(12) United States Patent
Dong et al.

(10) Patent No.: US 10,913,786 B2
(45) Date of Patent: Feb. 9, 2021

(54) COMPOSITIONS AND METHODS FOR INHIBITING WNT SIGNALING

(71) Applicant: Children's Medical Center Corporation, Boston, MA (US)

(72) Inventors: Min Dong, Weatogue, CT (US); Liang Tao, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 16/086,159

(22) PCT Filed: Mar. 21, 2017

(86) PCT No.: PCT/US2017/023381
§ 371 (c)(1),
(2) Date: Sep. 18, 2018

(87) PCT Pub. No.: WO2017/165398
PCT Pub. Date: Sep. 28, 2017

(65) Prior Publication Data
US 2019/0031734 A1 Jan. 31, 2019

Related U.S. Application Data

(60) Provisional application No. 62/311,381, filed on Mar. 21, 2016.

(51) Int. Cl.
| | | |
|---|---|---|
| *A61K 39/00* | (2006.01) | |
| *C07K 14/71* | (2006.01) | |
| *C07K 14/33* | (2006.01) | |
| *A61K 47/68* | (2017.01) | |
| *A61P 35/00* | (2006.01) | |
| *C07K 16/12* | (2006.01) | |
| *C07K 16/22* | (2006.01) | |
| *C12N 15/62* | (2006.01) | |
| *C12N 15/85* | (2006.01) | |
| *A61P 31/04* | (2006.01) | |
| *A61K 31/095* | (2006.01) | |
| *A61K 31/41* | (2006.01) | |

(52) U.S. Cl.
CPC .......... *C07K 14/71* (2013.01); *A61K 47/6849* (2017.08); *A61P 35/00* (2018.01); *C07K 14/33* (2013.01); *C07K 16/1282* (2013.01); *C07K 16/22* (2013.01); *C12N 15/62* (2013.01); *C12N 15/85* (2013.01); *A61K 31/095* (2013.01); *A61K 31/41* (2013.01); *A61K 2300/00* (2013.01); *A61P 31/04* (2018.01); *C07K 2319/00* (2013.01); *C07K 2319/21* (2013.01); *C07K 2319/23* (2013.01); *C07K 2319/24* (2013.01); *C07K 2319/30* (2013.01); *C07K 2319/31* (2013.01); *C12N 2015/8572* (2013.01)

(58) Field of Classification Search
CPC ...................................................... C07K 14/71
See application file for complete search history.

(56) References Cited

U.S. PATENT DOCUMENTS

| | | | |
|---|---|---|---|
| 2004/0053366 A1 | 3/2004 | Lo et al. | |
| 2006/0263368 A1* | 11/2006 | Rosenblum | ........ A61K 41/0038 424/155.1 |
| 2008/0241164 A1 | 10/2008 | Knopf et al. | |
| 2008/0299136 A1* | 12/2008 | Ernst | ...................... C07K 14/71 424/178.1 |
| 2010/0104574 A1* | 4/2010 | Gurney | .................. A61K 31/00 424/139.1 |
| 2015/0093389 A1 | 4/2015 | Shone et al. | |
| 2015/0140070 A1* | 5/2015 | Heartlein | ............... A61K 38/53 424/450 |

FOREIGN PATENT DOCUMENTS

| | | |
|---|---|---|
| WO | WO 2013/150309 A1 | 10/2013 |
| WO | WO 2014/086787 A1 | 6/2014 |
| WO | WO 2019/143552 A1 | 7/2019 |

OTHER PUBLICATIONS

Chen et al., Structural basis for recognition of frizzled proteins by Clostridium difficile toxin B. Science. May 11, 2018;360:664-669.
Debruine et al., Wnt5a promotes Frizzled-4 signalosome assembly by stabilizing cysteine-rich domain dimerization. Genes Dev. May 1, 2017;31(9):916-926.
Salnikova et al., Physical characterization of clostridium difficile toxins and toxoids: effect of the formaldehyde crosslinking on thermal stability. J Pharm Sci. Sep. 2008. 97(9)3735-3552.
Tao et al., Frizzled proteins are colonic epithelial receptors for C. difficile toxin B. Nature. Sep. 28, 2016;538(7625):350-355.
EP 17770971.4, Jul. 26, 2019, Extended European Search Report.
PCT/2017/023381, Jun. 7, 2017, Invitation to Pay Additional Fees.
PCT/2017/023381, Aug. 10, 2017, International Search Report and Written Opinion.
PCT/2017/023381, Oct. 4, 2018, International Preliminary Report on Patentability.
PCT/2019/013440, Apr. 25, 2019, Invitation to Pay Additional Fees.
PCT/2019/013440, Jul. 1, 2019, International Search Report and Written Opinion.
EP 17770971.4, Aug. 26, 2020, European Examination Report.
European Examination Report for Application No. EP 17770971.4 dated Aug. 26, 2020.

* cited by examiner

*Primary Examiner* — Albert M Navarro
(74) *Attorney, Agent, or Firm* — Wolf, Greenfield & Sacks, P.C.

(57) ABSTRACT

The present disclosure relates to isolated polypeptides that inhibit Wnt signaling, pharmaceutical compositions comprising the isolated polypeptides, and methods of use thereof. Nucleic acids, cells, and methods of production related to the isolated polypeptides and compositions are also disclosed.

18 Claims, 39 Drawing Sheets

Specification includes a Sequence Listing.

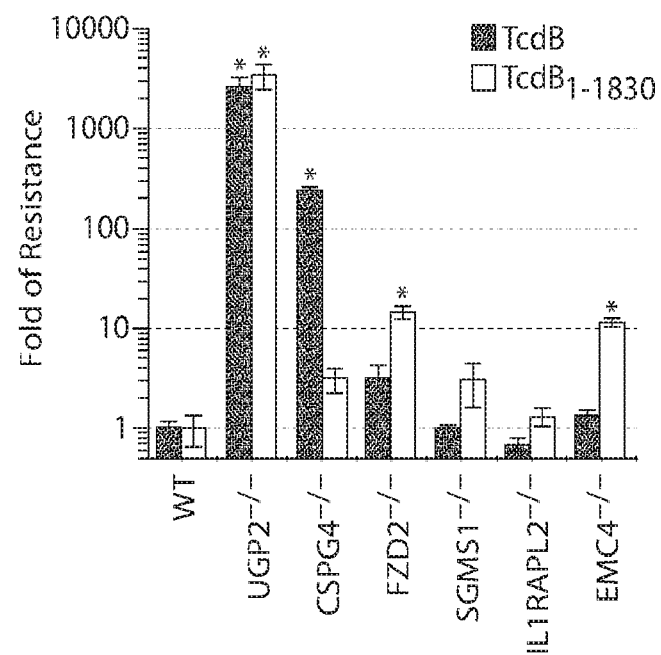
Figure 2A
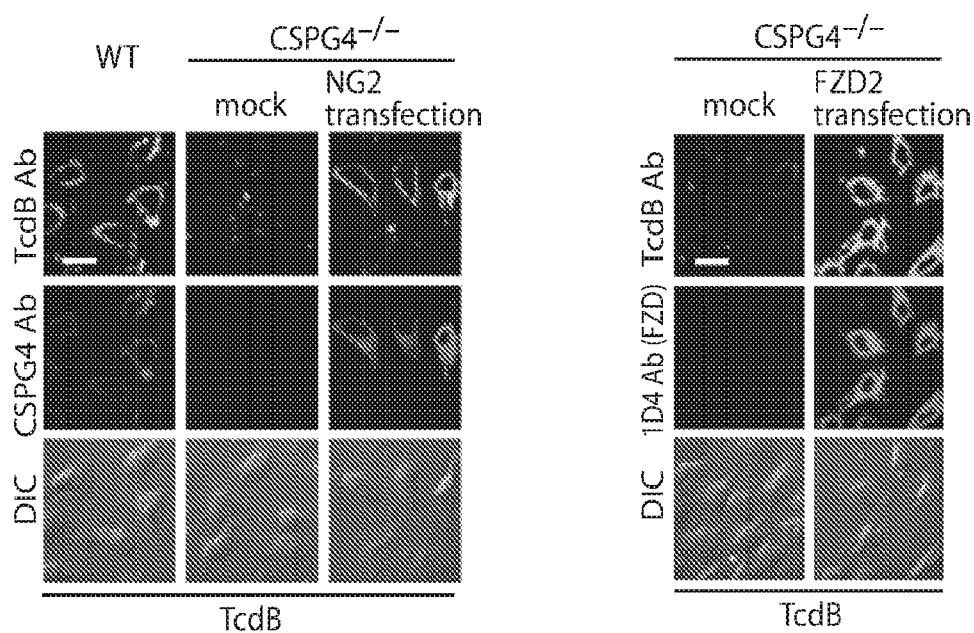
Figure 2B
Figure 2C

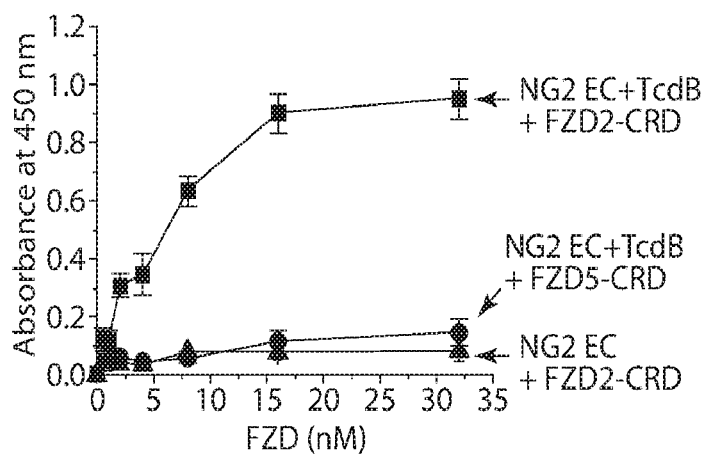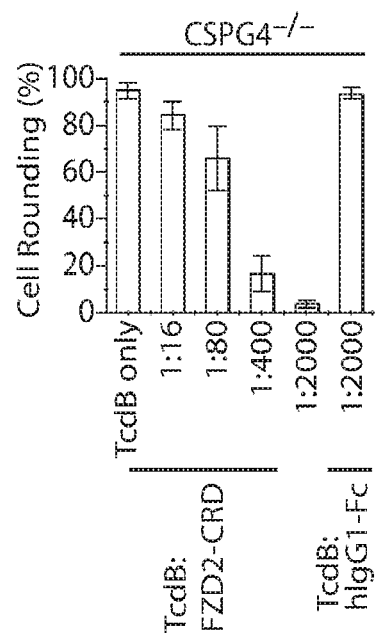
Figure 3A
Figure 3B
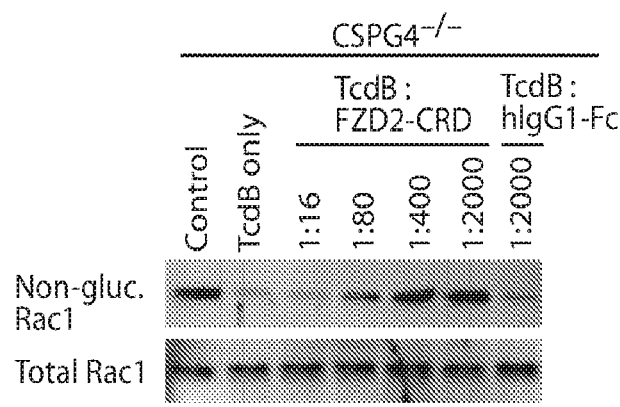
Figure 3C

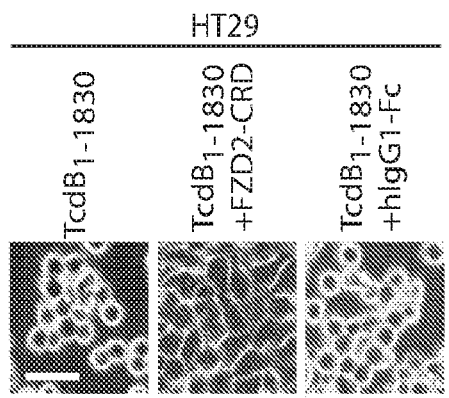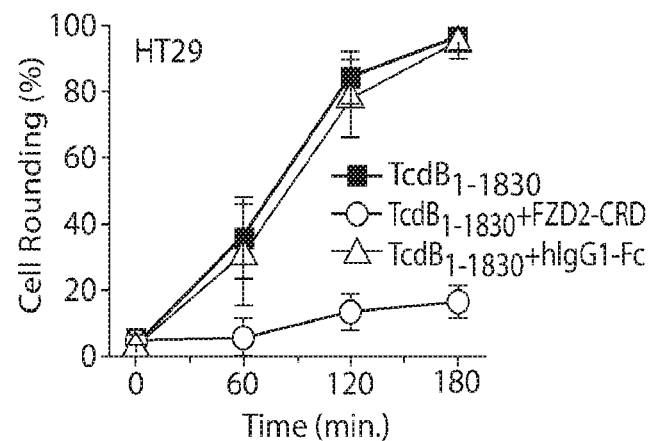
Figure 3D
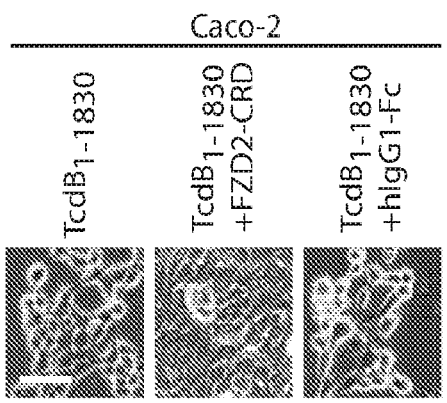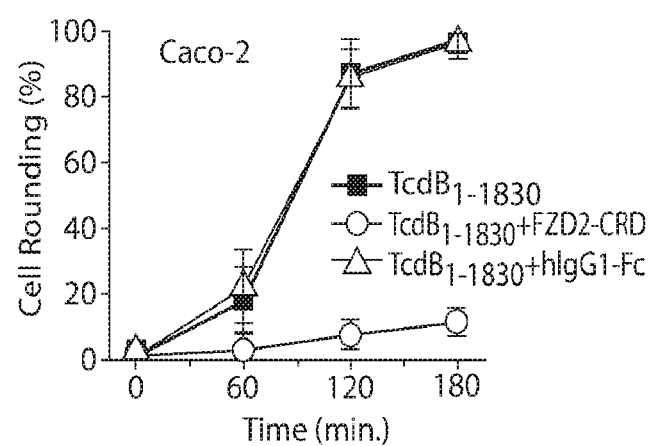
Figure 3E
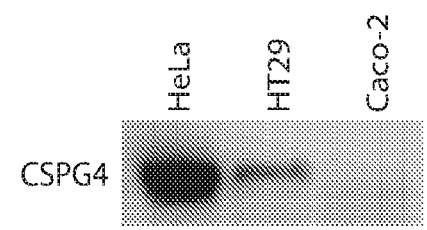
Figure 3F a = normal organoids
b = growth inhibited organoids

| Target gene | Mutation rate | Number of unique mutations |
|---|---|---|
| CSPG4 | 98.7% | 38,661 |
| FZD2 | 96.3% | 66,782 |
| UGP2 | 81.7% | 49,204 |
| EMC4 | 81.5% | 127,086 |
| SGMS1 | 91.1% | 110,938 |
| IL1RAPL2 | 72.4% | 82,797 |

Figure 8

| CR$_{50}$ (pM) | TcdB | TcdB$_{1-1830}$ |
|---|---|---|
| WT | 0.011±0.002 | 0.98±0.33 |
| UGP2-/- | 29.1±8.3 * | 3350±930 * |
| CSPG4-/- | 2.64±0.41 * | 3.09±0.77 |
| FZD2-/- | 0.035±0.014 | 14.3±2.1 * |
| SGMS1-/- | 0.011±0.001 | 2.99±1.40 |
| IL1RAPL2-/- | 0.0078±0.0014 | 1.29±0.27 |
| EMC4-/- | 0.015±0.002 | 11.22±1.18 * |

```
FZD1-CRD  YNGERGISVPDHGYCQPISIPLCTDIAYNQTIMPNLLGHTNQEDAGLEVH
FZD2-CRD  FHGEKGISIPDHGFCQPISIPLCTDIAYNQTIMPNLLGHTNQEDAGLEVH
FZD7-CRD  YHGEKGISVPDHGFCQPISIPLCTDIAYNQTILPNLLGHTNQEDAGLEVH
          YHGEKGISVPDHGFCQPISIPLCTDIAYNQTIMPNLLGHTNQEDAGLEVH

QFYPLVKVQCSAELKFFLCSMYAPVCTVLEQALPPCRSLCERARQGCEAL
          QFYPLVKVQCSRELRFFLCSMYAPVCTVLEQAIPPCRSICERARQGCEAL
          QFYPLVKVQCSPELRFFLCSMYAPVCTVLDQAIPPCRSLCERARQGCEAL
          QFYPLVKVQCSPELRFFLCSMYAPVCTVLDQAIPPCRSLCERARQGCEAL

MNKFGFQWPDTLKCEKFPVHGAGELCVGQNTSD
          MNKFGFQWPERLRCEHFPRHGAEQICVGQNHSE
          MNKFGFQWPERLRCENFPVHGAGEICVGQNTSD
          MNKFGFQWPERLRCE FPVHGAGEICVGQNTSD
```

Figure 13

| TcdB$_{1-1830}$ | K$_D$ (M) | K$_{on}$ (1/Ms) | K$_{on}$ Error | K$_{off}$ (1/s) | K$_{off}$ Error |
|---|---|---|---|---|---|
| FZD2 | 1.7x10$^{-8}$ | 1.13x10$^5$ | 3.29x10$^3$ | 1.89x10$^{-3}$ | 5.47x10$^{-5}$ |

```
                        SEQUENCE LISTING

<160> NUMBER OF SEQ ID NOS: 635

<210> SEQ ID NO 1
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 1
aatggactat catatgctta ccgtaacttg aaagtatttc g                            41

<210> SEQ ID NO 2
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 2
atgaatactg ccatttgtct caagatctag ttacgc                                  36

<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 3
ccggagacac ggagcagtgg                                                    20
```

```
<210> SEQ ID NO 4
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 4
gcgctgctgg gacatcgcct                                                 20

<210> SEQ ID NO 5
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 5
accttatacc acacaacatc                                                 20

<210> SEQ ID NO 6
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 6
tgcgagcact tcccgcgcca                                                 20

<210> SEQ ID NO 7
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 7
agcgcatgac cactacactg                                                 20

<210> SEQ ID NO 8
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 8
acaggcagaa aacggctcct                                                 20

<210> SEQ ID NO 9
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 9
gtgtaatgac aagttcgccg                                                 20

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide
```

```
<400> SEQUENCE: 10
gagaacggta aagagcgtcg                                              20

<210> SEQ ID NO 11
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 11
ctggacttcc agaagaaca                                               19

<210> SEQ ID NO 12
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 12
tggtgtgcaa cgacaagttt g                                            21

<210> SEQ ID NO 13
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 13
cgcttctcag aggacggtta t                                            21

<210> SEQ ID NO 14
<211> LENGTH: 133
<212> TYPE: PRT
<213> ORGANISM: Homo sapiens

<400> SEQUENCE: 14

Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
            20                  25                  30

Met Pro Asn Leu Leu Gly His Thr Asn Gln Glu Asp Ala Gly Leu Glu
        35                  40                  45

Val His Gln Phe Tyr Pro Leu Val Lys Val Gln Cys Ser Ala Glu Leu
    50                  55                  60

Lys Phe Phe Leu Cys Ser Met Tyr Ala Pro Val Cys Thr Val Leu Glu
65                  70                  75                  80

Gln Ala Leu Pro Pro Cys Arg Ser Leu Cys Glu Arg Ala Arg Gln Gly
                85                  90                  95

Cys Glu Ala Leu Met Asn Lys Phe Gly Phe Gln Trp Pro Asp Thr Leu
            100                 105                 110

Lys Cys Glu Lys Phe Pro Val His Gly Ala Gly Glu Leu Cys Val Gly
        115                 120                 125

Gln Asn Thr Ser Asp
    130

<210> SEQ ID NO 15
<211> LENGTH: 133
<212> TYPE: PRT
```

<213> ORGANISM: Homo sapiens

<400> SEQUENCE: 15

Phe His Gly Glu Lys Gly Ile Ser Ile Pro Asp His Gly Phe Cys Gln
1               5                   10                  15

Pro Ile Ser Ile Pro Leu Cys Thr Asp Ile Ala Tyr Asn Gln Thr Ile
            20                  25                  30

Met Pro Asn Leu Leu Gly His Thr Asn Gln Glu Asp Ala Gly Leu Glu
        35                  40                  45

Val His Gln Phe Tyr Pro Leu Val Lys Val Gln Cys Ser Pro Glu Leu
    50                  55                  60

Arg Phe Phe Leu Cys Ser Met Tyr Ala Pro Val Cys Thr Val Leu Glu
65                  70                  75                  80

Gln Ala Ile Pro Pro Cys Arg Ser Ile Cys Glu Arg Ala Arg Gln Gly
                85                  90                  95

Cys Glu Ala Leu Met Asn Lys Phe Gly Phe Gln Trp Pro Glu Arg Leu
            100                 105                 110

Arg Cys Glu His Phe Pro Arg His Gly Ala Glu Gln Ile Cys Val Gly
        115                 120                 125

Gln Asn His Ser Glu
    130

<210> SEQ ID NO 16
<211> LENGTH: 133
<212> TYPE: PRT
<213> ORGANISM: Homo sapiens

<400> SEQUENCE: 16

Tyr His Gly Glu Lys Gly Ile Ser Val Pro Asp His Gly Phe Cys Gln
1               5                   10                  15

Pro Ile Ser Ile Pro Leu Cys Thr Asp Ile Ala Tyr Asn Gln Thr Ile
            20                  25                  30

Leu Pro Asn Leu Leu Gly His Thr Asn Gln Glu Asp Ala Gly Leu Glu
        35                  40                  45

Val His Gln Phe Tyr Pro Leu Val Lys Val Gln Cys Ser Pro Glu Leu
    50                  55                  60

Arg Phe Phe Leu Cys Ser Met Tyr Ala Pro Val Cys Thr Val Leu Asp
65                  70                  75                  80

Gln Ala Ile Pro Pro Cys Arg Ser Leu Cys Glu Arg Ala Arg Gln Gly
                85                  90                  95

Cys Glu Ala Leu Met Asn Lys Phe Gly Phe Gln Trp Pro Glu Arg Leu
            100                 105                 110

Arg Cys Glu Asn Phe Pro Val His Gly Ala Gly Glu Ile Cys Val Gly
        115                 120                 125

Gln Asn Thr Ser Asp
    130

<210> SEQ ID NO 17
<211> LENGTH: 132
<212> TYPE: PRT
<213> ORGANISM: Homo sapiens

<400> SEQUENCE: 17

Tyr His Gly Glu Lys Gly Ile Ser Val Pro Asp His Gly Phe Cys Gln
1               5                   10                  15

Pro Ile Ser Ile Pro Leu Cys Thr Asp Ile Ala Tyr Asn Gln Thr Ile
            20                  25                  30

```
Met Pro Asn Leu Leu Gly His Thr Asn Gln Glu Asp Ala Gly Leu Glu
         35                  40                  45

Val His Gln Phe Tyr Pro Leu Val Lys Val Gln Cys Ser Pro Glu Leu
 50                  55                  60

Arg Phe Phe Leu Cys Ser Met Tyr Ala Pro Val Cys Thr Val Leu Glu
 65                  70                  75                  80

Gln Ala Ile Pro Pro Cys Arg Ser Leu Cys Glu Arg Ala Arg Gln Gly
                 85                  90                  95

Cys Glu Ala Leu Met Asn Lys Phe Gly Phe Gln Trp Pro Glu Arg Leu
             100                 105                 110

Arg Cys Glu Phe Pro Val His Gly Ala Gly Glu Ile Cys Val Gly Gln
             115                 120                 125

Asn Thr Ser Asp
     130

<210> SEQ ID NO 18
<211> LENGTH: 722
<212> TYPE: PRT
<213> ORGANISM: Artificial Sequence
<220> FEATURE:
<223> OTHER INFORMATION: Synthetic Polypeptide

<400> SEQUENCE: 18

Arg Asp Lys Ala Thr Lys Val Val Asp Tyr Phe Lys His Val Ser Leu
 1               5                  10                  15

Val Glu Thr Glu Gly Val Phe Thr Leu Leu Asp Asp Lys Ile Met Met
             20                  25                  30

Pro Gln Asp Asp Leu Val Ile Ser Glu Ile Asp Phe Asn Asn Asn Ser
         35                  40                  45

Ile Val Leu Gly Lys Cys Glu Ile Trp Arg Met Glu Gly Gly Ser Gly
 50                  55                  60

His Thr Val Thr Asp Asp Ile Asp His Phe Phe Ser Ala Pro Ser Ile
 65                  70                  75                  80

Thr Tyr Arg Glu Pro His Leu Ser Ile Tyr Asp Val Leu Glu Val Gln
                 85                  90                  95

Lys Glu Glu Leu Asp Leu Ser Lys Asp Leu Met Val Leu Pro Asn Ala
             100                 105                 110

Pro Asn Arg Val Phe Ala Trp Glu Thr Gly Trp Thr Pro Gly Leu Arg
             115                 120                 125

Ser Leu Glu Asn Asp Gly Thr Lys Leu Leu Asp Arg Ile Arg Asp Asn
     130                 135                 140

Tyr Glu Gly Glu Phe Tyr Trp Arg Tyr Phe Ala Phe Ile Ala Asp Ala
145                 150                 155                 160

Leu Ile Thr Thr Leu Lys Pro Arg Tyr Glu Asp Thr Asn Ile Arg Ile
                 165                 170                 175

Asn Leu Asp Ser Asn Thr Arg Ser Phe Ile Val Pro Ile Ile Thr Thr
             180                 185                 190

Glu Tyr Ile Arg Glu Lys Leu Ser Tyr Ser Phe Tyr Gly Ser Gly Gly
             195                 200                 205

Thr Tyr Ala Leu Ser Leu Ser Gln Tyr Asn Met Gly Ile Asn Ile Glu
     210                 215                 220

Leu Ser Glu Ser Asp Val Trp Ile Ile Asp Val Asp Asn Val Val Arg
225                 230                 235                 240

Asp Val Thr Ile Glu Ser Asp Lys Ile Lys Lys Gly Asp Leu Ile Glu
                 245                 250                 255
```

```
Gly Ile Leu Ser Thr Leu Ser Ile Glu Glu Asn Lys Ile Ile Leu Asn
            260                 265                 270

Ser His Glu Ile Asn Phe Ser Gly Glu Val Asn Gly Ser Asn Gly Phe
        275                 280                 285

Val Ser Leu Thr Phe Ser Ile Leu Glu Gly Ile Asn Ala Ile Ile Glu
    290                 295                 300

Val Asp Leu Leu Ser Lys Ser Tyr Lys Leu Leu Ile Ser Gly Glu Leu
305                 310                 315                 320

Lys Ile Leu Met Leu Asn Ser Asn His Ile Gln Gln Lys Ile Asp Tyr
                325                 330                 335

Ile Gly Phe Asn Ser Glu Leu Gln Lys Asn Ile Pro Tyr Ser Phe Val
            340                 345                 350

Asp Ser Glu Gly Lys Glu Asn Gly Phe Ile Asn Gly Ser Thr Lys Glu
        355                 360                 365

Gly Leu Phe Val Ser Glu Leu Pro Asp Val Val Leu Ile Ser Lys Val
    370                 375                 380

Tyr Met Asp Asp Ser Lys Pro Ser Phe Gly Tyr Tyr Ser Asn Asn Leu
385                 390                 395                 400

Lys Asp Val Lys Val Ile Thr Lys Asp Asn Val Asn Ile Leu Thr Gly
                405                 410                 415

Tyr Tyr Leu Lys Asp Asp Ile Lys Ile Ser Leu Ser Leu Thr Leu Gln
            420                 425                 430

Asp Glu Lys Thr Ile Lys Leu Asn Ser Val His Leu Asp Glu Ser Gly
        435                 440                 445

Val Ala Glu Ile Leu Lys Phe Met Asn Arg Lys Gly Asn Thr Asn Thr
    450                 455                 460

Ser Asp Ser Leu Met Ser Phe Leu Glu Ser Met Asn Ile Lys Ser Ile
465                 470                 475                 480

Phe Val Asn Phe Leu Gln Ser Asn Ile Lys Phe Ile Leu Asp Ala Asn
                485                 490                 495

Phe Ile Ile Ser Gly Thr Thr Ser Ile Gly Gln Phe Glu Phe Ile Cys
            500                 505                 510

Asp Glu Asn Asp Asn Ile Gln Pro Tyr Phe Ile Lys Phe Asn Thr Leu
        515                 520                 525

Glu Thr Asn Tyr Thr Leu Tyr Val Gly Asn Arg Gln Asn Met Ile Val
    530                 535                 540

Glu Pro Asn Tyr Asp Leu Asp Asp Ser Gly Asp Ile Ser Ser Thr Val
545                 550                 555                 560

Ile Asn Phe Ser Gln Lys Tyr Leu Tyr Gly Ile Asp Ser Cys Val Asn
                565                 570                 575

Lys Val Val Ile Ser Pro Asn Ile Tyr Thr Asp Glu Ile Asn Ile Thr
            580                 585                 590

Pro Val Tyr Glu Thr Asn Asn Thr Tyr Pro Glu Val Ile Val Leu Asp
        595                 600                 605

Ala Asn Tyr Ile Asn Glu Lys Ile Asn Val Asn Ile Asn Asp Leu Ser
    610                 615                 620

Ile Arg Tyr Val Trp Ser Asn Asp Gly Asn Asp Phe Ile Leu Met Ser
625                 630                 635                 640

Thr Ser Glu Glu Asn Lys Val Ser Gln Val Lys Ile Arg Phe Val Asn
                645                 650                 655

Val Phe Lys Asp Lys Thr Leu Ala Asn Lys Leu Ser Phe Asn Phe Ser
            660                 665                 670
```

-continued

```
Asp Lys Gln Asp Val Pro Val Ser Glu Ile Ile Leu Ser Phe Thr Pro
            675                 680                 685

Ser Tyr Tyr Glu Asp Gly Leu Ile Gly Tyr Asp Leu Gly Leu Val Ser
690                 695                 700

Leu Tyr Asn Glu Lys Phe Tyr Ile Asn Asn Phe Gly Met Met Val Ser
705                 710                 715                 720

Gly Leu
```

<210> SEQ ID NO 19
<211> LENGTH: 808
<212> TYPE: PRT
<213> ORGANISM: Artificial Sequence
<220> FEATURE:
<223> OTHER INFORMATION: Synthetic Polypeptide

<400> SEQUENCE: 19

```
Gly Leu Pro Ile Ile Ala Thr Ile Ile Asp Gly Val Ser Leu Gly Ala
1               5                   10                  15

Ala Ile Lys Glu Leu Ser Glu Thr Ser Asp Pro Leu Leu Arg Gln Glu
            20                  25                  30

Ile Glu Ala Lys Ile Gly Ile Met Ala Val Asn Leu Thr Thr Ala Thr
        35                  40                  45

Thr Ala Ile Ile Thr Ser Ser Leu Gly Ile Ala Ser Gly Phe Ser Ile
    50                  55                  60

Leu Leu Val Pro Leu Ala Gly Ile Ser Ala Gly Ile Pro Ser Leu Val
65                  70                  75                  80

Asn Asn Glu Leu Val Leu Arg Asp Lys Ala Thr Lys Val Val Asp Tyr
                85                  90                  95

Phe Lys His Val Ser Leu Val Glu Thr Glu Gly Val Phe Thr Leu Leu
            100                 105                 110

Asp Asp Lys Ile Met Met Pro Gln Asp Asp Leu Val Ile Ser Glu Ile
        115                 120                 125

Asp Phe Asn Asn Asn Ser Ile Val Leu Gly Lys Cys Glu Ile Trp Arg
    130                 135                 140

Met Glu Gly Gly Ser Gly His Thr Val Thr Asp Asp Ile Asp His Phe
145                 150                 155                 160

Phe Ser Ala Pro Ser Ile Thr Tyr Arg Glu Pro His Leu Ser Ile Tyr
                165                 170                 175

Asp Val Leu Glu Val Gln Lys Glu Glu Leu Asp Leu Ser Lys Asp Leu
            180                 185                 190

Met Val Leu Pro Asn Ala Pro Asn Arg Val Phe Ala Trp Glu Thr Gly
        195                 200                 205

Trp Thr Pro Gly Leu Arg Ser Leu Glu Asn Asp Gly Thr Lys Leu Leu
    210                 215                 220

Asp Arg Ile Arg Asp Asn Tyr Glu Gly Glu Phe Tyr Trp Arg Tyr Phe
225                 230                 235                 240

Ala Phe Ile Ala Asp Ala Leu Ile Thr Thr Leu Lys Pro Arg Tyr Glu
                245                 250                 255

Asp Thr Asn Ile Arg Ile Asn Leu Asp Ser Asn Thr Arg Ser Phe Ile
            260                 265                 270

Val Pro Ile Ile Thr Thr Glu Tyr Ile Arg Glu Lys Leu Ser Tyr Ser
        275                 280                 285

Phe Tyr Gly Ser Gly Gly Thr Tyr Ala Leu Ser Leu Ser Gln Tyr Asn
    290                 295                 300

Met Gly Ile Asn Ile Glu Leu Ser Glu Ser Asp Val Trp Ile Ile Asp
```

-continued

```
            305                 310                 315                 320
Val Asp Asn Val Val Arg Asp Val Thr Ile Glu Ser Asp Lys Ile Lys
                    325                 330                 335
Lys Gly Asp Leu Ile Glu Gly Ile Leu Ser Thr Leu Ser Ile Glu Glu
                    340                 345                 350
Asn Lys Ile Ile Leu Asn Ser His Glu Ile Asn Phe Ser Gly Glu Val
                    355                 360                 365
Asn Gly Ser Asn Gly Phe Val Ser Leu Thr Phe Ser Ile Leu Glu Gly
                    370                 375                 380
Ile Asn Ala Ile Ile Glu Val Asp Leu Ser Lys Ser Tyr Lys Leu
385                 390                 395                 400
Leu Ile Ser Gly Glu Leu Lys Ile Leu Met Leu Asn Ser Asn His Ile
                    405                 410                 415
Gln Gln Lys Ile Asp Tyr Ile Gly Phe Asn Ser Glu Leu Gln Lys Asn
                    420                 425                 430
Ile Pro Tyr Ser Phe Val Asp Ser Glu Gly Lys Glu Asn Gly Phe Ile
                    435                 440                 445
Asn Gly Ser Thr Lys Glu Gly Leu Phe Val Ser Glu Leu Pro Asp Val
                    450                 455                 460
Val Leu Ile Ser Lys Val Tyr Met Asp Asp Ser Lys Pro Ser Phe Gly
465                 470                 475                 480
Tyr Tyr Ser Asn Asn Leu Lys Asp Val Lys Val Ile Thr Lys Asp Asn
                    485                 490                 495
Val Asn Ile Leu Thr Gly Tyr Tyr Leu Lys Asp Asp Ile Lys Ile Ser
                    500                 505                 510
Leu Ser Leu Thr Leu Gln Asp Glu Lys Thr Ile Lys Leu Asn Ser Val
                    515                 520                 525
His Leu Asp Glu Ser Gly Val Ala Glu Ile Leu Lys Phe Met Asn Arg
                    530                 535                 540
Lys Gly Asn Thr Asn Thr Ser Asp Ser Leu Met Ser Phe Leu Glu Ser
545                 550                 555                 560
Met Asn Ile Lys Ser Ile Phe Val Asn Phe Leu Gln Ser Asn Ile Lys
                    565                 570                 575
Phe Ile Leu Asp Ala Asn Phe Ile Ile Ser Gly Thr Thr Ser Ile Gly
                    580                 585                 590
Gln Phe Glu Phe Ile Cys Asp Glu Asn Asp Asn Ile Gln Pro Tyr Phe
                    595                 600                 605
Ile Lys Phe Asn Thr Leu Glu Thr Asn Tyr Thr Leu Tyr Val Gly Asn
                    610                 615                 620
Arg Gln Asn Met Ile Val Glu Pro Asn Tyr Asp Leu Asp Asp Ser Gly
625                 630                 635                 640
Asp Ile Ser Ser Thr Val Ile Asn Phe Ser Gln Lys Tyr Leu Tyr Gly
                    645                 650                 655
Ile Asp Ser Cys Val Asn Lys Val Val Ile Ser Pro Asn Ile Tyr Thr
                    660                 665                 670
Asp Glu Ile Asn Ile Thr Pro Val Tyr Glu Thr Asn Asn Thr Tyr Pro
                    675                 680                 685
Glu Val Ile Val Leu Asp Ala Asn Tyr Ile Asn Glu Lys Ile Asn Val
                    690                 695                 700
Asn Ile Asn Asp Leu Ser Ile Arg Tyr Val Trp Ser Asn Asp Gly Asn
705                 710                 715                 720
Asp Phe Ile Leu Met Ser Thr Ser Glu Glu Asn Lys Val Ser Gln Val
                    725                 730                 735
```

-continued

```
Lys Ile Arg Phe Val Asn Val Phe Lys Asp Lys Thr Leu Ala Asn Lys
            740                 745                 750

Leu Ser Phe Asn Phe Ser Asp Lys Gln Asp Val Pro Val Ser Glu Ile
            755                 760                 765

Ile Leu Ser Phe Thr Pro Ser Tyr Tyr Glu Asp Gly Leu Ile Gly Tyr
            770                 775                 780

Asp Leu Gly Leu Val Ser Leu Tyr Asn Glu Lys Phe Tyr Ile Asn Asn
785                 790                 795                 800

Phe Gly Met Met Val Ser Gly Leu
                805

<210> SEQ ID NO 20
<211> LENGTH: 988
<212> TYPE: PRT
<213> ORGANISM: Artificial Sequence
<220> FEATURE:
<223> OTHER INFORMATION: Synthetic Polypeptide

<400> SEQUENCE: 20

Arg Asp Lys Ala Thr Lys Val Val Asp Tyr Phe Lys His Val Ser Leu
1               5                   10                  15

Val Glu Thr Glu Gly Val Phe Thr Leu Leu Asp Asp Lys Ile Met Met
            20                  25                  30

Pro Gln Asp Asp Leu Val Ile Ser Glu Ile Asp Phe Asn Asn Asn Ser
            35                  40                  45

Ile Val Leu Gly Lys Cys Glu Ile Trp Arg Met Glu Gly Gly Ser Gly
        50                  55                  60

His Thr Val Thr Asp Asp Ile Asp His Phe Phe Ser Ala Pro Ser Ile
65                  70                  75                  80

Thr Tyr Arg Glu Pro His Leu Ser Ile Tyr Asp Val Leu Glu Val Gln
                85                  90                  95

Lys Glu Glu Leu Asp Leu Ser Lys Asp Leu Met Val Leu Pro Asn Ala
            100                 105                 110

Pro Asn Arg Val Phe Ala Trp Glu Thr Gly Trp Thr Pro Gly Leu Arg
        115                 120                 125

Ser Leu Glu Asn Asp Gly Thr Lys Leu Leu Asp Arg Ile Arg Asp Asn
    130                 135                 140

Tyr Glu Gly Glu Phe Tyr Trp Arg Tyr Phe Ala Phe Ile Ala Asp Ala
145                 150                 155                 160

Leu Ile Thr Thr Leu Lys Pro Arg Tyr Glu Asp Thr Asn Ile Arg Ile
                165                 170                 175

Asn Leu Asp Ser Asn Thr Arg Ser Phe Ile Val Pro Ile Ile Thr Thr
            180                 185                 190

Glu Tyr Ile Arg Glu Lys Leu Ser Ser Phe Tyr Gly Ser Gly Gly
        195                 200                 205

Thr Tyr Ala Leu Ser Leu Ser Gln Tyr Asn Met Gly Ile Asn Ile Glu
    210                 215                 220

Leu Ser Glu Ser Asp Val Trp Ile Asp Val Asp Asn Val Val Arg
225                 230                 235                 240

Asp Val Thr Ile Glu Ser Asp Lys Ile Lys Lys Gly Asp Leu Ile Glu
                245                 250                 255

Gly Ile Leu Ser Thr Leu Ser Ile Glu Glu Asn Lys Ile Ile Leu Asn
            260                 265                 270

Ser His Glu Ile Asn Phe Ser Gly Glu Val Asn Gly Ser Asn Gly Phe
        275                 280                 285
```

```
Val Ser Leu Thr Phe Ser Ile Leu Glu Gly Ile Asn Ala Ile Ile Glu
    290                 295                 300

Val Asp Leu Leu Ser Lys Ser Tyr Lys Leu Leu Ile Ser Gly Glu Leu
305                 310                 315                 320

Lys Ile Leu Met Leu Asn Ser Asn His Ile Gln Gln Lys Ile Asp Tyr
                325                 330                 335

Ile Gly Phe Asn Ser Glu Leu Gln Lys Asn Ile Pro Tyr Ser Phe Val
                340                 345                 350

Asp Ser Glu Gly Lys Glu Asn Gly Phe Ile Asn Gly Ser Thr Lys Glu
            355                 360                 365

Gly Leu Phe Val Ser Glu Leu Pro Asp Val Val Leu Ile Ser Lys Val
    370                 375                 380

Tyr Met Asp Asp Ser Lys Pro Ser Phe Gly Tyr Tyr Ser Asn Asn Leu
385                 390                 395                 400

Lys Asp Val Lys Val Ile Thr Lys Asp Asn Val Asn Ile Leu Thr Gly
                405                 410                 415

Tyr Tyr Leu Lys Asp Asp Ile Lys Ile Ser Leu Ser Leu Thr Leu Gln
                420                 425                 430

Asp Glu Lys Thr Ile Lys Leu Asn Ser Val His Leu Asp Glu Ser Gly
            435                 440                 445

Val Ala Glu Ile Leu Lys Phe Met Asn Arg Lys Gly Asn Thr Asn Thr
    450                 455                 460

Ser Asp Ser Leu Met Ser Phe Leu Glu Ser Met Asn Ile Lys Ser Ile
465                 470                 475                 480

Phe Val Asn Phe Leu Gln Ser Asn Ile Lys Phe Ile Leu Asp Ala Asn
                485                 490                 495

Phe Ile Ile Ser Gly Thr Thr Ser Ile Gly Gln Phe Glu Phe Ile Cys
                500                 505                 510

Asp Glu Asn Asp Asn Ile Gln Pro Tyr Phe Ile Lys Phe Asn Thr Leu
            515                 520                 525

Glu Thr Asn Tyr Thr Leu Tyr Val Gly Asn Arg Gln Asn Met Ile Val
    530                 535                 540

Glu Pro Asn Tyr Asp Leu Asp Asp Ser Gly Asp Ile Ser Ser Thr Val
545                 550                 555                 560

Ile Asn Phe Ser Gln Lys Tyr Leu Tyr Gly Ile Asp Ser Cys Val Asn
                565                 570                 575

Lys Val Val Ile Ser Pro Asn Ile Tyr Thr Asp Glu Ile Asn Ile Thr
                580                 585                 590

Pro Val Tyr Glu Thr Asn Asn Thr Tyr Pro Glu Val Ile Val Leu Asp
            595                 600                 605

Ala Asn Tyr Ile Asn Glu Lys Ile Asn Val Asn Ile Asn Asp Leu Ser
    610                 615                 620

Ile Arg Tyr Val Trp Ser Asn Asp Gly Asn Asp Phe Ile Leu Met Ser
625                 630                 635                 640

Thr Ser Glu Glu Asn Lys Val Ser Gln Val Lys Ile Arg Phe Val Asn
                645                 650                 655

Val Phe Lys Asp Lys Thr Leu Ala Asn Lys Leu Ser Phe Asn Phe Ser
                660                 665                 670

Asp Lys Gln Asp Val Pro Val Ser Glu Ile Ile Leu Ser Phe Thr Pro
            675                 680                 685

Ser Tyr Tyr Glu Asp Gly Leu Ile Gly Tyr Asp Leu Gly Leu Val Ser
    690                 695                 700
```

Leu Tyr Asn Glu Lys Phe Tyr Ile Asn Asn Phe Gly Met Met Val Ser
705                 710                 715                 720

Gly Leu Ile Tyr Ile Asn Asp Ser Leu Tyr Tyr Phe Lys Pro Pro Val
                725                 730                 735

Asn Asn Leu Ile Thr Gly Phe Val Thr Val Gly Asp Asp Lys Tyr Tyr
            740                 745                 750

Phe Asn Pro Ile Asn Gly Gly Ala Ala Ser Ile Gly Glu Thr Ile Ile
        755                 760                 765

Asp Asp Lys Asn Tyr Tyr Phe Asn Gln Ser Gly Val Leu Gln Thr Gly
    770                 775                 780

Val Phe Ser Thr Glu Asp Gly Phe Lys Tyr Phe Ala Pro Ala Asn Thr
785                 790                 795                 800

Leu Asp Glu Asn Leu Glu Gly Glu Ala Ile Asp Phe Thr Gly Lys Leu
                805                 810                 815

Ile Ile Asp Glu Asn Ile Tyr Tyr Phe Asp Asp Asn Tyr Arg Gly Ala
                820                 825                 830

Val Glu Trp Lys Glu Leu Asp Gly Glu Met His Tyr Phe Ser Pro Glu
                835                 840                 845

Thr Gly Lys Ala Phe Lys Gly Leu Asn Gln Ile Gly Asp Tyr Lys Tyr
            850                 855                 860

Tyr Phe Asn Ser Asp Gly Val Met Gln Lys Gly Phe Val Ser Ile Asn
865                 870                 875                 880

Asp Asn Lys His Tyr Phe Asp Asp Ser Gly Val Met Lys Val Gly Tyr
                885                 890                 895

Thr Glu Ile Asp Gly Lys His Phe Tyr Phe Ala Glu Asn Gly Glu Met
                900                 905                 910

Gln Ile Gly Val Phe Asn Thr Glu Asp Gly Phe Lys Tyr Phe Ala His
            915                 920                 925

His Asn Glu Asp Leu Gly Asn Glu Glu Gly Glu Glu Ile Ser Tyr Ser
        930                 935                 940

Gly Ile Leu Asn Phe Asn Asn Lys Ile Tyr Tyr Phe Asp Asp Ser Phe
945                 950                 955                 960

Thr Ala Val Val Gly Trp Lys Asp Leu Glu Asp Gly Ser Lys Tyr Tyr
                965                 970                 975

Phe Asp Glu Asp Thr Ala Glu Ala Tyr Ile Gly Leu
            980                 985

<210> SEQ ID NO 21
<211> LENGTH: 947
<212> TYPE: PRT
<213> ORGANISM: Artificial Sequence
<220> FEATURE:
<223> OTHER INFORMATION: Synthetic Polypeptide

<400> SEQUENCE: 21

Arg Asp Lys Ala Thr Lys Val Val Asp Tyr Phe Lys His Val Ser Leu
1               5                   10                  15

Val Glu Thr Glu Gly Val Phe Thr Leu Leu Asp Asp Lys Ile Met Met
                20                  25                  30

Pro Gln Asp Asp Leu Val Ile Ser Glu Ile Asp Phe Asn Asn Asn Ser
            35                  40                  45

Ile Val Leu Gly Lys Cys Glu Ile Trp Arg Met Glu Gly Gly Ser Gly
        50                  55                  60

His Thr Val Thr Asp Asp Ile Asp His Phe Phe Ser Ala Pro Ser Ile
65                  70                  75                  80

-continued

```
Thr Tyr Arg Glu Pro His Leu Ser Ile Tyr Asp Val Leu Glu Val Gln
                85                  90                  95

Lys Glu Glu Leu Asp Leu Ser Lys Asp Leu Met Val Leu Pro Asn Ala
            100                 105                 110

Pro Asn Arg Val Phe Ala Trp Glu Thr Gly Trp Thr Pro Gly Leu Arg
        115                 120                 125

Ser Leu Glu Asn Asp Gly Thr Lys Leu Leu Asp Arg Ile Arg Asp Asn
    130                 135                 140

Tyr Glu Gly Glu Phe Tyr Trp Arg Tyr Phe Ala Phe Ile Ala Asp Ala
145                 150                 155                 160

Leu Ile Thr Thr Leu Lys Pro Arg Tyr Glu Asp Thr Asn Ile Arg Ile
                165                 170                 175

Asn Leu Asp Ser Asn Thr Arg Ser Phe Ile Val Pro Ile Ile Thr Thr
            180                 185                 190

Glu Tyr Ile Arg Glu Lys Leu Ser Tyr Ser Phe Tyr Gly Ser Gly Gly
        195                 200                 205

Thr Tyr Ala Leu Ser Leu Ser Gln Tyr Asn Met Gly Ile Asn Ile Glu
    210                 215                 220

Leu Ser Glu Ser Asp Val Trp Ile Ile Asp Val Asp Asn Val Val Arg
225                 230                 235                 240

Asp Val Thr Ile Glu Ser Asp Lys Ile Lys Lys Gly Asp Leu Ile Glu
                245                 250                 255

Gly Ile Leu Ser Thr Leu Ser Ile Glu Glu Asn Lys Ile Ile Leu Asn
            260                 265                 270

Ser His Glu Ile Asn Phe Ser Gly Glu Val Asn Gly Ser Asn Gly Phe
        275                 280                 285

Val Ser Leu Thr Phe Ser Ile Leu Glu Gly Ile Asn Ala Ile Ile Glu
    290                 295                 300

Val Asp Leu Leu Ser Lys Ser Tyr Lys Leu Leu Ile Ser Gly Glu Leu
305                 310                 315                 320

Lys Ile Leu Met Leu Asn Ser Asn His Ile Gln Gln Lys Ile Asp Tyr
                325                 330                 335

Ile Gly Phe Asn Ser Glu Leu Gln Lys Asn Ile Pro Tyr Ser Phe Val
            340                 345                 350

Asp Ser Glu Gly Lys Glu Asn Gly Phe Ile Asn Gly Ser Thr Lys Glu
        355                 360                 365

Gly Leu Phe Val Ser Glu Leu Pro Asp Val Val Leu Ile Ser Lys Val
    370                 375                 380

Tyr Met Asp Asp Ser Lys Pro Ser Phe Gly Tyr Tyr Ser Asn Asn Leu
385                 390                 395                 400

Lys Asp Val Lys Val Ile Thr Lys Asp Asn Val Asn Ile Leu Thr Gly
                405                 410                 415

Tyr Tyr Leu Lys Asp Asp Ile Lys Ile Ser Leu Ser Leu Thr Leu Gln
            420                 425                 430

Asp Glu Lys Thr Ile Lys Leu Asn Ser Val His Leu Asp Glu Ser Gly
        435                 440                 445

Val Ala Glu Ile Leu Lys Phe Met Asn Arg Lys Gly Asn Thr Asn Thr
    450                 455                 460

Ser Asp Ser Leu Met Ser Phe Leu Glu Ser Met Asn Ile Lys Ser Ile
465                 470                 475                 480

Phe Val Asn Phe Leu Gln Ser Asn Ile Lys Phe Ile Leu Asp Ala Asn
                485                 490                 495

Phe Ile Ile Ser Gly Thr Thr Ser Ile Gly Gln Phe Glu Phe Ile Cys
```

```
                500                 505                 510
Asp Glu Asn Asp Asn Ile Gln Pro Tyr Phe Ile Lys Phe Asn Thr Leu
            515                 520                 525
Glu Thr Asn Tyr Thr Leu Tyr Val Gly Asn Arg Gln Asn Met Ile Val
        530                 535                 540
Glu Pro Asn Tyr Asp Leu Asp Asp Ser Gly Asp Ile Ser Ser Thr Val
545                 550                 555                 560
Ile Asn Phe Ser Gln Lys Tyr Leu Tyr Gly Ile Asp Ser Cys Val Asn
            565                 570                 575
Lys Val Val Ile Ser Pro Asn Ile Tyr Thr Asp Glu Ile Asn Ile Thr
                580                 585                 590
Pro Val Tyr Glu Thr Asn Asn Thr Tyr Pro Glu Val Ile Val Leu Asp
            595                 600                 605
Ala Asn Tyr Ile Asn Glu Lys Ile Asn Val Asn Ile Asn Asp Leu Ser
        610                 615                 620
Ile Arg Tyr Val Trp Ser Asn Asp Gly Asn Asp Phe Ile Leu Met Ser
625                 630                 635                 640
Thr Ser Glu Glu Asn Lys Val Ser Gln Val Lys Ile Arg Phe Val Asn
            645                 650                 655
Val Phe Lys Asp Lys Thr Leu Ala Asn Lys Leu Ser Phe Asn Phe Ser
            660                 665                 670
Asp Lys Gln Asp Val Pro Val Ser Glu Ile Ile Leu Ser Phe Thr Pro
            675                 680                 685
Ser Tyr Tyr Glu Asp Gly Leu Ile Gly Tyr Asp Leu Gly Leu Val Ser
        690                 695                 700
Leu Tyr Asn Glu Lys Phe Tyr Ile Asn Asn Phe Gly Met Met Val Ser
705                 710                 715                 720
Gly Leu Thr His Thr Cys Pro Pro Cys Pro Ala Pro Glu Leu Leu Gly
            725                 730                 735
Gly Pro Ser Val Phe Leu Phe Pro Pro Lys Pro Lys Asp Thr Leu Met
            740                 745                 750
Ile Ser Arg Thr Pro Glu Val Thr Cys Val Val Val Asp Val Ser His
            755                 760                 765
Glu Asp Pro Glu Val Lys Phe Asn Trp Tyr Val Asp Gly Val Glu Val
        770                 775                 780
His Asn Ala Lys Thr Lys Pro Arg Glu Glu Gln Tyr Asn Ser Thr Tyr
785                 790                 795                 800
Arg Val Val Ser Val Leu Thr Val Leu His Gln Asp Trp Leu Asn Gly
            805                 810                 815
Lys Glu Tyr Lys Cys Lys Val Ser Asn Lys Ala Leu Pro Val Pro Ile
            820                 825                 830
Glu Lys Thr Ile Ser Lys Ala Lys Gly Gln Pro Arg Glu Pro Gln Val
            835                 840                 845
Tyr Thr Leu Pro Pro Ser Arg Glu Glu Met Thr Lys Asn Gln Val Ser
        850                 855                 860
Leu Thr Cys Leu Val Lys Gly Phe Tyr Pro Ser Asp Ile Ala Val Glu
865                 870                 875                 880
Trp Glu Ser Asn Gly Gln Pro Glu Asn Asn Tyr Lys Thr Thr Pro Pro
            885                 890                 895
Val Leu Asp Ser Asp Gly Pro Phe Phe Leu Tyr Ser Lys Leu Thr Val
            900                 905                 910
Asp Lys Ser Arg Trp Gln Gln Gly Asn Val Phe Ser Cys Ser Val Met
            915                 920                 925
```

-continued

```
His Glu Ala Leu His Asn His Tyr Thr Gln Lys Ser Leu Ser Leu Ser
            930                 935                 940
Pro Gly Lys
945

<210> SEQ ID NO 22
<211> LENGTH: 1033
<212> TYPE: PRT
<213> ORGANISM: Artificial Sequence
<220> FEATURE:
<223> OTHER INFORMATION: Synthetic Polypeptide

<400> SEQUENCE: 22

Gly Leu Pro Ile Ile Ala Thr Ile Ile Asp Gly Val Ser Leu Gly Ala
1               5                   10                  15

Ala Ile Lys Glu Leu Ser Glu Thr Ser Asp Pro Leu Leu Arg Gln Glu
            20                  25                  30

Ile Glu Ala Lys Ile Gly Ile Met Ala Val Asn Leu Thr Thr Ala Thr
        35                  40                  45

Thr Ala Ile Ile Thr Ser Ser Leu Gly Ile Ala Ser Gly Phe Ser Ile
    50                  55                  60

Leu Leu Val Pro Leu Ala Gly Ile Ser Ala Gly Ile Pro Ser Leu Val
65                  70                  75                  80

Asn Asn Glu Leu Val Leu Arg Asp Lys Ala Thr Lys Val Val Asp Tyr
                85                  90                  95

Phe Lys His Val Ser Leu Val Glu Thr Glu Gly Val Phe Thr Leu Leu
            100                 105                 110

Asp Asp Lys Ile Met Met Pro Gln Asp Leu Val Ile Ser Glu Ile
        115                 120                 125

Asp Phe Asn Asn Asn Ser Ile Val Leu Gly Lys Cys Glu Ile Trp Arg
    130                 135                 140

Met Glu Gly Gly Ser Gly His Thr Val Thr Asp Asp Ile Asp His Phe
145                 150                 155                 160

Phe Ser Ala Pro Ser Ile Thr Tyr Arg Glu Pro His Leu Ser Ile Tyr
                165                 170                 175

Asp Val Leu Glu Val Gln Lys Glu Glu Leu Asp Leu Ser Lys Asp Leu
            180                 185                 190

Met Val Leu Pro Asn Ala Pro Asn Arg Val Phe Ala Trp Glu Thr Gly
        195                 200                 205

Trp Thr Pro Gly Leu Arg Ser Leu Glu Asn Asp Gly Thr Lys Leu Leu
    210                 215                 220

Asp Arg Ile Arg Asp Asn Tyr Glu Gly Glu Phe Tyr Trp Arg Tyr Phe
225                 230                 235                 240

Ala Phe Ile Ala Asp Ala Leu Ile Thr Thr Leu Lys Pro Arg Tyr Glu
                245                 250                 255

Asp Thr Asn Ile Arg Ile Asn Leu Asp Ser Asn Thr Arg Ser Phe Ile
            260                 265                 270

Val Pro Ile Ile Thr Thr Glu Tyr Ile Arg Glu Lys Leu Ser Tyr Ser
        275                 280                 285

Phe Tyr Gly Ser Gly Gly Thr Tyr Ala Leu Ser Leu Ser Gln Tyr Asn
    290                 295                 300

Met Gly Ile Asn Ile Glu Leu Ser Glu Ser Asp Val Trp Ile Ile Asp
305                 310                 315                 320

Val Asp Asn Val Val Arg Asp Val Thr Ile Glu Ser Asp Lys Ile Lys
                325                 330                 335
```

```
Lys Gly Asp Leu Ile Glu Gly Ile Leu Ser Thr Leu Ser Ile Glu Glu
            340                 345                 350

Asn Lys Ile Ile Leu Asn Ser His Glu Ile Asn Phe Ser Gly Glu Val
            355                 360                 365

Asn Gly Ser Asn Gly Phe Val Ser Leu Thr Phe Ser Ile Leu Glu Gly
            370                 375                 380

Ile Asn Ala Ile Ile Glu Val Asp Leu Ser Lys Ser Tyr Lys Leu
385                 390                 395                 400

Leu Ile Ser Gly Glu Leu Lys Ile Leu Met Leu Asn Ser Asn His Ile
                405                 410                 415

Gln Gln Lys Ile Asp Tyr Ile Gly Phe Asn Ser Glu Leu Gln Lys Asn
            420                 425                 430

Ile Pro Tyr Ser Phe Val Asp Ser Glu Gly Lys Glu Asn Gly Phe Ile
            435                 440                 445

Asn Gly Ser Thr Lys Glu Gly Leu Phe Val Ser Glu Leu Pro Asp Val
            450                 455                 460

Val Leu Ile Ser Lys Val Tyr Met Asp Asp Ser Lys Pro Ser Phe Gly
465                 470                 475                 480

Tyr Tyr Ser Asn Asn Leu Lys Asp Val Lys Val Ile Thr Lys Asp Asn
                485                 490                 495

Val Asn Ile Leu Thr Gly Tyr Tyr Leu Lys Asp Asp Ile Lys Ile Ser
            500                 505                 510

Leu Ser Leu Thr Leu Gln Asp Glu Lys Thr Ile Lys Leu Asn Ser Val
            515                 520                 525

His Leu Asp Glu Ser Gly Val Ala Glu Ile Leu Lys Phe Met Asn Arg
            530                 535                 540

Lys Gly Asn Thr Asn Thr Ser Asp Ser Leu Met Ser Phe Leu Glu Ser
545                 550                 555                 560

Met Asn Ile Lys Ser Ile Phe Val Asn Phe Leu Gln Ser Asn Ile Lys
                565                 570                 575

Phe Ile Leu Asp Ala Asn Phe Ile Ile Ser Gly Thr Thr Ser Ile Gly
            580                 585                 590

Gln Phe Glu Phe Ile Cys Asp Glu Asn Asp Ile Gln Pro Tyr Phe
            595                 600                 605

Ile Lys Phe Asn Thr Leu Glu Thr Asn Tyr Thr Leu Tyr Val Gly Asn
            610                 615                 620

Arg Gln Asn Met Ile Val Glu Pro Asn Tyr Asp Leu Asp Asp Ser Gly
625                 630                 635                 640

Asp Ile Ser Ser Thr Val Ile Asn Phe Ser Gln Lys Tyr Leu Tyr Gly
                645                 650                 655

Ile Asp Ser Cys Val Asn Lys Val Val Ile Ser Pro Asn Ile Tyr Thr
            660                 665                 670

Asp Glu Ile Asn Ile Thr Pro Val Tyr Glu Thr Asn Asn Thr Tyr Pro
            675                 680                 685

Glu Val Ile Val Leu Asp Ala Asn Tyr Ile Asn Glu Lys Ile Asn Val
            690                 695                 700

Asn Ile Asn Asp Leu Ser Ile Arg Tyr Val Trp Ser Asn Asp Gly Asn
705                 710                 715                 720

Asp Phe Ile Leu Met Ser Thr Ser Glu Glu Asn Lys Val Ser Gln Val
                725                 730                 735

Lys Ile Arg Phe Val Asn Val Phe Lys Asp Lys Thr Leu Ala Asn Lys
            740                 745                 750
```

Leu Ser Phe Asn Phe Ser Asp Lys Gln Asp Val Pro Val Ser Glu Ile
        755                 760                 765

Ile Leu Ser Phe Thr Pro Ser Tyr Tyr Glu Asp Gly Leu Ile Gly Tyr
    770                 775                 780

Asp Leu Gly Leu Val Ser Leu Tyr Asn Glu Lys Phe Tyr Ile Asn Asn
785                 790                 795                 800

Phe Gly Met Met Val Ser Gly Leu Thr His Thr Cys Pro Cys Pro
                805                 810                 815

Ala Pro Glu Leu Leu Gly Gly Pro Ser Val Phe Leu Phe Pro Pro Lys
                820                 825                 830

Pro Lys Asp Thr Leu Met Ile Ser Arg Thr Pro Glu Val Thr Cys Val
            835                 840                 845

Val Val Asp Val Ser His Glu Asp Pro Glu Val Lys Phe Asn Trp Tyr
850                 855                 860

Val Asp Gly Val Glu Val His Asn Ala Lys Thr Lys Pro Arg Glu Glu
865                 870                 875                 880

Gln Tyr Asn Ser Thr Tyr Arg Val Val Ser Val Leu Thr Val Leu His
                885                 890                 895

Gln Asp Trp Leu Asn Gly Lys Glu Tyr Lys Cys Lys Val Ser Asn Lys
            900                 905                 910

Ala Leu Pro Val Pro Ile Glu Lys Thr Ile Ser Lys Ala Lys Gly Gln
        915                 920                 925

Pro Arg Glu Pro Gln Val Tyr Thr Leu Pro Pro Ser Arg Glu Glu Met
    930                 935                 940

Thr Lys Asn Gln Val Ser Leu Thr Cys Leu Val Lys Gly Phe Tyr Pro
945                 950                 955                 960

Ser Asp Ile Ala Val Glu Trp Glu Ser Asn Gly Gln Pro Glu Asn Asn
                965                 970                 975

Tyr Lys Thr Thr Pro Pro Val Leu Asp Ser Asp Gly Pro Phe Phe Leu
            980                 985                 990

Tyr Ser Lys Leu Thr Val Asp Lys Ser Arg Trp Gln Gln Gly Asn Val
        995                 1000                1005

Phe Ser Cys Ser Val Met His Glu Ala Leu His Asn His Tyr Thr
    1010                1015                1020

Gln Lys Ser Leu Ser Leu Ser Pro Gly Lys
        1025                1030

<210> SEQ ID NO 23
<211> LENGTH: 1213
<212> TYPE: PRT
<213> ORGANISM: Artificial Sequence
<220> FEATURE:
<223> OTHER INFORMATION: Synthetic Polypeptide

<400> SEQUENCE: 23

Arg Asp Lys Ala Thr Lys Val Val Asp Tyr Phe Lys His Val Ser Leu
1               5                   10                  15

Val Glu Thr Glu Gly Val Phe Thr Leu Leu Asp Asp Lys Ile Met Met
            20                  25                  30

Pro Gln Asp Asp Leu Val Ile Ser Glu Ile Asp Phe Asn Asn Asn Ser
        35                  40                  45

Ile Val Leu Gly Lys Cys Glu Ile Trp Arg Met Glu Gly Gly Ser Gly
    50                  55                  60

His Thr Val Thr Asp Asp Ile Asp His Phe Phe Ser Ala Pro Ser Ile
65                  70                  75                  80

-continued

Thr Tyr Arg Glu Pro His Leu Ser Ile Tyr Asp Val Leu Glu Val Gln
                85                  90                  95

Lys Glu Glu Leu Asp Leu Ser Lys Asp Leu Met Val Leu Pro Asn Ala
            100                 105                 110

Pro Asn Arg Val Phe Ala Trp Glu Thr Gly Trp Thr Pro Gly Leu Arg
        115                 120                 125

Ser Leu Glu Asn Asp Gly Thr Lys Leu Leu Asp Arg Ile Arg Asp Asn
130                 135                 140

Tyr Glu Gly Glu Phe Tyr Trp Arg Tyr Phe Ala Phe Ile Ala Asp Ala
145                 150                 155                 160

Leu Ile Thr Thr Leu Lys Pro Arg Tyr Glu Asp Thr Asn Ile Arg Ile
                165                 170                 175

Asn Leu Asp Ser Asn Thr Arg Ser Phe Ile Val Pro Ile Ile Thr Thr
            180                 185                 190

Glu Tyr Ile Arg Glu Lys Leu Ser Tyr Ser Phe Tyr Gly Ser Gly Gly
        195                 200                 205

Thr Tyr Ala Leu Ser Leu Ser Gln Tyr Asn Met Gly Ile Asn Ile Glu
    210                 215                 220

Leu Ser Glu Ser Asp Val Trp Ile Ile Asp Val Asp Asn Val Val Arg
225                 230                 235                 240

Asp Val Thr Ile Glu Ser Asp Lys Ile Lys Lys Gly Asp Leu Ile Glu
                245                 250                 255

Gly Ile Leu Ser Thr Leu Ser Ile Glu Glu Asn Lys Ile Ile Leu Asn
            260                 265                 270

Ser His Glu Ile Asn Phe Ser Gly Glu Val Asn Gly Ser Asn Gly Phe
        275                 280                 285

Val Ser Leu Thr Phe Ser Ile Leu Glu Gly Ile Asn Ala Ile Ile Glu
    290                 295                 300

Val Asp Leu Leu Ser Lys Ser Tyr Lys Leu Leu Ile Ser Gly Glu Leu
305                 310                 315                 320

Lys Ile Leu Met Leu Asn Ser Asn His Ile Gln Gln Lys Ile Asp Tyr
                325                 330                 335

Ile Gly Phe Asn Ser Glu Leu Gln Lys Asn Ile Pro Tyr Ser Phe Val
            340                 345                 350

Asp Ser Glu Gly Lys Glu Asn Gly Phe Ile Asn Gly Ser Thr Lys Glu
        355                 360                 365

Gly Leu Phe Val Ser Glu Leu Pro Asp Val Val Leu Ile Ser Lys Val
    370                 375                 380

Tyr Met Asp Asp Ser Lys Pro Ser Phe Gly Tyr Tyr Ser Asn Asn Leu
385                 390                 395                 400

Lys Asp Val Lys Val Ile Thr Lys Asp Asn Val Asn Ile Leu Thr Gly
                405                 410                 415

Tyr Tyr Leu Lys Asp Asp Ile Lys Ile Ser Leu Ser Leu Thr Leu Gln
            420                 425                 430

Asp Glu Lys Thr Ile Lys Leu Asn Ser Val His Leu Asp Glu Ser Gly
        435                 440                 445

Val Ala Glu Ile Leu Lys Phe Met Asn Arg Lys Gly Asn Thr Asn Thr
    450                 455                 460

Ser Asp Ser Leu Met Ser Phe Leu Glu Ser Met Asn Ile Lys Ser Ile
465                 470                 475                 480

Phe Val Asn Phe Leu Gln Ser Asn Ile Lys Phe Ile Leu Asp Ala Asn
                485                 490                 495

Phe Ile Ile Ser Gly Thr Thr Ser Ile Gly Gln Phe Glu Phe Ile Cys

```
              500                 505                 510
Asp Glu Asn Asp Asn Ile Gln Pro Tyr Phe Ile Lys Phe Asn Thr Leu
            515                 520                 525

Glu Thr Asn Tyr Thr Leu Tyr Val Gly Asn Arg Gln Asn Met Ile Val
            530                 535             540

Glu Pro Asn Tyr Asp Leu Asp Asp Ser Gly Asp Ile Ser Ser Thr Val
545                 550                 555                 560

Ile Asn Phe Ser Gln Lys Tyr Leu Tyr Gly Ile Asp Ser Cys Val Asn
                565                 570                 575

Lys Val Val Ile Ser Pro Asn Ile Tyr Thr Asp Glu Ile Asn Ile Thr
                    580                 585                 590

Pro Val Tyr Glu Thr Asn Thr Tyr Pro Glu Val Ile Val Leu Asp
                595                 600                 605

Ala Asn Tyr Ile Asn Glu Lys Ile Asn Val Asn Ile Asn Asp Leu Ser
            610                 615                 620

Ile Arg Tyr Val Trp Ser Asn Asp Gly Asn Asp Phe Ile Leu Met Ser
625                 630                 635                 640

Thr Ser Glu Glu Asn Lys Val Ser Gln Val Lys Ile Arg Phe Val Asn
                645                 650                 655

Val Phe Lys Asp Lys Thr Leu Ala Asn Lys Leu Ser Phe Asn Phe Ser
            660                 665                 670

Asp Lys Gln Asp Val Pro Val Ser Glu Ile Ile Leu Ser Phe Thr Pro
            675                 680                 685

Ser Tyr Tyr Glu Asp Gly Leu Ile Gly Tyr Asp Leu Gly Leu Val Ser
            690                 695                 700

Leu Tyr Asn Glu Lys Phe Tyr Ile Asn Asn Phe Gly Met Met Val Ser
705                 710                 715                 720

Gly Leu Ile Tyr Ile Asn Asp Ser Leu Tyr Tyr Phe Lys Pro Pro Val
                725                 730                 735

Asn Asn Leu Ile Thr Gly Phe Val Thr Val Gly Asp Asp Lys Tyr Tyr
                740                 745                 750

Phe Asn Pro Ile Asn Gly Gly Ala Ala Ser Ile Gly Glu Thr Ile Ile
            755                 760                 765

Asp Asp Lys Asn Tyr Tyr Phe Asn Gln Ser Gly Val Leu Gln Thr Gly
            770                 775             780

Val Phe Ser Thr Glu Asp Gly Phe Lys Tyr Phe Ala Pro Ala Asn Thr
785                 790                 795                 800

Leu Asp Glu Asn Leu Glu Gly Glu Ala Ile Asp Phe Thr Gly Lys Leu
                805                 810                 815

Ile Ile Asp Glu Asn Ile Tyr Tyr Phe Asp Asp Asn Tyr Arg Gly Ala
                820                 825                 830

Val Glu Trp Lys Glu Leu Asp Gly Glu Met His Tyr Phe Ser Pro Glu
            835                 840                 845

Thr Gly Lys Ala Phe Lys Gly Leu Asn Gln Ile Gly Asp Tyr Lys Tyr
            850                 855             860

Tyr Phe Asn Ser Asp Gly Val Met Gln Lys Gly Phe Val Ser Ile Asn
865                 870                 875                 880

Asp Asn Lys His Tyr Phe Asp Asp Ser Gly Val Met Lys Val Gly Tyr
                885                 890                 895

Thr Glu Ile Asp Gly Lys His Phe Tyr Phe Ala Glu Asn Gly Glu Met
                    900                 905                 910

Gln Ile Gly Val Phe Asn Thr Glu Asp Gly Phe Lys Tyr Phe Ala His
            915                 920                 925
```

His Asn Glu Asp Leu Gly Asn Glu Glu Gly Glu Ile Ser Tyr Ser
    930                 935                 940

Gly Ile Leu Asn Phe Asn Asn Lys Ile Tyr Tyr Phe Asp Ser Phe
945                 950                 955                 960

Thr Ala Val Val Gly Trp Lys Asp Leu Glu Asp Gly Ser Lys Tyr Tyr
            965                 970                 975

Phe Asp Glu Asp Thr Ala Glu Ala Tyr Ile Gly Leu Thr His Thr Cys
            980                 985                 990

Pro Pro Cys Pro Ala Pro Glu Leu Leu Gly Gly Pro Ser Val Phe Leu
        995                 1000                1005

Phe Pro Pro Lys Pro Lys Asp Thr Leu Met Ile Ser Arg Thr Pro
    1010                1015                1020

Glu Val Thr Cys Val Val Val Asp Val Ser His Glu Asp Pro Glu
    1025                1030                1035

Val Lys Phe Asn Trp Tyr Val Asp Gly Val Glu Val His Asn Ala
    1040                1045                1050

Lys Thr Lys Pro Arg Glu Glu Gln Tyr Asn Ser Thr Tyr Arg Val
    1055                1060                1065

Val Ser Val Leu Thr Val Leu His Gln Asp Trp Leu Asn Gly Lys
    1070                1075                1080

Glu Tyr Lys Cys Lys Val Ser Asn Lys Ala Leu Pro Val Pro Ile
    1085                1090                1095

Glu Lys Thr Ile Ser Lys Ala Lys Gly Gln Pro Arg Glu Pro Gln
    1100                1105                1110

Val Tyr Thr Leu Pro Pro Ser Arg Glu Glu Met Thr Lys Asn Gln
    1115                1120                1125

Val Ser Leu Thr Cys Leu Val Lys Gly Phe Tyr Pro Ser Asp Ile
    1130                1135                1140

Ala Val Glu Trp Glu Ser Asn Gly Gln Pro Glu Asn Asn Tyr Lys
    1145                1150                1155

Thr Thr Pro Pro Val Leu Asp Ser Asp Gly Pro Phe Phe Leu Tyr
    1160                1165                1170

Ser Lys Leu Thr Val Asp Lys Ser Arg Trp Gln Gln Gly Asn Val
    1175                1180                1185

Phe Ser Cys Ser Val Met His Glu Ala Leu His Asn His Tyr Thr
    1190                1195                1200

Gln Lys Ser Leu Ser Leu Ser Pro Gly Lys
    1205                1210

<210> SEQ ID NO 24
<211> LENGTH: 134
<212> TYPE: PRT
<213> ORGANISM: Artificial Sequence
<220> FEATURE:
<223> OTHER INFORMATION: Synthetic Polypeptide

<400> SEQUENCE: 24

Tyr Asn Gly Glu Arg Gly Ile Ser Val Pro Asp His Gly Tyr Cys Gln
1               5                   10                  15

Pro Ile Ser Ile Pro Leu Cys Thr Asp Ile Ala Tyr Asn Gln Thr Ile
            20                  25                  30

Met Pro Asn Leu Leu Gly His Thr Asn Gln Glu Asp Ala Gly Leu Glu
        35                  40                  45

Val His Gln Phe Tyr Pro Leu Val Lys Val Gln Cys Ser Ala Glu Leu
    50                  55                  60

```
Lys Phe Phe Leu Cys Ser Met Tyr Ala Pro Val Cys Thr Val Leu Glu
 65                  70                  75                  80

Gln Ala Leu Pro Pro Cys Arg Ser Leu Cys Glu Arg Ala Arg Gln Gly
                 85                  90                  95

Cys Glu Ala Leu Met Asn Lys Phe Gly Phe Gln Trp Pro Asp Thr Leu
            100                 105                 110

Lys Cys Glu Lys Phe Pro Val His Gly Ala Gly Glu Leu Cys Val Gly
        115                 120                 125

Gln Asn Thr Ser Asp Lys
    130

<210> SEQ ID NO 25
<211> LENGTH: 134
<212> TYPE: PRT
<213> ORGANISM: Artificial Sequence
<220> FEATURE:
<223> OTHER INFORMATION: Synthetic Polypeptide

<400> SEQUENCE: 25

Tyr Asn Gly Glu Arg Gly Ile Ser Val Pro Asp His Gly Tyr Cys Gln
  1               5                  10                  15

Pro Ile Ser Ile Pro Leu Cys Thr Asp Ile Ala Tyr Asn Gln Thr Ile
             20                  25                  30

Met Pro Asn Leu Leu Gly His Thr Asn Gln Glu Asp Ala Gly Leu Glu
            35                  40                  45

Val His Gln Phe Tyr Pro Leu Val Lys Val Gln Cys Ser Ala Glu Leu
        50                  55                  60

Lys Phe Phe Leu Cys Ser Met Tyr Ala Pro Val Cys Thr Val Leu Glu
 65                  70                  75                  80

Gln Ala Leu Pro Pro Cys Arg Ser Leu Cys Glu Arg Ala Arg Gln Gly
                 85                  90                  95

Cys Glu Ala Leu Met Asn Lys Phe Gly Phe Gln Trp Pro Asp Thr Leu
            100                 105                 110

Lys Cys Glu Lys Phe Pro Val His Gly Ala Gly Glu Leu Cys Val Gly
        115                 120                 125

Gln Asn Thr Ser Asp Lys
    130

<210> SEQ ID NO 26
<211> LENGTH: 134
<212> TYPE: PRT
<213> ORGANISM: Artificial Sequence
<220> FEATURE:
<223> OTHER INFORMATION: Synthetic Polypeptide

<400> SEQUENCE: 26

Tyr Asn Gly Glu Arg Gly Ile Ser Val Pro Asp His Gly Tyr Cys Gln
  1               5                  10                  15

Pro Ile Ser Ile Pro Leu Cys Thr Asp Ile Ala Tyr Asn Gln Thr Ile
             20                  25                  30

Met Pro Asn Leu Leu Gly His Thr Asn Gln Glu Asp Ala Gly Leu Glu
            35                  40                  45

Val His Gln Phe Tyr Pro Leu Val Lys Val Gln Cys Ser Ala Glu Leu
        50                  55                  60

Lys Phe Phe Leu Cys Ser Met Tyr Ala Pro Val Cys Thr Val Leu Glu
 65                  70                  75                  80

Gln Ala Leu Pro Pro Cys Arg Ser Leu Cys Glu Arg Ala Arg Gln Gly
```

```
                     85                  90                  95

Cys Glu Ala Leu Met Asn Lys Phe Gly Phe Gln Trp Pro Asp Thr Leu
            100                 105                 110

Lys Cys Glu Lys Phe Pro Val His Gly Ala Gly Glu Leu Cys Val Gly
            115                 120                 125

Gln Asn Thr Ser Asp Lys
    130

<210> SEQ ID NO 27
<211> LENGTH: 2366
<212> TYPE: PRT
<213> ORGANISM: Artificial Sequence
<220> FEATURE:
<223> OTHER INFORMATION: Synthetic Polypeptide

<400> SEQUENCE: 27

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
            115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
    210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asp
        275                 280                 285

Met Leu Pro Gly Ile Gln Pro Asp Leu Phe Glu Ser Ile Glu Lys Pro
    290                 295                 300

Ser Ser Val Thr Val Asp Phe Trp Glu Met Thr Lys Leu Glu Ala Ile
```

-continued

```
                305                 310                 315                 320
Met Lys Tyr Lys Glu Tyr Ile Pro Gly Tyr Thr Ser Glu His Phe Asp
                325                 330                 335

Met Leu Asp Glu Glu Val Gln Ser Ser Phe Glu Ser Val Leu Ala Ser
                340                 345                 350

Lys Ser Asp Lys Ser Glu Ile Phe Ser Ser Leu Gly Asp Met Glu Ala
                355                 360                 365

Ser Pro Leu Glu Val Lys Ile Ala Phe Asn Ser Lys Gly Ile Ile Asn
370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
                420                 425                 430

Asp Ser Ile Met Ala Glu Ala Asn Ala Asp Asn Gly Arg Phe Met Met
                435                 440                 445

Glu Leu Gly Lys Tyr Leu Arg Val Gly Phe Phe Pro Asp Val Lys Thr
                450                 455                 460

Thr Ile Asn Leu Ser Gly Pro Glu Ala Tyr Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
                500                 505                 510

Glu Gln Glu Met Ala Ser Leu Trp Ser Phe Asp Asp Ala Arg Ala Lys
                515                 520                 525

Ala Gln Phe Glu Glu Tyr Lys Arg Asn Tyr Phe Glu Gly Ser Leu Gly
                530                 535                 540

Glu Asp Asp Asn Leu Asp Phe Ser Gln Asn Ile Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
                580                 585                 590

Ala Ala Cys Asn Leu Phe Ala Lys Thr Pro Tyr Asp Ser Val Leu Phe
                595                 600                 605

Gln Lys Asn Ile Glu Asp Ser Glu Ile Ala Tyr Tyr Tyr Asn Pro Gly
                610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Phe Asp Val Asp Ser Leu Ser
                660                 665                 670

Thr Glu Ile Glu Ala Ala Ile Asp Leu Ala Lys Glu Asp Ile Ser Pro
                675                 680                 685

Lys Ser Ile Glu Ile Asn Leu Leu Gly Cys Asn Met Phe Ser Tyr Ser
                690                 695                 700

Ile Asn Val Glu Glu Thr Tyr Pro Gly Lys Leu Leu Leu Lys Val Lys
705                 710                 715                 720

Asp Lys Ile Ser Glu Leu Met Pro Ser Ile Ser Gln Asp Ser Ile Ile
                725                 730                 735
```

```
Val Ser Ala Asn Gln Tyr Glu Val Arg Ile Asn Ser Glu Gly Arg Arg
                740                 745                 750

Glu Leu Leu Asp His Ser Gly Glu Trp Ile Asn Lys Glu Ser Ile
            755                 760                 765

Ile Lys Asp Ile Ser Ser Lys Glu Tyr Ile Ser Phe Asn Pro Lys Glu
        770                 775                 780

Asn Lys Ile Thr Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
                805                 810                 815

Glu Lys Val Met Leu Thr Glu Cys Glu Ile Asn Val Ile Ser Asn Ile
                820                 825                 830

Asp Thr Gln Ile Val Glu Glu Arg Ile Glu Glu Ala Lys Asn Leu Thr
            835                 840                 845

Ser Asp Ser Ile Asn Tyr Ile Lys Asp Glu Phe Lys Leu Ile Glu Ser
        850                 855                 860

Ile Ser Asp Ala Leu Cys Asp Leu Lys Gln Gln Asn Glu Leu Glu Asp
865                 870                 875                 880

Ser His Phe Ile Ser Phe Glu Asp Ile Ser Glu Thr Asp Glu Gly Phe
                885                 890                 895

Ser Ile Arg Phe Ile Asn Lys Glu Thr Gly Glu Ser Ile Phe Val Glu
            900                 905                 910

Thr Glu Lys Thr Ile Phe Ser Glu Tyr Ala Asn His Ile Thr Glu Glu
        915                 920                 925

Ile Ser Lys Ile Lys Gly Thr Ile Phe Asp Thr Val Asn Gly Lys Leu
            930                 935                 940

Val Lys Lys Val Asn Leu Asp Thr Thr His Glu Val Asn Thr Leu Asn
945                 950                 955                 960

Ala Ala Phe Phe Ile Gln Ser Leu Ile Glu Tyr Asn Ser Ser Lys Glu
                965                 970                 975

Ser Leu Ser Asn Leu Ser Val Ala Met Lys Val Gln Val Tyr Ala Gln
            980                 985                 990

Leu Phe Ser Thr Gly Leu Asn Thr Ile Thr Asp Ala Ala Lys Val Val
        995                 1000                1005

Glu Leu Val Ser Thr Ala Leu Asp Glu Thr Ile Asp Leu Leu Pro
    1010                1015                1020

Thr Leu Ser Glu Gly Leu Pro Ile Ile Ala Thr Ile Ile Asp Gly
    1025                1030                1035

Val Ser Leu Gly Ala Ala Ile Lys Glu Leu Ser Glu Thr Ser Asp
    1040                1045                1050

Pro Leu Leu Arg Gln Glu Ile Glu Ala Lys Ile Gly Ile Met Ala
    1055                1060                1065

Val Asn Leu Thr Thr Ala Thr Thr Ala Ile Ile Thr Ser Ser Leu
    1070                1075                1080

Gly Ile Ala Ser Gly Phe Ser Ile Leu Leu Val Pro Leu Ala Gly
    1085                1090                1095

Ile Ser Ala Gly Ile Pro Ser Leu Val Asn Asn Glu Leu Val Leu
    1100                1105                1110

Arg Asp Lys Ala Thr Lys Val Val Asp Tyr Phe Lys His Val Ser
    1115                1120                1125

Leu Val Glu Thr Glu Gly Val Phe Thr Leu Leu Asp Asp Lys Ile
    1130                1135                1140
```

-continued

```
Met Met Pro Gln Asp Asp Leu Val Ile Ser Glu Ile Asp Phe Asn
    1145               1150               1155

Asn Asn Ser Ile Val Leu Gly Lys Cys Glu Ile Trp Arg Met Glu
    1160               1165               1170

Gly Gly Ser Gly His Thr Val Thr Asp Asp Ile Asp His Phe Phe
    1175               1180               1185

Ser Ala Pro Ser Ile Thr Tyr Arg Glu Pro His Leu Ser Ile Tyr
    1190               1195               1200

Asp Val Leu Glu Val Gln Lys Glu Glu Leu Asp Leu Ser Lys Asp
    1205               1210               1215

Leu Met Val Leu Pro Asn Ala Pro Asn Arg Val Phe Ala Trp Glu
    1220               1225               1230

Thr Gly Trp Thr Pro Gly Leu Arg Ser Leu Glu Asn Asp Gly Thr
    1235               1240               1245

Lys Leu Leu Asp Arg Ile Arg Asp Asn Tyr Glu Gly Glu Phe Tyr
    1250               1255               1260

Trp Arg Tyr Phe Ala Phe Ile Ala Asp Ala Leu Ile Thr Thr Leu
    1265               1270               1275

Lys Pro Arg Tyr Glu Asp Thr Asn Ile Arg Ile Asn Leu Asp Ser
    1280               1285               1290

Asn Thr Arg Ser Phe Ile Val Pro Ile Ile Thr Thr Glu Tyr Ile
    1295               1300               1305

Arg Glu Lys Leu Ser Tyr Ser Phe Tyr Gly Ser Gly Gly Thr Tyr
    1310               1315               1320

Ala Leu Ser Leu Ser Gln Tyr Asn Met Gly Ile Asn Ile Glu Leu
    1325               1330               1335

Ser Glu Ser Asp Val Trp Ile Ile Asp Val Asp Asn Val Val Arg
    1340               1345               1350

Asp Val Thr Ile Glu Ser Asp Lys Ile Lys Lys Gly Asp Leu Ile
    1355               1360               1365

Glu Gly Ile Leu Ser Thr Leu Ser Ile Glu Glu Asn Lys Ile Ile
    1370               1375               1380

Leu Asn Ser His Glu Ile Asn Phe Ser Gly Glu Val Asn Gly Ser
    1385               1390               1395

Asn Gly Phe Val Ser Leu Thr Phe Ser Ile Leu Glu Gly Ile Asn
    1400               1405               1410

Ala Ile Ile Glu Val Asp Leu Leu Ser Lys Ser Tyr Lys Leu Leu
    1415               1420               1425

Ile Ser Gly Glu Leu Lys Ile Leu Met Leu Asn Ser Asn His Ile
    1430               1435               1440

Gln Gln Lys Ile Asp Tyr Ile Gly Phe Asn Ser Glu Leu Gln Lys
    1445               1450               1455

Asn Ile Pro Tyr Ser Phe Val Asp Ser Glu Gly Lys Glu Asn Gly
    1460               1465               1470

Phe Ile Asn Gly Ser Thr Lys Glu Gly Leu Phe Val Ser Glu Leu
    1475               1480               1485

Pro Asp Val Val Leu Ile Ser Lys Val Tyr Met Asp Asp Ser Lys
    1490               1495               1500

Pro Ser Phe Gly Tyr Tyr Ser Asn Asn Leu Lys Asp Val Lys Val
    1505               1510               1515

Ile Thr Lys Asp Asn Val Asn Ile Leu Thr Gly Tyr Tyr Leu Lys
    1520               1525               1530

Asp Asp Ile Lys Ile Ser Leu Ser Leu Thr Leu Gln Asp Glu Lys
```

```
            1535                1540                1545

Thr Ile Lys Leu Asn Ser Val His Leu Asp Glu Ser Gly Val Ala
        1550                1555                1560

Glu Ile Leu Lys Phe Met Asn Arg Lys Gly Asn Thr Asn Thr Ser
        1565                1570                1575

Asp Ser Leu Met Ser Phe Leu Glu Ser Met Asn Ile Lys Ser Ile
        1580                1585                1590

Phe Val Asn Phe Leu Gln Ser Asn Ile Lys Phe Ile Leu Asp Ala
        1595                1600                1605

Asn Phe Ile Ile Ser Gly Thr Thr Ser Ile Gly Gln Phe Glu Phe
        1610                1615                1620

Ile Cys Asp Glu Asn Asp Asn Ile Gln Pro Tyr Phe Ile Lys Phe
        1625                1630                1635

Asn Thr Leu Glu Thr Asn Tyr Thr Leu Tyr Val Gly Asn Arg Gln
        1640                1645                1650

Asn Met Ile Val Glu Pro Asn Tyr Asp Leu Asp Asp Ser Gly Asp
        1655                1660                1665

Ile Ser Ser Thr Val Ile Asn Phe Ser Gln Lys Tyr Leu Tyr Gly
        1670                1675                1680

Ile Asp Ser Cys Val Asn Lys Val Val Ile Ser Pro Asn Ile Tyr
        1685                1690                1695

Thr Asp Glu Ile Asn Ile Thr Pro Val Tyr Glu Thr Asn Asn Thr
        1700                1705                1710

Tyr Pro Glu Val Ile Val Leu Asp Ala Asn Tyr Ile Asn Glu Lys
        1715                1720                1725

Ile Asn Val Asn Ile Asn Asp Leu Ser Ile Arg Tyr Val Trp Ser
        1730                1735                1740

Asn Asp Gly Asn Asp Phe Ile Leu Met Ser Thr Ser Glu Glu Asn
        1745                1750                1755

Lys Val Ser Gln Val Lys Ile Arg Phe Val Asn Val Phe Lys Asp
        1760                1765                1770

Lys Thr Leu Ala Asn Lys Leu Ser Phe Asn Phe Ser Asp Lys Gln
        1775                1780                1785

Asp Val Pro Val Ser Glu Ile Ile Leu Ser Phe Thr Pro Ser Tyr
        1790                1795                1800

Tyr Glu Asp Gly Leu Ile Gly Tyr Asp Leu Gly Leu Val Ser Leu
        1805                1810                1815

Tyr Asn Glu Lys Phe Tyr Ile Asn Asn Phe Gly Met Met Val Ser
        1820                1825                1830

Gly Leu Ile Tyr Ile Asn Asp Ser Leu Tyr Tyr Phe Lys Pro Pro
        1835                1840                1845

Val Asn Asn Leu Ile Thr Gly Phe Val Thr Val Gly Asp Asp Lys
        1850                1855                1860

Tyr Tyr Phe Asn Pro Ile Asn Gly Gly Ala Ala Ser Ile Gly Glu
        1865                1870                1875

Thr Ile Ile Asp Asp Lys Asn Tyr Tyr Phe Asn Gln Ser Gly Val
        1880                1885                1890

Leu Gln Thr Gly Val Phe Ser Thr Glu Asp Gly Phe Lys Tyr Phe
        1895                1900                1905

Ala Pro Ala Asn Thr Leu Asp Glu Asn Leu Glu Gly Glu Ala Ile
        1910                1915                1920

Asp Phe Thr Gly Lys Leu Ile Ile Asp Glu Asn Ile Tyr Tyr Phe
        1925                1930                1935
```

Asp Asp Asn Tyr Arg Gly Ala Val Glu Trp Lys Glu Leu Asp Gly
    1940            1945                1950

Glu Met His Tyr Phe Ser Pro Glu Thr Gly Lys Ala Phe Lys Gly
    1955            1960                1965

Leu Asn Gln Ile Gly Asp Tyr Lys Tyr Tyr Phe Asn Ser Asp Gly
    1970            1975                1980

Val Met Gln Lys Gly Phe Val Ser Ile Asn Asp Asn Lys His Tyr
    1985            1990                1995

Phe Asp Asp Ser Gly Val Met Lys Val Gly Tyr Thr Glu Ile Asp
    2000            2005                2010

Gly Lys His Phe Tyr Phe Ala Glu Asn Gly Glu Met Gln Ile Gly
    2015            2020                2025

Val Phe Asn Thr Glu Asp Gly Phe Lys Tyr Phe Ala His His Asn
    2030            2035                2040

Glu Asp Leu Gly Asn Glu Glu Gly Glu Ile Ser Tyr Ser Gly
    2045            2050                2055

Ile Leu Asn Phe Asn Asn Lys Ile Tyr Tyr Phe Asp Asp Ser Phe
    2060            2065                2070

Thr Ala Val Val Gly Trp Lys Asp Leu Glu Asp Gly Ser Lys Tyr
    2075            2080                2085

Tyr Phe Asp Glu Asp Thr Ala Glu Ala Tyr Ile Gly Leu Ser Leu
    2090            2095                2100

Ile Asn Asp Gly Gln Tyr Tyr Phe Asn Asp Asp Gly Ile Met Gln
    2105            2110                2115

Val Gly Phe Val Thr Ile Asn Asp Lys Val Phe Tyr Phe Ser Asp
    2120            2125                2130

Ser Gly Ile Ile Glu Ser Gly Val Gln Asn Ile Asp Asp Asn Tyr
    2135            2140                2145

Phe Tyr Ile Asp Asp Asn Gly Ile Val Gln Ile Gly Val Phe Asp
    2150            2155                2160

Thr Ser Asp Gly Tyr Lys Tyr Phe Ala Pro Ala Asn Thr Val Asn
    2165            2170                2175

Asp Asn Ile Tyr Gly Gln Ala Val Glu Tyr Ser Gly Leu Val Arg
    2180            2185                2190

Val Gly Glu Asp Val Tyr Tyr Phe Gly Glu Thr Tyr Thr Ile Glu
    2195            2200                2205

Thr Gly Trp Ile Tyr Asp Met Glu Asn Glu Ser Asp Lys Tyr Tyr
    2210            2215                2220

Phe Asn Pro Glu Thr Lys Lys Ala Cys Lys Gly Ile Asn Leu Ile
    2225            2230                2235

Asp Asp Ile Lys Tyr Tyr Phe Asp Glu Lys Gly Ile Met Arg Thr
    2240            2245                2250

Gly Leu Ile Ser Phe Glu Asn Asn Asn Tyr Tyr Phe Asn Glu Asn
    2255            2260                2265

Gly Glu Met Gln Phe Gly Tyr Ile Asn Ile Glu Asp Lys Met Phe
    2270            2275                2280

Tyr Phe Gly Glu Asp Gly Val Met Gln Ile Gly Val Phe Asn Thr
    2285            2290                2295

Pro Asp Gly Phe Lys Tyr Phe Ala His Gln Asn Thr Leu Asp Glu
    2300            2305                2310

Asn Phe Glu Gly Glu Ser Ile Asn Tyr Thr Gly Trp Leu Asp Leu
    2315            2320                2325

Asp Glu Lys Arg Tyr Tyr Phe Thr Asp Glu Tyr Ile Ala Ala Thr
    2330                2335                2340

Gly Ser Val Ile Ile Asp Gly Glu Glu Tyr Tyr Phe Asp Pro Asp
    2345                2350                2355

Thr Ala Gln Leu Val Ile Ser Glu
    2360                2365

<210> SEQ ID NO 28
<211> LENGTH: 225
<212> TYPE: PRT
<213> ORGANISM: Homo sapiens

<400> SEQUENCE: 28

Thr His Thr Cys Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
                20                  25                  30

Arg Thr Pro Glu Val Thr Cys Val Val Asp Val Ser His Glu Asp
            35                  40                  45

Pro Glu Val Lys Phe Asn Trp Tyr Val Asp Gly Val Glu Val His Asn
50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Val Pro Ile Glu Lys
            100                 105                 110

Thr Ile Ser Lys Ala Lys Gly Gln Pro Arg Glu Pro Gln Val Tyr Thr
            115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Pro Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 29
<211> LENGTH: 2166
<212> TYPE: DNA
<213> ORGANISM: Artificial Sequence
<220> FEATURE:
<223> OTHER INFORMATION: Synthetic Polynucleotide

<400> SEQUENCE: 29
cgagataagg caacaaaggt tgtagattat tttaaacatg tttcattagt tgaaactgaa     60
ggagtattta ctttattaga tgataaaata atgatgccac aagatgattt agtgatatca    120
gaaatagatt taataataa ttcaatagtt ttaggtaaat gtgaaatctg gagaatggaa    180
ggtggttcag gtcatactgt aactgatgat atagatcact tcttttcagc accatcaata    240

```
acatatagag agccacactt atctatatat gacgtattgg aagtacaaaa agaagaactt      300
gatttgtcaa aagatttaat ggtattacct aatgctccaa atagagtatt tgcttgggaa      360
acaggatgga caccaggttt aagaagctta gaaaatgatg cacaaaact gttagaccgt       420 ataagagata actatgaagg tgagttttat tggagatatt ttgcttttat agctgatgct      480
ttaataacaa cattaaaacc aagatatgaa gatactaata taagaataaa tttagatagt      540
aatactagaa gttttatagt tccaataata actacagaat atataagaga aaaattatca      600
tattctttct atggttcagg aggaacttat gcattgtctc tttctcaata taatatgggt      660
ataaatatag aattaagtga aagtgatgtt tggattatag atgttgataa tgttgtgaga      720
gatgtaacta tagaatctga taaaattaaa aaaggtgatt aatagaagg tatttttatct      780 acactaagta ttgaagagaa taaaattatc ttaaatagcc atgagattaa tttttctggt      840
gaggtaaatg gaagtaatgg atttgtttct ttaacatttt caattttaga aggaataaat      900
gcaattatag aagttgattt attatctaaa tcatataaat tacttatttc tggcgaatta      960
aaaatattga tgttaaattc aaatcatatt caacagaaaa tagattatat aggattcaat     1020
agcgaattac agaaaaatat accatatagc tttgtagata gtgaaggaaa agagaatggt     1080
tttattaatg gttcaacaaa agaaggttta tttgtatctg aattacctga tgtagttctt     1140
ataagtaagg tttatatgga tgatagtaag ccttcatttg gatattatag taataatttg     1200
aaagatgtca aagttataac taaagataat gttaatatat taacaggtta ttatcttaag     1260
gatgatataa aaatctctct ttctttgact ctacaagatg aaaaaactat aaagttaaat     1320
agtgtgcatt tagatgaaag tggagtagct gagattttga agttcatgaa tagaaaaggt     1380
aatacaaata cttcagattc tttaatgagc tttttagaaa gtatgaatat aaaaagtatt     1440
ttcgttaatt tcttacaatc taatattaag tttatattag atgctaatttt tataataagt    1500 ggtactactt ctattggcca atttgagttt atttgtgatg aaaatgataa tatacaacca     1560
tatttcatta agtttaatac actagaaact aattatactt tatatgtagg aaatagacaa     1620
aatatgatag tggaaccaaa ttatgattta gatgattctg gagatatatc ttcaactgtt     1680
atcaatttct ctcaaaagta tctttatgga atagacagtt gtgttaataa agttgtaatt     1740
tcaccaaata tttatacaga tgaaataaat ataacgcctg tatatgaaac aaataatact     1800
tatccagaag ttattgtatt agatgcaaat tatataaatg aaaaaataaa tgttaatatc     1860
aatgatctat ctatacgata tgtatggagt aatgatggta atgattttat tcttatgtca     1920
actagtgaag aaaataaggt gtcacaagtt aaaataagat tcgttaatgt ttttaaagat     1980
aagactttgg caaataagct atcttttaac tttagtgata aacaagatgt acctgtaagt     2040
gaaataatct tatcatttac accttcatat tatgaggatg gattgattgg ctatgatttg     2100
ggtctagttt ctttatataa tgagaaattt tatattaata actttggaat gatggtatct     2160
ggatta                                                                2166
```

<210> SEQ ID NO 30
<211> LENGTH: 214
<212> TYPE: DNA
<213> ORGANISM: Artificial Sequence
<220> FEATURE:
<223> OTHER INFORMATION: Synthetic Polynucleotide

<400> SEQUENCE: 30

```
tgagggtcct ggcttgaggt ccgtcctcct tctgcagggc tccatgctgg ggtggctcca       60
```

```
gcacctgcag gctgaggccc aggagagtgg ggaagtaggg cccggagaca cggagcagtg      120
gaggggccag ggtgaggctg ccaccctcag ggacgctgaa gttttgcgcc tctagtggga      180
tggcagcggg cagcacctcc agctccacaa ggac                                 214

<210> SEQ ID NO 31
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 31
tgagggtcct ggcttgaggt ccgtcctcct tctgcagggc tccatgctgg ggtggctcca      60
gcacctgcag gctgaggccc aggagagtgg ggaagtaggg cccggagaca cggaggggcc      120
agggtgaggc tgccaccctc aggacgctg aagttttgcg cctctagtgg gatggcagcg      180
ggcagcacct ccagctccac aaggac                                          206

<210> SEQ ID NO 32
<211> LENGTH: 215
<212> TYPE: DNA
<213> ORGANISM: Artificial Sequence
<220> FEATURE:
<223> OTHER INFORMATION: Synthetic Polynucleotide

<400> SEQUENCE: 32
tgagggtcct ggcttgaggt ccgtcctcct tctgcagggc tccatgctgg ggtggctcca      60
gcacctgcag gctgaggccc aggagagtgg ggaagtaggg cccggagaca cggagcaagt      120
ggaggggcca gggtgaggct gccaccctca gggacgctga agttttgcgc ctctagtggg      180
atggcagcgg gcagcacctc cagctccaca aggac                                215

<210> SEQ ID NO 33
<211> LENGTH: 212
<212> TYPE: DNA
<213> ORGANISM: Artificial Sequence
<220> FEATURE:
<223> OTHER INFORMATION: Synthetic Polynucleotide

<400> SEQUENCE: 33
tgagggtcct ggcttgaggt ccgtcctcct tctgcagggc tccatgctgg ggtggctcca      60
gcacctgcag gctgaggccc aggagagtgg ggaagtaggg cccggagaca cggagcagga      120
ggggccaggg tgaggctgcc accctcaggg acgctgaagt tttgcgcctc tagtgggatg      180
gcagcgggca gcacctccag ctccacaagg ac                                   212

<210> SEQ ID NO 34
<211> LENGTH: 230
<212> TYPE: DNA
<213> ORGANISM: Artificial Sequence
<220> FEATURE:
<223> OTHER INFORMATION: Synthetic Polynucleotide

<400> SEQUENCE: 34
tgagggtcct ggcttgaggt ccgtcctcct tctgcagggc tccatgctgg ggtggctcca      60
gcacctgcag gctgaggccc aggagagtgg ggaagtaggg cccggagaca cggagggccg      120
gcgatgcaga gcagtggagg ggccagggtg aggctgccac cctcagggac gctgaagttt      180
tgcgcctcta gtgggatggc agcgggcagc acctccagct ccacaaggac                230
```

```
<210> SEQ ID NO 35
<211> LENGTH: 214
<212> TYPE: DNA
<213> ORGANISM: Artificial Sequence
<220> FEATURE:
<223> OTHER INFORMATION: Synthetic Polynucleotide

<400> SEQUENCE: 35
tgagggtcct ggcttgaggt ccgtcctcct tctgcagggc tccatgctgg ggtggctcca      60
gcacctgcag gccgaggccc gggagagtgg ggaagtaggg gccggcgatg cagagcagtg     120
gaggggccag ggtgaagctg ccaccctcag ggacactgaa gttttgcacc tccggtggga    180
tgacagtggg cagcacctcc agctccacaa ggac                                 214

<210> SEQ ID NO 36
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 36
tgagggtcct ggcttgaggt ccgtcctcct tctgcagggc tccatgctgg ggtggctcca      60
gcacctgcag gctgaggccc aggagagtgg ggaagtaggg cccggagaca cggaggggcc     120
agggtgaggc tgccaccctc agggacgctg aagttttgca cctccggtgg gatgacagtg    180
ggcagcacct ccagctccac aaggac                                          206

<210> SEQ ID NO 37
<211> LENGTH: 214
<212> TYPE: DNA
<213> ORGANISM: Artificial Sequence
<220> FEATURE:
<223> OTHER INFORMATION: Synthetic Polynucleotide

<400> SEQUENCE: 37
tgagggtcct ggcttgaggt ccgtcctcct tctgcagggc tccatgctgg ggtggctcca      60
gcacctgcag gctgaggccc aggagagtgg ggaagtaggg gccggcgatg cagagcagtg    120
gaggggccag ggtgaagctg ccaccctcag ggacactgaa gttttgcacc tccggtggga   180
tgacagtggg cagcacctcc agctccacaa ggac                                214

<210> SEQ ID NO 38
<211> LENGTH: 215
<212> TYPE: DNA
<213> ORGANISM: Artificial Sequence
<220> FEATURE:
<223> OTHER INFORMATION: Synthetic Polynucleotide

<400> SEQUENCE: 38
tgagggtcct ggcttgaggt ccgtcctcct tctgcagggc tccatgctgg ggtggctcca      60
gcacctgcag gctgaggccc aggagagtgg ggaagtaggg cccggagaca cggagcaagt    120
ggaggggcca gggtgaggct gccaccctca gggacgctga agttttgcac ctccggtggg   180
atgacagtgg gcagcacctc cagctccaca aggac                               215

<210> SEQ ID NO 39
<211> LENGTH: 206
<212> TYPE: DNA
<213> ORGANISM: Artificial Sequence
<220> FEATURE:
<223> OTHER INFORMATION: Synthetic Polynucleotide
```

<400> SEQUENCE: 39

```
tgagggtcct ggcttgaggt ccgtcctcct tctgcagggc tccatgctgg ggtggctcca      60
gcacctgcag gctgaggccc aggagagtgg ggaagtaggg cccggagaca cggaggggcc     120
agggtgaggc tgccaccctc agggacactg aagttttgca cctccggtgg gatgacagtg     180
ggcagcacct ccagctccac aaggac                                          206
```

<210> SEQ ID NO 40
<211> LENGTH: 214
<212> TYPE: DNA
<213> ORGANISM: Artificial Sequence
<220> FEATURE:
<223> OTHER INFORMATION: Synthetic Polynucleotide

<400> SEQUENCE: 40

```
tgagggtcct ggcttgaggt ccgtcctcct tctgcagggc tccatgctgg ggtggctcca      60
gcacctgcag gctgaggccc aggagagtgg ggaagtaggg cccggagaca cggagcagtg     120
gaggggccag ggtgaggctg ccaccctcag ggacgctgaa gttttgcgcc tctagtggga     180
tggcagcggg cagcacctcc agctccacaa ggac                                 214
```

<210> SEQ ID NO 41
<211> LENGTH: 230
<212> TYPE: DNA
<213> ORGANISM: Artificial Sequence
<220> FEATURE:
<223> OTHER INFORMATION: Synthetic Polynucleotide

<400> SEQUENCE: 41

```
tgagggtcct ggcttgaggt ccgtcctcct tctgcagggc tccatgctgg ggtggctcca      60
gcacctgcag gctgaggccc aggagagtgg ggaagtaggg cccggagaca cggagggccg     120
gcgatgcaga gcagtggagg ggccagggtg aagctgccac cctcagggac actgaagttt     180
tgcacctccg gtgggatgac agtgggcagc acctccagct ccacaaggac                230
```

<210> SEQ ID NO 42
<211> LENGTH: 214
<212> TYPE: DNA
<213> ORGANISM: Artificial Sequence
<220> FEATURE:
<223> OTHER INFORMATION: Synthetic Polynucleotide

<400> SEQUENCE: 42

```
tgagggtcct ggcttgaggt ccgtcctcct tctgcagggc tccatgctgg ggtggctcca      60
gcacctgcag gccgaggccc gggagagtgg ggaagtaggg gccggcgatg cagagcagtg     120
gaggggccag ggtgaggctg ccaccctcag ggacgctgaa gttttgcgcc tctagtggga     180
tggcagcggg cagcacctcc agctccacaa ggac                                 214
```

<210> SEQ ID NO 43
<211> LENGTH: 214
<212> TYPE: DNA
<213> ORGANISM: Artificial Sequence
<220> FEATURE:
<223> OTHER INFORMATION: Synthetic Polynucleotide

<400> SEQUENCE: 43

```
tgagggtcct ggcttgaggt ccgtcctcct tctgcagggc tccatgctgg ggtggctcca      60
gcacctgcag gctgaggccc aggagagtgg ggaagtaggg gccggcgatg cagagcagtg     120
gaggggccag ggtgaggctg ccaccctcag ggacgctgaa gttttgcgcc tctagtggga     180
```
tggcagcggg cagcacctcc agctccacaa ggac                                      214

<210> SEQ ID NO 44
<211> LENGTH: 214
<212> TYPE: DNA
<213> ORGANISM: Artificial Sequence
<220> FEATURE:
<223> OTHER INFORMATION: Synthetic Polynucleotide

<400> SEQUENCE: 44
tgagggtcct ggcttgaggt ccgtcctcct tctgcagggc tccatgctgg ggtggctcca    60
gcacctgcag gccgaggccc gggagagtgg ggaagtaggg gccggcgatg cagagcagtg   120
gaggggccag ggtgaagctg ccaccctcag ggacactgaa gttttgcgcc tctagtggga   180
tggcagcggg cagcacctcc agctccacaa ggac                                214

<210> SEQ ID NO 45
<211> LENGTH: 212
<212> TYPE: DNA
<213> ORGANISM: Artificial Sequence
<220> FEATURE:
<223> OTHER INFORMATION: Synthetic Polynucleotide

<400> SEQUENCE: 45
tgagggtcct ggcttgaggt ccgtcctcct tctgcagggc tccatgctgg ggtggctcca    60
gcacctgcag gctgaggccc aggagagtgg ggaagtaggg cccggagaca cggagcagga   120
ggggccaggg tgaggctgcc accctcaggg acgctgaagt tttgcacctc cggtgggatg   180
acagtgggca gcacctccag ctccacaagg ac                                  212

<210> SEQ ID NO 46
<211> LENGTH: 230
<212> TYPE: DNA
<213> ORGANISM: Artificial Sequence
<220> FEATURE:
<223> OTHER INFORMATION: Synthetic Polynucleotide

<400> SEQUENCE: 46
tgagggtcct ggcttgaggt ccgtcctcct tctgcagggc tccatgctgg ggtggctcca    60
gcacctgcag gctgaggccc aggagagtgg ggaagtaggg cccggagaca cggagggccg   120
gcgatgcaga gcagtggagg ggccagggtg aggctgccac cctcagggac gctgaagttt   180
tgcacctccg gtgggatgac agtgggcagc acctccagct ccacaaggac              230

<210> SEQ ID NO 47
<211> LENGTH: 215
<212> TYPE: DNA
<213> ORGANISM: Artificial Sequence
<220> FEATURE:
<223> OTHER INFORMATION: Synthetic Polynucleotide

<400> SEQUENCE: 47
tgagggtcct ggcttgaggt ccgtcctcct tctgcagggc tccatgctgg ggtggctcca    60
gcacctgcag gctgaggccc aggagagtgg ggaagtaggg cccggagaca cggagcaagt   120
ggaggggcca gggtgaggct gccaccctca ggacactga agttttgcac ctccggtggg   180
atgacagtgg gcagcacctc cagctccaca aggac                               215

<210> SEQ ID NO 48
<211> LENGTH: 214
<212> TYPE: DNA

```
<213> ORGANISM: Artificial Sequence
<220> FEATURE:
<223> OTHER INFORMATION: Synthetic Polynucleotide

<400> SEQUENCE: 48
tgagggtcct ggcttgaggt ccgtcctcct tctgcagggc tccatgctgg ggtggctcca      60
gcacctgcag gctgaggccc aggagagtgg ggaagtaggg gccggcgatg cagagcagtg     120
gaggggccag ggtgaagctg ccaccctcag gacactgaa gttttgcgcc tctagtggga     180
tggcagcggg cagcacctcc agctccacaa ggac                                  214

<210> SEQ ID NO 49
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 49
tgagggtcct ggcttgaggt ccgtcctcct tctgcagggc tccatgctgg ggtggctcca      60
gcacctgcag gccgaggccc gggagagtgg ggaagtaggg cccggagaca cggaggggcc     120
agggtgaggc tgccaccctc agggacgctg aagttttgcg cctctagtgg gatggcagcg     180
ggcagcacct ccagctccac aaggac                                           206

<210> SEQ ID NO 50
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 50
tgagggtcct ggcttgaggt ccgtcctcct tctgcagggc tccatgctgg ggtggctcca      60
gcacctgcag gctgaggccc aggagagtgg ggaagtaggg cccggagaca cggaggggcc     120
agggtgaagc tgccaccctc agggacactg aagttttgca cctccggtgg gatgacagtg     180
ggcagcacct ccagctccac aaggac                                           206

<210> SEQ ID NO 51
<211> LENGTH: 214
<212> TYPE: DNA
<213> ORGANISM: Artificial Sequence
<220> FEATURE:
<223> OTHER INFORMATION: Synthetic Polynucleotide

<400> SEQUENCE: 51
tgagggtcct ggcttgaggt ccgtcctcct tctgcagggc tccatgctgg ggtggctcca      60
gcacctgcag gccgaggccc gggagagtgg ggaagtaggg gccggcgatg cagagcagtg     120
gaggggccag ggtgaagctg ccaccctcag gacgctgaa gttttgcgcc tctagtggga     180
tggcagcggg cagcacctcc agctccacaa ggac                                  214

<210> SEQ ID NO 52
<211> LENGTH: 214
<212> TYPE: DNA
<213> ORGANISM: Artificial Sequence
<220> FEATURE:
<223> OTHER INFORMATION: Synthetic Polynucleotide

<400> SEQUENCE: 52
tgagggtcct ggcttgaggt ccgtcctcct tctgcagggc tccatgctgg ggtggctcca      60
```

```
gcacctgcag gctgaggccc aggagagtgg ggaagtaggg gccggcgatg cagagcagtg      120
gaggggccag ggtgaagctg ccaccctcag ggacgctgaa gttttgcgcc tctagtggga      180
tggcagcggg cagcacctcc agctccacaa ggac                                  214

<210> SEQ ID NO 53
<211> LENGTH: 215
<212> TYPE: DNA
<213> ORGANISM: Artificial Sequence
<220> FEATURE:
<223> OTHER INFORMATION: Synthetic Polynucleotide

<400> SEQUENCE: 53
tgagggtcct ggcttgaggt ccgtcctcct tctgcagggc tccatgctgg ggtggctcca       60
gcacctgcag gctgaggccc aggagagtgg ggaagtaggg cccggagaca cggagcaagt      120
ggaggggcca gggtgaagct gccaccctca ggacactga agttttgcac ctccggtggg       180
atgacagtgg gcagcacctc cagctccaca aggac                                 215

<210> SEQ ID NO 54
<211> LENGTH: 214
<212> TYPE: DNA
<213> ORGANISM: Artificial Sequence
<220> FEATURE:
<223> OTHER INFORMATION: Synthetic Polynucleotide

<400> SEQUENCE: 54
tgagggtcct ggcttgaggt ccatcctcct tctgcagggc tccatgctgg ggtggctcca       60
gcacctgcag gccgaggccc gggagagtgg ggaagtaggg gccggcgatg cagagcagtg      120
gaggggccag ggtgaagctg ccaccctcag ggacactgaa gttttgcacc tccggtggga      180
tgacagtggg cagcacctcc agctccacaa ggac                                  214

<210> SEQ ID NO 55
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 55
tgagggtcct ggcttgaggt ccgtcctcct tctgcagggc tccatgctgg ggtggctcca       60
gcacctgcag gctgaggccc aggagagtgg ggaagtaggg cccggagaca cggaggggcc      120
agggtgaggc tgccaccctc agggacactg aagttttgcg cctctagtgg gatggcagcg      180
ggcagcacct ccagctccac aaggac                                           206

<210> SEQ ID NO 56
<211> LENGTH: 214
<212> TYPE: DNA
<213> ORGANISM: Artificial Sequence
<220> FEATURE:
<223> OTHER INFORMATION: Synthetic Polynucleotide

<400> SEQUENCE: 56
tgagggtcct ggcttgaggt ccgtcctcct tctgcagggc tccatgctgg ggtggctcca       60
gcacctgcag gctgaggccc gggagagtgg ggaagtaggg gccggcgatg cagagcagtg      120
gaggggccag ggtgaagctg ccaccctcag ggacactgaa gttttgcacc tccggtggga      180
tgacagtggg cagcacctcc agctccacaa ggac                                  214
```

<210> SEQ ID NO 57
<211> LENGTH: 230
<212> TYPE: DNA
<213> ORGANISM: Artificial Sequence
<220> FEATURE:
<223> OTHER INFORMATION: Synthetic Polynucleotide

<400> SEQUENCE: 57

```
tgagggtcct ggcttgaggt ccgtcctcct tctgcagggc tccatgctgg ggtggctcca      60
gcacctgcag gctgaggccc aggagagtgg ggaagtaggg cccggagaca cggagggccg     120
gcgatgcaga gcagtggagg ggccagggtg aggctgccac cctcagggac actgaagttt     180
tgcacctccg gtgggatgac agtgggcagc acctccagct ccacaaggac                230
```

<210> SEQ ID NO 58
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 58

```
tgagggtcct ggcttgaggt ccgtcctcct tctgcagggc tccatgctgg ggtggctcca      60
gcacctgcag gctgaggccc aggagagtgg ggaagtaggg cccggagaca cggaggggcc     120
agggtgaggc tgccaccctc agggacgctg aagttttgcg cctctagtgg gatgacagtg     180
ggcagcacct ccagctccac aaggac                                          206
```

<210> SEQ ID NO 59
<211> LENGTH: 212
<212> TYPE: DNA
<213> ORGANISM: Artificial Sequence
<220> FEATURE:
<223> OTHER INFORMATION: Synthetic Polynucleotide

<400> SEQUENCE: 59

```
tgagggtcct ggcttgaggt ccgtcctcct tctgcagggc tccatgctgg ggtggctcca      60
gcacctgcag gctgaggccc aggagagtgg ggaagtaggg cccggagaca cggagcagga     120
ggggccaggg tgaggctgcc accctcaggg acactgaagt tttgcacctc cggtgggatg     180
acagtgggca gcacctccag ctccacaagg ac                                   212
```

<210> SEQ ID NO 60
<211> LENGTH: 215
<212> TYPE: DNA
<213> ORGANISM: Artificial Sequence
<220> FEATURE:
<223> OTHER INFORMATION: Synthetic Polynucleotide

<400> SEQUENCE: 60

```
tgagggtcct ggcttgaggt ccgtcctcct tctgcagggc tccatgctgg ggtggctcca      60
gcacctgcag gccgaggccc gggagagtgg ggaagtaggg cccggagaca cggagcaagt     120
ggaggggcca gggtgaggct gccaccctca gggacgctga agttttgcgc ctctagtggg     180
atggcagcgg gcagcacctc cagctccaca aggac                                215
```

<210> SEQ ID NO 61
<211> LENGTH: 230
<212> TYPE: DNA
<213> ORGANISM: Artificial Sequence
<220> FEATURE:
<223> OTHER INFORMATION: Synthetic Polynucleotide

<400> SEQUENCE: 61

| tgagggtcct ggcttgaggt ccgtcctcct tctgcaggc tccatgctgg ggtggctcca | 60 |
| gcacctgcag gctgaggccc aggagagtgg ggaagtaggg cccggagaca cggagggccg | 120 |
| gcgatgcaga gcagtggagg ggccaggtg aagctgccac cctcagggac actgaagttt | 180 |
| tgcgcctcta gtgggatggc agcgggcagc acctccagct ccacaaggac | 230 |

<210> SEQ ID NO 62
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 62

| tgagggtcct ggcttgaggt ccgtcctcct tctgcaggc tccatgctgg ggtggctcca | 60 |
| gcacctgcag gccgaggccc aggagagtgg ggaagtaggg cccggagaca cggaggggcc | 120 |
| agggtgaggc tgccaccctc agggacgctg aagttttgcg cctctagtgg gatggcagcg | 180 |
| ggcagcacct ccagctccac aaggac | 206 |

<210> SEQ ID NO 63
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 63

| tgagggtcct ggcttgaggt ccgtcctcct tctgcaggc tccatgctgg ggtggctcca | 60 |
| gcacctgcag gctgaggccc aggagagtgg ggaagtaggg cccggagaca cggaggggcc | 120 |
| agggtgaggc tgccaccctc agggacgctg aagttttgcg cctctagtgg gatggcagtg | 180 |
| ggcagcacct ccagctccac aaggac | 206 |

<210> SEQ ID NO 64
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 64

| tgagggtcct ggcttgaggt ccatcctcct tctgcaggc tccatgctgg ggtggctcca | 60 |
| gcacctgcag gctgaggccc aggagagtgg ggaagtaggg cccggagaca cggaggggcc | 120 |
| agggtgaggc tgccaccctc agggacgctg aagttttgcg cctctagtgg gatggcagcg | 180 |
| ggcagcacct ccagctccac aaggac | 206 |

<210> SEQ ID NO 65
<211> LENGTH: 230
<212> TYPE: DNA
<213> ORGANISM: Artificial Sequence
<220> FEATURE:
<223> OTHER INFORMATION: Synthetic Polynucleotide

<400> SEQUENCE: 65

| tgagggtcct ggcttgaggt ccgtcctcct tctgcaggc tccatgctgg ggtggctcca | 60 |
| gcacctgcag gctgaggccc aggagagtgg ggaagtaggg cccggagaca cggagggccg | 120 |

```
gcgatgcaga gcagtggagg ggccagggtg aagctgccac cctcagggac gctgaagttt      180
tgcgcctcta gtgggatggc agcgggcagc acctccagct ccacaaggac                 230

<210> SEQ ID NO 66
<211> LENGTH: 215
<212> TYPE: DNA
<213> ORGANISM: Artificial Sequence
<220> FEATURE:
<223> OTHER INFORMATION: Synthetic Polynucleotide

<400> SEQUENCE: 66
tgagggtcct ggcttgaggt ccgtcctcct tctgcagggc tccatgctgg ggtggctcca       60
gcacctgcag gctgaggccc aggagagtgg ggaagtaggg cccggagaca cggagcaagt     120
ggaggggcca gggtgaggct gccaccctca gggacactga agttttgcgc ctctagtggg     180
atggcagcgg gcagcacctc cagctccaca aggac                                215

<210> SEQ ID NO 67
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 67
tgagggtcct ggcttgaggt ccgtcctcct tctgcagggc tccatgctgg ggtggctcca       60
gcacctgcag gctgaggccc gggagagtgg ggaagtaggg cccggagaca cggaggggcc     120
agggtgaggc tgccaccctc agggacgctg aagttttgcg cctctagtgg gatggcagcg     180
ggcagcacct ccagctccac aaggac                                          206

<210> SEQ ID NO 68
<211> LENGTH: 212
<212> TYPE: DNA
<213> ORGANISM: Artificial Sequence
<220> FEATURE:
<223> OTHER INFORMATION: Synthetic Polynucleotide

<400> SEQUENCE: 68
tgagggtcct ggcttgaggt ccgtcctcct tctgcagggc tccatgctgg ggtggctcca       60
gcacctgcag gctgaggccc aggagagtgg ggaagtaggg cccggagaca cggagcagga     120
ggggccaggg tgaagctgcc accctcaggg acactgaagt tttgcacctc cggtgggatg     180
acagtgggca gcacctccag ctccacaagg ac                                   212

<210> SEQ ID NO 69
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 69
tgagggtcct ggcttgaggt ccgtcctcct tctgcagggc tccatgctgg ggcggctcca       60
gcacctgcag gctgaggccc aggagagtgg ggaagtaggg cccggagaca cggaggggcc     120
agggtgaggc tgccaccctc agggacgctg aagttttgcg cctctagtgg gatggcagcg     180
ggcagcacct ccagctccac aaggac                                          206

<210> SEQ ID NO 70
<211> LENGTH: 206
```

<212> TYPE: DNA
<213> ORGANISM: Artificial Sequence
<220> FEATURE:
<223> OTHER INFORMATION: Synthetic Polynucleotide

<400> SEQUENCE: 70

```
tgagggtcct ggcttgaggt ccgtcctcct tctgcaggqc tccatgctgg ggtggctcca      60
gcacctgcag gctgaggccc aggagagtgg ggaagtaggg cccggagaca cggaggggcc     120
agggtgaagc tgccaccctc agggacgctg aagttttgcg cctctagtgg gatggcagcg     180
ggcagcacct ccagctccac aaggac                                          206
```

<210> SEQ ID NO 71
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 71

```
tgagggtcct ggcttgaggt ccgtcctcct tctgcaggqc tccatgctgg ggtggctcca      60
gcacctgcag gctgaggccc aggagagtgg ggaagtaggg cccggagaca cggaggggcc     120
agggtgaggc tgccaccctc agggacgctg aagttttgcg cctctagtgg gatggcagcg     180
ggcagcccct ccagctccac aaggac                                          206
```

<210> SEQ ID NO 72
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 72

```
tgagggtcct ggcttgaggt ccgtcctcct tctgcaggqc tccatgctgg ggtggctcca      60
gcacctgcag gctgaggccc aggagagtgg ggaagtaggg cccggagaca cggaggggcc     120
agggtgaggc tgccaccctc agggacgctg aagttttgcg cctctagtgg gatggcggcg     180
ggcagcacct ccagctccac aaggac                                          206
```

<210> SEQ ID NO 73
<211> LENGTH: 215
<212> TYPE: DNA
<213> ORGANISM: Artificial Sequence
<220> FEATURE:
<223> OTHER INFORMATION: Synthetic Polynucleotide

<400> SEQUENCE: 73

```
tgagggtcct ggcttgaggt ccgtcctcct tctgcaggqc tccatgctgg ggtggctcca      60
gcacctgcag gctgaggccc aggagagtgg ggaagtaggg cccggagaca cggagcaagt     120
ggaggggcca gggtgaggct gccaccctca gggacgctga agttttgcgc ctctagtggg     180
atgacagtgg gcagcacctc cagctccaca aggac                                215
```

<210> SEQ ID NO 74
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 74

```
tgagggtcct ggcttgaggt ccgtcctcct tctgcagggc tccatgctgg ggtggctcca      60
gcacctgcag gctgaggccc aggagagtgg ggaagtaggg cccggagaca cggaggggcc     120
agggtgaggc tgccaccctc agggacgctg aagttttgcg cctctagtgg gatggcagcg     180
ggcagcgcct ccagctccac aaggac                                          206
```

<210> SEQ ID NO 75
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 75

```
tgagggtcct ggcttgaggt ccgtcctcct tctgcagggc tccatgctgg ggtggcccca      60
gcacctgcag gctgaggccc aggagagtgg ggaagtaggg cccggagaca cggaggggcc     120
agggtgaggc tgccaccctc agggacgctg aagttttgcg cctctagtgg gatggcagcg     180
ggcagcacct ccagctccac aaggac                                          206
```

<210> SEQ ID NO 76
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 76

```
tgagggtcct ggcttgaggt ccgtcctcct tctgcagggc tccatgctgg ggtggctcca      60
gcacctgcag gctgaggccc aggagagtgg ggaagtaggg cccggagaca cggaggggcc     120
agggtgaggc tgccaccctc agggacgctg aagttttgcg cctctagtgg ggtggcagcg     180
ggcagcacct ccagctccac aaggac                                          206
```

<210> SEQ ID NO 77
<211> LENGTH: 212
<212> TYPE: DNA
<213> ORGANISM: Artificial Sequence
<220> FEATURE:
<223> OTHER INFORMATION: Synthetic Polynucleotide

<400> SEQUENCE: 77

```
tgagggtcct ggcttgaggt ccgtcctcct tctgcagggc tccatgctgg ggtggctcca      60
gcacctgcag gccgaggccc gggagagtgg ggaagtaggg cccggagaca cggagcagga     120
ggggccaggg tgaggctgcc accctcaggg acgctgaagt tttgcgcctc tagtgggatg     180
gcagcgggca gcacctccag ctccacaagg ac                                   212
```

<210> SEQ ID NO 78
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 78

```
tgagggtcct ggcttgaggt ccgtcctcct tctgcagggc tccatgctgg ggtggctcca      60
gcacctgcag gctgaggccc aggagagtgg ggaagtaggg cccggagaca cggaggggcc     120
agggtgaagc tgccaccctc agggacactg aagttttgcg cctctagtgg gatggcagcg     180
ggcagcacct ccagctccac aaggac                                          206
```

-continued

<210> SEQ ID NO 79
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 79
tgagggtcct ggcttgaggt ccgtcctcct tctgcagggc tccatgctgg ggtggctcca      60
gcacctgcag gctgaggccc aggagagtgg ggaagtaggg cccggaggca cggaggggcc     120
agggtgaggc tgccaccctc agggacgctg aagttttgcg cctctagtgg gatggcagcg     180
ggcagcacct ccagctccac aaggac                                          206

<210> SEQ ID NO 80
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 80
tgagggtcct ggcttgaggt ccgtcctcct tctgcagggc tccatgctgg ggtggctcca      60
gcacctgcag gctgaggccc aggagggtgg ggaagtaggg cccggagaca cggaggggcc     120
agggtgaggc tgccaccctc agggacgctg aagttttgcg cctctagtgg gatggcagcg     180
ggcagcacct ccagctccac aaggac                                          206

<210> SEQ ID NO 81
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 81
tgagggtcct ggcttgaggt ccgtcctcct tctgcagggc tccatgctgg ggtggctcca      60
gcacctgcag gctgaggccc aggagagtgg ggaagtaggg cccggagaca cggaggggcc     120
agggtgaggc tgccaccctc agggacgctg aagttttgcg cctccggtgg gatgacagtg     180
ggcagcacct ccagctccac aaggac                                          206

<210> SEQ ID NO 82
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 82
tgagggtcct ggcttgaggt ccgtcctccc tctgcagggc tccatgctgg ggtggctcca      60
gcacctgcag gctgaggccc aggagagtgg ggaagtaggg cccggagaca cggaggggcc     120
agggtgaggc tgccaccctc agggacgctg aagttttgcg cctctagtgg gatggcagcg     180
ggcagcacct ccagctccac aaggac                                          206

<210> SEQ ID NO 83
<211> LENGTH: 206
<212> TYPE: DNA
<213> ORGANISM: Artificial Sequence
<220> FEATURE:

<223> OTHER INFORMATION: Synthetic Polynucleotide

<400> SEQUENCE: 83

| tgagggtcct ggcttgaggt ccgtcctcct tctgcagggc tccatgctgg ggtggctcca | 60 |
| gcacctgcag gctgaggccc aggagagtgg ggaagtaggg cccggagaca cggaggggcc | 120 |
| agggtggggc tgccacccte agggacgctg aagttttgcg cctctagtgg gatggcagcg | 180 |
| ggcagcacct ccagctccac aaggac | 206 |

<210> SEQ ID NO 84
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 84

| tgagggtcct ggcttgaggt ccgtcctcct tctgcagggc tccatgctgg ggtggctcca | 60 |
| gcacctgcag gctgaggccc aggagagtgg ggaagtaggg cccggagaca cggaggggcc | 120 |
| agggtgaggc tgccgcccte agggacgctg aagttttgcg cctctagtgg gatggcagcg | 180 |
| ggcagcacct ccagctccac aaggac | 206 |

<210> SEQ ID NO 85
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 85

| tgagggtcct ggcttgaggt ccgtcctcct tctgcagggc tccatgctgg ggtggctcca | 60 |
| gcacctgcag gctgaggccc aggagagtgg ggaagtaggg cccggagaca cggaggggcc | 120 |
| agggtgaggc tgccacccte agggacgctg aggttttgcg cctctagtgg gatggcagcg | 180 |
| ggcagcacct ccagctccac aaggac | 206 |

<210> SEQ ID NO 86
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 86

| tgagggtcct ggcttgaggt ccgtcctcct tccgcagggc tccatgctgg ggtggctcca | 60 |
| gcacctgcag gctgaggccc aggagagtgg ggaagtaggg cccggagaca cggaggggcc | 120 |
| agggtgaggc tgccacccte agggacgctg aagttttgcg cctctagtgg gatggcagcg | 180 |
| ggcagcacct ccagctccac aaggac | 206 |

<210> SEQ ID NO 87
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 87

| tgagggtcct ggcttgaggt ccgtcctcct tctgcagggc tccatgctgg ggtggctcca | 60 |
| gcacctgcag gctgaggccc aggagagtgg ggaggtaggg cccggagaca cggaggggcc | 120 | agggtgaggc tgccaccctc agggacgctg aagttttgcg cctctagtgg gatggcagcg        180 ggcagcacct ccagctccac aaggac                                              206

<210> SEQ ID NO 88
<211> LENGTH: 215
<212> TYPE: DNA
<213> ORGANISM: Artificial Sequence
<220> FEATURE:
<223> OTHER INFORMATION: Synthetic Polynucleotide

<400> SEQUENCE: 88
tgagggtcct ggcttgaggt ccgtcctcct tctgcagggc tccatgctgg ggtggctcca        60
gcacctgcag gctgaggccc aggagagtgg ggaagtaggg cccggagaca cggagcaagt        120
ggaggggcca gggtgaagct gccaccctca gggacactga agttttgcgc ctctagtggg        180
atggcagcgg gcagcaccct cagctccaca aggac                                    215

<210> SEQ ID NO 89
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 89
tgagggtcct ggcttgaggt ccgtcctcct tctgcagggc tccatgctgg ggtggctcca        60
gcacccgcag gctgaggccc aggagagtgg ggaagtaggg cccggagaca cggaggggcc        120
agggtgaggc tgccaccctc agggacgctg aagttttgcg cctctagtgg gatggcagcg        180
ggcagcacct ccagctccac aaggac                                              206

<210> SEQ ID NO 90
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 90
tgagggtcct ggcttgaggt ccgtcctcct tctgcagggc tccatgctgg ggtggctcca        60
gcacctgcag gctgaggccc aggagagtgg ggaagtaggg cccggagaca cggaggggcc        120
agggtgaggc cgccaccctc agggacgctg aagttttgcg cctctagtgg gatggcagcg        180
ggcagcacct ccagctccac aaggac                                              206

<210> SEQ ID NO 91
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 91
tgagggtcct ggcttgaggt ccgtcctcct tctgcagggc tccatgctgg ggtggctcca        60
gcacctgcag gctgaggccc aggagagtgg ggaagtaggg cccggagacg cggaggggcc        120
agggtgaggc tgccaccctc agggacgctg aagttttgcg cctctagtgg gatggcagcg        180
ggcagcacct ccagctccac aaggac                                              206

<210> SEQ ID NO 92

```
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 92
tgagggtcct ggcttgaggt ccgtcctcct tctgcagggc tccatgctgg ggtggctcca      60
gcacctgcag gctgaggccc aggggagtgg ggaagtaggg cccggagaca cggaggggcc     120
agggtgaggc tgccaccctc agggacgctg aagttttgcg cctctagtgg gatggcagcg     180
ggcagcacct ccagctccac aaggac                                          206

<210> SEQ ID NO 93
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 93
tgagggtcct ggcttgaggt ccgtcctcct tctgcagggc tccatgctgg ggtggctcca      60
gcacctgcag gctgaggccc aggagagtgg ggaagtaggg cccggagaca cggaggggcc     120
agggtgaggc tgccaccctc aggggcgctg aagttttgcg cctctagtgg gatggcagcg     180
ggcagcacct ccagctccac aaggac                                          206

<210> SEQ ID NO 94
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 94
tgagggtcct ggcttgaggt ccgtccccct tctgcagggc tccatgctgg ggtggctcca      60
gcacctgcag gctgaggccc aggagagtgg ggaagtaggg cccggagaca cggaggggcc     120
agggtgaggc tgccaccctc agggacgctg aagttttgcg cctctagtgg gatggcagcg     180
ggcagcacct ccagctccac aaggac                                          206

<210> SEQ ID NO 95
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 95
tgagggtcct ggcttgaggt ccgtcctcct tctgcggggc tccatgctgg ggtggctcca      60
gcacctgcag gctgaggccc aggagagtgg ggaagtaggg cccggagaca cggaggggcc     120
agggtgaggc tgccaccctc agggacgctg aagttttgcg cctctagtgg gatggcagcg     180
ggcagcacct ccagctccac aaggac                                          206

<210> SEQ ID NO 96
<211> LENGTH: 215
<212> TYPE: DNA
<213> ORGANISM: Artificial Sequence
<220> FEATURE:
<223> OTHER INFORMATION: Synthetic Polynucleotide

<400> SEQUENCE: 96
```

```
tgagggtcct ggcttgaggt ccgtcctcct tctgcagggc tccatgctgg ggtggctcca    60
gcacctgcag gccgaggccc aggagagtgg ggaagtaggg cccggagaca cggagcaagt   120
ggaggggcca gggtgaggct gccaccctca gggacgctga agttttgcgc ctctagtggg   180
atggcagcgg gcagcacctc cagctccaca aggac                              215
```

<210> SEQ ID NO 97
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 97

```
tgagggtcct ggcttgaggt ccgtcctcct tctgcagggc tccatgctgg ggtggctcca    60
gcacctgcag gctgaggccc aggagagtgg ggaagtaggg cccggagaca cggaggggcc   120
agggtgaggc tgccaccctc aggacgctg aagttttgcg ccctagtgg gatggcagcg    180 ggcagcacct ccagctccac aaggac                                        206
```

<210> SEQ ID NO 98
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 98

```
tgagggtcct ggcttgaggt ccgtcctcct tctgcagggc tccatgctgg ggtggctcca    60
gcacctgcag gctgaggccc aggagagtgg ggaagtaggg cccggagaca cggaggggcc   120
agggtgaggc tgccaccctc aggacgctg aagttttgcg cctctagtgg gatggcagcg   180
ggcggcacct ccagctccac aaggac                                        206
```

<210> SEQ ID NO 99
<211> LENGTH: 215
<212> TYPE: DNA
<213> ORGANISM: Artificial Sequence
<220> FEATURE:
<223> OTHER INFORMATION: Synthetic Polynucleotide

<400> SEQUENCE: 99

```
tgagggtcct ggcttgaggt ccgtcctcct tctgcagggc tccatgctgg ggtggctcca    60
gcacctgcag gctgaggccc aggagagtgg ggaagtaggg cccggagaca cggagcaagt   120
ggaggggcca gggtgaagct gccaccctca gggacgctga agttttgcgc ctctagtggg   180
atggcagcgg gcagcacctc cagctccaca aggac                              215
```

<210> SEQ ID NO 100
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 100

```
tgagggtcct ggcttgaggc ccgtcctcct tctgcagggc tccatgctgg ggtggctcca    60
gcacctgcag gctgaggccc aggagagtgg ggaagtaggg cccggagaca cggaggggcc   120
agggtgaggc tgccaccctc agggacgctg aagttttgcg cctctagtgg gatggcagcg   180
```

```
ggcagcacct ccagctccac aaggac                                           206

<210> SEQ ID NO 101
<211> LENGTH: 214
<212> TYPE: DNA
<213> ORGANISM: Artificial Sequence
<220> FEATURE:
<223> OTHER INFORMATION: Synthetic Polynucleotide

<400> SEQUENCE: 101
tgagggtcct ggcttgaggt ccgtcctcct tctgcagggc tccatgctgg ggtggctcca      60
gcacctgcag gctgaggccc gggagagtgg ggaagtaggg gccggcgatg cagagcagtg     120
gaggggccag ggtgaggctg ccaccctcag ggacgctgaa gttttgcgcc tctagtggga     180
tggcagcggg cagcacctcc agctccacaa ggac                                 214

<210> SEQ ID NO 102
<211> LENGTH: 215
<212> TYPE: DNA
<213> ORGANISM: Artificial Sequence
<220> FEATURE:
<223> OTHER INFORMATION: Synthetic Polynucleotide

<400> SEQUENCE: 102
tgagggtcct ggcttgaggt ccatcctcct tctgcagggc tccatgctgg ggtggctcca      60
gcacctgcag gctgaggccc aggagagtgg ggaagtaggg cccggagaca cggagcaagt     120
ggaggggcca gggtgaggct gccaccctca gggacgctga agttttgcgc ctctagtggg     180
atggcagcgg gcagcacctc cagctccaca aggac                                215

<210> SEQ ID NO 103
<211> LENGTH: 212
<212> TYPE: DNA
<213> ORGANISM: Artificial Sequence
<220> FEATURE:
<223> OTHER INFORMATION: Synthetic Polynucleotide

<400> SEQUENCE: 103
tgagggtcct ggcttgaggt ccgtcctcct tctgcagggc tccatgctgg ggtggctcca      60
gcacctgcag gctgaggccc aggagagtgg ggaagtaggg cccggagaca cggagcagga     120
ggggccaggg tgaggctgcc accctcaggg acactgaagt tttgcgcctc tagtgggatg     180
gcagcgggca gcacctccag ctccacaagg ac                                   212

<210> SEQ ID NO 104
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 104
tgagggtcct ggcttgaggt ccgtcctcct tctgcagggc tccatgctgg ggtggctcca      60
gcacctgcag gctggggccc aggagagtgg ggaagtaggg cccggagaca cggaggggcc     120
agggtgaggc tgccaccctc agggacgctg aagttttgcg cctctagtgg gatggcagcg     180
ggcagcacct ccagctccac aaggac                                          206

<210> SEQ ID NO 105
<211> LENGTH: 206
<212> TYPE: DNA
<213> ORGANISM: Artificial Sequence
```

```
<220> FEATURE:
<223> OTHER INFORMATION: Synthetic Polynucleotide

<400> SEQUENCE: 105
tgagggtcct ggcttgaggt ccgtcctcct tctgcagggc tccatgctgg ggtggctcca      60
gcacctgcag gctgaggccc aggagagtgg ggaagtaggg cccggagaca cggaggggcc     120
agggtgaggc tgccaccctc agggacgctg aagttttgca cctccggtgg gatggcagcg     180
ggcagcacct ccagctccac aaggac                                          206

<210> SEQ ID NO 106
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 106
tgagggtcct ggcttgaggt ccgtcctcct tctgcagggc tccatgctgg ggtggctcca      60
gcacctgcag gctgaggccc aggagagtgg ggaagtaggg cccggagaca cggaggggcc     120
agggtgaggc tgccaccctc agggacgccg aagttttgcg cctctagtgg gatggcagcg     180
ggcagcacct ccagctccac aaggac                                          206

<210> SEQ ID NO 107
<211> LENGTH: 215
<212> TYPE: DNA
<213> ORGANISM: Artificial Sequence
<220> FEATURE:
<223> OTHER INFORMATION: Synthetic Polynucleotide

<400> SEQUENCE: 107
tgagggtcct ggcttgaggt ccgtcctcct tctgcagggc tccatgctgg ggtggctcca      60
gcacctgcag gctgaggccc aggagagtgg ggaagtaggg cccggagaca cggagcaagt     120
ggaggggcca gggtgaggct gccaccctca gggacgctga agttttgcgc ctctagtggg     180
atggcagtgg gcagcacctc agctccaca aggac                                 215

<210> SEQ ID NO 108
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 108
tgagggtcct ggcttgaggg ccgtcctcct tctgcagggc tccatgctgg ggtggctcca      60
gcacctgcag gctgaggccc aggagagtgg ggaagtaggg cccggagaca cggaggggcc     120
agggtgaggc tgccaccctc agggacgctg aagttttgcg cctctagtgg gatggcagcg     180
ggcagcacct ccagctccac aaggac                                          206

<210> SEQ ID NO 109
<211> LENGTH: 230
<212> TYPE: DNA
<213> ORGANISM: Artificial Sequence
<220> FEATURE:
<223> OTHER INFORMATION: Synthetic Polynucleotide

<400> SEQUENCE: 109
tgagggtcct ggcttgaggt ccgtcctcct tctgcagggc tccatgctgg ggtggctcca      60
```

```
gcacctgcag gctgaggccc aggagagtgg ggaagtaggg cccggagaca cggagggccg      120
gcgatgcaga gcagtggagg ggccaggtg aggctgccac cctcagggac actgaagttt       180
tgcgcctcta gtgggatggc agcgggcagc acctccagct ccacaaggac                 230
```

<210> SEQ ID NO 110
<211> LENGTH: 230
<212> TYPE: DNA
<213> ORGANISM: Artificial Sequence
<220> FEATURE:
<223> OTHER INFORMATION: Synthetic Polynucleotide

<400> SEQUENCE: 110

```
tgagggtcct ggcttgaggt ccgtcctcct tctgcagggc tccatgctgg ggtggctcca      60
gcacctgcag gccgaggccc gggagagtgg ggaagtaggg cccggagaca cggagggccg      120
gcgatgcaga gcagtggagg ggccaggtg aggctgccac cctcagggac gctgaagttt      180
tgcgcctcta gtgggatggc agcgggcagc acctccagct ccacaaggac                 230
```

<210> SEQ ID NO 111
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 111

```
tgagggtcct ggcttgaggt ccgtcctcct tctgcagggc cccatgctgg ggtggctcca      60
gcacctgcag gctgaggccc aggagagtgg ggaagtaggg cccggagaca cggaggggcc      120
agggtgaggc tgccaccctc agggacgctg aagttttgcg cctctagtgg gatggcagcg      180
ggcagcacct ccagctccac aaggac                                           206
```

<210> SEQ ID NO 112
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 112

```
tgagggtcct ggcttgaggt ccgtcctcct tctgcagggc tccatgctgg ggtggctcca      60
gcacctgcag gctgaggccc aggagagtgg ggaagtaggg cccggagaca cggaggggcc      120
agggtgaggc tgccaccccc agggacgctg aagttttgcg cctctagtgg gatggcagcg      180
ggcagcacct ccagctccac aaggac                                           206
```

<210> SEQ ID NO 113
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 113

```
tgagggtcct ggcttgaggt ccgtcctcct tctgcagggc tccatgctgg ggtggctccg      60
gcacctgcag gctgaggccc aggagagtgg ggaagtaggg cccggagaca cggaggggcc      120
agggtgaggc tgccaccctc agggacgctg aagttttgcg cctctagtgg gatggcagcg      180
ggcagcacct ccagctccac aaggac                                           206
```

<210> SEQ ID NO 114
<211> LENGTH: 214
<212> TYPE: DNA
<213> ORGANISM: Artificial Sequence
<220> FEATURE:
<223> OTHER INFORMATION: Synthetic Polynucleotide

<400> SEQUENCE: 114

```
tgagggtcct ggcttgaggt ccgtcctcct tctgcagggc tccatgctgg ggtggctcca      60
gcacctgcag gctgaggccc gggagagtgg ggaagtaggg gccggcgatg cagagcagtg     120
gaggggccag ggtgaagctg ccaccctcag ggacactgaa gttttgcgcc tctagtggga     180
tggcagcggg cagcacctcc agctccacaa ggac                                 214
```

<210> SEQ ID NO 115
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 115

```
tgagggtcct ggcttgaggt ccgtcctcct tctgcagggc tccatgctgg ggtggctcca      60
gcacctgcag gctgaggccc aggagagtgg ggaagtaggg cccggagaca cgggggggcc     120
agggtgaggc tgccaccctc agggacgctg aagttttgcg cctctagtgg gatggcagcg     180
ggcagcacct ccagctccac aaggac                                          206
```

<210> SEQ ID NO 116
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 116

```
tgagggtcct ggcttgaggt ccgtcctcct tctgcagggc tccatgctgg ggtggctcca      60
gcacctgcag gctgaggccc aggagagtgg ggaagtaggg cccggggaca cggaggggcc     120
agggtgaggc tgccaccctc agggacgctg aagttttgcg cctctagtgg gatggcagcg     180
ggcagcacct ccagctccac aaggac                                          206
```

<210> SEQ ID NO 117
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 117

```
tgagggtcct ggcttgaggt ccgccctcct tctgcagggc tccatgctgg ggtggctcca      60
gcacctgcag gctgaggccc aggagagtgg ggaagtaggg cccggagaca cggaggggcc     120
agggtgaggc tgccaccctc agggacgctg aagttttgcg cctctagtgg gatggcagcg     180
ggcagcacct ccagctccac aaggac                                          206
```

<210> SEQ ID NO 118
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 118

```
tgagggtcct ggcttgaggt ccgtcctcct tctgcagggc tccatgctgg ggtggctcca        60
gcacctgcag gctgaggccc aggagagtgg ggaagtaggg cccggagaca cggagggggcc      120 agggcgaggc tgccacccte agggacgctg aagttttgcg cctctagtgg gatggcagcg       180
ggcagcacct ccagctccac aaggac                                            206
```

<210> SEQ ID NO 119
<211> LENGTH: 214
<212> TYPE: DNA
<213> ORGANISM: Artificial Sequence
<220> FEATURE:
<223> OTHER INFORMATION: Synthetic Polynucleotide

<400> SEQUENCE: 119

```
tgagggtcct ggcttgaggt ccgtcctcct tctgcagggc tccatgctgg ggtggctcca        60
gcacctgcag gccgaggccc gggagagtgg ggaagtaggg gccggcgatg cagagcagtg      120
gaggggccag ggtgaagctg ccaccctcag ggacactgaa gttttgcacc tccggtggga     180
tggcagcggg cagcacctcc agctccacaa ggac                                   214
```

<210> SEQ ID NO 120
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 120

```
tgagggtcct ggcttgaggt ccgtcctcct tctgcagggc tccgtgctgg ggtggctcca        60
gcacctgcag gctgaggccc aggagagtgg ggaagtaggg cccggagaca cggagggggcc      120 agggtgaggc tgccacccte agggacgctg aagttttgcg cctctagtgg gatggcagcg       180
ggcagcacct ccagctccac aaggac                                            206
```

<210> SEQ ID NO 121
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 121

```
tgagggtcct ggcttgaggt ccgtcctcct tctgcagggc tccatgctgg ggtggctcca        60
gcacctgcag gctgaggccc aggagagtgg ggaagtaggg cccggagaca cggagggggcc      120 ggggtgaggc tgccacccte agggacgctg aagttttgcg cctctagtgg gatggcagcg       180
ggcagcacct ccagctccac aaggac                                            206
```

<210> SEQ ID NO 122
<211> LENGTH: 203
<212> TYPE: DNA
<213> ORGANISM: Artificial Sequence
<220> FEATURE:
<223> OTHER INFORMATION: Synthetic Polynucleotide

<400> SEQUENCE: 122

```
tgagggtcct ggcttgaggt ccgtcctcct tctgcagggc tccatgctgg ggtggctcca        60
gcacctgcag gctgaggccc aggagagtgg ggaagtaggg cccggagaca cggagccagg      120
gtgaggctgc caccctcagg gacgctgaag ttttgcgcct ctagtgggat ggcagcgggc       180
```
agcacctcca gctccacaag gac       203

<210> SEQ ID NO 123
<211> LENGTH: 215
<212> TYPE: DNA
<213> ORGANISM: Artificial Sequence
<220> FEATURE:
<223> OTHER INFORMATION: Synthetic Polynucleotide

<400> SEQUENCE: 123
tgagggtcct ggcttgaggt ccgtcctcct tctgcagggc tccatgctgg ggtggctcca       60
gcacctgcag gctgaggccc aggagagtgg ggaagtaggg cccggagaca cggagcaagt      120
ggaggggcca gggtgaggct gccaccctca gggacgctga agttttgcgc ctctagtggg      180
atggcagcgg gcagcgcctc cagctccaca aggac      215

<210> SEQ ID NO 124
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 124
tgagggtcct ggcttgaggt ccgtcctcct tctgcagggc tccatgctgg ggtggctcca       60
gcacctgcag gctgaggccc aggagagtgg ggaagtaggg cccggagaca cggaggggcc      120
agggtgaggc tgccaccctc ggggacgctg aagttttgcg cctctagtgg gatggcagcg      180
ggcagcacct ccagctccac aaggac      206

<210> SEQ ID NO 125
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 125
tgagggtcct ggcttgaggt ccgtcctcct tctgcagggc tccatgctgg ggtggctcca       60
gcacctgcag gctgaggccc aggagagtgg ggaagtaggg cccggagaca cggaggggcc      120
agggtgaggc tgccaccctc agggacgctg aagctttgcg cctctagtgg gatggcagcg      180
ggcagcacct ccagctccac aaggac      206

<210> SEQ ID NO 126
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 126
tgagggtcct ggcttgaggt ccgtcctcct tctgcagggc tccatgctgg ggtggctcca       60
gcgcctgcag gctgaggccc aggagagtgg ggaagtaggg cccggagaca cggaggggcc      120
agggtgaggc tgccaccctc agggacgctg aagttttgcg cctctagtgg gatggcagcg      180
ggcagcacct ccagctccac aaggac      206

<210> SEQ ID NO 127
<211> LENGTH: 215
<212> TYPE: DNA

```
<213> ORGANISM: Artificial Sequence
<220> FEATURE:
<223> OTHER INFORMATION: Synthetic Polynucleotide

<400> SEQUENCE: 127
tgagggtcct ggcttgaggt ccgtcctcct tctgcagggc tccatgctgg ggtggctcca      60
gcacctgcag gctgaggccc gggagagtgg ggaagtaggg cccggagaca cggagcaagt     120
ggaggggcca gggtgaggct gccaccctca gggacgctga agttttgcgc ctctagtggg     180
atggcagcgg gcagcaccte cagctccaca aggac                                215

<210> SEQ ID NO 128
<211> LENGTH: 212
<212> TYPE: DNA
<213> ORGANISM: Artificial Sequence
<220> FEATURE:
<223> OTHER INFORMATION: Synthetic Polynucleotide

<400> SEQUENCE: 128
tgagggtcct ggcttgaggt ccgtcctcct tctgcagggc tccatgctgg ggtggctcca      60
gcacctgcag gctgaggccc aggagagtgg ggaagtaggg cccggagaca cggagcagga     120
ggggccaggg tgaggctgcc accctcaggg acgctgaagt tttgcgcctc tagtgggatg     180
acagtgggca gcacctccag ctccacaagg ac                                   212

<210> SEQ ID NO 129
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 129
tgagggtcct ggcttgaggt ccgtcctcct tctgcagggc tccatgctgg ggtggctcca      60
gcacctgcag gctgaggccc aggagagtgg ggaagtaggg cccggagaca cggaggggcc     120
agggtgaggc tgccaccctc agggacgctg aagttttgcg cctctagtgg gacggcagcg     180
ggcagcacct ccagctccac aaggac                                          206

<210> SEQ ID NO 130
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 130
tgagggtcct ggcttgaggt ccgtcctcct tctgcagggc tccatgccgg ggtggctcca      60
gcacctgcag gctgaggccc aggagagtgg ggaagtaggg cccggagaca cggaggggcc     120
agggtgaggc tgccaccctc agggacgctg aagttttgcg cctctagtgg gatggcagcg     180
ggcagcacct ccagctccac aaggac                                          206

<210> SEQ ID NO 131
<211> LENGTH: 210
<212> TYPE: DNA
<213> ORGANISM: Artificial Sequence
<220> FEATURE:
<223> OTHER INFORMATION: Synthetic Polynucleotide

<400> SEQUENCE: 131
ttcctgtgct ccatgtacgc accgtgtgc accgtgctgg aacaggccat cccgccgtgc      60
```

```
cgctctatct gtgagcgcgc gcgccagggc tgcgaagccc tcatgaacaa gttcggtttt    120
cagtggcccg agcgcctgcg ctgcgagcac ttcccgcgcc acggcgccga gcagatctgc    180
gtcggccaga accactccga ggacggagct                                     210
```

```
<210> SEQ ID NO 132
<211> LENGTH: 202
<212> TYPE: DNA
<213> ORGANISM: Artificial Sequence
<220> FEATURE:
<223> OTHER INFORMATION: Synthetic Polynucleotide

<400> SEQUENCE: 132
```

```
ttcctgtgct ccatgtacgc acccgtgtgc accgtgctgg aacaggccat cccgccgtgc     60
cgctctatct gtgagcgcgc gcgccagggc tgcgaagccc tcatgaacaa gttcggtttt    120
cagtggcccg agcgcctgcg ctgcgagcac ttcccgcgcc gagcagatct gcgtcggcca    180
gaaccactcc gaggacggag ct                                             202
```

```
<210> SEQ ID NO 133
<211> LENGTH: 205
<212> TYPE: DNA
<213> ORGANISM: Artificial Sequence
<220> FEATURE:
<223> OTHER INFORMATION: Synthetic Polynucleotide

<400> SEQUENCE: 133
```

```
ttcctgtgct ccatgtacgc acccgtgtgc accgtgctgg aacaggccat cccgccgtgc     60
cgctctatct gtgagcgcgc gcgccagggc tgcgaagccc tcatgaacaa gttcggtttt    120
cagtggcccg agcgcctgcg ctgcgagcac ttcccgcggc gccgagcaga tctgcgtcgg    180
ccagaaccac tccgaggacg gagct                                          205
```

```
<210> SEQ ID NO 134
<211> LENGTH: 205
<212> TYPE: DNA
<213> ORGANISM: Artificial Sequence
<220> FEATURE:
<223> OTHER INFORMATION: Synthetic Polynucleotide

<400> SEQUENCE: 134
```

```
ttcctgtgct ccatgtacgc acccgtgtgc accgtgctgg aacaggccat cccgccgtgc     60
cgctctatct gtgagcgcgc gcgccagggc tgcgaagccc tcatgaacaa gttcggtttt    120
cagtggcccg agcgcctgcg ctgcgagcac ttcccacggc gccgagcaga tctgcgtcgg    180
ccagaaccac tccgaggacg gagct                                          205
```

```
<210> SEQ ID NO 135
<211> LENGTH: 204
<212> TYPE: DNA
<213> ORGANISM: Artificial Sequence
<220> FEATURE:
<223> OTHER INFORMATION: Synthetic Polynucleotide

<400> SEQUENCE: 135
```

```
ttcctgtgct ccatgtacgc acccgtgtgc accgtgctgg aacaggccat cccgccgtgc     60
cgctctatct gtgagcgcgc gcgccagggc tgcgaagccc tcatgaacaa gttcggtttt    120
cagtggcccg agcgcctgcg ctgcgagcac ttccacggcg ccgagcagat ctgcgtcggc    180
cagaaccact ccgaggacgg agct                                           204
```

<210> SEQ ID NO 136
<211> LENGTH: 210
<212> TYPE: DNA
<213> ORGANISM: Artificial Sequence
<220> FEATURE:
<223> OTHER INFORMATION: Synthetic Polynucleotide

<400> SEQUENCE: 136
ttcctgtgct ccatgtacgc acccgtgtgc accgtgctgg aacaggccat cccgccgtgc     60
cgctctatct gtgagcgcgc gcgccagggc tgcgaagccc tcatgaacaa gttcggtttt    120
cagtggcccg agcgcctgcg ctgcgagcac ttcccgcgcc acggcgccga gcagatctgc    180
gtcggccaga accactccga ggacggagct                                     210

<210> SEQ ID NO 137
<211> LENGTH: 200
<212> TYPE: DNA
<213> ORGANISM: Artificial Sequence
<220> FEATURE:
<223> OTHER INFORMATION: Synthetic Polynucleotide

<400> SEQUENCE: 137
ttcctgtgct ccatgtacgc acccgtgtgc accgtgctgg aacaggccat cccgccgtgc     60
cgctctatct gtgagcgcgc gcgccagggc tgcgaagccc tcatgaacaa gttcggtttt    120
cagtggcccg agcgcctgcg ctgcgagcac ttcccgccga gcagatctgc gtcggccaga    180
accactccga ggacggagct                                                200

<210> SEQ ID NO 138
<211> LENGTH: 197
<212> TYPE: DNA
<213> ORGANISM: Artificial Sequence
<220> FEATURE:
<223> OTHER INFORMATION: Synthetic Polynucleotide

<400> SEQUENCE: 138
ttcctgtgct ccatgtacgc acccgtgtgc accgtgctgg aacaggccat cccgccgtgc     60
cgctctatct gtgagcgcgc gcgccagggc tgcgaagccc tcatgaacaa gttcggtttt    120
cagtggcccg agcgcctgcg ctgcgagcac ttcccgagca gatctgcgtc ggccagaacc    180
actccgagga cggagct                                                   197

<210> SEQ ID NO 139
<211> LENGTH: 199
<212> TYPE: DNA
<213> ORGANISM: Artificial Sequence
<220> FEATURE:
<223> OTHER INFORMATION: Synthetic Polynucleotide

<400> SEQUENCE: 139
ttcctgtgct ccatgtacgc acccgtgtgc accgtgctgg aacaggccat cccgccgtgc     60
cgctctatct gtgagcgcgc gcgccagggc tgcgaagccc tcatgaacaa gttcggtttt    120
cagtggcccg agcgcctgcg ctgcgagcac ttcccgcgag cagatctgcg tcggccagaa    180
ccactccgag gacggagct                                                 199

<210> SEQ ID NO 140
<211> LENGTH: 186
<212> TYPE: DNA
<213> ORGANISM: Artificial Sequence
<220> FEATURE:
<223> OTHER INFORMATION: Synthetic Polynucleotide

```
<400> SEQUENCE: 140
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ctgcgagcag atctgcgtcg ccagaaccac tccgaggac     180 ggagct                                                                186

<210> SEQ ID NO 141
<211> LENGTH: 202
<212> TYPE: DNA
<213> ORGANISM: Artificial Sequence
<220> FEATURE:
<223> OTHER INFORMATION: Synthetic Polynucleotide

<400> SEQUENCE: 141
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ctgcgagcac ttcccgcgcc gagcagatct gcgtcggcca     180
gaaccactca gaggacggag ct                                              202

<210> SEQ ID NO 142
<211> LENGTH: 204
<212> TYPE: DNA
<213> ORGANISM: Artificial Sequence
<220> FEATURE:
<223> OTHER INFORMATION: Synthetic Polynucleotide

<400> SEQUENCE: 142
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ctgcgagcac ttcccgcgcg ccgagcagat ctgcgtcggc     180
cagaaccact ccgaggacgg agct                                            204

<210> SEQ ID NO 143
<211> LENGTH: 201
<212> TYPE: DNA
<213> ORGANISM: Artificial Sequence
<220> FEATURE:
<223> OTHER INFORMATION: Synthetic Polynucleotide

<400> SEQUENCE: 143
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ctgcgagcac ttcggcgccg agcagatctg cgtcggccag     180
aaccactccg aggacggagc t                                               201

<210> SEQ ID NO 144
<211> LENGTH: 207
<212> TYPE: DNA
<213> ORGANISM: Artificial Sequence
<220> FEATURE:
<223> OTHER INFORMATION: Synthetic Polynucleotide

<400> SEQUENCE: 144
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
```

```
cagtggcccg agcgcctgcg ctgcgagcac ttcccgctcg gcgccgagca gatctgcgtc    180
ggccagaacc actccgagga cggagct                                        207

<210> SEQ ID NO 145
<211> LENGTH: 209
<212> TYPE: DNA
<213> ORGANISM: Artificial Sequence
<220> FEATURE:
<223> OTHER INFORMATION: Synthetic Polynucleotide

<400> SEQUENCE: 145
ttcctgtgct ccatgtacgc acccgtgtgc accgtgctgg aacaggccat cccgccgtgc     60
cgctctatct gtgagcgcgc gcgccagggc tgcgaagccc tcatgaacaa gttcggtttt    120
cagtggcccg agcgcctgcg ctgcgagcac ttcccgcgca cggcgccgag cagatctgcg    180
tcggccagaa ccactccgag gacggagct                                      209

<210> SEQ ID NO 146
<211> LENGTH: 203
<212> TYPE: DNA
<213> ORGANISM: Artificial Sequence
<220> FEATURE:
<223> OTHER INFORMATION: Synthetic Polynucleotide

<400> SEQUENCE: 146
ttcctgtgct ccatgtacgc acccgtgtgc accgtgctgg aacaggccat cccgccgtgc     60
cgctctatct gtgagcgcgc gcgccagggc tgcgaagccc tcatgaacaa gttcggtttt    120
cagtggcccg agcgcctgcg ctgcgagcac ttcccggcgc cgagcagatc tgcgtcggcc    180
agaaccactc cgaggacgga gct                                            203

<210> SEQ ID NO 147
<211> LENGTH: 207
<212> TYPE: DNA
<213> ORGANISM: Artificial Sequence
<220> FEATURE:
<223> OTHER INFORMATION: Synthetic Polynucleotide

<400> SEQUENCE: 147
ttcctgtgct ccatgtacgc acccgtgtgc accgtgctgg aacaggccat cccgccgtgc     60
cgctctatct gtgagcgcgc gcgccagggc tgcgaagccc tcatgaacaa gttcggtttt    120
cagtggcccg agcgcctgcg ctgcgagcac ttcccgcgcg gcgccgagca gatctgcgtc    180
ggccagaacc actccgagga cggagct                                        207

<210> SEQ ID NO 148
<211> LENGTH: 208
<212> TYPE: DNA
<213> ORGANISM: Artificial Sequence
<220> FEATURE:
<223> OTHER INFORMATION: Synthetic Polynucleotide

<400> SEQUENCE: 148
ttcctgtgct ccatgtacgc acccgtgtgc accgtgctgg aacaggccat cccgccgtgc     60
cgctctatct gtgagcgcgc gcgccagggc tgcgaagccc tcatgaacaa gttcggtttt    120
cagtggcccg agcgcctgcg ctgcgagcac ttcccgccac ggcgccgagc agatctgcgt    180
cggccagaac cactccgagg acggagct                                       208

<210> SEQ ID NO 149
<211> LENGTH: 211
```

```
<212> TYPE: DNA
<213> ORGANISM: Artificial Sequence
<220> FEATURE:
<223> OTHER INFORMATION: Synthetic Polynucleotide

<400> SEQUENCE: 149
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ctgcgagcac ttcccgcggc cacggcgccg agcagatctg     180
cgtcggccag aaccactccg aggacggagc t                                    211

<210> SEQ ID NO 150
<211> LENGTH: 118
<212> TYPE: DNA
<213> ORGANISM: Artificial Sequence
<220> FEATURE:
<223> OTHER INFORMATION: Synthetic Polynucleotide

<400> SEQUENCE: 150
ttcctgtgct ccatgtacgc acccgtgtgc accgtgctgg aacaggccat cccgccgtgc      60
cgctctgcac ggcgccgagc agatctgcgt cggccagaac cactccgagg acggagct      118

<210> SEQ ID NO 151
<211> LENGTH: 205
<212> TYPE: DNA
<213> ORGANISM: Artificial Sequence
<220> FEATURE:
<223> OTHER INFORMATION: Synthetic Polynucleotide

<400> SEQUENCE: 151
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ctgcgagcac tgcccgcggc gccgagcaga tctgcgtcgg     180
ccagaaccac tccgaggacg gagct                                          205

<210> SEQ ID NO 152
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 152
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ctgcgagcac ttcccgcggg cgccgagcag atctgcgtcg     180
gccagaacca ctccgaggac ggagct                                         206

<210> SEQ ID NO 153
<211> LENGTH: 205
<212> TYPE: DNA
<213> ORGANISM: Artificial Sequence
<220> FEATURE:
<223> OTHER INFORMATION: Synthetic Polynucleotide

<400> SEQUENCE: 153
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
```

```
cagtggcccg agcgcctgcg ctgcgagcac ttcccgcggc gccgagcaga tctgcgtcgg    180
ccagaaccac tcagaggacg gagct                                          205

<210> SEQ ID NO 154
<211> LENGTH: 199
<212> TYPE: DNA
<213> ORGANISM: Artificial Sequence
<220> FEATURE:
<223> OTHER INFORMATION: Synthetic Polynucleotide

<400> SEQUENCE: 154
ttcctgtgct ccatgtacgc acccgtgtgc accgtgctgg aacaggccat cccgccgtgc     60
cgctctatct gtgagcgcgc gcgccagggc tgcgaagccc tcatgaacaa gttcggtttt    120
cagtggcccg agcgcctgcg ctgcgagcac ttcccgcggg cagatctgcg tcggccagaa    180
ccactccgag gacggagct                                                 199

<210> SEQ ID NO 155
<211> LENGTH: 203
<212> TYPE: DNA
<213> ORGANISM: Artificial Sequence
<220> FEATURE:
<223> OTHER INFORMATION: Synthetic Polynucleotide

<400> SEQUENCE: 155
ttcctgtgct ccatgtacgc acccgtgtgc accgtgctgg aacaggccat cccgccgtgc     60
cgctctatct gtgagcgcgc gcgccagggc tgcgaagccc tcatgaacaa gttcggtttt    120
cagtggcccg agcgcctgcg ctgcgagcac ttcacggcgc cgagcagatc tgcgtcggcc    180
agaaccactc cgaggacgga gct                                            203

<210> SEQ ID NO 156
<211> LENGTH: 200
<212> TYPE: DNA
<213> ORGANISM: Artificial Sequence
<220> FEATURE:
<223> OTHER INFORMATION: Synthetic Polynucleotide

<400> SEQUENCE: 156
ttcctgtgct ccatgtacgc acccgtgtgc accgtgctgg aacaggccat cccgccgtgc     60
cgctctatct gtgagcgcgc gcgccagggc tgcgaagccc tcatgaacaa gttcggtttt    120
cagtggcccg agcgcctgcg ctgcgagcac ttcccgcggg ccagatctgc gtcggccaga    180
accactccga ggacggagct                                                200

<210> SEQ ID NO 157
<211> LENGTH: 195
<212> TYPE: DNA
<213> ORGANISM: Artificial Sequence
<220> FEATURE:
<223> OTHER INFORMATION: Synthetic Polynucleotide

<400> SEQUENCE: 157
ttcctgtgct ccatgtacgc acccgtgtgc accgtgctgg aacaggccat cccgccgtgc     60
cgctctatct gtgagcgcgc gcgccagggc tgcgaagccc tcatgaacaa gttcggtttt    120
cagtggcccg agcgcctgcg ctgcgagcac ttcccgcgga tctgcgtcgg ccagaaccac    180
tccgaggacg gagct                                                     195

<210> SEQ ID NO 158
<211> LENGTH: 208
```

<210> SEQ ID NO 158
<211> LENGTH: 208
<212> TYPE: DNA
<213> ORGANISM: Artificial Sequence
<220> FEATURE:
<223> OTHER INFORMATION: Synthetic Polynucleotide

<400> SEQUENCE: 158

```
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ctgcgagcac ttcccgcgac ggcgccgagc agatctgcgt     180
cggccagaac cactccgagg acggagct                                        208
```

<210> SEQ ID NO 159
<211> LENGTH: 205
<212> TYPE: DNA
<213> ORGANISM: Artificial Sequence
<220> FEATURE:
<223> OTHER INFORMATION: Synthetic Polynucleotide

<400> SEQUENCE: 159

```
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ctgcgagcac tgcccacggc gccgagcaga tctgcgtcgg     180
ccagaaccac tccgaggacg gagct                                           205
```

<210> SEQ ID NO 160
<211> LENGTH: 178
<212> TYPE: DNA
<213> ORGANISM: Artificial Sequence
<220> FEATURE:
<223> OTHER INFORMATION: Synthetic Polynucleotide

<400> SEQUENCE: 160

```
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgccgagc agatctgcgt cggccagaac cactccgagg acggagct      178
```

<210> SEQ ID NO 161
<211> LENGTH: 187
<212> TYPE: DNA
<213> ORGANISM: Artificial Sequence
<220> FEATURE:
<223> OTHER INFORMATION: Synthetic Polynucleotide

<400> SEQUENCE: 161

```
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ctgcgagcac ttcccgcgtc ggccagaacc actccgagga     180
cggagct                                                              187
```

<210> SEQ ID NO 162
<211> LENGTH: 151
<212> TYPE: DNA
<213> ORGANISM: Artificial Sequence
<220> FEATURE:
<223> OTHER INFORMATION: Synthetic Polynucleotide

<400> SEQUENCE: 162

```
ttcctgtgct ccatgtacgc acccgtgtgc accgtgctgg aacaggccat cccgccgtgc      60
```
cgctctatct gtgagcgcgc gcgccagggc tgcgaagccc tcatgaacaa gttcgatctg    120
cgtcggccag aaccactccg aggacggagc t                                    151

<210> SEQ ID NO 163
<211> LENGTH: 171
<212> TYPE: DNA
<213> ORGANISM: Artificial Sequence
<220> FEATURE:
<223> OTHER INFORMATION: Synthetic Polynucleotide

<400> SEQUENCE: 163
ttcctgtgct ccatgtacgc acccgtgtgc accgtgctgg aacaggccat cccgccgtgc     60
cgctctatct gtgagcgcgc gcgccagggc tgcgaagccc tcatgaacaa gttcggtttt    120
cagtggcccg agcagatctg cgtcggccag aaccactccg aggacggagc t             171

<210> SEQ ID NO 164
<211> LENGTH: 193
<212> TYPE: DNA
<213> ORGANISM: Artificial Sequence
<220> FEATURE:
<223> OTHER INFORMATION: Synthetic Polynucleotide

<400> SEQUENCE: 164
ttcctgtgct ccatgtacgc acccgtgtgc accgtgctgg aacaggccat cccgccgtgc     60
cgctctatct gtgagcgcgc gcgccagggc tgcgaagccc tcatgaacaa gttcggtttt    120
cagtggcccg agcgcctgcg ctgcgagcgc cgagcagatc tgcgtcggcc agaaccactc    180
cgaggacgga gct                                                       193

<210> SEQ ID NO 165
<211> LENGTH: 205
<212> TYPE: DNA
<213> ORGANISM: Artificial Sequence
<220> FEATURE:
<223> OTHER INFORMATION: Synthetic Polynucleotide

<400> SEQUENCE: 165
ttcctgtgct ccatgtacgc acccgtgtgc accgtgctgg aacaggccat cccgccgtgc     60
cgctctatct gtgagcgcgc gcgccagggc tgcgaagccc tcatgaacaa gttcggtttt    120
cagtggcccg agcgcctgcg ctgcgagcac ttcccacggc gccgagcaga tctgcgtcgg    180
ccagaaccac tcagaggacg gagct                                          205

<210> SEQ ID NO 166
<211> LENGTH: 195
<212> TYPE: DNA
<213> ORGANISM: Artificial Sequence
<220> FEATURE:
<223> OTHER INFORMATION: Synthetic Polynucleotide

<400> SEQUENCE: 166
ttcctgtgct ccatgtacgc acccgtgtgc accgtgctgg aacaggccat cccgccgtgc     60
cgctctatct gtgagcgcgc gcgccagggc tgcgaagccc tcatgaacaa gttcggtttt    120
cagtggcccg agcgcctgcg ctgcgagcac ttcccgcaga tctgcgtcgg ccagaaccac    180
tccgaggacg gagct                                                     195

<210> SEQ ID NO 167
<211> LENGTH: 75
<212> TYPE: DNA
<213> ORGANISM: Artificial Sequence

```
<220> FEATURE:
<223> OTHER INFORMATION: Synthetic Polynucleotide

<400> SEQUENCE: 167
ttcctgtgct ccatgtacgc acccgtgtgc accgagcaga tctgcgtcgg ccagaaccac      60
tccgaggacg gagct                                                       75

<210> SEQ ID NO 168
<211> LENGTH: 190
<212> TYPE: DNA
<213> ORGANISM: Artificial Sequence
<220> FEATURE:
<223> OTHER INFORMATION: Synthetic Polynucleotide

<400> SEQUENCE: 168
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ctgcgagcac ttcgatctgc gtcggccaga accactccga     180
ggacggagct                                                            190

<210> SEQ ID NO 169
<211> LENGTH: 204
<212> TYPE: DNA
<213> ORGANISM: Artificial Sequence
<220> FEATURE:
<223> OTHER INFORMATION: Synthetic Polynucleotide

<400> SEQUENCE: 169
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ctgcgagcac ttccacggcg ccgagcagat ctgcgtcggc     180
cagaaccact cagaggacgg agct                                            204

<210> SEQ ID NO 170
<211> LENGTH: 198
<212> TYPE: DNA
<213> ORGANISM: Artificial Sequence
<220> FEATURE:
<223> OTHER INFORMATION: Synthetic Polynucleotide

<400> SEQUENCE: 170
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ctgcgagcac ttccccgagc agatctgcgt cggccagaac     180
cactccgagg acggagct                                                   198

<210> SEQ ID NO 171
<211> LENGTH: 197
<212> TYPE: DNA
<213> ORGANISM: Artificial Sequence
<220> FEATURE:
<223> OTHER INFORMATION: Synthetic Polynucleotide

<400> SEQUENCE: 171
ttcctgtgct ccatgtacgc acccgtgtgc accgtgctgg aacaggccat cccgccgtgc      60
cgctctatct gtgagcgtgc gcgccagggc tgcgaagccc tcatgaacaa gttcggtttt     120
cagtggcccg agcgcctgcg ctgcgagcac ttcccgagca gatctgcgtc ggccagaacc     180
```
actccgagga cggagct                                                          197

<210> SEQ ID NO 172
<211> LENGTH: 119
<212> TYPE: DNA
<213> ORGANISM: Artificial Sequence
<220> FEATURE:
<223> OTHER INFORMATION: Synthetic Polynucleotide

<400> SEQUENCE: 172
ttcctgtgct ccatgtacgc acccgtgtgc accgtgctgg aacaggccat cccgccgtgc      60
cgctctatct gtgagccgag cagatctgcg tcggccagaa ccactccgag gacggagct      119

<210> SEQ ID NO 173
<211> LENGTH: 179
<212> TYPE: DNA
<213> ORGANISM: Artificial Sequence
<220> FEATURE:
<223> OTHER INFORMATION: Synthetic Polynucleotide

<400> SEQUENCE: 173
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg cagatctgcg tcggccagaa ccactccgag gacggagct     179

<210> SEQ ID NO 174
<211> LENGTH: 187
<212> TYPE: DNA
<213> ORGANISM: Artificial Sequence
<220> FEATURE:
<223> OTHER INFORMATION: Synthetic Polynucleotide

<400> SEQUENCE: 174
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ctgcgacgca gatctgcgtc ggccagaacc actccgagga     180
cggagct                                                              187

<210> SEQ ID NO 175
<211> LENGTH: 185
<212> TYPE: DNA
<213> ORGANISM: Artificial Sequence
<220> FEATURE:
<223> OTHER INFORMATION: Synthetic Polynucleotide

<400> SEQUENCE: 175
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ctcgagcaga tctgcgtcgg ccagaaccac tccgaggacg     180
gagct                                                                185

<210> SEQ ID NO 176
<211> LENGTH: 210
<212> TYPE: DNA
<213> ORGANISM: Artificial Sequence
<220> FEATURE:
<223> OTHER INFORMATION: Synthetic Polynucleotide

<400> SEQUENCE: 176
ttcctgtgct ccatgtacgc acccgtgtgc accgtgctgg aacaggccat cccgccgtgc      60

```
cgctctatct gtgagcgcgc gcgccagggc tgcgaagccc tcatgaacaa gttcggtttt    120
cagtggcccg agcgcctgcg ctgcgagcac ttcccgcgcc acggcgccga gcagatctgc    180
gtcggccaga accactcaga ggacggagct                                     210
```

<210> SEQ ID NO 177
<211> LENGTH: 177
<212> TYPE: DNA
<213> ORGANISM: Artificial Sequence
<220> FEATURE:
<223> OTHER INFORMATION: Synthetic Polynucleotide

<400> SEQUENCE: 177

```
ttcctgtgct ccatgtacgc acccgtgtgc accgtgctgg aacaggccat cccgccgtgc     60
cgctctatct gtgagcgcgc gcgccagggc tgcgaagccc tcatgaacaa gttcggtttt    120
cagtggcacg gcgccgagca gatctgcgtc ggccagaacc actccgagga cggagct      177
```

<210> SEQ ID NO 178
<211> LENGTH: 202
<212> TYPE: DNA
<213> ORGANISM: Artificial Sequence
<220> FEATURE:
<223> OTHER INFORMATION: Synthetic Polynucleotide

<400> SEQUENCE: 178

```
ttcctgtgct ccatgtacgc acccgtgtgc accgtgctgg aacaggccat cccgccgtgc     60
cgctctatct gtgagcgcgc gcgccagggc tgcgaagccc tcatgaacaa gttcggtttt    120
cagtggcccg agcgcctgcg ctgcgagcac ttcccgcgcc gtgcagatct gcgtcggcca    180
gaaccactcc gaggacggag ct                                            202
```

<210> SEQ ID NO 179
<211> LENGTH: 203
<212> TYPE: DNA
<213> ORGANISM: Artificial Sequence
<220> FEATURE:
<223> OTHER INFORMATION: Synthetic Polynucleotide

<400> SEQUENCE: 179

```
ttcctgtgct ccatgtacgc acccgtgtgc accgtgctgg aacaggccat cccgccgtgc     60
cgctctatct gtgagcgcgc gcgccagggc tgcgaagccc tcatgaacaa gttcggtttt    120
cagtggcccg agcgcctgcg ctgcgagcac ttctcggcgc cgagcagatc tgcgtcggcc    180
agaaccactc cgaggacgga gct                                           203
```

<210> SEQ ID NO 180
<211> LENGTH: 153
<212> TYPE: DNA
<213> ORGANISM: Artificial Sequence
<220> FEATURE:
<223> OTHER INFORMATION: Synthetic Polynucleotide

<400> SEQUENCE: 180

```
ttcctgtgct ccatgtacgc acccgtgtgc accgtgctgg aacaggccat cccgccgtgc     60
cgctctatct gtgagcgcgc gcgccagggc tgcgaagccc tcatgaacac cgagcagatc    120
tgcgtcggcc agaaccactc cgaggacgga gct                                153
```

<210> SEQ ID NO 181
<211> LENGTH: 202
<212> TYPE: DNA

<213> ORGANISM: Artificial Sequence
<220> FEATURE:
<223> OTHER INFORMATION: Synthetic Polynucleotide

<400> SEQUENCE: 181
ttcctgtgct ccatgtacgc acccgtgtgc accgtgctgg aacaggccat cccgccgtgc    60
cgctctatct gtgagcgcgc gcgccagggc tgcgaagccc tcatgaacaa gttcggtttt   120
cagtggcccg agcgcctgcg ctgcgagcac ttcccgcggc gagcagatct gcgtcggcca   180
gaaccactcc gaggacggag ct                                            202

<210> SEQ ID NO 182
<211> LENGTH: 203
<212> TYPE: DNA
<213> ORGANISM: Artificial Sequence
<220> FEATURE:
<223> OTHER INFORMATION: Synthetic Polynucleotide

<400> SEQUENCE: 182
ttcctgtgct ccatgtacgc acccgtgtgc accgtgctgg aacaggccat cccgccgtgc    60
cgctctatct gtgagcgcgc gcgccagggc tgcgaagccc tcatgaacaa gttcggtttt   120
cagtggcccg agcgcctgcg ctgcgagcac tccacggcgc gagcagatc tgcgtcggcc    180 agaaccactc cgaggacgga gct                                           203

<210> SEQ ID NO 183
<211> LENGTH: 75
<212> TYPE: DNA
<213> ORGANISM: Artificial Sequence
<220> FEATURE:
<223> OTHER INFORMATION: Synthetic Polynucleotide

<400> SEQUENCE: 183
ttcctgtgct ccatgtacgc acccgtgtgc accgtgcaga tctgcgtcgg ccagaaccac    60
tccgaggacg gagct                                                    75

<210> SEQ ID NO 184
<211> LENGTH: 198
<212> TYPE: DNA
<213> ORGANISM: Artificial Sequence
<220> FEATURE:
<223> OTHER INFORMATION: Synthetic Polynucleotide

<400> SEQUENCE: 184
ttcctgtgct ccatgtacgc acccgtgtgc accgtgctgg aacaggccat cccgccgtgc    60
cgctctatct gtgagcgcgc gcgccagggc tgcgaagccc tcatgaacaa gttcggtttt   120
cagtggcccg agcgcctgcg ctgcgagcac ggcgccgagc agatctgcgt cggccagaac   180
cactccgagg acggagct                                                 198

<210> SEQ ID NO 185
<211> LENGTH: 197
<212> TYPE: DNA
<213> ORGANISM: Artificial Sequence
<220> FEATURE:
<223> OTHER INFORMATION: Synthetic Polynucleotide

<400> SEQUENCE: 185
ttcctgtgct ccatgtacgc acccgtgtgc accgtgctgg aacaggccat cccgccgtgc    60
cgctctatct gtgagcgcgc gcgccagggc tgcgaagccc tcatgaacaa gttcggtttt   120
cagtggcccg agcgcctgcg ctgcgagcac ttcccgcgcg gatctgcgtc ggccagaacc   180

```
actccgagga cggagct                                              197

<210> SEQ ID NO 186
<211> LENGTH: 186
<212> TYPE: DNA
<213> ORGANISM: Artificial Sequence
<220> FEATURE:
<223> OTHER INFORMATION: Synthetic Polynucleotide

<400> SEQUENCE: 186
ttcctgtgct ccatgtacgc acccgtgtgc accgtgctgg aacaggccat cccgccgtgc    60
cgctctatct gtgagcgcgc gcgccagggc tgcgaagccc tcatgaacaa gttcggtttt   120
cagtggcccg agcgcctgcg ctgcgagcac ttcccgatcg gccagaacca ctccgaggac   180
ggagct                                                             186

<210> SEQ ID NO 187
<211> LENGTH: 211
<212> TYPE: DNA
<213> ORGANISM: Artificial Sequence
<220> FEATURE:
<223> OTHER INFORMATION: Synthetic Polynucleotide

<400> SEQUENCE: 187
ttcctgtgct ccatgtacgc acccgtgtgc accgtgctgg aacaggccat cccgccgtgc    60
cgctctatct gtgagcgcgc gcgccagggc tgcgaagccc tcatgaacaa gttcggtttt   120
cagtggcccg agcgcctgcg ctgcgagcac ttcccgccgc cacggcgccg agcagatctg   180
cgtcggccag aaccactccg aggacggagc t                                  211

<210> SEQ ID NO 188
<211> LENGTH: 195
<212> TYPE: DNA
<213> ORGANISM: Artificial Sequence
<220> FEATURE:
<223> OTHER INFORMATION: Synthetic Polynucleotide

<400> SEQUENCE: 188
ttcctgtgct ccatgtacgc acccgtgtgc accgtgctgg aacaggccat cccgccgtgc    60
cgctctatct gtgagcgcgc gcgccagggc tgcgaagccc tcatgaacaa gttcggtttt   120
cagtggcccg agcgcctgcg ctgccacggc gccgagcaga tctgcgtcgg ccagaaccac   180
tccgaggacg gagct                                                   195

<210> SEQ ID NO 189
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 189
ttcctgtgct ccatgtacgc acccgtgtgc accgtgctgg aacaggccat cccgccgtgc    60
cgctctatct gtgagcgcgc gcgccagggc tgcgaagccc tcatgaacaa gttcggtttt   120
cagtggcccg agcgcctgcg ctgcgagcac ttccccacgg cgccgagcag atctgcgtcg   180
gccagaacca ctccgaggac ggagct                                        206

<210> SEQ ID NO 190
<211> LENGTH: 204
<212> TYPE: DNA
```

<213> ORGANISM: Artificial Sequence
<220> FEATURE:
<223> OTHER INFORMATION: Synthetic Polynucleotide

<400> SEQUENCE: 190

```
ttcctgtgct ccatgtacgc acccgtgtgc accgtgctgg aacaggccat cccgccgtgc        60
cgctctatct gtgagcgcgc gcgccagggc tgcgaagccc tcatgaacaa gttcggtttt       120
cagtggcccg agcgcctgcg ctgcgagcac tcccacggcg ccgagcagat ctgcgtcggc       180
cagaaccact ccgaggacgg agct                                              204
```

<210> SEQ ID NO 191
<211> LENGTH: 185
<212> TYPE: DNA
<213> ORGANISM: Artificial Sequence
<220> FEATURE:
<223> OTHER INFORMATION: Synthetic Polynucleotide

<400> SEQUENCE: 191

```
ttcctgtgct ccatgtacgc acccgtgtgc accgtgctgg aacaggccat cccgccgtgc        60
cgctctatct gtgagcgcgc gcgccagggc tgcgaagccc tcatgaacaa gttcggtttt       120
cagtggcccg agcgcctgcg ctgcgagcac ttcccgcggg ccagaaccac tccgaggacg       180
gagct                                                                   185
```

<210> SEQ ID NO 192
<211> LENGTH: 207
<212> TYPE: DNA
<213> ORGANISM: Artificial Sequence
<220> FEATURE:
<223> OTHER INFORMATION: Synthetic Polynucleotide

<400> SEQUENCE: 192

```
ttcctgtgct ccatgtacgc acccgtgtgc accgtgctgg aacaggccat cccgccgtgc        60
cgctctatct gtgagcgcgc gcgccagggc tgcgaagccc tcatgaacaa gttcggtttt       120
cagtggcccg agcgcctgcg ctgcgagcac ttcccgcacg cgccgagca gatctgcgtc        180
ggccagaacc actccgagga cggagct                                           207
```

<210> SEQ ID NO 193
<211> LENGTH: 174
<212> TYPE: DNA
<213> ORGANISM: Artificial Sequence
<220> FEATURE:
<223> OTHER INFORMATION: Synthetic Polynucleotide

<400> SEQUENCE: 193

```
ttcctgtgct ccatgtacgc acccgtgtgc accgtgctgg aacaggccat cccgccgtgc        60
cgctctatct gtgagcgcgc gcgccagggc tgcgaagccc tcatgaacaa gttcggtttt       120
cagtggcccg agcgcctgcg ctgcgtcggc cagaaccact ccgaggacgg agct             174
```

<210> SEQ ID NO 194
<211> LENGTH: 205
<212> TYPE: DNA
<213> ORGANISM: Artificial Sequence
<220> FEATURE:
<223> OTHER INFORMATION: Synthetic Polynucleotide

<400> SEQUENCE: 194

```
ttcctgtgct ccatgtacgc acccgtgtgc accgtgctgg aacaggccat cccgccgtgc        60
cgctctatct gtgagcgcgc gcgccagggc tgcgaagccc tcatgaacaa gttcggtttt       120
```

```
cagtggcccg agcgcctgcg ctgcgagcac tttccacggc gccgagcaga tctgcgtcgg    180
ccagaaccac tccgaggacg gagct                                          205

<210> SEQ ID NO 195
<211> LENGTH: 184
<212> TYPE: DNA
<213> ORGANISM: Artificial Sequence
<220> FEATURE:
<223> OTHER INFORMATION: Synthetic Polynucleotide

<400> SEQUENCE: 195
ttcctgtgct ccatgtacgc acccgtgtgc accgtgctgg aacaggccat cccgccgtgc    60
cgctctatct gtgagcgcgc gcgccagggc tgcgaagccc tcatgaacaa gttcggtttt   120
cagtggcccg agcgcctgcg ctgcgagcac ttcccgcggc cagaaccact ccgaggacgg   180
agct                                                                184

<210> SEQ ID NO 196
<211> LENGTH: 156
<212> TYPE: DNA
<213> ORGANISM: Artificial Sequence
<220> FEATURE:
<223> OTHER INFORMATION: Synthetic Polynucleotide

<400> SEQUENCE: 196
ttcctgtgct ccatgtacgc acccgtgtgc accgtgctgg aacaggccat cccgccgtgc    60
cgctctatct gtgagcgcgc gcgccagggc tgcgaagccc tcatgaacaa gttcgagcag   120
atctgcgtcg gccagaacca ctccgaggac ggagct                             156

<210> SEQ ID NO 197
<211> LENGTH: 202
<212> TYPE: DNA
<213> ORGANISM: Artificial Sequence
<220> FEATURE:
<223> OTHER INFORMATION: Synthetic Polynucleotide

<400> SEQUENCE: 197
ttcctgtgct ccatgtacgc acccgtgtgc accgtgctgg aacaggccat cccgccgtgc    60
cgctctatct gtgagcgcgc gcgccagggc tgcgaagccc tcatgaacaa gttcggtttt   120
cagtggcccg agcgcctgcg ctgcgagcac ttcccgcggg aagcagatct gcgtcggcca   180
gaaccactcc gaggacggag ct                                            202

<210> SEQ ID NO 198
<211> LENGTH: 181
<212> TYPE: DNA
<213> ORGANISM: Artificial Sequence
<220> FEATURE:
<223> OTHER INFORMATION: Synthetic Polynucleotide

<400> SEQUENCE: 198
ttcctgtgct ccatgtacgc acccgtgtgc accgtgctgg aacaggccat cccgccgtgc    60
cgctctatct gtgagcgcgc gcgccagggc tgcgaagccc tcatgaacaa gttcggtttt   120
cagtggcccg agcgcctgcg ctgcgagcac ttccctcatg aaccactccg aggacggagc   180
t                                                                   181

<210> SEQ ID NO 199
<211> LENGTH: 209
<212> TYPE: DNA
```

<213> ORGANISM: Artificial Sequence
<220> FEATURE:
<223> OTHER INFORMATION: Synthetic Polynucleotide

<400> SEQUENCE: 199

```
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ctgcgagcac ttcccgccca ggcgccgag  cagatctgcg     180 tcggccagaa ccactccgag gacggagct                                       209
```

<210> SEQ ID NO 200
<211> LENGTH: 201
<212> TYPE: DNA
<213> ORGANISM: Artificial Sequence
<220> FEATURE:
<223> OTHER INFORMATION: Synthetic Polynucleotide

<400> SEQUENCE: 200

```
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ctgcgagcac ttcccgcgcc ggaagatctg cgtcggccag     180
aaccactccg aggacggagc t                                               201
```

<210> SEQ ID NO 201
<211> LENGTH: 220
<212> TYPE: DNA
<213> ORGANISM: Artificial Sequence
<220> FEATURE:
<223> OTHER INFORMATION: Synthetic Polynucleotide

<400> SEQUENCE: 201

```
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ctgcgagcac ttcccgcgcc gagcacttcc acggcgccga     180
gcagatctgc gtcggccaga accactccga ggacggagct                           220
```

<210> SEQ ID NO 202
<211> LENGTH: 197
<212> TYPE: DNA
<213> ORGANISM: Artificial Sequence
<220> FEATURE:
<223> OTHER INFORMATION: Synthetic Polynucleotide

<400> SEQUENCE: 202

```
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ctgcgagcac ttcccgcgca gatctgcgtc ggccagaacc     180
actccgagga cggagct                                                    197
```

<210> SEQ ID NO 203
<211> LENGTH: 205
<212> TYPE: DNA
<213> ORGANISM: Artificial Sequence
<220> FEATURE:
<223> OTHER INFORMATION: Synthetic Polynucleotide

<400> SEQUENCE: 203

```
ttcctgtgct ccatgtacgc acccgtgtgc accgtgctgg aacaggccat cccgccgtgc      60
```

```
cgctctatct gtgagcgcgc gcgccagggc tgcgaagccc tcatgaacaa gttcggtttt      120
cagtggcccg agcgcctgcg ctgcgagcac ttcccgcgcg tccgagcaga tctgcgtcgg      180
ccagaaccac tccgaggacg gagct                                            205
```

<210> SEQ ID NO 204
<211> LENGTH: 204
<212> TYPE: DNA
<213> ORGANISM: Artificial Sequence
<220> FEATURE:
<223> OTHER INFORMATION: Synthetic Polynucleotide

<400> SEQUENCE: 204

```
ttcctgtgct ccatgtacgc acccgtgtgc accgtgctgg aacaggccat cccgccgtgc       60
cgctctatct gtgagcgcgc gcgccagggc tgcgaagccc tcatgaacaa gttcggtttt      120
cagtggcccg agcgcctgcg ctgcgagcac ttcccgcgag ccgagcagat ctgcgtcggc      180
cagaaccact ccgaggacgg agct                                             204
```

<210> SEQ ID NO 205
<211> LENGTH: 178
<212> TYPE: DNA
<213> ORGANISM: Artificial Sequence
<220> FEATURE:
<223> OTHER INFORMATION: Synthetic Polynucleotide

<400> SEQUENCE: 205

```
ttcctgtgct ccatgtacgc acccgtgtgc accgtgctgg aacaggccat cccgccgtgc       60
cgctctatct gtgagcgcgc gcgccagggc tgcgaagccc tcatgaacaa gttcggtttt      120
cagtggccac ggcgccgagc agatctgcgt cggccagaac cactccgagg acggagct        178
```

<210> SEQ ID NO 206
<211> LENGTH: 200
<212> TYPE: DNA
<213> ORGANISM: Artificial Sequence
<220> FEATURE:
<223> OTHER INFORMATION: Synthetic Polynucleotide

<400> SEQUENCE: 206

```
ttcctgtgct ccatgtacgc acccgtgtgc accgtgctgg aacaggccat cccgccgtgc       60
cgctctatct gtgagcgcgc gcgccagggc tgcgaagccc tcatgaacaa gttcggtttt      120
cagtggcccg agcgcctgcg ctgcgagcac ttcccgccga gcagatctgc gtcggccaga     180
accactcaga ggacggagct                                                  200
```

<210> SEQ ID NO 207
<211> LENGTH: 195
<212> TYPE: DNA
<213> ORGANISM: Artificial Sequence
<220> FEATURE:
<223> OTHER INFORMATION: Synthetic Polynucleotide

<400> SEQUENCE: 207

```
ttcctgtgct ccatgtacgc acccgtgtgc accgtgctgg aacaggccat cccgccgtgc       60
cgctctatct gtgagcgcgc gcgccagggc tgcgaagccc tcatgaacaa gttcggtttt      120
cagtggcccg agcgcctgcg ctgcgagcac ttcgagcaga tctgcgtcgg ccagaaccac     180
tccgaggacg gagct                                                       195
```

<210> SEQ ID NO 208

-continued

```
<211> LENGTH: 98
<212> TYPE: DNA
<213> ORGANISM: Artificial Sequence
<220> FEATURE:
<223> OTHER INFORMATION: Synthetic Polynucleotide

<400> SEQUENCE: 208
ttcctgtgct ccatgtacgc acccgtgtgc accgtgctgg aacaggccat cccgccgagc      60
agatctgcgt cggccagaac cactccgagg acggagct                             98

<210> SEQ ID NO 209
<211> LENGTH: 200
<212> TYPE: DNA
<213> ORGANISM: Artificial Sequence
<220> FEATURE:
<223> OTHER INFORMATION: Synthetic Polynucleotide

<400> SEQUENCE: 209
ttcctgtgct ccatgtacgc acccgtgtgc accgtgctgg aacaggccat cccgccgtgc      60
cgctctatct gtgagcgcgc gccagggctg cgaagccctc atgaacaagt tcggttttca    120
gtggcccgag cgcctgcgct gcgagcactt cccgcgccga gcagatctgc gtcggccaga    180
accactccga ggacggagct                                                200

<210> SEQ ID NO 210
<211> LENGTH: 201
<212> TYPE: DNA
<213> ORGANISM: Artificial Sequence
<220> FEATURE:
<223> OTHER INFORMATION: Synthetic Polynucleotide

<400> SEQUENCE: 210
ttcctgtgct ccatgtacgc acccgtgtgc accgtgctgg aacaggccat cccgccgtgc      60
cgctctatct gtgagcgcgc gcgccaggct gcgaagccct catgaacaag ttcggttttc    120
agtggcccga gcgcctgcgc tgcgagcact cccgcgccg agcagatctg cgtcggccag    180
aaccactccg aggacggagc t                                             201

<210> SEQ ID NO 211
<211> LENGTH: 212
<212> TYPE: DNA
<213> ORGANISM: Artificial Sequence
<220> FEATURE:
<223> OTHER INFORMATION: Synthetic Polynucleotide

<400> SEQUENCE: 211
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt    120
cagtggcccg agcgcctgcg ctgcgagcac ttcccgcgcg ccacggcgcc gagcagatct    180
gcgtcggcca gaaccactcc gaggacggag ct                                 212

<210> SEQ ID NO 212
<211> LENGTH: 207
<212> TYPE: DNA
<213> ORGANISM: Artificial Sequence
<220> FEATURE:
<223> OTHER INFORMATION: Synthetic Polynucleotide

<400> SEQUENCE: 212
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt    120
```
cagtggcccg agcgcctgcg ctgcgagcac ttcccgctcg cgccgtgca gatctgcgtc        180 ggccagaacc actccgagga cggagct                                           207

<210> SEQ ID NO 213
<211> LENGTH: 215
<212> TYPE: DNA
<213> ORGANISM: Artificial Sequence
<220> FEATURE:
<223> OTHER INFORMATION: Synthetic Polynucleotide

<400> SEQUENCE: 213
ttcctgtgct ccatgtacgc acccgtgtgc accgtgctgg aacaggccat cccgccgtgc        60
cgctctatct gtgagcgcgc gcgccagggc tgcgaagccc tcatgaacaa gttcggtttt       120
cagtggcccg agcgcctgcg ctgcgagcac ttcccgggca gatccacggc gccgagcaga       180
tctgcgtcgg ccagaaccac tccgaggacg gagct                                  215

<210> SEQ ID NO 214
<211> LENGTH: 189
<212> TYPE: DNA
<213> ORGANISM: Artificial Sequence
<220> FEATURE:
<223> OTHER INFORMATION: Synthetic Polynucleotide

<400> SEQUENCE: 214
ttcctgtgct ccatgtacgc acccgtgtgc accgtgctgg aacaggccat cccgccgtgc        60
cgctctatct gtgagcgcgc gcgccagggc tgcgaagccc tcatgaacaa gttcggtttt       120
cagtggcccg agcgcctgcg ctgcgccgag cagatctgcg tcggccagaa ccactccgag       180
gacggagct                                                               189

<210> SEQ ID NO 215
<211> LENGTH: 197
<212> TYPE: DNA
<213> ORGANISM: Artificial Sequence
<220> FEATURE:
<223> OTHER INFORMATION: Synthetic Polynucleotide

<400> SEQUENCE: 215
ttcctgtgct ccatgtacgc acccgtgtgc accgtgctgg aacaggccat cccgccgtgc        60
cgctctatct gtgagcgcgc gcgccagggc tgcgaagccc tcatgaacaa gttcggtttt       120
cagtggcccg agcgcctgcg ctgcgagcac ttcccgagca gatctgcgtc ggccagaacc       180
actcagagga cggagct                                                      197

<210> SEQ ID NO 216
<211> LENGTH: 202
<212> TYPE: DNA
<213> ORGANISM: Artificial Sequence
<220> FEATURE:
<223> OTHER INFORMATION: Synthetic Polynucleotide

<400> SEQUENCE: 216
ttcctgtgct ccatgtacgc acccgtgtgc accgtgctgg aacaggccat cccgccgtgc        60
cgctctatct gtgagcgcgc gcgccagggc tgcgaagccc tcatgaacaa gttcggtttt       120
cagtggcccg agcgcctgcg ctgcgagcac ttcccgcgcc gagcagatct gcgtcggccg       180
gaaccactcc gaggacggag ct                                                202

<210> SEQ ID NO 217

```
<211> LENGTH: 186
<212> TYPE: DNA
<213> ORGANISM: Artificial Sequence
<220> FEATURE:
<223> OTHER INFORMATION: Synthetic Polynucleotide

<400> SEQUENCE: 217
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ctgcgagcac ttctgcgtcg gccagaacca ctccgaggac     180
ggagct                                                                186

<210> SEQ ID NO 218
<211> LENGTH: 218
<212> TYPE: DNA
<213> ORGANISM: Artificial Sequence
<220> FEATURE:
<223> OTHER INFORMATION: Synthetic Polynucleotide

<400> SEQUENCE: 218
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ctgcaagcac ttcccgcgcc agatctgctc ggcgccgtgg     180
agatctgcgt cggccagaac cactccgagg acggagct                             218

<210> SEQ ID NO 219
<211> LENGTH: 204
<212> TYPE: DNA
<213> ORGANISM: Artificial Sequence
<220> FEATURE:
<223> OTHER INFORMATION: Synthetic Polynucleotide

<400> SEQUENCE: 219
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ctgcgagcac gtccacggcg ccgagcagat ctgcgtcggc     180
cagaaccact ccgaggacgg agct                                            204

<210> SEQ ID NO 220
<211> LENGTH: 199
<212> TYPE: DNA
<213> ORGANISM: Artificial Sequence
<220> FEATURE:
<223> OTHER INFORMATION: Synthetic Polynucleotide

<400> SEQUENCE: 220
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ctgcgagcac ttcccgcgag cagatctgcg tcggccagaa     180
ccactcagag gacggagct                                                  199

<210> SEQ ID NO 221
<211> LENGTH: 186
<212> TYPE: DNA
<213> ORGANISM: Artificial Sequence
<220> FEATURE:
<223> OTHER INFORMATION: Synthetic Polynucleotide

<400> SEQUENCE: 221
```

```
ttcctgtgct ccatgtacgc acccgtgtgc accgtgctgg aacaggccat cccgccgtgc    60
cgctctatct gtgagcgcgc gcgccagggc tgcgaagccc tcatgaacaa gttcggtttt   120
cagtggcccg agcgcctgcg ctgcgagcag atctgcgtcg gccagaacca ctcagaggac   180
ggagct                                                              186
```

<210> SEQ ID NO 222
<211> LENGTH: 199
<212> TYPE: DNA
<213> ORGANISM: Artificial Sequence
<220> FEATURE:
<223> OTHER INFORMATION: Synthetic Polynucleotide

<400> SEQUENCE: 222

```
ttcctgtgct ccatgtacgc acccgtgtgc accgtgctgg aacaggccat cccgccgtgc    60
cgctctatct gtgagcgcgc gcgccagggc tgcgaagccc tcatgaacaa gttcggtttt   120
cagtggcccg agcgcctgcg ctgcgagcca cggcgccgag cagatctgcg tcggccagaa   180
ccactccgag gacggagct                                                199
```

<210> SEQ ID NO 223
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 223

```
ttcctgtgct ccatgtacgc cgagcagatc tgcgtcggcc agaaccactc cgaggacgga    60
gct                                                                  63
```

<210> SEQ ID NO 224
<211> LENGTH: 202
<212> TYPE: DNA
<213> ORGANISM: Artificial Sequence
<220> FEATURE:
<223> OTHER INFORMATION: Synthetic Polynucleotide

<400> SEQUENCE: 224

```
ttcctgtgct ccatgtacgc acccgtgtgc accgtgctgg aacaggccat cccgccgtgc    60
cgctctatct gtgagcgcgc gcgccagggc tgcggagccc tcatgaacaa gttcggtttt   120
cagtggcccg agcgcctgcg ctgcgagcac ttcccgcgcc gagcagatct gcgtcggcca   180
gaaccactcc gaggacggag ct                                            202
```

<210> SEQ ID NO 225
<211> LENGTH: 204
<212> TYPE: DNA
<213> ORGANISM: Artificial Sequence
<220> FEATURE:
<223> OTHER INFORMATION: Synthetic Polynucleotide

<400> SEQUENCE: 225

```
ttcctgtgct ccatgtacgc acccgtgtgc accgtgctgg aacaggccat cccgccgtgc    60
cgctctatct gtgagagcgc gcgccagggc tgcgaagccc tcatgaacaa gttcggtttt   120
cagtggcccg agcgcctgcg ctgcgagcac ttccacggcg ccgagcagat ctgcgtcggc   180
cagagccact ccgaggacgg agct                                          204
```

<210> SEQ ID NO 226

```
<211> LENGTH: 205
<212> TYPE: DNA
<213> ORGANISM: Artificial Sequence
<220> FEATURE:
<223> OTHER INFORMATION: Synthetic Polynucleotide

<400> SEQUENCE: 226
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ctgcgagcgc ttcccacggc gccgagcaga tctgcgtcgg     180
ccagaaccac tccgaggacg gagct                                           205

<210> SEQ ID NO 227
<211> LENGTH: 184
<212> TYPE: DNA
<213> ORGANISM: Artificial Sequence
<220> FEATURE:
<223> OTHER INFORMATION: Synthetic Polynucleotide

<400> SEQUENCE: 227
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
cagtggcccg agcgcctgcg ccgagcagat ctgcgtcggc cagaaccact ccgaggacgg     180
agct                                                                  184

<210> SEQ ID NO 228
<211> LENGTH: 114
<212> TYPE: DNA
<213> ORGANISM: Artificial Sequence
<220> FEATURE:
<223> OTHER INFORMATION: Synthetic Polynucleotide

<400> SEQUENCE: 228
ttcctgtgct ccatgtacgc acccgtgtgc accgtgctgg aacaggccat cccgccgtgc      60
cgctctatct gtgagcagat ctgcgtcggc cagaaccact ccgaggacgg agct           114

<210> SEQ ID NO 229
<211> LENGTH: 185
<212> TYPE: DNA
<213> ORGANISM: Artificial Sequence
<220> FEATURE:
<223> OTHER INFORMATION: Synthetic Polynucleotide

<400> SEQUENCE: 229
ttcctgtgct ccatgtacgc acccgtgtgc accgtgctgg aacaggccat cccgccgtgc      60
cgctctatct gtgagcgcgc gcgccagggc tgcgaaccct catgaacaag ttcggttttc     120
agtggcccga gcgcctgcgc tgcgagcact tctgcgtcgg ccagaaccac tccgaggacg     180
gagct                                                                 185

<210> SEQ ID NO 230
<211> LENGTH: 205
<212> TYPE: DNA
<213> ORGANISM: Artificial Sequence
<220> FEATURE:
<223> OTHER INFORMATION: Synthetic Polynucleotide

<400> SEQUENCE: 230
ttcctgtgct ccatgtacgc acccgtgtgc accgtgctgg aacaggccat cccgccgtgc      60
cgctctatct gtgagcgcgc gcgccagggc tgcgaagccc tcatgaacaa gttcggtttt     120
```

```
cagtggcccg agcgcctgcg ctgcgagcac ttcccgcggc gccgagcaga tctgcgtcgg    180
tcagaaccac tccgaggacg gagct                                          205
```

<210> SEQ ID NO 231
<211> LENGTH: 204
<212> TYPE: DNA
<213> ORGANISM: Artificial Sequence
<220> FEATURE:
<223> OTHER INFORMATION: Synthetic Polynucleotide

<400> SEQUENCE: 231

```
ttcctgtgct ccatgtacgc acccgtgtgc accgtgctgg aacaggccat cccgccgtgc    60
cgctctatct gtgagcgcgc gcgccagggc tgcgaagccc tcatgaacaa gttcggtttt   120
cagtggcccg agcgcctgcg ctgcgagcac ttccacggcg ccgagcagat ctgcgtcggc   180
cagagccact ccgaggacgg agct                                          204
```

<210> SEQ ID NO 232
<211> LENGTH: 249
<212> TYPE: DNA
<213> ORGANISM: Artificial Sequence
<220> FEATURE:
<223> OTHER INFORMATION: Synthetic Polynucleotide

<400> SEQUENCE: 232

```
aattttcatt gtaacaacat acctttaatg aaacattttt tccaaatgtc acatctcctg    60
aaactgtgag gtgatccaat tcaagcatat ctggtatact ttcaaatctt cttagataat   120
cttgaacctt acagaaaagg agaaacataa aaatttgtct caaatgggtt caaagaaaga   180
caggaaaaat attaacaaga agtttaact gaactgtaga acctttttt ggcaaagctc    240 aggtcctct                                                           249
```

<210> SEQ ID NO 233
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 233

```
aattttcatt gtaacaacat acctttaatg aaacattttt tccaaatgtc acatctcctg    60
aaactgtgag gtgatccaat tcaagcattc tggtatactt tcaaatcttc ttagataatc   120
ttgaacctta cagaaaagga gaaacataaa aatttgtctc aaatgggttc aaagaaagac   180
aggaaaaata ttaacaagaa gtttaactg aactgtagaa ccttttttg gcaaagctca    240 ggtcctct                                                            248
```

<210> SEQ ID NO 234
<211> LENGTH: 258
<212> TYPE: DNA
<213> ORGANISM: Artificial Sequence
<220> FEATURE:
<223> OTHER INFORMATION: Synthetic Polynucleotide

<400> SEQUENCE: 234

```
aattttcatt gtaacaacat acctttaatg aaacattttt tccaaatgtc acatctcctg    60
aaactgtgag gtgatccaat tcaagcatat acttgaattc tggtatactt tcaaatcttc   120
ttagataatc ttgaacctta cagaaaagga gaaacataaa aatttgtctc aaatgggttc   180
```

-continued

| | |
|---|---|
| aaagaaagac aggaaaaata ttaacaagaa agtttaactg aactgtagaa accttttttg | 240 |
| gcaaagctca ggtcctct | 258 |

<210> SEQ ID NO 235
<211> LENGTH: 249
<212> TYPE: DNA
<213> ORGANISM: Artificial Sequence
<220> FEATURE:
<223> OTHER INFORMATION: Synthetic Polynucleotide

<400> SEQUENCE: 235

| | |
|---|---|
| aattttcatt gtaacaacat acctttaatg aaacattttt tccaaatgtc acatctcctg | 60 |
| aaactgtgag gtgatccaat tcaagcatat ctggtatact ttcaaatctt cttagataat | 120 |
| cttgaacctt acagaaaagg agaaacataa aaatttgtct caaatgggtt caaagaaaga | 180 |
| caggaaaaat attaacaaga aagtttaact gaactgtaga aaccttttttt ggcaaagctc | 240 |
| aggtcctct | 249 |

<210> SEQ ID NO 236
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 236

| | |
|---|---|
| aattttcatt gtaacaacat acctttaatg aaacattttt tccaaatgtc acatctcctg | 60 |
| aaactgtgag gtgatccaat tcaagcattc tggtatactt tcaaatcttc ttagataatc | 120 |
| ttgaacctta cagaaaggga gaaacataaa aatttgtctc aaatgggttc aaagaaagac | 180 |
| aggaaaaata ttaacaagaa agtttaactg aactgtagaa accttttttg gcaaagctca | 240 |
| ggtcctct | 248 |

<210> SEQ ID NO 237
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 237

| | |
|---|---|
| aattttcatt gtaacaacat acctttaatg aaacattttt tccaaatgtc acatctcctg | 60 |
| aaactgtgag gtgatccaat tcaagcattc tggtatactt tcaaatcttc ttagataatc | 120 |
| ttgaacctta cagaaaagga gaaacataaa aatttgtctc aaatgggttc aaagaaggac | 180 |
| aggaaaaata ttaacaagaa agtttaactg aactgtagaa accttttttg gcaaagctca | 240 |
| ggtcctct | 248 |

<210> SEQ ID NO 238
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 238

| | |
|---|---|
| aattttcatt gtaacaacat acctttaatg aaacattttt tccaaatgtc acatctcctg | 60 |
| aaactgtgag gtgatccaat tcaagcattc tggtatactt tcaaatcttc ttagataatc | 120 |
| ttgaacctta cagaaaagga gaaacataaa aatttgtctc aaatgggttc aaagaaagac | 180 |

```
aggaaaaata ttaacaagaa agtttaactg aactgtagaa gccttttttg gcaaagctca    240
ggtcctct                                                             248
```

<210> SEQ ID NO 239
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 239

```
aattttcatt gtaacaacat acctttaatg aaacattttt tccaaatgtc acatctcctg    60
aaactgtgag gtgatccaat tcaagcattc tggtatactt tcaaatcttc ttagataatc    120 ttgaaccttna cagaaaagga gaaacataaa aatttgtctc aaatgggttc aaggaaagac   180
aggaaaaata ttaacaagaa agtttaactg aactgtagaa accttttttg gcaaagctca    240
ggtcctct                                                             248
```

<210> SEQ ID NO 240
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 240

```
aattttcatt gtaacaacat acctttaatg aaacattttt tccaaatgtc acatctcctg    60
aaactgtgag gtgatccaat tcaagcattc tggtatactt tcaaatcttc ttagataatc    120 ttgaaccttna cagaaaagga gaaacataaa aatttgtctc aaatgggttc aaagaaagac   180
aggaaaaata ttaacaagaa agtttaactg agctgtagaa accttttttg gcaaagctca    240
ggtcctct                                                             248
```

<210> SEQ ID NO 241
<211> LENGTH: 244
<212> TYPE: DNA
<213> ORGANISM: Artificial Sequence
<220> FEATURE:
<223> OTHER INFORMATION: Synthetic Polynucleotide

<400> SEQUENCE: 241

```
aattttcatt gtaacaacat acctttaatg aaacattttt tccaaatgtc acatctcctg    60
aaactgtgag gtgatccaat tcaatctggt atactttcaa atcttcttag ataatcttga    120
accttacaga aaggagaaa cataaaaatt tgtctcaaat gggttcaaag aaagacagga    180 aaatattaa caagaaagtt taactgaact gtagaaacct ttttggcaa agctcaggtc     240 ctct                                                                 244
```

<210> SEQ ID NO 242
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 242

```
aattttcatt gtaacaacat acctttaatg aaacattttt tccaaatgtc acatctcctg    60
aaactgtgag gtgatccaat tcaagcattc tggtatactt tcaaatcttc ttagataatc    120
```

```
ttgagcctta cagaaaagga gaaacataaa aatttgtctc aaatgggttc aaagaaagac        180
aggaaaaata ttaacaagaa agtttaactg aactgtagaa accttttttg gcaaagctca       240
ggtcctct                                                                248
```

<210> SEQ ID NO 243
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 243

```
aattttcatt gtaacaacat acctttaatg aaacattttt tccaaatgtc acatctcctg        60
aaactgtgag gtgatccaat tcaagcattc tggtatactt tcaaatcttc ttagataatc       120
ttgaacctta cagaaaagga gaaacataaa aatttgtctc aaatgggttc aaagaaaggc       180
aggaaaaata ttaacaagaa agtttaactg aactgtagaa accttttttg gcaaagctca       240
ggtcctct                                                                248
```

<210> SEQ ID NO 244
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 244

```
aattttcatt gtaacaacat acctttaatg aaacattttt tccaaatgcc acatctcctg        60
aaactgtgag gtgatccaat tcaagcattc tggtatactt tcaaatcttc ttagataatc       120
ttgaacctta cagaaaagga gaaacataaa aatttgtctc aaatgggttc aaagaaagac       180
aggaaaaata ttaacaagaa agtttaactg aactgtagaa accttttttg gcaaagctca       240
ggtcctct                                                                248
```

<210> SEQ ID NO 245
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 245

```
aattttcatt gtaacaacat acctttaatg aaacattttt tccaaatgtc acatctcctg        60
aaactgtgag gtgatccaat tcaagcattc tggtatactt tcaaatcttc ttagataatc       120
ttgaacctta cagaaaagga gaaacataaa aatttgtctc aaatgggttc aaagaaagac       180
gggaaaaata ttaacaagaa agtttaactg aactgtagaa accttttttg gcaaagctca       240
ggtcctct                                                                248
```

<210> SEQ ID NO 246
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 246

```
aattttcatt gtaacaacat acctttaatg aaacattttt tccaaatgtc acatctcctg        60
aaactgtgag gtgatccaat tcaagcattc tggtatactt tcaaatcttc ttagataatc       120
```
ttgaacctta cagaaaagga gaaacataaa aatttgcctc aaatgggttc aaagaaagac    180
aggaaaaata ttaacaagaa agtttaactg aactgtagaa accttttttg gcaaagctca    240
ggtcctct                                                            248

<210> SEQ ID NO 247
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 247
aattttcatt gtaacaacat acctttaatg aaacattttt tccaaatgtc acatctcctg     60
aaactgtgag gtgatccaat tcaagcattc tggtatactt tcaaatcttc ttagataatc    120
ttgaacctta cagaaaagga gaagcataaa aatttgtctc aaatgggttc aaagaaagac    180
aggaaaaata ttaacaagaa agtttaactg aactgtagaa accttttttg gcaaagctca    240
ggtcctct                                                            248

<210> SEQ ID NO 248
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 248
aattttcatt gtaacaacat acctttaatg aaacattttt tccaaatgtc acatctcctg     60
aaactgtgag gtgatccaat tcaagcattc tggtatactt tcaaatcttc ttagataatc    120
ttgaacctta cagaaaagga gaaacataaa aatttgtctc aaatgggttc aaagaaagac    180
aggaaaaata ttaacaagaa ggtttaactg aactgtagaa accttttttg gcaaagctca    240
ggtcctct                                                            248

<210> SEQ ID NO 249
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 249
aattttcatt gtaacaacat acctttaatg aaacattttt tccaaatgtc acatctcctg     60
aaactgtgag gtgatccaat tcaagcattc tggtatactt tcaaatcttc ttagataatc    120
ttgaacctta cagaaaagga gaaacataaa aatttgtctc aaatgggctc aaagaaagac    180
aggaaaaata ttaacaagaa agtttaactg aactgtagaa accttttttg gcaaagctca    240
ggtcctct                                                            248

<210> SEQ ID NO 250
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 250
aattttcatt gtaacaacat acctttaatg aaacattttt tccaaatgtc acatctcctg     60

```
aaactgtgag gtgatccaat tcaagcattc tggtatactt tcaaatcttc ttagataatc      120
ttgaacctta cagagaagga gaaacataaa aatttgtctc aaatgggttc aaagaaagac      180
aggaaaaata ttaacaagaa agtttaactg aactgtagaa acctttttg gcaaagctca       240 ggtcctct                                                                248
```

<210> SEQ ID NO 251
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 251

```
aattttcatt gtaacaacat acctttaatg aaacattttt tccaaatgtc acatctcctg       60
aaactgtgag gtgatccaat tcaagcattc tggtatactt tcaaatcttc ttagataatc      120
ttgaacctta cggaaaagga gaaacataaa aatttgtctc aaatgggttc aaagaaagac      180
aggaaaaata ttaacaagaa agtttaactg aactgtagaa acctttttg gcaaagctca       240 ggtcctct                                                                248
```

<210> SEQ ID NO 252
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 252

```
aattttcatt gtaacaacat acctttaatg aaacattttt tccaaatgtc acatctcctg       60
aaactgtgag gtgatccaat tcaagcattc tggtatactt tcaaatcttc ttagataatc      120
ttgaacctta cagaaaagga gaaacataaa aatttgtctc aaatgggttc aaagaaagac      180
aggaaaaata ttaacaagaa agtttaactg aactgtagag acctttttg gcaaagctca       240 ggtcctct                                                                248
```

<210> SEQ ID NO 253
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 253

```
aattttcatt gtaacaacat acctttaatg aaacattttt tccaaatgtc acatctcctg       60
aaactgtgag gtgatccaat tcaagcattc tggtatactt tcaaatcttc ttagataatc      120
ttgaacctta cagaaaagga ggaacataaa aatttgtctc aaatgggttc aaagaaagac      180
aggaaaaata ttaacaagaa agtttaactg aactgtagaa acctttttg gcaaagctca       240 ggtcctct                                                                248
```

<210> SEQ ID NO 254
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 254

```
aattttcatt gtaacaacat acctttaatg aaacattttt tccaaatgtc acatctcctg       60
```
aaactgtgag gtgatccaat tcaagcattc tggtatactt tcaaatcttc ttagataatc    120
ttgaacctta cagaaaagga gaaacataaa aatttgtctc aaatgggtcc aaagaaagac    180
aggaaaaata ttaacaagaa agtttaactg aactgtagaa accttttttg gcaaagctca    240
ggtcctct                                                             248

<210> SEQ ID NO 255
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 255
aattttcatt gtaacaacat acctttaatg aaacattttt tccaaatgtc acatctcctg     60
aaactgtgag gtgatccaat tcaagcattc tggtatactt tcaaatcttc ttagataatc    120
ttgaacctta cagaaaagga gaaacataaa aatttgtctc aaatgggttc aaagagagac    180
aggaaaaata ttaacaagaa agtttaactg aactgtagaa accttttttg gcaaagctca    240
ggtcctct                                                             248

<210> SEQ ID NO 256
<211> LENGTH: 258
<212> TYPE: DNA
<213> ORGANISM: Artificial Sequence
<220> FEATURE:
<223> OTHER INFORMATION: Synthetic Polynucleotide

<400> SEQUENCE: 256
aattttcatt gtaacaacat acctttaatg aaacattttt tccaaatgtc acatctcctg     60
aaactgtgag gtgatccaat tcaagcatat acttgaattc tggtatactt tcaaatcttc    120
ttagataatc ttgaacctta cagaaaggga gaaacataaa aatttgtctc aaatgggttc    180
aaagaaagac aggaaaaata ttaacaagaa agtttaactg aactgtagaa accttttttg    240
gcaaagctca ggtcctct                                                  258

<210> SEQ ID NO 257
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 257
aattttcatt gtaacaacat acctttaatg aaacattttt tccaaatgtc acatctcctg     60
aaactgtgag gtgatccaat tcaagcattc tggtatacct tcaaatcttc ttagataatc    120
ttgaacctta cagaaaagga gaaacataaa aatttgtctc aaatgggttc aaagaaagac    180
aggaaaaata ttaacaagaa agtttaactg aactgtagaa accttttttg gcaaagctca    240
ggtcctct                                                             248

<210> SEQ ID NO 258
<211> LENGTH: 247
<212> TYPE: DNA
<213> ORGANISM: Artificial Sequence
<220> FEATURE:
<223> OTHER INFORMATION: Synthetic Polynucleotide

<400> SEQUENCE: 258

```
aattttcatt gtaacaacat acctttaatg aaacattttt tccaaatgtc acatctcctg    60
aaactgtgag gtgatccaat tcaagcattc tggtatactt tcaaatcttc ttagataatc   120
ttgaacctta cagaaaagga gaaacataaa aatttgtctc aaatgggttc aaagaaagac   180
aggaaaaata ttaacaagaa agtttaactg aactgtagaa acctttttgg caaagctcag   240
gtcctct                                                             247

<210> SEQ ID NO 259
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 259
aattttcatt gtaacaacat acctttaatg aaacattttt tccaaatgtc acatctcctg    60
aaactgtgag gtgatccaat tcaagcattc tggtatactt tcaaatcttc ttagataatc   120
ttgaacctta cagaaaagga gaaacataaa aatttgtctc aaatgggttc aaagaaagac   180
aggaaaaata ttaacaagaa agtttaactg aactgtagaa acccttttg gcaaagctca   240 ggtcctct                                                            248

<210> SEQ ID NO 260
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 260
aattttcatt gtaacaacat acctttaatg aaacattttt tccaaatgtc gcatctcctg    60
aaactgtgag gtgatccaat tcaagcattc tggtatactt tcaaatcttc ttagataatc   120
ttgaacctta cagaaaagga gaaacataaa aatttgtctc aaatgggttc aaagaaagac   180
aggaaaaata ttaacaagaa agtttaactg aactgtagaa acccttttg gcaaagctca   240 ggtcctct                                                            248

<210> SEQ ID NO 261
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 261
aattttcatt gtaacaacat acctttaatg aaacattttt tccaaatgtc acatctcctg    60
aaactgtgag gtgatccaat tcaagcattc tggtatactt tcaaatcttc ttagataatc   120
ttgaacctta cagaaaagga gaaacataaa aatttgtctc aaatgggttc gaagaaagac   180
aggaaaaata ttaacaagaa agtttaactg aactgtagaa acccttttg gcaaagctca   240 ggtcctct                                                            248

<210> SEQ ID NO 262
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 262
```

```
aatttcatt gtaacaacat acctttaatg aaacatttt tccaaatgtc acatctcctg    60
aaactgtgag gtgatccaat tcaagcattc tggtatactt tcaaatcttc ttagataatc  120 ttgaaccta cagaaaagga gaaacataaa aatttgtctc aaatgggttc aaagaaagac  180
aggaagaata ttaacaagaa agtttaactg aactgtagaa ccttttttg gcaaagctca   240 ggtcctct                                                          248
```

<210> SEQ ID NO 263
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 263

```
aatttcatt gtaacaacat acctttaatg aaacatttt tccaaatgtc acatctcctg    60
aaactgtgag gtgatccaat tcaagcattc tggtatactt tcaaatcttc ttagataatc  120 ttgaaccta cagaaaagga gaaacataaa aatttgtctc aaatgggttc aaagaaagac  180
aggaaaaata ttaacaagaa agtttaactg aactgtagga ccttttttg gcaaagctca   240 ggtcctct                                                          248
```

<210> SEQ ID NO 264
<211> LENGTH: 249
<212> TYPE: DNA
<213> ORGANISM: Artificial Sequence
<220> FEATURE:
<223> OTHER INFORMATION: Synthetic Polynucleotide

<400> SEQUENCE: 264

```
aatttcatt gtaacaacat acctttaatg aaacatttt tccaaatgtc acatctcctg    60
aaactgtgag gtgatccaat tcaagcatat ctggtatact ttcaaatctt cttagataat  120
cttgaacctt acagaaaggg agaaacataa aaatttgtct caaatgggtt caagaaaga   180 caggaaaaat attaacaaga agtttaact gaactgtaga acctttttt ggcaaagctc    240 aggtcctct                                                         249
```

<210> SEQ ID NO 265
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 265

```
aatttcatt gtaacaacat acctttaatg aaacatttt tccaaatgtc acatctcctg    60
aaactgtgag gtgatccaat tcaagcattc tggtatactt tcaaatcttc ttagataatc  120 ttgaaccta cagaaaagga gaaacataaa aatttgtctc aaatgggttc aaagaaagac  180
aggaaaaata ttaacaagaa agtttaactg gactgtagaa ccttttttg gcaaagctca   240 ggtcctct                                                          248
```

<210> SEQ ID NO 266
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 266

```
aattttcatt gtaacaacat acctttaatg aaacattttt tccaaatgtc acatccctg    60
aaactgtgag gtgatccaat tcaagcattc tggtatactt tcaaatcttc ttagataatc   120
ttgaaccta cagaaaagga gaaacataaa aatttgtctc aaatgggttc aaagaaagac   180
aggaaaaata ttaacaagaa agtttaactg aactgtagaa acctttttg gcaaagctca   240
ggtcctct                                                           248
```

<210> SEQ ID NO 267
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 267

```
aattttcatt gtaacaacat acctttaatg aaacattttt tccaaatgtc acatctcctg   60
aaactgtgag gtgatccaat tcaagcattc tggtatactt tcaaatcttc ttagataatc   120
ttgaaccta cagaaaagga gaaacataaa aatttgtctc aaatgggttc aaagaaagac   180
aggaaaaata ttaacaagga agtttaactg aactgtagaa acctttttg gcaaagctca   240
ggtcctct                                                           248
```

<210> SEQ ID NO 268
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 268

```
aattttcatt gtaacaacat acctttaatg aaacattttt tccaaatgtc acatctcctg   60
aaactgtgag gtgatccaat tcaagcattc tggtatactt tcaaatcttc ttagataatc   120
ttgaaccta cagaaaagga gaaacataaa aatttgtctc aaatgggttc aaaggaagac   180
aggaaaaata ttaacaagaa agtttaactg aactgtagaa acctttttg gcaaagctca   240
ggtcctct                                                           248
```

<210> SEQ ID NO 269
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 269

```
aattttcatt gtaacaacat acctttaatg aaacattttt tccaaatgtc acatctcctg   60
aaactgtggg gtgatccaat tcaagcattc tggtatactt tcaaatcttc ttagataatc   120
ttgaaccta cagaaaagga gaaacataaa aatttgtctc aaatgggttc aaagaaagac   180
aggaaaaata ttaacaagaa agtttaactg aactgtagaa acctttttg gcaaagctca   240
ggtcctct                                                           248
```

<210> SEQ ID NO 270
<211> LENGTH: 258
<212> TYPE: DNA
<213> ORGANISM: Artificial Sequence
<220> FEATURE:
<223> OTHER INFORMATION: Synthetic Polynucleotide

<400> SEQUENCE: 270
aattttcatt gtaacaacat acctttaatg aaacattttt tccaaatgtc acatctcctg     60
aaactgtgag gtgatccaat tcaagcatat acttgaattc tggtatactt tcaaatcttc    120
ttagataatc ttgaaccttc agaaaagga gaaacataaa aatttgtctc aaatgggttc    180
aaagaaggac aggaaaaata ttaacaagaa agtttaactg aactgtagaa acctttttg     240 gcaaagctca ggtcctct                                                  258

<210> SEQ ID NO 271
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 271
aattttcatt gtaacaacat acctttaatg aaacattttt tccaaatgtc acatctcctg     60
aaactgtgag gtgatccaat tcaagcattc tggtatactt tcaaatcttc ttagataatc    120
ttgaaccttc agaagagga gaaacataaa aatttgtctc aaatgggttc aaagaaagac    180
aggaaaaata ttaacaagaa agtttaactg aactgtagaa acctttttg gcaaagctca    240 ggtcctct                                                             248

<210> SEQ ID NO 272
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 272
aattttcatt gtaacaacat acctttaatg aaacattttt tccaaatgtc acatctcctg     60
aaactgtgag gtgatccaat tcaagcattc tggtatactt tcaaatcttc ttagataatc    120
ttgaaccttc agaaaagga gaaacataaa aatttgtctc aaatgggttc aaagaaagac    180
agggaaaata ttaacaagaa agtttaactg aactgtagaa acctttttg gcaaagctca    240 ggtcctct                                                             248

<210> SEQ ID NO 273
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 273
aattttcatt gtaacaacat acctttaatg aaacattttt tccaaatgtc acatctcctg     60
aaactgtgag gtgatccaat tcaagcattc tggtatactt tcaaatcttc ttagataatc    120
ttgaaccttc agaaaagga gaaacataaa aattcgtctc aaatgggttc aaagaaagac    180
aggaaaaata ttaacaagaa agtttaactg aactgtagaa acctttttg gcaaagctca    240 ggtcctct                                                             248

<210> SEQ ID NO 274
<211> LENGTH: 248
<212> TYPE: DNA
<213> ORGANISM: Artificial Sequence
<220> FEATURE:

<223> OTHER INFORMATION: Synthetic Polynucleotide

<400> SEQUENCE: 274

```
aattttcatt gtaacaacat acctttaatg aaacattttt tccaaatgtc acatctcctg    60
aaactgcgag gtgatccaat tcaagcattc tggtatactt tcaaatcttc ttagataatc   120
ttgaaccttta cagaaaagga gaaacataaa aatttgtctc aaatgggttc aaagaaagac  180
aggaaaaata ttaacaagaa agtttaactg aactgtagaa accttttttg gcaaagctca   240
ggtcctct                                                           248
```

<210> SEQ ID NO 275
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 275

```
aattttcatt gtaacaaaat acctttaatg aaacattttt tccaaatgtc acatctcctg    60
aaactgtgag gtgatccaat tcaagcattc tggtatactt tcaaatcttc ttagataatc   120
ttgaaccttta cagaaaagga gaaacataaa aatttgtctc aaatgggttc aaagaaagac  180
aggaaaaata ttaacaagaa agtttaactg aactgtagaa accttttttg gcaaagctca   240
ggtcctct                                                           248
```

<210> SEQ ID NO 276
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 276

```
aattttcatt gtaacaacat acctttaatg aaacattttt tccaaatgtc acatctcctg    60
aaactgtgag gcgatccaat tcaagcattc tggtatactt tcaaatcttc ttagataatc   120
ttgaaccttta cagaaaagga gaaacataaa aatttgtctc aaatgggttc aaagaaagac  180
aggaaaaata ttaacaagaa agtttaactg aactgtagaa accttttttg gcaaagctca   240
ggtcctct                                                           248
```

<210> SEQ ID NO 277
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 277

```
aattttcatt gtaacaacat acctttaatg aaacattttt tccaaatgtc acatctcctg    60
aaactgtgag gtgatccaat tcaagcattc tggtatactt tcaaatcttc ttagataatc   120
ttgaaccttta cagaaaagga gaaacgtaaa aatttgtctc aaatgggttc aaagaaagac  180
aggaaaaata ttaacaagaa agtttaactg aactgtagaa accttttttg gcaaagctca   240
ggtcctct                                                           248
```

<210> SEQ ID NO 278
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 278

```
aattttcatt gtaacaacat acctttaatg aaacattttt tccaaatgtc acatctcctg    60
aaactgtgag gtgatccaat tcaagcattc tggtatactt tcaaatcttc ttagataatc   120
ttgaaccttta cagaaaaggg gaaacataaa aatttgtctc aaatggggttc aaagaaagac  180
aggaaaaata ttaacaagaa agtttaactg aactgtagaa acctttttg gcaaagctca    240
ggtcctct                                                            248
```

<210> SEQ ID NO 279
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 279

```
aattttcatt gtaacaacat acctttaatg aaacattttt tccaaatgtc acatctcctg    60
aaactgtgag gtgatccaat tcaagcattc tggtatactt tcaaatcttc ttagataatc   120
ttgaaccttta cagaaaagga gaaacataaa aatttgtccc aaatgggttc aaagaaagac  180
aggaaaaata ttaacaagaa agtttaactg aactgtagaa acctttttg gcaaagctca    240
ggtcctct                                                            248
```

<210> SEQ ID NO 280
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 280

```
aattttcatt gtaacaacat acctttaatg aaacattttt tccaaatgtc acacctcctg    60
aaactgtgag gtgatccaat tcaagcattc tggtatactt tcaaatcttc ttagataatc   120
ttgaaccttta cagaaaagga gaaacataaa aatttgtctc aaatgggttc aaagaaagac  180
aggaaaaata ttaacaagaa agtttaactg aactgtagaa acctttttg gcaaagctca    240
ggtcctct                                                            248
```

<210> SEQ ID NO 281
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 281

```
aattttcatt gtaacaacat acctttaatg aaacattttt tccaaatgtc acatctcctg    60
aaactgtgag gtgatccaat tcaagcattc tggtatactt tcaaatcttc ttagataatc   120
ttggacctta cagaaaagga gaaacataaa aatttgtctc aaatgggttc aaagaaagac   180
aggaaaaata ttaacaagaa agtttaactg aactgtagaa acctttttg gcaaagctca    240
ggtcctct                                                            248
```

<210> SEQ ID NO 282
<211> LENGTH: 249
<212> TYPE: DNA

<213> ORGANISM: Artificial Sequence
<220> FEATURE:
<223> OTHER INFORMATION: Synthetic Polynucleotide

<400> SEQUENCE: 282

```
aattttcatt gtaacaacat acctttaatg aaacattttt tccaaatgtc acatctcctg    60
aaactgtgag gtgatccaat tcaagcatat ctggtatact ttcaaatctt cttagataat   120
cttgaacctt acagaaaagg agaaacataa aatttgtct caaatgggtt caaagaagga   180
caggaaaaat attaacaaga aagtttaact gaactgtaga aaccttttt ggcaaagctc    240
aggtcctct                                                           249
```

<210> SEQ ID NO 283
<211> LENGTH: 258
<212> TYPE: DNA
<213> ORGANISM: Artificial Sequence
<220> FEATURE:
<223> OTHER INFORMATION: Synthetic Polynucleotide

<400> SEQUENCE: 283

```
aattttcatt gtaacaacat acctttaatg aaacattttt tccaaatgtc acatctcctg    60
aaactgtgag gtgatccaat tcaagcatat acttgaattc tggtatactt tcaaatcttc   120
ttagataatc ttgaacctta cagaaaagga gaaacataaa atttgtctc aaatgggctc    180
aaagaaagac aggaaaaata ttaacaagaa agtttaactg aactgtagaa accttttttg   240
gcaaagctca ggtcctct                                                 258
```

<210> SEQ ID NO 284
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 284

```
aattttcatt gtaacaacat acctttaatg aaacattttt tccaaatgtc acatctcctg    60
aaactgtgag gtgatccaat tcaagcattc tggtatactt tcaaatcttc ttagataatc   120
ttgaacctta cagaaaagga gaaacataaa atttgtctc aagtgggttc aaagaaagac    180
aggaaaaata ttaacaagaa agtttaactg aactgtagaa accttttttg gcaaagctca   240
ggtcctct                                                            248
```

<210> SEQ ID NO 285
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 285

```
aattttcatt gtaacaacat acctttaatg aaacattttt tccaaatgtc acatctcctg    60
aaaccgtgag gtgatccaat tcaagcattc tggtatactt tcaaatcttc ttagataatc   120
ttgaacctta cagaaaagga gaaacataaa atttgtctc aaatgggttc aaagaaagac    180
aggaaaaata ttaacaagaa agtttaactg aactgtagaa accttttttg gcaaagctca   240
ggtcctct                                                            248
```

<210> SEQ ID NO 286
<211> LENGTH: 248

<212> TYPE: DNA
<213> ORGANISM: Artificial Sequence
<220> FEATURE:
<223> OTHER INFORMATION: Synthetic Polynucleotide

<400> SEQUENCE: 286
aattttcatt gtaacaacat acctttaatg aaacattttt tccaaatgtc acgtctcctg    60
aaactgtgag gtgatccaat tcaagcattc tggtatactt tcaaatcttc ttagataatc    120 ttgaaccttta cagaaaagga gaaacataaa aatttgtctc aaatgggttc aaagaaagac    180
aggaaaaata ttaacaagaa agtttaactg aactgtagaa accttttttg gcaaagctca    240
ggtcctct    248

<210> SEQ ID NO 287
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 287
aattttcatt gtaacaacat acctttaatg aaacattttt tccaaatgtc acatctcctg    60
aaactgtgag gtgatccaat tcaagcattc tggtatactt tcaaatcttc ttagataatc    120 ttgaaccttta cagaaaagga gagacataaa aatttgtctc aaatgggttc aaagaaagac    180
aggaaaaata ttaacaagaa agtttaactg aactgtagaa accttttttg gcaaagctca    240
ggtcctct    248

<210> SEQ ID NO 288
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 288
aattttcatt gtaacaacat acctttaatg aaacattttt tccaaatgta acatctcctg    60
aaactgtgag gtgatccaat tcaagcattc tggtatactt tcaaatcttc ttagataatc    120 ttgaaccttta cagaaaagga gaaacataaa aatttgtctc aaatgggttc aaagaaagac    180
aggaaaaata ttaacaagaa agtttaactg aactgtagaa accttttttg gcaaagctca    240
ggtcctct    248

<210> SEQ ID NO 289
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 289
aattttcatt gtaacaacat acctttaatg aaacattttt tccaaatgtc acatctcctg    60
aaactgtgag gtgatccaat tcaagcattc tggtatactt tcaaatcttc ttagataatc    120 ttgaaccttta cagaaaagga gaaacataaa aatttgtctc aaatgggttc aaagaaagac    180
aggaaaaata ttaacaagaa agtttaactg aaccgtagaa accttttttg gcaaagctca    240
ggtcctct    248

<210> SEQ ID NO 290

```
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 290
aattttcatt gtaacaacat acctttaatg aagcattttt tccaaatgtc acatctcctg      60
aaactgtgag gtgatccaat tcaagcattc tggtatactt tcaaatcttc ttagataatc     120 ttgaaccttta cagaaaagga gaaacataaa aatttgtctc aaatgggttc aaagaaagac    180
aggaaaaata ttaacaagaa agtttaactg aactgtagaa accttttttg gcaaagctca     240
ggtcctct                                                              248

<210> SEQ ID NO 291
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 291
aattttcatt gtaacaacat acctttaatg aaacattttt tccaaatgtc acatctcctg      60
aaactgtgag gtgatccaat tcgagcattc tggtatactt tcaaatcttc ttagataatc     120 ttgaaccttta cagaaaagga gaaacataaa aatttgtctc aaatgggttc aaagaaagac    180
aggaaaaata ttaacaagaa agtttaactg aactgtagaa accttttttg gcaaagctca     240
ggtcctct                                                              248

<210> SEQ ID NO 292
<211> LENGTH: 258
<212> TYPE: DNA
<213> ORGANISM: Artificial Sequence
<220> FEATURE:
<223> OTHER INFORMATION: Synthetic Polynucleotide

<400> SEQUENCE: 292
aattttcatt gtaacaacat acctttaatg aaacattttt tccaaatgtc acatctcctg      60
aaactgtgag gtgatccaat tcaagcatat acttgaattc tggtatactt tcaaatcttc     120
ttagataatc ttgaacctta cagaaaagga gaaacataaa aatttgtctc aaatgggttc     180
aaagaaagac aggaaaaata ttaacaagaa agtttaactg agctgtagaa accttttttg     240
gcaaagctca ggtcctct                                                   258

<210> SEQ ID NO 293
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 293
aattttcatt gtaacaacat acctttaatg aaacattttt tccaaatgtc acatctcctg      60
aaactgtgag gtgatccaat tcaagcattc tggtatactt tcaaatcttc ttagataacc     120 ttgaaccttta cagaaaagga gaaacataaa aatttgtctc aaatgggttc aaagaaagac    180
aggaaaaata ttaacaagaa agtttaactg aactgtagaa accttttttg gcaaagctca     240
ggtcctct                                                              248
```

```
<210> SEQ ID NO 294
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 294
aattttcatt gtaacaacat acctttaatg aaacattttt tccaaatgtc acatctcctg      60
aaactgtgag gtgatccaat tcaagcattc tggtatactt tcaaatcttc ttagataatc     120 ttgaaccta cagaaaagga gaaacataaa aatttgtctc aaatgggttc aaagaaagac      180
aggaaaaata ttaacaagaa agtttaactg aactgtagaa accttttttg gcaaagctca     240
ggtcctct                                                              248

<210> SEQ ID NO 295
<211> LENGTH: 258
<212> TYPE: DNA
<213> ORGANISM: Artificial Sequence
<220> FEATURE:
<223> OTHER INFORMATION: Synthetic Polynucleotide

<400> SEQUENCE: 295
aattttcatt gtaacaacat acctttaatg aaacattttt tccaaatgtc acatctcctg      60
aaactgtgag gtgatccaat tcaagcatat acttgaattc tggtatactt tcaaatcttc     120
ttagataatc ttgaacctta cagaaaagga gaaacataaa aatttgtctc aaatgggttc     180
aaagaaagac aggaaaaata ttaacaagaa agtttaactg aactgtagaa gccttttttg     240
gcaaagctca ggtcctct                                                   258

<210> SEQ ID NO 296
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 296
aattttcatt gtaacaacat acctttaatg aaacattttt tccaaatgtc acatctcccg      60
aaactgtgag gtgatccaat tcaagcattc tggtatactt tcaaatcttc ttagataatc     120 ttgaaccta cagaaaagga gaaacataaa aatttgtctc aaatgggttc aaagaaagac      180
aggaaaaata ttaacaagaa agtttaactg aactgtagaa accttttttg gcaaagctca     240
ggtcctct                                                              248

<210> SEQ ID NO 297
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 297
aattttcatt gtaacaacat acctttaatg aaacattttt tccaaatgtc acatctcctg      60
agactgtgag gtgatccaat tcaagcattc tggtatactt tcaaatcttc ttagataatc     120 ttgaaccta cagaaaagga gaaacataaa aatttgtctc aaatgggttc aaagaaagac      180
aggaaaaata ttaacaagaa agtttaactg aactgtagaa accttttttg gcaaagctca     240
ggtcctct                                                              248
```

<210> SEQ ID NO 298
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 298
aattttcatt gtaacaacat acctttaatg aaacattttt tccaaatgtc acatctcctg    60
aaactgtgag gtgatccaat tcaagcattc tggtatactt tcaaatcttc ttagataatc   120 ttgaaccttta cagaaaagga gaaacataaa aatttgtctc aaatgggttc aaagaaagac   180
aggaaaaata ttaacaagaa agcttaactg aactgtagaa acctttttg gcaaagctca    240 ggtcctct                                                             248

<210> SEQ ID NO 299
<211> LENGTH: 258
<212> TYPE: DNA
<213> ORGANISM: Artificial Sequence
<220> FEATURE:
<223> OTHER INFORMATION: Synthetic Polynucleotide

<400> SEQUENCE: 299
aattttcatt gtaacaacat acctttaatg aaacattttt tccaaatgtc acatctcctg    60
aaactgtgag gtgatccaat tcaagcatat acttgaattc tggtatactt tcaaatcttc   120
ttagataatc ttgaaccttta cagaaaagga gaaacataaa aatttgtctc aaatgggttc   180
aaggaaagac aggaaaaata ttaacaagaa agtttaactg aactgtagaa acctttttg    240 gcaaagctca ggtcctct                                                  258

<210> SEQ ID NO 300
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 300
aattttcatt gtaacaacat acctttaatg aaacattttt tccaaatgtc acatctcctg    60
aaactgtgag gtgatccaat tcaagcattc tggtatactt tcaaatcttc ttagataatc   120 tcgaaccttta cagaaaagga gaaacataaa aatttgtctc aaatgggttc aaagaaagac   180
aggaaaaata ttaacaagaa agtttaactg aactgtagaa acctttttg gcaaagctca    240 ggtcctct                                                             248

<210> SEQ ID NO 301
<211> LENGTH: 258
<212> TYPE: DNA
<213> ORGANISM: Artificial Sequence
<220> FEATURE:
<223> OTHER INFORMATION: Synthetic Polynucleotide

<400> SEQUENCE: 301
aattttcatt gtaacaacat acctttaatg aaacattttt tccaaatgtc acatctcctg    60
aaactgtgag gtgatccaat tcaagcatat acttgaattc tggtatactt tcaaatcttc   120
ttagataatc ttgaaccttta cagaaaagga gaaacataaa aatttgtctc aaatgggttc   180
aaagaaagac gggaaaaata ttaacaagaa agtttaactg aactgtagaa acctttttg    240 gcaaagctca ggtcctct                                                  258

<210> SEQ ID NO 302
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 302
aattttcatt gtaacaacat acctttaatg aaacattttt tccaaatgtc acatctcctg    60
aagctgtgag gtgatccaat tcaagcattc tggtatactt tcaaatcttc ttagataatc   120
ttgaacctta cagaaaagga gaaacataaa aatttgtctc aaatgggttc aaagaaagac   180
aggaaaaata ttaacaagaa agtttaactg aactgtagaa accttttttg gcaaagctca   240
ggtcctct                                                            248

<210> SEQ ID NO 303
<211> LENGTH: 249
<212> TYPE: DNA
<213> ORGANISM: Artificial Sequence
<220> FEATURE:
<223> OTHER INFORMATION: Synthetic Polynucleotide

<400> SEQUENCE: 303
aattttcatt gtaacaacat acctttaatg aaacattttt tccaaatgtc acatctcctg    60
aaactgtgag gtgatccaat tcaagcatat ctggtatact ttcaaatctt cttagataat   120
cttgaacctt acagaaaagg agaaacataa aatttgtctc aaatgggttc aaagaaaga   180 caggaaaaat attaacaaga aagtttaact gaactgtaga agcctttttt ggcaaagctc   240
aggtcctct                                                           249

<210> SEQ ID NO 304
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 304
aattttcatt gtaacaacat acctttaatg aaacattttt tccaaatgtc acatctcctg    60
aaactgtgag gtggtccaat tcaagcattc tggtatactt tcaaatcttc ttagataatc   120
ttgaacctta cagaaaagga gaaacataaa aatttgtctc aaatgggttc aaagaaagac   180
aggaaaaata ttaacaagaa agtttaactg aactgtagaa accttttttg gcaaagctca   240
ggtcctct                                                            248

<210> SEQ ID NO 305
<211> LENGTH: 258
<212> TYPE: DNA
<213> ORGANISM: Artificial Sequence
<220> FEATURE:
<223> OTHER INFORMATION: Synthetic Polynucleotide

<400> SEQUENCE: 305
aattttcatt gtaacaacat acctttaatg aaacattttt tccaaatgtc acatctcctg    60
aaactgtgag gtgatccaat tcaagcatat acttgaattc tggtatactt tcaaatcttc   120
ttagataatc ttgagcctta cagaaaagga gaaacataaa aatttgtctc aaatgggttc   180
aaagaaagac aggaaaaata ttaacaagaa agtttaactg aactgtagaa accttttttg   240

```
gcaaagctca ggtcctct                                                  258

<210> SEQ ID NO 306
<211> LENGTH: 258
<212> TYPE: DNA
<213> ORGANISM: Artificial Sequence
<220> FEATURE:
<223> OTHER INFORMATION: Synthetic Polynucleotide

<400> SEQUENCE: 306
aattttcatt gtaacaacat acctttaatg aaacattttt tccaaatgtc acatctcctg    60
aaactgtgag gtgatccaat tcaagcatat acttgaattc tggtatactt tcaaatcttc   120
ttagataatc ttgaacctta cagaaaagga gaagcataaa aatttgtctc aaatgggttc   180
aaagaaagac aggaaaaata ttaacaagaa agtttaactg aactgtagaa acctttttg    240 gcaaagctca ggtcctct                                                  258

<210> SEQ ID NO 307
<211> LENGTH: 249
<212> TYPE: DNA
<213> ORGANISM: Artificial Sequence
<220> FEATURE:
<223> OTHER INFORMATION: Synthetic Polynucleotide

<400> SEQUENCE: 307
aattttcatt gtaacaacat acctttaatg aaacattttt tccaaatgtc acatctcctg    60
aaactgtgag gtgatccaat tcaagcatat ctggtatact ttcaaatctt cttagataat   120
cttgaacctt acagaaaagg agaaacataa aaatttgtct caaatgggtt caaggaaaga   180
caggaaaaat attaacaaga agtttaact gaactgtaga aaccttttttt ggcaaagctc   240 aggtcctct                                                            249

<210> SEQ ID NO 308
<211> LENGTH: 258
<212> TYPE: DNA
<213> ORGANISM: Artificial Sequence
<220> FEATURE:
<223> OTHER INFORMATION: Synthetic Polynucleotide

<400> SEQUENCE: 308
aattttcatt gtaacaacat acctttaatg aaacattttt tccaaatgcc acatctcctg    60
aaactgtgag gtgatccaat tcaagcatat acttgaattc tggtatactt tcaaatcttc   120
ttagataatc ttgaacctta cagaaaagga gaaacataaa aatttgtctc aaatgggttc   180
aaagaaagac aggaaaaata ttaacaagaa agtttaactg aactgtagaa accttttttg   240
gcaaagctca ggtcctct                                                  258

<210> SEQ ID NO 309
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 309
aattttcatt gtaacaacat acctttaatg aaacattttt tccaaatgtc acatctcctg    60
aaactgtgag gtgatccaat tcaagcattc tggtatactt tcaaatcttc ttagataatc   120
ttgaacctta cagaaaagga gaaacataaa aatttgtctc aaatgggttc aaagaaagac   180
aggaaaaata ttaacaagaa agtttagctg aactgtagaa accttttttg gcaaagctca   240
```

```
<210> SEQ ID NO 310
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 310
aattttcatt gtaacaacat acctttaatg aaacattttt tccaaatgtc acatctcctg    60
aaactgtgag gtgatccaat tcaagcattc tggtatactc tcaaatcttc ttagataatc   120
ttgaacctta cagaaaagga gaaacataaa aatttgtctc aaatgggttc aaagaaagac   180
aggaaaaata ttaacaagaa agtttaactg aactgtagaa accttttttg gcaaagctca   240
ggtcctct                                                            248

<210> SEQ ID NO 311
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 311
aattttcatt gtaacaacat acctttaatg aaacattttt tccaaatgtc acatctcctg    60
aaactgtgag gtgatccaat tcaagcattc tggtatactt tcaaatcttc ttagataatc   120
ttgaacctta cagaaaagga gaaacataaa aatttgtctc aaatgggttc aaagaaagac   180
aggaaaaata ttaacaagaa agtttaactg aactgtggaa accttttttg gcaaagctca   240
ggtcctct                                                            248

<210> SEQ ID NO 312
<211> LENGTH: 258
<212> TYPE: DNA
<213> ORGANISM: Artificial Sequence
<220> FEATURE:
<223> OTHER INFORMATION: Synthetic Polynucleotide

<400> SEQUENCE: 312
aattttcatt gtaacaacat acctttaatg aaacattttt tccaaatgtc acatctcctg    60
aaactgtgag gtgatccaat tcaagcatat acttgaattc tggtatacct tcaaatcttc   120
ttagataatc ttgaacctta cagaaaagga gaaacataaa aatttgtctc aaatgggttc   180
aaagaaagac aggaaaaata ttaacaagaa agtttaactg aactgtagaa accttttttg   240
gcaaagctca ggtcctct                                                 258

<210> SEQ ID NO 313
<211> LENGTH: 249
<212> TYPE: DNA
<213> ORGANISM: Artificial Sequence
<220> FEATURE:
<223> OTHER INFORMATION: Synthetic Polynucleotide

<400> SEQUENCE: 313
aattttcatt gtaacaacat acctttaatg aaacattttt tccaaatgtc acatctcctg    60
aaactgtgag gtgatccaat tcaagcatat ctggtatact ttcaaatctt cttagataat   120
cttgaacctt acagaaaagg agaaacataa aatttgtct caaatgggct caagaaaaga   180
```

```
caggaaaaat attaacaaga aagtttaact gaactgtaga aaccttttt ggcaaagctc    240 aggtcctct                                                           249
```

<210> SEQ ID NO 314
<211> LENGTH: 248
<212> TYPE: DNA
<213> ORGANISM: Artificial Sequence
<220> FEATURE:
<223> OTHER INFORMATION: Synthetic Polynucleotide
<400> SEQUENCE: 314

```
aattttcatt gtaacaacat acccttaatg aaacatttt tccaaatgtc acatctcctg     60
aaactgtgag gtgatccaat tcaagcattc tggtatactt tcaaatcttc ttagataatc   120
ttgaacctta cagaaaagga gaaacataaa aatttgtctc aaatgggttc aaagaaagac   180
aggaaaaata ttaacaagaa agtttaactg aactgtagaa ccttttttg gcaaagctca   240 ggtcctct                                                           248
```

<210> SEQ ID NO 315
<211> LENGTH: 249
<212> TYPE: DNA
<213> ORGANISM: Artificial Sequence
<220> FEATURE:
<223> OTHER INFORMATION: Synthetic Polynucleotide
<400> SEQUENCE: 315

```
aattttcatt gtaacaacat acctttaatg aaacatttt tccaaatgtc acatctcctg     60
aaactgtgag gtgatccaat tcaagcatat ctggtatact ttcaaatctt cttagataat   120
cttgaacctt acagaaaagg agaaacataa aaatttgtct caaatgggtt caaagaaaga   180
cgggaaaaat attaacaaga aagtttaact gaactgtaga aaccttttt ggcaaagctc   240 aggtcctct                                                           249
```

<210> SEQ ID NO 316
<211> LENGTH: 258
<212> TYPE: DNA
<213> ORGANISM: Artificial Sequence
<220> FEATURE:
<223> OTHER INFORMATION: Synthetic Polynucleotide
<400> SEQUENCE: 316

```
aattttcatt gtaacaacat acctttaatg aaacatttt tccaaatgtc acatctcctg     60
aaactgtgag gtgatccaat tcaagcatat acttgaattc tggtatactt tcaaatcttc   120
ttagataatc ttgaacctta cggaaaagga gaaacataaa aatttgtctc aaatgggttc   180
aaagaaagac aggaaaaata ttaacaagaa agtttaactg aactgtagaa cctttttg    240 gcaaagctca ggtcctct                                                 258
```

<210> SEQ ID NO 317
<211> LENGTH: 248
<212> TYPE: DNA
<213> ORGANISM: Artificial Sequence
<220> FEATURE:
<223> OTHER INFORMATION: Synthetic Polynucleotide
<400> SEQUENCE: 317

```
aattttcatt gtaacaacat acctttaatg aaacatttt tccaaacgtc acatctcctg     60
aaactgtgag gtgatccaat tcaagcattc tggtatactt tcaaatcttc ttagataatc   120
ttgaacctta cagaaaagga gaaacataaa aatttgtctc aaatgggttc aaagaaagac   180
```
aggaaaaata ttaacaagaa agtttaactg aactgtagaa accttttttg gcaaagctca    240
ggtcctct                                                            248

<210> SEQ ID NO 318
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 318
aattttcatt gtaacaacat acctttaatg agacattttt tccaaatgtc acatctcctg    60
aaactgtgag gtgatccaat tcaagcattc tggtatactt tcaaatcttc ttagataatc    120 ttgaaccttta cagaaaagga gaaacataaa aatttgtctc aaatgggttc aaagaaagac    180
aggaaaaata ttaacaagaa agtttaactg aactgtagaa accttttttg gcaaagctca    240
ggtcctct                                                            248

<210> SEQ ID NO 319
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 319
aattttcatt gtaacaacat acctttaatg aaacattttt tccaaatgtc acatctcctg    60
aaactgtgag gtgatccaat tcaagcattc tggtatactt tcaaatcctc ttagataatc    120 ttgaaccttta cagaaaagga gaaacataaa aatttgtctc aaatgggttc aaagaaagac    180
aggaaaaata ttaacaagaa agtttaactg aactgtagaa accttttttg gcaaagctca    240
ggtcctct                                                            248

<210> SEQ ID NO 320
<211> LENGTH: 249
<212> TYPE: DNA
<213> ORGANISM: Artificial Sequence
<220> FEATURE:
<223> OTHER INFORMATION: Synthetic Polynucleotide

<400> SEQUENCE: 320
aattttcatt gtaacaacat acctttaatg aaacattttt tccaaatgtc acatctcctg    60
aaactgtgag gtgatccaat tcaagcatat ctggtatact ttcaaatctt cttagataat    120
cttgaacctt acagaaaagg agaaacataa aaatttgtct caaatgggtt caaagaaaga    180
caggaaaaat attaacaaga aagtttaact gagctgtaga aaccttttttt ggcaaagctc    240 aggtcctct                                                           249

<210> SEQ ID NO 321
<211> LENGTH: 258
<212> TYPE: DNA
<213> ORGANISM: Artificial Sequence
<220> FEATURE:
<223> OTHER INFORMATION: Synthetic Polynucleotide

<400> SEQUENCE: 321
aattttcatt gtaacaacat acctttaatg aaacattttt tccaaatgtc acatctcctg    60
aaactgtgag gtgatccaat tcaagcatat acttgaattc tggtatactt tcaaatcttc    120

```
ttagataatc ttgaacctta cagaaaagga gaaacataaa aatttgcctc aaatgggttc    180
aaagaaagac aggaaaaata ttaacaagaa agtttaactg aactgtagaa acctttttg     240 gcaaagctca ggtcctct                                                  258

<210> SEQ ID NO 322
<211> LENGTH: 258
<212> TYPE: DNA
<213> ORGANISM: Artificial Sequence
<220> FEATURE:
<223> OTHER INFORMATION: Synthetic Polynucleotide

<400> SEQUENCE: 322
aattttcatt gtaacaacat acctttaatg aaacattttt tccaaatgtc acatctcctg    60
aaactgtgag gtgatccaat tcaagcatat acttgaattc tggtatactt tcaaatcttc    120
ttagataatc ttgaacctta cagaaaagga gaaacataaa aatttgtctc aaatgggttc    180
aaagaaagac aggaaaaata ttaacaagaa ggtttaactg aactgtagaa acctttttg     240 gcaaagctca ggtcctct                                                  258

<210> SEQ ID NO 323
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 323
aattttcatt gtaacaacat acctttaatg aaacattttc tccaaatgtc acatctcctg    60
aaactgtgag gtgatccaat tcaagcattc tggtatactt tcaaatcttc ttagataatc    120
ttgaacctta cagaaaagga gaaacataaa aatttgtctc aaatgggttc aaagaaagac    180
aggaaaaata ttaacaagaa agtttaactg aactgtagaa acctttttg gcaaagctca     240 ggtcctct                                                             248

<210> SEQ ID NO 324
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 324
aattttcatt gtaacaacat acctttaacg aaacattttt tccaaatgtc acatctcctg    60
aaactgtgag gtgatccaat tcaagcattc tggtatactt tcaaatcttc ttagataatc    120
ttgaacctta cagaaaagga gaaacataaa aatttgtctc aaatgggttc aaagaaagac    180
aggaaaaata ttaacaagaa agtttaactg aactgtagaa acctttttg gcaaagctca     240 ggtcctct                                                             248

<210> SEQ ID NO 325
<211> LENGTH: 258
<212> TYPE: DNA
<213> ORGANISM: Artificial Sequence
<220> FEATURE:
<223> OTHER INFORMATION: Synthetic Polynucleotide

<400> SEQUENCE: 325
aattttcatt gtaacaacat acctttaatg aaacattttt tccaaatgtc acatctcctg    60
aaactgtgag gtgatccaat tcaagcatat acttgaattc tggtatactt tcaaatcttc    120
```

```
ttagataatc ttgaacctta cagaaaagga gaaacataaa aatttgtctc aaatgggttc    180
aaagaaaggc aggaaaaata ttaacaagaa agtttaactg aactgtagaa acctttttg    240 gcaaagctca ggtcctct                                                   258
```

<210> SEQ ID NO 326
<211> LENGTH: 258
<212> TYPE: DNA
<213> ORGANISM: Artificial Sequence
<220> FEATURE:
<223> OTHER INFORMATION: Synthetic Polynucleotide

<400> SEQUENCE: 326

```
aattttcatt gtaacaacat acctttaatg aaacatttt tccaaatgtc acatctcctg    60
aaactgtgag gtgatccaat tcaagcatat acttgaattc tggtatactt tcaaatcttc   120
ttagataatc ttgaacctta cagaaaagga ggaacataaa aatttgtctc aaatgggttc    180
aaagaaagac aggaaaaata ttaacaagaa agtttaactg aactgtagaa acctttttg    240 gcaaagctca ggtcctct                                                   258
```

<210> SEQ ID NO 327
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 327

```
aattttcatt gtaacaacat acctttaatg aaacatttt tccaaatgtc acatctcctg    60
aaactgtgag gtgatccaat tcaagcattc tggcatactt tcaaatcttc ttagataatc   120
ttgaacctta cagaaaagga gaaacataaa aatttgtctc aaatgggttc aaagaaagac   180
aggaaaaata ttaacaagaa agtttaactg aactgtagaa acctttttg gcaaagctca    240 ggtcctct                                                              248
```

<210> SEQ ID NO 328
<211> LENGTH: 258
<212> TYPE: DNA
<213> ORGANISM: Artificial Sequence
<220> FEATURE:
<223> OTHER INFORMATION: Synthetic Polynucleotide

<400> SEQUENCE: 328

```
aattttcatt gtaacaacat acctttaatg aaacatttt tccaaatgtc acatctcctg    60
aaactgtgag gtgatccaat tcaagcatat acttgaattc tggtatactt tcaaatcttc   120
ttagataatc ttgaacctta cagaaaagga gaaacataaa aatttgtctc aaatgggttc    180
aaagagagac aggaaaaata ttaacaagaa agtttaactg aactgtagaa acctttttg    240 gcaaagctca ggtcctct                                                   258
```

<210> SEQ ID NO 329
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 329

```
aattttcatt gtaacaacat acctttaatg aaacatttt tccaaatgtc acatctcctg    60
```

```
aaactgtgag gtgatccaat tcaagcattc tggtatactt tcaaatcttc ttaggtaatc    120
ttgaacctta cagaaaagga gaaacataaa aatttgtctc aaatgggttc aaagaaagac    180
aggaaaaata ttaacaagaa agtttaactg aactgtagaa accttttttg gcaaagctca    240
ggtcctct                                                             248
```

```
<210> SEQ ID NO 330
<211> LENGTH: 248
<212> TYPE: DNA
<213> ORGANISM: Artificial Sequence
<220> FEATURE:
<223> OTHER INFORMATION: Synthetic Polynucleotide

<400> SEQUENCE: 330
aattttcatt gtaacaacat acctttaatg aaacattttt tccaaatgtc acatctcctg     60
aaactgtgag gtgatccaat tcaagcatcc tggtatactt tcaaatcttc ttagataatc    120
ttgaacctta cagaaaagga gaaacataaa aatttgtctc aaatgggttc aaagaaagac    180
aggaaaaata ttaacaagaa agtttaactg aactgtagaa accttttttg gcaaagctca    240
ggtcctct                                                             248
```

```
<210> SEQ ID NO 331
<211> LENGTH: 249
<212> TYPE: DNA
<213> ORGANISM: Artificial Sequence
<220> FEATURE:
<223> OTHER INFORMATION: Synthetic Polynucleotide

<400> SEQUENCE: 331
aattttcatt gtaacaacat acctttaatg aaacattttt tccaaatgtc acatctcctg     60
aaactgtgag gtgatccaat tcaagcatat ctggtatact ttcaaatctt cttagataat    120
cttgagcctt acagaaaagg agaaacataa aaatttgtct caaatgggtt caaagaaaga    180
caggaaaaat attaacaaga aagtttaact gaactgtaga accttttttt ggcaaagctc    240
aggtcctct                                                            249
```

```
<210> SEQ ID NO 332
<211> LENGTH: 249
<212> TYPE: DNA
<213> ORGANISM: Artificial Sequence
<220> FEATURE:
<223> OTHER INFORMATION: Synthetic Polynucleotide

<400> SEQUENCE: 332
aattttcatt gtaacaacat acctttaatg aaacattttt tccaaatgtc acatctcctg     60
aaactgtgag gtgatccaat tcaagcatat ctggtatact ttcaaatctt cttagataat    120
cttgaacctt acggaaaagg agaaacataa aaatttgtct caaatgggtt caaagaaaga    180
caggaaaaat attaacaaga aagtttaact gaactgtaga acctttttt ggcaaagctc     240 aggtcctct                                                            249
```

```
<210> SEQ ID NO 333
<211> LENGTH: 237
<212> TYPE: DNA
<213> ORGANISM: Artificial Sequence
<220> FEATURE:
<223> OTHER INFORMATION: Synthetic Polynucleotide

<400> SEQUENCE: 333
agctcagtta gaagcaggga gttgggaatt ccgttcatgt gatttagcat cagtgatatg     60
```
gcaaatgtgg gactaagggt agtgatcaga gggttaaaat tgtgtgtttt gttttagcgc    120
tgctgggaca tcgccttggg tcccctcaaa cagattccca tgaatctctt catcatgtac    180
atggcaggca atactatctc catcttccct actatgatgg tgtgtatgat ggcctgg      237

<210> SEQ ID NO 334
<211> LENGTH: 237
<212> TYPE: DNA
<213> ORGANISM: Artificial Sequence
<220> FEATURE:
<223> OTHER INFORMATION: Synthetic Polynucleotide

<400> SEQUENCE: 334
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc    120
tgctgggaca tcgccttggg tcccctcaaa cagattccca tgaatctctt catcatgtac    180
atggcaggca atactatctc catcttccct actatgatgg tgtgtatgat ggcctgg      237

<210> SEQ ID NO 335
<211> LENGTH: 235
<212> TYPE: DNA
<213> ORGANISM: Artificial Sequence
<220> FEATURE:
<223> OTHER INFORMATION: Synthetic Polynucleotide

<400> SEQUENCE: 335
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc    120
tgctgggaca tcgttgggtc ccctcaaaca gattcccatg aatctcttca tcatgtacat    180
ggcaggcaat actatctcca tcttccctac tatgatggtg tgtatgatgg cctgg        235

<210> SEQ ID NO 336
<211> LENGTH: 225
<212> TYPE: DNA
<213> ORGANISM: Artificial Sequence
<220> FEATURE:
<223> OTHER INFORMATION: Synthetic Polynucleotide

<400> SEQUENCE: 336
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc    120
tgcttgggtc ccctcaaaca gattcccatg aatctcttca tcatgtacat ggcaggcaat    180
actatctcca tcttccctac tatgatggtg tgtatgatgg cctgg                   225

<210> SEQ ID NO 337
<211> LENGTH: 224
<212> TYPE: DNA
<213> ORGANISM: Artificial Sequence
<220> FEATURE:
<223> OTHER INFORMATION: Synthetic Polynucleotide

<400> SEQUENCE: 337
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc    120
tgctgggtcc cctcaaacag attcccatga atctcttcat catgtacatg gcaggcaata    180
ctatctccat cttccctact atgatggtgt gtatgatggc ctgg                    224

<210> SEQ ID NO 338
<211> LENGTH: 222
<212> TYPE: DNA
<213> ORGANISM: Artificial Sequence
<220> FEATURE:
<223> OTHER INFORMATION: Synthetic Polynucleotide

<400> SEQUENCE: 338

```
agctcagtta gaagcaggga gttgggaatt ccgttcatgt gatttagcat cagtgatatg      60
gcaaatgtgg gactaagggt agtgatcaga gggttaaaat tgtgtgtttt gttttagcgc     120
tgctgggaca tcaaacagat tcccatgaat ctcttcatca gtacatggc aggcaatact      180
atctccatct tccctactat gatggtgtgt atgatggcct gg                        222
```

<210> SEQ ID NO 339
<211> LENGTH: 235
<212> TYPE: DNA
<213> ORGANISM: Artificial Sequence
<220> FEATURE:
<223> OTHER INFORMATION: Synthetic Polynucleotide

<400> SEQUENCE: 339

```
agctcagtta gaagcaggga gttgggaatt ccgttcatgt gatttagcat cagtgatatg      60
gcaaatgtgg gactaagggt agtgatcaga gggttaaaat tgtgtgtttt gttttagcgc     120
tgctgggaca tccttgggtc ccctcaaaca gattcccatg aatctcttca tcatgtacat     180
ggcaggcaat actatctcca tcttccctac tatgatggtg tgtatgatgg cctgg           235
```

<210> SEQ ID NO 340
<211> LENGTH: 236
<212> TYPE: DNA
<213> ORGANISM: Artificial Sequence
<220> FEATURE:
<223> OTHER INFORMATION: Synthetic Polynucleotide

<400> SEQUENCE: 340

```
agctcagtta gaagcaggga gttgggaatt ccgttcatgt gatttagcat cagtgatatg      60
gcaaatgtgg gactaagggt agtgatcaga gggttaaaat tgtgtgtttt gttttagcgc     120
tgctgggaca tcgcttgggt cccctcaaac agattcccat gaatctcttc atcatgtaca     180
tggcaggcaa tactatctcc atcttcccta ctatgatggt gtgtatgatg gcctgg          236
```

<210> SEQ ID NO 341
<211> LENGTH: 234
<212> TYPE: DNA
<213> ORGANISM: Artificial Sequence
<220> FEATURE:
<223> OTHER INFORMATION: Synthetic Polynucleotide

<400> SEQUENCE: 341

```
agctcagtta gaagcaggga gttgggaatt ccgttcatgt gatttagcat cagtgatatg      60
gcaaatgtgg gactaagggt agtgatcaga gggttaaaat tgtgtgtttt gttttagcgc     120
tgctgggaca tcgtgggtcc cctcaaacag attcccatga atctcttcat catgtacatg     180
gcaggcaata ctatctccat cttccctact atgatggtgt gtatgatggc ctgg            234
```

<210> SEQ ID NO 342
<211> LENGTH: 232
<212> TYPE: DNA
<213> ORGANISM: Artificial Sequence
<220> FEATURE:
<223> OTHER INFORMATION: Synthetic Polynucleotide

<400> SEQUENCE: 342
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggacc ttgggtcccc tcaaacagat tcccatgaat ctcttcatca tgtacatggc   180
aggcaatact atctccatct tccctactat gatggtgtgt atgatggcct gg           232

<210> SEQ ID NO 343
<211> LENGTH: 237
<212> TYPE: DNA
<213> ORGANISM: Artificial Sequence
<220> FEATURE:
<223> OTHER INFORMATION: Synthetic Polynucleotide

<400> SEQUENCE: 343
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tctgtttggg tcccctcaaa cagattccca tgaatctctt catcatgtac   180
atggcaggca atactatctc atcttccct actatgatgg tgtgtatgat ggcctgg      237

<210> SEQ ID NO 344
<211> LENGTH: 227
<212> TYPE: DNA
<213> ORGANISM: Artificial Sequence
<220> FEATURE:
<223> OTHER INFORMATION: Synthetic Polynucleotide

<400> SEQUENCE: 344
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tccctcaaa cagattccca tgaatctctt catcatgtac atggcaggca   180
atactatctc atcttccct actatgatgg tgtgtatgat ggcctgg                  227

<210> SEQ ID NO 345
<211> LENGTH: 223
<212> TYPE: DNA
<213> ORGANISM: Artificial Sequence
<220> FEATURE:
<223> OTHER INFORMATION: Synthetic Polynucleotide

<400> SEQUENCE: 345
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctggtccc ctcaaacaga ttcccatgaa tctcttcatc atgtacatgg caggcaatac   180
tatctccatc ttccctacta tgatggtgtg tatgatggcc tgg                     223

<210> SEQ ID NO 346
<211> LENGTH: 234
<212> TYPE: DNA
<213> ORGANISM: Artificial Sequence
<220> FEATURE:
<223> OTHER INFORMATION: Synthetic Polynucleotide

<400> SEQUENCE: 346
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120

```
tgctgggaca ccttgggtcc cctcaaacag attcccatga atctcttcat catgtacatg    180
gcaggcaata ctatctccat cttccctact atgatggtgt gtatgatggc ctgg          234
```

<210> SEQ ID NO 347
<211> LENGTH: 232
<212> TYPE: DNA
<213> ORGANISM: Artificial Sequence
<220> FEATURE:
<223> OTHER INFORMATION: Synthetic Polynucleotide

<400> SEQUENCE: 347

```
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc    120
tgctgggaca tcgggtcccc tcaaacagat tcccatgaat ctcttcatca tgtacatggc    180
aggcaatact atctccatct tccctactat gatggtgtgt atgatggcct gg            232
```

<210> SEQ ID NO 348
<211> LENGTH: 224
<212> TYPE: DNA
<213> ORGANISM: Artificial Sequence
<220> FEATURE:
<223> OTHER INFORMATION: Synthetic Polynucleotide

<400> SEQUENCE: 348

```
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc    120
tgctgggacc cctcaaacag attcccatga atctcttcat catgtacatg gcaggcaata    180
ctatctccat cttccctact atgatggtgt gtatgatggc ctgg                     224
```

<210> SEQ ID NO 349
<211> LENGTH: 225
<212> TYPE: DNA
<213> ORGANISM: Artificial Sequence
<220> FEATURE:
<223> OTHER INFORMATION: Synthetic Polynucleotide

<400> SEQUENCE: 349

```
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc    120
tgtttgggtc ccctcaaaca gattcccatg aatctcttca tcatgtacat ggcaggcaat    180
actatctcca tcttccctac tatgatggtg tgtatgatgg cctgg                    225
```

<210> SEQ ID NO 350
<211> LENGTH: 226
<212> TYPE: DNA
<213> ORGANISM: Artificial Sequence
<220> FEATURE:
<223> OTHER INFORMATION: Synthetic Polynucleotide

<400> SEQUENCE: 350

```
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc    120
tgccttgggt cccctcaaac agattcccat gaatctcttc atcatgtaca tggcaggcaa    180
tactatctcc atcttcccta ctatgatggt gtgtatgatg gcctgg                   226
```

<210> SEQ ID NO 351
<211> LENGTH: 224

```
<212> TYPE: DNA
<213> ORGANISM: Artificial Sequence
<220> FEATURE:
<223> OTHER INFORMATION: Synthetic Polynucleotide

<400> SEQUENCE: 351
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tctcaaacag attcccatga atctcttcat catgtacatg gcaggcaata   180
ctatctccat cttccctact atgatggtgt gtatgatggc ctgg                    224

<210> SEQ ID NO 352
<211> LENGTH: 231
<212> TYPE: DNA
<213> ORGANISM: Artificial Sequence
<220> FEATURE:
<223> OTHER INFORMATION: Synthetic Polynucleotide

<400> SEQUENCE: 352
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tcggtcccct caaacagatt cccatgaatc tcttcatcat gtacatggca   180
ggcaatacta tctccatctt ccctactatg atggtgtgta tgatggcctg g            231

<210> SEQ ID NO 353
<211> LENGTH: 232
<212> TYPE: DNA
<213> ORGANISM: Artificial Sequence
<220> FEATURE:
<223> OTHER INFORMATION: Synthetic Polynucleotide

<400> SEQUENCE: 353
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca ttgggtcccc tcaaacagat tcccatgaat ctcttcatca tgtacatggc   180
aggcaatact atctccatct tccctactat gatggtgtgt atgatggcct gg           232

<210> SEQ ID NO 354
<211> LENGTH: 215
<212> TYPE: DNA
<213> ORGANISM: Artificial Sequence
<220> FEATURE:
<223> OTHER INFORMATION: Synthetic Polynucleotide

<400> SEQUENCE: 354
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca gattcccatg aatctcttca tcatgtacat ggcaggcaat actatctcca   180
tcttccctac tatgatggtg tgtatgatgg cctgg                              215

<210> SEQ ID NO 355
<211> LENGTH: 238
<212> TYPE: DNA
<213> ORGANISM: Artificial Sequence
<220> FEATURE:
<223> OTHER INFORMATION: Synthetic Polynucleotide

<400> SEQUENCE: 355
```

```
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tcggccttgg gtcccctcaa acagattccc atgaatctct tcatcatgta   180
catggcaggc aatactatct ccatcttccc tactatgatg gtgtgtatga tggcctgg    238
```

<210> SEQ ID NO 356
<211> LENGTH: 222
<212> TYPE: DNA
<213> ORGANISM: Artificial Sequence
<220> FEATURE:
<223> OTHER INFORMATION: Synthetic Polynucleotide

<400> SEQUENCE: 356

```
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tcgaacagat tcccatgaat ctcttcatca gtacatggc aggcaatact   180 atctccatct tccctactat gatggtgtgt atgatggcct gg                     222
```

<210> SEQ ID NO 357
<211> LENGTH: 233
<212> TYPE: DNA
<213> ORGANISM: Artificial Sequence
<220> FEATURE:
<223> OTHER INFORMATION: Synthetic Polynucleotide

<400> SEQUENCE: 357

```
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggacc cttgggtccc ctcaaacaga ttcccatgaa tctcttcatc atgtacatgg   180
caggcaatac tatctccatc ttccctacta tgatggtgtg tatgatggcc tgg          233
```

<210> SEQ ID NO 358
<211> LENGTH: 165
<212> TYPE: DNA
<213> ORGANISM: Artificial Sequence
<220> FEATURE:
<223> OTHER INFORMATION: Synthetic Polynucleotide

<400> SEQUENCE: 358

```
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tcttccctac tatgatggtg tgtatgatgg cctgg                  165
```

<210> SEQ ID NO 359
<211> LENGTH: 237
<212> TYPE: DNA
<213> ORGANISM: Artificial Sequence
<220> FEATURE:
<223> OTHER INFORMATION: Synthetic Polynucleotide

<400> SEQUENCE: 359

```
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tctgcttggg tcccctcaaa cagattccca tgaatctctt catcatgtac   180
atggcaggca atactatctc catcttccct actatgatgg tgtgtatgat ggcctgg     237
```

```
<210> SEQ ID NO 360
<211> LENGTH: 225
<212> TYPE: DNA
<213> ORGANISM: Artificial Sequence
<220> FEATURE:
<223> OTHER INFORMATION: Synthetic Polynucleotide

<400> SEQUENCE: 360
agctcagtta gaagcaggga gttgggaatt ccgttcatgt gatttagcat cagtgatatg      60
gcaaatgtgg gactaagggt agtgatcaga gggttaaaat tgtgtgtttt gttttagcgc     120
tgctggggtc ccctcaaaca gattcccatg aatctcttca tcatgtacat ggcaggcaat     180
actatctcca tcttccctac tatgatggtg tgtatgatgg cctgg                    225

<210> SEQ ID NO 361
<211> LENGTH: 228
<212> TYPE: DNA
<213> ORGANISM: Artificial Sequence
<220> FEATURE:
<223> OTHER INFORMATION: Synthetic Polynucleotide

<400> SEQUENCE: 361
agctcagtta gaagcaggga gttgggaatt ccgttcatgt gatttagcat cagtgatatg      60
gcaaatgtgg gactaagggt agtgatcaga gggttaaaat tgtgtgtttt gttttagcgc     120
tgctgtttgg gtcccctcaa acagattccc atgaatctct tcatcatgta catggcaggc     180
aatactatct ccatcttccc tactatgatg gtgtgtatga tggcctgg                 228

<210> SEQ ID NO 362
<211> LENGTH: 233
<212> TYPE: DNA
<213> ORGANISM: Artificial Sequence
<220> FEATURE:
<223> OTHER INFORMATION: Synthetic Polynucleotide

<400> SEQUENCE: 362
agctcagtta gaagcaggga gttgggaatt ccgttcatgt gatttagcat cagtgatatg      60
gcaaatgtgg gactaagggt agtgatcaga gggttaaaat tgtgtgtttt gttttagcgc     120
tgctgggaca tcggggtccc ctcaaacaga ttcccatgaa tctcttcatc atgtacatgg     180
caggcaatac tatctccatc ttccctacta tgatggtgtg tatgatggcc tgg           233

<210> SEQ ID NO 363
<211> LENGTH: 238
<212> TYPE: DNA
<213> ORGANISM: Artificial Sequence
<220> FEATURE:
<223> OTHER INFORMATION: Synthetic Polynucleotide

<400> SEQUENCE: 363
agctcagtta gaagcaggga gttgggaatt ccgttcatgt gatttagcat cagtgatatg      60
gcaaatgtgg gactaagggt agtgatcaga gggttaaaat tgtgtgtttt gttttagcgc     120
tgctgggaca tcgcccttgg gtcccctcaa acagattccc atgaatctct tcatcatgta     180
catggcaggc aatactatct ccatcttccc tactatgatg gtgtgtatga tggcctgg     238

<210> SEQ ID NO 364
<211> LENGTH: 236
<212> TYPE: DNA
<213> ORGANISM: Artificial Sequence
<220> FEATURE:
<223> OTHER INFORMATION: Synthetic Polynucleotide
```

<400> SEQUENCE: 364
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tcccttgggt cccctcaaac agattcccat gaatctcttc atcatgtaca   180
tggcaggcaa tactatctcc atcttcccta ctatgatggt gtgtatgatg gcctgg       236

<210> SEQ ID NO 365
<211> LENGTH: 219
<212> TYPE: DNA
<213> ORGANISM: Artificial Sequence
<220> FEATURE:
<223> OTHER INFORMATION: Synthetic Polynucleotide

<400> SEQUENCE: 365
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca aacagattcc catgaatctc ttcatcatgt acatggcagg caatactatc   180
tccatcttcc ctactatgat ggtgtgtatg atggcctgg                          219

<210> SEQ ID NO 366
<211> LENGTH: 223
<212> TYPE: DNA
<213> ORGANISM: Artificial Sequence
<220> FEATURE:
<223> OTHER INFORMATION: Synthetic Polynucleotide

<400> SEQUENCE: 366
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggacc ctcaaacaga ttcccatgaa tctcttcatc atgtacatgg caggcaatac   180
tatctccatc ttccctacta tgatggtgtg tatgatggcc tgg                     223

<210> SEQ ID NO 367
<211> LENGTH: 222
<212> TYPE: DNA
<213> ORGANISM: Artificial Sequence
<220> FEATURE:
<223> OTHER INFORMATION: Synthetic Polynucleotide

<400> SEQUENCE: 367
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgtcccc tcaaacagat tcccatgaat ctcttcatca tgtacatggc aggcaatact   180
atctccatct tccctactat ggtgtgtgt atgatggcct gg                       222

<210> SEQ ID NO 368
<211> LENGTH: 224
<212> TYPE: DNA
<213> ORGANISM: Artificial Sequence
<220> FEATURE:
<223> OTHER INFORMATION: Synthetic Polynucleotide

<400> SEQUENCE: 368
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tcgcaaacag attcccatga atctcttcat catgtacatg gcaggcaata   180

```
ctatctccat cttccctact atgatggtgt gtatgatggc ctgg          224

<210> SEQ ID NO 369
<211> LENGTH: 214
<212> TYPE: DNA
<213> ORGANISM: Artificial Sequence
<220> FEATURE:
<223> OTHER INFORMATION: Synthetic Polynucleotide

<400> SEQUENCE: 369
agctcagtta gaagcaggga gttgggaatt ccgttcatgt gatttagcat cagtgatatg    60
gcaaatgtgg gactaagggt agtgatcaga gggttaaaat tgtgtgtttt gtttgggtcc   120
cctcaaacag attcccatga atctcttcat catgtacatg gcaggcaata ctatctccat   180
cttccctact atgatggtgt gtatgatggc ctgg                               214

<210> SEQ ID NO 370
<211> LENGTH: 227
<212> TYPE: DNA
<213> ORGANISM: Artificial Sequence
<220> FEATURE:
<223> OTHER INFORMATION: Synthetic Polynucleotide

<400> SEQUENCE: 370
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tcgcctcaaa cagattccca tgaatctctt catcatgtac atggcaggca   180
atactatctc catcttccct actatgatgg tgtgtatgat ggcctgg                 227

<210> SEQ ID NO 371
<211> LENGTH: 203
<212> TYPE: DNA
<213> ORGANISM: Artificial Sequence
<220> FEATURE:
<223> OTHER INFORMATION: Synthetic Polynucleotide

<400> SEQUENCE: 371
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tctcttcatc atgtacatgg caggcaatac tatctccatc ttccctacta   180
tgatggtgtg tatgatggcc tgg                                           203

<210> SEQ ID NO 372
<211> LENGTH: 207
<212> TYPE: DNA
<213> ORGANISM: Artificial Sequence
<220> FEATURE:
<223> OTHER INFORMATION: Synthetic Polynucleotide

<400> SEQUENCE: 372
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tgaatctctt catcatgtac atggcaggca atactatctc catcttccct   180
actatgatgg tgtgtatgat ggcctgg                                       207

<210> SEQ ID NO 373
<211> LENGTH: 234
<212> TYPE: DNA
```

<213> ORGANISM: Artificial Sequence
<220> FEATURE:
<223> OTHER INFORMATION: Synthetic Polynucleotide

<400> SEQUENCE: 373

```
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tcttgggtcc cctcaaacag attcccatga atctcttcat catgtacatg   180
gcaggcaata ctatctccat cttccctact atgatggtgt gtatgatggc ctgg         234
```

<210> SEQ ID NO 374
<211> LENGTH: 223
<212> TYPE: DNA
<213> ORGANISM: Artificial Sequence
<220> FEATURE:
<223> OTHER INFORMATION: Synthetic Polynucleotide

<400> SEQUENCE: 374

```
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
cttgggtccc ctcaaacaga ttcccatgaa tctcttcatc atgtacatgg caggcaatac   180
tatctccatc ttccctacta tgatggtgtg tatgatggcc tgg                     223
```

<210> SEQ ID NO 375
<211> LENGTH: 195
<212> TYPE: DNA
<213> ORGANISM: Artificial Sequence
<220> FEATURE:
<223> OTHER INFORMATION: Synthetic Polynucleotide

<400> SEQUENCE: 375

```
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tcatgtacat ggcaggcaat actatctcca tcttccctac tatgatggtg   180
tgtatgatgg cctgg                                                    195
```

<210> SEQ ID NO 376
<211> LENGTH: 230
<212> TYPE: DNA
<213> ORGANISM: Artificial Sequence
<220> FEATURE:
<223> OTHER INFORMATION: Synthetic Polynucleotide

<400> SEQUENCE: 376

```
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tcgtccctc aaacagattc catgaatct cttcatcatg tacatggcag    180
gcaatactat ctccatcttc cctactatga tggtgtgtat gatggcctgg              230
```

<210> SEQ ID NO 377
<211> LENGTH: 229
<212> TYPE: DNA
<213> ORGANISM: Artificial Sequence
<220> FEATURE:
<223> OTHER INFORMATION: Synthetic Polynucleotide

<400> SEQUENCE: 377

```
agctcagtta gaagcaggga gttgggaatt ccgttcatgt gatttagcat cagtgatatg    60
```

```
gcaaatgtgg gactaagggt agtgatcaga gggttaaaat tgtgtgtttt gttttagcgc    120
tgctgccttg ggtcccctca aacagattcc catgaatctc ttcatcatgt acatggcagg    180
caatactatc tccatcttcc ctactatgat ggtgtgtatg atggcctgg               229
```

<210> SEQ ID NO 378
<211> LENGTH: 186
<212> TYPE: DNA
<213> ORGANISM: Artificial Sequence
<220> FEATURE:
<223> OTHER INFORMATION: Synthetic Polynucleotide

<400> SEQUENCE: 378

```
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tggcaggcaa tactatctcc atcttcccta ctatgatggt gtgtatgatg   180
gcctgg                                                              186
```

<210> SEQ ID NO 379
<211> LENGTH: 215
<212> TYPE: DNA
<213> ORGANISM: Artificial Sequence
<220> FEATURE:
<223> OTHER INFORMATION: Synthetic Polynucleotide

<400> SEQUENCE: 379

```
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctcaaaca gattcccatg aatctcttca tcatgtacat ggcaggcaat actatctcca   180
tcttccctac tatgatggtg tgtatgatgg cctgg                              215
```

<210> SEQ ID NO 380
<211> LENGTH: 171
<212> TYPE: DNA
<213> ORGANISM: Artificial Sequence
<220> FEATURE:
<223> OTHER INFORMATION: Synthetic Polynucleotide

<400> SEQUENCE: 380

```
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tctccatctt ccctactatg atggtgtgta tgatggcctg g            171
```

<210> SEQ ID NO 381
<211> LENGTH: 228
<212> TYPE: DNA
<213> ORGANISM: Artificial Sequence
<220> FEATURE:
<223> OTHER INFORMATION: Synthetic Polynucleotide

<400> SEQUENCE: 381

```
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tcgccctcaa acagattccc atgaatctct tcatcatgta catggcaggc   180
aatactatct ccatcttccc tactatgatg gtgtgtatga tggcctgg                228
```

<210> SEQ ID NO 382

```
<211> LENGTH: 229
<212> TYPE: DNA
<213> ORGANISM: Artificial Sequence
<220> FEATURE:
<223> OTHER INFORMATION: Synthetic Polynucleotide

<400> SEQUENCE: 382
agctcagtta gaagcaggga gttgggaatt ccgttcatgt gatttagcat cagtgatatg     60
gcaaatgtgg gactaagggt agtgatcaga gggttaaaat tgtgtgtttt gttttagcgc    120
tgctgggaca tcgcccctca aacagattcc catgaatctc ttcatcatgt acatggcagg   180
caatactatc tccatcttcc ctactatgat ggtgtgtatg atggcctgg               229

<210> SEQ ID NO 383
<211> LENGTH: 221
<212> TYPE: DNA
<213> ORGANISM: Artificial Sequence
<220> FEATURE:
<223> OTHER INFORMATION: Synthetic Polynucleotide

<400> SEQUENCE: 383
agctcagtta gaagcaggga gttgggaatt ccgttcatgt gatttagcat cagtgatatg     60
gcaaatgtgg gactaagggt agtgatcaga gggttaaaat tgtgtgtttt gttttagcgc    120
tgctgggaca tcgacagatt cccatgaatc tcttcatcat gtacatggca ggcaatacta   180
tctccatctt ccctactatg atggtgtgta tgatggcctg g                       221

<210> SEQ ID NO 384
<211> LENGTH: 212
<212> TYPE: DNA
<213> ORGANISM: Artificial Sequence
<220> FEATURE:
<223> OTHER INFORMATION: Synthetic Polynucleotide

<400> SEQUENCE: 384
agctcagtta gaagcaggga gttgggaatt ccgttcatgt gatttagcat cagtgatatg     60
gcaaatgtgg gactaagggt agtgatcaga gggttaaaat tgtgtgtttt gttttagcgc    120
tgctgggaca tcccatgaat ctcttcatca tgtacatggc aggcaatact atctccatct   180
tccctactat gatggtgtgt atgatggcct gg                                 212

<210> SEQ ID NO 385
<211> LENGTH: 226
<212> TYPE: DNA
<213> ORGANISM: Artificial Sequence
<220> FEATURE:
<223> OTHER INFORMATION: Synthetic Polynucleotide

<400> SEQUENCE: 385
agctcagtta gaagcaggga gttgggaatt ccgttcatgt gatttagcat cagtgatatg     60
gcaaatgtgg gactaagggt agtgatcaga gggttaaaat tgtgtgtttt gttttagcgc    120
tgctgggaca tcgctcaaac agattcccat gaatctcttc atcatgtaca tggcaggcaa   180
tactatctcc atcttcccta ctatgatggt gtgtatgatg gcctgg                  226

<210> SEQ ID NO 386
<211> LENGTH: 236
<212> TYPE: DNA
<213> ORGANISM: Artificial Sequence
<220> FEATURE:
<223> OTHER INFORMATION: Synthetic Polynucleotide

<400> SEQUENCE: 386
```

```
agctcagtta gaagcaggga gttgggaatt ccgttcatgt gatttagcat cagtgatatg      60
gcaaatgtgg gactaagggt agtgatcaga gggttaaaat tgtgtgtttt gttttagcgc     120
tgctgggaca tcgtttgggt ccactcaaac agattcccat gaatctcttc atcatgtaca     180
tggcaggcaa tactatctcc atcttcccta ctatgatggt gtgtatgatg gcctgg        236

<210> SEQ ID NO 387
<211> LENGTH: 190
<212> TYPE: DNA
<213> ORGANISM: Artificial Sequence
<220> FEATURE:
<223> OTHER INFORMATION: Synthetic Polynucleotide

<400> SEQUENCE: 387
agctcagtta gaagcaggga gttgggaatt ccgttcatgt gatttagcat cagtgatatg      60
gcaaatgtgg gactaagggt agtgatcaga gggtccccctc aaacagattc ccatgaatct    120
cttcatcatg tacatggcag gcaatactat ctccatcttc cctactatga tggtgtgtat    180
gatggcctgg                                                            190

<210> SEQ ID NO 388
<211> LENGTH: 224
<212> TYPE: DNA
<213> ORGANISM: Artificial Sequence
<220> FEATURE:
<223> OTHER INFORMATION: Synthetic Polynucleotide

<400> SEQUENCE: 388
agctcagtta gaagcaggga gttgggaatt ccgttcatgt gatttagcat cagtgatatg      60
gcaaatgtgg gactaagggt agtgatcaga gggttaaaat tgtgtgtttt gttttagcgc     120
tgttgggtcc cctcaaacag attcccatga atctcttcat catgtacatg gcaggcaata     180
ctatctccat cttccctact atgatggtgt gtatgatggc ctgg                       224

<210> SEQ ID NO 389
<211> LENGTH: 211
<212> TYPE: DNA
<213> ORGANISM: Artificial Sequence
<220> FEATURE:
<223> OTHER INFORMATION: Synthetic Polynucleotide

<400> SEQUENCE: 389
agctcagtta gaagcaggga gttgggaatt ccgttcatgt gatttagcat cagtgatatg      60
gcaaatgtgg gactaagggt agtgatcaga gggttaaaat tgtgtgtttt gttttagcgc     120
tgctgggatt cccatgaatc tcttcatcat gtacatggca ggcaatacta tctccatctt    180
ccctactatg atggtgtgta tgatggcctg g                                    211

<210> SEQ ID NO 390
<211> LENGTH: 177
<212> TYPE: DNA
<213> ORGANISM: Artificial Sequence
<220> FEATURE:
<223> OTHER INFORMATION: Synthetic Polynucleotide

<400> SEQUENCE: 390
agctcagtta gaagcaggga gttgggaatt ccgttcatgt gatttagcat cagtgatatg      60
gcaaatgtgg gactaagggt agtgatcaga gggttaaaat tgtgtgtttt gttttagcgc     120
tgctgggaca atactatctc catcttccct actatgatgg tgtgtatgat ggcctgg        177
```

<210> SEQ ID NO 391
<211> LENGTH: 225
<212> TYPE: DNA
<213> ORGANISM: Artificial Sequence
<220> FEATURE:
<223> OTHER INFORMATION: Synthetic Polynucleotide

<400> SEQUENCE: 391
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tccttgggtc ccctcaaaca gattcccatg aatctcttca tcatgtacat ggcaggcaat   180
actatctcca tcttccctac tatgatggtg tgtatgatgg cctgg                   225

<210> SEQ ID NO 392
<211> LENGTH: 209
<212> TYPE: DNA
<213> ORGANISM: Artificial Sequence
<220> FEATURE:
<223> OTHER INFORMATION: Synthetic Polynucleotide

<400> SEQUENCE: 392
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgcagattcc catgaatctc ttcatcatgt acatggcagg caatactatc tccatcttcc   180
ctactatgat ggtgtgtatg atggcctgg                                      209

<210> SEQ ID NO 393
<211> LENGTH: 233
<212> TYPE: DNA
<213> ORGANISM: Artificial Sequence
<220> FEATURE:
<223> OTHER INFORMATION: Synthetic Polynucleotide

<400> SEQUENCE: 393
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tcgatgtccc ctcaaacaga ttcccatgaa tctcttcatc atgtacatgg   180
caggcaatac tatctccatc ttccctacta tgatggtgtg tatgatggcc tgg          233

<210> SEQ ID NO 394
<211> LENGTH: 237
<212> TYPE: DNA
<213> ORGANISM: Artificial Sequence
<220> FEATURE:
<223> OTHER INFORMATION: Synthetic Polynucleotide

<400> SEQUENCE: 394
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tcgctttggg tcccctcaaa cagattccca tgaatctctt catcatgtac   180
atggcaggca atactatctc catcttccct actatgatgg tgtgtatgat ggcctgg      237

<210> SEQ ID NO 395
<211> LENGTH: 225
<212> TYPE: DNA
<213> ORGANISM: Artificial Sequence
<220> FEATURE:
<223> OTHER INFORMATION: Synthetic Polynucleotide

<400> SEQUENCE: 395
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tcctcaaaca gattcccatg aatctcttca tcatgtacat ggcaggcaat   180
actatctcca tcttccctac tatgatggtg tgtatgatgg cctgg                  225

<210> SEQ ID NO 396
<211> LENGTH: 218
<212> TYPE: DNA
<213> ORGANISM: Artificial Sequence
<220> FEATURE:
<223> OTHER INFORMATION: Synthetic Polynucleotide

<400> SEQUENCE: 396
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tcagattccc atgaatctct tcatcatgta catggcaggc aatactatct   180
ccatcttccc tactatgatg gtgtgtatga tggcctgg                          218

<210> SEQ ID NO 397
<211> LENGTH: 228
<212> TYPE: DNA
<213> ORGANISM: Artificial Sequence
<220> FEATURE:
<223> OTHER INFORMATION: Synthetic Polynucleotide

<400> SEQUENCE: 397
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctccttgg gtcccctcaa acagattccc atgaatctct tcatcatgta catggcaggc   180
aatactatct ccatcttccc tactatgatg gtgtgtatga tggcctgg                228

<210> SEQ ID NO 398
<211> LENGTH: 220
<212> TYPE: DNA
<213> ORGANISM: Artificial Sequence
<220> FEATURE:
<223> OTHER INFORMATION: Synthetic Polynucleotide

<400> SEQUENCE: 398
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tcgcagattc ccatgaatct cttcatcatg tacatggcag gcaatactat   180
ctccatcttc cctactatga tggtgtgtat gatggcctgg                        220

<210> SEQ ID NO 399
<211> LENGTH: 222
<212> TYPE: DNA
<213> ORGANISM: Artificial Sequence
<220> FEATURE:
<223> OTHER INFORMATION: Synthetic Polynucleotide

<400> SEQUENCE: 399
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120

```
ttgggtcccc tcaaacagat tcccatgaat ctcttcatca tgtacatggc aggcaatact    180
atctccatct tccctactat gatggtgtgt atgatggcct gg                       222
```

<210> SEQ ID NO 400
<211> LENGTH: 223
<212> TYPE: DNA
<213> ORGANISM: Artificial Sequence
<220> FEATURE:
<223> OTHER INFORMATION: Synthetic Polynucleotide

<400> SEQUENCE: 400

```
agctcagtta gaagcaggga gttgggaatt ccgttcatgt gatttagcat cagtgatatg     60
gcaaatgtgg gactaagggt agtgatcaga gggttaaaat tgtgtgtttt gttttagcgc    120
tgctgggaca tcgaaacaga ttcccatgaa tctcttcatc atgtacatgg caggcaatac    180
tatctccatc ttccctacta tgatggtgtg tatgatggcc tgg                     223
```

<210> SEQ ID NO 401
<211> LENGTH: 222
<212> TYPE: DNA
<213> ORGANISM: Artificial Sequence
<220> FEATURE:
<223> OTHER INFORMATION: Synthetic Polynucleotide

<400> SEQUENCE: 401

```
agctcagtta gaagcaggga gttgggaatt ccgttcatgt gatttagcat cagtgatatg     60
gcaaatgtgg gactaagggt agtgatcaga gggttaaaat tgtgtgtttt gttttagcgc    120
tgctgggacc tcaaacagat tcccatgaat ctcttcatca tgtacatggc aggcaatact    180
atctccatct tccctactat gatggtgtgt atgatggcct gg                       222
```

<210> SEQ ID NO 402
<211> LENGTH: 221
<212> TYPE: DNA
<213> ORGANISM: Artificial Sequence
<220> FEATURE:
<223> OTHER INFORMATION: Synthetic Polynucleotide

<400> SEQUENCE: 402

```
agctcagtta gaagcaggga gttgggaatt ccgttcatgt gatttagcat cagtgatatg     60
gcaaatgtgg gactaagggt agtgatcaga gggttaaaat tgtgtgtttt gttttagcct    120
tgggtcccct caaacagatt cccatgaatc tcttcatcat gtacatggca ggcaatacta    180
tctccatctt ccctactatg atggtgtgta tgatggcctg g                        221
```

<210> SEQ ID NO 403
<211> LENGTH: 210
<212> TYPE: DNA
<213> ORGANISM: Artificial Sequence
<220> FEATURE:
<223> OTHER INFORMATION: Synthetic Polynucleotide

<400> SEQUENCE: 403

```
agctcagtta gaagcaggga gttgggaatt ccgttcatgt gatttagcat cagtgatatg     60
gcaaatgtgg gactaagggt agtgatcaga gggttaaaat tgtgtgtttt gggtcccctc    120
aaacagattc ccatgaatct cttcatcatg tacatggcag gcaatactat ctccatcttc    180
cctactatga tggtgtgtat gatggcctgg                                     210
```

<210> SEQ ID NO 404
<211> LENGTH: 208

```
<212> TYPE: DNA
<213> ORGANISM: Artificial Sequence
<220> FEATURE:
<223> OTHER INFORMATION: Synthetic Polynucleotide

<400> SEQUENCE: 404
agctcagtta gaagcaggga gttgggaatt ccgttcatgt gatttagcat cagtgatatg      60
gcaaatgtgg gactaagggt agtgatcaga gggttaaaat tgtgtgtttt gtcccctcaa     120
acagattccc atgaatctct tcatcatgta catggcaggc aatactatct ccatcttccc     180
tactatgatg gtgtgtatga tggcctgg                                        208

<210> SEQ ID NO 405
<211> LENGTH: 143
<212> TYPE: DNA
<213> ORGANISM: Artificial Sequence
<220> FEATURE:
<223> OTHER INFORMATION: Synthetic Polynucleotide

<400> SEQUENCE: 405
agctcagtta gaagcaggga gttgggaatt ccgttcatgt gatttagcat cagtgatatg      60
gcaaatgtgg gactaagggt agtgatcaga gggttaaaat tgtgtgtttt gttttagcgc     120
tgctggtgtg tatgatggcc tgg                                             143

<210> SEQ ID NO 406
<211> LENGTH: 176
<212> TYPE: DNA
<213> ORGANISM: Artificial Sequence
<220> FEATURE:
<223> OTHER INFORMATION: Synthetic Polynucleotide

<400> SEQUENCE: 406
agctcagtta gaagcaggga gttgggaatt ccgttcatgt gatttagcat cagtgatatg      60
gcaaatgtgg gactaagggt agtgatcaga gggttaaaat tgtgtgtttt gttttagcgc     120
tgctgggaca tactatctcc atcttcccta ctatgatggt gtgtatgatg gcctgg         176

<210> SEQ ID NO 407
<211> LENGTH: 237
<212> TYPE: DNA
<213> ORGANISM: Artificial Sequence
<220> FEATURE:
<223> OTHER INFORMATION: Synthetic Polynucleotide

<400> SEQUENCE: 407
agctcagtta gaagcaggga gttgggaatt ccgttcatgt gatttagcat cagtgatatg      60
gcaaatgtgg gactaagggt agtgatcaga gggttaaaat tgtgtgtttt gttttagcgc     120
tgctgggaca tcgccttggg tcccctcaaa cagattccca tgaatctctt catcatgtac     180
atggcgggca atactatctc catcttccct actatgatgg tgtgtatgat ggcctgg        237

<210> SEQ ID NO 408
<211> LENGTH: 217
<212> TYPE: DNA
<213> ORGANISM: Artificial Sequence
<220> FEATURE:
<223> OTHER INFORMATION: Synthetic Polynucleotide

<400> SEQUENCE: 408
agctcagtta gaagcaggga gttgggaatt ccgttcatgt gatttagcat cagtgatatg      60
gcaaatgtgg gactaagggt agtgatcaga gggttaaaat tgtgtgtttt gttttagcgc     120
```
tgctgggaca tcgattccca tgaatctctt catcatgtac atggcaggca atactatctc   180
catcttccct actatgatgg tgtgtatgat ggcctgg                            217

<210> SEQ ID NO 409
<211> LENGTH: 202
<212> TYPE: DNA
<213> ORGANISM: Artificial Sequence
<220> FEATURE:
<223> OTHER INFORMATION: Synthetic Polynucleotide

<400> SEQUENCE: 409
agctcagtta gaagcaggga gttgggaatt ccgttcatgt gatttagcat cagtgatatg   60
gcaaatgtgg gactaagggt agtgatcaga gggttaaaat tgtgtgtttt gttttagcgc   120
tgccatgaat ctcttcatca tgtacatggc aggcaatact atctccatct tccctactat   180
gatggtgtgt atgatggcct gg                                            202

<210> SEQ ID NO 410
<211> LENGTH: 213
<212> TYPE: DNA
<213> ORGANISM: Artificial Sequence
<220> FEATURE:
<223> OTHER INFORMATION: Synthetic Polynucleotide

<400> SEQUENCE: 410
agctcagtta gaagcaggga gttgggaatt ccgttcatgt gatttagcat cagtgatatg   60
gcaaatgtgg gactaagggt agtgatcaga gggttaaaat tgtgtgtttt gttttagcgc   120
tgcaaacaga ttcccatgaa tctcttcatc atgtacatgg caggcaatac tatctccatc   180
ttccctacta tgatggtgtg tatgatggcc tgg                                213

<210> SEQ ID NO 411
<211> LENGTH: 237
<212> TYPE: DNA
<213> ORGANISM: Artificial Sequence
<220> FEATURE:
<223> OTHER INFORMATION: Synthetic Polynucleotide

<400> SEQUENCE: 411
agctcagtta gaagcaggga gttgggaatt ccgttcatgt gatttagcat cagtgatatg   60
gcaaatgtgg gactaagggt agtgatcaga gggttaaaat tgtgtgtttt gttttagcgc   120
tgctggggca tcgccttggg tcccctcaaa cagattccca tgaatctctt catcatgtac   180
atggcaggca atactatctc catcttccct actatgatgg tgtgtatgat ggcctgg     237

<210> SEQ ID NO 412
<211> LENGTH: 237
<212> TYPE: DNA
<213> ORGANISM: Artificial Sequence
<220> FEATURE:
<223> OTHER INFORMATION: Synthetic Polynucleotide

<400> SEQUENCE: 412
agctcagtta gaagcaggga gttgggaatt ccgttcacgt gatttagcat cagtgatatg   60
gcaaatgtgg gactaagggt agtgatcaga gggttaaaat tgtgtgtttt gttttagcgc   120
tgctgggaca tcgccttggg tcccctcaaa cagattccca tgaatctctt catcatgtac   180
atggcaggca atactatctc catcttccct actatgatgg tgtgtatgat ggcctgg     237

<210> SEQ ID NO 413
<211> LENGTH: 238

<210> SEQ ID NO 413
<211> LENGTH: 238
<212> TYPE: DNA
<213> ORGANISM: Artificial Sequence
<220> FEATURE:
<223> OTHER INFORMATION: Synthetic Polynucleotide

<400> SEQUENCE: 413

```
agctcagtta gaagcaggga gttgggaatt ccgttcatgt gatttagcat cagtgatatg      60
gcaaatgtgg gactaagggt agtgatcaga gggttaaaat tgtgtgtttt gttttagcgc     120
tgctgggaca tcgtccttgg gtcccctcaa acagattccc atgaatctct tcatcatgta     180
catggcaggc aatactatct ccatcttccc tactatgatg gtgtgtatga tggcctgg      238
```

<210> SEQ ID NO 414
<211> LENGTH: 237
<212> TYPE: DNA
<213> ORGANISM: Artificial Sequence
<220> FEATURE:
<223> OTHER INFORMATION: Synthetic Polynucleotide

<400> SEQUENCE: 414

```
agctcagtta gaagcaggga gttgggaatt ccgttcatgt gatttagcat cagtgatatg      60
gcaaatgtgg gactaagggt agtgatcaga gggttaaaat tgtgtgtttt gttttagcgc     120
tgctgggaca tcgccttggg tcccctcaaa cagattccca tgaatctcct catcatgtac     180
atggcaggca atactatctc catcttccct actatgatgg tgtgtatgat ggcctgg       237
```

<210> SEQ ID NO 415
<211> LENGTH: 231
<212> TYPE: DNA
<213> ORGANISM: Artificial Sequence
<220> FEATURE:
<223> OTHER INFORMATION: Synthetic Polynucleotide

<400> SEQUENCE: 415

```
agctcagtta gaagcaggga gttgggaatt ccgttcatgt gatttagcat cagtgatatg      60
gcaaatgtgg gactaagggt agtgatcaga gggttaaaat tgtgtgtttt gttttagcgc     120
tgctgggaca tctgtcccct caaacagatt cccatgaatc tcttcatcat gtacatggca     180
ggcaatacta tctccatctt ccctactatg atggtgtgta tgatggcctg g             231
```

<210> SEQ ID NO 416
<211> LENGTH: 218
<212> TYPE: DNA
<213> ORGANISM: Artificial Sequence
<220> FEATURE:
<223> OTHER INFORMATION: Synthetic Polynucleotide

<400> SEQUENCE: 416

```
agctcagtta gaagcaggga gttgggaatt ccgttcatgt gatttagcat cagtgatatg      60
gcaaatgtgg gactaagggt agtgatcaga gggttaaaat tgtgtgtttt gttttagcgc     120
tgcccctcaa acagattccc atgaatctct tcatcatgta catggcaggc aatactatct     180
ccatcttccc tactatgatg gtgtgtatga tggcctgg                            218
```

<210> SEQ ID NO 417
<211> LENGTH: 165
<212> TYPE: DNA
<213> ORGANISM: Artificial Sequence
<220> FEATURE:
<223> OTHER INFORMATION: Synthetic Polynucleotide

<400> SEQUENCE: 417
agctcagtta gaagcaggga gttgggaatt ccgttcatgt gatttagcat cagtgatatg    60
gcaaatgtgg gactaagggt agtgatcaga gggttaaaat tgtgtgtttt ggtaggcaat   120
actatctcca tcttccctac tatgatggtg tgtatgatgg cctgg                   165

<210> SEQ ID NO 418
<211> LENGTH: 237
<212> TYPE: DNA
<213> ORGANISM: Artificial Sequence
<220> FEATURE:
<223> OTHER INFORMATION: Synthetic Polynucleotide

<400> SEQUENCE: 418
agctcagtta gaagcaggga gttgggaatt ccgctcatgt gatttagcat cagtgatatg    60
gcaaatgtgg gactaagggt agtgatcaga gggttaaaat tgtgtgtttt gttttagcgc   120
tgctgggaca tcgccttggg tcccctcaaa cagattccca tgaatctctt catcatgtac   180
atggcaggca atactatctc catcttccct actatgatgg tgtgtatgat ggcctgg      237

<210> SEQ ID NO 419
<211> LENGTH: 230
<212> TYPE: DNA
<213> ORGANISM: Artificial Sequence
<220> FEATURE:
<223> OTHER INFORMATION: Synthetic Polynucleotide

<400> SEQUENCE: 419
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctggcctt gggtcccctc aaacagattc ccatgaatct cttcatcatg tacatggcag   180
gcaatactat ctccatcttc cctactatga tggtgtgtat gatggcctgg              230

<210> SEQ ID NO 420
<211> LENGTH: 203
<212> TYPE: DNA
<213> ORGANISM: Artificial Sequence
<220> FEATURE:
<223> OTHER INFORMATION: Synthetic Polynucleotide

<400> SEQUENCE: 420
agctcagtta gaagcaggga gttgggaatt ccgttcatgt gatttagcat cagtgatatg    60
gcaaatgtgg gactaagggt agtgatcaga gggttaaaat tgtgtgtccc ctcaaacaga   120
ttcccatgaa tctcttcatc atgtacatgg caggcaatac tatctccatc ttccctacta   180
tgatggtgtg tatgatggcc tgg                                           203

<210> SEQ ID NO 421
<211> LENGTH: 221
<212> TYPE: DNA
<213> ORGANISM: Artificial Sequence
<220> FEATURE:
<223> OTHER INFORMATION: Synthetic Polynucleotide

<400> SEQUENCE: 421
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgggtcccct caaacagatt cccatgaatc tcttcatcat gtacatggca ggcaatacta   180
tctccatctt ccctactatg atggtgtgta tgatggcctg g                       221

```
<210> SEQ ID NO 422
<211> LENGTH: 237
<212> TYPE: DNA
<213> ORGANISM: Artificial Sequence
<220> FEATURE:
<223> OTHER INFORMATION: Synthetic Polynucleotide

<400> SEQUENCE: 422
agctcagtta gaagcaggga gttgggaatt ccgttcatgt gatttagcat cagtgatatg      60
gcaaatgtgg gactaagggt agtgatcaga gggttaaaat tgtgtgtttt gttttagcgc     120
tgctgggaca tcgccttggg tcccctcaaa cagattccca tgaatctctt catcatgtac     180
gtggcaggca atactatctc catcttccct actatgatgg tgtgtatgat ggcctgg        237

<210> SEQ ID NO 423
<211> LENGTH: 231
<212> TYPE: DNA
<213> ORGANISM: Artificial Sequence
<220> FEATURE:
<223> OTHER INFORMATION: Synthetic Polynucleotide

<400> SEQUENCE: 423
agctcagtta gaagcaggga gttgggaatt ccgttcatgt gatttagcat cagtgatatg      60
gcaaatgtgg gactaagggt agtgatcaga gggttaaaat tgtgtgtttt gttttagcgc     120
tgctgggaca tgggtcccct caaacagatt cccatgaatc tcttcatcat gtacatggca     180
ggcaatacta tctccatctt ccctactatg atggtgtgta tgatggcctg g              231

<210> SEQ ID NO 424
<211> LENGTH: 201
<212> TYPE: DNA
<213> ORGANISM: Artificial Sequence
<220> FEATURE:
<223> OTHER INFORMATION: Synthetic Polynucleotide

<400> SEQUENCE: 424
agctcagtta gaagcaggga gttgggaatt ccgttcatgt gatttagcat cagtgatatg      60
gcaaatgtgg gactaagggt agtgatcaga gggttaaaat tgtgtgtttt gttttagcgc     120
tgctgggaca tcttcatcat gtacatggca ggcaatacta tctccatctt ccctactatg     180
atggtgtgta tgatggcctg g                                               201

<210> SEQ ID NO 425
<211> LENGTH: 237
<212> TYPE: DNA
<213> ORGANISM: Artificial Sequence
<220> FEATURE:
<223> OTHER INFORMATION: Synthetic Polynucleotide

<400> SEQUENCE: 425
agctcagtta gaagcaggga gttgggaatt ccgttcatgc gatttagcat cagtgatatg      60
gcaaatgtgg gactaagggt agtgatcaga gggttaaaat tgtgtgtttt gttttagcgc     120
tgctgggaca tcgccttggg tcccctcaaa cagattccca tgaatctctt catcatgtac     180
atggcaggca atactatctc catcttccct actatgatgg tgtgtatgat ggcctgg        237

<210> SEQ ID NO 426
<211> LENGTH: 237
<212> TYPE: DNA
<213> ORGANISM: Artificial Sequence
<220> FEATURE:
<223> OTHER INFORMATION: Synthetic Polynucleotide
```

<400> SEQUENCE: 426

```
agctcagtta gaagcaggga gttgggaatt ccgtccatgt gatttagcat cagtgatatg    60
gcaaatgtgg gactaagggt agtgatcaga gggttaaaat tgtgtgtttt gttttagcgc   120
tgctgggaca tcgccttggg tcccctcaaa cagattccca tgaatctctt catcatgtac   180
atggcaggca atactatctc catcttccct actatgatgg tgtgtatgat ggcctgg      237
```

<210> SEQ ID NO 427
<211> LENGTH: 238
<212> TYPE: DNA
<213> ORGANISM: Artificial Sequence
<220> FEATURE:
<223> OTHER INFORMATION: Synthetic Polynucleotide

<400> SEQUENCE: 427

```
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tcgaccttgg gtcccctcaa acagattccc atgaatctct tcatcatgta   180
catggcaggc aatactatct ccatcttccc tactatgatg gtgtgtatga tggcctgg    238
```

<210> SEQ ID NO 428
<211> LENGTH: 237
<212> TYPE: DNA
<213> ORGANISM: Artificial Sequence
<220> FEATURE:
<223> OTHER INFORMATION: Synthetic Polynucleotide

<400> SEQUENCE: 428

```
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tcgccttggg tcccctcaaa cagattccca tgaatctctt catcatgtac   180
atggcaggca atactatctc catcttccct actatggtgg tgtgtatgat ggcctgg      237
```

<210> SEQ ID NO 429
<211> LENGTH: 237
<212> TYPE: DNA
<213> ORGANISM: Artificial Sequence
<220> FEATURE:
<223> OTHER INFORMATION: Synthetic Polynucleotide

<400> SEQUENCE: 429

```
agctcagtta gaagcaggga gttgggaatt ccgttcatgt gatttagcat cagtgatatg    60
gcaaatgtgg gactaagggt agtgatcaga gggttaaaat tgcgtgtttt gttttagcgc   120
tgctgggaca tcgccttggg tcccctcaaa cagattccca tgaatctctt catcatgtac   180
atggcaggca atactatctc catcttccct actatgatgg tgtgtatgat ggcctgg      237
```

<210> SEQ ID NO 430
<211> LENGTH: 226
<212> TYPE: DNA
<213> ORGANISM: Artificial Sequence
<220> FEATURE:
<223> OTHER INFORMATION: Synthetic Polynucleotide

<400> SEQUENCE: 430

```
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggaca tccctcaaac agattcccat gaatctcttc atcatgtaca tggcaggcaa   180
```

```
tactatctcc atcttccta ctatgatggt gtgtatgatg gcctgg            226
```

```
<210> SEQ ID NO 431
<211> LENGTH: 237
<212> TYPE: DNA
<213> ORGANISM: Artificial Sequence
<220> FEATURE:
<223> OTHER INFORMATION: Synthetic Polynucleotide

<400> SEQUENCE: 431
agctcagtta gaagcaggga gttgggaatt ccgttcatgt gatttagcat cagtgatatg    60
gcaaatgtgg gactaagggt agtgatcaga gggttaaaat tgtgtgcttt gttttagcgc   120
tgctgggaca tcgccttggg tcccctcaaa cagattccca tgaatctctt catcatgtac   180
atggcaggca atactatctc catcttccct actatgatgg tgtgtatgat ggcctgg     237
```

```
<210> SEQ ID NO 432
<211> LENGTH: 231
<212> TYPE: DNA
<213> ORGANISM: Artificial Sequence
<220> FEATURE:
<223> OTHER INFORMATION: Synthetic Polynucleotide

<400> SEQUENCE: 432
agctcagtta gaagcaggga gttgggaatt ccgttcatgt gatttagcat cagtgatatg    60
gcaaatgtgg gactaagggt agtgatcaga gggttaaaat tgtgtgtttt gttttagcgc   120
tgctgggcct tgggtcccct caaacagatt cccatgaatc tcttcatcat gtacatggca   180
ggcaatacta tctccatctt ccctactatg atggtgtgta tgatggcctg g           231
```

```
<210> SEQ ID NO 433
<211> LENGTH: 123
<212> TYPE: DNA
<213> ORGANISM: Artificial Sequence
<220> FEATURE:
<223> OTHER INFORMATION: Synthetic Polynucleotide

<400> SEQUENCE: 433
agctcagtta gaagcaggga gttgggtccc ctcaaacaga ttcccatgaa tctcttcatc    60
atgtacatgg caggcaatac tatctccatc ttccctacta tgatggtgtg tatgatggcc   120
tgg                                                                 123
```

```
<210> SEQ ID NO 434
<211> LENGTH: 240
<212> TYPE: DNA
<213> ORGANISM: Artificial Sequence
<220> FEATURE:
<223> OTHER INFORMATION: Synthetic Polynucleotide

<400> SEQUENCE: 434
gactattgca aatctctccc cctttcagat tcccctcggc gactctggtg gtatcactgg    60
atttgctggc ttctcagcgt agttggaatc ttctgtattc tcttagcgca tgaccactac   120
actgtggacg tggtggtggc atattacatc accacgagac tcttctggtg gtatcacact   180
atggccaatc agcaagtgag tttccccgct tttgatttta gcttctgttg tttctggctt   240
```

```
<210> SEQ ID NO 435
<211> LENGTH: 241
<212> TYPE: DNA
<213> ORGANISM: Artificial Sequence
<220> FEATURE:
```

<223> OTHER INFORMATION: Synthetic Polynucleotide

<400> SEQUENCE: 435

| gactattgca aatctctccc cctttcagat tcccctcggc gactctggtg gtatcactgg | 60 |
| atttgctggc ttctcagcgt agttggaatc ttctgtattc tcttagcgca tgaccactac | 120 |
| aactgtggac gtggtggtgg catattacat caccacgaga ctcttctggt ggtatcacac | 180 |
| tatggccaat cagcaagtga gtttccccgc ttttgatttt agcttctgtt gtttctggct | 240 |
| t | 241 |

<210> SEQ ID NO 436
<211> LENGTH: 240
<212> TYPE: DNA
<213> ORGANISM: Artificial Sequence
<220> FEATURE:
<223> OTHER INFORMATION: Synthetic Polynucleotide

<400> SEQUENCE: 436

| gactattgca aatctctccc cctttcagat tcccctcggc gactctggtg gtatcactgg | 60 |
| atttgctggc ttctcagcgt agttggaatc ttctgtattc tcttagcgca tgaccactac | 120 |
| actgtggacg tggtggtggc atattacatc accacgagac tcttctggtg gtatcacact | 180 |
| atggccaatc agcaagtgag tttccccgct tttgatttta gcttctgttg tttctggctt | 240 |

<210> SEQ ID NO 437
<211> LENGTH: 235
<212> TYPE: DNA
<213> ORGANISM: Artificial Sequence
<220> FEATURE:
<223> OTHER INFORMATION: Synthetic Polynucleotide

<400> SEQUENCE: 437

| gactattgca aatctctccc cctttcagat tcccctcggc gactctggtg gtatcactgg | 60 |
| atttgctggc ttctcagcgt agttggaatc ttctgtattc tcttagcgca tgaccactgt | 120 |
| ggacgtggtg gtggcatatt acatcaccac gagactcttc tggtggtatc acactatggc | 180 |
| caatcagcaa gtgagtttcc ccgcttttga ttttagcttc tgttgtttct ggctt | 235 |

<210> SEQ ID NO 438
<211> LENGTH: 238
<212> TYPE: DNA
<213> ORGANISM: Artificial Sequence
<220> FEATURE:
<223> OTHER INFORMATION: Synthetic Polynucleotide

<400> SEQUENCE: 438

| gactattgca aatctctccc cctttcagat tcccctcggc gactctggtg gtatcactgg | 60 |
| atttgctggc ttctcagcgt agttggaatc ttctgtattc tcttagcgca tgaccactac | 120 |
| tgtggacgtg gtggtggcat attacatcac cacgagactc ttctggtggt atcacactat | 180 |
| ggccaatcag caagtgagtt tccccgcttt tgattttagc ttctgttgtt tctggctt | 238 |

<210> SEQ ID NO 439
<211> LENGTH: 225
<212> TYPE: DNA
<213> ORGANISM: Artificial Sequence
<220> FEATURE:
<223> OTHER INFORMATION: Synthetic Polynucleotide

<400> SEQUENCE: 439

| gactattgca aatctctccc cctttcagat tcccctcggc gactctggtg gtatcactgg | 60 |

```
atttgctggc ttctcagcgt agttggaatc ttctgtattc tcttagcgca tgacgtggtg    120
gtggcatatt acatcaccac gagactcttc tggtggtatc acactatggc caatcagcaa    180
gtgagtttcc ccgcttttga ttttagcttc tgttgtttct ggctt                    225
```

<210> SEQ ID NO 440
<211> LENGTH: 239
<212> TYPE: DNA
<213> ORGANISM: Artificial Sequence
<220> FEATURE:
<223> OTHER INFORMATION: Synthetic Polynucleotide

<400> SEQUENCE: 440

```
gactattgca aatctctccc cctttcagat tcccctcggc gactctggtg gtatcactgg     60
atttgctggc ttctcagcgt agttggaatc ttctgtattc tcttagcgca tgaccactac    120
atgtggacgt ggtggtggca tattacatca ccacgagact cttctggtgg tatcacacta    180
tggccaatca gcaagtgagt tccccgctt ttgattttag cttctgttgt ttctggctt     239
```

<210> SEQ ID NO 441
<211> LENGTH: 226
<212> TYPE: DNA
<213> ORGANISM: Artificial Sequence
<220> FEATURE:
<223> OTHER INFORMATION: Synthetic Polynucleotide

<400> SEQUENCE: 441

```
gactattgca aatctctccc cctttcagat tcccctcggc gactctggtg gtatcactgg     60
atttgctggc ttctcagcgt agttggaatc ttctgtattc tcttagcgca tggacgtggt    120
ggtggcatat acatcacca cgagactctt ctggtggtat cacactatgg ccaatcagca    180
agtgagtttc cccgctttg attttagctt ctgttgtttc tggctt                   226
```

<210> SEQ ID NO 442
<211> LENGTH: 228
<212> TYPE: DNA
<213> ORGANISM: Artificial Sequence
<220> FEATURE:
<223> OTHER INFORMATION: Synthetic Polynucleotide

<400> SEQUENCE: 442

```
gactattgca aatctctccc cctttcagat tcccctcggc gactctggtg gtatcactgg     60
atttgctggc ttctcagcgt agttggaatc ttctgtattc tcttagcgca tgtggacgtg    120
gtggtggcat attacatcac cacgagactc ttctggtgg atcacactat ggccaatcag    180
caagtgagtt ccccgctttt tgattttagc ttctgttgtt tctggctt                 228
```

<210> SEQ ID NO 443
<211> LENGTH: 233
<212> TYPE: DNA
<213> ORGANISM: Artificial Sequence
<220> FEATURE:
<223> OTHER INFORMATION: Synthetic Polynucleotide

<400> SEQUENCE: 443

```
gactattgca aatctctccc cctttcagat tcccctcggc gactctggtg gtatcactgg     60
atttgctggc ttctcagcgt agttggaatc ttctgtattc tcttagcgca tgaccactac    120
acgtggtggt ggcatattac atcaccacga gactcttctg gtggtatcac actatggcca    180
atcagcaagt gagtttcccc gctttgatt ttagcttctg ttgtttctgg ctt            233
```

<210> SEQ ID NO 444
<211> LENGTH: 236
<212> TYPE: DNA
<213> ORGANISM: Artificial Sequence
<220> FEATURE:
<223> OTHER INFORMATION: Synthetic Polynucleotide

<400> SEQUENCE: 444

```
gactattgca aatctctccc cctttcagat tccctcggc gactctggtg gtatcactgg      60
atttgctggc ttctcagcgt agttggaatc ttctgtattc tcttagcgca tgaccactac     120
aggacgtggt ggtggcatat tacatcacca cgagactctt ctggtggtat cacactatgg    180
ccaatcagca agtgagtttc cccgcttttg attttagctt ctgttgtttc tggctt         236
```

<210> SEQ ID NO 445
<211> LENGTH: 235
<212> TYPE: DNA
<213> ORGANISM: Artificial Sequence
<220> FEATURE:
<223> OTHER INFORMATION: Synthetic Polynucleotide

<400> SEQUENCE: 445

```
gactattgca aatctctccc cctttcagat tccctcggc gactctggtg gtatcactgg      60
atttgctggc ttctcagcgt agttggaatc ttctgtattc tcttagcgca tgaccactac     120
agacgtggtg gtggcatatt acatcaccac gagactcttc tggtggtatc acactatggc    180
caatcagcaa gtgagtttcc ccgcttttga ttttagcttc tgttgtttct ggctt          235
```

<210> SEQ ID NO 446
<211> LENGTH: 232
<212> TYPE: DNA
<213> ORGANISM: Artificial Sequence
<220> FEATURE:
<223> OTHER INFORMATION: Synthetic Polynucleotide

<400> SEQUENCE: 446

```
gactattgca aatctctccc cctttcagat tccctcggc gactctggtg gtatcactgg      60
atttgctggc ttctcagcgt agttggaatc ttctgtattc tcttagcgca tgactgtgga    120
cgtggtggtg gcatattaca tcaccacgag actcttctgg tggtatcaca ctatggccaa    180
tcagcaagtg agtttccccg cttttgattt tagcttctgt tgtttctggc tt             232
```

<210> SEQ ID NO 447
<211> LENGTH: 231
<212> TYPE: DNA
<213> ORGANISM: Artificial Sequence
<220> FEATURE:
<223> OTHER INFORMATION: Synthetic Polynucleotide

<400> SEQUENCE: 447

```
gactattgca aatctctccc cctttcagat tccctcggc gactctggtg gtatcactgg      60
atttgctggc ttctcagcgt agttggaatc ttctgtattc tcttagcgca tgaccactac     120
gtggtggtgg catattacat caccacgaga ctcttctggt ggtatcacac tatggccaat    180
cagcaagtga gtttccccgc ttttgatttt agcttctgtt gtttctggct t              231
```

<210> SEQ ID NO 448
<211> LENGTH: 209
<212> TYPE: DNA
<213> ORGANISM: Artificial Sequence
<220> FEATURE:
<223> OTHER INFORMATION: Synthetic Polynucleotide

<400> SEQUENCE: 448

```
gactattgca aatctctccc cctttcagat tccccctcggc gactctggtg gtatcactgg    60
atttgctggc ttctcagcgt agttggaatc ttctgtattc tcttagcgca tattacatca   120
ccacgagact cttctggtgg tatcacacta tggccaatca gcaagtgagt ttccccgctt   180
ttgattttag cttctgttgt ttctggctt                                     209
```

<210> SEQ ID NO 449
<211> LENGTH: 238
<212> TYPE: DNA
<213> ORGANISM: Artificial Sequence
<220> FEATURE:
<223> OTHER INFORMATION: Synthetic Polynucleotide

<400> SEQUENCE: 449

```
gactattgca aatctctccc cctttcagat tccccctcggc gactctggtg gtatcactgg    60
atttgctggc ttctcagcgt agttggaatc ttctgtattc tcttagcgca tgaccaccac   120
tgtggacgtg gtggtggcat attacatcac cacgagactc ttctggtggt atcacactat   180
ggccaatcag caagtgagtt tccccgcttt tgattttagc ttctgttgtt tctggctt     238
```

<210> SEQ ID NO 450
<211> LENGTH: 237
<212> TYPE: DNA
<213> ORGANISM: Artificial Sequence
<220> FEATURE:
<223> OTHER INFORMATION: Synthetic Polynucleotide

<400> SEQUENCE: 450

```
gactattgca aatctctccc cctttcagat tccccctcggc gactctggtg gtatcactgg    60
atttgctggc ttctcagcgt agttggaatc ttctgtattc tcttagcgca tgaccactac   120
atggacgtgg tggtggcata ttacatcacc acgagactct tctggtggta tcacactatg   180
gccaatcagc aagtgagttt ccccgctttt gattttagct tctgttgttt ctggctt      237
```

<210> SEQ ID NO 451
<211> LENGTH: 220
<212> TYPE: DNA
<213> ORGANISM: Artificial Sequence
<220> FEATURE:
<223> OTHER INFORMATION: Synthetic Polynucleotide

<400> SEQUENCE: 451

```
gactattgca aatctctccc cctttcagat tccccctcggc gactctggtg gtatcactgg    60
atttgctggc ttctcagcgt agttggaatc ttctgtattc tcttagcgca tgaccactac   120
atattcatc accacgagac tcttctggtg gtatcacact atggccaatc agcaagtgag   180
tttccccgct tttgatttta gcttctgttg tttctggctt                         220
```

<210> SEQ ID NO 452
<211> LENGTH: 213
<212> TYPE: DNA
<213> ORGANISM: Artificial Sequence
<220> FEATURE:
<223> OTHER INFORMATION: Synthetic Polynucleotide

<400> SEQUENCE: 452

```
gactattgca aatctctccc cctttcagat tccccctcggc gactctggtg gtatcactgg    60
atttgctggc ttctcagcgt agttggaatc ttctgtattc tcttagcgca tgaccactac   120
```

```
atcaccacga gactcttctg gtggtatcac actatggcca atcagcaagt gagtttcccc    180
gcttttgatt ttagcttctg ttgtttctgg ctt                                 213
```

<210> SEQ ID NO 453
<211> LENGTH: 239
<212> TYPE: DNA
<213> ORGANISM: Artificial Sequence
<220> FEATURE:
<223> OTHER INFORMATION: Synthetic Polynucleotide

<400> SEQUENCE: 453

```
gactattgca aatctctccc cctttcagat tccctcggc gactctggtg gtatcactgg     60
atttgctggc ttctcagcgt agttggaatc ttctgtattc tcttagcgca tgaccactac   120
ctgtggacgt ggtggtggca tattacatca ccacgagact cttctggtgg tatcacacta   180
tggccaatca gcaagtgagt tccccgctt tgatttag cttctgttgt ttctggctt       239
```

<210> SEQ ID NO 454
<211> LENGTH: 241
<212> TYPE: DNA
<213> ORGANISM: Artificial Sequence
<220> FEATURE:
<223> OTHER INFORMATION: Synthetic Polynucleotide

<400> SEQUENCE: 454

```
gactattgca aatctctccc cctttcagat tccctcggc gactctggtg gtatcactgg     60
atttgctggc ttctcagcgt agttggaatc ttctgtattc tcttagcgca tgaccactac   120
aactgtggac gtggtggtgg catattacat caccacgaga ctcttctggt ggtatcacac   180
tatggccaat cagcaagtga gtttccccga ttttgatttt agcttctgtt gtttctggct   240
t                                                                   241
```

<210> SEQ ID NO 455
<211> LENGTH: 234
<212> TYPE: DNA
<213> ORGANISM: Artificial Sequence
<220> FEATURE:
<223> OTHER INFORMATION: Synthetic Polynucleotide

<400> SEQUENCE: 455

```
gactattgca aatctctccc cctttcagat tccctcggc gactctggtg gtatcactgg     60
atttgctggc ttctcagcgt agttggaatc ttctgtattc tcttagcgca tgaccactac   120
aacgtggtgg tggcatatta catcaccacg agactcttct ggtggtatca cactatggcc   180
aatcagcaag tgagtttccc cgcttttgat tttagcttct gttgtttctg gctt         234
```

<210> SEQ ID NO 456
<211> LENGTH: 238
<212> TYPE: DNA
<213> ORGANISM: Artificial Sequence
<220> FEATURE:
<223> OTHER INFORMATION: Synthetic Polynucleotide

<400> SEQUENCE: 456

```
gactattgca aatctctccc cctttcagat tccctcggc gactctggtg gtatcactgg     60
atttgctggc ttctcagcgt agttggaatc ttctgtattc tcttagcgca tgaccactac   120
agtggacgtg gtggtggcat attacatcac cacgagactc ttctggtggt atcacactat   180
ggccaatcag caagtgagtt tccccgcttt tgatttagc ttctgttgtt tctggctt      238
```

```
<210> SEQ ID NO 457
<211> LENGTH: 228
<212> TYPE: DNA
<213> ORGANISM: Artificial Sequence
<220> FEATURE:
<223> OTHER INFORMATION: Synthetic Polynucleotide

<400> SEQUENCE: 457
gactattgca aatctctccc cctttcagat tcccctcggc gactctggtg gtatcactgg      60
atttgctggc ttctcagcgt agttggaatc ttctgtattc tcttagcgca tgaccacgtg     120
gtggtggcat attacatcac cacgagactc ttctggtggt atcacactat ggccaatcag     180
caagtgagtt tccccgcttt tgattttagc ttctgttgtt tctggctt                  228

<210> SEQ ID NO 458
<211> LENGTH: 242
<212> TYPE: DNA
<213> ORGANISM: Artificial Sequence
<220> FEATURE:
<223> OTHER INFORMATION: Synthetic Polynucleotide

<400> SEQUENCE: 458
gactattgca aatctctccc cctttcagat tcccctcggc gactctggtg gtatcactgg      60
atttgctggc ttctcagcgt agttggaatc ttctgtattc tcttagcgca tgaccactac     120
acactgtgga cgtggtggtg gcatattaca tcaccacgag actcttctgg tggtatcaca     180
ctatggccaa tcagcaagtg agtttccccg cttttgattt tagcttctgt tgtttctggc     240
tt                                                                    242

<210> SEQ ID NO 459
<211> LENGTH: 202
<212> TYPE: DNA
<213> ORGANISM: Artificial Sequence
<220> FEATURE:
<223> OTHER INFORMATION: Synthetic Polynucleotide

<400> SEQUENCE: 459
gactattgca aatctctccc cctttcagat tcccctcggc gactctggtg gtatcactgg      60
atttgctggc ttctcagcgt agttggaatc ttctgtattc tcttagcgca tgaccacgag     120
actcttctgg tggtatcaca ctatggccaa tcagcaagtg agtttccccg cttttgattt     180
tagcttctgt tgtttctggc tt                                              202

<210> SEQ ID NO 460
<211> LENGTH: 211
<212> TYPE: DNA
<213> ORGANISM: Artificial Sequence
<220> FEATURE:
<223> OTHER INFORMATION: Synthetic Polynucleotide

<400> SEQUENCE: 460
gactattgca aatctctccc cctttcagat tcccctcggc gactctggtg gtatcactgg      60
atttgctggc ttctcagcgt agttggaatc ttctgtggac gtggtggtgg catattacat     120
caccacgaga ctcttctggt ggtatcacac tatggccaat cagcaagtga gtttccccgc     180
ttttgatttt agcttctgtt gtttctggct t                                    211

<210> SEQ ID NO 461
<211> LENGTH: 238
<212> TYPE: DNA
<213> ORGANISM: Artificial Sequence
<220> FEATURE:
```

<223> OTHER INFORMATION: Synthetic Polynucleotide

<400> SEQUENCE: 461

| gactattgca aatctctccc cctttcagat tcccctcggc gactctggtg gtatcactgg | 60 |
| atttgctggc ttctcagcgt agttggaatc ttctgtattc tcttagcgca tgtccactac | 120 |
| tgtggacgtg gtggtggcat attacatcac cacgagactc ttctggtggt atcacactat | 180 |
| ggccaatcag caagtgagtt tccccgcttt tgattttagc ttctgttgtt tctggctt | 238 |

<210> SEQ ID NO 462
<211> LENGTH: 232
<212> TYPE: DNA
<213> ORGANISM: Artificial Sequence
<220> FEATURE:
<223> OTHER INFORMATION: Synthetic Polynucleotide

<400> SEQUENCE: 462

| gactattgca aatctctccc cctttcagat tcccctcggc gactctggtg gtatcactgg | 60 |
| atttgctggc ttctcagcgt agttggaatc ttctgtattc tcttagcgca tgaccactac | 120 |
| agtggtggtg gcatattaca tcaccacgag actcttctgg tggtatcaca ctatggccaa | 180 |
| tcagcaagtg agtttccccg cttttgattt tagcttctgt tgtttctggc tt | 232 |

<210> SEQ ID NO 463
<211> LENGTH: 230
<212> TYPE: DNA
<213> ORGANISM: Artificial Sequence
<220> FEATURE:
<223> OTHER INFORMATION: Synthetic Polynucleotide

<400> SEQUENCE: 463

| gactattgca aatctctccc cctttcagat tcccctcggc gactctggtg gtatcactgg | 60 |
| atttgctggc ttctcagcgt agttggaatc ttctgtattc tcttagcgca tgaccactac | 120 |
| aggtggtggc atattacatc accacgagac tcttctggtg gtatcacact atggccaatc | 180 |
| agcaagtgag tttccccgct tttgatttta gcttctgttg tttctggctt | 230 |

<210> SEQ ID NO 464
<211> LENGTH: 241
<212> TYPE: DNA
<213> ORGANISM: Artificial Sequence
<220> FEATURE:
<223> OTHER INFORMATION: Synthetic Polynucleotide

<400> SEQUENCE: 464

| gactattgca aatctctccc cctttcagat tcccctcggc gactctggtg gtatcactgg | 60 |
| atttgctggc ttctcagcgt agttggaatc ttctgtattc tcttagcgca tgaccactac | 120 |
| acctgtggac gtggtggtgg catattacat caccacgaga ctcttctggt ggtatcacac | 180 |
| tatggccaat cagcaagtga gtttccccgc ttttgatttt agcttctgtt gtttctggct | 240 |
| t | 241 |

<210> SEQ ID NO 465
<211> LENGTH: 240
<212> TYPE: DNA
<213> ORGANISM: Artificial Sequence
<220> FEATURE:
<223> OTHER INFORMATION: Synthetic Polynucleotide

<400> SEQUENCE: 465

| gactattgca aatctctccc cctttcagat tcccctcggc gactctggtg gtatcactgg | 60 |

```
atttgctggc ttctcagcgt agttggaatc ttctgtattc tcttagcgca tgaccactac    120
actgtggacg tggtggtggc atattacatc accacgagac tcttctggtg gtatcacact    180
atggccaatc agcaagtgag tttccccgat tttgatttta gcttctgttg tttctggctt    240
```

<210> SEQ ID NO 466
<211> LENGTH: 218
<212> TYPE: DNA
<213> ORGANISM: Artificial Sequence
<220> FEATURE:
<223> OTHER INFORMATION: Synthetic Polynucleotide

<400> SEQUENCE: 466

```
gactattgca aatctctccc cctttcagat tcccctcggc gactctggtg gtatcactgg     60
atttgctggc ttctcagcgt agttggaatc ttctgtattc tcttagcgtg gtggtggcat    120
attacatcac cacgagactc ttctggtggt atcacactat ggccaatcag caagtgagtt    180
tccccgcttt tgattttagc ttctgttgtt tctggctt                             218
```

<210> SEQ ID NO 467
<211> LENGTH: 233
<212> TYPE: DNA
<213> ORGANISM: Artificial Sequence
<220> FEATURE:
<223> OTHER INFORMATION: Synthetic Polynucleotide

<400> SEQUENCE: 467

```
gactattgca aatctctccc cctttcagat tcccctcggc gactctggtg gtatcactgg     60
atttgctggc ttctcagcgt agttggaatc ttctgtattc tcttagcgca tgacctgtgg    120
acgtggtggt ggcatattac atcaccacga gactcttctg gtggtatcac actatggcca    180
atcagcaagt gagtttcccc gcttttgatt ttagcttctg ttgtttctgg ctt           233
```

<210> SEQ ID NO 468
<211> LENGTH: 220
<212> TYPE: DNA
<213> ORGANISM: Artificial Sequence
<220> FEATURE:
<223> OTHER INFORMATION: Synthetic Polynucleotide

<400> SEQUENCE: 468

```
gactattgca aatctctccc cctttcagat tcccctcggc gactctggtg gtatcactgg     60
atttgctggc ttctcagcgt agttggaatc ttctgtattc tcttagcgca tggtggtggc    120
atattacatc accacgagac tcttctggtg gtatcacact atggccaatc agcaagtgag    180
tttccccgct tttgatttta gcttctgttg tttctggctt                          220
```

<210> SEQ ID NO 469
<211> LENGTH: 231
<212> TYPE: DNA
<213> ORGANISM: Artificial Sequence
<220> FEATURE:
<223> OTHER INFORMATION: Synthetic Polynucleotide

<400> SEQUENCE: 469

```
gactattgca aatctctccc cctttcagat tcccctcggc gactctggtg gtatcactgg     60
atttgctggc ttctcagcgt agttggaatc ttctgtattc tcttagcgca tgctgtggac    120
gtggtggtgg catattacat caccacgaga ctcttctggt ggtatcacac tatggccaat    180
cagcaagtga gtttccccgc ttttgatttt agcttctgtt gtttctggct t             231
```

<210> SEQ ID NO 470
<211> LENGTH: 215
<212> TYPE: DNA
<213> ORGANISM: Artificial Sequence
<220> FEATURE:
<223> OTHER INFORMATION: Synthetic Polynucleotide

<400> SEQUENCE: 470

```
gactattgca aatctctccc cctttcagat tcccctcggc gactctggtg gtatcactgg       60
atttgctggc ttctcagcgt agttggaatc ttctgtattc tcttagcgca tgaccatatt      120
acatcaccac gagactcttc tggtggtatc acactatggc caatcagcaa gtgagtttcc      180 ccgctttga ttttagcttc tgttgtttct ggctt                                  215
```

<210> SEQ ID NO 471
<211> LENGTH: 237
<212> TYPE: DNA
<213> ORGANISM: Artificial Sequence
<220> FEATURE:
<223> OTHER INFORMATION: Synthetic Polynucleotide

<400> SEQUENCE: 471

```
gactattgca aatctctccc cctttcagat tcccctcggc gactctggtg gtatcactgg       60
atttgctggc ttctcagcgt agttggaatc ttctgtattc tcttagcgca tgaccactac      120
gtggacgtgg tggtggcata ttacatcacc acgagactct tctggtggta tcacactatg      180
gccaatcagc aagtgagttt ccccgctttt gattttagct tctgttgttt ctggctt         237
```

<210> SEQ ID NO 472
<211> LENGTH: 241
<212> TYPE: DNA
<213> ORGANISM: Artificial Sequence
<220> FEATURE:
<223> OTHER INFORMATION: Synthetic Polynucleotide

<400> SEQUENCE: 472

```
gactattgca aatctctccc cctttcagat tcccctcggc gactctggtg gtatcactgg       60
atttgctggc ttctcagcgt agttggaatc ttctgtattc tcttagcgca tgaccactac      120
tactgtggac gtggtggtgg catattacat caccacgaga ctcttctggt ggtatcacac      180
tatggccaat cagcaagtga gtttccccgc ttttgatttt agcttctgtt gtttctggct      240
t                                                                      241
```

<210> SEQ ID NO 473
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 473

```
gactattgca aatctctccc cctttcagat tcccctcggc gactctggtg gtatcacact       60
atggccaatc agcaagtgag tttccccgct tttgatttta gcttctgttg tttctggctt      120
```

<210> SEQ ID NO 474
<211> LENGTH: 235
<212> TYPE: DNA
<213> ORGANISM: Artificial Sequence
<220> FEATURE:
<223> OTHER INFORMATION: Synthetic Polynucleotide

<400> SEQUENCE: 474

```
gactattgca aatctctccc cctttcagat tccsctcggc gactctggtg gtatcactgg    60
atttgctggc ttctcagcgt agttggaatc ttctgtattc tcttagcgca tgaccactgt   120
ggacgtggtg gtggcatatt acatcaccac gagactcttc tggtggtatc acactatggc   180
caatcagcaa gtgagtttcc ccgatttga ttttagcttc tgttgtttct ggctt         235
```

<210> SEQ ID NO 475
<211> LENGTH: 234
<212> TYPE: DNA
<213> ORGANISM: Artificial Sequence
<220> FEATURE:
<223> OTHER INFORMATION: Synthetic Polynucleotide

<400> SEQUENCE: 475

```
gactattgca aatctctccc cctttcagat tccsctcggc gactctggtg gtatcactgg    60
atttgctggc ttctcagcgt agttggaatc ttctgtattc tcttagcgca tgacactgtg   120
gacgtggtgg tggcatatta catcaccacg agactcttct ggtggtatca cactatggcc   180
aatcagcaag tgagtttccc cgcttttgat tttagcttct gttgtttctg gctt          234
```

<210> SEQ ID NO 476
<211> LENGTH: 217
<212> TYPE: DNA
<213> ORGANISM: Artificial Sequence
<220> FEATURE:
<223> OTHER INFORMATION: Synthetic Polynucleotide

<400> SEQUENCE: 476

```
gactattgca aatctctccc cctttcagat tccsctcggc gactctggtg gtatcactgg    60
atttgctggc ttctcagcgt agttggaatc ttctgtattc tcttagcgca tggtggcata   120
ttacatcacc acgagactct tctggtggta tcacactatg gccaatcagc aagtgagttt   180
ccccgctttt gatttagct tctgttgttt ctggctt                              217
```

<210> SEQ ID NO 477
<211> LENGTH: 242
<212> TYPE: DNA
<213> ORGANISM: Artificial Sequence
<220> FEATURE:
<223> OTHER INFORMATION: Synthetic Polynucleotide

<400> SEQUENCE: 477

```
gactattgca aatctctccc cctttcagat tccsctcggc gactctggtg gtatcactgg    60
atttgctggc ttctcagcgt agttggaatc ttctgtattc tcttagcgca tgaccactac   120
aaactgtgga cgtggtggtg gcatattaca tcaccacgag actcttctgg tggtatcaca   180
ctatggccaa tcagcaagtg agtttccccg cttttgattt tagcttctgt tgtttctggc   240
tt                                                                  242
```

<210> SEQ ID NO 478
<211> LENGTH: 232
<212> TYPE: DNA
<213> ORGANISM: Artificial Sequence
<220> FEATURE:
<223> OTHER INFORMATION: Synthetic Polynucleotide

<400> SEQUENCE: 478

```
gactattgca aatctctccc cctttcagat tccsctcggc gactctggtg gtatcactgg    60
atttgctggc ttctcagcgt agttggaatc ttctgtattc tcttagcgca tgaccatgga   120
```
cgtggtggtg gcatattaca tcaccacgag actcttctgg tggtatcaca ctatggccaa    180
tcagcaagtg agtttccccg cttttgattt tagcttctgt tgtttctggc tt            232

<210> SEQ ID NO 479
<211> LENGTH: 220
<212> TYPE: DNA
<213> ORGANISM: Artificial Sequence
<220> FEATURE:
<223> OTHER INFORMATION: Synthetic Polynucleotide

<400> SEQUENCE: 479
gactattgca aatctctccc cctttcagat tcccctcggc gactctggtg gtatcactgg    60
atttgctggc ttctcagcgt agttggaatc ttctgtattc tctgtggacg tggtggtggc    120
atattacatc accacgagac tcttctggtg gtatcacact atggccaatc agcaagtgag    180
tttccccgct tttgatttta gcttctgttg tttctggctt                          220

<210> SEQ ID NO 480
<211> LENGTH: 234
<212> TYPE: DNA
<213> ORGANISM: Artificial Sequence
<220> FEATURE:
<223> OTHER INFORMATION: Synthetic Polynucleotide

<400> SEQUENCE: 480
gactattgca aatctctccc cctttcagat tcccctcggc gactctggtg gtatcactgg    60
atttgctggc ttctcagcgt agttggaatc ttctgtattc tcttagcgca tgaccatgtg    120
gacgtggtgg tggcatatta catcaccacg agactcttct ggtggtatca cactatggcc    180
aatcagcaag tgagtttccc cgcttttgat tttagcttct gttgtttctg gctt          234

<210> SEQ ID NO 481
<211> LENGTH: 202
<212> TYPE: DNA
<213> ORGANISM: Artificial Sequence
<220> FEATURE:
<223> OTHER INFORMATION: Synthetic Polynucleotide

<400> SEQUENCE: 481
gactattgca aatctctccc cctttcagat tcccctcggc gactctggtg gtatcactgg    60
atttgctggc ttctcagcgt agttggaatc ttctgtattc tcttagcgca tcaccacgag    120
actcttctgg tggtatcaca ctatggccaa tcagcaagtg agtttccccg cttttgattt    180
tagcttctgt tgtttctggc tt                                             202

<210> SEQ ID NO 482
<211> LENGTH: 238
<212> TYPE: DNA
<213> ORGANISM: Artificial Sequence
<220> FEATURE:
<223> OTHER INFORMATION: Synthetic Polynucleotide

<400> SEQUENCE: 482
gactattgca aatctctccc cctttcagat tcccctcggc gactctggtg gtatcactgg    60
atttgctggc ttctcagcgt agttggaatc ttctgtattc tcttagcgca tgaccactac    120
tgtggacgtg gtggtggcat attacatcac cacgagactc ttctggtggt atcacactat    180
ggccaatcag caagtgagtt tccccgattt tgatttagc ttctgttgtt tctggctt       238

<210> SEQ ID NO 483
<211> LENGTH: 218

```
<212> TYPE: DNA
<213> ORGANISM: Artificial Sequence
<220> FEATURE:
<223> OTHER INFORMATION: Synthetic Polynucleotide

<400> SEQUENCE: 483
gactattgca aatctctccc cctttcagat tcccctcggc gactctggtg gtatcactgg      60
atttgctggc ttctcagcgt agttggaatc ttctgtattc tgtggacgtg gtggtggcat     120
attacatcac cacgagactc ttctggtggt atcacactat ggccaatcag caagtgagtt     180
tccccgcttt tgattttagc ttctgttgtt ctggctt                              218

<210> SEQ ID NO 484
<211> LENGTH: 236
<212> TYPE: DNA
<213> ORGANISM: Artificial Sequence
<220> FEATURE:
<223> OTHER INFORMATION: Synthetic Polynucleotide

<400> SEQUENCE: 484
gactattgca aatctctccc cctttcagat tcccctcggc gactctggtg gtatcactgg      60
atttgctggc ttctcagcgt agttggaatc ttctgtattc tcttagcgca tgaccactag     120
tggacgtggt ggtggcatat tacatcacca cgagactctt ctggtggtat cacactatgg     180
ccaatcagca agtgagtttc cccgcttttg attttagctt ctgttgtttc tggctt         236

<210> SEQ ID NO 485
<211> LENGTH: 234
<212> TYPE: DNA
<213> ORGANISM: Artificial Sequence
<220> FEATURE:
<223> OTHER INFORMATION: Synthetic Polynucleotide

<400> SEQUENCE: 485
gactattgca aatctctccc cctttcagat tcccctcggc gactctggtg gtatcactgg      60
atttgctggc ttctcagcgt agttggaatc ttctgtattc tcttagcgca tgaccactaa     120
gacgtggtgg tggcatatta catcaccacg agactcttct ggtggtatca cactatggcc     180
aatcagcaag tgagtttccc cgcttttgat tttagcttct gttgtttctg gctt           234

<210> SEQ ID NO 486
<211> LENGTH: 241
<212> TYPE: DNA
<213> ORGANISM: Artificial Sequence
<220> FEATURE:
<223> OTHER INFORMATION: Synthetic Polynucleotide

<400> SEQUENCE: 486
gactattgca aatctctccc cctttcagat tcccctcggc gactctggtg gtatcactgg      60
atttgctggc ttctcagcgt agttggaatc ttctgtattc tcttagcgca tgaccactac     120
atctgtggac gtggtggtgg catattacat caccacgaga ctcttctggt ggtatcacac     180
tatggccaat cagcaagtga gtttccccgc ttttgatttt agcttctgtt gtttctggct     240
t                                                                     241

<210> SEQ ID NO 487
<211> LENGTH: 241
<212> TYPE: DNA
<213> ORGANISM: Artificial Sequence
<220> FEATURE:
<223> OTHER INFORMATION: Synthetic Polynucleotide
```

<400> SEQUENCE: 487

```
gactattgca aatctctccc cctttcagat tccccteggc gactctggtg gtatcactgg      60
atttgctggc ttctcagcgt agttggaatc ttctgtattc tcttagcgca tgaccactac     120
agctgtggac gtggtggtgg catattacat caccacgaga ctcttctggt ggtatcacac     180
tatggccaat cagcaagtga gtttccccgc ttttgatttt agcttctgtt gtttctggct     240
t                                                                      241
```

<210> SEQ ID NO 488
<211> LENGTH: 233
<212> TYPE: DNA
<213> ORGANISM: Artificial Sequence
<220> FEATURE:
<223> OTHER INFORMATION: Synthetic Polynucleotide

<400> SEQUENCE: 488

```
gactattgca aatctctccc cctttcagat tccccteggc gactctggtg gtatcactgg      60
atttgctggc ttctcagcgt agttggaatc ttctgtattc tcttagcgca tgaccactgg     120
acgtggtggt ggcatattac atcaccacga gactcttctg gtggtatcac actatggcca     180
atcagcaagt gagtttcccc gcttttgatt ttagcttctg ttgtttctgg ctt            233
```

<210> SEQ ID NO 489
<211> LENGTH: 227
<212> TYPE: DNA
<213> ORGANISM: Artificial Sequence
<220> FEATURE:
<223> OTHER INFORMATION: Synthetic Polynucleotide

<400> SEQUENCE: 489

```
gactattgca aatctctccc cctttcagat tccccteggc gactctggtg gtatcactgg      60
atttgctggc ttctcagcgt agttggaatc ttctgtattc tcttagcgct gtggacgtgg     120
tggtggcata ttcatcacc acgagactct tctggtggta tcacactatg gccaatcagc     180
aagtgagttt ccccgctttt gatttagct tctgttgttt ctggctt                   227
```

<210> SEQ ID NO 490
<211> LENGTH: 237
<212> TYPE: DNA
<213> ORGANISM: Artificial Sequence
<220> FEATURE:
<223> OTHER INFORMATION: Synthetic Polynucleotide

<400> SEQUENCE: 490

```
gactattgca aatctctccc cctttcagat tccccteggc gactctggtg gtatcactgg      60
atttgctggc ttctcagcgt agttggaatc ttctgtattc tcttagcgca tgaccactct     120
gtggacgtgg tggtggcata ttacatcacc acgagactct tctggtggta tcacactatg     180
gccaatcagc aagtgagttt ccccgctttt gatttagct tctgttgttt ctggctt        237
```

<210> SEQ ID NO 491
<211> LENGTH: 229
<212> TYPE: DNA
<213> ORGANISM: Artificial Sequence
<220> FEATURE:
<223> OTHER INFORMATION: Synthetic Polynucleotide

<400> SEQUENCE: 491

```
gactattgca aatctctccc cctttcagat tccccteggc gactctggtg gtatcactgg      60
atttgctggc ttctcagcgt agttggaatc ttctgtattc tcttagcgca ctgtggacgt     120
```
ggtggtggca tattacatca ccacgagact cttctggtgg tatcacacta tggccaatca    180
gcaagtgagt ttccccgctt ttgattttag cttctgttgt ttctggctt                229

<210> SEQ ID NO 492
<211> LENGTH: 199
<212> TYPE: DNA
<213> ORGANISM: Artificial Sequence
<220> FEATURE:
<223> OTHER INFORMATION: Synthetic Polynucleotide

<400> SEQUENCE: 492
gactattgca aatctctccc cctttcagat tcccctcggc gactctggtg gtatcactgg    60
atttgctggc ttctcagcgt agttggacgt ggtggtggca tattacatca ccacgagact    120
cttctggtgg tatcacacta tggccaatca gcaagtgagt ttccccgctt ttgattttag    180
cttctgttgt ttctggctt                                                 199

<210> SEQ ID NO 493
<211> LENGTH: 231
<212> TYPE: DNA
<213> ORGANISM: Artificial Sequence
<220> FEATURE:
<223> OTHER INFORMATION: Synthetic Polynucleotide

<400> SEQUENCE: 493
gactattgca aatctctccc cctttcagat tcccctcggc gactctggtg gtatcactgg    60
atttgctggc ttctcagcgt agttggaatc ttctgtattc tcttagcgca tgaccactac    120
atggtggtgg catattacat caccacgaga ctcttctggt ggtatcacac tatggccaat    180
cagcaagtga gtttccccgc ttttgatttt agcttctgtt gtttctggct t             231

<210> SEQ ID NO 494
<211> LENGTH: 222
<212> TYPE: DNA
<213> ORGANISM: Artificial Sequence
<220> FEATURE:
<223> OTHER INFORMATION: Synthetic Polynucleotide

<400> SEQUENCE: 494
gactattgca aatctctccc cctttcagat tcccctcggc gactctggtg gtatcactgg    60
atttgctggc ttctcagcgt agttggaatc ttctgtattc tcttagcgca tgaccactac    120
acatattaca tcaccacgag actcttctgg tggtatcaca ctatggccaa tcagcaagtg    180
agtttccccg cttttgattt tagcttctgt tgtttctggc tt                       222

<210> SEQ ID NO 495
<211> LENGTH: 226
<212> TYPE: DNA
<213> ORGANISM: Artificial Sequence
<220> FEATURE:
<223> OTHER INFORMATION: Synthetic Polynucleotide

<400> SEQUENCE: 495
gactattgca aatctctccc cctttcagat tcccctcggc gactctggtg gtatcactgg    60
atttgctggc ttctcagcgt agttggaatc ttctgtattc tcttagcgca tgaccgtggt    120
ggtggcatat tacatcacca cgagactctt ctggtggtat cacactatgg ccaatcagca    180
agtgagtttc ccgcttttg attttagctt ctgttgtttc tggctt                    226

<210> SEQ ID NO 496

```
<211> LENGTH: 231
<212> TYPE: DNA
<213> ORGANISM: Artificial Sequence
<220> FEATURE:
<223> OTHER INFORMATION: Synthetic Polynucleotide

<400> SEQUENCE: 496
gactattgca aatctctccc cctttcagat tcccctcggc gactctggtg gtatcactgg      60
atttgctggc ttctcagcgt agttggaatc ttctgtattc tcttagcgca tgacgtggac     120
gtggtggtgg catattacat caccacgaga ctcttctggt ggtatcacac tatggccaat    180
cagcaagtga gtttccccgc ttttgatttt agcttctgtt gtttctggct t              231

<210> SEQ ID NO 497
<211> LENGTH: 235
<212> TYPE: DNA
<213> ORGANISM: Artificial Sequence
<220> FEATURE:
<223> OTHER INFORMATION: Synthetic Polynucleotide

<400> SEQUENCE: 497
gactattgca aatctctccc cctttcagat tcccctcggc gactctggtg gtatcactgg      60
atttgctggc ttctcagcgt agttggaatc ttctgtattc tcttagcgca tgactactgt     120
ggacgtggtg gtggcatatt acatcaccac gagactcttc tggtggtatc acactatggc    180
caatcagcaa gtgagtttcc ccgcttttga ttttagcttc tgttgtttct ggctt          235

<210> SEQ ID NO 498
<211> LENGTH: 216
<212> TYPE: DNA
<213> ORGANISM: Artificial Sequence
<220> FEATURE:
<223> OTHER INFORMATION: Synthetic Polynucleotide

<400> SEQUENCE: 498
gactattgca aatctctccc cctttcagat tcccctcggc gactctggtg gtatcactgg      60
atttgctggc ttctcagcgt agttggaatc ttctgtattc tcttagcgca tgaccactat    120
tacatcacca cgagactctt ctggtggtat cacactatgg ccaatcagca agtgagtttc    180
cccgcttttg attttagctt ctgttgtttc tggctt                               216

<210> SEQ ID NO 499
<211> LENGTH: 222
<212> TYPE: DNA
<213> ORGANISM: Artificial Sequence
<220> FEATURE:
<223> OTHER INFORMATION: Synthetic Polynucleotide

<400> SEQUENCE: 499
gactattgca aatctctccc cctttcagat tcccctcggc gactctggtg gtatcactgg      60
atttgctggc ttctcagcgt agttggaatc ttctgtattc tcttagcgca tgtggtggtg    120
gcatattaca tcaccacgag actcttctgg tggtatcaca ctatggccaa tcagcaagtg    180
agtttccccg cttttgattt tagcttctgt tgtttctggc tt                        222

<210> SEQ ID NO 500
<211> LENGTH: 222
<212> TYPE: DNA
<213> ORGANISM: Artificial Sequence
<220> FEATURE:
<223> OTHER INFORMATION: Synthetic Polynucleotide

<400> SEQUENCE: 500
```

```
gactattgca aatctctccc cctttcagat tcccctcggc gactctggtg gtatcactgg    60
atttgctggc ttctcagcgt agttggaatc ttctgtattc tcttagcgca cgtggtggtg   120
gcatattaca tcaccacgag actcttctgg tggtatcaca ctatggccaa tcagcaagtg   180
agtttccccg cttttgattt tagcttctgt tgtttctggc tt                      222
```

<210> SEQ ID NO 501
<211> LENGTH: 220
<212> TYPE: DNA
<213> ORGANISM: Artificial Sequence
<220> FEATURE:
<223> OTHER INFORMATION: Synthetic Polynucleotide

<400> SEQUENCE: 501

```
gactattgca aatctctccc cctttcagat tcccctcggc gactctggtg gtatcactgg    60
atttgctggc ttctcagcgt agttggaatc ttctgtattc tcttagcgcg tggtggtggc   120
atattacatc accacgagac tcttctggtg gtatcacact atggccaatc agcaagtgag   180
tttccccgct tttgatttta gcttctgttg tttctggctt                         220
```

<210> SEQ ID NO 502
<211> LENGTH: 239
<212> TYPE: DNA
<213> ORGANISM: Artificial Sequence
<220> FEATURE:
<223> OTHER INFORMATION: Synthetic Polynucleotide

<400> SEQUENCE: 502

```
gactattgca aatctctccc cctttcagat tcccctcggc gactctggtg gtatcactgg    60
atttgctggc ttctcagcgt agttggaatc ttctgtattc tcttagcgca tgaccactaa   120
ctgtggacgt ggtggtggca tattacatca ccacgagact cttctggtgg tatcacacta   180
tggccaatca gcaagtgagt tccccgctt tgattttag cttctgttgt ttctggctt     239
```

<210> SEQ ID NO 503
<211> LENGTH: 228
<212> TYPE: DNA
<213> ORGANISM: Artificial Sequence
<220> FEATURE:
<223> OTHER INFORMATION: Synthetic Polynucleotide

<400> SEQUENCE: 503

```
gactattgca aatctctccc cctttcagat tcccctcggc gactctggtg gtatcactgg    60
atttgctggc ttctcagcgt agttggaatc ttctgtattc tcttagcgca tgaccactac   120
atggtggcat attacatcac cacgagactc ttctggtggt atcacactat ggccaatcag   180
caagtgagtt tccccgcttt tgattttagc ttctgttgtt tctggctt                228
```

<210> SEQ ID NO 504
<211> LENGTH: 223
<212> TYPE: DNA
<213> ORGANISM: Artificial Sequence
<220> FEATURE:
<223> OTHER INFORMATION: Synthetic Polynucleotide

<400> SEQUENCE: 504

```
gactattgca aatctctccc cctttcagat tcccctcggc gactctggtg gtatcactgg    60
atttgctggc ttctcagcgt agttggaatc ttctgtattc tcttagcgca tgaccactac   120
agcatattac atcaccacga gactcttctg gtggtatcac actatggcca atcagcaagt   180
```
gagtttcccc gcttttgatt ttagcttctg ttgtttctgg ctt    223

<210> SEQ ID NO 505
<211> LENGTH: 241
<212> TYPE: DNA
<213> ORGANISM: Artificial Sequence
<220> FEATURE:
<223> OTHER INFORMATION: Synthetic Polynucleotide

<400> SEQUENCE: 505
gactattgca aatctctccc cctttcagat tcccctcggc gactctggtg gtatcactgg    60
atttgctggc ttctcagcgt agttggaatc ttctgtattc tcttagcgca tgaccactac    120
aactgtggac gtggtggtgg catattacat caccacgaga ctcttctggt ggtatcacgc    180
tatggccaat cagcaagtga gtttccccgc ttttgatttt agcttctgtt gtttctggct    240
t    241

<210> SEQ ID NO 506
<211> LENGTH: 238
<212> TYPE: DNA
<213> ORGANISM: Artificial Sequence
<220> FEATURE:
<223> OTHER INFORMATION: Synthetic Polynucleotide

<400> SEQUENCE: 506
gactattgca aatctctccc cctttcagat tcccctcggc gactctggtg gtatcactgg    60
atttgctggc ttctcagcgt agttggaatc ttctgtattc tcttagcgca tgaccacgtc    120
tgtggacgtg gtggtggcat attacatcac cacgagactc ttctggtggt atcacactat    180
ggccaatcag caagtgagtt tccccgcttt tgattttagc ttctgttgtt tctggctt    238

<210> SEQ ID NO 507
<211> LENGTH: 236
<212> TYPE: DNA
<213> ORGANISM: Artificial Sequence
<220> FEATURE:
<223> OTHER INFORMATION: Synthetic Polynucleotide

<400> SEQUENCE: 507
gactattgca aatctctccc cctttcagat tcccctcggc gactctggtg gtatcactgg    60
atttgctggc ttctcagcgt agttggaatc ttctgtattc tcttagcgca tgaccacctg    120
tggacgtggt ggtggcatat tacatcacca cgagactctt ctggtggtat cacactatgg    180
ccaatcagca agtgagtttc ccgcttttga ttttagcttc tgttgtttc tggctt    236

<210> SEQ ID NO 508
<211> LENGTH: 227
<212> TYPE: DNA
<213> ORGANISM: Artificial Sequence
<220> FEATURE:
<223> OTHER INFORMATION: Synthetic Polynucleotide

<400> SEQUENCE: 508
gactattgca aatctctccc cctttcagat tcccctcggc gactctggtg gtatcactgg    60
atttgctggc ttctcagcgt agttggaatc ttctgtattc tcttagcgca tgaccactgg    120
tggtggcata ttacatcacc acgagactct tctggtggta tcacactatg gccaatcagc    180
aagtgagttt ccccgctttt gattttagct tctgttgttt ctggctt    227

<210> SEQ ID NO 509
<211> LENGTH: 241

```
<212> TYPE: DNA
<213> ORGANISM: Artificial Sequence
<220> FEATURE:
<223> OTHER INFORMATION: Synthetic Polynucleotide

<400> SEQUENCE: 509
gactattgca aatctctccc cctttcagat tcccctcggc gactctggtg gtatcactgg      60
atttgctggc ttctcagcgt agttggaatc ttctgtattc tcttagcgca tgaccactac     120
aactgtggac gtggtggtgg catattacat cgccacgaga ctcttctggt ggtatcacac     180
tatggccaat cagcaagtga gtttccccgc ttttgatttt agcttctgtt gtttctggct     240
t                                                                    241

<210> SEQ ID NO 510
<211> LENGTH: 231
<212> TYPE: DNA
<213> ORGANISM: Artificial Sequence
<220> FEATURE:
<223> OTHER INFORMATION: Synthetic Polynucleotide

<400> SEQUENCE: 510
gactattgca aatctctccc cctttcagat tcccctcggc gactctggtg gtatcactgg      60
atttgctggc ttctcagcgt agttggaatc ttctgtattc tcttagcgca tactgtggac     120
gtggtggtgg catattacat caccacgaga ctcttctggt ggtatcacac tatggccaat     180
cagcaagtga gtttccccgc ttttgatttt agcttctgtt gtttctggct t              231

<210> SEQ ID NO 511
<211> LENGTH: 208
<212> TYPE: DNA
<213> ORGANISM: Artificial Sequence
<220> FEATURE:
<223> OTHER INFORMATION: Synthetic Polynucleotide

<400> SEQUENCE: 511
gactattgca aatctctccc cctttcagat tcccctcggc gactctggtg gtatcactgg      60
atttgctggc ttctcagcgt agttggaatc ttctgtattc tcttagcgca tgaccatcac     120
cacgagactc ttctggtggt atcacactat ggccaatcag caagtgagtt tccccgcttt     180
tgattttagc ttctgttgtt tctggctt                                       208

<210> SEQ ID NO 512
<211> LENGTH: 209
<212> TYPE: DNA
<213> ORGANISM: Artificial Sequence
<220> FEATURE:
<223> OTHER INFORMATION: Synthetic Polynucleotide

<400> SEQUENCE: 512
gactattgca aatctctccc cctttcagat tcccctcggc gactctggtg gtatcactgg      60
atttgctggc ttctcagcgt agttggaatc ttctggacgt ggtggtggca tattacatca     120
ccacgagact cttctggtgg tatcacacta tggccaatca gcaagtgagt tccccgcttt     180
ttgattttag cttctgttgt ttctggctt                                      209

<210> SEQ ID NO 513
<211> LENGTH: 224
<212> TYPE: DNA
<213> ORGANISM: Artificial Sequence
<220> FEATURE:
<223> OTHER INFORMATION: Synthetic Polynucleotide
```

<400> SEQUENCE: 513
gactattgca aatctctccc cctttcagat tccctcggc gactctggtg gtatcactgg      60
atttgctggc ttctcagcgt agttggaatc ttctgtattc tcttagcgtg gacgtggtgg     120
tggcatatta catcaccacg agactcttct ggtggtatca cactatggcc aatcagcaag     180
tgagtttccc cgcttttgat tttagcttct gttgtttctg gctt                      224

<210> SEQ ID NO 514
<211> LENGTH: 235
<212> TYPE: DNA
<213> ORGANISM: Artificial Sequence
<220> FEATURE:
<223> OTHER INFORMATION: Synthetic Polynucleotide

<400> SEQUENCE: 514
gactattgca aatctctccc cctttcagat tccctcggc gactctggtg gtatcactgg      60
atttgctggc ttctcagcgt agttggaatc ttctgtattc tcttagcgca tgaccactat     120
ggacgtggtg gtggcatatt acatcaccac gagactcttc tggtggtatc acactatggc    180
caatcagcaa gtgagtttcc ccgctttga ttttagcttc tgttgtttct ggctt           235

<210> SEQ ID NO 515
<211> LENGTH: 233
<212> TYPE: DNA
<213> ORGANISM: Artificial Sequence
<220> FEATURE:
<223> OTHER INFORMATION: Synthetic Polynucleotide

<400> SEQUENCE: 515
gactattgca aatctctccc cctttcagat tccctcggc gactctggtg gtatcactgg      60
atttgctggc ttctcagcgt agttggaatc ttctgtattc tcttagcgca tgaactgtgg     120
acgtggtggt ggcatattac atcaccacga gactcttctg gtggtatcac actatggcca    180
atcagcaagt gagtttcccc gcttttgatt ttagcttctg ttgtttctgg ctt            233

<210> SEQ ID NO 516
<211> LENGTH: 235
<212> TYPE: DNA
<213> ORGANISM: Artificial Sequence
<220> FEATURE:
<223> OTHER INFORMATION: Synthetic Polynucleotide

<400> SEQUENCE: 516
gactattgca aatctctccc cctttcagat tccctcggc gactctggtg gtatcactgg      60
atttgctggc ttctcagcgt agttggaatc ttctgtattc tcttagcgca cgtccactgt     120
ggacgtggtg gtggcatatt acatcaccac gagactcttc tggtggtatc acactatggc    180
caatcagcaa gtgagtttcc ccgcttttga ttttagcttc tgttgtttct ggctt          235

<210> SEQ ID NO 517
<211> LENGTH: 214
<212> TYPE: DNA
<213> ORGANISM: Artificial Sequence
<220> FEATURE:
<223> OTHER INFORMATION: Synthetic Polynucleotide

<400> SEQUENCE: 517
gactattgca aatctctccc cctttcagat tccctcggc gactctggtg gtatcactgg      60
atttgctggc ttctcagcgt agttggaatc ttctgtattc tcttagcgca tggcatatta     120
catcaccacg agactcttct ggtggtatca cactatggcc aatcagcaag tgagtttccc    180

```
cgcttttgat tttagcttct gttgtttctg gctt                                214
```

<210> SEQ ID NO 518
<211> LENGTH: 237
<212> TYPE: DNA
<213> ORGANISM: Artificial Sequence
<220> FEATURE:
<223> OTHER INFORMATION: Synthetic Polynucleotide

<400> SEQUENCE: 518

```
gactattgca aatctctccc cctttcagat tcccctcggc gactctggtg gtatcactgg    60
atttgctggc ttctcagcgt agttggaatc ttctgtattc tcttagcgca tgaccactat   120
gtggacgtgg tggtggcata ttacatcacc acgagactct tctggtggta tcacactatg   180
gccaatcagc aagtgagttt ccccgctttt gattttagct tctgttgttt ctggctt     237
```

<210> SEQ ID NO 519
<211> LENGTH: 237
<212> TYPE: DNA
<213> ORGANISM: Artificial Sequence
<220> FEATURE:
<223> OTHER INFORMATION: Synthetic Polynucleotide

<400> SEQUENCE: 519

```
gactattgca aatctctccc cctttcagat tcccctcggc gactctggtg gtatcactgg    60
atttgctggc ttctcagcgt agttggaatc ttctgtattc tcttagcgca tgaccacact   120
gtggacgtgg tggtggcata ttacatcacc acgagactct tctggtggta tcacactatg   180
gccaatcagc aagtgagttt ccccgctttt gattttagct tctgttgttt ctggctt     237
```

<210> SEQ ID NO 520
<211> LENGTH: 234
<212> TYPE: DNA
<213> ORGANISM: Artificial Sequence
<220> FEATURE:
<223> OTHER INFORMATION: Synthetic Polynucleotide

<400> SEQUENCE: 520

```
gactattgca aatctctccc cctttcagat tcccctcggc gactctggtg gtatcactgg    60
atttgctggc ttctcagcgt agttggaatc ttctgtattc tcttagcgca tgaccctgtg   120
gacgtggtgg tggcatatta catcaccacg agactcttct ggtggtatca cactatggcc   180
aatcagcaag tgagtttccc cgcttttgat tttagcttct gttgtttctg gctt        234
```

<210> SEQ ID NO 521
<211> LENGTH: 234
<212> TYPE: DNA
<213> ORGANISM: Artificial Sequence
<220> FEATURE:
<223> OTHER INFORMATION: Synthetic Polynucleotide

<400> SEQUENCE: 521

```
gactattgca aatctctccc cctttcagat tcccctcggc gactctggtg gtatcactgg    60
atttgctggc ttctcagcgt agttggaatc ttctgtattc tcttagcgca tgaccacgtg   120
gacgtggtgg tggcatatta catcaccacg agactcttct ggtggtatca cactatggcc   180
aatcagcaag tgagtttccc cgcttttgat tttagcttct gttgtttctg gctt        234
```

<210> SEQ ID NO 522
<211> LENGTH: 234
<212> TYPE: DNA

<210> SEQ ID NO 522
<211> LENGTH: 234
<212> TYPE: DNA
<213> ORGANISM: Artificial Sequence
<220> FEATURE:
<223> OTHER INFORMATION: Synthetic Polynucleotide

<400> SEQUENCE: 522

```
gactattgca aatctctccc cctttcagat tcccctcggc gactctggtg gtatcactgg      60
atttgctggc ttctcagcgt agttggaatc ttctgtattc tcttagcgca tgaccactac     120
gacgtggtgg tggcatatta catcaccacg agactcttct ggtggtatca cactatggcc     180
aatcagcaag tgagtttccc cgcttttgat tttagcttct gttgtttctg gctt           234
```

<210> SEQ ID NO 523
<211> LENGTH: 227
<212> TYPE: DNA
<213> ORGANISM: Artificial Sequence
<220> FEATURE:
<223> OTHER INFORMATION: Synthetic Polynucleotide

<400> SEQUENCE: 523

```
gactattgca aatctctccc cctttcagat tcccctcggc gactctggtg gtatcactgg      60
atttgctggc ttctcagcgt agttggaatc ttctgtattc tcttagcgca tgaccactac     120
aggtggcata ttacatcacc acgagactct tctggtggta tcacactatg gccaatcagc     180
aagtgagttt ccccgctttt gattttagct tctgttgttt ctggctt                   227
```

<210> SEQ ID NO 524
<211> LENGTH: 241
<212> TYPE: DNA
<213> ORGANISM: Artificial Sequence
<220> FEATURE:
<223> OTHER INFORMATION: Synthetic Polynucleotide

<400> SEQUENCE: 524

```
gactattgca aatctctccc cctttcagat tcccctcggc gactctggtg gtatcactgg      60
atttgctggc ttctcagcgt agttggaatc ttctgtattc tcttagcgca tgaccactac     120
aactgtggac gtggtggtgg catattacat caccacgaga ctcttctggt ggtatcacac     180
tatggccaat cagcaagtgg gtttccccgc ttttgatttt agcttctgtt gtttctggct     240
t                                                                     241
```

<210> SEQ ID NO 525
<211> LENGTH: 241
<212> TYPE: DNA
<213> ORGANISM: Artificial Sequence
<220> FEATURE:
<223> OTHER INFORMATION: Synthetic Polynucleotide

<400> SEQUENCE: 525

```
gactattgca aatctctccc cctttcagat tcccctcggc gactctggtg gtatcactgg      60
atttgctggc ttctcagcgt agttggaatc ttccgtattc tcttagcgca tgaccactac     120
aactgtggac gtggtggtgg catattacat caccacgaga ctcttctggt ggtatcacac     180
tatggccaat cagcaagtga gtttccccgc ttttgatttt agcttctgtt gtttctggct     240
t                                                                     241
```

<210> SEQ ID NO 526
<211> LENGTH: 241
<212> TYPE: DNA
<213> ORGANISM: Artificial Sequence
<220> FEATURE:
<223> OTHER INFORMATION: Synthetic Polynucleotide

<400> SEQUENCE: 526

```
gactattgca aatctctccc cctttcagat tccctcggc gactctggtg gtatcactgg      60
atttgctggc ttctcagcgt agttggaatc ttctgtattc tcttagcgca tggccactac    120
aactgtggac gtggtggtgg catattacat caccacgaga ctcttctggt ggtatcacac    180
tatggccaat cagcaagtga gtttccccgc ttttgatttt agcttctgtt gtttctggct    240
t                                                                     241
```

<210> SEQ ID NO 527
<211> LENGTH: 241
<212> TYPE: DNA
<213> ORGANISM: Artificial Sequence
<220> FEATURE:
<223> OTHER INFORMATION: Synthetic Polynucleotide

<400> SEQUENCE: 527

```
gactattgca aatctctccc cctttcagat tccctcggc gactctggtg gtatcactgg      60
atttgctggc ctctcagcgt agttggaatc ttctgtattc tcttagcgca tgaccactac    120
aactgtggac gtggtggtgg catattacat caccacgaga ctcttctggt ggtatcacac    180
tatggccaat cagcaagtga gtttccccgc ttttgatttt agcttctgtt gtttctggct    240
t                                                                     241
```

<210> SEQ ID NO 528
<211> LENGTH: 235
<212> TYPE: DNA
<213> ORGANISM: Artificial Sequence
<220> FEATURE:
<223> OTHER INFORMATION: Synthetic Polynucleotide

<400> SEQUENCE: 528

```
gactattgca aatctctccc cctttcagat tccctcggc gactctggtg gtatcactgg      60
atttgctggc ttctcagcgt agttggaatc ttctgtattc tcttagcgca tgaccacagt    120
ggacgtggtg gtggcatatt acatcaccac gagactcttc tggtggtatc acactatggc    180
caatcagcaa gtgagtttcc ccgcttttga ttttagcttc tgttgtttct ggctt          235
```

<210> SEQ ID NO 529
<211> LENGTH: 241
<212> TYPE: DNA
<213> ORGANISM: Artificial Sequence
<220> FEATURE:
<223> OTHER INFORMATION: Synthetic Polynucleotide

<400> SEQUENCE: 529

```
gactattgca aatctctccc cctttcagat tccctcggc gactctggtg gtatcactgg      60
atttgctggc tcctcagcgt agttggaatc ttctgtattc tcttagcgca tgaccactac    120
aactgtggac gtggtggtgg catattacat caccacgaga ctcttctggt ggtatcacac    180
tatggccaat cagcaagtga gtttccccgc ttttgatttt agcttctgtt gtttctggct    240
t                                                                     241
```

<210> SEQ ID NO 530
<211> LENGTH: 230
<212> TYPE: DNA
<213> ORGANISM: Artificial Sequence
<220> FEATURE:
<223> OTHER INFORMATION: Synthetic Polynucleotide

<400> SEQUENCE: 530

```
gactattgca aatctctccc cctttcagat tccccctcggc gactctggtg gtatcactgg     60
atttgctggc ttctcagcgt agttggaatc ttctgtattc tcttagcgca tctgtggacg    120
tggtggtggc atattacatc accacgagac tcttctggtg gtatcacact atggccaatc    180
agcaagtgag tttccccgct tttgatttta gcttctgttg tttctggctt              230
```

<210> SEQ ID NO 531
<211> LENGTH: 235
<212> TYPE: DNA
<213> ORGANISM: Artificial Sequence
<220> FEATURE:
<223> OTHER INFORMATION: Synthetic Polynucleotide

<400> SEQUENCE: 531

```
gactattgca aatctctccc cctttcagat tccccctcggc gactctggtg gtatcactgg     60
atttgctggc ttctcagcgt agttggaatc ttctgtattc tcttagcgca tgaccactac    120
ggacgtggtg gtggcatatt acatcaccac gagactcttc tggtggtatc acactatggc    180
caatcagcaa gtgagtttcc ccgcttttga ttttagcttc tgttgtttct ggctt         235
```

<210> SEQ ID NO 532
<211> LENGTH: 241
<212> TYPE: DNA
<213> ORGANISM: Artificial Sequence
<220> FEATURE:
<223> OTHER INFORMATION: Synthetic Polynucleotide

<400> SEQUENCE: 532

```
gactattgca aatctctccc cctttcagat tccccctcggc gactctggtg gtatcactgg     60
atttgctggc ttctcagcgt agttggaatc ttctgtattc tcttagcgca tgaccactac    120
cactgtggac gtggtggtgg catattacat caccacgaga ctcttctggt ggtatcacac    180
tatggccaat cagcaagtga gtttccccgc ttttgatttt agcttctgtt gtttctggct    240
t                                                                    241
```

<210> SEQ ID NO 533
<211> LENGTH: 241
<212> TYPE: DNA
<213> ORGANISM: Artificial Sequence
<220> FEATURE:
<223> OTHER INFORMATION: Synthetic Polynucleotide

<400> SEQUENCE: 533

```
gactattgca aatctctccc cctttcagat tccccctcggc gactctggtg gtatcactgg     60
atttgctggc ttctcagcgt agttggaatc ttctgtattc tcttagcgca tgaccactac    120
aactgtggac gtggtggtgg catattacat caccacgaga ctcttctggt ggtatcacac    180
tatggccaat cggcaagtga gtttccccgc ttttgatttt agcttctgtt gtttctggct    240
t                                                                    241
```

<210> SEQ ID NO 534
<211> LENGTH: 240
<212> TYPE: DNA
<213> ORGANISM: Artificial Sequence
<220> FEATURE:
<223> OTHER INFORMATION: Synthetic Polynucleotide

<400> SEQUENCE: 534

```
gactattgca aatctctccc cctttcagat tccccctcggc gactctggtg gtatcactgg     60
```

```
atttgctggc ttctcagcgt agttggaatc ttctgtattc tcttagcgca tgaccactac    120
gctgtggacg tggtggtggc atattacatc accacgagac tcttctggtg gtatcacact    180
atggccaatc agcaagtgag tttccccgct tttgatttta gcttctgttg tttctggctt    240
```

<210> SEQ ID NO 535
<211> LENGTH: 221
<212> TYPE: DNA
<213> ORGANISM: Artificial Sequence
<220> FEATURE:
<223> OTHER INFORMATION: Synthetic Polynucleotide

<400> SEQUENCE: 535

```
tcctcatccc caagactgct attgactgag gtaaaatatg aatttgacac catgctgagt     60
taccttatac cacacaacat caggctcctg atcggacttt ttaaagtcat ccatgtctgg    120
acaggagatc tccttcttt  tagtgacttc agattttct  aaatagcgga tcctgctgtt    180
gtagcacagg cctgattcat tctctgcaac agtcaaggac a                        221
```

<210> SEQ ID NO 536
<211> LENGTH: 221
<212> TYPE: DNA
<213> ORGANISM: Artificial Sequence
<220> FEATURE:
<223> OTHER INFORMATION: Synthetic Polynucleotide

<400> SEQUENCE: 536

```
tcctcatccc caagactgct attgactgag gtaaaatatg aatttgacac catgctgagt     60
taccttatac cacacaacat caggctcctg atcggacttt ttaaagtcat ccatgtctgg    120
acaggagatc tccttcttt  tagtgacttc agattttct  aaatagcgga tcctgctgtt    180
gtagcacagg cctgattcat tctctgcaac agtcaaggac a                        221
```

<210> SEQ ID NO 537
<211> LENGTH: 222
<212> TYPE: DNA
<213> ORGANISM: Artificial Sequence
<220> FEATURE:
<223> OTHER INFORMATION: Synthetic Polynucleotide

<400> SEQUENCE: 537

```
tcctcatccc caagactgct attgactgag gtaaaatatg aatttgacac catgctgagt     60
taccttatac cacacaacca tcaggctcct gatcggactt tttaaagtca tccatgtctg    120
gacaggagat ctcctttctt ttagtgactt cagattttc  taaatagcgg atcctgctgt    180
tgtagcacag gcctgattca ttctctgcaa cagtcaagga ca                       222
```

<210> SEQ ID NO 538
<211> LENGTH: 215
<212> TYPE: DNA
<213> ORGANISM: Artificial Sequence
<220> FEATURE:
<223> OTHER INFORMATION: Synthetic Polynucleotide

<400> SEQUENCE: 538

```
tcctcatccc caagactgct attgactgag gtaaaatatg aatttgacac catgctgagt     60
taccttatac cacacaggct cctgatcgga cttttttaaag tcatccatgt ctggacagga    120
gatctccttt cttttagtga cttcagattt ttctaaatag cggatcctgc tgttgtagca    180
caggcctgat tcattctctg caacagtcaa ggaca                               215
```

<210> SEQ ID NO 539
<211> LENGTH: 222
<212> TYPE: DNA
<213> ORGANISM: Artificial Sequence
<220> FEATURE:
<223> OTHER INFORMATION: Synthetic Polynucleotide

<400> SEQUENCE: 539

```
tcctcatccc caagactgct attgactgag gtaaaatatg aatttgacac catgctgagt    60
taccttatac cacacaacta tcaggctcct gatcggactt tttaaagtca tccatgtctg   120
gacaggagat ctcctttctt ttagtgactt cagattttc taaatagcgg atcctgctgt   180
tgtagcacag gcctgattca ttctctgcaa cagtcaagga ca                     222
```

<210> SEQ ID NO 540
<211> LENGTH: 222
<212> TYPE: DNA
<213> ORGANISM: Artificial Sequence
<220> FEATURE:
<223> OTHER INFORMATION: Synthetic Polynucleotide

<400> SEQUENCE: 540

```
tcctcatccc caagactgct attgactgag gtaaaatatg aatttgacac catgctgagt    60
taccttatac cacacaacaa tcaggctcct gatcggactt tttaaagtca tccatgtctg   120
gacaggagat ctcctttctt ttagtgactt cagattttc taaatagcgg atcctgctgt   180
tgtagcacag gcctgattca ttctctgcaa cagtcaagga ca                     222
```

<210> SEQ ID NO 541
<211> LENGTH: 218
<212> TYPE: DNA
<213> ORGANISM: Artificial Sequence
<220> FEATURE:
<223> OTHER INFORMATION: Synthetic Polynucleotide

<400> SEQUENCE: 541

```
tcctcatccc caagactgct attgactgag gtaaaatatg aatttgacac catgctgagt    60
taccttatac cacacatcag gctcctgatc ggactttta aagtcatcca tgtctggaca   120
ggagatctcc tttcttttag tgacttcaga tttttctaaa tagcggatcc tgctgttgta   180
gcacaggcct gattcattct ctgcaacagt caaggaca                           218
```

<210> SEQ ID NO 542
<211> LENGTH: 219
<212> TYPE: DNA
<213> ORGANISM: Artificial Sequence
<220> FEATURE:
<223> OTHER INFORMATION: Synthetic Polynucleotide

<400> SEQUENCE: 542

```
tcctcatccc caagactgct attgactgag gtaaaatatg aatttgacac catgctgagt    60
taccttatac cacacaatca ggctcctgat cggacttttt aaagtcatcc atgtctggac   120
aggagatctc ctttctttta gtgacttcag attttctaa atagcggatc ctgctgttgt   180
agcacaggcc tgattcattc tctgcaacag tcaaggaca                          219
```

<210> SEQ ID NO 543
<211> LENGTH: 222
<212> TYPE: DNA
<213> ORGANISM: Artificial Sequence
<220> FEATURE:
<223> OTHER INFORMATION: Synthetic Polynucleotide

<400> SEQUENCE: 543

| | | |
|---|---|---|
| tcctcatccc caagactgct attgactgag gtaaaatatg aatttgacac catgctgagt | 60 |
| taccttatac cacacaacga tcaggctcct gatcggactt tttaaagtca tccatgtctg | 120 |
| gacaggagat ctcctttctt ttagtgactt cagattttc taaatagcgg atcctgctgt | 180 |
| tgtagcacag gcctgattca ttctctgcaa cagtcaagga ca | 222 |

<210> SEQ ID NO 544
<211> LENGTH: 213
<212> TYPE: DNA
<213> ORGANISM: Artificial Sequence
<220> FEATURE:
<223> OTHER INFORMATION: Synthetic Polynucleotide

<400> SEQUENCE: 544

| | | |
|---|---|---|
| tcctcatccc caagactgct attgactgag gtaaaatatg aatttgacac catgctgagt | 60 |
| taccttatac cacaggctcc tgatcggact ttttaaagtc atccatgtct ggacaggaga | 120 |
| tctcctttct tttagtgact tcagattttt ctaaatagcg gatcctgctg ttgtagcaca | 180 |
| ggcctgattc attctctgca acagtcaagg aca | 213 |

<210> SEQ ID NO 545
<211> LENGTH: 219
<212> TYPE: DNA
<213> ORGANISM: Artificial Sequence
<220> FEATURE:
<223> OTHER INFORMATION: Synthetic Polynucleotide

<400> SEQUENCE: 545

| | | |
|---|---|---|
| tcctcatccc caagactgct attgactgag gtaaaatatg aatttgacac catgctgagt | 60 |
| taccttatac cacacaacca ggctcctgat cggacttttt aaagtcatcc atgtctggac | 120 |
| aggagatctc ctttctttta gtgacttcag attttctaa atagcggatc ctgctgttgt | 180 |
| agcacaggcc tgattcattc tctgcaacag tcaaggaca | 219 |

<210> SEQ ID NO 546
<211> LENGTH: 221
<212> TYPE: DNA
<213> ORGANISM: Artificial Sequence
<220> FEATURE:
<223> OTHER INFORMATION: Synthetic Polynucleotide

<400> SEQUENCE: 546

| | | |
|---|---|---|
| tcctcatccc caagactgct attgactgag gtaaaatatg aatttgacac catgctgagt | 60 |
| taccttatac cacacaacat caggctcctg atcggacttt ttaaagtcat ccatgtctgg | 120 |
| acaggagatc tcctttcttt tagtgacttc agattttct aaatagcgga tcctgctgtt | 180 |
| gtagcacagg cctgattcat tatctgcaac agtcaaggac a | 221 |

<210> SEQ ID NO 547
<211> LENGTH: 216
<212> TYPE: DNA
<213> ORGANISM: Artificial Sequence
<220> FEATURE:
<223> OTHER INFORMATION: Synthetic Polynucleotide

<400> SEQUENCE: 547

| | | |
|---|---|---|
| tcctcatccc caagactgct attgactgag gtaaaatatg aatttgacac catgctgagt | 60 |
| taccttatac cacatcaggc tcctgatcgg acttttaaa gtcatccatg tctggacagg | 120 |

```
agatctcctt tcttttagtg acttcagatt tttctaaata gcggatcctg ctgttgtagc      180
acaggcctga ttcattctct gcaacagtca aggaca                                216

<210> SEQ ID NO 548
<211> LENGTH: 217
<212> TYPE: DNA
<213> ORGANISM: Artificial Sequence
<220> FEATURE:
<223> OTHER INFORMATION: Synthetic Polynucleotide

<400> SEQUENCE: 548
tcctcatccc caagactgct attgactgag gtaaaatatg aatttgacac catgctgagt      60
taccttatac cacaatcagg ctcctgatcg gacttttta a agtcatccat gtctggacag     120
gagatctcct ttcttttagt gacttcagat ttttctaaat agcggatcct gctgttgtag      180
cacaggcctg attcattctc tgcaacagtc aaggaca                               217

<210> SEQ ID NO 549
<211> LENGTH: 218
<212> TYPE: DNA
<213> ORGANISM: Artificial Sequence
<220> FEATURE:
<223> OTHER INFORMATION: Synthetic Polynucleotide

<400> SEQUENCE: 549
tcctcatccc caagactgct attgactgag gtaaaatatg aatttgacac catgctgagt      60
taccttatac cacacaacag gctcctgatc ggacttttta aagtcatcca tgtctggaca      120
ggagatctcc tttcttttag tgacttcaga ttttttctaaa tagcggatcc tgctgttgta     180
gcacaggcct gattcattct ctgcaacagt caaggaca                              218

<210> SEQ ID NO 550
<211> LENGTH: 211
<212> TYPE: DNA
<213> ORGANISM: Artificial Sequence
<220> FEATURE:
<223> OTHER INFORMATION: Synthetic Polynucleotide

<400> SEQUENCE: 550
tcctcatccc caagactgct attgactgag gtaaaatatg aatttgacac catgctgagt      60
taccttatac caggctcctg atcggacttt ttaaagtcat ccatgtctgg acaggagatc      120
tcctttcttt tagtgacttc agatttttct aaatagcgga tcctgctgtt gtagcacagg      180
cctgattcat tctctgcaac agtcaaggac a                                     211

<210> SEQ ID NO 551
<211> LENGTH: 214
<212> TYPE: DNA
<213> ORGANISM: Artificial Sequence
<220> FEATURE:
<223> OTHER INFORMATION: Synthetic Polynucleotide

<400> SEQUENCE: 551
tcctcatccc caagactgct attgactgag gtaaaatatg aatttgacac catgctgagt      60
taccttatac cacacaactc ctgatcggac ttttaaagt catccatgtc tggacaggag       120
atctcctttc ttttagtgac ttcagatttt tctaaatagc ggatcctgct gttgtagcac      180
aggcctgatt cattctctgc aacagtcaag gaca                                  214

<210> SEQ ID NO 552
<211> LENGTH: 204
```

<212> TYPE: DNA
<213> ORGANISM: Artificial Sequence
<220> FEATURE:
<223> OTHER INFORMATION: Synthetic Polynucleotide

<400> SEQUENCE: 552
tcctcatccc caagactgct attgactgag gtaaaatatg aatttgacac catgctgagt       60
taccttatac ctgatcggac tttttaaagt catccatgtc tggacaggag atctcctttc     120
ttttagtgac ttcagatttt tctaaatagc ggatcctgct gttgtagcac aggcctgatt     180
cattctctgc aacagtcaag gaca                                              204

<210> SEQ ID NO 553
<211> LENGTH: 211
<212> TYPE: DNA
<213> ORGANISM: Artificial Sequence
<220> FEATURE:
<223> OTHER INFORMATION: Synthetic Polynucleotide

<400> SEQUENCE: 553
tcctcatccc caagactgct attgactgag gtaaaatatg aatttgacac catgctgagt       60
taccttatat caggctcctg atcggacttt ttaaagtcat ccatgtctgg acaggagatc     120
tcctttcttt tagtgacttc agattttttct aaatagcgga tcctgctgtt gtagcacagg     180
cctgattcat tctctgcaac agtcaaggac a                                      211

<210> SEQ ID NO 554
<211> LENGTH: 197
<212> TYPE: DNA
<213> ORGANISM: Artificial Sequence
<220> FEATURE:
<223> OTHER INFORMATION: Synthetic Polynucleotide

<400> SEQUENCE: 554
tcctcatccc caagactgct attgactgag gtaaaatatg aatttgacac catgctgagt       60
tacctgatcg gactttttaa agtcatccat gtctggacag gagatctcct ttcttttagt     120
gacttcagat ttttctaaat agcggatcct gctgttgtag cacaggcctg attcattctc     180
tgcaacagtc aaggaca                                                      197

<210> SEQ ID NO 555
<211> LENGTH: 197
<212> TYPE: DNA
<213> ORGANISM: Artificial Sequence
<220> FEATURE:
<223> OTHER INFORMATION: Synthetic Polynucleotide

<400> SEQUENCE: 555
tcctcatccc caagactgct attgactgag gtaaaatatg aatttgacac catgctgagt       60
taccttatcg gactttttaa agtcatccat gtctggacag gagatctcct ttcttttagt     120
gacttcagat ttttctaaat agcggatcct gctgttgtag cacaggcctg attcattctc     180
tgcaacagtc aaggaca                                                      197

<210> SEQ ID NO 556
<211> LENGTH: 211
<212> TYPE: DNA
<213> ORGANISM: Artificial Sequence
<220> FEATURE:
<223> OTHER INFORMATION: Synthetic Polynucleotide

<400> SEQUENCE: 556

```
tcctcatccc caagactgct attgactgag gtaaaatatg aatttgacac catgctgagt    60
taccttatac cacactcctg atcggacttt ttaaagtcat ccatgtctgg acaggagatc   120
tcctttcttt tagtgacttc agattttttct aaatagcgga tcctgctgtt gtagcacagg  180
cctgattcat tctctgcaac agtcaaggac a                                  211

<210> SEQ ID NO 557
<211> LENGTH: 216
<212> TYPE: DNA
<213> ORGANISM: Artificial Sequence
<220> FEATURE:
<223> OTHER INFORMATION: Synthetic Polynucleotide

<400> SEQUENCE: 557
tcctcatccc caagactgct attgactgag gtaaaatatg aatttgacac catgctgagt    60
taccttatac cacacaaggc tcctgatcgg acttttttaaa gtcatccatg tctggacagg  120
agatctcctt tcttttagtg acttcagatt tttctaaata gcggatcctg ctgttgtagc   180
acaggcctga ttcattctct gcaacagtca aggaca                             216

<210> SEQ ID NO 558
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 558
tcctcatccc caagactgct attgactgag gtaaaatatg aatttgacac catgctgagt    60
taccttatac tcctgatcgg acttttttaaa gtcatccatg tctggacagg agatctcctt  120
tcttttagtg acttcagatt tttctaaata gcggatcctg ctgttgtagc acaggcctga   180
ttcattctct gcaacagtca aggaca                                        206

<210> SEQ ID NO 559
<211> LENGTH: 214
<212> TYPE: DNA
<213> ORGANISM: Artificial Sequence
<220> FEATURE:
<223> OTHER INFORMATION: Synthetic Polynucleotide

<400> SEQUENCE: 559
tcctcatccc caagactgct attgactgag gtaaaatatg aatttgacac catgctgagt    60
taccttatac catcaggctc ctgatcggac tttttaaagt catccatgtc tggacaggag   120
atctcctttc ttttagtgac ttcagatttt tctaaatagc ggatcctgct gttgtagcac   180
aggcctgatt cattctctgc aacagtcaag gaca                               214

<210> SEQ ID NO 560
<211> LENGTH: 209
<212> TYPE: DNA
<213> ORGANISM: Artificial Sequence
<220> FEATURE:
<223> OTHER INFORMATION: Synthetic Polynucleotide

<400> SEQUENCE: 560
tcctcatccc caagactgct attgactgag gtaaaatatg aatttgacac catgctgagt    60
taccttatca ggctcctgat cggacttttt aaagtcatcc atgtctggac aggagatctc   120
ctttctttta gtgacttcag atttttctaa atagcggatc ctgctgttgt agcacaggcc   180
tgattcattc tctgcaacag tcaaggaca                                     209
```

<210> SEQ ID NO 561
<211> LENGTH: 220
<212> TYPE: DNA
<213> ORGANISM: Artificial Sequence
<220> FEATURE:
<223> OTHER INFORMATION: Synthetic Polynucleotide

<400> SEQUENCE: 561

```
tcctcatccc caagactgct attgactgag gtaaaatatg aatttgacac catgctgagt     60
taccttatac cacacaaatc aggctcctga tcggactttt taaagtcatc catgtctgga    120
caggagatct cctttctttt agtgacttca gattttttcta aatagcggat cctgctgttg   180
tagcacaggc ctgattcatt ctctgcaaca gtcaaggaca                          220
```

<210> SEQ ID NO 562
<211> LENGTH: 211
<212> TYPE: DNA
<213> ORGANISM: Artificial Sequence
<220> FEATURE:
<223> OTHER INFORMATION: Synthetic Polynucleotide

<400> SEQUENCE: 562

```
tcctcatccc caagactgct attgactgag gtaaaatatg aatttgacac catgctgagt     60
taccttatac cacacaactg atcggacttt ttaaagtcat ccatgtctgg acaggagatc    120
tcctttcttt tagtgacttc agattttttct aaatagcgga tcctgctgtt gtagcacagg   180
cctgattcat tctctgcaac agtcaaggac a                                   211
```

<210> SEQ ID NO 563
<211> LENGTH: 219
<212> TYPE: DNA
<213> ORGANISM: Artificial Sequence
<220> FEATURE:
<223> OTHER INFORMATION: Synthetic Polynucleotide

<400> SEQUENCE: 563

```
tcctcatccc caagactgct attgactgag gtaaaatatg aatttgacac catgctgagt     60
taccttatac cacaccatca ggctcctgat cggacttttt aaagtcatcc atgtctggac    120
aggagatctc ctttctttta gtgacttcag attttttctaa atagcggatc ctgctgttgt   180
agcacaggcc tgattcattc tctgcaacag tcaaggaca                           219
```

<210> SEQ ID NO 564
<211> LENGTH: 197
<212> TYPE: DNA
<213> ORGANISM: Artificial Sequence
<220> FEATURE:
<223> OTHER INFORMATION: Synthetic Polynucleotide

<400> SEQUENCE: 564

```
tcctcatccc caagactgct attgactgag gtaaaatatg aatttgacac catgctgagg     60
ctcctgatcg gactttttaa agtcatccat gtctggacag gagatctcct ttcttttagt    120
gacttcagat ttttctaaat agcggatcct gctgttgtag cacaggcctg attcattctc    180
tgcaacagtc aaggaca                                                   197
```

<210> SEQ ID NO 565
<211> LENGTH: 215
<212> TYPE: DNA
<213> ORGANISM: Artificial Sequence
<220> FEATURE:

<223> OTHER INFORMATION: Synthetic Polynucleotide

<400> SEQUENCE: 565

| tcctcatccc caagactgct attgactgag gtaaaatatg aatttgacac catgctgagt | 60 |
| taccttatac cgatcaggct cctgatcgga ctttttaaag tcatccatgt ctggacagga | 120 |
| gatctccttt cttttagtga cttcagattt ttctaaatag cggatcctgc tgttgtagca | 180 |
| caggcctgat tcattctctg caacagtcaa ggaca | 215 |

<210> SEQ ID NO 566
<211> LENGTH: 213
<212> TYPE: DNA
<213> ORGANISM: Artificial Sequence
<220> FEATURE:
<223> OTHER INFORMATION: Synthetic Polynucleotide

<400> SEQUENCE: 566

| tcctcatccc caagactgct attgactgag gtaaaatatg aatttgacac catgctgagt | 60 |
| taccttatac atcaggctcc tgatcggact ttttaaagtc atccatgtct ggacaggaga | 120 |
| tctcctttct tttagtgact tcagattttt ctaaatagcg gatcctgctg ttgtagcaca | 180 |
| ggcctgattc attctctgca acagtcaagg aca | 213 |

<210> SEQ ID NO 567
<211> LENGTH: 209
<212> TYPE: DNA
<213> ORGANISM: Artificial Sequence
<220> FEATURE:
<223> OTHER INFORMATION: Synthetic Polynucleotide

<400> SEQUENCE: 567

| tcctcatccc caagactgct attgactgag gtaaaatatg aatttgacac catgctgagt | 60 |
| taccttatac cactcctgat cggacttttt aaagtcatcc atgtctggac aggagatctc | 120 |
| cttcttttta gtgacttcag attttctaa atagcggatc ctgctgttgt agcacaggcc | 180 |
| tgattcattc tctgcaacag tcaaggaca | 209 |

<210> SEQ ID NO 568
<211> LENGTH: 190
<212> TYPE: DNA
<213> ORGANISM: Artificial Sequence
<220> FEATURE:
<223> OTHER INFORMATION: Synthetic Polynucleotide

<400> SEQUENCE: 568

| tcctcatccc caagactgct attgactgag gtaaaatatg aatttgacac catgctgaga | 60 |
| tcggactttt taaagtcatc catgtctgga caggagatct cctttctttt agtgacttca | 120 |
| gattttctta aatagcggat cctgctgttg tagcacaggc ctgattcatt ctctgcaaca | 180 |
| gtcaaggaca | 190 |

<210> SEQ ID NO 569
<211> LENGTH: 277
<212> TYPE: DNA
<213> ORGANISM: Artificial Sequence
<220> FEATURE:
<223> OTHER INFORMATION: Synthetic Polynucleotide

<400> SEQUENCE: 569

| tcctcatccc caagactgct gaccaaagcc tatattttgg gacgtggatg atgagagtaa | 60 |
| actacacctt ctgcccattt tagcttcctg ctctcacctc caacaagaat aagagatgtg | 120 |

```
ccaactttct ctgggtgcat acttgctgcc atgcactgtt ctgggtacca ggatagagca    180 ttaaagggc agatgcagtc cctgcttcca tgaagggtca taaattcctt cctgggcctt    240
atagttagcc ttcatcactc tgcaacagtc aaggaca                            277
```

<210> SEQ ID NO 570
<211> LENGTH: 202
<212> TYPE: DNA
<213> ORGANISM: Artificial Sequence
<220> FEATURE:
<223> OTHER INFORMATION: Synthetic Polynucleotide

<400> SEQUENCE: 570

```
tcctcatccc caagactgct attgactgag gtaaaatatg aatttgacac catgctgagt     60
taccttatac cacacaactt tttaaagtca tccatgtctg gacaggagat ctcctttctt    120
ttagtgactt cagattttc taaatagcgg atcctgctgt tgtagcacag gcctgattca    180
ttctctgcaa cagtcaagga ca                                            202
```

<210> SEQ ID NO 571
<211> LENGTH: 196
<212> TYPE: DNA
<213> ORGANISM: Artificial Sequence
<220> FEATURE:
<223> OTHER INFORMATION: Synthetic Polynucleotide

<400> SEQUENCE: 571

```
tcctcatccc caagactgct attgactgag gtaaaatatg aatttgacac catgctgagc     60
tcctgatcgg acttttaaa gtcatccatg tctggacagg agatctcctt tcttttagtg    120
acttcagatt tttctaaata gcggatcctg ctgttgtagc acaggcctga ttcattctct    180
gcaacagtca aggaca                                                   196
```

<210> SEQ ID NO 572
<211> LENGTH: 200
<212> TYPE: DNA
<213> ORGANISM: Artificial Sequence
<220> FEATURE:
<223> OTHER INFORMATION: Synthetic Polynucleotide

<400> SEQUENCE: 572

```
tcctcatccc caagactgct attgactgag gtaaaatatg aatttgacac catgctgagt     60
taccttatga tcggactttt taaagtcatc catgtctgga caggagatct cctttctttt    120
agtgacttca gattttcta aatagcggat cctgctgttg tagcacaggc ctgattcatt    180
ctctgcaaca gtcaaggaca                                               200
```

<210> SEQ ID NO 573
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 573

```
tcctcatccc caagactgct attgactgag gtaaaatatg aatttgacac catgctgagt     60
taccttatac cacacatcgg acttttaaa gtcatccatg tctggacagg agatctcctt    120
tcttttagtg acttcagatt tttctaaata gcggatcctg ctgttgtagc acaggcctga    180
ttcattctct gcaacagtca aggaca                                        206
```

```
<210> SEQ ID NO 574
<211> LENGTH: 199
<212> TYPE: DNA
<213> ORGANISM: Artificial Sequence
<220> FEATURE:
<223> OTHER INFORMATION: Synthetic Polynucleotide

<400> SEQUENCE: 574
tcctcatccc caagactgct attgactgag gtaaaatatg aatttgacac catgctgagt      60
taccttatac cacactttt aaagtcatcc atgtctggac aggagatctc ctttcttta     120 gtgacttcag attttctaa atagcggatc ctgctgttgt agcacaggcc tgattcattc     180
tctgcaacag tcaaggaca                                                  199

<210> SEQ ID NO 575
<211> LENGTH: 188
<212> TYPE: DNA
<213> ORGANISM: Artificial Sequence
<220> FEATURE:
<223> OTHER INFORMATION: Synthetic Polynucleotide

<400> SEQUENCE: 575
tcctcatccc caagactgct attgactgag gtaaaatatg aatttgacac catgctgatc      60 ggactttta aagtcatcca tgtctggaca ggagatctcc tttcttttag tgacttcaga     120 ttttctaaa tagcggatcc tgctgttgta gcacaggcct gattcattct ctgcaacagt     180
caaggaca                                                              188

<210> SEQ ID NO 576
<211> LENGTH: 200
<212> TYPE: DNA
<213> ORGANISM: Artificial Sequence
<220> FEATURE:
<223> OTHER INFORMATION: Synthetic Polynucleotide

<400> SEQUENCE: 576
tcctcatccc caagactgct attgactgag gtaaaatatg aatttgacac catgctgagt      60
tacctcctga tcggactttt taaagtcatc catgtctgga caggagatct cctttctttt    120
agtgacttca gattttccta aatagcggat cctgctgttg tagcacaggc ctgattcatt    180
ctctgcaaca gtcaaggaca                                                 200

<210> SEQ ID NO 577
<211> LENGTH: 192
<212> TYPE: DNA
<213> ORGANISM: Artificial Sequence
<220> FEATURE:
<223> OTHER INFORMATION: Synthetic Polynucleotide

<400> SEQUENCE: 577
tcctcatccc caagactgct attgactgag gtaaaatatg aatttgacac catgctgagt      60
gatcggactt tttaaagtca tccatgtctg gacaggagat ctcctttctt ttagtgactt    120 cagattttc taaatagcgg atcctgctgt tgtagcacag gcctgattca ttctctgcaa    180
cagtcaagga ca                                                         192

<210> SEQ ID NO 578
<211> LENGTH: 203
<212> TYPE: DNA
<213> ORGANISM: Artificial Sequence
<220> FEATURE:
<223> OTHER INFORMATION: Synthetic Polynucleotide
```

<400> SEQUENCE: 578

```
tcctcatccc caagactgct attgactgag gtaaaatatg aatttgacac catgctgagt    60
taccttatcc tgatcggact ttttaaagtc atccatgtct ggacaggaga tctccttttct  120
tttagtgact tcagattttt ctaaatagcg gatcctgctg ttgtagcaca ggcctgattc   180
attctctgca acagtcaagg aca                                           203
```

<210> SEQ ID NO 579
<211> LENGTH: 220
<212> TYPE: DNA
<213> ORGANISM: Artificial Sequence
<220> FEATURE:
<223> OTHER INFORMATION: Synthetic Polynucleotide

<400> SEQUENCE: 579

```
tcctcatccc caagactgct attgactgag gtaaaatatg aatttgacac catgctgagt    60
taccttatac cacacaactc aggctcctga tcggactttt taaagtcatc catgtctgga  120
caggagatct cctttctttt agtgacttca gattttttcta atagcggat cctgctgttg   180
tagcacaggc ctgattcatt ctctgcaaca gtcaaggaca                         220
```

<210> SEQ ID NO 580
<211> LENGTH: 219
<212> TYPE: DNA
<213> ORGANISM: Artificial Sequence
<220> FEATURE:
<223> OTHER INFORMATION: Synthetic Polynucleotide

<400> SEQUENCE: 580

```
tcctcatccc caagactgct attgactgag gtaaaatatg aatttgacac catgctgagt    60
taccttatac cacacgatca ggctcctgat cggactttt aaagtcatcc atgtctggac   120
aggagatctc ctttctttta gtgacttcag attttttctaa atagcggatc ctgctgttgt  180
agcacaggcc tgattcattc tctgcaacag tcaaggaca                          219
```

<210> SEQ ID NO 581
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 581

```
tcctcatccc caagactgct attgactgag gtaaaatatg aatttgacac catgctgagt    60
taccttatac cactgatcgg acttttttaaa gtcatccatg tctggacagg agatctcctt  120
tcttttagtg acttcagatt tttctaaata gcggatcctg ctgttgtagc acaggcctga   180
ttcattctct gcaacagtca aggaca                                        206
```

<210> SEQ ID NO 582
<211> LENGTH: 222
<212> TYPE: DNA
<213> ORGANISM: Artificial Sequence
<220> FEATURE:
<223> OTHER INFORMATION: Synthetic Polynucleotide

<400> SEQUENCE: 582

```
tcctcatccc caagactgct attgactgag gtaaaatatg aatttgacac catgctgagt    60
taccttatac cacacaacca tcaggctcct gatcggactt tttaaagtca tccatgtctg   120
```

```
gacaggagat ctcctttctt ttagtgactt cagattttc taaatagcgg atcctgctgt    180
tgtagcacag gcctgattca ttatctgcaa cagtcaagga ca                      222

<210> SEQ ID NO 583
<211> LENGTH: 215
<212> TYPE: DNA
<213> ORGANISM: Artificial Sequence
<220> FEATURE:
<223> OTHER INFORMATION: Synthetic Polynucleotide

<400> SEQUENCE: 583
tcctcatccc caagactgct attgactgag gtaaaatatg aatttgacac catgctgagt    60
taccttatac caatcaggct cctgatcgga cttttaaag tcatccatgt ctggacagga    120
gatctccttt cttttagtga cttcagattt ttctaaatag cggatcctgc tgttgtagca    180
caggcctgat tcattctctg caacagtcaa ggaca                               215

<210> SEQ ID NO 584
<211> LENGTH: 217
<212> TYPE: DNA
<213> ORGANISM: Artificial Sequence
<220> FEATURE:
<223> OTHER INFORMATION: Synthetic Polynucleotide

<400> SEQUENCE: 584
tcctcatccc caagactgct attgactgag gtaaaatatg aatttgacac catgctgagt    60
taccttatac cacacacagg ctcctgatcg gacttttaa agtcatccat gtctggacag    120
gagatctcct ttcttttagt gacttcagat ttttctaaat agcggatcct gctgttgtag    180
cacaggcctg attcattctc tgcaacagtc aaggaca                             217

<210> SEQ ID NO 585
<211> LENGTH: 215
<212> TYPE: DNA
<213> ORGANISM: Artificial Sequence
<220> FEATURE:
<223> OTHER INFORMATION: Synthetic Polynucleotide

<400> SEQUENCE: 585
tcctcatccc caagactgct attgactgag gtaaaatatg aatttgacac catgctgagt    60
taccttatac cacacaacct cctgatcgga cttttaaag tcatccatgt ctggacagga    120
gatctccttt cttttagtga cttcagattt ttctaaatag cggatcctgc tgttgtagca    180
caggcctgat tcattctctg caacagtcaa ggaca                               215

<210> SEQ ID NO 586
<211> LENGTH: 203
<212> TYPE: DNA
<213> ORGANISM: Artificial Sequence
<220> FEATURE:
<223> OTHER INFORMATION: Synthetic Polynucleotide

<400> SEQUENCE: 586
tcctcatccc caagactgct attgactgag gtaaaatatg aatttgacac catgctgagt    60
taccttatac tgatcggact ttttaaagtc atccatgtct ggacaggaga tctcctttct    120
tttagtgact tcagattttt ctaaatagcg gatcctgctg ttgtagcaca ggcctgattc    180
attctctgca acagtcaagg aca                                            203

<210> SEQ ID NO 587
<211> LENGTH: 204
```

```
<212> TYPE: DNA
<213> ORGANISM: Artificial Sequence
<220> FEATURE:
<223> OTHER INFORMATION: Synthetic Polynucleotide

<400> SEQUENCE: 587
tcctcatccc caagactgct attgactgag gtaaaatatg aatttgacac catgctgagt    60
tatcaggctc ctgatcggac tttttaaagt catccatgtc tggacaggag atctcctttc   120
ttttagtgac ttcagatttt tctaaatagc ggatcctgct gttgtagcac aggcctgatt   180
cattctctgc aacagtcaag gaca                                          204

<210> SEQ ID NO 588
<211> LENGTH: 195
<212> TYPE: DNA
<213> ORGANISM: Artificial Sequence
<220> FEATURE:
<223> OTHER INFORMATION: Synthetic Polynucleotide

<400> SEQUENCE: 588
tcctcatccc caagactgct attgactgag gtaaaatatg aatttgacac catgctgagt    60
cctgatcgga ctttttaaag tcatccatgt ctggacagga gatctccttt cttttagtga   120
cttcagattt ttctaaatag cggatcctgc tgttgtagca caggcctgat tcattctctg   180
caacagtcaa ggaca                                                    195

<210> SEQ ID NO 589
<211> LENGTH: 212
<212> TYPE: DNA
<213> ORGANISM: Artificial Sequence
<220> FEATURE:
<223> OTHER INFORMATION: Synthetic Polynucleotide

<400> SEQUENCE: 589
tcctcatccc caagactgct attgactgag gtaaaatatg aatttgacac catgctgagt    60
taccttatac cacacaacct gatcggactt tttaaagtca tccatgtctg gacaggagat   120
ctcctttctt ttagtgactt cagattttc taaatagcgg atcctgctgt tgtagcacag    180
gcctgattca ttctctgcaa cagtcaagga ca                                 212

<210> SEQ ID NO 590
<211> LENGTH: 193
<212> TYPE: DNA
<213> ORGANISM: Artificial Sequence
<220> FEATURE:
<223> OTHER INFORMATION: Synthetic Polynucleotide

<400> SEQUENCE: 590
tcctcatccc caagactgct attgactgag gtaaaatatg aatttgacac catgctgagt    60
tgatcggact ttttaaagtc atccatgtct ggacaggaga tctcctttct tttagtgact   120
tcagattttt ctaaatagcg gatcctgctg ttgtagcaca ggcctgattc attctctgca   180
acagtcaagg aca                                                      193

<210> SEQ ID NO 591
<211> LENGTH: 210
<212> TYPE: DNA
<213> ORGANISM: Artificial Sequence
<220> FEATURE:
<223> OTHER INFORMATION: Synthetic Polynucleotide

<400> SEQUENCE: 591
```

```
tcctcatccc caagactgct attgactgag gtaaaatatg aatttgacac catgctgagt      60
taccttatac aggctcctga tcggactttt taaagtcatc catgtctgga caggagatct     120
cctttctttt agtgacttca gattttctaa atagcggat cctgctgttg tagcacaggc      180
ctgattcatt ctctgcaaca gtcaaggaca                                      210

<210> SEQ ID NO 592
<211> LENGTH: 198
<212> TYPE: DNA
<213> ORGANISM: Artificial Sequence
<220> FEATURE:
<223> OTHER INFORMATION: Synthetic Polynucleotide

<400> SEQUENCE: 592
tcctcatccc caagactgct attgactgag gtaaaatatg aatttgacac catgctgagt      60
taccttgatc ggacttttta aagtcatcca tgtctggaca ggagatctcc tttcttttag     120
tgacttcaga ttttctaaa tagcggatcc tgctgttgta gcacaggcct gattcattct      180
ctgcaacagt caaggaca                                                   198

<210> SEQ ID NO 593
<211> LENGTH: 207
<212> TYPE: DNA
<213> ORGANISM: Artificial Sequence
<220> FEATURE:
<223> OTHER INFORMATION: Synthetic Polynucleotide

<400> SEQUENCE: 593
tcctcatccc caagactgct attgactgag gtaaaatatg aatttgacac catgctgagt      60
taccttatac tcctgatcg gacttttta agtcatccat gtctggacag gagatctcct      120
ttcttttagt gacttcagat ttttctaaat agcggatcct gctgttgtag cacaggcctg     180
attcattctc tgcaacagtc aaggaca                                         207

<210> SEQ ID NO 594
<211> LENGTH: 180
<212> TYPE: DNA
<213> ORGANISM: Artificial Sequence
<220> FEATURE:
<223> OTHER INFORMATION: Synthetic Polynucleotide

<400> SEQUENCE: 594
tcctcatccc caagactgct attgactgag gtaaaatatg aatttgacac catgctgagt      60
taaagtcatc catgtctgga caggagatct cctttctttt agtgacttca gattttctca    120
aatagcggat cctgctgttg tagcacaggc ctgattcatt ctctgcaaca gtcaaggaca    180

<210> SEQ ID NO 595
<211> LENGTH: 187
<212> TYPE: DNA
<213> ORGANISM: Artificial Sequence
<220> FEATURE:
<223> OTHER INFORMATION: Synthetic Polynucleotide

<400> SEQUENCE: 595
tcctcatccc caagactgct attgactgag gtaaaatatg aatttgacac catgctgagt      60
tactttttaa agtcatccat gtctggacag gagatctcct ttcttttagt gacttcagat     120
ttttctaaat agcggatcct gctgttgtag cacaggcctg attcattctc tgcaacagtc     180
aaggaca                                                               187
```

```
<210> SEQ ID NO 596
<211> LENGTH: 209
<212> TYPE: DNA
<213> ORGANISM: Artificial Sequence
<220> FEATURE:
<223> OTHER INFORMATION: Synthetic Polynucleotide

<400> SEQUENCE: 596
tcctcatccc caagactgct attgactgag gtaaaatatg aatttgacac catgctgagt      60
taccttatac cacacaacat cggacttttt aaagtcatcc atgtctggac aggagatctc     120 ctttcttta gtgacttcag attttctaa atagcggatc ctgctgttgt agcacaggcc     180
tgattcattc tctgcaacag tcaaggaca                                        209

<210> SEQ ID NO 597
<211> LENGTH: 208
<212> TYPE: DNA
<213> ORGANISM: Artificial Sequence
<220> FEATURE:
<223> OTHER INFORMATION: Synthetic Polynucleotide

<400> SEQUENCE: 597
tcctcatccc caagactgct attgactgag gtaaaatatg aatttgacac catgctgagt      60
taccttatac cacactgatc ggactttta aagtcatcca tgtctggaca ggagatctcc     120
tttcttttag tgacttcaga tttttctaaa tagcggatcc tgctgttgta gcacaggcct     180
gattcattct ctgcaacagt caaggaca                                         208

<210> SEQ ID NO 598
<211> LENGTH: 216
<212> TYPE: DNA
<213> ORGANISM: Artificial Sequence
<220> FEATURE:
<223> OTHER INFORMATION: Synthetic Polynucleotide

<400> SEQUENCE: 598
tcctcatccc caagactgct attgactgag gtaaaatatg aatttgacac catgctgagt      60
taccttatac cacacaacgc tcctgatcgg acttttaaa gtcatccatg tctggacagg     120
agatctcctt tcttttagtg acttcagatt tttctaaata gcggatcctg ctgttgtagc     180
acaggcctga ttcattctct gcaacagtca aggaca                                216

<210> SEQ ID NO 599
<211> LENGTH: 223
<212> TYPE: DNA
<213> ORGANISM: Artificial Sequence
<220> FEATURE:
<223> OTHER INFORMATION: Synthetic Polynucleotide

<400> SEQUENCE: 599
tcctcatccc caagactgct attgactgag gtaaaatatg aatttgacac catgctgagt      60
taccttatac cacacaacaa atcaggctcc tgatcggact ttaaagtc atccatgtct     120 ggacaggaga tctcctttct tttagtgact tcagattttt ctaaatagcg gatcctgctg     180
ttgtagcaca ggcctgattc attctctgca acagtcaagg aca                        223

<210> SEQ ID NO 600
<211> LENGTH: 190
<212> TYPE: DNA
<213> ORGANISM: Artificial Sequence
<220> FEATURE:
<223> OTHER INFORMATION: Synthetic Polynucleotide
```

```
<400> SEQUENCE: 600
tcctcatccc caagactgct attgactgag gtaaaatatg aatttgacac catgctgagt    60
tcggactttt taaagtcatc catgtctgga caggagatct cctttctttt agtgacttca   120
gattttctta aatagcggat cctgctgttg tagcacaggc ctgattcatt ctctgcaaca   180
gtcaaggaca                                                         190

<210> SEQ ID NO 601
<211> LENGTH: 221
<212> TYPE: DNA
<213> ORGANISM: Artificial Sequence
<220> FEATURE:
<223> OTHER INFORMATION: Synthetic Polynucleotide

<400> SEQUENCE: 601
tcctcatccc caagactgct attgactgag ggaaaatatg aatttgacac catgctgagt    60
taccttatac cacacaacat caggctcctg atcggacttt ttaaagtcat ccatgtctgg   120
acaggagatc tcctttcttt tagtgacttc agattttcct aaatagcgga tcctgctgtt   180
gtagcacagg cctgattcat tctctgcaac agtcaaggac a                      221

<210> SEQ ID NO 602
<211> LENGTH: 185
<212> TYPE: DNA
<213> ORGANISM: Artificial Sequence
<220> FEATURE:
<223> OTHER INFORMATION: Synthetic Polynucleotide

<400> SEQUENCE: 602
tcctcatccc caagactgct attgactgag gtaaaatatg aatttgacac catgctgagt    60
taccttaaag tcatccatgt ctggacagga gatctccttt cttttagtga cttcagattt   120
ttctaaatag cggatcctgc tgttgtagca caggcctgat tcattctctg caacagtcaa   180
ggaca                                                              185

<210> SEQ ID NO 603
<211> LENGTH: 215
<212> TYPE: DNA
<213> ORGANISM: Artificial Sequence
<220> FEATURE:
<223> OTHER INFORMATION: Synthetic Polynucleotide

<400> SEQUENCE: 603
tcctcatccc caagactgct attgactgag gtaaaatatg aatttgacac catgctgagt    60
taccttatac cacacaggct cctgatcgga cttttaaag tcatccatgt ctggacagga   120
gatctccttt cttttagtga cttcagattt ttctaaatag cggatcctgc tgttgtagca   180
caggcctgat tcattatctg caacagtcaa ggaca                             215

<210> SEQ ID NO 604
<211> LENGTH: 109
<212> TYPE: DNA
<213> ORGANISM: Artificial Sequence
<220> FEATURE:
<223> OTHER INFORMATION: Synthetic Polynucleotide

<400> SEQUENCE: 604
tcctcatccc caagactgct attgactgag gtaaaatatg aatttgacac catgctgagt    60
taccttatac cacacaggcc tgattcattc tctgcaacag tcaaggaca              109
```

```
<210> SEQ ID NO 605
<211> LENGTH: 199
<212> TYPE: DNA
<213> ORGANISM: Artificial Sequence
<220> FEATURE:
<223> OTHER INFORMATION: Synthetic Polynucleotide

<400> SEQUENCE: 605
tcctcatccc caagactgct attgactgag gtaaaatatg aatttgacac catgctgagt    60
tactcctgat cggactttt aaagtcatcc atgtctggac aggagatctc ctttcttta    120 gtgacttcag attttctaa atagcggatc ctgctgttgt agcacaggcc tgattcattc    180
tctgcaacag tcaaggaca                                                199

<210> SEQ ID NO 606
<211> LENGTH: 204
<212> TYPE: DNA
<213> ORGANISM: Artificial Sequence
<220> FEATURE:
<223> OTHER INFORMATION: Synthetic Polynucleotide

<400> SEQUENCE: 606
tcctcatccc caagactgct attgactgag gtaaaatatg aatttgacac catgctgagt    60
taccttatac cacatcggac tttttaaagt catccatgtc tggacaggag atctcctttc    120
ttttagtgac ttcagatttt ctaaatagc ggatcctgct gttgtagcac aggcctgatt    180
cattctctgc aacagtcaag gaca                                          204

<210> SEQ ID NO 607
<211> LENGTH: 220
<212> TYPE: DNA
<213> ORGANISM: Artificial Sequence
<220> FEATURE:
<223> OTHER INFORMATION: Synthetic Polynucleotide

<400> SEQUENCE: 607
tcctcatccc caagactgct attgactgag gtaaaatatg aatttgacac catgctgagt    60
taccttatac cacacacatc aggctcctga tcggactttt taaagtcatc catgtctgga    120
caggagatct cctttctttt agtgacttca gattttctta aatagcggat cctgctgttg    180
tagcacaggc ctgattcatt ctctgcaaca gtcaaggaca                         220

<210> SEQ ID NO 608
<211> LENGTH: 210
<212> TYPE: DNA
<213> ORGANISM: Artificial Sequence
<220> FEATURE:
<223> OTHER INFORMATION: Synthetic Polynucleotide

<400> SEQUENCE: 608
tcctcatccc caagactgct attgactgag gtaaaatatg aatttgacac catgctgagt    60
taccttatac cacacaacga tcggactttt taaagtcatc catgtctgga caggagatct    120
cctttctttt agtgacttca gattttctta aatagcggat cctgctgttg tagcacaggc    180
ctgattcatt ctctgcaaca gtcaaggaca                                    210

<210> SEQ ID NO 609
<211> LENGTH: 199
<212> TYPE: DNA
<213> ORGANISM: Artificial Sequence
<220> FEATURE:
<223> OTHER INFORMATION: Synthetic Polynucleotide
```

<400> SEQUENCE: 609

```
tcctcatccc caagactgct attgactgag gtaaaatatg aatttgacac catgctgagt      60
taccttatat cggacttttt aaagtcatcc atgtctggac aggagatctc ctttcttta      120
gtgacttcag atttttctaa atagcggatc ctgctgttgt agcacaggcc tgattcattc     180
tctgcaacag tcaaggaca                                                  199
```

<210> SEQ ID NO 610
<211> LENGTH: 221
<212> TYPE: DNA
<213> ORGANISM: Artificial Sequence
<220> FEATURE:
<223> OTHER INFORMATION: Synthetic Polynucleotide

<400> SEQUENCE: 610

```
tcctcatccc caagactgct attgactgag gcaaaatatg aatttgacac catgctgagt      60
taccttatac cacacaacat caggctcctg atcggacttt ttaaagtcat ccatgtctgg     120
acaggagatc tcctttcttt tagtgacttc agatttttct aaatagcgga tcctgctgtt     180
gtagcacagg cctgattcat tctctgcaac agtcaaggac a                        221
```

<210> SEQ ID NO 611
<211> LENGTH: 186
<212> TYPE: DNA
<213> ORGANISM: Artificial Sequence
<220> FEATURE:
<223> OTHER INFORMATION: Synthetic Polynucleotide

<400> SEQUENCE: 611

```
tcctcatccc caagactgct attgactgag gtaaaatatg aatttgacac catgctgagg      60
acttttaaa gtcatccatg tctggacagg agatctcctt tcttttagtg acttcagatt     120
tttctaaata gcggatcctg ctgttgtagc acaggcctga ttcattctct gcaacagtca    180
aggaca                                                               186
```

<210> SEQ ID NO 612
<211> LENGTH: 197
<212> TYPE: DNA
<213> ORGANISM: Artificial Sequence
<220> FEATURE:
<223> OTHER INFORMATION: Synthetic Polynucleotide

<400> SEQUENCE: 612

```
tcctcatccc caagactgct attgactgag gtaaaatatg aatttgacac catgctgagt      60
taccttatac cacttttaa agtcatccat gtctggacag gagatctcct ttcttttagt     120
gacttcagat ttttctaaat agcggatcct gctgttgtag cacaggcctg attcattctc    180
tgcaacagtc aaggaca                                                   197
```

<210> SEQ ID NO 613
<211> LENGTH: 191
<212> TYPE: DNA
<213> ORGANISM: Artificial Sequence
<220> FEATURE:
<223> OTHER INFORMATION: Synthetic Polynucleotide

<400> SEQUENCE: 613

```
tcctcatccc caagactgct attgactgag gtaaaatatg aatttgacac catgctcctg      60
atcggacttt ttaaagtcat ccatgtctgg acaggagatc tcctttcttt tagtgacttc     120
agatttttct aaatagcgga tcctgctgtt gtagcacagg cctgattcat tctctgcaac    180
```
agtcaaggac a 191

<210> SEQ ID NO 614
<211> LENGTH: 217
<212> TYPE: DNA
<213> ORGANISM: Artificial Sequence
<220> FEATURE:
<223> OTHER INFORMATION: Synthetic Polynucleotide

<400> SEQUENCE: 614

| | |
|---|---|
| tcctcatccc caagactgct attgactgag gtaaaatatg aatttgacac catgctgagt | 60 |
| taccttatac caccatcagg ctcctgatcg gacttttta agtcatccat gtctggacag | 120 |
| gagatctcct ttcttttagt gacttcagat ttttctaaat agcggatcct gctgttgtag | 180 |
| cacaggcctg attcattctc tgcaacagtc aaggaca | 217 |

<210> SEQ ID NO 615
<211> LENGTH: 209
<212> TYPE: DNA
<213> ORGANISM: Artificial Sequence
<220> FEATURE:
<223> OTHER INFORMATION: Synthetic Polynucleotide

<400> SEQUENCE: 615

| | |
|---|---|
| tcctcatccc caagactgct attgactgag gtaaaatatg aatttgacac catgctgagt | 60 |
| taccttatac cacacctgat cggactttttt aaagtcatcc atgtctggac aggagatctc | 120 |
| ctttcttta gtgacttcag attttttctaa atagcggatc tgctgttgt agcacaggcc | 180 |
| tgattcattc tctgcaacag tcaaggaca | 209 |

<210> SEQ ID NO 616
<211> LENGTH: 210
<212> TYPE: DNA
<213> ORGANISM: Artificial Sequence
<220> FEATURE:
<223> OTHER INFORMATION: Synthetic Polynucleotide

<400> SEQUENCE: 616

| | |
|---|---|
| tcctcatccc caagactgct attgactgag gtaaaatatg aatttgacac catgctgagt | 60 |
| taccttaatc aggctcctga tcggactttt taaagtcatc catgtctgga caggagatct | 120 |
| cctttctttt agtgacttca gattttttcta aatagcggat cctgctgttg tagcacaggc | 180 |
| ctgattcatt ctctgcaaca gtcaaggaca | 210 |

<210> SEQ ID NO 617
<211> LENGTH: 185
<212> TYPE: DNA
<213> ORGANISM: Artificial Sequence
<220> FEATURE:
<223> OTHER INFORMATION: Synthetic Polynucleotide

<400> SEQUENCE: 617

| | |
|---|---|
| tcctcatccc caagactgct attgactgag gtaaaatatg aatttgacac catgctgaga | 60 |
| cttttttaaag tcatccatgt ctggacagga gatctccttt cttttagtga cttcagatttt | 120 |
| ttctaaatag cggatcctgc tgttgtagca caggcctgat tcattctctg caacagtcaa | 180 |
| ggaca | 185 |

<210> SEQ ID NO 618
<211> LENGTH: 213
<212> TYPE: DNA

```
<213> ORGANISM: Artificial Sequence
<220> FEATURE:
<223> OTHER INFORMATION: Synthetic Polynucleotide

<400> SEQUENCE: 618
tcctcatccc caagactgct attgactgag gtaaaatatg aatttgacac catgctgagt      60
taccttatac cacacactcc tgatcggact ttttaaagtc atccatgtct ggacaggaga     120
tctcctttct tttagtgact tcagattttt ctaaatagcg gatcctgctg ttgtagcaca     180
ggcctgattc attctctgca acagtcaagg aca                                  213

<210> SEQ ID NO 619
<211> LENGTH: 206
<212> TYPE: DNA
<213> ORGANISM: Artificial Sequence
<220> FEATURE:
<223> OTHER INFORMATION: Synthetic Polynucleotide

<400> SEQUENCE: 619
tcctcatccc caagactgct attgactgag gtaaaatatg aatttgacac catgctgagt      60
tacatcaggc tcctgatcgg acttttaaa gtcatccatg tctggacagg agatctcctt     120
tcttttagtg acttcagatt tttctaaata gcggatcctg ctgttgtagc acaggcctga     180
ttcattctct gcaacagtca aggaca                                          206

<210> SEQ ID NO 620
<211> LENGTH: 199
<212> TYPE: DNA
<213> ORGANISM: Artificial Sequence
<220> FEATURE:
<223> OTHER INFORMATION: Synthetic Polynucleotide

<400> SEQUENCE: 620
tcctcatccc caagactgct attgactgag gtaaaatatg aatttgacac catgctgagt      60
taccttatac cggactttt aaagtcatcc atgtctggac aggagatctc ctttcttta     120 gtgacttcag attttctaa atagcggatc ctgctgttgt agcacaggcc tgattcattc     180
tctgcaacag tcaaggaca                                                  199

<210> SEQ ID NO 621
<211> LENGTH: 221
<212> TYPE: DNA
<213> ORGANISM: Artificial Sequence
<220> FEATURE:
<223> OTHER INFORMATION: Synthetic Polynucleotide

<400> SEQUENCE: 621
tcctcatccc caagactgct attgactgag gtaaaatatg aatttgacac catgctgagt      60
taccttatac cacacaacat caggctcctg atcggacctt ttaaagtcat ccatgtctgg     120
acaggagatc tcctttcttt tagtgacttc agattttct aaatagcgga tcctgctgtt     180
gtagcacagg cctgattcat tctctgcaac agtcaaggac a                         221

<210> SEQ ID NO 622
<211> LENGTH: 221
<212> TYPE: DNA
<213> ORGANISM: Artificial Sequence
<220> FEATURE:
<223> OTHER INFORMATION: Synthetic Polynucleotide

<400> SEQUENCE: 622
tcctcatccc caagactgct attgactgag gtaaaatatg aatttgacgc catgctgagt      60
```
taccttatac cacacaacat caggctcctg atcggacttt ttaaagtcat ccatgtctgg    120
acaggagatc tcctttcttt tagtgacttc agatttttct aaatagcgga tcctgctgtt    180
gtagcacagg cctgattcat tctctgcaac agtcaaggac a                         221

<210> SEQ ID NO 623
<211> LENGTH: 221
<212> TYPE: DNA
<213> ORGANISM: Artificial Sequence
<220> FEATURE:
<223> OTHER INFORMATION: Synthetic Polynucleotide

<400> SEQUENCE: 623
tcctcatccc caagactgct attgactgag gtaaaatatg aatttgacac catgctgagt    60
taccttatac cacacaacat caggctcctg atcggacttt ttaaagtcat ccatgtctgg    120
acaggagatc tcctttcttt tagtgacttc agatttttct aaatagcgga tcctgctgtt    180
gtagcgcagg cctgattcat tctctgcaac agtcaaggac a                         221

<210> SEQ ID NO 624
<211> LENGTH: 221
<212> TYPE: DNA
<213> ORGANISM: Artificial Sequence
<220> FEATURE:
<223> OTHER INFORMATION: Synthetic Polynucleotide

<400> SEQUENCE: 624
tcctcatccc caagactgct attgactgag gtaaaatatg aatttgacac catgctgagt    60
taccttatac cacacaacat caggctcctg atcggacttt ttaaagtcat ccatgtctgg    120
acaggagatc tcctttcctt tagtgacttc agatttttct aaatagcgga tcctgctgtt    180
gtagcacagg cctgattcat tctctgcaac agtcaaggac a                         221

<210> SEQ ID NO 625
<211> LENGTH: 221
<212> TYPE: DNA
<213> ORGANISM: Artificial Sequence
<220> FEATURE:
<223> OTHER INFORMATION: Synthetic Polynucleotide

<400> SEQUENCE: 625
tcctcatccc caagactgct attgactgag gtaaaatatg aatttgacac catgctgagt    60
taccttatac cacacaacat caggctcctg atcggacttt ttaaagtcat ccatgtctgg    120
acaggagatc tcctttcttt tagtgacttc agatttttct aaatagcgga tcctgctgtc    180
gtagcacagg cctgattcat tctctgcaac agtcaaggac a                         221

<210> SEQ ID NO 626
<211> LENGTH: 215
<212> TYPE: DNA
<213> ORGANISM: Artificial Sequence
<220> FEATURE:
<223> OTHER INFORMATION: Synthetic Polynucleotide

<400> SEQUENCE: 626
tcctcatccc caagactgct attgactgag gtaaaatatg aatttgacac catgctgagt    60
taccttatac cacacaagct cctgatcgga ctttttaaag tcatccatgt ctggacagga    120
gatctccttt cttttagtga cttcagattt ttctaaatag cggatcctgc tgttgtagca    180
caggcctgat tcattctctg caacagtcaa ggaca                                215

<210> SEQ ID NO 627
<211> LENGTH: 223
<212> TYPE: DNA
<213> ORGANISM: Artificial Sequence
<220> FEATURE:
<223> OTHER INFORMATION: Synthetic Polynucleotide

<400> SEQUENCE: 627

```
tcctcatccc caagactgct attgactgag gtaaaatatg aatttgacac catgctgagt     60
taccttatac cacacaactt atcaggctcc tgatcggact ttttaaagtc atccatgtct    120
ggacaggaga tctcctttct tttagtgact tcagatttttt ctaaatagcg gatcctgctg    180
ttgtagcaca ggcctgattc attctctgca acagtcaagg aca                      223
```

<210> SEQ ID NO 628
<211> LENGTH: 203
<212> TYPE: DNA
<213> ORGANISM: Artificial Sequence
<220> FEATURE:
<223> OTHER INFORMATION: Synthetic Polynucleotide

<400> SEQUENCE: 628

```
tcctcatccc caagactgct attgactgag gtaaaatatg aatttgacac catgctgagt     60
taccttatac cacacggact ttttaaagtc atccatgtct ggacaggaga tctcctttct    120
tttagtgact tcagatttttt ctaaatagcg gatcctgctg ttgtagcaca ggcctgattc    180
attctctgca acagtcaagg aca                                             203
```

<210> SEQ ID NO 629
<211> LENGTH: 192
<212> TYPE: DNA
<213> ORGANISM: Artificial Sequence
<220> FEATURE:
<223> OTHER INFORMATION: Synthetic Polynucleotide

<400> SEQUENCE: 629

```
tcctcatccc caagactgct attgactgag gtaaaatatg aatttgacac catgctgagt     60
tatcggactt tttaaagtca tccatgtctg gacaggagat ctcctttctt ttagtgactt    120 cagattttttc taaatagcgg atcctgctgt tgtagcacag gcctgattca ttctctgcaa    180
cagtcaagga ca                                                         192
```

<210> SEQ ID NO 630
<211> LENGTH: 222
<212> TYPE: DNA
<213> ORGANISM: Artificial Sequence
<220> FEATURE:
<223> OTHER INFORMATION: Synthetic Polynucleotide

<400> SEQUENCE: 630

```
tcctcatccc caagactgct attgactgag gtaaaatatg aatttgacac catgctgagt     60
taccttatac cacacaacta tcaggctcct gatcggactt tttaaagtca tccatgtctg    120
gacaggagat ctcctttctt ttagtgactt cagattttttc taaatagcgg atcctgctgt    180
tgtagcacag gcctgattca ttatctgcaa cagtcaagga ca                       222
```

<210> SEQ ID NO 631
<211> LENGTH: 221
<212> TYPE: DNA
<213> ORGANISM: Artificial Sequence
<220> FEATURE:
<223> OTHER INFORMATION: Synthetic Polynucleotide

<400> SEQUENCE: 631

```
tcctcatccc caagactgct attgactgag gtaaaatatg aatttgacac catgctgagt      60
taccttatac cacacaacat caggctcctg atcggacttt ttaaagtcat ccatgtctgg     120
acaggagatc tcccttcttt tagtgacttc agatttttct aaatagcgga tcctgctgtt     180
gtagcacagg cctgattcat tctctgcaac agtcaaggac a                        221
```

<210> SEQ ID NO 632
<211> LENGTH: 193
<212> TYPE: DNA
<213> ORGANISM: Artificial Sequence
<220> FEATURE:
<223> OTHER INFORMATION: Synthetic Polynucleotide

<400> SEQUENCE: 632

```
tcctcatccc caagactgct attgactgag gtaaaatatg aatttgacac catgctgagt      60
taccttatac cacacaagtc atccatgtct ggacaggaga tctcctttct tttagtgact     120
tcagattttt ctaaatagcg gatcctgctg ttgtagcaca ggcctgattc attctctgca     180
acagtcaagg aca                                                        193
```

<210> SEQ ID NO 633
<211> LENGTH: 200
<212> TYPE: DNA
<213> ORGANISM: Artificial Sequence
<220> FEATURE:
<223> OTHER INFORMATION: Synthetic Polynucleotide

<400> SEQUENCE: 633

```
tcctcatccc caagactgct attgactgag gtaaaatatg aatttgacac catgctgatc      60
aggctcctga tcggactttt taaagtcatc catgtctgga caggagatct cctttctttt     120
agtgacttca gatttttcta aatagcggat cctgctgttg tagcacaggc ctgattcatt     180
ctctgcaaca gtcaaggaca                                                 200
```

<210> SEQ ID NO 634
<211> LENGTH: 222
<212> TYPE: DNA
<213> ORGANISM: Artificial Sequence
<220> FEATURE:
<223> OTHER INFORMATION: Synthetic Polynucleotide

<400> SEQUENCE: 634

```
tcctcatccc caagactgct attgactgag gtaaaatatg aatttgacac catgctgagt      60
taccttatac cacacaacaa tcaggctcct gatcggactt tttaaagtca tccatgtctg     120
gacaggagat ctcctttctt ttagtgactt cagattttc taaatagcgg atcctgctgt     180
tgtagcacag gcctgattca ttatctgcaa cagtcaagga ca                       222
```

<210> SEQ ID NO 635
<211> LENGTH: 174
<212> TYPE: DNA
<213> ORGANISM: Artificial Sequence
<220> FEATURE:
<223> OTHER INFORMATION: Synthetic Polynucleotide

```
<400> SEQUENCE: 635
tcctcatccc caagactgct attgactgag gtaaaatatg aatttgacac catgctgagt        60
taccttatac cacacaggag atctcctttc ttttagtgac ttcagatttt tctaaatagc       120
ggatcctgct gttgtagcac aggcctgatt cattctctgc aacagtcaag gaca            174
```

COMPOSITIONS AND METHODS FOR INHIBITING WNT SIGNALING

RELATED APPLICATIONS

This application is a national stage filing under 35 U.S.C. 371 of International Patent Application Serial No. PCT/US2017/023381, filed Mar. 21, 2017, entitled "COMPOSITIONS AND METHODS FOR INHIBITING WNT SIGNALING", which claims the benefit of the filing date under 35 U.S.C. § 119 of U.S. Provisional Application Ser. No. 62/311,381, filed Mar. 21, 2016, and entitled Compositions and Methods for Inhibiting WNT Signaling, the entire contents of which are incorporated herein by reference. International Patent Application PCT/US2017/023381 was published under PCT Article 21(2) in English.

GOVERNMENT SUPPORT

This disclosure was made with government support under grant 1R01NS080833, awarded by the National Institutes of Health. The government has certain rights in the disclosure.

BACKGROUND OF THE DISCLOSURE

*Clostridium difficile* toxin B (TcdB) is a critical virulence factor causing diseases associated with *C. difficile* infections (CDI). CDI is the most common cause for antibiotic-associated diarrhea and the leading cause of gastroenteritis-associated death in developed countries. Existing treatment regimens of CDI with antibiotics are ineffective and the rate of reoccurrence for the disease is high.

SUMMARY

*Clostridium difficile* toxin B (TcdB) is a critical virulence factor causing diseases associated with *C. difficile* infections (CDI). Utilizing genome-wide CRISPR/Cas9 mediated knockout screen, we identified the Wnt receptors Frizzled (FZD) as TcdB receptors. TcdB competes with Wnt for binding to the conserved cysteine-rich domain (CRD) in FZDs, with the highest affinity toward FZD1, 2, and 7, and is a potent inhibitor of Wnt signaling. A recombinant FZD2-CRD fragment protected cells from TcdB. Triple FZD1/2/7 knockout (KO) cells were dramatically resistant to toxin entry. Thus, FZDs as physiologically relevant epithelial receptors for TcdB and play a role in Wnt signaling blockage in CDI pathogenesis and diseases associated with increased Wnt signaling, e.g., cancer.

One aspect of the present disclosure provides isolated polypeptides comprising an amino acid sequence of SEQ ID NO: 18, SEQ ID NO: 19, or SEQ ID NO: 20, wherein the polypeptide does not have the amino acid sequence of SEQ ID NO: 27.

Another aspect of the present disclosure provides isolated polypeptides containing an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to SEQ ID NO: 18.

Another aspect of the present disclosure provides isolated polypeptides containing an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to SEQ ID NO: 19.

Another aspect of the present disclosure provides isolated polypeptides containing an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to SEQ ID NO: 20.

In some embodiments, the polypeptide has the amino acid sequence of SEQ ID NO: 18, SEQ ID NO: 19, or SEQ ID NO: 20.

In some embodiments, the polypeptide is cross-linked, cyclized, conjugated, acylated, carboxylated, lipidated, acetylated, thioglycolic acid amidated, alkylated, methylated, polyglycylated, glycosylated, polysialylated, phosphorylated, adenylylated, PEGylated, or combinations thereof. In some embodiments, the polypeptide has a modification at the C-terminus or at the N-terminus.

In some embodiments, the polypeptide further contains a fusion domain. In some embodiments, the fusion domain is selected from the group consisting of polyhistidine, Glu-Glu, glutathione S transferase (GST), thioredoxin, protein A, protein G, an immunoglobulin heavy chain constant region (Fc), maltose binding protein (MBP), or human serum albumin. In some embodiments, the polypeptide further contains an Fc portion of human IgG1.

Further provided herein are fusion proteins containing: a polypeptide comprising an amino acid sequence that has at least 95%, at least 96, at least 97, at least 98, at least 99, or at least 99.5% identity to SEQ ID NO: 18, SEQ ID NO: 19, or SEQ ID NO: 20, which polypeptide is fused to an Fc portion of an immunoglobulin. In some embodiments, the Fc portion is an Fc portion of a human IgG1. In some embodiments, the fusion protein consists of the amino acid sequence of SEQ ID NO:21, SEQ ID NO: 22, or SEQ ID NO: 23.

Another aspect of the present disclosure provides chimeric molecules containing a first portion and a second portion, wherein the first portion is an isolated polypeptide disclosed herein, and wherein in the second portion is a molecule that is not the isolated polypeptide disclosed herein.

In some embodiments, the isolated polypeptide binds Frizzled (FZD). In some embodiments, the isolated polypeptide blocks Wnt signaling. In some embodiments, the isolated polypeptide is a dimer, trimer, tetramer, or pentamer. In some embodiments, the isolated polypeptide is attached to a polymer. In some embodiments, the polymer prolongs the serum half-life of the isolated polypeptide. In some embodiments, the polymer prolongs the shelf-life of the isolated polypeptide. In some embodiments, the isolated polypeptide has 1-100 conservative amino acid substitutions.

In some embodiments, the second portion is an anti-bacterial agent. In some embodiments, the anti-bacterial agent is an antibiotic. In some embodiments, the second portion is an antibody that binds Frizzled co-receptors. In some embodiments, the Frizzled co-receptor is lipoprotein receptor-related protein (LRP)-5/6, receptor tyrosine kinase (RTK), or tyrosine-protein kinase transmembrane receptor (ROR2).

In some embodiments, the second portion contains an amino acid sequence of SEQ ID NO: 24, SEQ ID NO: 25, or SEQ ID NO: 26. In some embodiments, the second portion contains an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to SEQ ID NO: 24, SEQ ID NO: 25, or SEQ ID NO: 26.

Further provided herein are isolated nucleic acid molecules containing a polynucleotide encoding a polypeptide containing an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity, or 100% identity of SEQ ID NO: 18.

Further provided herein are nucleic acid molecules comprising a polynucleotide encoding a polypeptide containing an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity, or 100% identity of SEQ ID NO: 19.

Further provided herein are nucleic acid molecules comprising a polynucleotide encoding a polypeptide containing an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity, or 100% identity of SEQ ID NO: 20.

Further provided herein are nucleic acid molecules containing a polynucleotide encoding a polypeptide containing an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity, or 100% identity of SEQ ID NO: 21.

Further provided herein are nucleic acid molecules comprising a polynucleotide encoding a polypeptide comprising an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity, or 100% identity of SEQ ID NO: 22.

Further provided herein are nucleic acid molecules containing a polynucleotide encoding a polypeptide comprising an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity, or 100% identity of SEQ ID NO: 23.

Another aspect of the present disclosure provides pharmaceutical compositions comprising the isolated polypeptides or the chimeric molecules disclosed herein.

In some embodiments, the pharmaceutical composition further contains an additional isolated polypeptide containing an amino acid sequence of SEQ ID NO: 24, SEQ ID NO: 25, or SEQ ID NO: 26. In some embodiments, the additional isolated polypeptide contains an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to SEQ ID NO: 24, SEQ ID NO: 25, or SEQ ID NO: 26. In some embodiments, the additional isolated polypeptide consists of the amino acid sequence of SEQ ID NO: 24, SEQ ID NO: 25, or SEQ ID NO: 26.

In some embodiments, the polypeptide is acetylated, carboxylated, glycosylated, phosphorylated, lipidated, acylated, PEGylated, thioglycolic acid amidated, or combinations thereof.

In some embodiments, the polypeptide further comprises a fusion domain. In some embodiments, the fusion domain is selected from the group consisting of polyhistidine, Glu-Glu, glutathione S transferase (GST), thioredoxin, protein A, protein G, an immunoglobulin heavy chain constant region (Fc), maltose binding protein (MBP), or human serum albumin. In some embodiments, the additional polypeptide comprises an Fc portion of human IgG1. In some embodiments, the fusion domain is an Fc portion of human IgG1.

Another aspect of the present disclosure provides a method of treating *Clostridium difficile* infection (CDI), the method comprising administering to a subject in need thereof, a therapeutically effective amount of the isolated polypeptide, the chimeric molecule, or the pharmaceutical composition disclosed herein. In some embodiments, the pharmaceutical composition further contains an agent that induces Wnt signaling downstream of Frizzled (FZD) in a cell. In some embodiments, the agent is a GSK-3 inhibitor. In some embodiments, the GSK-3 inhibitor is Lithium (LiCl), CHIR99021, SB 216763, BIO, TCS 2002, TC-G 24, TWS 119, SB 415286, A 1070722, AR-A 014418, L803-mts, or combination thereof.

In some embodiments, the pharmaceutical composition further comprises an agent that inhibits the cysteine protease activity of TcdB in a cell. In some embodiments, the agent is ebselen. In some embodiments, the pharmaceutical composition further comprises Frizzled antibodies.

In some embodiments, the cell is a colonic epithelial cell.

Yet another aspect of the present disclosure provides a method of treating cancer, the method comprising administering to a subject in need thereof, a therapeutically effective amount of the isolated polypeptide, the chimeric molecule, or the pharmaceutical composition disclosed herein. In some embodiments, the cancer is colon cancer, lung cancer, liver cancer, or breast cancer.

In some embodiments, the pharmaceutical composition further comprises an agent that blocks Wnt signaling. In some embodiments, the agent is a Dkk family protein, a Secreted Frizzled Related Protein (sFRP), Draxin, IGFBP-4, SOST/Sclerostin, USAG1, or WIF-1. In some embodiments, the agent is an Frizzled antibody. In some embodiments, the cancer is metastatic cancer.

Each of the limitations of the disclosure can encompass various embodiments of the disclosure. It is, therefore, anticipated that each of the limitations of the disclosure involving any one element or combinations of elements can be included in each aspect of the disclosure. This disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 3, Panels D and E show that FZD2-CRD protected HT29 (Panel D) and Caco-2 cells (Panel E) from TcdB1-1830 (300 pM, 3 hours). Panel F shows the examination of endogenous CSPG4 in HeLa, HT29, and Caco-2 cell expression via immunoblot analysis of cell lysates (200 μg). Panels G through I show an analysis and quantification of the degree of protection from TcdB using recombinant FZD2-CRD and CSPG4/NG2-EC on HeLa (Panel G, 5 pM TcdB), HT29 (Panel H, 50 pM TcdB), and Caco-2 (Panel I, 150 pM TcdB) by cytopathic cell-rounding assays at indicated time points. Representative images of cells are shown in FIG. 15. CSPG4/NG2-EC alone reduced TcdB entry into HeLa cells, suggesting that CSPG4 is the dominant receptor in HeLa cells. A combination of CSPG4/NG2-EC and FZD2-CRD provided significant protection of HT29 cells from TcdB, suggesting that CSPG4 and FZDs likely contribute equivalently for toxin entry in HT29 cells. FZD2-CRD alone protected Caco-2 cells from TcdB, indicating that FZDs are the dominant receptors for TcdB in Caco-2 cells.

FIG. 8 shows deep sequencing of targeted mutation sites in CRISPR/Cas9 mediated knockout HeLa cells. HeLa-Cas9 cells were transduced with lentiviruses that express sgRNAs targeting indicated genes. Cells were further selected with 2.5 µg/ml puromycin (Gibco) and 200 µg/ml hygromycin B to generate mixed populations of stable cells. Genomic DNAs of these cells were extracted and the sequences for targeted mutation sites were amplified via PCR and subjected to NGS. The total percentage of mutated genes and the total number of unique mutations for each cell population are listed. Top 100 specific sequences for each cell population are listed in Tables 1-6. Deep sequencing revealed that mutagenesis rates are high (e.g. 98.7% for $CSPG4^{-/-}$ and 96.3% for $FZD2^{-/-}$), with the majority of them being frameshift mutations (Tables S1-6). Each sgRNA induced highly diverse mutations in the cell population, due to random NHEJ (non-homologous end joining) repair processes in individual cells.

FIG. 13 shows sequence alignment of the CRDs of FZD1, 2, and 7. The CRD domains of human FZD1 (residues 102-235), FZD2 (residues 25-158), and FZD7 (residues 35-168) were aligned. Sequence alignment was performed with Vector NTI software. The sequences, from top to bottom, correspond to SEQ ID NOs: 14-17.

Figure 1A:
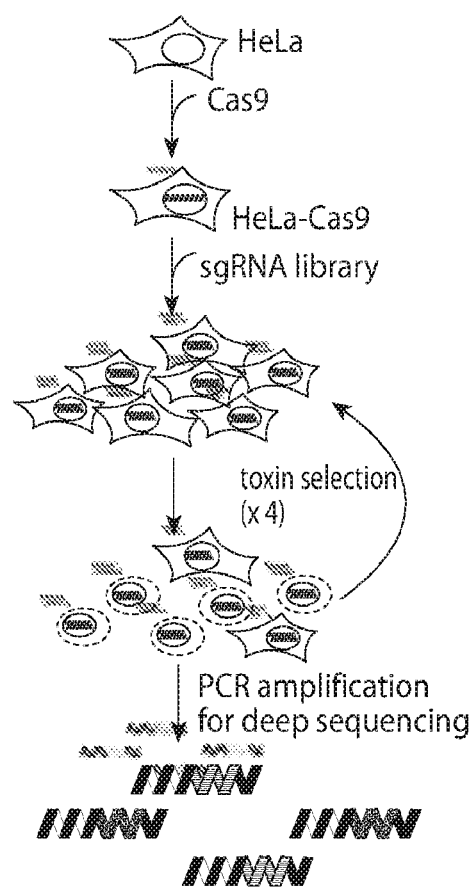
FIG. 1 shows genome-wide CRISPR/Cas9-mediated screens to identify host factors for TcdB. Panel A is a schematic drawing of the CRISPR/Cas9 screen. Four rounds of screenings were carried out with TcdB (0.05 pM, 0.1 pM, 0.2 pM, and 0.5 pM) and $TcdB_{1-1830}$ (5 pM, 10 pM, 20 pM, and 50 pM), respectively. Panels B and C show ranked and plotted genes identified in the screens with TcdB (panel B) or $TcdB_{1-1830}$ (panel C). The CRISPR library contains six unique sgRNAs per gene. As genes identified with multiple unique sgRNAs are less likely false-positives, the Y-axis is based on the number of unique sgRNAs identified for each gene. The X-axis is the total sgRNA NGS reads for a gene, which reflects the abundance of cells harboring mutated genes after selection. The percentages noted in the plot represent the relative abundance of sgRNA reads for indicated genes among total sgRNA reads.

Described in the Examples and Figures of the present disclosure are the identification and validation of TcdB receptors in colonic epithelia cells using a CRISPR/Cas9 mediated knockout screening system. The CRISPR/Cas9 system and its use is known in the art, e.g., US Patent Publication US20140357530, the entire contents of which is hereby incorporated by reference. Several Frizzled family proteins (FZDs) are identified and validated as novel and pathologically relevant TcdB receptors in the present disclosure. Among the 10 know FZD proteins, FZD 1, 2, and 7 are identified as the most important TcdB receptors that mediate the pathogenesis of *Clostridium difficile*. Further, FZD 1, 2, and 7 are redundant receptors for TcdB and have overlapping functions. Binding of TcdB to FZDs mediates the entry of the toxin into the cells. TcdB catalyzes the glycosylation of small GTPases inside epithelial cells, causing cell rounding and death. Accordingly, illustrated herein is a novel mechanism independent of the intracellular mechanism of TcdB pathogenesis, relating to the inhibition of Wnt signaling via competition for the FZD receptors.

FZDs are trans-membrane protein known to be involved in Wnt signaling. These receptors span the plasma membrane seven times and constitute a distinct family of G-protein coupled receptors (GPCRs). FZDs play key roles in governing cell polarity, embryonic development, formation of neural synapses, cell proliferation, and many other processes in developing and adult organisms, many of which relate to the Wnt signaling pathways.

The Wnt signaling pathways are a group of signal transduction pathways comprising proteins that pass signals into a cell through cell surface receptors. Three Wnt signaling pathways have been characterized: the canonical Wnt pathway, the noncanonical planar cell polarity pathway, and the noncanonical Wnt/calcium pathway. All three pathways are activated by binding a Wnt-protein ligand to a Frizzled family receptor, which passes the biological signal to proteins inside the cell. The canonical Wnt pathway leads to regulation of gene transcription. The noncanonical planar cell polarity pathway regulates the cytoskeleton that is responsible for the shape of the cell. The noncanonical Wnt/calcium pathway regulates calcium inside the cell. Wnt signaling pathways use either nearby cell-cell communication (paracrine) or same-cell communication (autocrine).

Wnt signaling was first identified for its role in carcinogenesis, then for its function in embryonic development. Wnt signaling also controls tissue regeneration in adult bone marrow, skin and intestine. For example, Wnt signaling is essential for maintaining colonic stem cells in vivo, which continuously give rise to new epithelial cells. The health of stem cells is critical for maintaining and repairing the epithelium, which turns over at an extraordinary rate: the entire colonic epithelium undergoes complete replacement every 5-7 days. Thus, as illustrated in the present disclosure, during *Clostridium difficile* infection, inhibition of Wnt signaling pathway led to depletion of colonic stem cells and greatly amplified the damage to the epithelium.

Further provided herein are the regions of FZD that interact with both TcdB and Wnt, resulting in competition. Both TcdB and Wnt bind to an N-terminal extracellular cysteine-rich domain of FZDs (FZD-CRD). TcdB is shown to preferentially bind FZDs 1, 2, and 7. The CRDs of FZDs 1, 2, and 7 are highly conserved with over 98% sequence similarity (See FIG. 13 for sequence alignment). The amino acid sequences of the CRDs of FZD 1, 2, and 7 are provided herein.

```
FZD1-CRD
                                           (SEQ ID NO: 24)
YNGERGISVPDHGYCQPISIPLCTDIAYNQTIMPNLLGHTNQEDAGLEVH
QFYPLVKVQCSAELKFFLCSMYAPVCTVLEQALPPCRSLCERARQGCEAL
MNKFGFQWPDTLKCEKFPVHGAGELCVGQNTSDK

FZD2-CRD
                                           (SEQ ID NO: 25)
YNGERGISVPDHGYCQPISIPLCTDIAYNQTIMPNLLGHTNQEDAGLEVH
QFYPLVKVQCSAELKFFLCSMYAPVCTVLEQALPPCRSLCERARQGCEAL
MNKFGFQWPDTLKCEKFPVHGAGELCVGQNTSDK

FZD3-CRD
                                           (SEQ ID NO: 26)
YNGERGISVPDHGYCQPISIPLCTDIAYNQTIMPNLLGHTNQEDAGLEVH
QFYPLVKVQCSAELKFFLCSMYAPVCTVLEQALPPCRSLCERARQGCEAL
MNKFGFQWPDTLKCEKFPVHGAGELCVGQNTSDK
```

The region of TcdB that interacts with FZD-CRD is identified to be between amino acid 1501-1830 of the TcdB protein (full-length TcdB protein, SEQ ID NO: 27). Polypeptide fragments corresponding to the region of TcdB that interacts with FZD-CRD, e.g., a polypeptide fragment of TcdB between amino 1114 to 1835 (hereafter termed "TcdB$_{1114\text{-}1835}$", SEQ ID NO: 18), is able to compete with Wnt and inhibit Wnt signaling, and is lacking the cysteine protease activity and the glucosyltransferase activity of TcdB. Such TcdB$_{1114\text{-}1835}$ polypeptide fragments, prevents the entry of wild-type, pathogenic TcdB from entering the cells. Further, the TcdB$_{1114\text{-}1835}$ fragments that enter the cells, are non-toxic due to its lacking the cysteine protease activity and the glucosyltransferase activity. Additionally, two other non-toxic polypeptides that have similar activity as the TcdB$_{1114\text{-}1835}$ are also provided: TcdB$_{1028\text{-}1835}$ (SEQ ID NO: 19) and TcdB$_{1114\text{-}2101}$ (SEQ ID NO: 20).

```
Full-length TcdB amino acid sequence
                                           (SEQ ID NO: 27)
MSLVNRKQLEKMANVRFRTQEDEYVAILDALEEYHNMSENTVVEKYLKLK

DINSLTDIYIDTYKKSGRNKALKKFKEYLVTEVLELKNNNLTPVEKNLHF

VWIGGQINDTAINYINQWKDVNSDYNVNVFYDSNAFLINTLKKTVVESAI

NDTLESFRENLNDPRFDYNKFFRKRMEIIYDKQKNFINYYKAQREENPEL

IIDDIVKTYLSNEYSKEIDELNTYIEESLNKITQNSGNDVRNFEEFKNGE

SFNLYEQELVERWNLAAASDILRISALKEIGGMYLDVDMLPGIQPDLFES

IEKPSSVTVDFWEMTKLEAIMKYKEYIPEYTSEHFDMLDEEVQSSFESVL

ASKSDKSEIFSSLGDMEASPLEVKIAFNSKGIINQGLISVKDSYCSNLIV

KQIENRYKILNNSLNPAISEDNDFNTTTNTFIDSIMAEANADNGRFMMEL

GKYLRVGFFPDVKTTINLSGPEAYAAAYQDLLMFKEGSMNIHLIEADLRN

FEISKTNISQSTEQEMASLWSFDDARAKAQFEEYKRNYFEGSLGEDDNLD

FSQNIVVDKEYLLEKISSLARSSERGYIHYIVQLQGDKISYEAACNLFAK

TPYDSVLFQKNIEDSEIAYYYNPGDGEIQEIDKYKIPSIISDRPKIKLTF

IGHGKDEFNTDIFAGFDVDSLSTEIEAAIDLAKEDISPKSIEINLLGCNM

FSYSINVEETYPGKLLLKVKDKISELMPSISQDSIIVSANQYEVRINSEG
```

-continued

RRELLDHSGEWINKEESIIKDISSKEYISFNPKENKITVKSKNLPELSTL
LQEIRNNSNSSDIELEEKVMLTECEINVISNIDTQIVEERIEEAKNLTSD
SINYIKDEFKLIESISDALCDLKQQNELEDSHFISFEDISETDEGFSIRF
INKETGESIFVETEKTIFSEYANHITEEISKIKGTIFDTVNGKLVKKVNL
DTTHEVNTLNAAFFIQSLIEYNSSKESLSNLSVAMKVQVYAQLFSTGLNT
ITDAAKVVELVSTALDETIDLLPTLSEGLPIIATIIDGVSLGAAIKELSE
TSDPLLRQEIEAKIGIMAVNLTTATTAIITSSLGIASGFSILLVPLAGIS
AGIPSLVNNELVLRDKATKVVDYFKHVSLVETEGVFTLLDDKIMMPQDDL
VISEIDFNNNSIVLGKCEIWRMEGGSGHTVTDDIDHFFSAPSITYREPHL
SIYDVLEVQKEELDLSKDLMVLPNAPNRVFAWETGWTPGLRSLENDGTKL
LDRIRDNYEGEFYWRYFAFIADALTTTLKPRYEDTNIRINLDSNTRSFIV
PIITTEYIREKLSYSFYGSGGTYALSLSQYNMGINIELSESDVWIIDVDN
VVRDVTIESDKIKKGDLIEGILSTLSIEENKIILNSHEINFSGEVNGSNG
FVSLTFSILEGINAIIEVDLLSKSYKLLISGELKILMLNSNHIQQKIDYI
GFNSELQKNIPYSFVDSEGKENGFINGSTKEGLFVSELPDVVLISKVYMD
DSKPSFGYYSNNLKDVKVITKDNVNILTGYYLKDDIKISLSLTLQDEKTI
KLNSVHLDESGVAEILKFMNRKGNTNTSDSLMSFLESMNIKSIFVNFLQS
NIKFILDANFIISGTTSIGQFEFICDENDNIQPYFIKFNTLETNYTLYVG
NRQNMIVEPNYDLDDSGDISSTVINFSQKYLYGIDSCVNKVVISPNIYTD
EINITPVYETNNTYPEVIVLDANYINEKINVNINDLSIRYVWSNDGNDFI
LMSTSEENKVSQVKIRFVNVFKDKTLANKLSFNFSDKQDVPVSEIILSFT
PSYYEDGLIGYDLGLVSLYNEKFYINNFGMMVSGLIYINDSLYYFKPPVN
NLITGFVTVGDDKYYFNPINGGAASIGETIIDDKNYYFNQSGVLQTGVFS
TEDGFKYFAPANTLDENLEGEAIDFTGKLIIDENIYYFDDNYRGAVEWKE
LDGEMHYFSPETGKAFKGLNQIGDYKYYFNSDGVMQKGFVSINDNKHYFD
DSGVMKVGYTEIDGKHFYFAENGEMQIGVFNTEDGFKYFAHHNEDLGNEE
GEEISYSGILNFNNKIYYFDDSFTAVVGWKDLEDGSKYYFDEDTAEAYIG
LSLINDGQYYFNDDGIMQVGFVTINDKVFYFSDSGIIESGVQNIDDNYFY
IDDNGIVQIGVFDTSDGYKYFAPANTVNDNIYGQAVEYSGLVRVGEDVYY

FGETYTIETGWIYDMENESDKYYFNPETKKACKGINLIDDIKYYFDEKGI

MRTGLISFENNNYYFNENGEMQFGYINIEDKMFYFGEDGVMQIGVFNTPD

GFKYFAHQNTLDENFEGESINYTGWLDLDEKRYYFTDEYIAATGSVIIDG

EEYYFDPDTAQLVISE $TcdB_{1114-1835}$ amino acid sequence (SEQ ID NO: 18)

RDKATKVVDYFKHVSLVETEGVFTLLDDKIMMPQDDLVISEIDFNNNSIV

LGKCEIWRMEGGSGHTVTDDIDHFFSAPSITYREPHLSIYDVLEVQKEEL

DLSKDLMVLPNAPNRVFAWETGWTPGLRSLENDGTKLLDRIRDNYEGEFY

WRYFAFIADALITTLKPRYEDTNIRINLDSNTRSFIVPIITTEYIREKLS

YSFYGSGGTYALSLSQYNMGINIELSESDVWIIDVDNVVRDVTIESDKIK

KGDLIEGILSTLSIEENKIILNSHEINFSGEVNGSNGFVSLTFSILEGIN

-continued

AIIEVDLLSKSYKLLISGELKILMLNSNHIQQKIDYIGFNSELQKNIPYS

FVDSEGKENGFINGSTKEGLFVSELPDVVLISKVYMDDSKPSFGYYSNNL

KDVKVITKDNVNILTGYYLKDDIKISLSLTLQDEKTIKLNSVHLDESGVA

EILKFMNRKGNTNTSDSLMSFLESMNIKSIFVNFLQSNIKFILDANFIIS

GTTSIGQFEFICDENDNIQPYFIKFNTLETNYTLYVGNRQNMIVEPNYDL

DDSGDISSTVINFSQKYLYGIDSCVNKVVISPNIYTDEINITPVYETNNT

YPEVIVLDANYINEKINVNINDLSIRYVWSNDGNDFILMSTSEENKVSQV

KIRFVNVFKDKTLANKLSFNFSDKQDVPVSEIILSFTPSYYEDGLIGYDL

GLVSLYNEKFYINNFGMMVSGL $TcdB_{1028-1835}$ amino acid sequence (SEQ ID NO: 19)

GLPIIATIIDGVSLGAAIKELSETSDPLLRQEIEAKIGIMAVNLTTATTA

IITSSLGIASGFSILLVPLAGISAGIPSLVNNELVLRDKATKVVDYFKHV

SLVETEGVFTLLDDKIMMPQDDLVISEIDFNNNSIVLGKCEIWRMEGGSG

HTVTDDIDHFFSAPSITYREPHLSIYDVLEVQKEELDLSKDLMVLPNAPN

RVFAWETGWTPGLRSLENDGTKLLDRIRDNYEGEFYWRYFAFIADALITT

LKPRYEDTNIRINLDSNTRSFIVPIITTEYIREKLSYSFYGSGGTYALSL

SQYNMGINIELSESDVWIIDVDNVVRDVTIESDKIKKGDLIEGILSTLSI

EENKIILNSHEINFSGEVNGSNGFVSLTFSILEGINAIIEVDLLSKSYKL

LISGELKILMLNSNHIQQKIDYIGFNSELQKNIPYSFVDSEGKENGFING

STKEGLFVSELPDVVLISKVYMDDSKPSFGYYSNNLKDVKVITKDNVNIL

TGYYLKDDIKISLSLTLQDEKTIKLNSVHLDESGVAEILKFMNRKGNTNT

SDSLMSFLESMNIKSIFVNFLQSNIKFILDANFIISGTTSIGQFEFICDE

NDNIQPYFIKFNTLETNYTLYVGNRQNMIVEPNYDLDDSGDISSTVINFS

QKYLYGIDSCVNKVVISPNIYTDEINITPVYETNNTYPEVIVLDANYINE

KINVNINDLSIRYVWSNDGNDFILMSTSEENKVSQVKIRFVNVFKDKTLA

NKLSFNFSDKQDVPVSEIILSFTPSYYEDGLIGYDLGLVSLYNEKFYINN

FGMMVSGL $TcdB_{1114-2101}$ amino acid sequence (SEQ ID NO: 20)

RDKATKVVDYFKHVSLVETEGVFTLLDDKIMMPQDDLVISEIDFNNNSIV

LGKCEIWRMEGGSGHTVTDDIDHFFSAPSITYREPHLSIYDVLEVQKEEL

DLSKDLMVLPNAPNRVFAWETGWTPGLRSLENDGTKLLDRIRDNYEGEFY

WRYFAFIADALITTLKPRYEDTNIRINLDSNTRSFIVPIITTEYIREKLS

YSFYGSGGTYALSLSQYNMGINIELSESDVWIIDVDNVVRDVTIESDKIK

KGDLIEGILSTLSIEENKIILNSHEINFSGEVNGSNGFVSLTFSILEGIN

AIIEVDLLSKSYKLLISGELKILMLNSNHIQQKIDYIGFNSELQKNIPYS

FVDSEGKENGFINGSTKEGLFVSELPDVVLISKVYMDDSKPSFGYYSNNL

KDVKVITKDNVNILTGYYLKDDIKISLSLTLQDEKTIKLNSVHLDESGVA

EILKFMNRKGNTNTSDSLMSFLESMNIKSIFVNFLQSNIKFILDANFIIS

GTTSIGQFEFICDENDNIQPYFIKFNTLETNYTLYVGNRQNMIVEPNYDL

DDSGDISSTVINFSQKYLYGIDSCVNKVVISPNIYTDEINITPVYETNNT

YPEVIVLDANYINEKINVNINDLSIRYVWSNDGNDFILMSTSEENKVSQV

-continued

KIRFVNVFKDKTLANKLSFNFSDKQDVPVSEIILSFTPSYYEDGLIGYDL

GLVSLYNEKFYINNFGMMVSGLIYINDSLYYFKPPVNNLITGFVTVGDDK

YYFNPINGGAASIGETIIDDKNYYFNQSGVLQTGVFSTEDGFKYFAPANT

LDENLEGEAIDFTGKLIIDENIYYFDDNYRGAVEWKELDGEMHYFSPETG

KAFKGLNQIGDYKYYFNSDGVMQKGFVSINDNKHYFDDSGVMKVGYTEID

GKHFYFAENGEMQIGVFNTEDGFKYFAHHNEDLGNEEGEEISYSGILNFN

NKIYYFDDSFTAVVGWKDLEDGSKYYFDEDTAEAYIGL

In some embodiments, the present disclosure makes available isolated and/or purified forms of polypeptides. "An isolated polypeptide", as used herein, refers to a polypeptide that is isolated from, or is otherwise substantially free of (e.g., at least 80%, 90%, 95%, 97%, 99%, or 99.5% free of), other protein(s) and/or other polypeptide(s) (e.g., TcdB polypeptide species). In some embodiments, the isolated polypeptides is 100% free of other protein(s) and/or other polypeptide(s) (e.g., TcdB polypeptide species).

The isolated polypeptides of the present disclosure, block or inhibit Wnt signaling in cells. "Block", or "inhibit", as used herein, means the amplitude of Wnt signaling is decreased compared to normal physiological condition. Inhibition of Wnt signaling exacerbates the pathological outcome of CDI. Conversely, in certain abnormal or pathological conditions, e.g., cancer, Wnt signaling may also be elevated, or hyperactive compared to normal physiological condition. The amplitude of Wnt signaling under normal physiological condition in different cell types may vary and are known in the art. Abnormal Wnt signaling, or the dysfunction of Wnt signaling pathway, is the underlying mechanism of a variety of diseases. Thus, later in the present disclosure, methods of treating such diseases are contemplated.

In some embodiments, the isolated polypeptides of the present disclosure, comprise an amino acid sequence of SEQ ID NO: 18, SEQ ID NO: 19, or SEQ ID NO: 20, wherein the polypeptide does not have the amino acid sequence of SEQ ID NO: 27. In some embodiments, the isolated polypeptide comprises an amino acid sequence that has at least 85% identity to SEQ ID NO: 18. For example, the isolated polypeptide comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to SEQ ID NO: 18. In some embodiments, the isolated polypeptide comprises an amino acid sequence that has at least 85% identity to SEQ ID NO: 19. For example, the isolated polypeptide comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to SEQ ID NO: 19. In some embodiments, the isolated polypeptide comprises an amino acid sequence that has at least 85% identity to SEQ ID NO: 20. For example, the isolated polypeptide comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to SEQ ID NO: 20. In some embodiments, the isolated polypeptide comprises an amino acid sequence that has 85%, 86%, 87%, 88%, 89%, 90%, 91%, 92%, 93%, 94%, 95%, 96%, 97%, 98%, 99%, 99.5%, or 100% identity to SEQ ID NO: 18. In some embodiments, the isolated polypeptide comprises an amino acid sequence that has 85%, 86%, 87&, 88%, 89%, 90%, 91%, 92%, 93%, 94%, 95%, 96%, 97%, 98%, 99%, 99.5%, or 100% identity to SEQ ID NO: 19. In some embodiments, the isolated polypeptide comprises an amino acid sequence that has 85%, 86%, 87&, 88%, 89%, 90%, 91%, 92%, 93%, 94%, 95%, 96%, 97%, 98%, 99%, 99.5%, or 100% identity to SEQ ID NO: 20. In some embodiments, the isolated polypeptide consists of an amino acid sequence of SEQ ID NO: 18, SEQ ID NO: 19, or SEQ ID NO: 20.

The "percent identity" of two amino acid sequences is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NB LAST) can be used.

The polypeptides described herein can be conjugated or otherwise covalently attached to other molecules (e.g., using a chemical linker). One such form of attachment is through a non-amide linkage (e.g., a disulfide bond). In some embodiments, the polypeptide is covalently attached (e.g., via a linker molecule) to an antibody or a domain thereof suitable for enhancing the half-life of the molecule (e.g., one or more constant domains in an Fc domain). In some embodiments, the polypeptide is linked to an Fc domain disclosed herein (e.g., IgG, IgA, IgM, IgD, or IgE).

In some embodiments, the isolated polypeptide of the present disclosure, further comprises a fusion domain. Thus, also provided herein are functional variants or modified forms of the polypeptide fragments having one or more fusion domains. Well known examples of such fusion domains include, without limitation, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS6) fusion partners. In some embodiments, the isolated polypeptide fragment is fused with a domain that stabilizes the isolated polypeptide fragment in vivo (a "stabilizer" domain). "Stabilizing", as used herein, means an increase in the half-life of the polypeptide in vivo, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains.

In some embodiments, the isolated polypeptides of the present disclosure, further comprises an Fc portion of human IgG1 (SEQ ID NO: 28). Thus, fusion proteins an Fc portion of an immunoglobulin are also contemplated herein. In some embodiments, the fusion protein comprises a polypeptide comprising an amino acid sequence that has at least 95% identity to SEQ ID NO: 18, wherein the said polypeptide is fused to an Fc portion of an immunoglobulin. For example, the polypeptide in the fusion protein of the present disclosure, may comprise an amino acid sequence that has at least 95%, at least 96%, at least 97%, at least 98%, at least 99%, or at least 99.5% identity to SEQ ID NO: 18. In some embodiments, the fusion protein comprises a polypeptide comprising an amino acid sequence that has 95%, 96%, 97%, 98%, 99%, or 100% identity to SEQ ID NO: 18. In some embodiments, the fusion protein comprises a polypeptide comprising an amino acid sequence that has at least 95% identity to SEQ ID NO: 19, wherein the said polypeptide is fused to an Fc portion of an immunoglobulin. For example, the polypeptide in the fusion protein of the present disclosure, may comprise an amino acid sequence that has at least 95%, at least 96%, at least 97%, at least 98%, at least 99%, or at least 99.5% identity to SEQ ID NO: 19. In some embodiments, the fusion protein comprises a polypeptide comprising an amino acid sequence that has 95%, 96%, 97%, 98%, 99%, or 100% identity to SEQ ID NO: 19. In some embodiments, the fusion protein comprises a polypeptide comprising an amino acid sequence that has at least 95% identity to SEQ ID NO: 20, wherein the said polypeptide is fused to an Fc portion of an immunoglobulin. For example, the polypeptide in the fusion protein of the present disclosure, may comprise an amino acid sequence that has at least 95%, at least 96%, at least 97%, at least 98%, at least 99%, or at least 99.5% identity to SEQ ID NO: 20. In some embodiments, the fusion protein comprises a polypeptide comprising an amino acid sequence that has 95%, 96%, 97%, 98%, 99%, or 100% identity to SEQ ID NO: 20. In some embodiments, the fusion protein comprises a polypeptide consisting of the amino acid sequence of SEQ ID NO: 18, SEQ ID NO: 19, or SEQ ID NO: 20, fused to the Fc portion of a human IgG1. Also provided herein are exemplary fusion proteins comprising a TcdB$_{1114-1835}$ polypeptide fused to an Fc domain (SEQ ID NO: 21), a TcdB$_{1028-1835}$ polypeptide fused to an Fc domain (SEQ ID NO: 22), and a TcdB$_{1114-2101}$ polypeptide fused to an Fc domain (SEQ ID NO: 23). The exemplary isolated polypeptide fragment is provided for the sole purpose of illustration and is not meant to be limiting.

Fc portion of human IgG1
(SEQ ID NO: 28)
THTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCK

VSNKALPVPIEKTISKAKGQPREPQVYTLPPSREEMTKNQVSLTCLVKGF

YPSDIAVEWESNGQPENNYKTTPPVLDSDGPFFLYSKLTVDKSRWQQGNV

FSCSVMHEALHNHYTQKSLSLSPGK

TcdB$_{1114-1835}$-Fc fusion protein
(SEQ ID NO: 21)
RDKATKVVDYFKHVSLVETEGVFTLLDDKIMMPQDDLVISEIDFNNNSIV

LGKCEIWRMEGGSGHTVTDDIDHFFSAPSITYREPHLSIYDVLEVQKEEL

DLSKDLMVLPNAPNRVFAWETGWTPGLRSLENDGTKLLDRIRDNYEGEFY

WRYFAFIADALITTLKPRYEDTNIRINLDSNTRSFIVPIITTEYIREKLS

YSFYGSGGTYALSLSQYNMGINIELSESDVWIIDVDNVVRDVTIESDKIK

KGDLIEGILSTLSIEENKIILNSHEINFSGEVNGSNGFVSLTFSILEGIN

AIIEVDLLSKSYKLLISGELKILMLNSNHIQQKIDYIGFNSELQKNIPYS

FVDSEGKENGFINGSTKEGLFVSELPDVVLISKVYMDDSKPSFGYYSNNL

KDVKVITKDNVNILTGYYLKDDIKISLSLTLQDEKTIKLNSVHLDESGVA

EILKFMNRKGNTNTSDSLMSFLESMNIKSIFVNFLQSNIKFILDANFIIS

GTTSIGQFEFICDENDNIQPYFIKFNTLETNYTLYVGNRQNMIVEPNYDL

DDSGDISSTVINFSQKYLYGIDSCVNKVVISPNIYTDEINITPVYETNNT

YPEVIVLDANYINEKINVNINDLSIRYVWSNDGNDFILMSTSEENKVSQV

KIRFVNVFKDKTLANKLSFNFSDKQDVPVSEIILSFTPSYYEDGLIGYDL

GLVSLYNEKFYINNFGMMVSGL<u>THTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPVPIEKTISKAKGQPREPQVYT

LPPSREEMTKNQVSLTCLVKGFYPSDIAVEWESNGQPENNYKTTPPVLDS

DGPFFLYSKLTVDKSRWQQGNVFSCSVMHEALHNHYTQKSLSLSPGK</u>

(Fc domain is underlined)

TcdB$_{1028-1835}$-Fc fusion protein
(SEQ ID NO: 22)
GLPIIATIIDGVSLGAAIKELSETSDPLLRQEIEAKIGIMAVNLTTATTA

IITSSLGIASGFSILLVPLAGISAGIPSLVNNELVLRDKATKVVDYFKHV

SLVETEGVFTLLDDKIMMPQDDLVISEIDFNNNSIVLGKCEIWRMEGGSG

HTVTDDIDHFFSAPSITYREPHLSIYDVLEVQKEELDLSKDLMVLPNAPN

RVFAWETGWTPGLRSLENDGTKLLDRIRDNYEGEFYWRYFAFIADALITT

LKPRYEDTNIRINLDSNTRSFIVPIITTEYIREKLSYSFYGSGGTYALSL

SQYNMGINIELSESDVWIIDVDNVVRDVTIESDKIKKGDLIEGILSTLSI

EENKIILNSHEINFSGEVNGSNGFVSLTFSILEGINAIIEVDLLSKSYKL

LISGELKILMLNSNHIQQKIDYIGFNSELQKNIPYSFVDSEGKENGFING

STKEGLFVSELPDVVLISKVYMDDSKPSFGYYSNNLKDVKVITKDNVNIL

TGYYLKDDIKISLSLTLQDEKTIKLNSVHLDESGVAEILKFMNRKGNTNT

SDSLMSFLESMNIKSIFVNFLQSNIKFILDANFIISGTTSIGQFEFICDE

NDNIQPYFIKFNTLETNYTLYVGNRQNMIVEPNYDLDDSGDISSTVINFS

QKYLYGIDSCVNKVVISPNIYTDEINITPVYETNNTYPEVIVLDANYINE

KINVNINDLSIRYVWSNDGNDFILMSTSEENKVSQVKIRFVNVFKDKTLA

NKLSFNFSDKQDVPVSEIILSFTPSYYEDGLIGYDLGLVSLYNEKFYINN

FGMMVSGL<u>THTCPPCPAPELLGGPSVFLFPPKPKDTLMISRTPEVTCVVV

DVSHEDPEVKFNWYVDGVEVHNAKTKPREEQYNSTYRVVSVLTVLHQDWL

NGKEYKCKVSNKALPVPIEKTISKAKGQPREPQVYTLPPSREEMTKNQVS</u>

-continued

LTCLVKGFYPSDIAVEWESNGQPENNYKTTPPVLDSDGPFFLYSKLTVDK

SRWQQGNVFSCSVMHEALHNHYTQKSLSLSPGK (Fc domain is underlined)

TcdB$_{1114-2101}$-Fc fusion protein
(SEQ ID NO: 23)
RDKATKVVDYFKHVSLVETEGVFTLLDDKIMMPQDDLVISEIDFNNNSIV

LGKCEIWRMEGGSGHTVTDDIDHFFSAPSITYREPHLSIYDVLEVQKEEL

DLSKDLMVLPNAPNRVFAWETGWTPGLRSLENDGTKLLDRIRDNYEGEFY

WRYFAFIADALITTLKPRYEDTNIRINLDSNTRSFIVPIITTEYIREKLS

YSFYGSGGTYALSLSQYNMGINIELSESDVWIIDVDNVVRDVTIESDKIK

KGDLIEGILSTLSIEENKIILNSHEINFSGEVNGSNGFVSLTFSILEGIN

AIIEVDLLSKSYKLLISGELKILMLNSNHIQQKIDYIGFNSELQKNIPYS

FVDSEGKENGFINGSTKEGLFVSELPDVVLISKVYMDDSKPSFGYYSNNL

KDVKVITKDNVNILTGYYLKDDIKISLSLTLQDEKTIKLNSVHLDESGVA

EILKFMNRKGNTNTSDSLMSFLESMNIKSIFVNFLQSNIKFILDANFIIS

GTTSIGQFEFICDENDNIQPYFIKFNTLETNYTLYVGNRQNMIVEPNYDL

DDSGDISSTVINFSQKYLYGIDSCVNKVVISPNIYTDEINITPVYETNNT

YPEVIVLDANYINEKINVNINDLSIRYVWSNDGNDFILMSTSEENKVSQV

KIRFVNVFKDKTLANKLSFNFSDKQDVPVSEIILSFTPSYYEDGLIGYDL

GLVSLYNEKFYINNFGMMVSGLIYINDSLYYFKPPVNNLITGFVTVGDDK

YYFNPINGGAASIGETIIDDKNYYFNQSGVLQTGVFSTEDGFKYFAPANT

LDENLEGEAIDFTGKLIIDENIYYFDDNYRGAVEWKELDGEMHYFSPETG

KAFKGLNQIGDYKYYFNSDGVMQKGFVSINDNKHYFDDSGVMKVGYTEID

GKHFYFAENGEMQIGVFNTEDGFKYFAHHNEDLGNEEGEEISYSGILNFN

NKIYYFDDSFTAVVGWKDLEDGSKYYFDEDTAEAYIGLTHTCPPCPAPEL

LGGPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPVPIEK

TISKAKGQPREPQVYTLPPSREEMTKNQVSLTCLVKGFYPSDIAVEWESN

GQPENNYKTTPPVLDSDGPFFLYSKLTVDKSRWQQGNVFSCSVMHEALHN

HYTQKSLSLSPGK (Fc domain is underlined)

Optionally, the Fc domain may have one or more mutations at residues such as Asp-265, lysine 322, and Asn-434. In certain cases, the mutant Fc domain having one or more of these mutations (e.g., Asp-265 mutation) has reduced ability of binding to the Fc receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wildtype Fc domain.

It is understood that different elements of the fusion proteins may be arranged in any manner that is consistent with the desired functionality. For example, the TcdB$_{1114-1835}$ polypeptide may be placed C-terminal to a heterologous domain, or, alternatively, a heterologous domain may be placed C-terminal to a TcdB$_{1114-1835}$ polypeptide. The TcdB$_{1114-1835}$ polypeptide domain and the heterologous domain need not be adjacent in a fusion protein, and additional domains or amino acid sequences may be included C- or N-terminal to either domain or between the domains.

As used herein, the term, "immunoglobulin Fc region" or simply "Fc" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In a preferred embodiment the immunoglobulin Fc region comprises at least an immunoglobulin hinge region a CH2 domain and a CH3 domain, and preferably lacks the CH1 domain.

In some embodiments, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igμ), may be used. The choice of appropriate immunoglobulin heavy chain constant region is discussed in detail in U.S. Pat. Nos. 5,541,087, and 5,726,044. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably comprises at least a portion of a hinge domain, and preferably at least a portion of a CH3 domain of Fc γ or the homologous domains in any of IgA, IgD, IgE, or IgM.

Furthermore, it is contemplated that substitution or deletion of amino acids within the immunoglobulin heavy chain constant regions may be useful in the practice of the methods and compositions disclosed herein. One example would be to introduce amino acid substitutions in the upper CH2 region to create an Fc variant with reduced affinity for Fc receptors (Cole et al. (1997) J. Immunol. 159:3613).

Optionally, the isolated polypeptides of the present disclosure, may comprise modifications. Polypeptides comprising modifications have additional features other than amino acid contents. As used herein, a "modification" or "derivative" of a peptide produces a modified or derivatized polypeptide, which is a form of a given peptide that is chemically modified relative to the reference peptide, the modification including, but not limited to, oligomerization or polymerization, modifications of amino acid residues or peptide backbone, cross-linking, cyclization, conjugation, pegylation, glycosylation, acetylation, phosphorylation, acylation, carboxylation, lipidation, thioglycolic acid amidation, alkylation, methylation, polyglycylation, glycosylation, polysialylation, adenylylation, PEGylation, fusion to additional heterologous amino acid sequences, or other modifications that substantially alter the stability, solubility, or other properties of the peptide while substantially retaining the activity of the polypeptides described herein. It is to be understood that the isolated polypeptides comprising such modifications, are cross-linked, cyclized, conjugated, acylated, carboxylated, lipidated, acetylated, thioglycolic acid amidated, alkylated, methylated, polyglycylated, glycosylated, polysialylated, phosphorylated, adenylylated, PEGylated, or combination thereof. As a result, the modified polypeptide fragments of the present disclosure may contain non-amino acid elements, such as polyethylene glycols, lipids, poly- or mono-saccharide, and phosphates. The isolated polypeptides of the present disclosure, may comprise the modifications disclosed herein at the C-terminus (e.g., C-terminal amidation), N-terminus (e.g., N-terminal acetylation). Terminal modifications are useful, and are well known, to reduce susceptibility to proteinase digestion, and therefore serve to prolong half-life of the polypeptides in solutions, particularly biological fluids where proteases may be present. In some embodiments, the polypeptides or fusion proteins described herein are further modified within the sequence, such as, modification by terminal-NH2 acylation, e.g., acetylation, or thioglycolic acid amidation, by terminal-carboxylamidation, e.g., with ammonia, methylamine, and the like terminal modifications.

Terminal modifications are useful, to reduce susceptibility by proteinase digestion, and therefore can serve to prolong half-life of the polypeptides in solution, particularly in biological fluids where proteases may be present. Amino terminus modifications include methylation (e.g., —NHCH3 or —N(CH3)2), acetylation (e.g., with acetic acid or a halogenated derivative thereof such as a-chloroacetic acid, a-bromoacetic acid, or a-iodoacetic acid), adding a benzyloxycarbonyl (Cbz) group, or blocking the amino terminus with any blocking group containing a carboxylate functionality defined by RCOO— or sulfonyl functionality defined by R—SO2-, where R is selected from the group consisting of alkyl, aryl, heteroaryl, alkyl aryl, and the like, and similar groups. One can also incorporate a desamino acid at the N-terminus (so that there is no N-terminal amino group) to decrease susceptibility to proteases or to restrict the conformation of the polypeptide. In certain embodiments, the N-terminus is acetylated with acetic acid or acetic anhydride.

Carboxy terminus modifications include replacing the free acid with a carboxamide group or forming a cyclic lactam at the carboxy terminus to introduce structural constraints. One can also cyclize the peptides described herein, or incorporate a desamino or descarboxy residue at the termini of the peptide, so that there is no terminal amino or carboxyl group, to decrease susceptibility to proteases or to restrict the conformation of the peptide. Methods of circular peptide synthesis are known in the art, for example, in U.S. Patent Application No. 20090035814; Muralidharan and Muir, 2006, Nat Methods, 3:429-38; and Lockless and Muir, 2009, Proc Natl Acad Sci USA. June 18, Epub. C-terminal functional groups of the peptides described herein include amide, amide lower alkyl, amide di(lower alkyl), lower alkoxy, hydroxy, and carboxy, and the lower ester derivatives thereof, and the pharmaceutically acceptable salts thereof.

In some embodiments, the polypeptides or the fusion proteins described herein are phosphorylated. One can also readily modify peptides by phosphorylation, and other methods (e.g., as described in Hruby, et al. (1990) Biochem J. 268:249-262). One can also replace the naturally occurring side chains of the genetically encoded amino acids (or the stereoisomeric D amino acids) with other side chains, for instance with groups such as alkyl, lower (C1-6) alkyl, cyclic 4-, 5-, 6-, to 7-membered alkyl, amide, amide lower alkyl amide di(lower alkyl), lower alkoxy, hydroxy, carboxy and the lower ester derivatives thereof, and with 4-, 5-, 6-, to 7-membered heterocycles. In particular, proline analogues in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl groups. These heterocyclic groups can be substituted or unsubstituted. Where a group is substituted, the substituent can be alkyl, alkoxy, halogen, oxygen, or substituted or unsubstituted phenyl.

In some embodiments, the isolated polypeptide of the present disclosure is multimeric, e.g., a dimer, trimer, tetramer, or pentamer. In some embodiments, the molecular linker used for forming the oligomeric polypeptides is a peptide linker molecule. In some embodiments, the peptide linking molecule comprises at least one amino acid residue which links at least two peptides according to the disclosure. The peptide linker comprises, e.g., at least 2, 3, 4, 5, 6, 7, 8, 9, 10 or more amino acids residues and preferably less than 50 amino acids residues. The peptide linking molecule can couple polypeptides or proteins covalently or non-covalently. Typical amino acid residues used for linking are glycine, tyrosine, cysteine, lysine, glutamic and aspartic acid, or the like. A peptide linker is attached on its amino-terminal end to one peptide, polypeptide or polypeptide domain (e.g., a C-peptide) and on its carboxyl-terminal end to another peptide, polypeptide or polypeptide domain (again, e.g., a C-peptide). Examples of useful linker peptides include, but are not limited to, glycine polymers ((G)n) including glycine-serine and glycine-alanine polymers (e.g., a (Gly4Ser)n repeat where n=1-8, preferably, n=3, 4, 5, or 6). Other examples of peptide linker molecules are described in U.S. Pat. No. 5,856,456 and are hereby incorporated by reference.

In another embodiment, the molecular linker is a chemical linker such as linkages by disulfide bonds between cysteine amino acid residues or by chemical bridges formed by amine crosslinkers, for example, glutaraldehyde, bis(imido ester), bis(succinimidyl esters), diisocyanates and diacid chlorides. Extensive data on chemical cross-linking agents can be found at INVITROGEN's Molecular Probe under section 5.2.

In certain embodiments, the peptide monomers described herein are dimerized or multimerized by covalent attachment to at least one linker moiety. The linker moiety is preferably, although not necessarily, a C1-12 linking moiety optionally terminated with one or two —NH— linkages and optionally substituted at one or more available carbon atoms with a lower alkyl substituent. Preferably the linker comprises —NH—R—NH— wherein R is a lower (C1-6) alkylene substituted with a functional group, such as a carboxyl group or an amino group, that enables binding to another molecular moiety (e.g., as may be present on the surface of a solid support during peptide synthesis or to a pharmacokinetic-modifying agent such as PEG). In certain embodiments the linker is a lysine residue. In certain other embodiments, the linker bridges the C-termini of two peptide monomers, by simultaneous attachment to the C-terminal amino acid of each monomer. In other embodiments, the linker bridges the peptides by attaching to the side chains of amino acids not at the C-termini. When the linker attaches to a side chain of an amino acid not at the C-termini of the peptides, the side chain preferably contains an amine, such as those found in lysine, and the linker contains two or more carboxy groups capable of forming an amide bond with the peptides.

The polypeptides, fusion proteins, and polypeptide multimers as described herein may be attached to one or more polymer moieties. Preferably, these polymers are covalently attached to the polypeptides of the disclosure. Preferably, for therapeutic use of the end product preparation, the polymer is pharmaceutically acceptable. One skilled in the art will be able to select the desired polymer based on such considerations as whether the polymer-peptide conjugate will be used therapeutically, and if so, the desired dosage, circulation time, resistance to proteolysis, and other considerations.

Suitable polymers include, for example, polyethylene glycol (PEG), polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polyoxyethylated polyol, heparin, heparin fragments, polysaccharides, cellulose and cellulose derivatives, including methylcellulose and carboxymethyl cellulose, starch and starch derivatives, polyalkylene glycol and derivatives thereof, copolymers of polyalkylene glycols and derivatives thereof, polyvinyl ethyl ethers, and α,β-Poly[(2-hydroxyethyl)-DL-aspartamide, and the like, or mixtures thereof. Such a polymer may or may not have its own biological activity. The polymers can be covalently or non-covalently conjugated to the polypeptide. Methods of conjugation for increasing serum half-life and for radiotherapy are known in the art, for example, in U.S. Pat. Nos. 5,180,816, 6,423,685, 6,884,780, and 7,022,673, which are hereby incorporated by reference in their entirety.

In some embodiments, the polypeptides monomers, dimers, or multimers as described herein may be attached to one or more water soluble polymer moieties. The water soluble polymer may be, for example, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), poly(n-vinylpyrrolidone)polyethylene glycol, propropylene glycol homopolymers, polypropylene oxide/ethylene oxide copolymers, and polyoxyethylated polyols. A preferred water soluble polymer is PEG.

The polymer may be of any molecular weight, and may be branched or unbranched. The average molecular weight of the reactant PEG is preferably between about 3,000 and about 50,000 daltons (the term "about" indicating that in preparations of PEG, some molecules will weigh more, and some less, than the stated molecular weight). More preferably, the PEG has a molecular weight of from about 10 kDa to about 40 kDa, and even more preferably, the PEG has a molecular weight from 15 to 30 kDa. Other sizes may be used, depending on the desired therapeutic profile (e.g., duration of sustained release desired; effects, if any, on biological activity; ease in handling; degree or lack of antigenicity; and other effects of PEG on a therapeutic peptide known to one skilled in the art).

The number of polymer molecules attached may vary; for example, one, two, three, or more water-soluble polymers may be attached to a peptide of the disclosure. The multiple attached polymers may be the same or different chemical moieties (e.g., PEGs of different molecular weight).

In certain embodiments, PEG may be attached to at least one terminus (N-terminus or C-terminus) of a peptide monomer or dimer. In other embodiments, PEG may be attached to a linker moiety of a peptide monomer or dimer. In a preferred embodiment, PEG is attached to the linker moiety of a peptide dimer. Optionally, the linker contains more than one reactive amine capable of being derivatized with a suitably activated PEG species.

In some embodiments, the isolated polypeptides, fusion proteins, or polypeptide multimers described herein, whether monomeric, oligomeric or cyclic, is PEGylated.

PEGylation is the process of covalent attachment of Polyethylene glycol polymer chains to another molecule, normally a drug or therapeutic protein. PEGylation is routinely achieved by incubation of a reactive derivative of PEG with the target macromolecule. The covalent attachment of PEG to a drug or therapeutic protein can "mask" the agent from the host's immune system (reduced immunogenicity and antigenicity), and increase the hydrodynamic size (size in solution) of the agent which prolongs its circulatory time by reducing renal clearance. PEGylation can also provide water solubility to hydrophobic drugs and proteins. PEGylation, by increasing the molecular weight of a molecule, can impart several significant pharmacological advantages over the unmodified form, such as: improved drug solubility, reduced dosage frequency, without diminished efficacy with potentially reduced toxicity, extended circulating life, increased drug stability, and enhanced protection from proteolytic degradation. In addition, PEGylated drugs are have wider opportunities for new delivery formats and dosing regimens. Methods of PEGylating molecules, proteins and peptides are well known in the art, e.g., as described in U.S. Pat. Nos. 5,766,897; 7,610,156; 7,256,258 and the International Application No. WO/1998/032466.

Encompassed herein are conjugates of the polypeptide described herein or of a variant or derivative thereof. These polypeptides can be conjugated to other polymers in addition to polyethylene glycol (PEG). The polymer may or may not have its own biological activity. Further examples of polymer conjugation include but are not limited to polymers such as polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polyoxyethylated polyol, heparin, heparin fragments, polysaccharides, cellulose and cellulose derivatives, including methylcellulose and carboxymethyl cellulose, starch and starch derivatives, polyalkylene glycol and derivatives thereof, copolymers of polyalkylene glycols and derivatives thereof, polyvinyl ethyl ethers, and α,β-Poly[(2-hydroxyethyl)-DL-aspartamide, and the like, or mixtures thereof. Conjugation to a polymer can improve serum half-life, among other effects. A variety of chelating agents can be used to conjugate the peptides described herein. These chelating agents include but are not limited to ethylenediaminetetraacetic acid (EDTA), diethylenetriaminopentaacetic acid (DTPA), ethyleneglycol-0,0'-bis(2-aminoethyl)-N,N,N',N'-tetraacetic acid (EGTA), N,N'-bis(hydroxybenzyl)ethylenediamine-N,N'-diacetic acid (HBED), triethylenetetraminehexaacetic acid (TTHA), 1,4,7,10-tetra-azacyclododecane-N,N',N'',N'''-tetraacetic acid (DOTA), 1,4,7,10-tetraazacyclotridecane-1,4,7,10-tetraacetic acid (TITRA), 1,4,8,11-tetraazacyclotetradecane-N,N',N'',N'''-tetraacetic acid (TETA), and 1,4,8,11-tetraazacyclotetradecane (TETRA). Methods of conjugation are well known in the art, for example, P. E. Thorpe, et. al, 1978, Nature 271, 752-755; Harokopakis E., et. al., 1995, Journal of Immunological Methods, 185:31-42; S. F. Atkinson, et. al., 2001, J. Biol. Chem., 276:27930-27935; and U.S. Pat. Nos. 5,601,825, 5,180,816, 6,423,685, 6,706,252, 6,884, 780, and 7,022,673, which are hereby incorporated by reference in their entirety.

In some embodiments, the polymer prolongs the serum half-life of the isolated polypeptide when attached to the isolated polypeptide. In some embodiments, the polymer prolongs the shelf-life of the isolated polypeptide when attached to the isolated polypeptide. The "serum half-life" of an isolated polypeptide, as used herein, refers to the period of time required for the concentration or amount of the polypeptides in the body to be reduced by one-half. A polypeptide's serum half-life depends on how quickly it is eliminated from the serum. The longer the serum half-life is, the more stable the polypeptide is in the body. The "shelf-life", refers to the period of time, from the date of manufacture, that a product is expected to remain within its approved product specification while stored under defined conditions. It is desirable for a therapeutic agent, e.g., the isolated polypeptide of the present disclosure, to have a longer shelf-life.

Other methods for stabilizing peptides known in the art may be used with the methods and compositions described herein. For example, using D-amino acids, using reduced amide bonds for the peptide backbone, and using non-peptide bonds to link the side chains, including, but not limited to, pyrrolinone and sugar mimetics can each provide stabilization. The design and synthesis of sugar scaffold peptide mimetics are described by Hirschmann et al. (*J. Med. Chem.*, 1996, 36, 2441-2448, which is incorporated herein by reference in its entirety). Further, pyrrolinone-based peptide mimetics present the peptide pharmacophore on a stable background that has improved bioavailability characteristics (see, for example, Smith et al., *J. Am. Chem. Soc.* 2000, 122, 11037-11038), which is incorporated herein by reference in its entirety.

The isolated polypeptides of the present disclosure, may comprise conservative amino acid substitutions. A "conservative amino acid substitution", refers to an amino acid substitution that changes an amino acid to a different amino acid with similar biochemical properties (e.g. charge, hydrophobicity and size). Conservative substitutions of amino acids include, for example, substitutions made amongst amino acids within the following groups: (a) M, I, L, V; (b) F, Y, W; (c) K, R, H; (d) A, G; (e) S, T; (f) Q, N; and (g) E, D. Conservative amino acid substitutions do not alter the relative charge or size characteristics of the protein in which the amino acid substitutions are made. Conservative amino acid substitutions typically do not change the overall structure of the peptide and/or the type of amino acid side chains available for forming van der Waals bonds with a binding partner. In some embodiments, the isolated polypeptide may comprise 1-100 conservative amino acid substitutions. For example, the isolated polypeptide may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69. 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 conservative amino acid substitutions.

Amino acid substitution can be achieved during chemical synthesis of the peptide by adding the desired substitute amino acid at the appropriate sequence in the synthesis process. Alternatively, molecular biology methods can be used. Non-conservative substitutions are also encompassed to the extent that they substantially retain the activities of those peptides described herein.

The amino acid substituted polypeptide will substantially retain the activity of the non-substituted polypeptide. By "substantially retain" means one or more activity of the variant is at least 50% compared to the activity of the original polypeptide in a similar assay, under similar conditions; preferably the activity is at least 60%, at least 70%, at least 80%, at least 90%, at least 95%, at least 99%, at least 100%, at least 2-fold, at least 5-fold, at least 10-fold, at least 100-fold or higher activity compared to the original polypeptide.

All combinations of the different modifications and derivativizations are envisioned for the polypeptides, fusion proteins and oligomer polypeptides described herein. Modifications, derivatives and methods of derivatizing polypeptides are described in Published International Application WO 2010/014616, the contents of which are incorporated herein by reference.

Other aspects of the present disclosure provide chimeric molecules comprising a first portion and a second portion, wherein the first portion is any isolated polypeptides, fusion proteins, multimeric polypeptides, or variants/derivatives disclosed herein. It is to be understood that the second portion of the chimeric molecule is not the same polypeptide as the first portion of the chimeric molecule. In some embodiments, the first portion of the chimeric molecule is an isolated polypeptide binds Frizzled (FZD). In some embodiments, binding of the isolated polypeptides to FZDs blocks Wnt signaling pathways.

In some embodiments, the second portion of the chimeric molecule comprises a therapeutic agent. In some embodiments, the therapeutic agent may be an anti-bacterial agent. In some embodiments, the therapeutic agent may be an antibiotic. Classes of anti-bacterial agents that may be used in accordance with the present disclosure include, without limitation, aminoglycosides, ansamycins, carbacephems, carbapenems, cephalosporins, glycopeptides, lincosamides, lipopeptides, macrolides, monobactams, nitrofurans, oxazolidinones, penicillins, quinolones, sulfonamides, and tetracyclines. It is to be understood that any known anti-bacterial agent in the art that can be attached to a polypeptide may be used herein.

In some embodiments, the second portion of the chimeric molecule may be a binder or antibody that binds the Frizzled co-receptors. It is known in the art that to facilitate Wnt signaling, co-receptors may be required alongside the interaction between the Wnt protein and FZDs. Upon activation of the receptor, a signal is sent to the phosphoprotein Dishevelled (Dsh), which is located in the cytoplasm. Blocking of the Frizzled co-receptors via binding of an antibody also blocks Wnt signaling. Examples of Frizzled co-receptors include, without limitation, lipoprotein receptor-related protein (LRP)-5/6, receptor tyrosine kinase (RTK), and tyrosine-protein kinase transmembrane receptor (ROR2). Thus, antibodies to the Frizzled co-receptors described herein, may be used as the second portion of the chimeric molecule of the present disclosure, the facilitate the blocking of Wnt signaling at the receptor level.

In some embodiments, the second portion of the chimeric molecule may be a FZD-CRD fused to the polypeptide of the first portion. In some embodiments, the second portion comprises an amino acid sequence of SEQ ID NO: 24, SEQ ID NO: 25, or SEQ ID NO: 26. In some embodiments, the second portion of the chimeric molecule comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to SEQ ID NO: 24. In some embodiments, the second portion of the chimeric molecule comprises an amino acid sequence that has 85%, 86%, 87%, 88%, 89%, 90%, 91%, 92%, 93%, 94%, 95%, 96%, 97%, 98%, 99%, or 100% to SEQ ID NO: 24. In some embodiments, the second portion of the chimeric molecule comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to SEQ ID NO: 25. In some embodiments, the second portion of the chimeric molecule comprises an amino acid sequence that has 85%, 86%, 87%, 88%, 89%, 90%, 91%, 92%, 93%, 94%, 95%, 96%, 97%, 98%, 99%, or 100% to SEQ ID NO: 25. SEQ ID NO: 25. In some embodiments, the second portion of the chimeric molecule comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity to SEQ ID NO: 26. In some embodiments, the second portion of the chimeric molecule comprises an amino acid sequence that has 85%, 86%, 87%, 88%, 89%, 90%, 91%, 92%, 93%, 94%, 95%, 96%, 97%, 98%, 99%, or 100% to SEQ ID NO: 26.

The isolated polypeptides of the present disclosure (e.g., polypeptides comprising amino acid sequence of any of SEQ ID NOs: 18-26), will generally be produced by expression form recombinant nucleic acids in appropriate cells (e.g., *E. coli*, or insect cells) and isolated. The nucleic acids encoding the polypeptides described herein may be obtained, and the nucleotide sequence of the nucleic acids determined, by any method known in the art. Further provided herein are isolated and/or recombinant nucleic acids encoding any of the isolated polypeptide fragments disclosed herein. For example, SEQ ID NO: 29 encodes the TcdB$_{1114-1835}$ polypeptide. The nucleic acids encoding the isolated polypeptide fragments of the present disclosure, may be DNA or RNA, double-stranded or single stranded.

TcdB$_{1114-1835}$ nucleic acid sequence
(SEQ ID NO: 29)
CGAGATAAGGCAACAAAGGTTGTAGATTATTTTAAACATGTTTCATTAGTT

GAAACTGAAGGAGTATTTACTTTATTAGATGATAAAATAATGATGCCACAA

GATGATTTAGTGATATCAGAAATAGATTTTAATAATAATTCAATAGTTTTA

GGTAAATGTGAAATCTGGAGAATGGAAGGTGGTTCAGGTCATACTGTAACT

GATGATATAGATCACTTCTTTTCAGCACCATCAATAACATATAGAGAGCCA

CACTTATCTATATATGACGTATTGGAAGTACAAAAAGAAGAACTTGATTTG

TCAAAAGATTTAATGGTATTACCTAATGCTCCAAATAGAGTATTTGCTTGG

GAAACAGGATGGACACCAGGTTTAAGAAGCTTAGAAAATGATGGCACAAAA

CTGTTAGACCGTATAAGAGATAACTATGAAGGTGAGTTTTATTGGAGATAT

TTTGCTTTTATAGCTGATGCTTTAATAACAACATTAAAACCAAGATATGAA

GATACTAATATAAGAATAAATTTAGATAGTAATACTAGAAGTTTTATAGTT

CCAATAATAACTACAGAATATATAAGAGAAAAATTATCATATTCTTTCTAT

GGTTCAGGAGGAACTTATGCATTGTCTCTTTCTCAATATAATATGGGTATA

AATATAGAATTAAGTGAAAGTGATGTTTGGATTATAGATGTTGATAATGTT

GTGAGAGATGTAACTATAGAATCTGATAAAATTAAAAAAGGTGATTTAATA

GAAGGTATTTTATCTACACTAAGTATTGAAGAGAATAAAATTATCTTAAAT

AGCCATGAGATTAATTTTTCTGGTGAGGTAAATGGAAGTAATGGATTTGTT

TCTTTAACATTTTCAATTTTAGAAGGAATAAATGCAATTATAGAAGTTGAT

TTATTATCTAAATCATATAAATTACTTATTTCTGGCGAATTAAAAATATTG

ATGTTAAATTCAAATCATATTCAACAGAAAATAGATTATATAGGATTCAAT

AGCGAATTACAGAAAAATATACCATATAGCTTTGTAGATAGTGAAGGAAAA

GAGAATGGTTTTATTAATGGTTCAACAAAAGAAGGTTTATTTGTATCTGAA

TTACCTGATGTAGTTCTTATAAGTAAGGTTTATATGGATGATAGTAAGCCT

TCATTTGGATATTATAGTAATAATTTGAAAGATGTCAAAGTTATAACTAAA

GATAATGTTAATATATTAACAGGTTATTATCTTAAGGATGATATAAAAATC

TCTCTTTCTTTGACTCTACAAGATGAAAAAACTATAAAGTTAAATAGTGTG

CATTTAGATGAAAGTGGAGTAGCTGAGATTTTGAAGTTCATGAATAGAAAA

GGTAATACAAATACTTCAGATTCTTTAATGAGCTTTTTAGAAAGTATGAAT

ATAAAAAGTATTTTCGTTAATTTCTTACAATCTAATATTAAGTTTATATTA

GATGCTAATTTTATAATAAGTGGTACTACTTCTATTGGCCAATTTGAGTTT

ATTTGTGATGAAAATGATAATATACAACCATATTTCATTAAGTTTAATACA

CTAGAAACTAATTATACTTTATATGTAGGAAATAGACAAAATATGATAGTG

GAACCAAATTATGATTTAGATGATTCTGGAGATATATCTTCAACTGTTATC

AATTTCTCTCAAAAGTATCTTTATGGAATAGACAGTTGTGTTAATAAAGTT

GTAATTTCACCAAATATTTATACAGATGAAATAAATATAACGCCTGTATAT

GAAACAAATAATACTTATCCAGAAGTTATTGTATTAGATGCAAATTATATA

AATGAAAAAATAAATGTTAATATCAATGATCTATCTATACGATATGTATGG

AGTAATGATGGTAATGATTTTATTCTTATGTCAACTAGTGAAGAAAATAAG

GTGTCACAAGTTAAAATAAGATTCGTTAATGTTTTTAAAGATAAGACTTTG

GCAAATAAGCTATCTTTTAACTTTAGTGATAAACAAGATGTACCTGTAAGT

GAAATAATCTTATCATTTACACCTTCATATTATGAGGATGGATTGATTGGC

TATGATTTGGGTCTAGTTTCTTTATATAATGAGAAATTTTATATTAATAAC

TTTGGAATGATGGTATCTGGATTA

In certain aspects, the subject nucleic acids encoding the isolated polypeptide fragments are further understood to include nucleic acids encoding polypeptides that are variants of SEQ ID NOs: 18 to 23. Variant nucleotide sequences include sequences that differ by one or more nucleotide substitutions, additions or deletions, such as allelic variants. In some embodiments, the isolated nucleic acid molecule of the present disclosure comprising a polynucleotide encoding a polypeptide comprising an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity of SEQ ID NO: 18. In some embodiments, the isolated nucleic acid molecule of the present disclosure comprising a polynucleotide encoding a polypeptide comprising an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity of SEQ ID NO: 19. In some embodiments, the isolated nucleic acid molecule of the present disclosure comprising a polynucleotide encoding a polypeptide comprising an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity of SEQ ID NO: 20. In embodiments, the isolated nucleic acid molecule of the present disclosure comprising a polynucleotide encoding a polypeptide comprising an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity of SEQ ID NO: 21. In some embodiments, the isolated nucleic acid molecule of the present disclosure comprising a polynucleotide encoding a polypeptide comprising an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity of SEQ ID NO: 22. In some embodiments, the isolated nucleic acid molecule of the present disclosure comprising a polynucleotide encoding a polypeptide comprising an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identity of SEQ ID NO: 23. In some embodiments, the isolated nucleic acid molecule of the present disclosure comprising a polynucleotide encoding a polypeptide comprising an amino acid sequence that has 85%, 86%, 87%, 88%, 89%, 90%, 91%, 92%, 93%, 94%, 95%, 96%, 97%, 98%, 99%, or 100% identity of SEQ ID NO: 18. In some embodiments, the isolated nucleic acid molecule of the present disclosure comprising a polynucleotide encoding a polypeptide comprising an amino acid sequence that has 85%, 86%, 87%, 88%, 89%, 90%, 91%, 92%, 93%, 94%, 95%, 96%, 97%, 98%, 99%, or 100% identity of SEQ ID NO: 19. In some embodiments, the isolated nucleic acid molecule of the present disclosure comprising a polynucleotide encoding a polypeptide comprising an amino acid sequence that has 85%, 86%, 87%, 88%, 89%, 90%, 91%, 92%, 93%, 94%, 95%, 96%, 97%, 98%, 99%, or 100% identity of SEQ ID NO: 20. In some embodiments, the isolated nucleic acid molecule of the present disclosure comprising a polynucleotide encoding a polypeptide comprising an amino acid sequence that has 85%, 86%, 87%, 88%, 89%, 90%, 91%, 92%, 93%, 94%, 95%, 96%, 97%, 98%, 99%, or 100% identity of SEQ ID NO: 21. In some embodiments, the isolated nucleic acid molecule of the present disclosure comprising a polynucleotide encoding a polypeptide comprising an amino acid sequence that has 85%, 86%, 87%, 88%, 89%, 90%, 91%, 92%, 93%, 94%, 95%, 96%, 97%, 98%, 99%, or 100% identity of SEQ ID NO: 22. In some embodiments, the isolated nucleic acid molecule of the present disclosure comprising a polynucleotide encoding a polypeptide comprising an amino acid sequence that has 85%, 86%, 87%, 88%, 89%, 90%, 91%, 92%, 93%, 94%, 95%, 96%, 97%, 98%, 99%, or 100% identity of SEQ ID NO: 23.

In some embodiments, the nucleic acid is comprised within a vector, such as an expression vector. In some embodiments, the vector comprises a promoter operably linked to the nucleic acid.

A variety of promoters can be used for expression of the polypeptides described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter, and the herpes simplex tk virus promoter.

Regulatable promoters can also be used. Such regulatable promoters include those using the lac repressor from *E. coli* as a transcription modulator to regulate transcription from lac operator-bearing mammalian cell promoters [Brown, M. et al., *Cell,* 49:603-612 (1987)], those using the tetracycline repressor (tetR) [Gossen, M., and Bujard, H., *Proc. Natl. Acad. Sci. USA* 89:5547-5551 (1992); Yao, F. et al., *Human Gene Therapy,* 9:1939-1950 (1998); Shockelt, P., et al., *Proc. Natl. Acad. Sci. USA,* 92:6522-6526 (1995)]. Other systems include FK506 dimer, VP16 or p65 using astradiol, RU486, diphenol murislerone, or rapamycin. Inducible systems are available from Invitrogen, Clontech and Ariad.

Regulatable promoters that include a repressor with the operon can be used. In one embodiment, the lac repressor from *Escherichia coli* can function as a transcriptional modulator to regulate transcription from lac operator-bearing mammalian cell promoters [M. Brown et al., *Cell,* 49:603-612 (1987)]; Gossen and Bujard (1992); [M. Gossen et al., Natl. Acad. Sci. USA, 89:5547-5551 (1992)] combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used (Yao et al., *Human Gene Therapy*; Gossen et al., *Natl. Acad. Sci. USA,* 89:5547-5551 (1992); Shockett et al., *Proc. Natl. Acad. Sci. USA,* 92:6522-6526 (1995)).

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art.

An expression vector comprising the nucleic acid can be transferred to a host cell by conventional techniques (e.g., electroporation, liposomal transfection, and calcium phosphate precipitation) and the transfected cells are then cultured by conventional techniques to produce the polypeptides described herein. In some embodiments, the expression of the polypeptides described herein is regulated by a constitutive, an inducible or a tissue-specific promoter.

The host cells used to express the isolated polypeptides described herein may be either bacterial cells such as *Escherichia coli*, or, preferably, eukaryotic cells. In particular, mammalian cells, such as Chinese hamster ovary cells (CHO), in conjunction with a vector such as the major intermediate early gene promoter element from human cytomegalovirus is an effective expression system for immunoglobulins (Foecking et al. (1986) "Powerful And Versatile Enhancer-Promoter Unit For Mammalian Expression Vectors," *Gene* 45:101-106; Cockett et al. (1990) "High Level Expression Of Tissue Inhibitor Of Metalloproteinases In Chinese Hamster Ovary Cells Using Glutamine Synthetase Gene Amplification," *Biotechnology* 8:662-667).

A variety of host-expression vector systems may be utilized to express the isolated polypeptides described herein. Such host-expression systems represent vehicles by which the coding sequences of the isolate d polypeptides described herein may be produced and subsequently purified, but also represent cells which may, when transformed or transfected with the appropriate nucleotide coding sequences, express the isolated polypeptides described herein in situ. These include, but are not limited to, microorganisms such as bacteria (e.g., *E. coli* and *B. subtilis*) transformed with recombinant bacteriophage DNA, plasmid DNA or cosmid DNA expression vectors containing coding sequences for the isolated polypeptides described herein; yeast (e.g., *Saccharomyces pichia*) transformed with recombinant yeast expression vectors containing sequences encoding the isolated polypeptides described herein; insect cell systems infected with recombinant virus expression vectors (e.g., baclovirus) containing the sequences encoding the isolated polypeptides described herein; plant cell systems infected with recombinant virus expression vectors (e.g., cauliflower mosaic virus (CaMV) and tobacco mosaic virus (TMV) or transformed with recombinant plasmid expression vectors (e.g., Ti plasmid) containing sequences encoding the isolated polypeptides described herein; or mammalian cell systems (e.g., COS, CHO, BHK, 293, 293T, 3T3 cells, lymphotic cells (see U.S. Pat. No. 5,807,715), Per C.6 cells (human retinal cells developed by Crucell) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the polypeptides being expressed. For example, when a large quantity of such a protein is to be produced, for the generation of pharmaceutical compositions of polypeptides described herein, vectors which direct the expression of high levels of fusion protein products that are readily purified may be desirable. Such vectors include, but are not limited, to the *E. coli* expression vector pUR278 (Rüther et al. (1983) "Easy Identification Of cDNA Clones," *EMBO J.* 2:1791-1794), in which the coding sequence may be ligated individually into the vector in frame with the lac Z coding region so that a fusion protein is produced; pIN vectors (Inouye et al. (1985) "Up-Promoter Mutations In The lpp Gene Of *Escherichia Coli*," *Nucleic Acids Res.* 13:3101-3110; Van Heeke et al. (1989) "Expression Of Human Asparagine Synthetase In *Escherichia Coli*," *J. Biol. Chem.* 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts (e.g., see Logan et al. (1984) "Adenovirus Tripartite Leader Sequence Enhances Translation Of mRNAs Late After Infection," *Proc. Natl. Acad. Sci. USA* 81:3655-3659). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al. (1987) "Expression And Secretion Vectors For Yeast," *Methods in Enzymol.* 153:516-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. For example, in certain embodiments, the polypeptides described herein may be expressed as a single gene product (e.g., as a single polypeptide chain, i.e., as a polyprotein precursor), requiring proteolytic cleavage by native or recombinant cellular mechanisms to form separate polypeptides described herein. The disclosure thus encompasses engineering a nucleic acid sequence to encode a polyprotein precursor molecule comprising the polypeptides described herein, which includes coding sequences capable of directing post translational cleavage of said polyprotein precursor. Post-translational cleavage of the polyprotein precursor results in the polypeptides described herein. The post translational cleavage of the precursor molecule comprising the polypeptides described herein may occur in vivo (i.e., within the host cell by native or recombinant cell systems/mechanisms, e.g. furin cleavage at an appropriate site) or may occur in vitro (e.g. incubation of said polypeptide chain in a composition comprising proteases or peptidases of known activity and/or in a composition comprising conditions or reagents known to foster the desired proteolytic action). Purification and modification of recombinant proteins is well known in the art such that the design of the polyprotein precursor could include a number of embodiments readily appreciated by a skilled worker. Any known proteases or peptidases known in the art can be used for the described modification of the precursor molecule, e.g., thrombin or factor Xa (Nagai et al. (1985) "Oxygen Binding Properties Of Human Mutant Hemoglobins Synthesized In *Escherichia Coli,*" *Proc. Nat. Acad. Sci. USA* 82:7252-7255, and reviewed in Jenny et al. (2003) "A Critical Review Of The Methods For Cleavage Of Fusion Proteins With Thrombin And Factor Xa," *Protein Expr. Purif.* 31:1-11, each of which is incorporated by reference herein in its entirety)), enterokinase (Collins-Racie et al. (1995) "Production Of Recombinant Bovine Enterokinase Catalytic Subunit In *Escherichia Coli* Using The Novel Secretory Fusion Partner DsbA," *Biotechnology* 13:982-987 hereby incorporated by reference herein in its entirety)), furin, and AcTEV (Parks et al. (1994) "Release Of Proteins And Peptides From Fusion Proteins Using A Recombinant Plant Virus Proteinase," *Anal. Biochem.* 216:413-417 hereby incorporated by reference herein in its entirety)) and the Foot and Mouth Disease Virus Protease C3.

Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines which stably express polypeptides described herein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the polypeptides described herein. Such engineered cell lines may be particularly useful in screening and evaluation of polypeptides that interact directly or indirectly with the polypeptides described herein.

A number of selection systems may be used, including but not limited to the herpes simplex virus thymidine kinase (Wigler et al. (1977) "Transfer Of Purified Herpes Virus Thymidine Kinase Gene To Cultured Mouse Cells," *Cell* 11: 223-232), hypoxanthine-guanine phosphoribosyltransferase (Szybalska et al. (1992) "Use Of The HPRT Gene And The HAT Selection Technique In DNA-Mediated Transformation Of Mammalian Cells First Steps Toward Developing Hybridoma Techniques And Gene Therapy," *Bioessays* 14: 495-500), and adenine phosphoribosyltransferase (Lowy et al. (1980) "Isolation Of Transforming DNA: Cloning The Hamster aprt Gene," *Cell* 22: 817-823) genes can be employed in tk-, hgprt- or aprt-cells, respectively. Also, antimetabolite resistance can be used as the basis of selection for the following genes: dhfr, which confers resistance to methotrexate (Wigler et al. (1980) "Transformation Of Mammalian Cells With An Amplifiable Dominant-Acting Gene," *Proc. Natl. Acad. Sci. USA* 77:3567-3570; O'Hare et al. (1981) "Transformation Of Mouse Fibroblasts To Methotrexate Resistance By A Recombinant Plasmid Expressing A Prokaryotic Dihydrofolate Reductase," *Proc. Natl. Acad. Sci. USA* 78: 1527-1531); gpt, which confers resistance to mycophenolic acid (Mulligan et al. (1981) "Selection For Animal Cells That Express The *Escherichia coli* Gene Coding For Xanthine-Guanine Phosphoribosyltransferase," *Proc. Natl. Acad. Sci. USA* 78: 2072-2076); neo, which confers resistance to the aminoglycoside G-418 (Tolstoshev (1993) "Gene Therapy, Concepts, Current Trials And Future Directions," *Ann. Rev. Pharmacol. Toxicol.* 32:573-596; Mulligan (1993) "The Basic Science Of Gene Therapy," *Science* 260:926-932; and Morgan et al. (1993) "Human Gene Therapy," *Ann. Rev. Biochem.* 62:191-217) and hygro, which confers resistance to hygromycin (Santerre et al. (1984) "Expression Of Prokaryotic Genes For Hygromycin B And G418 Resistance As Dominant-Selection Markers In Mouse L Cells," *Gene* 30:147-156). Methods commonly known in the art of recombinant DNA technology which can be used are described in Ausubel et al. (eds.), 1993, *Current Protocols in Molecular Biology*, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al. (1981) "A New Dominant Hybrid Selective Marker For Higher Eukaryotic Cells," *J. Mol. Biol.* 150:1-14.

The expression levels of polypeptides described herein can be increased by vector amplification (for a review, see Bebbington and Hentschel, The use of vectors based on gene amplification for the expression of cloned genes in mammalian cells in DNA cloning, Vol. 3 (Academic Press, New York, 1987). When a marker in the vector system expressing a polypeptide described herein is amplifiable, increase in the level of inhibitor present in culture of host cell will increase the number of copies of the marker gene. Since the amplified region is associated with the nucleotide sequence of a polypeptide described herein or a polypeptide described herein, production of the polypeptide will also increase (Crouse et al. (1983) "Expression And Amplification Of Engineered Mouse Dihydrofolate Reductase Minigenes," *Mol. Cell. Biol.* 3:257-266).

Once a polypeptide described herein has been recombinantly expressed, it may be purified by any method known in the art for purification of polypeptides, polyproteins or antibodies (e.g., analogous to antibody purification schemes based on antigen selectivity) for example, by chromatography (e.g., ion exchange, affinity, particularly by affinity for the specific antigen (optionally after Protein A selection where the polypeptide comprises an Fc domain (or portion thereof)), and sizing column chromatography), centrifugation, differential solubility, or by any other standard technique for the purification of polypeptides or antibodies.

Other aspects of the present disclosure relate to a cell comprising a nucleic acid described herein or a vector described herein. The cell may be a prokaryotic or eukaryotic cell. In some embodiments, the cell in a mammalian cell. Exemplary cell types are described herein.

Yet other aspects of the disclosure relate to a method of producing a polypeptide described herein, the method comprising obtaining a cell described herein and expressing nucleic acid described herein in said cell. In some embodiments, the method further comprises isolating and purifying a polypeptide described herein.

Other aspects of the present disclosure relate to pharmaceutical compositions comprising the isolated polypeptides or the chimeric molecules described herein. The term "pharmaceutical composition", as used herein, refers to the formulation of an isolated polypeptide described herein in combination with a pharmaceutically acceptable carrier. The pharmaceutical composition can further comprise additional agents (e.g. for specific delivery, increasing half-life, or other therapeutic agents).

In some embodiments, the pharmaceutical composition of the present disclosure comprise other therapeutic agents. In some embodiments, such other therapeutic agents comprise an additional isolated polypeptide fragment. In some embodiments, the additional isolated polypeptide fragment comprises the amino acid sequence of the cysteine-rich domain of FZD (FZD-CRD). Also illustrated in the Examples of the present disclosure, is the inhibitory effect of FZD-CRD on TcdB binding to cell surface FZDs via competition. By preventing TcdB from binding to FZDs, the FZD-CRD polypeptides not only block the entry of TcdB into the cells, but also prevent the inhibition of Wnt signaling by TcdB. Thus, further provided herein are examples of how the FZD-CRD polypeptides protect cells in from TcdB induced CDI. As illustrated herein, Triple FZD1/2/7 knockout (KO) cells were dramatically resistant to toxin entry. Furthermore, colonic organoids with reduced FZD1/2/7 were less sensitive to TcdB. Finally, FZD2-CRD prevented TcdB binding to colonic tissues in mice and the colonic epithelium in FZD7 KO mice was less susceptible to TcdB-induced tissue damage. These findings establish FZDs as physiologically relevant epithelial receptors for TcdB, point to a role of Wnt signaling blockage in CDI pathogenesis, and provide novel therapeutic targets for treating CDI. Recombinant human FZD-CRD proteins and variants are commercially available (e.g., from ACRO Biosystems).

In some embodiments, the additional isolated polypeptide fragment of the present disclosure, may comprise an amino acid sequence of SEQ ID NO: 24, SEQ ID NO: 25, or SEQ ID NO: 26. In some embodiments, the isolated polypeptide fragment comprises an amino acid sequence that has at least 85% identity to SEQ ID NO: 24. For example, the isolated polypeptide fragment comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or even 100% identity to SEQ ID NO: 24. In some embodiments, the isolated polypeptide fragment comprises an amino acid sequence that has at least 85% identity to SEQ ID NO: 25. For example, the isolated polypeptide fragment comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or even 100% identity to SEQ ID NO: 25. In some embodiments, the isolated polypeptide fragment comprises an amino acid sequence that has at least 85% identity to SEQ ID NO: 26. For example, the isolated polypeptide fragment comprises an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or even 100% identity to SEQ ID NO: 26.

The additional isolated polypeptide fragments of the present disclosure, may comprise any modifications or derivatizations disclosed herein. Such additional isolated polypeptide fragments may also be fused to any heterologous partners described herein, e.g., an Fc domain.

As it may also become clear later in the present disclosure, the pharmaceutical composition of the present disclosure, may further comprise other therapeutic agents suitable for the specific disease such composition is designed to treat.

The term "pharmaceutically-acceptable carrier", as used herein, means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the polypeptide from one site (e.g., the delivery site) of the body, to another site (e.g., organ, tissue or portion of the body). A pharmaceutically acceptable carrier is "acceptable" in the sense of being compatible with the other ingredients of the formulation and not injurious to the tissue of the subject (e.g., physiologically compatible, sterile, physiologic pH, etc.). Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

In some embodiments, an isolated polypeptide of the present disclosure in a composition is administered by injection, by means of a catheter, by means of a suppository, or by means of an implant, the implant being of a porous, non-porous, or gelatinous material, including a membrane, such as a sialastic membrane, or a fiber. Typically, when administering the composition, materials to which the polypeptide of the disclosure does not absorb are used.

In other embodiments, the isolated polypeptides of the present disclosure are delivered in a controlled release system. In one embodiment, a pump may be used (see, e.g., Langer, 1990, Science 249:1527-1533; Sefton, 1989, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used. (See, e.g., Medical Applications of Controlled Release (Langer and Wise eds., CRC Press, Boca Raton, Fla., 1974); Controlled Drug Bioavailability, Drug Product Design and Performance (Smolen and Ball eds., Wiley, New York, 1984); Ranger and Peppas, 1983, Macromol. Sci. Rev. Macromol. Chem. 23:61. See also Levy et al., 1985, Science 228:190; During et al., 1989, Ann. Neurol. 25:351; Howard et al., 1989, J. Neurosurg. 71:105.) Other controlled release systems are discussed, for example, in Langer, supra.

Isolated polypeptides of the present disclosure can be administered as pharmaceutical compositions comprising a therapeutically effective amount of a binding agent and one or more pharmaceutically compatible ingredients.

In typical embodiments, the pharmaceutical composition is formulated in accordance with routine procedures as a pharmaceutical composition adapted for intravenous or subcutaneous administration to a subject, e.g., a human being. Typically, compositions for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

A pharmaceutical composition for systemic administration may be a liquid, e.g., sterile saline, lactated Ringer's or Hank's solution. In addition, the pharmaceutical composition can be in solid forms and re-dissolved or suspended immediately prior to use. Lyophilized forms are also contemplated.

The pharmaceutical composition can be contained within a lipid particle or vesicle, such as a liposome or microcrystal, which is also suitable for parenteral administration. The particles can be of any suitable structure, such as unilamellar or plurilamellar, so long as compositions are contained therein. The polypeptides of the present disclosure can be entrapped in 'stabilized plasmid-lipid particles' (SPLP) containing the fusogenic lipid dioleoylphosphatidylethanolamine (DOPE), low levels (5-10 mol %) of cationic lipid, and stabilized by a polyethyleneglycol (PEG) coating (Zhang Y. P. et al., Gene Ther. 1999, 6:1438-47). Positively charged lipids such as N-[1-(2,3-dioleoyloxi)propyl]-N,N, N-trimethyl-amoniummethylsulfate, or "DOTAP," are particularly preferred for such particles and vesicles. The preparation of such lipid particles is well known. See, e.g., U.S. Pat. Nos. 4,880,635; 4,906,477; 4,911,928; 4,917,951; 4,920,016; and 4,921,757.

The pharmaceutical compositions of the present disclosure may be administered or packaged as a unit dose, for example. The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent; i.e., carrier, or vehicle.

In some embodiments, the isolated polypeptides described herein may be conjugated to a therapeutic moiety, e.g., an antibiotic. Techniques for conjugating such therapeutic moieties to polypeptides, including e.g., Fc domains, are well known; see, e.g., Amon et al., "Monoclonal Antibodies For Immunotargeting Of Drugs In Cancer Therapy", in Monoclonal Antibodies And Cancer Therapy, Reisfeld et al. (eds.), 1985, pp. 243-56, Alan R. Liss, Inc.); Hellstrom et al., "Antibodies For Drug Delivery", in Controlled Drug Delivery (2nd Ed.), Robinson et al. (eds.), 1987, pp. 623-53, Marcel Dekker, Inc.); Thorpe, "Antibody Carriers Of Cytotoxic Agents In Cancer Therapy: A Review", in Monoclonal Antibodies '84: Biological And Clinical Applications, Pinchera et al. (eds.), 1985, pp. 475-506); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), 1985, pp. 303-16, Academic Press; and Thorpe et al. (1982) "The Preparation And Cytotoxic Properties Of Antibody-Toxin Conjugates," Immunol. Rev., 62:119-158.

Further, the pharmaceutical composition can be provided as a pharmaceutical kit comprising (a) a container containing a polypeptide of the disclosure in lyophilized form and (b) a second container containing a pharmaceutically acceptable diluent (e.g., sterile water) for injection. The pharmaceutically acceptable diluent can be used for reconstitution or dilution of the lyophilized polypeptide of the disclosure. Optionally associated with such container(s) can be a notice in the form prescribed by a governmental agency regulating the manufacture, use or sale of pharmaceuticals or biological products, which notice reflects approval by the agency of manufacture, use or sale for human administration.

In another aspect, an article of manufacture containing materials useful for the treatment of the diseases described above is included. In some embodiments, the article of manufacture comprises a container and a label. Suitable containers include, for example, bottles, vials, syringes, and test tubes. The containers may be formed from a variety of materials such as glass or plastic. In some embodiments, the container holds a composition that is effective for treating a disease described herein and may have a sterile access port. For example, the container may be an intravenous solution bag or a vial having a stopper pierceable by a hypodermic injection needle. The active agent in the composition is an isolated polypeptide of the disclosure. In some embodiments, the label on or associated with the container indicates that the composition is used for treating the disease of choice. The article of manufacture may further comprise a second container comprising a pharmaceutically-acceptable buffer, such as phosphate-buffered saline, Ringer's solution, or dextrose solution. It may further include other materials desirable from a commercial and user standpoint, including other buffers, diluents, filters, needles, syringes, and package inserts with instructions for use.

The isolated polypeptides, chimeric molecules, and the pharmaceutical compositions comprising such isolated polypeptides of the present disclosure, may be used to treat a variety of diseases. In some embodiments, the diseases are caused, at least in part, by the dysregulation of Wnt signaling pathways. In some embodiments, the disease is *Clostridium difficile* infection. Thus, further provided herein are methods of treating *Clostridium difficile* infection, comprising administering to a subject in need thereof, a therapeutically effective amount of the isolated polypeptides or the pharmaceutical composition comprising such isolated polypeptides disclosed herein. The isolated polypeptides of or the pharmaceutical composition comprising such isolated polypeptides, is effective in blocking TcdB binding to FZDs.

In some embodiments, the pharmaceutically composition used for treating CDI of the present disclosure, further comprises additional therapeutic agents or polypeptides. For example, the isolated TcdB$_{1114-1835}$ polypeptide fragment of the present disclosure, while being able to block the wild-type TcdB from entering the cells, still inhibits Wnt signaling due to its occupancy of the FZD receptors. Thus, agents that activate Wnt signaling downstream of the FZD receptors may afford additional therapeutic effects against CDI. Agents that activate Wnt signaling downstream of the FZD receptors are known in the art. Non-limiting examples of such agents include GSK-3 inhibitors such as Lithium (LiCl) and CHIR99021. GSK-3 inhibits Wnt signaling downstream of the FZD receptors. Therefore, GSK-3 inhibitors are able to activate Wnt signaling downstream of the FZD receptors. Other non-limiting examples of agents that induce Wnt signaling include, without limitation, SB 216763 (Tocris Bioscience, catalog #1616), BIO (Tocris Bioscience, catalog #3194), TCS 2002 (Tocris Bioscience, catalog #3869), TC-G 24 (Tocris Bioscience, catalog #4353), TWS 119 (Tocris Bioscience, catalog #3835), SB 415286 (Tocris Bioscience, catalog #1617), A 1070722 (Tocris Bioscience, catalog #4431), AR-A 014418 (Tocris Bioscience, catalog #3966), L803-mts (Tocris Bioscience, catalog #2256). The activating of Wnt signaling occurs in a cell. In some embodiments, the cell is a colonic epithelial cell.

In some embodiments, the pharmaceutically composition used for treating CDI of the present disclosure, further comprises an agent that inhibits the cysteine protease activity of TcdB. In some embodiments, the agent is ebselen. Ebselen (also called PZ 51, DR3305, and SPI-1005), is a synthetic organoselenium drug molecule with anti-inflammatory, anti-oxidant and cytoprotective activity. It acts as a mimic of glutathione peroxidase and can also react with peroxynitrite. Ebselen is a potent scavenger of hydrogen peroxide as well as hydroperoxides including membrane bound phospholipid and cholesterylester hydroperoxides. Several ebselen analogues have been shown to scavenge hydrogen peroxide in the presence of thiols. Ebselen is known in the art to be inhibiting the cysteine protease activity of TcdB. Other non-limiting examples of cysteine protease inhibitors include serpins, stefins, and Inhibitors of apoptosis (IAPs).

Yet in other embodiments, the pharmaceutically composition used for treating CDI of the present disclosure, further comprises agents that facilitate blocking TcdB binding to FZDs. Such agents may be, for example, an FZD antibody. It is to be understood that any agents that competes with TcdB for binding to FZD may be used herein.

In other embodiments, the disease caused by the dysregulation of Wnt signaling is cancer. The dysregulation of Wnt signaling pathway is a known cause of cancer and is a central mechanism in cancer biology. For example, Wnt overexpression could lead to malignant transformation of mouse mammary tissue. Therefore, the inhibition of Wnt signaling has been a focus for developing cancer therapeutics. As described herein, the isolated polypeptides of the present disclosure, e.g., the $TdcB_{1114-1835}$ polypeptide, is able to inhibit/block Wnt signaling by competing with Wnt for the FZD receptors. Thus, other aspects of the present disclosure relate methods of treating cancer. Such methods comprise administering to the subject in need thereof a therapeutically effective amount of the isolated polypeptides, or the pharmaceutical composition comprising the isolated polypeptides of the present disclosure.

In some embodiments, the method of treating cancer of the present disclosure, further comprises administering to the subject an agent that blocks Wnt signaling. Non-limiting examples of agents that block Wnt signaling include Dkk family proteins, Secreted Frizzled Related Proteins (sFRP), Draxin, IGFBP-4, SOST/Sclerostin, USAG1, and WIF-1. In some embodiments, the agent that blocks Wnt signaling is an FZD antibody. The use of these agents in blocking Wnt signaling is known in the art.

Many types of cancer are characterized with over-activated Wnt signaling and over-expression of Frizzled. For instance, >90% of colon cancers feature aberrant Wnt signaling. Recent study (Gujral et al, Cell, 2014, 159, 844-856) showed that Frizzled 2 is over expressed in metastatic liver, lung, colon and breast cancers. The expression is highly correlated with the markers of epithelial-mesenchymal transition. Thus, types of cancer that may be treated using the methods disclosed herein include, without limitation neoplasms, malignant tumors, metastases, or any disease or disorder characterized by uncontrolled cell growth such that it would be considered cancerous. The cancer may be a primary or metastatic cancer. Cancers include, but are not limited to, biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemias; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma, teratomas, choriocarcinomas; stromal tumors and germ cell tumors; thyroid cancer including thyroid adenocarcinoma and medullar carcinoma; and renal cancer including adenocarcinoma and Wilms' tumor. Commonly encountered cancers include breast, prostate, lung, ovarian, colorectal, and brain cancer. In some preferred embodiments, the methods of the present disclosure may be used to treat colon cancer, liver cancer, lung cancer, breast cancer. In some embodiments, the cancer cells are metastatic. It is to be understood that the examples are not meant to be limiting and that any types of cancer that shows hyperactive Wnt signaling or overexpression of Frizzled may be treated using the methods disclosed herein.

"A therapeutically effective amount" as used herein refers to the amount of each therapeutic agent of the present disclosure (e.g., the isolated polypeptide fragment, the additional isolated polypeptide fragment, and the agent that activates Wnt signaling) required to confer therapeutic effect on the subject, either alone or in combination with one or more other therapeutic agents. Effective amounts vary, as recognized by those skilled in the art, depending on the particular condition being treated, the severity of the condition, the individual subject parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a subject may insist upon a lower dose or tolerable dose for medical reasons, psychological reasons or for virtually any other reasons.

Empirical considerations, such as the half-life, generally will contribute to the determination of the dosage. For example, therapeutic agents that are compatible with the human immune system, such as polypeptides comprising regions from humanized antibodies or fully human antibodies, may be used to prolong half-life of the polypeptide and to prevent the polypeptide being attacked by the host's immune system. Frequency of administration may be determined and adjusted over the course of therapy, and is generally, but not necessarily, based on treatment and/or suppression and/or amelioration and/or delay of a disease. Alternatively, sustained continuous release formulations of a polypeptide may be appropriate. Various formulations and devices for achieving sustained release are known in the art.

In some embodiments, dosage is daily, every other day, every three days, every four days, every five days, or every six days. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the polypeptide used) can vary over time. In some embodiments, for an adult subject of normal weight, doses ranging from about 0.01 to 1000 mg/kg may be administered. In some embodiments, the dose is between 1 to 200 mg. The particular dosage regimen, i.e., dose, timing and repetition, will depend on the particular subject and that subject's medical history, as well as the properties of the polypeptide (such as the half-life of the polypeptide, and other considerations well known in the art).

For the purpose of the present disclosure, the appropriate dosage of a therapeutic agent as described herein will depend on the specific agent (or compositions thereof) employed, the formulation and route of administration, the type and severity of the disease, whether the polypeptide is administered for preventive or therapeutic purposes, previous therapy, the subject's clinical history and response to the antagonist, and the discretion of the attending physician. Typically the clinician will administer a polypeptide until a dosage is reached that achieves the desired result. Administration of one or more polypeptides can be continuous or intermittent, depending, for example, upon the recipient's physiological condition, whether the purpose of the administration is therapeutic or prophylactic, and other factors known to skilled practitioners. The administration of a polypeptide may be essentially continuous over a preselected period of time or may be in a series of spaced dose, e.g., either before, during, or after developing a disease.

As used herein, the term "treating" refers to the application or administration of a polypeptide or composition including the polypeptide to a subject in need thereof. "A subject in need thereof", refers to an individual who has a disease, a symptom of the disease, or a predisposition toward the disease, with the purpose to cure, heal, alleviate, relieve, alter, remedy, ameliorate, improve, or affect the disease, the symptom of the disease, or the predisposition toward the disease. In some embodiments, the subject has CDI. In some embodiments, the subject has cancer. In some embodiments, the subject is a mammal. In some embodiments, the subject is a non-human primate. In some embodiments, the subject is human.

Alleviating a disease includes delaying the development or progression of the disease, or reducing disease severity. Alleviating the disease does not necessarily require curative results. As used therein, "delaying" the development of a disease means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a disease includes initial onset and/or recurrence.

In some embodiments, the pharmaceutical composition comprising the therapeutic agents (e.g., an isolated polypeptide) described herein is administered to a subject in need of the treatment at an amount sufficient to inhibit the activity of TcdB by at least 20% (e.g., 30%, 40%, 50%, 60%, 70%, 80%, 90% or greater) in vivo or in vitro.

Conventional methods, known to those of ordinary skill in the art of medicine, can be used to administer the isolated polypeptide or pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

EXAMPLES

Genome-wide CRISPR/Cas9 Screen Reveals Frizzled as Receptors for *Clostridium difficile* Toxin B To identify the physiologically relevant receptor and other host factors involved in TcdB actions, two unbiased genome-wide mutagenesis screens using the CRISPR (clustered regularly interspaced short palindromic repeats)/Cas9 approach were performed (15, 16). The C-terminal part of TcdA and TcdB contains a region known as combined repetitive oligopeptides (CROPs, FIG. 6, Panel A), which can bind carbohydrates and may mediate toxin binding to cells (17). Recent studies suggest the existence of an additional receptor binding region beyond the CROPs (18-21). Indeed, a truncated toxin ($TcdB_{1-1830}$) that lacks the CROPs still induced cell-rounding at clinically relevant picomolar toxin concentrations on various cell lines (FIG. 6, Panels B-E) (22). As CROPs-carbohydrate interactions may mask the contribution of specific protein receptors, two separate screens were performed, using full-length TcdB and $TcdB_{1-1830}$, respectively (FIG. 1, Panel A).

HeLa cells that stably express RNA-guided endonuclease Cas9 were transduced with lentivirus libraries that express small guide RNA (sgRNA) targeting 19,052 genes, with six sgRNAs per gene (15). After four rounds of selection with increasing concentrations of toxins, the sgRNA sequences from the remaining cells were identified via next-generation sequencing (NGS). Candidate genes were ranked based on the number of unique sgRNAs identified for each gene (Y-axis) versus its total NGS reads (X-axis), which represents the abundance of cells harboring sgRNA targeting that gene (FIG. 1, panel B and FIG. 7 Tables 1-4).

Figure 1B:
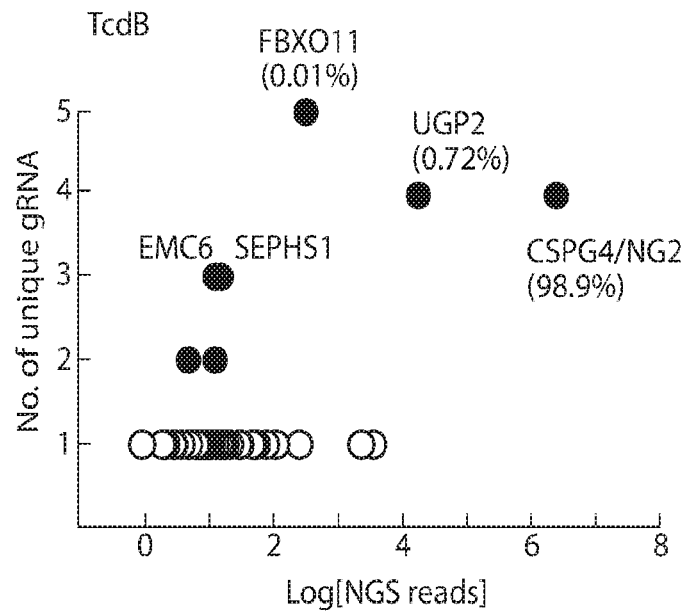
Figure 1C:
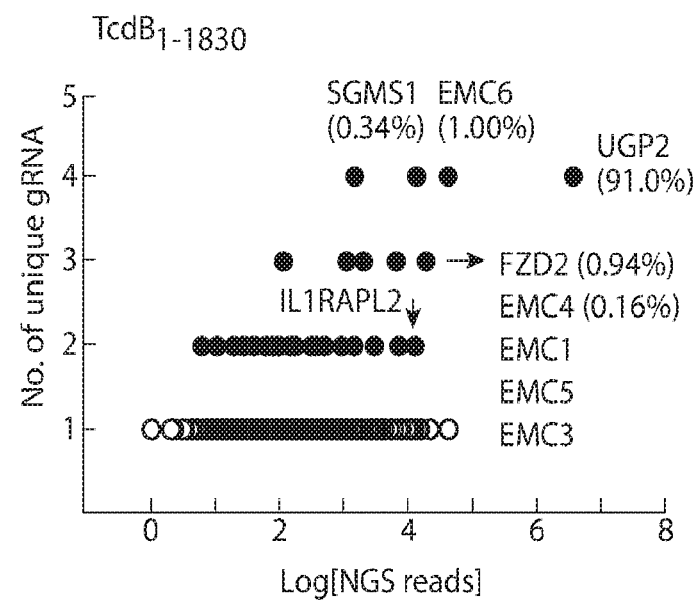
Figure 2D:
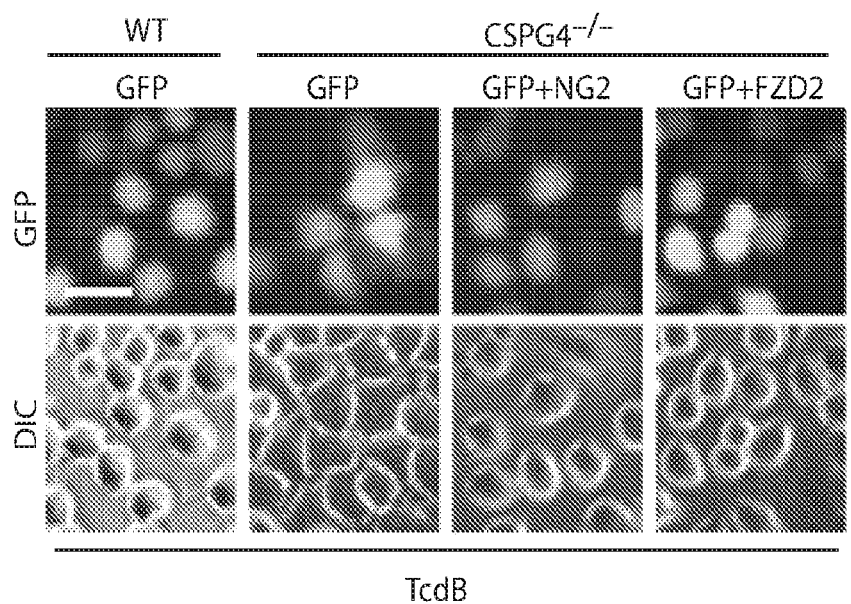
FIG. 2 demonstrates that FZDs are CROPs-independent receptors for TcdB. In Panel A, HeLa cells with the indicated genes mutated via CRISPR/Cas9 were exposed to a series of concentrations of TcdB or $TcdB_{1-1830}$, and the percentages of rounded cells were quantified as described in FIG. 9, panels A-C. Their sensitivities to toxins, defined as the toxin centration that induced 50% cell-rounding ($CR_{50}$, listed in FIG. 9, panel C), were normalized to WT HeLa cells and plotted (*P<0.005, one-way ANOVA). Panel B shows that the binding of TcdB (10 nM, 10 min) was greatly reduced in $CSPG4^{-/-}$ cells compared to WT cells assayed by immunostaining. Ectopic expression of rat NG2 increased binding of TcdB. Scale bar=20 μm. NG2 was detected using a polyclonal anti-CSPG4/NG2 antibody. TcdB was detected using a polyclonal chicken anti-TcdB antibody. Panel C shows that the transfection of FZD2 increased TcdB binding to $CSPG4^{-/-}$ cells. Transfected FZD2 was identified by 1D4 tag fused to its C-terminal cytoplasmic domain. Scale bar=20 μm. Panel D illustrates that the ectopic expression of NG2 or FZD2 both restored TcdB entry into $CSPG4^{-/-}$ cells, which resulted in cell-rounding for nearly all transfected cells when $CSPG4^{-/-}$ cells have yet to show any cell-rounding effect after exposure to TcdB (5 pM, 3 hours). Co-transfected GFP was used to mark transfected cells. Scale bar=50 μm. Panel E shows $CSPG4^{-/-}$ cells transfected with the indicated FZD members exposed to TcdB (10 nM, 10 min). Cells were washed and cell lysates were subjected to immunoblot analysis. Expression of FZDs was confirmed by 1D4 tag fused to their cytoplasmic domains. Actin served as a loading control. Transfection of FZD1, 2, and 7 greatly increased binding of TcdB to cells. Panel F shows the assessed sensitivities of $FZD1^{-/-}$, $FZD2^{-/-}$, $FZD7^{-/-}$, as well as triple $FZD1/2/7^{-/-}$ cells to TcdB and $TcdB_{1-1830}$ using cytopathic cell-rounding assays as described in FIG. 2, Panel A (*P<0.005, one-way ANOVA). Panel G shows that ectopic expression of FZD1, 2, or 7 restored entry of $TcdB_{1-1830}$ into $FZD1/2/7^{-/-}$ cells, resulting in cell-rounding for nearly all transfected cells (300 pM, 3 hours). Co-transfected GFP marked the transfected cells. Scale bar=50 μm. Panel H is a schematic illustration of FZD. Recombinant Fc-tagged FZD2-CRD binds directly to immobilized GST-tagged $TcdB_{1501-2366}$, but not GST-tagged CROP region (residues 1831-2366) in pull-down assays. Panel I is a characterization of interactions between TcdB and Fc-tagged CRDs of FZD1, 2, 5, and 7 using a bio-layer interferometry (BLI) assay. The binding curve between FZD1/2/7 and TcdB fits a single binding site with low nanomolar Kd (see FIG. 14 for detailed Kd analysis). Panel J shows that FZD7-CRD, but not FZD8-CRD, when expressed on the surface of $CSPG4^{-/-}$ cells via a GPI anchor, mediated binding of TcdB to cells.
Figure 2E:
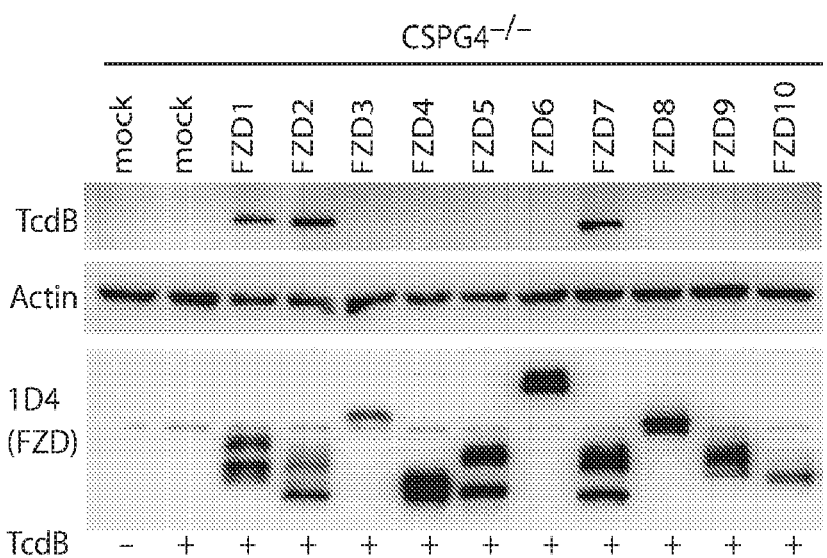
Figure 2F:
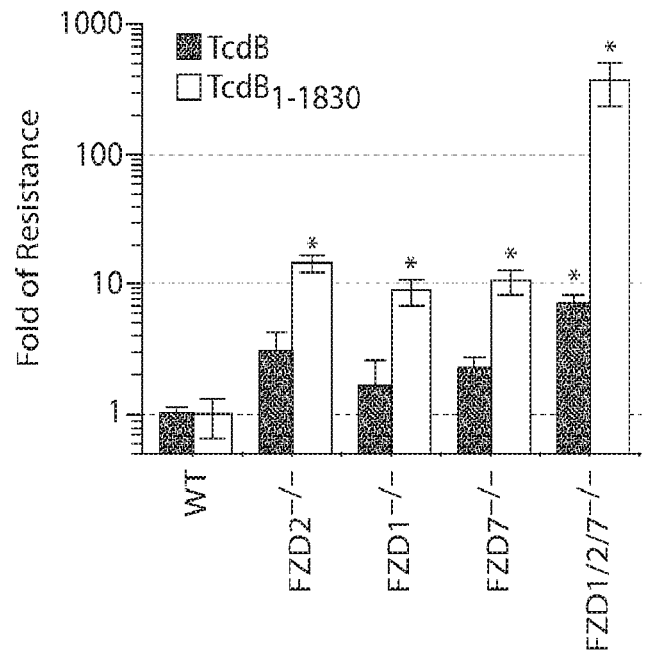
Figure 2G:
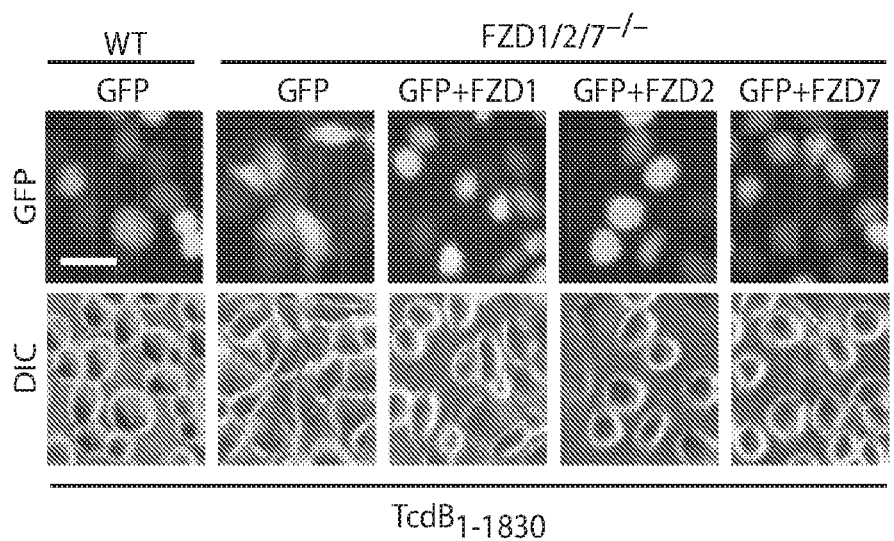
Figure 2H:
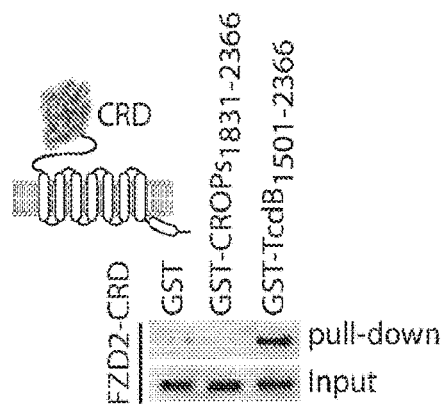
Figure 2I:
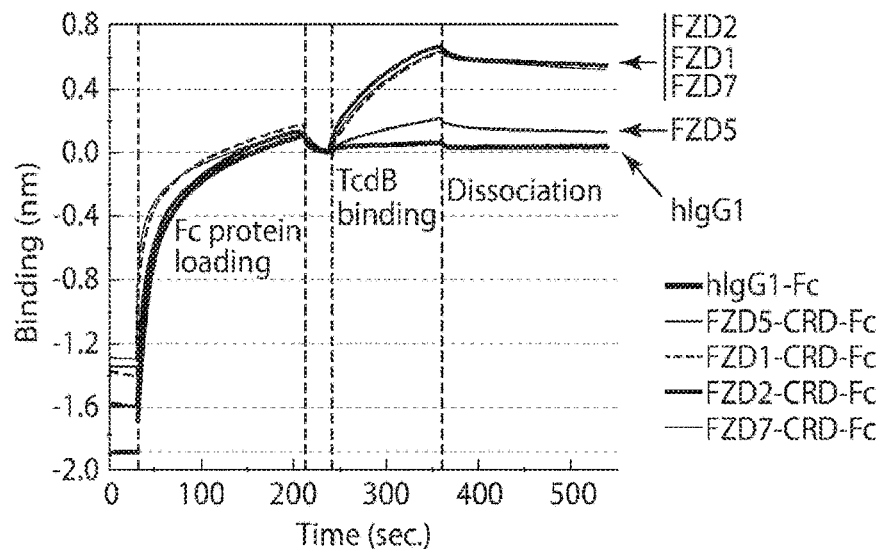
Figure 2J:
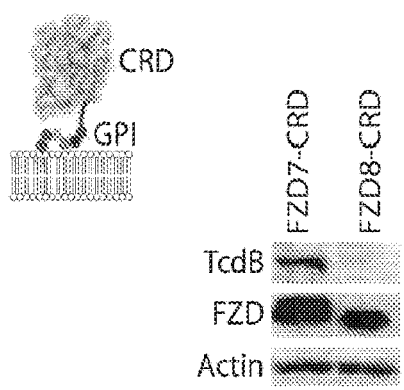

UDP-glucose pyrophosphorylase (UGP2) stood out in both screens (FIG. 1, panels B and C). UGP2 is a cytosolic enzyme producing UDP-glucose, which is the essential substrate used by TcdA and TcdB to glucosylate small GTPases (23). CSPG4 was a top hit from the full-length TcdB screen (FIG. 1, Panel B), confirming a previous report that identified CSPG4 using a shRNA-based screen in HeLa cells (12). An intriguing hit was Frizzled 2 (FZD2), which was the highest-ranking membrane protein from the $TcdB_{1-1830}$ screen (FIG. 1, Panel C). FZD2 is a well-known receptor for Wnt signaling, which is the central pathway regulating proliferation and self-renewal of colonic epithelial cells (24, 25). In addition to FZD2, an unusual group of high-ranking hits were the subunits of the ER membrane protein complex (EMC), including EMC1, 3, 4, 5, and 6 (FIG. 1, Panels B and C).

Figure 9A:
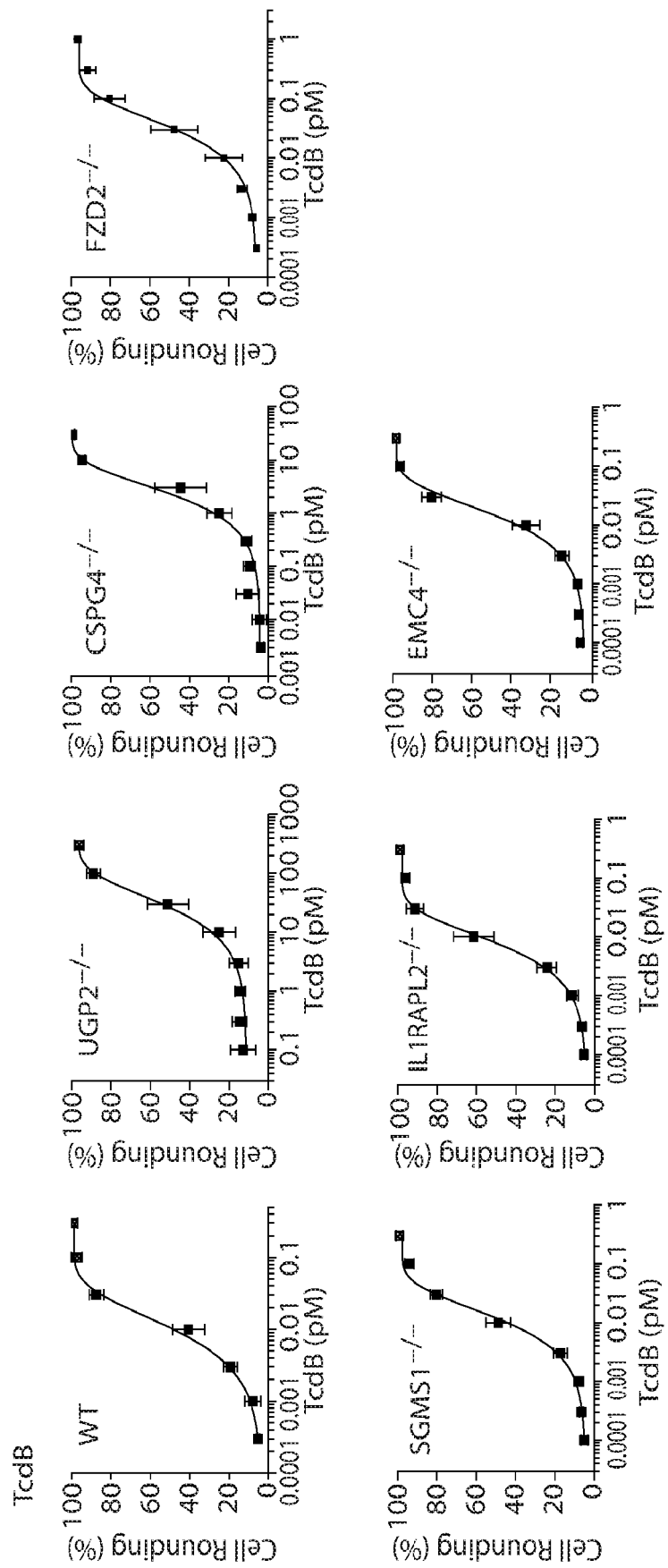
FIG. 9 shows assessments of the sensitivities of CRISPR/Cas9 mediated knockout HeLa cells to TcdB and $TcdB_{1-1830}$. Panels A and B show HeLa-Cas9 cells with the indicated genes mutated via CRISPR/Cas9, as well as WT Hela-Cas9 cells, exposed to titrations of TcdB and $TcdB_{1-1830}$ for 24 hrs. The percentages of cell rounding for each indicated cell lines were quantified and plotted against the concentrations of TcdB (Panel A) or $TcdB_{1-1830}$ (Panel B). Panel C shows the determination of toxin concentrations that induce 50% of cells to become round after 24 hours, defined as $CR_{50}$, from the fitting curves in Panels A and B. Errors represent SD. *P<0.005, one-way ANOVA. Panel D shows HeLa cells with the indicated genes mutated exposed to TcdB (top panel) or $TcdB_{1-1830}$ (lower panel) for 3 hours. Cell lysates were subjected to immunoblot analysis for total levels of Rac1, and for non-glucosylated Rac1 that was not modified by TcdB. $UGP2^{-/-}$ cells have significant levels of Rac1 that remains non-glucosylated after exposure to TcdB or $TcdB_{1-1830}$. $CSPG4^{-/-}$ cells have significant levels of non-glucosylated Rac1 after exposure to TcdB. $FZD2^{-/-}$ and $EMC4^{-/-}$ cells both have slightly higher levels of non-glucosylated Rac1 compared to WT cells after exposure to $TcdB_{1-1830}$.
Figure 9B:
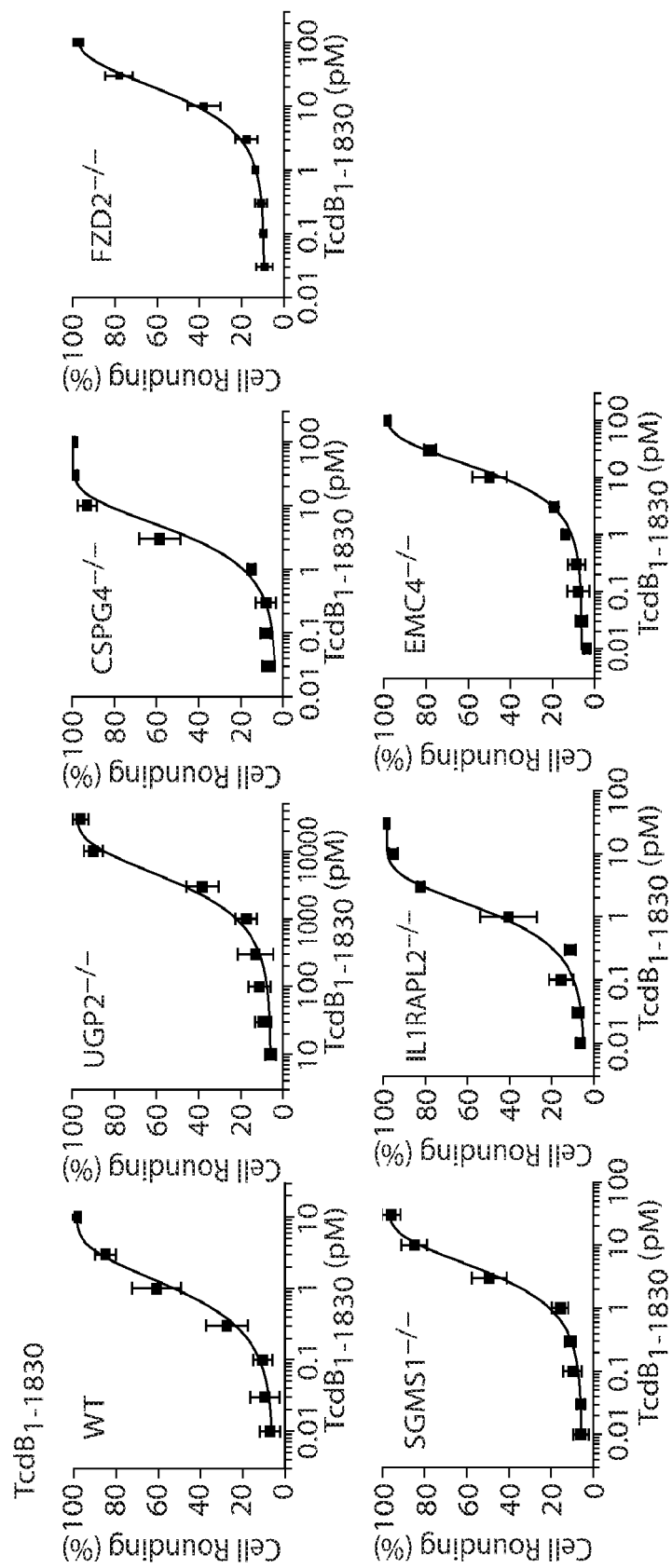
Figures 9C, 9D:
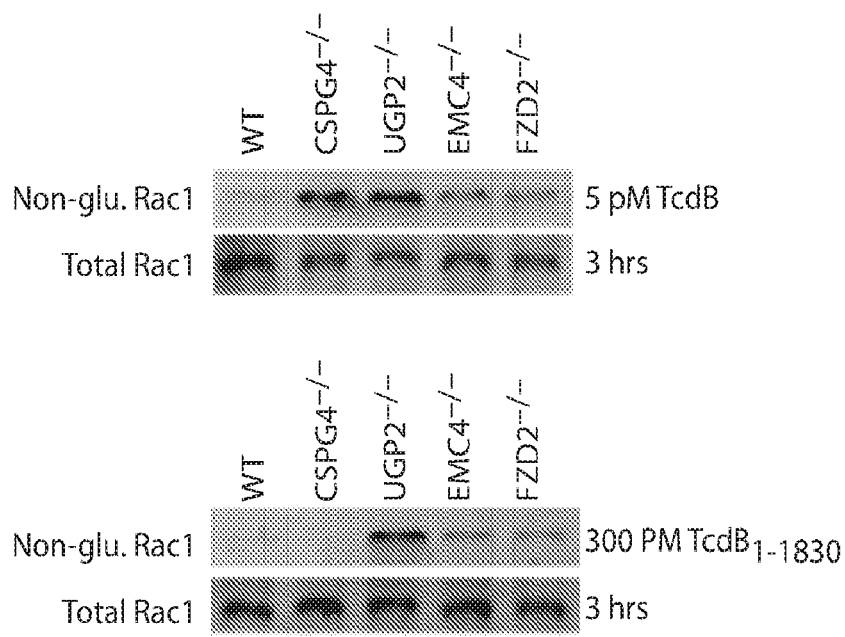
Figure 10A:
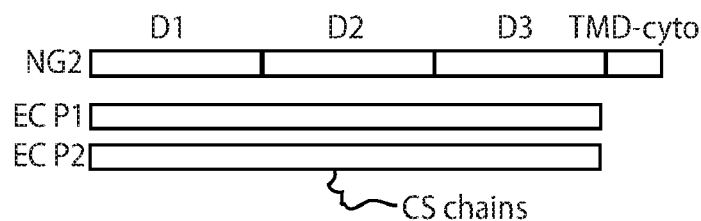
FIG. 10 demonstrates that the CROPs of TcdB is essential for its binding to CSPG4/NG2-EC. Panel A shows schematic drawings of CSPG4/NG2. Two fractions of recombinant extracellular domain (EC) fragments were used: one that does not contain chondroitin sulfate (CS) chains (EC P1), and the other that contains CS (EC P2). TMD-cyto: transmembrane and cytoplasmic domain. Panel B shows that TcdB, but not $TcdB_{1-1830}$, binds directly to both EC P1 and EC P2 of CSPG4/NG2 in a micro-titer plate based binding assay. Panel C shows $CSPG4^{-/-}$ cells transfected with the indicated constructs exposed to TcdB (upper panel, 10 nM, 10 min) or $TcdB_{1-1830}$ (lower panel, 10 nM, 10 min). Cells were washed and lysates were subjected to immunoblot analysis. IL1RAPL2 and Synaptotagmin II (Syt II, a receptor for botulinum neurotoxins) served as negative controls. Expression of CSPG4 increased binding of TcdB, but not $TcdB_{1-1830}$, whereas expression of FZD2 increased binding of both TcdB and $TcdB_{1-1830}$. Panel D shows that the CROPs fragment binds to CSPG4/NG2 on cell surfaces in a concentration-dependent manner. This binding is dependent on CSPG4/NG2 because it is largely abolished in $CSPG4^{-/-}$ cells. High concentrations of CROPs fragment reduced CSPG4/NG2-dependent binding of full-length TcdB to cells, indicating that CROPs can compete with full-length TcdB for binding to CSPG4/NG2.
Figure 10B:
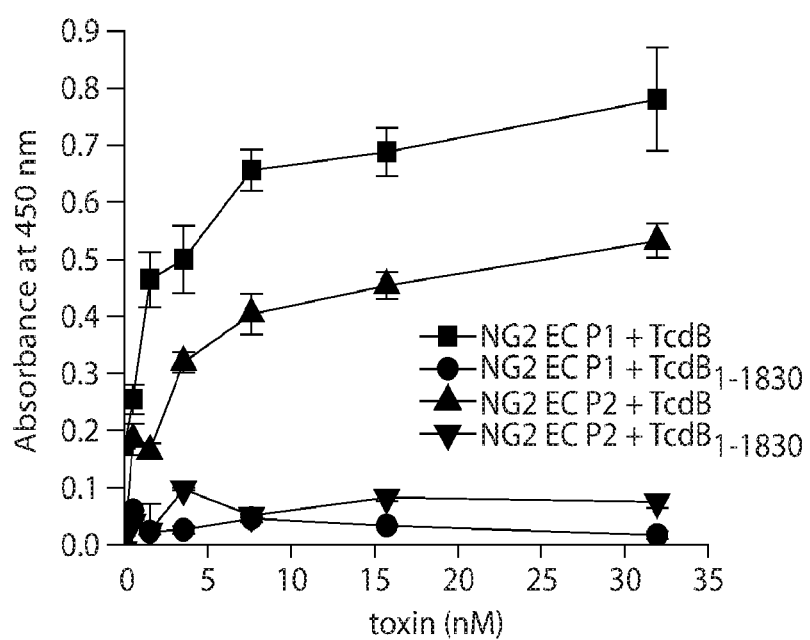
Figure 10C:
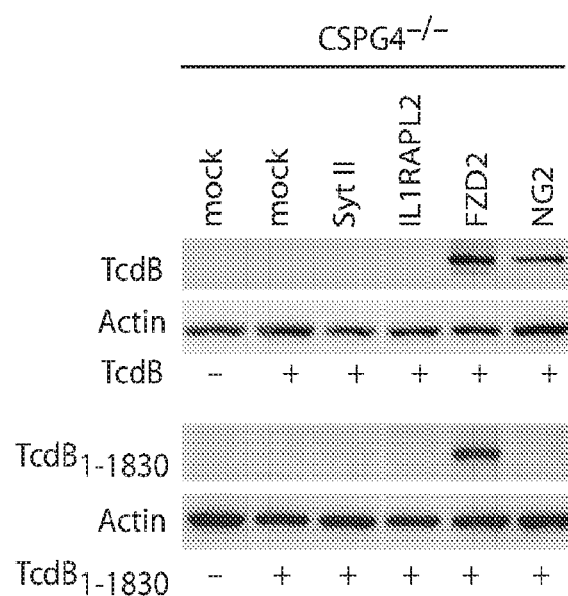
Figure 10D:
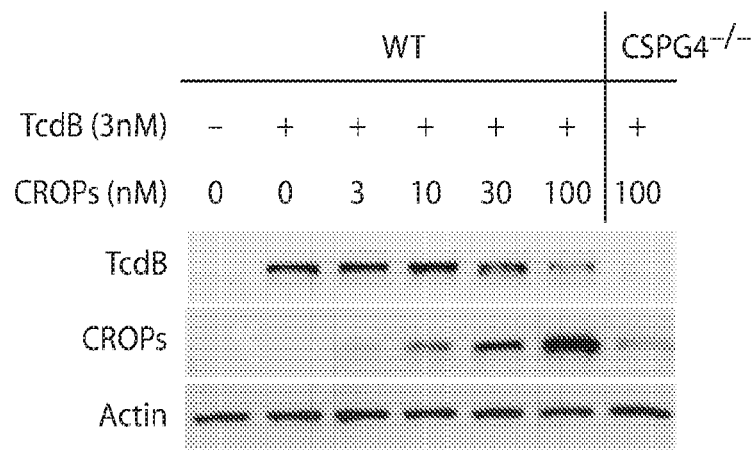

To validate the screening results, individual knockout HeLa cell lines for top candidates, including UGP2$^{-/-}$, CSPG4$^{-/-}$, FZD2$^{-/-}$, and EMC4$^{-/-}$, were generated using the CRISPR/Cas9 approach (FIG. 8, Tables 1-6). Two additional genes that appeared in the screen, SGMS1$^{-/-}$ (sphingomyelin synthase 1) and IL1RAPL2$^{-/-}$ (Interleukin-1 receptor accessory protein-like 2) were also tested. The above six knockout cell lines were challenged with either TcdB or TcdB$_{1-1830}$, using the well-established cytopathic assay (1), by quantifying the percentages of rounded cells after exposure to a series of concentrations of toxins (FIG. 9, Panels A-C). UGP2$^{-/-}$ were highly resistant (3000-fold) to both TcdB and TcdB$_{1-1830}$ compared to wild type (WT) HeLa cells. CSPG4$^{-/-}$ showed increased resistance to TcdB (~240-fold), but not to TcdB$_{1-1830}$. FZD2$^{-/-}$ and EMC4$^{-/-}$ both showed modest resistance (~15 and ~11-fold, respectively) to TcdB$_{1-1830}$, but not to TcdB (FIG. 2, Panel A, FIG. 9, Panel C). SGMS1$^{-/-}$ and IL1RAPL2$^{-/-}$ were not significantly resistant to TcdB or TcdB$_{1-1830}$ (P<0.005). Increased resistance of UGP2$^{-/-}$, CSPG4$^{-/-}$, FZD2$^{-/-}$, and EMC4$^{-/-}$ to TcdB or TcdB$_{1-1830}$ was further confirmed by immunoblot analysis for the levels of glucosylation of toxin substrate Rac1 (FIG. 9, Panel D).

CSPG4/NG2 and FZD2 were investigated for their potential as receptors. Binding of TcdB to CSPG4$^{-/-}$ cells was drastically reduced and ectopic expression of rat NG2 restored binding (FIG. 2, Panel B). TcdB binds directly to purified extracellular domain (EC) of CSPG4/NG2, independent of the glycosaminoglycan (GAG) on CSPG4/NG2 (26) (FIG. 10, Panels A and B). The above results are consistent with the previous report (12). In contrast to the previous suggestion that CSPG4 might be a CROPs-independent receptor (12), it was found that the CROPs region of TcdB is essential for binding to CSPG4/NG2 because TcdB$_{1-1830}$ does not bind to either purified CSPG4/NG2-EC or CSPG4/NG2 on cell surfaces (FIG. 10, Panel B and C), and the isolated CROPs domain alone binds to CSPG4/NG2 and can compete with TcdB for binding to CSPG4/NG2 on cell surfaces (FIG. 10, Panel D). These results explain why CSPG4$^{-/-}$ remains sensitive to TcdB$_{1-1830}$ (FIG. 2, Panel A). The previous conclusion was based on the findings that CSPG4 binds to TcdB$_{1500-2366}$, but not TcdB$_{1851-2366}$ (12). The recent structural studies confirmed that the CROP domain starts at residue 1831 instead of 1851 (27), thus the full CROP domain was used in the present study (residues 1831-2366). It is possible that the first repeat of CROPs is critical for binding to CSPG4/NG2.

Figure 11:
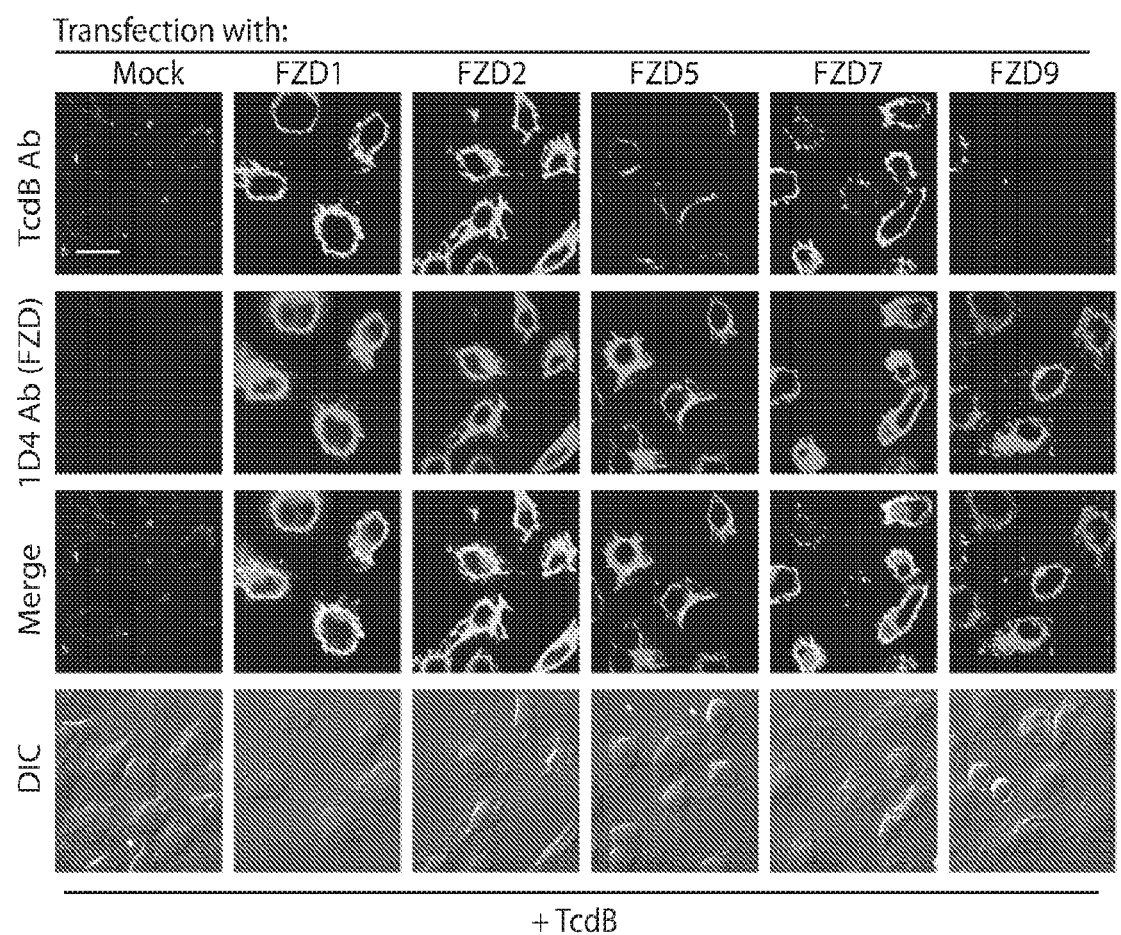
FIG. 11 shows FZD1, 2, and 7 can mediate binding of TcdB to $CSPG4^{-/-}$ cells. $CSPG4^{-/-}$ HeLa cells were transfected with 1D4 tagged FZD1, 2, 5, 7, and 9. Cells were exposed to TcdB (10 nM, 10 minutes). Cells were washed, fixed, permeabilized, and subjected to immunostaining analysis. Scale bar=20 µm.

Transfecting CSPG4$^{-/-}$ cells with full-length FZD2 also increased binding of TcdB (FIG. 2, Panel C). Consistently, transfection of either CSPG4/NG2 or FZD2 restored entry of TcdB into CSPG4$^{-/-}$ cells, resulting in rounding of transfected cells (FIG. 2, Panel D). These results suggest that FZD2 can mediate binding and entry of TcdB into cells independently of CSPG4. The FZD family has ten members (FZD1-10) and HeLa cells express multiple FZDs at low levels (28). CSPG4$^{-/-}$ cells were transfected with FZD1-10 and found that over-expression of FZD1, 2, and 7 each drastically increased binding of TcdB to cells (FIG. 2, Panel E, FIG. 11). FZD1, 2, and 7 are highly homologous to each other and form a subgroup within the FZD family (24). FZD7 was also identified in the screen (Table 3). To confirm the redundancy of FZDs, FZD1 and FZD7 single KO HeLa cells, as well as triple FZD1/2/7 KO HeLa cells, were generated. FZD1$^{-/-}$ and FZD7$^{-/-}$ cells behaved similarly to FZD2$^{-/-}$ cells: each showed a modest reduction in sensitivity to TcdB$_{1-1830}$, but not to TcdB. Strikingly, the FZD1/2/7 triple KO was highly resistant to TcdB$_{1-1830}$ (~300-fold). These cells, which still express CSPG4, also become significantly resistant to TcdB (~10-fold, FIG. 2, Panel F). Transfection of FZD1, 2, or 7 restored TcdB$_{1-1830}$ entry into FZD1/2/7 triple KO cells (FIG. 2, Panel G), demonstrating that FZD1/2/7 are redundant receptors.

Figure 12:
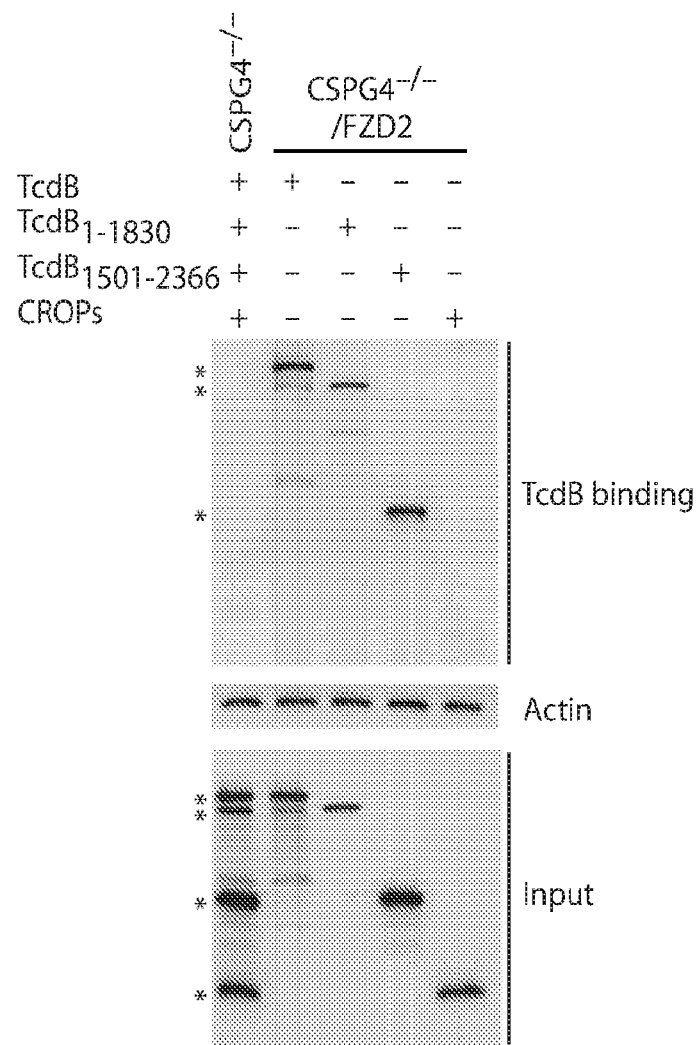
FIG. 12 shows FZD2 can mediate binding of $TcdB_{1501-2366}$, but not the CROPs region to cells. $CSPG4^{-/-}$ Hela cells were transfected with FZD2 and then exposed to TcdB or the indicated TcdB fragments. Cells were washed and cell lysates were subjected to immunoblot analysis. FZD2 mediated binding of TcdB, $TcdB_{1-1830}$, and $TcdB_{1501-2366}$, but not the CROPs region ($TcdB_{1831-2366}$).

In contrast to CSPG4, transfecting FZD2 in CSPG4$^{-/-}$ cells increased binding of both TcdB and TcdB$_{1-1830}$ (FIG. 10, Panel C). Further mapping showed that FZD2 mediated binding of TcdB$_{1501-2366}$, but not the isolated CROPs domain (FIG. 12). FZDs are 7-pass transmembrane proteins with a sole distinct extracellular domain known as cysteine-rich domain (CRD, FIG. 2, Panel H, upper panel), which is also the Wnt binding site (24). Recombinant Fc-tagged FZD2-CRD bound directly to GST-tagged TcdB$_{1501-2366}$, but not to the GST-tagged CROPs domain (FIG. 2, Panel H), demonstrating a direct interaction between FZD2-CRD with the region 1501-1830 of TcdB.

Figure 14A:
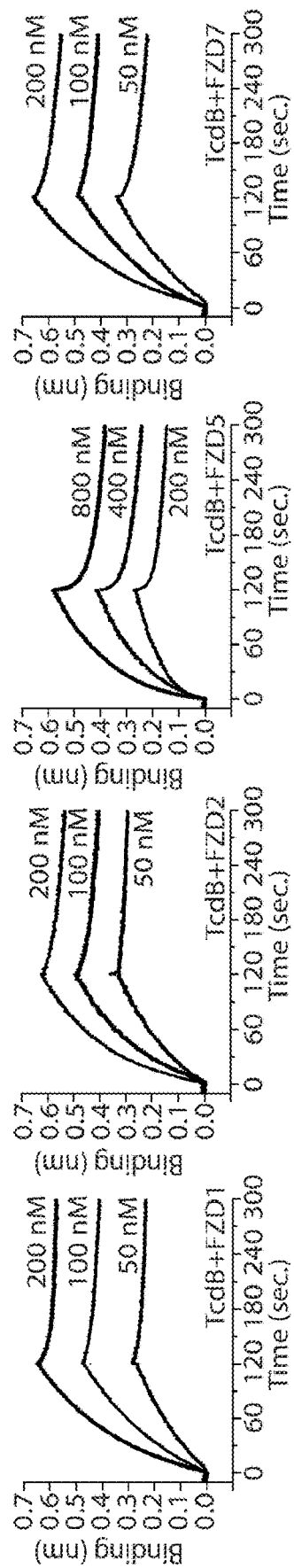
FIG. 14 shows binding affinities between FZD isoforms and TcdB determined using BLI assays. Panel A shows representative binding/dissociation curves for different concentrations of TcdB to Fc-tagged CRDs of FZD1, 2, 5, and 7. Parameters characterizing binding of the Fc-tagged FZD isoforms to TcdB are calculated from these binding curves and are listed in the table. Panel B shows representative binding/dissociation curves for TcdB$_{1-1830 expressed in colonic epithelial cells. Poliovirus receptor-like 3 (PVRL3) was recently suggested as a cellular factor contributing to necrotic cell death process (cytotoxicity) after exposure to high concentrations of TcdB in HeLa cells and in a colorectal cell line Caco-2, but whether PVRL3 is a relevant TcdB receptor in the colonic epithelium remains unknown and its role in directly mediating TcdB entry into cells has not been established.
Figure 14B:
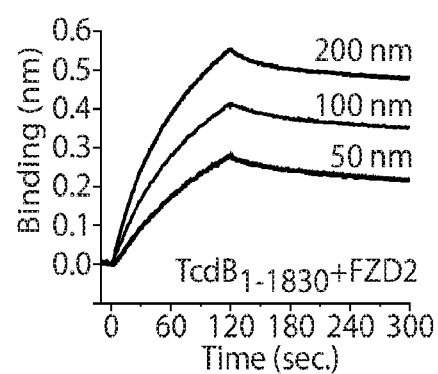

The CRDs of FZD1, 2, and 7 are highly conserved, with ~98% sequence similarity and ~84% identity (FIG. 13) (24). Using bio-layer interferometry (BLI) assay, it was confirmed that the CRDs of FZD1, 2, and 7 all bind to TcdB with nanomolar affinities ($K_D$=32 nM for FZD1, 19 nM for FZD2, and 21 nM for FZD7) (FIG. 2, Panel I, FIG. 14, Panel A). Consistently, an isolated FZD7-CRD, but not FZD8-CRD, when expressed on cell surfaces via a GPI anchor, was able to mediate strong binding of TcdB to cells (FIG. 2, Panel J). Furthermore, FZD2-CRD showed the same binding affinity to TcdB$_{1-1830}$ ($K_D$=17 nM) as to full-length TcdB (FIG. 14, Panel B), confirming that the CROPs region is not involved in binding to FZDs. CRD of other FZDs such as FZDS-CRD also bind to TcdB, but with a weaker affinity ($K_D$=670 nM, FIG. 2, Panel I, FIG. 14, Panel A), suggesting that FZDs other than FZD1/2/7 may still function as additional receptors at high toxin concentrations, which may explain why FZD1/2/7 KO cells are not completely resistant to TcdB$_{1-1830}$. Indeed, FZD6 was also identified in the screen, albeit with only one sgRNA (Table 3).

Figure 3G:
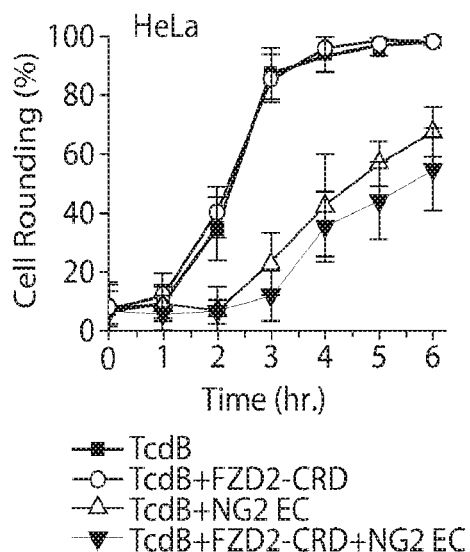
FIG. 3 shows that FZDs can function as TcdB receptors independent of CSPG4. Panel A shows CSPG4/NG2-E immobilized on micro-titer plates, followed by binding of TcdB, washing away unbound TcdB, and the addition of FZD-CRD. FZD2-CRD binds robustly to TcdB that is pre-bound by CSPG4/NG2-EC on the micro-titer plate. FZD2-CRD did not bind to CSPG4/NG2-EC without TcdB, and FZDS-CRD showed no detectable binding to CSPG4/NG2-TcdB complex in this assay. Panels B and C show that excessive amounts of recombinant FZD2-CRD prevented TcdB (300 pM, 3 hrs) entry into CSPG4-/- cells, measured by both cytopathic cell-rounding assays (Panel B) and glucosylation of Rac1 (Panel C). Human IgG1-Fc served as a negative control.
Figure 3H:
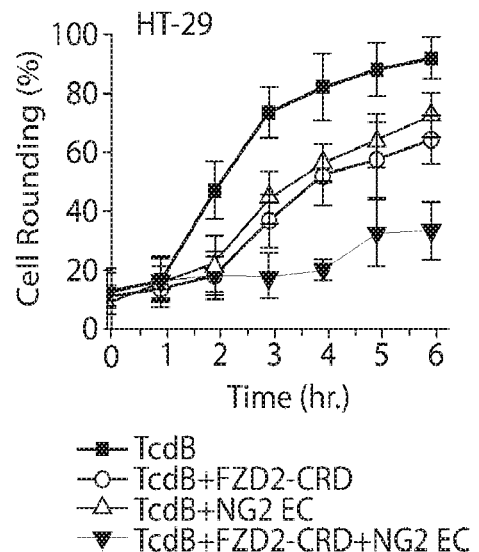
Figure 3I:
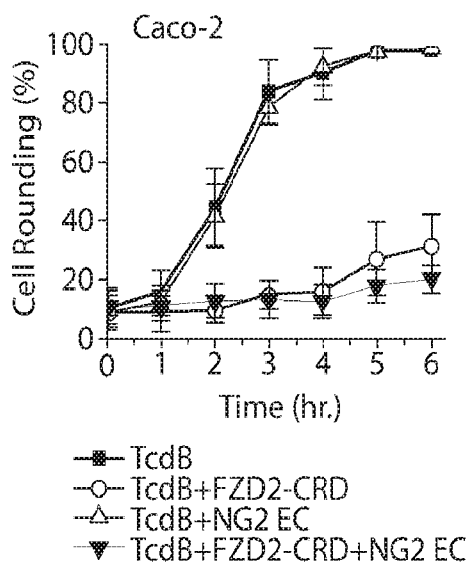
Figure 4A:
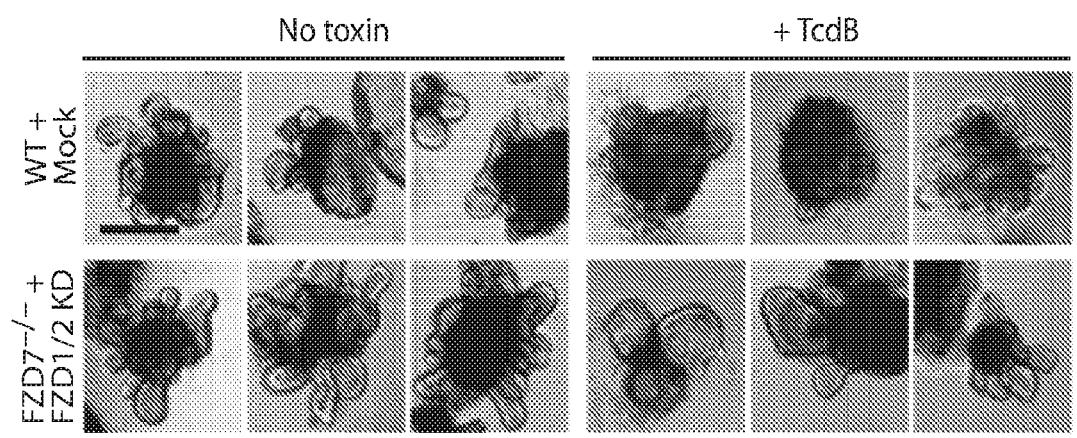
FIG. 4 shows FZDs are functional receptors for TcdB in colonic organoids. Panel A shows differential interference contrast (DIC) images of WT and $FZD7^{-/-}/FZD1/2$ KD organoids, with and without exposure to TcdB (0.5 pM, 3 days), showing that TcdB induced atrophy and death of WT organoids. Scale bar represents 200 μm. Panel B shows quantification of the viability of organoids with MTT assays for WT and $FZD7^{-/-}/FZD1/2$ KD organoids when they were exposed to a titrations of TcdB (*p<0.005, n=4). Panel C shows the $IC_{50}$ of TcdB (defined as the TcdB concentration that results in 50% viability after three days) on WT, $FZD7^{-/-}$ and $FZD7^{-/-}/FZD1/2$ KD organoids (*p<0.005, n=4). Panel D demonstrates that a non-toxic fragment of TcdB (residues 1114-1835) blocked Wnt3a mediated signaling in cells, which was analyzed using TOPFLASH/TK-Renilla dual luciferase reporter assay. Panel E shows that a non-toxic fragment $TcdB_{1114-1835}$ inhibited the growth of WT colon organoids and resulted in death of organoids, which was rescued with the addition of CHIR99021. Normal organoids (indicated by letter "a"), growth inhibited organoids (indicated by letter "b"), and disrupted/dead organoids (*) were marked. Scale bar represents 200 μm. Panel F shows the viabilities of organoids after exposure to 25 nM $TcdB_{1114-1835}$, with and without the presence of 5 μM CHIR99021, as measured with MTT assays and plotted (*p<0.005, n=4).
Figure 4B:
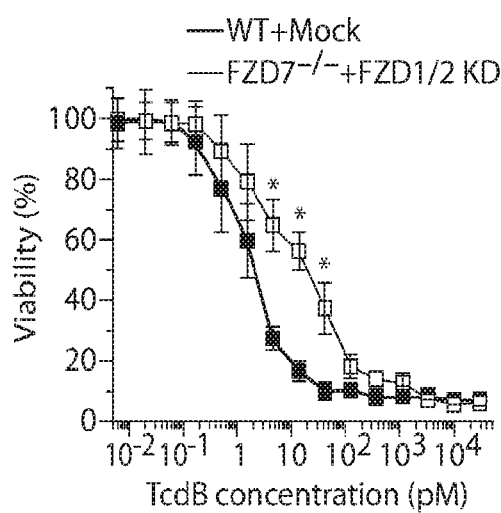
Figure 4C:
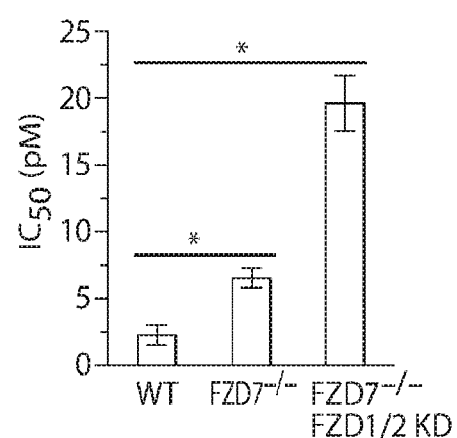
Figure 4D:
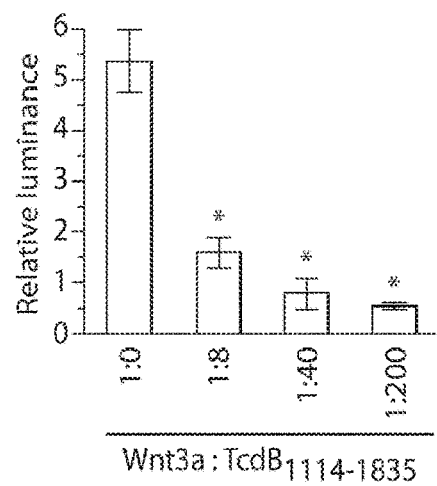
Figure 4E:
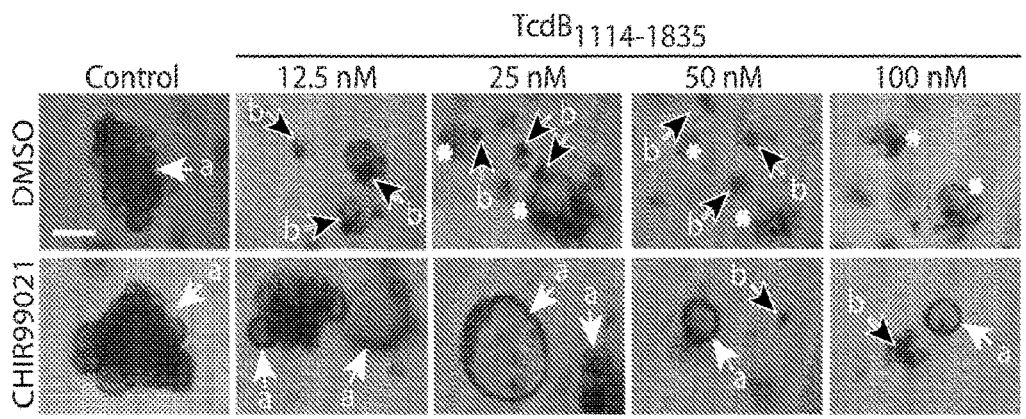
Figure 4F:
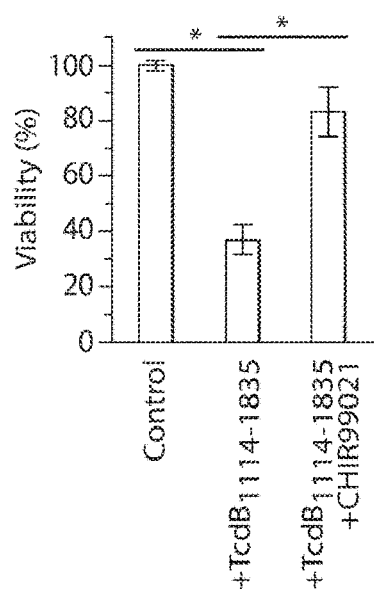
Figure 5A:
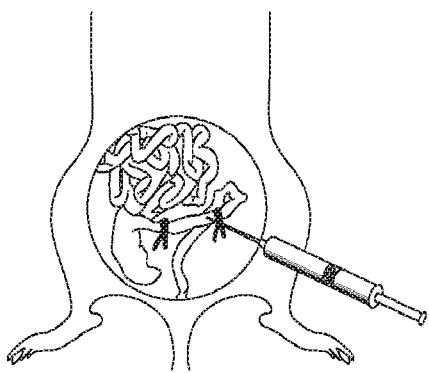
FIG. 5 demonstrate that FZDs are physiologically relevant receptors in the colonic epithelium in vivo. Panel A is a schematic illustration for colon loop ligation assay. In Panel B, TcdB was injected into the ligated colonic segments in WT mice, together with either FZD2-CRD or IgG1-Fc control, and incubated for 2 hours. The colonic segment was then excised, washed with PBS, and subjected to immunohistochemical analysis to detect binding of TcdB to colonic tissues. Location of TcdB is marked by arrows. PBS injection served as a negative control (left panel). TcdB bound to the colon epithelium (middle panel). Co-injection of FZD2-CRD abolished binding of TcdB to the colonic epithelium (right panel). Panel C shows $TcdB_{1-1830}$ injected into the ligated colonic segments in WT and $FZD7^{-/-}$ KO mice. Saline injection served as a negative control. Mice were allowed to recover and survive for 8 hours before the ligated colon segments were excised. Fluid accumulations in the excised colon segments were recorded by measuring weight versus length. Boxes represent mean±SE and the bars represent SD (*p<0.005). Panel D shows experiments carried out as described in Panel C, except that the excised colon segments were fixed, sectioned, and subjected to H&E staining. Scale bar represents 100 µm. Panel E shows histological scores of H&E stained colon sections described in FIG. 5, Panel D (Mean±SE, *p<0.005). Panel F shows experiments were carried out as described in Panel C, except that the excised colon segments were fixed, sectioned, and subjected to immunohistochemical analysis detecting Claudin3. Right panels are enlarged from the areas marked in the left panels to show the detail of tight junctions. Claudin3 is marked by arrows. Scale bar represents 200 µm.
Figure 5B:
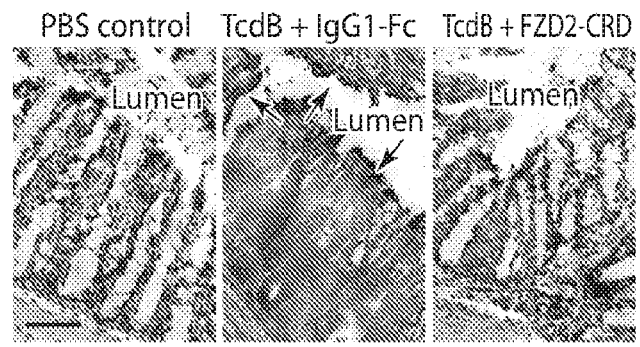
Figure 5C:
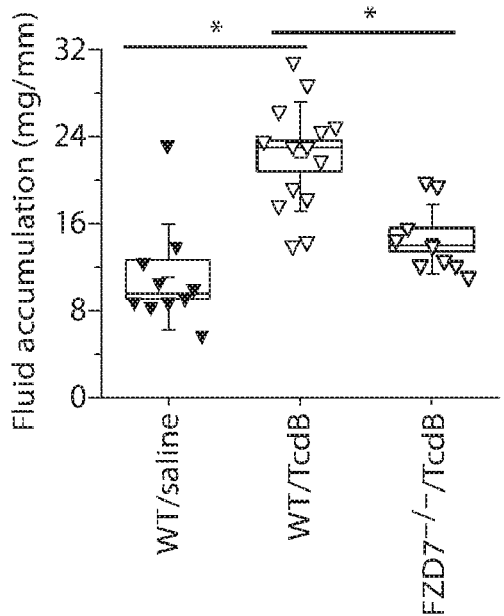
Figure 5D:
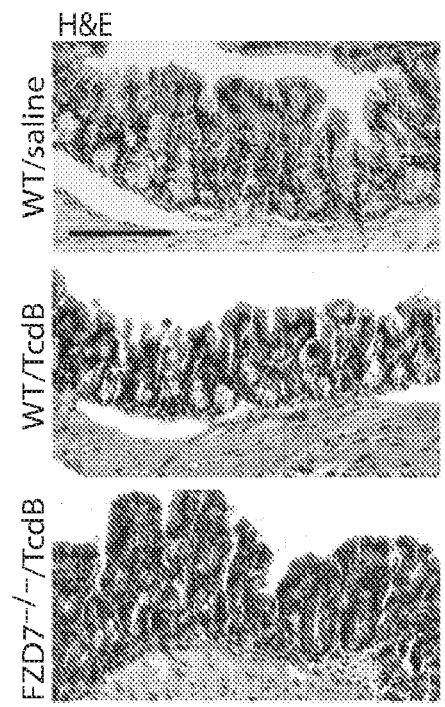
Figure 5E:
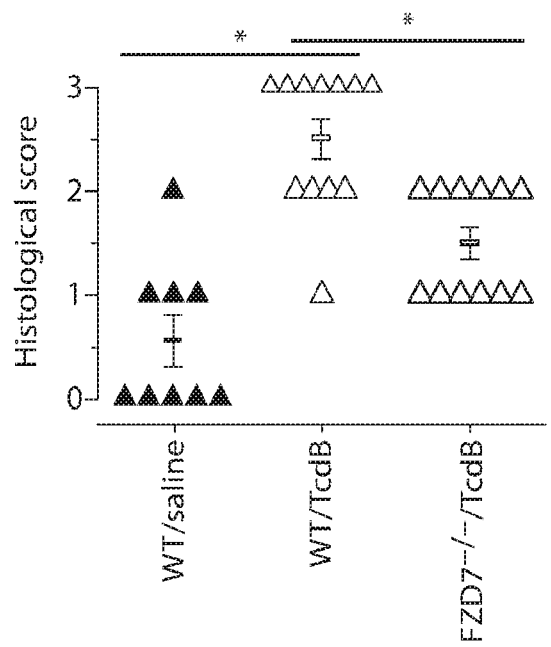
Figure 5F:
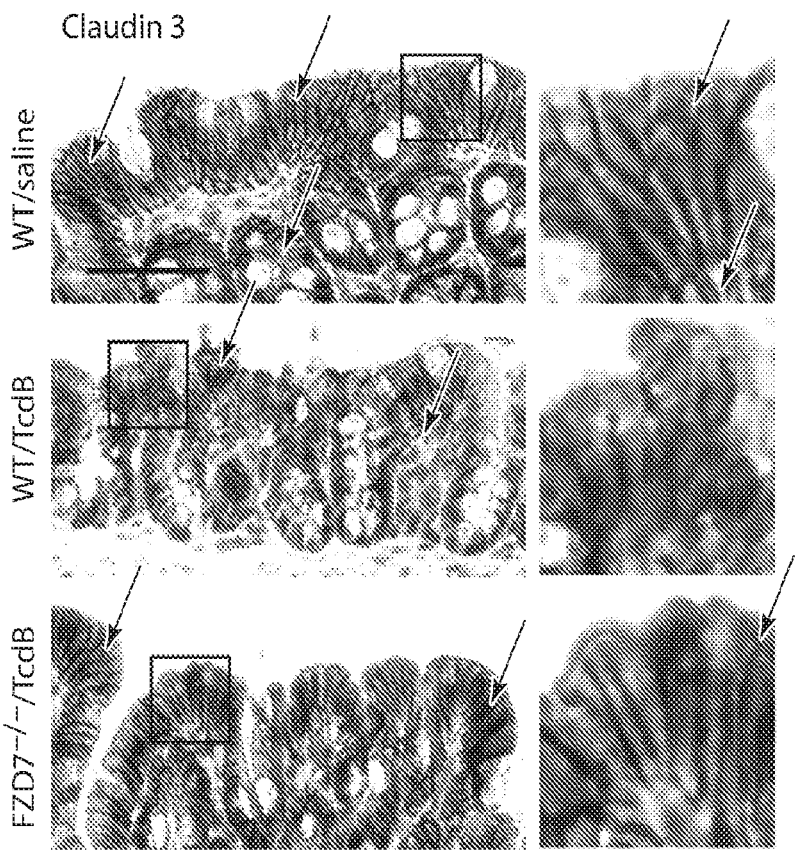
Figure 6A:
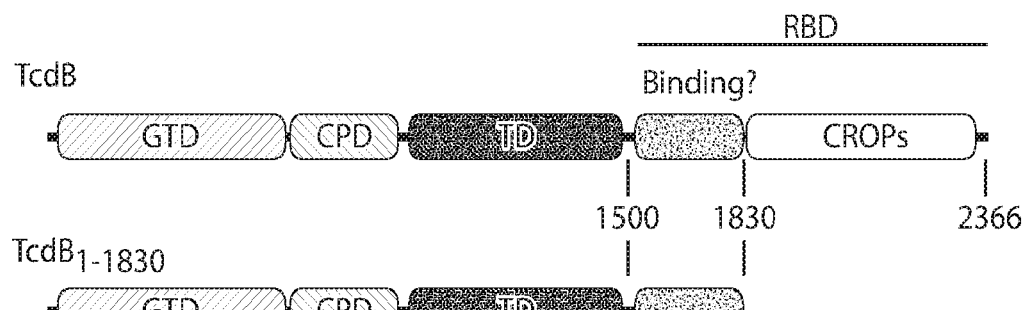
FIG. 6 shows that $TcdB_{1-1830}$ remains a potent toxin that can induce cell-rounding in a variety of cell lines. Panel A presents schematic drawings of TcdB and a truncated TcdB lacking the CROPs region ($TcdB_{1-1830}$). GTD: glucosyltransferase domain; CPD: cysteine protease domain; TD: translocation domain; RBD: receptor binding domain, including a putative receptor binding region and the CROPs region. Panel B shows HeLa cells exposed to titrations of TcdB and $TcdB_{1-1830}$ as indicated for 24 hrs. Cell rounding can be easily observed. HeLa cells were less sensitive to $TcdB_{1-1830}$ than to TcdB, but $TcdB_{1-1830}$ remained a potent toxin that induced cell rounding at picomolar concentrations. Scale bar=50 µm. Panels C-E show CHO (Panel C), HT-29 (Panel D) and Caco-2 (Panel E) cells exposed to titrations of TcdB and $TcdB_{1-1830}$ as indicated for 24 hrs. Scale bars=25 (Panel D) or 50 µm (Panels C, E).
Figure 6B:
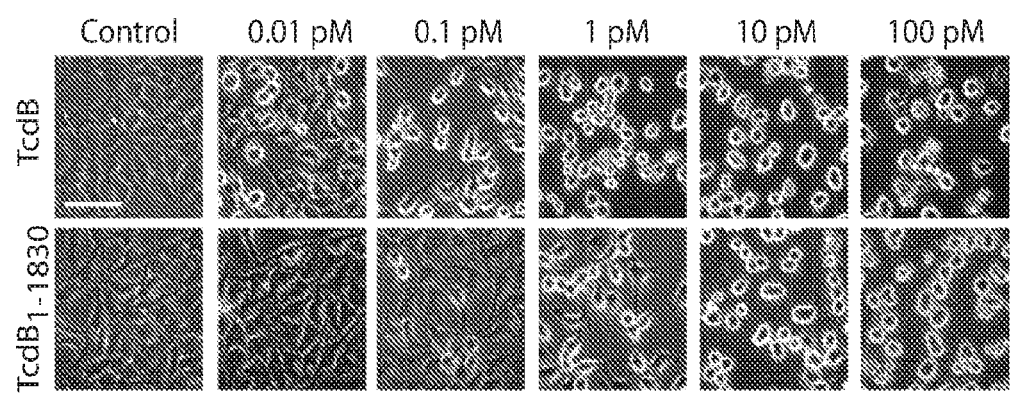
Figure 6C:
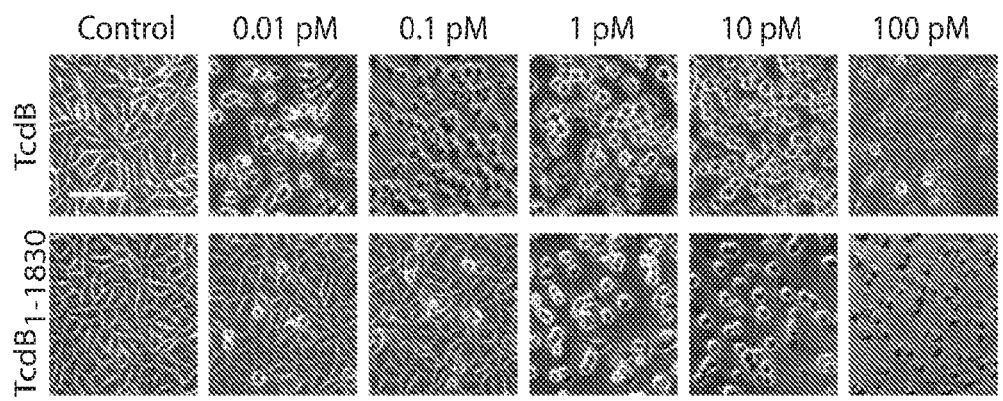
Figure 6D:
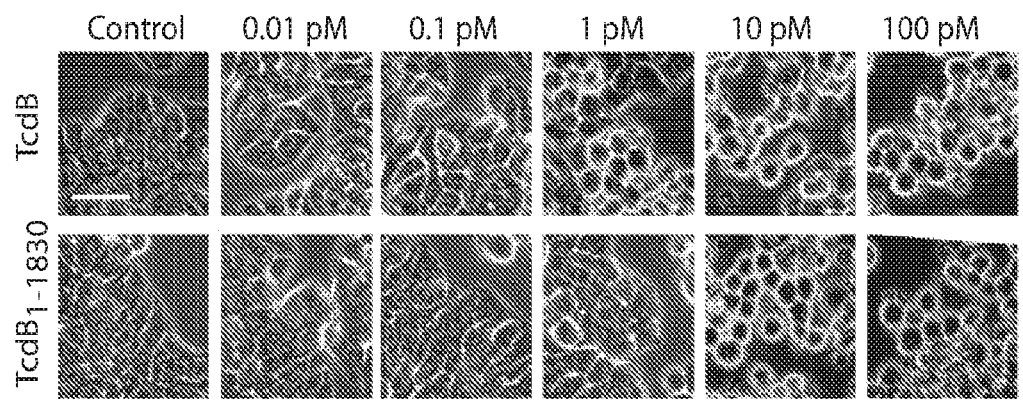
Figure 6E:
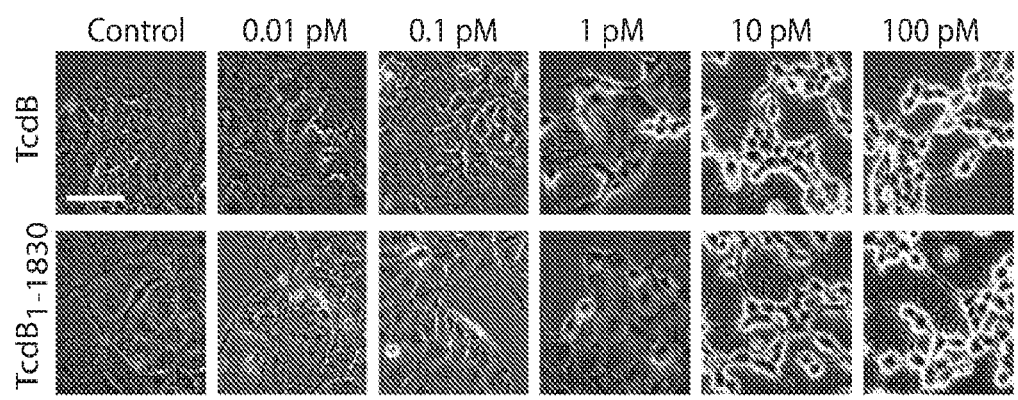
Figure 7A:
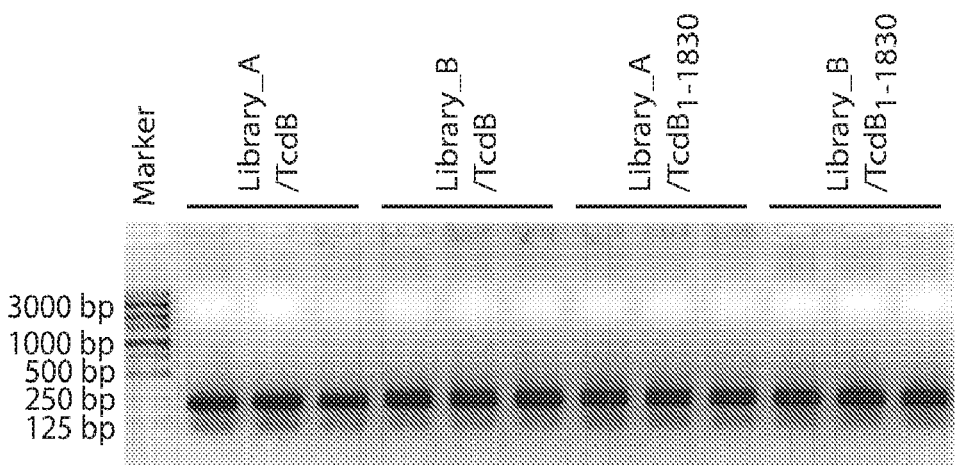
FIG. 7 shows the ranks of sgRNAs in the four libraries of cells after screening with TcdB and $TcdB_{1-1830}$. Panel A shows the sequences of sgRNA were amplified by PCR and subjected to NGS. Panels B-E are lists of top-ranking sgRNAs and their relative abundance among total sgRNA reads.
Figure 7B:
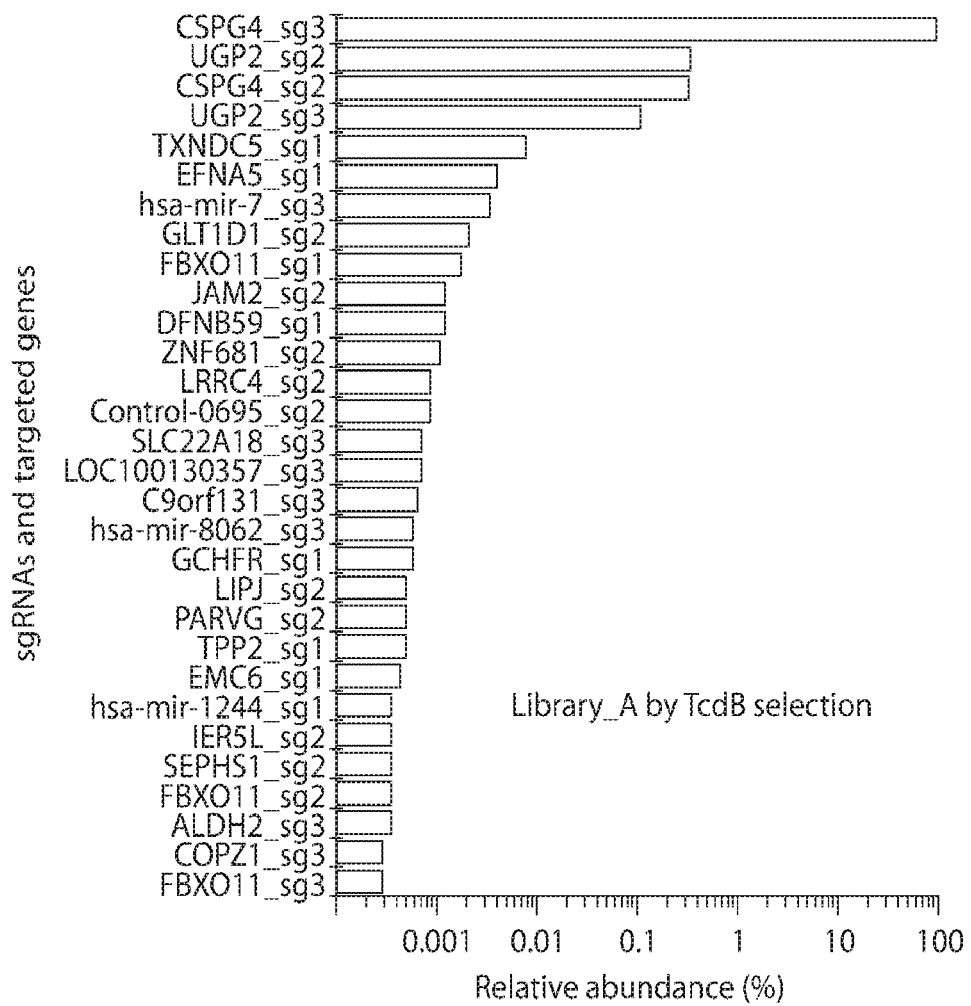
Figure 7C:
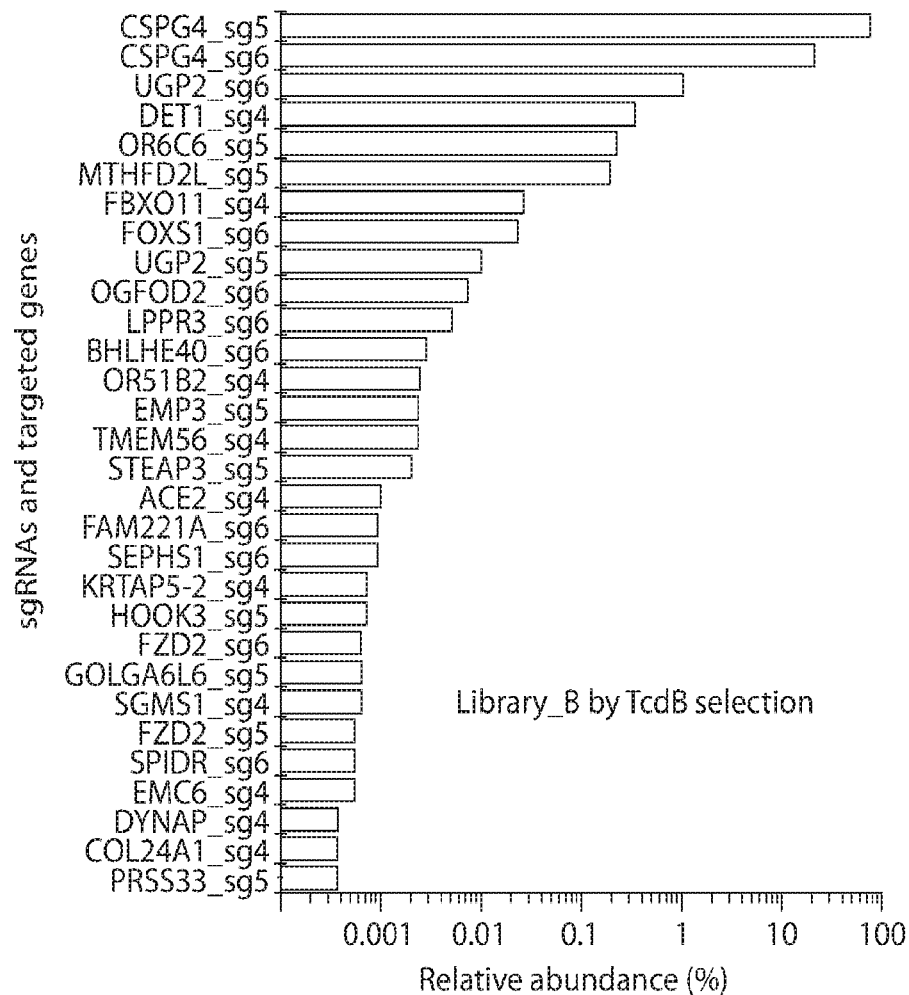
Figure 7D:
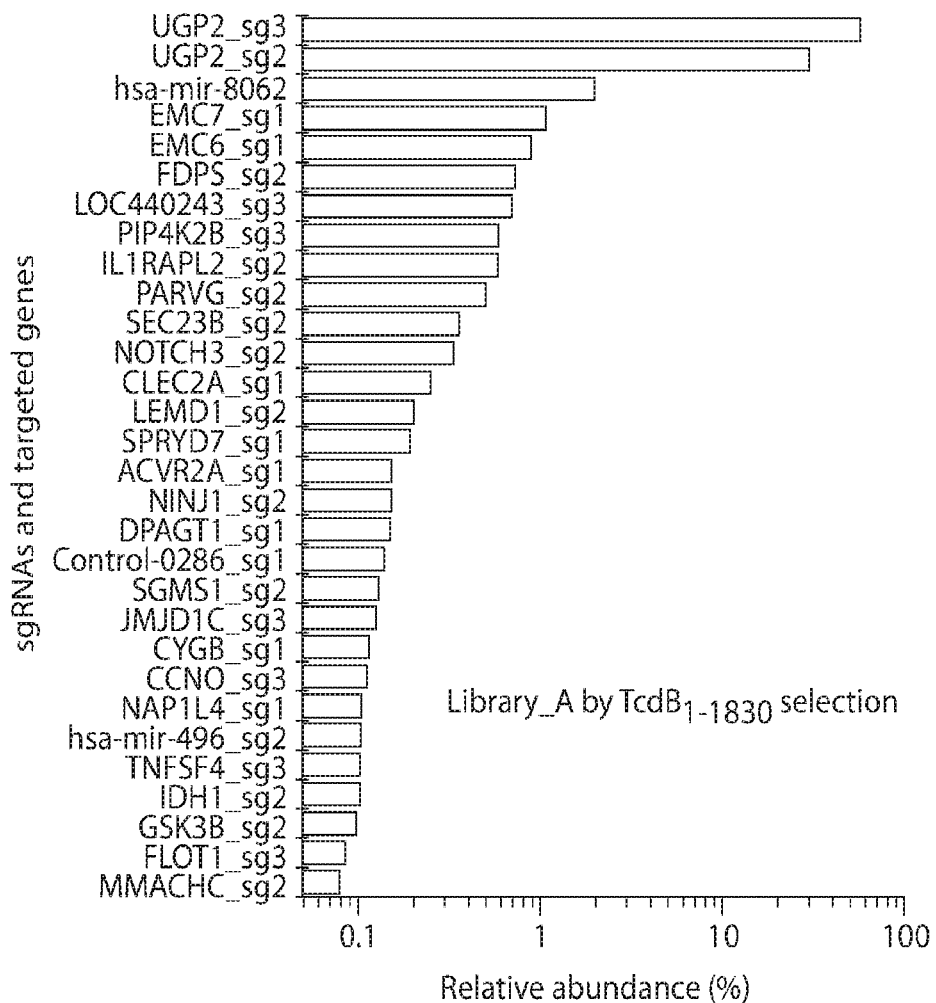
Figure 7E:
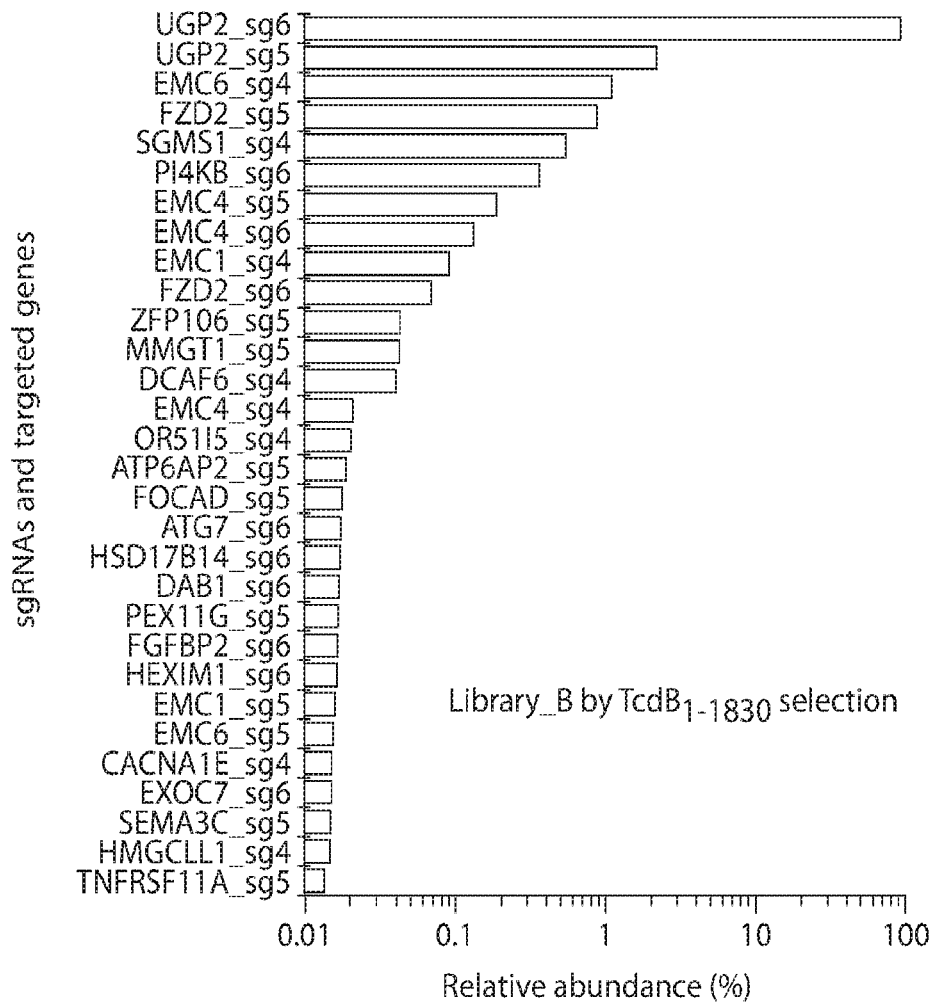

As FZDs and CSPG4 are recognized by distinct regions of TcdB, the present data support a previously proposed two-receptor model for TcdB (19). Consistent with this model, FZD2-CRD binds robustly to TcdB that is pre-bound by immobilized CSPG4/NG2-EC on the micro-titer plate (FIG. 3, Panel A), confirming that TcdB can bind to CSPG4 and FZDs simultaneously. On the other hand, picomolar levels of TcdB can still enter CSPG4$^{-/-}$ cells (FIG. 9, Panel C). This entry is blocked by recombinant FZD2-CRD, as evidenced by lack of cell-rounding and Rac1 glucosylation (FIG. 3, Panels B and C). Thus, endogenous FZDs alone can mediate entry of TcdB independent of CSGP4 at clinically relevant picomolar concentrations.

Figure 15A:
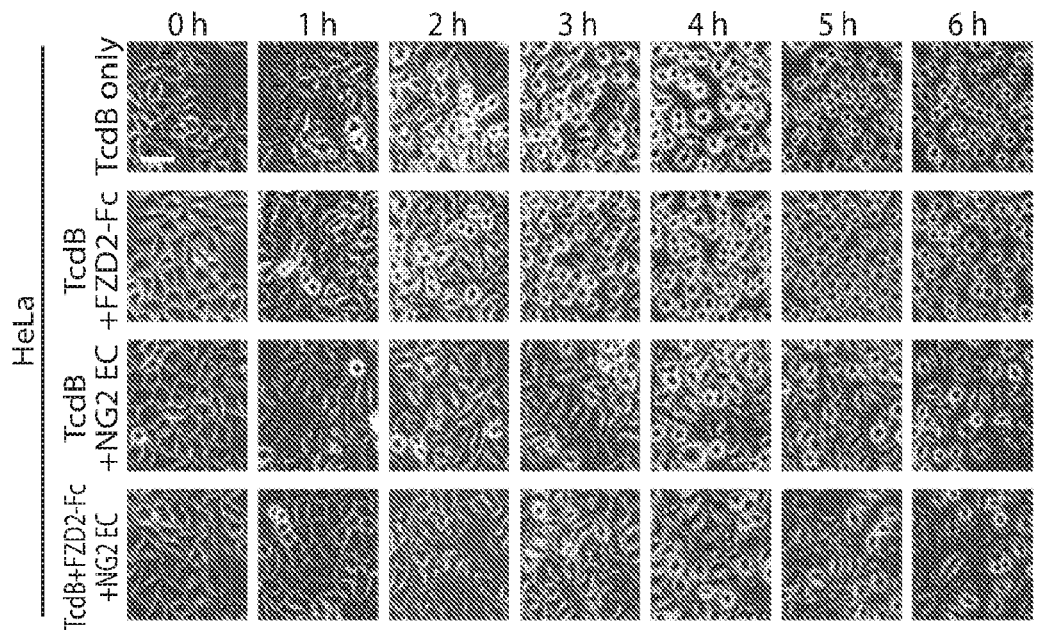
Figure 15B:
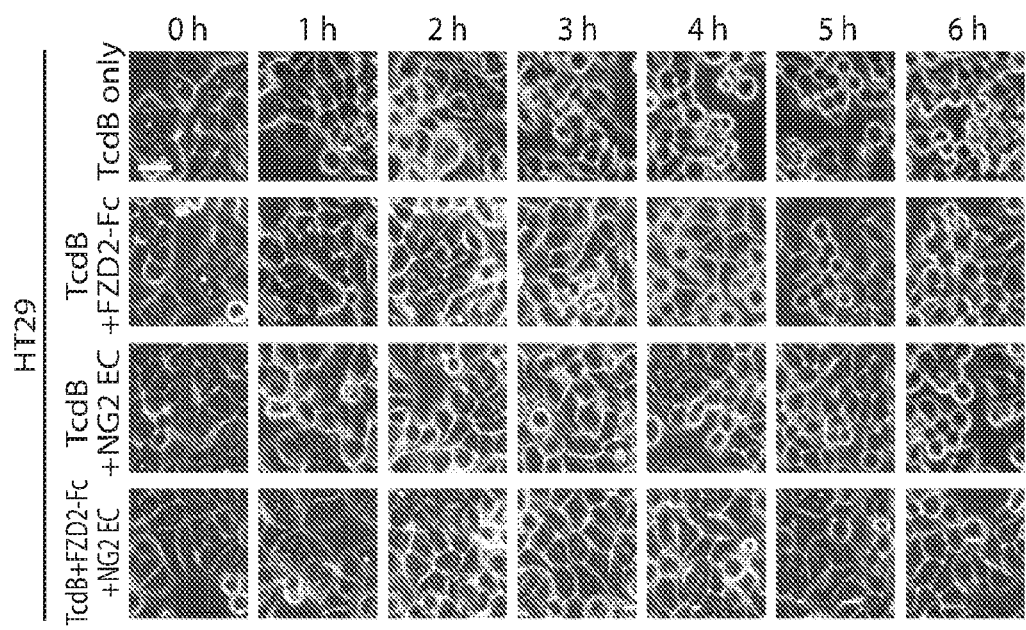
Figure 15C:
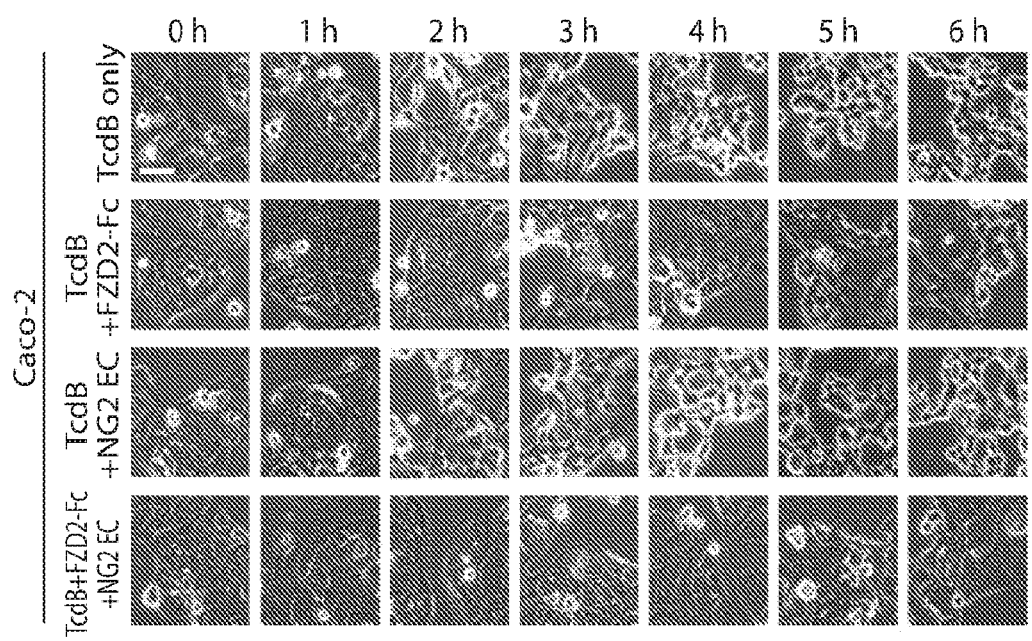

The role of FZDs and CSPG4 in human colorectal cell lines HT-29 and Caco-2, which express multiple FZDs was further examined (29). FZD2-CRD fully protected both cell types from TcdB$_{1-1830}$ (FIG. 3, Panels D and E), confirming the role of FZDs as toxin receptors in these cells. Interestingly, CSPG4 is highly expressed in HeLa cells, which may explain why loss of CSPG4 alone resulted in a drastic decrease of TcdB entry in HeLa cells. CSPG4 expression was much lower in HT-29 and undetectable in Caco-2 cells (FIG. 3, Panel F). Consistent with this expression profile, CSPG4/NG2-EC alone was able to reduce TcdB entry in HeLa cells (FIG. 3, Panel G, FIG. 15, Panel A). FZD2-CRD or CSPG4/NG2-EC demonstrated modest protection of HT-29 cells, and a combination of the two produced a stronger protection, suggesting that FZDs and CSPG4 might contribute to toxin entry equivalently in HT-29 cells (FIG. 3, Panel H, FIG. 15, Panel B). Finally, FZD2-CRD alone protected Caco-2 cells from full-length TcdB, indicating that FZDs are the dominant receptors in Caco-2 cells (FIG. 3, Panel I, FIG. 15, Panel C). Together, these results indicate that relative contributions of FZDs versus CSPG4 for TcdB entry in a particular cell type depend on their relative expression levels.

Figure 16A:
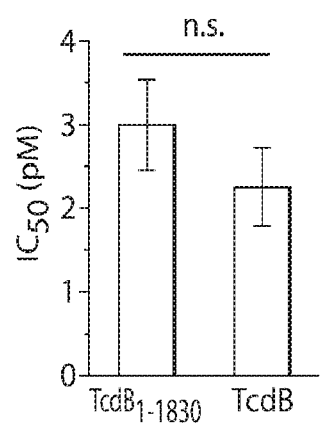
Figure 16B:
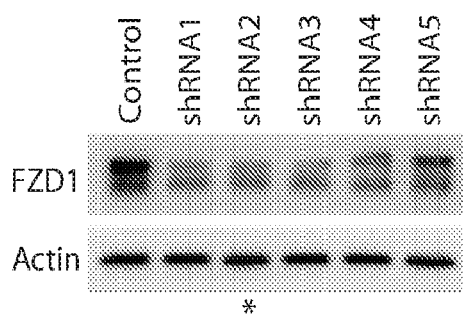
Figure 16C:
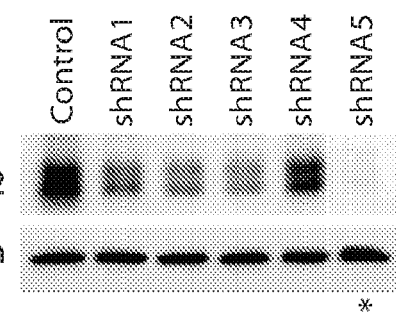

Whether FZDs are the pathologically relevant TcdB receptors in colonic epithelial cells was next examined. First, primary colonic organoid models, which develop into a "mini-gut" when cultured in 3-D matrix and display many important features of normal colonic epithelium, were used (30). Exposure to TcdB caused a concentration-dependent atrophy and death of organoids, which was quantified with a viability assay (FIG. 4, Panels A and B). $TcdB_{1-1830}$ is equally potent as TcdB on colonic organoids (FIG. 16, Panel A), indicating that CROPs-CSPG4 interactions does not contribute significantly to TcdB entry in colonic organoids, which is consistent with the previous report that CSPG4 is not expressed in the colonic epithelium (13). To reduce expression of FZDs, we utilized colonic organoids cultured from FZD7 KO mice, combined with adenovirus-mediated knock-down (KD) of FZD1 and FZD2 (FIG. 16, Panels B and C). It was recently shown that FZD7 is critical for maintaining intestinal organoids, but $FZD7^{-/-}$ organoids can be cultured in the presence of the small molecule inhibitor CHIR99021, which inhibits the GSK3 kinase and activates the Wnt/β-catenin signaling pathway downstream of FZDs (31). It was found that $FZD7^{-/-}$/FZD1/2 KD organoids showed a clear resistance to TcdB compared to WT organoids, with the TcdB concentration that resulted in 50% viability after three days (defined as $IC_{50}$) at 19.7 pM versus 2.2 pM for WT organoids (FIG. 4, Panels B and C). Indeed, even before the adenovirus-mediated KD of FZD1/2, the $FZD7^{-/-}$ organoids already showed ~3-fold increase in $IC_{50}$ compared to WT organoids (FIG. 4, Panel C). Incomplete depletion of FZD1/2 and/or the expression of other FZDs may account for the residual toxin sensitivity of the colon organoids.

Figure 17A:
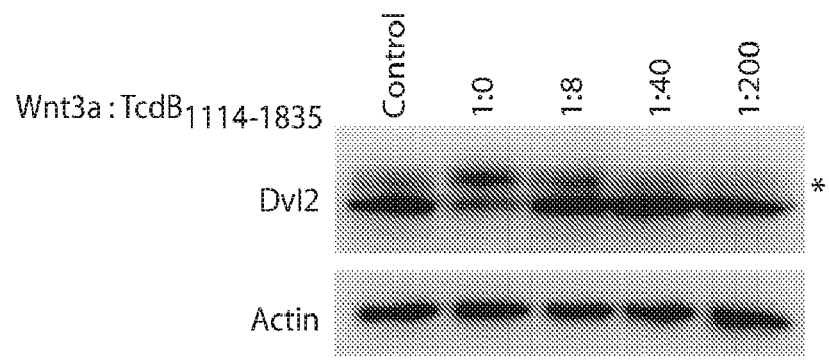
Figure 17B:
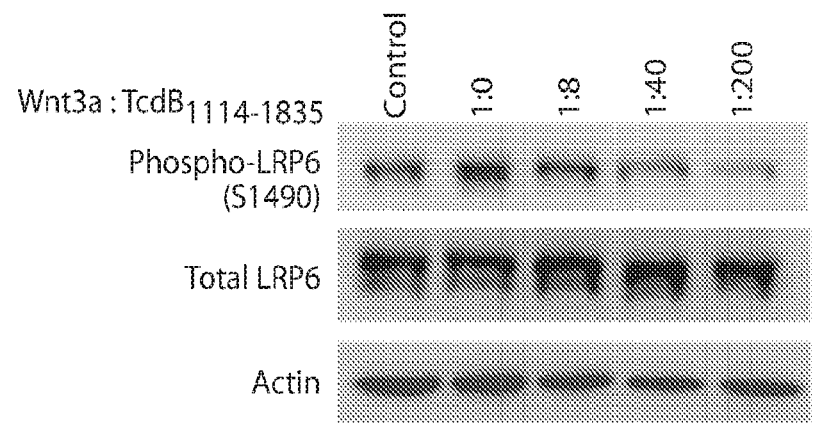
Figure 18A:
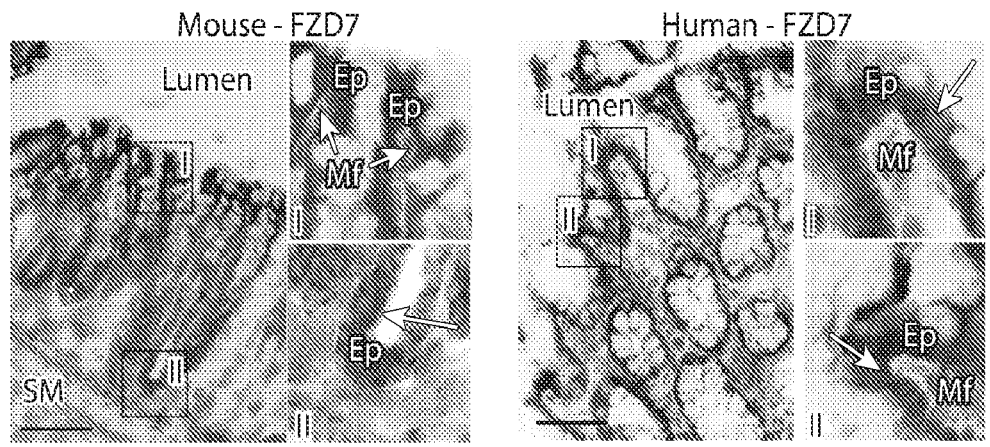
Figure 18B:
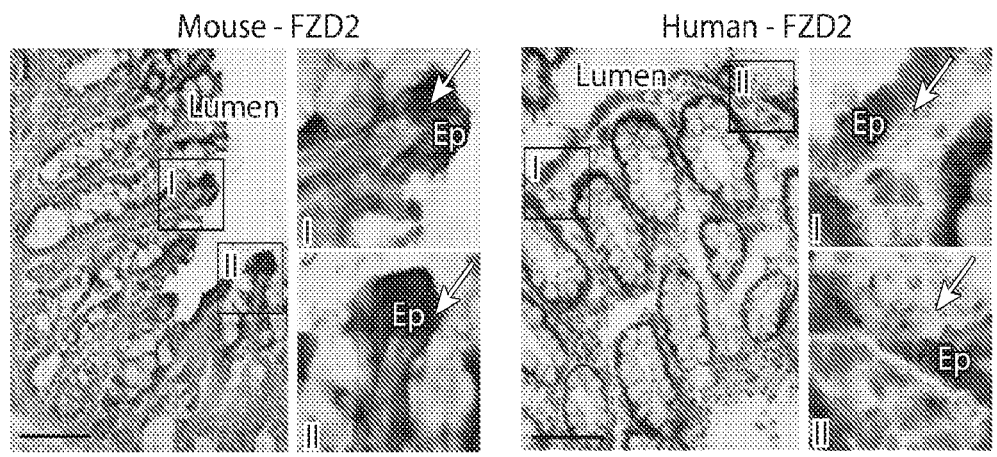
Figure 18C:
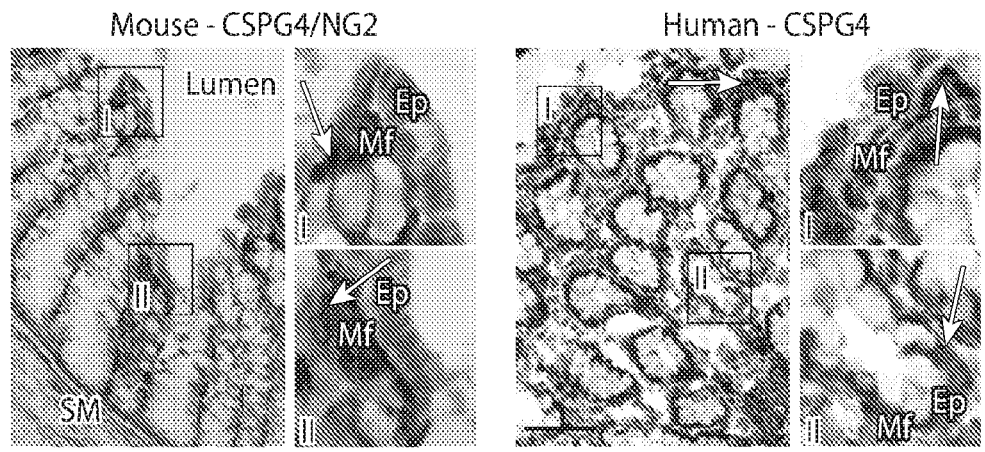
Figure 18D:
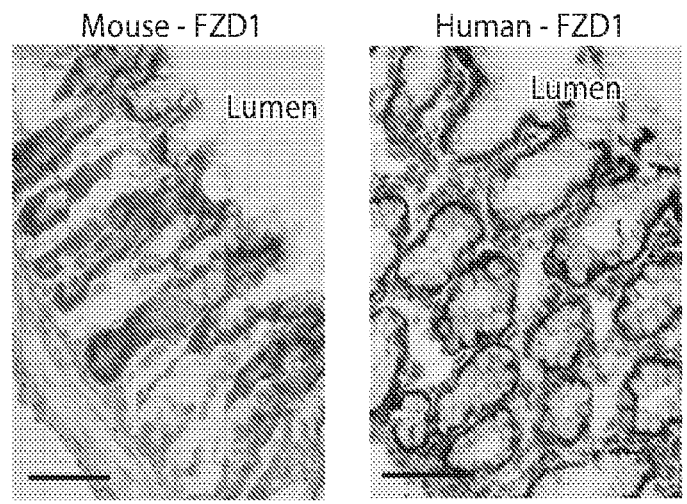

Wnt signaling plays a critical role for growth and survival of intestinal and colonic organoids. Both TcdB and Wnt bind to the FZD-CRD. It was found that a non-toxic fragment of TcdB (residues 1114-1835) potently blocked Wnt3a-mediated signaling in cultured cells, as demonstrated by the TOPFLASH luciferase reporter assay as well as phosphorylation levels of LRP6 and Dvl2, which are the FZD co-receptors and a downstream component, respectively (FIG. 4, Panel D, FIG. 17) (24). $TcdB_{1114-1835}$ strongly inhibited growth of colonic organoids and induced organoid death at nanomolar concentrations (FIG. 4, Panels E and F). The death of colonic organoids was rescued when Wnt/β-catenin signaling was directly activated by CHIR99021 (FIG. 4, Panels E and F). These data revealed a potential new mechanism for TcdB in CDI: binding of TcdB to FZDs may directly disrupt the integrity of the colon epithelium and its self-renewal by inhibiting Wnt signaling, independent and in parallel of glucosylation of small GTPases inside epithelial cells.

The role of FZDs in vivo using mouse models was examined next. Because TcdB is naturally released into the lumen of the colon during CDI, a model was developed by injecting TcdB directly into the lumen of ligated colon segments in mice (FIG. 5, Panel A), which resulted in specific binding and entry of TcdB into colonic epithelial cells. Co-injection of FZD2-CRD largely prevented binding of TcdB to colonic tissues (FIG. 5, Panel B), indicating that FZDs are the dominant receptors in the colonic epithelium. Consistently, it was found that both FZD2 and FZD7 are expressed in epithelial cells in mouse and human colon tissues (FIG. 18, Panels A and B). In contrast, CSPG4 expression is limited to the multi-nucleated sub-epithelial cells termed ISEMFs (intestinal sub-epithelial myofibroblasts) and is absent from epithelial cells in both mice and humans (FIG. 18, Panel C), which is consistent with a previous report (13).

FZD2/7 double KO mice are embryonic lethal (25, 32). As FZD7 appears to be a dominant Wnt receptor in the intestinal epithelium (31), $FZD7^{-/-}$ mice were utilized as a model to determine whether depletion of FZD7 may reduce toxicity of TcdB on the colonic epithelium in vivo. To detect the damage to colonic tissues, $TcdB_{1-1830}$ was injected directly into ligated colon segments of live mice, followed by an 8 hour incubation period. $TcdB_{1-1830}$ was used instead of TcdB, in order to focus on the colonic epithelium and avoid complications from potential TcdB entry into CSPG4-expressing ISEMFs after the colonic epithelium is damaged. Accumulation of fluids was observed in the lumen of the ligated colon segments in the WT mice after exposure to $TcdB_{1-1830}$, but was significantly reduced in that of $FZD7^{-/-}$ mice (FIG. 5, Panel C). Examining colonic tissues by hematoxylin and eosin stain (H&E) showed extensive damage to the epithelium layer in WT mice, but much less so in $FZD7^{-/-}$ mice (FIG. 5, Panels D and E). Finally, immunohistochemical staining for a tight junction marker, Claudin3, showed that tight junctions were disrupted in WT mice, but remained largely intact in $FZD7^{-/-}$ mice (FIG. 5, Panel F). Together, these data established FZD7 as a physiologically relevant receptor for TcdB in the colonic epithelium in vivo.

Figure 19A:
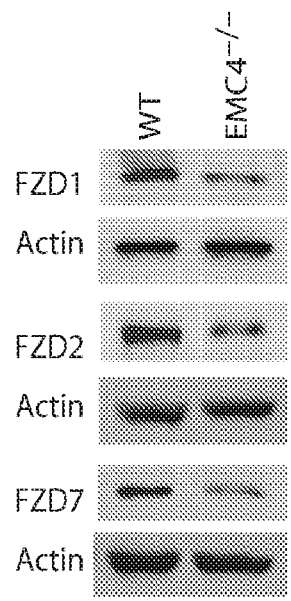
Figure 19B:
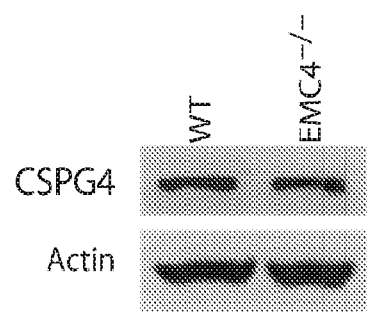

In addition to receptors, the screen also revealed other cellular factors, such as the EMC complex (FIG. 1, Panels B and C). Although its function remains unknown, recent studies suggested that the EMC might be critical for biosynthesis and/or folding of multi-transmembrane proteins (33, 34). Indeed, expression of transiently transfected FZD1, 2, or 7 was drastically reduced in $EMC4^{-/-}$ cells as compared to WT cells (FIG. 19). Thus, reduction of FZDs in EMC-deficient cells is a potential explanation for their increased resistance to $TcdB_{1-1830}$ (FIG. 2, Panel A). Besides EMC, the other protein complex identified includes five subunits of Vacuolar-type $H^+$-ATPase. This is consistent with acidification being required for triggering toxin translocation across the endosomal membranes (5).

Figure 20A:
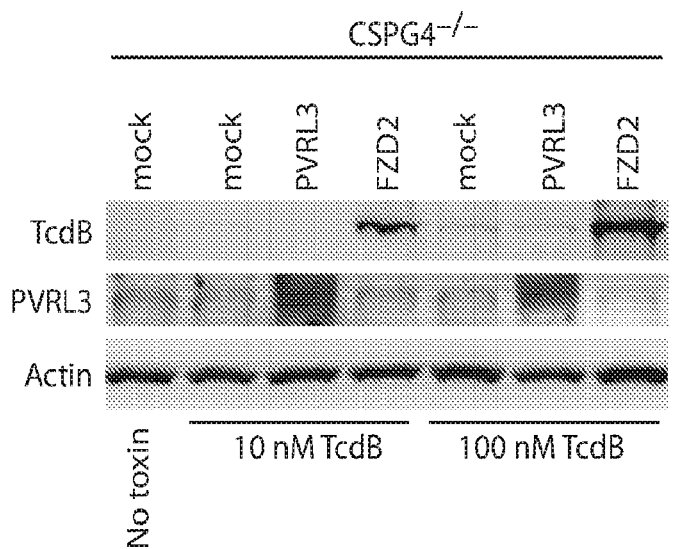
Figure 20B:
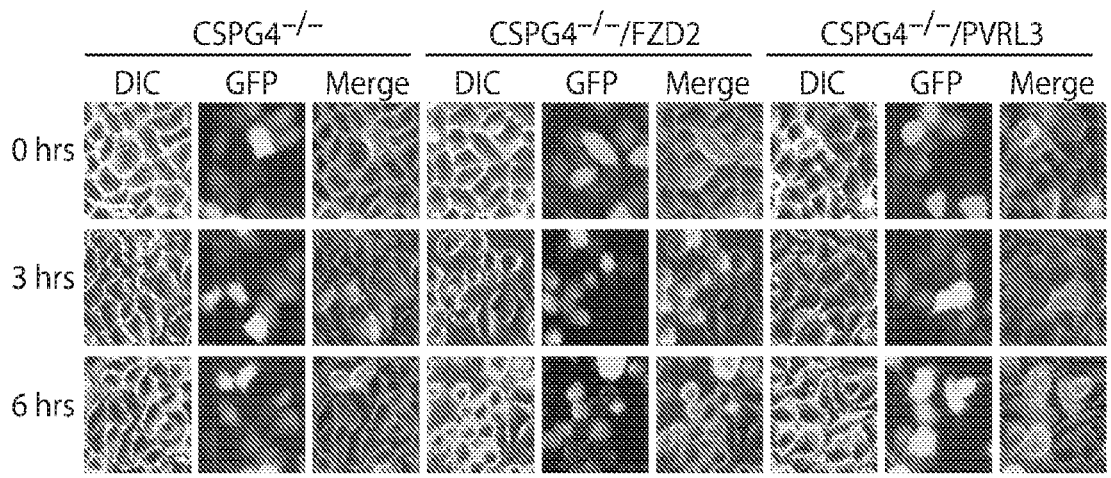
Figure 20C:
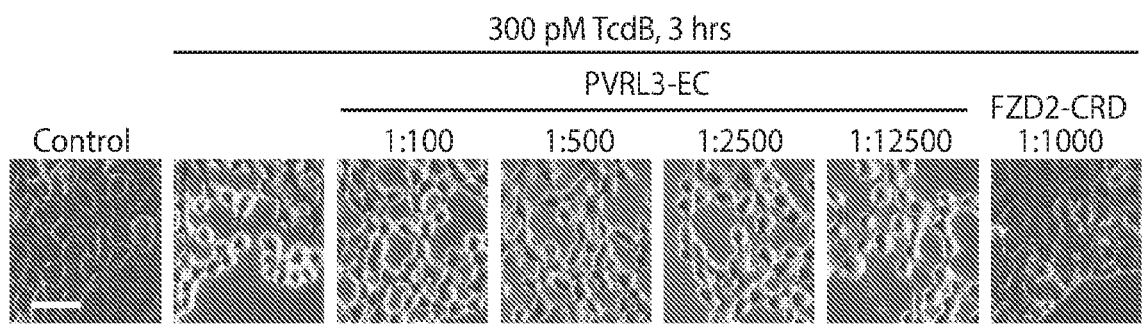

PVRL3 did not appear in the screens, which may not be surprising as PVRL3 was identified in a screen for factors involved in necrotic cell death induced by toxin concentrations several orders of magnitude higher than what was used in the present study to screen for cytopathic cell-rounding and apoptosis (14). The role of PVRL3 was examined experimentally and it was found that ectopically expressed PVRL3 did not mediate binding or entry of TcdB into $CSPG4^{-/-}$ HeLa cells (FIG. 20, Panels A and B). Furthermore, the recombinant ecto-domain of PVRL3 failed to protect Caco-2 cells from TcdB in cytopathic cell-rounding assays, whereas FZD2-CRD offered full protection (FIG. 20, Panel C). Thus, PVRL3 is not likely a relevant receptor for cytopathic cell-rounding effects and apoptosis induced by TcdB.

Figure 21:
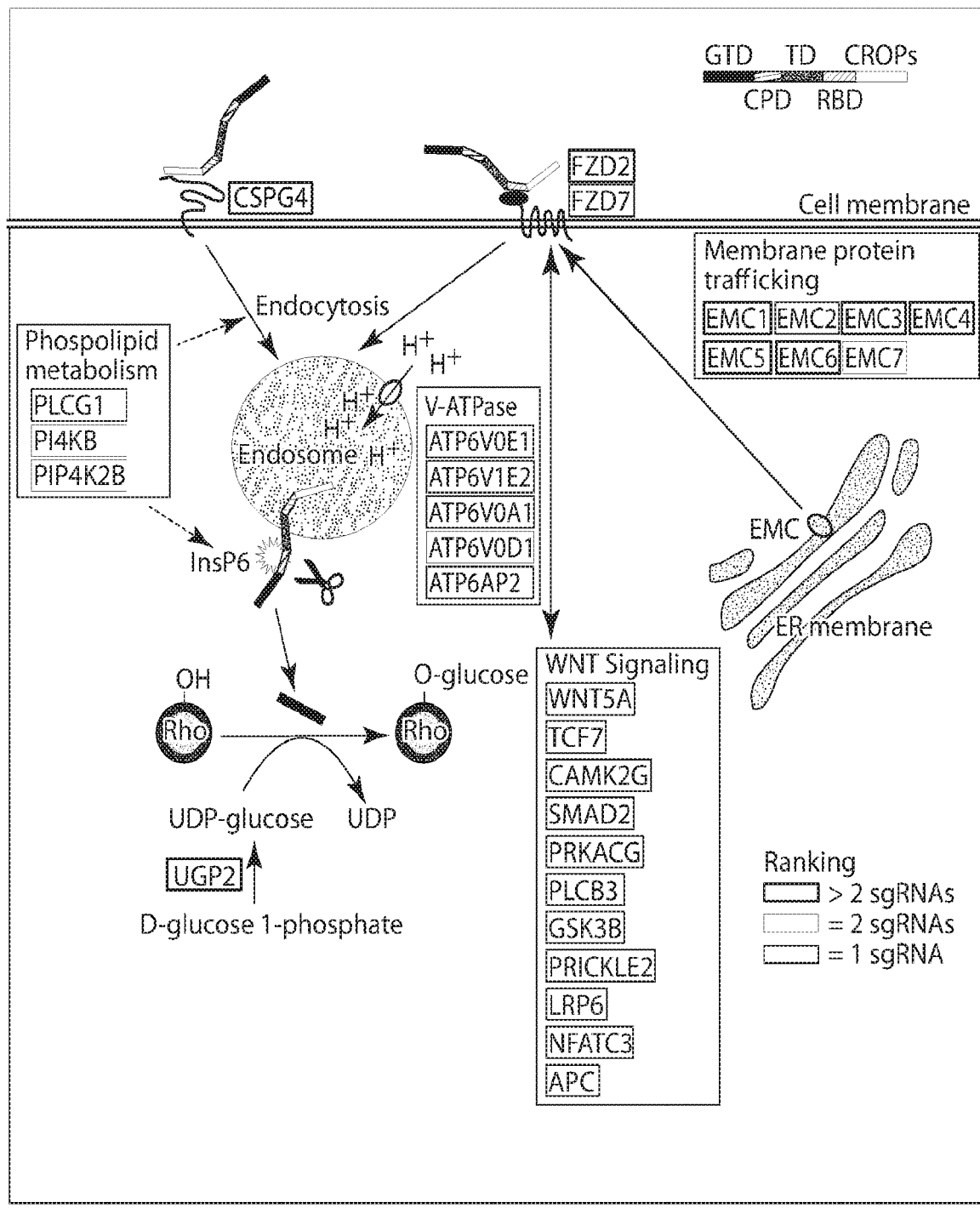

The unbiased genome-wide CRISPR-mediated screens revealed multiple host factors involved in all major steps of toxin actions, from surface receptors (FZDs and CSPG4) to acidification in endosomes (vacuolar-type $H^+$-ATPase), and to toxin enzymatic activities in the cytosol (UGP2). The screens also suggested EMC as a key factor for folding/trafficking of Wnt receptors. Interestingly, the screen identified a total of eleven proteins involved in Wnt signaling pathways, including APC, GSK-3β, Wnt5a, and LRP6 (FIG. 21).

The present study showed FZDs are physiologically relevant receptors for TcdB in colonic epithelial cells, suggesting a potential new mechanism: TcdB may disrupt the colonic epithelium by directly blocking Wnt signaling. The present study also provided novel therapeutic targets for treating CDI. Furthermore, dysregulation of Wnt signaling pathways is associated with many cancers, particularly colorectal cancers. Therefore, the receptor binding domain of TcdB, or its homologs, are believed to be valuable tools and therapeutics for targeting Wnt pathways.

Materials and Methods

Cell Lines, Antibodies, and Constructs.

HeLa (H1), CHO (K1), HT-29, Caco-2, and HEK293T cells were obtained from ATCC. The following mouse monoclonal antibodies were purchased from indicated vendors: Rac1 (23A8, Abcam), non-glucosylated Rac1 (Clone 102, BD Biosciences), 1D4 tag (MA1-722, ThermoFisher Scientific), HA tag (16B12, Covance), β-actin (AC-15, Sigma). Rabbit monoclonal IgG against human CSPG4 (ab139406) and rabbit polyclonal antibodies against FZD1 (ab150553), FZD2 (ab150477), FZD7 (ab51049), PVRL3 (ab63931), and Claudin3 (ab15102) were all purchased from Abcam. Rabbit monoclonal antibodies against Dvl2 (30D2) and LRP6 (C5C7), and a rabbit polyclonal antibody against phosphorylated LRP6 (Ser1490) were all purchased from Cell Signaling. Chicken polyclonal IgY (#754A) against TcdB was purchased from List Biological Labs. A rabbit polyclonal antibody against rodent CSPG4/NG2 and a construct express full-length rat CSPG4/NG2 (in pcDNA vector) were both generated in W. Stallcup's lab. 1D4 tagged full length FZD1-10 constructs in pRK5 vectors were originally generated in J. Nathans's lab (Baltimore, Md.) and were obtained from Addgene. FZD7 and FZD8 CRD-myc-GPI constructs were generously provided by J. Nathan's lab and have been described previously (35). Constructs expressing full-length human IL1RAPL2 and full-length PVRL3 were purchased from Vigene Biosciences. A construct expressing full-length mouse Syt II in pcDNA3.1 vector was described previously (36).

TcdB and Other Recombinant Proteins.

Recombinant TcdB (from *C. difficile* strain VPI 10463) was expressed in *Bacillus megaterium* as previously described (37) and purified as a His6 tagged protein. TcdB$_{1-1830}$ was cloned into the pHis1522 vector (MoBiTec) and expressed in *Bacillus megaterium* following the same procedure used for TcdB. TcdB$_{1831-2366}$, TcdB$_{1501}$-2366, and TcdB$_{1114-1835}$ were cloned into pGEX-6P-1 or pET28a vectors and were purified as GST-tagged or His6-tagged proteins in *E. coli*. CSPG4/NG2 EC (P1 and P2) was expressed in HEK293 cells, purified from medium with DEAE-Sepharose columns, and eluted with a gradient buffer (NaCl from 0.2 to 0.8 M, 50 mM Tris-Cl, pH 8.6) as previously described (38). The following recombinant human proteins were purchased from ACRO Biosystems (IgG1 Fc and FZD2-CRD-Fc), R&D Systems (FZD1-CRD-Fc, FZD5-CRD-Fc, and FZD7-CRD-Fc), and Sino Biologics (PVRL3-EC).

Generating Stable HeLa-Cas9 Cells and Lentivirus sgRNA Libraries.

The human codon-optimized sequence of *S. pyogenes* Cas9 was subcloned from plasmid lentiCas9-Blast (Addgene #52962) into pQCXIH retroviral vector (Clontech), which was used to generate retroviruses to transduce into H1 HeLa cells (ATCC CRL-1958). Mixed stable cells were selected in the presence of 200 μg/ml hygromycin B (Life Technologies). Lentivirus sgRNA libraries were generated following published protocols using the human GeCKO v2 sgRNA library (Addgene #1000000049), which targets 19,052 genes in the human genome (15). The GeCKO v2 library is delivered from Addgene in two half-libraries (library A and library B). Each half library contains three unique sgRNA per gene and two half-libraries were subjected to screens with toxins independently. Cells were transduced with lentivirus-packaged GeCKO v2 sgRNA library at a MOI of 0.2.

Screening CRISPR libraries with TcdB and TcdB$_{1-1830}$. For each half CRISPR library of cells, $4\times10^7$ cells were plated onto two 15-cm culture dishes to ensure sufficient coverage of sgRNAs, with each sgRNA on average being represented about 650 times (i.e., there are on average 650 cells transduced with the same sgRNA). This over-representation rate was calculated from titration plates that were set up in parallel with the library. These cells were exposed to either TcdB or TcdB$_{1-1830}$, respectively, for 48 hours. Cells were then washed three times with PBS to remove loosely attached round-shaped cells. The remaining cells were re-seeded onto new dishes and cultured with normal media without toxins until the cells reach ~70% confluence. Cells were then subjected to the next round of screening with increased concentrations of toxins. Four rounds of screenings were carried out with TcdB (0.05 pM, 0.1 pM, 0.2 pM, and 0.5 pM) and TcdB$_{1-1830}$ (5 pM, 10 pM, 20 pM, and 50 pM), respectively. The remaining cells were harvested and their genomic DNA was extracted using Blood and Cell Culture DNA mini kit (Qiagen). DNA fragments containing the sgRNA sequences were amplified by PCR with primers lentiGP-1_F (AATGGACTATCATATGCTTACCGTAAC-TTGAAAGTATTTCG) (SEQ ID NO: 1) and lentiGP-3_R (ATGAATACTGCCATTTGTCTCAAGATCTAGTTAC-GC) (SEQ ID NO: 2). Next generation sequencing (Illumina MiSeq) was performed by a commercial vendor (Genewiz).

Generating Knockout Cell Lines Via CRISPR.

The following sgRNA sequences were cloned into LentiGuide-Puro vectors (Addgene) to target indicated genes: ccggagacacggagcagtgg (cspg4) (SEQ ID NO: 3), gcgctgc-tgggacatcgcct (emc4) (SEQ ID NO: 4), accttataccacacaacatc (illrap12) (SEQ ID NO: 5), tgcgagcacttcccgcgcca (fzd2) (SEQ ID NO: 6), agcgcatgaccactacactg (sgms1) (SEQ ID NO: 7), acaggcagaaaacggctcct (ugp2) (SEQ ID NO: 8), GTGTAATGACAAGTTCGCCG (FZD1) (SEQ ID NO: 9), and GAGAACGGTAAAGAGCGTCG (FZD7) (SEQ ID NO: 10). HeLa-Cas9 cells were transduced with lentiviruses that express these sgRNAs. Mixed populations of stable cells were selected with 2.5 μg/ml puromycin (Gibco) and 200 μg/ml hygromycin B. Triple knockout cells of FZD1/2/7 were created by sequentially transducing FZD1 and 7 sgRNA lentiviruses into FZD2$^{-/-}$ cells, followed by selection with 50 pM TcdB$_{1-1830}$. The knockout efficiency was demonstrated by NGS (FIG. 8, Tables 1-6).

Cytopathic Assay.

The cytopathic effect (cell-rounding) of TcdB and TcdB$_{1-1830}$ was monitored using well established standard cell-rounding assay as previously described (1). Briefly, cells were exposed to a gradient of TcdB and TcdB$_{1-1830}$ added into media for 24 hours as shown in FIG. 9, Panel A and B. Phase-contrast images of cells were taken using a microscope (Olympus IX51, 10-20× objectives). Three randomly selected images per condition were used for analysis. The numbers of round-shaped and normal shaped cells were counted manually. The ratio of round-shaped cells over the total number of cells is plotted and fitted with the Origin software. Statistical analysis was carried out with one-way ANOVA test. The experiments described here and thereafter have been repeated at least three times.

Blocking TcdB Entry into Cells with Extracellular Domains of CSPG4/NG2 and FZD2.

Recombinant proteins used for cell protection assays were pre-filtered (0.22 µM filter, Millipore). Toxins were pre-incubated with FZD2-CRD-Fc and/or CSPG4-EC (P1) for 30 minutes on ice with a toxin:protein ratio of 1:400 except when noted in the figure legend. The mixtures were added into cell culture medium. The cytopathic effects were analyzed by cell-rounding assay as described above.

Transfection and Detection of TcdB Binding.

Transient transfection of HeLa cells was carried out with POLYJET™ transfection reagent (SignaGen) following the manufacturer's instruction. Binding of TcdB to cells was analyzed by exposing cells to TcdB or truncated TcdB fragments (10 nM, unless noted in the figure) for 10 min at room temperature, followed by washing three times with PBS. Cells were then either fixed and subjected to immunostaining, or harvested and subjected to immunoblot analysis.

GST Pull-Down Assays.

GST pull-down assays were performed using glutathione Sepharose 4B as previously described (36). Briefly, 5 µg of GST-tagged $TcdB_{1831-2366}$ and $TcdB_{1501-2366}$ were immobilized on glutathione beads and were incubated with 10 nM FZD2-CRD-Fc for one hour at 4° C. Beads were then washed, pelleted, and boiled in SDS sample buffers. Samples were subjected to immunoblot analysis.

Biolayer Interferometry Assay.

The binding affinities between TcdB and FZDs were measured by BLI assay with the Blitz system (ForteBio). Briefly, the CRDs-Fc of FZD1, 2, 5, 7 or human IgG1 Fc (20 µg/ml) were immobilized onto DIP AND READ™ Anti-hIgG Fc Capture Biosensors (ForteBio) and balanced with PBS buffer. The biosensors were then exposed to series concentrations of TcdB or $TcdB_{1-1830}$, followed by washing with PBS. Binding affinities ($K_D$) were calculated using the Blitz system software (ForteBio).

Wnt Signaling Assay.

The TOPFLASH/TK-*Renilla* dual luciferase reporter assay was utilized to detect Wnt signaling activities as previously described (39). Briefly, HEK 293T cells in 24-well plates were co-transfected with TOPFLASH (50 ng/well), TK-*Renilla* (internal control, 10 ng/well), and pcDNA3 (200 ng/well). After 24 hours, cells were exposed to Wnt3a (50 ng/ml) and $TcdB_{1114-1835}$ (with molar ratio 1:8, 1:40, and 1:200 to Wnt3a, respectively) in culture medium for 6 hours. Cell lysates were harvested and subjected to the firefly/*renilla* dual luciferase assay, as well as immunoblot analysis detecting phosphorylated Dvl2 and LRP6. Wnt signaling activates expression of TOPFLASH luciferase reporter (firefly luciferase). Co-transfected *renilla* luciferase serves as an internal control.

Micro-Titer Plate Based Binding Assay.

Binding assays were performed on EIA/RIA Half Area 96-well plates (high-binding, Corning Costar) as described previously (38). Briefly, micro-titer plates were coated with 10 µg/ml CSPG4/NG2 proteins in coating buffer (0.1 M $NaHCO_3$, pH 8.3) at 4° C. overnight, and then blocked with 1% bovine serum albumin in PBS for 1 hour. Plates were then incubates with the indicated proteins for 1 hour in PBS.

Wells were washed three times with PBS plus 0.05% tween-20 at room temperature. One-step Turbo TMB (Thermo Scientific) was used as the substrate and absorbance at 450 nm was measured with a microplate reader.

Organoid Culture, Adenoviral Transduction, and TcdB Challenge Assay.

Crypt isolation from WT or $FZD7^{-/-}$ mouse colon was carried out as previously described and organoids were expanded as spheroid cultures using conditioned medium (40). Except for WT organoids used for Wnt-Signaling inhibition assay, 3 µM CHIR99021 was supplemented to the medium (31). Five days after passaging, organoids were re-suspended with Cell Recovery Solution (Fisher Scientific) and mechanically fragmented. Fragments were transduced with adenovirus expressing shRNA for FZD1, shRNA for FZD2, or a control sequence using transduction medium supplemented with Nicotinamide (10 mM, Sigma), Polybrene (8 ug/ml, Sigma) and Y-27632 (10 uM, Sigma), washed and plated in growth factor reduced Matrigel (Corning) (41). Three days following viral transduction, organoids were challenged with series diluted TcdB by directly adding the toxin into the medium. The MTT assay was performed to measure the viability of cells 72-hours post-exposure to the toxin.

Wnt Signaling Inhibition Assay in WT Colon Organoids.

$TcdB_{1114-1835}$ of indicated concentration was directly added into the culture media of WT colon organoids. For rescue experiments, 5 µM CHIR99021 was added to the media. The media were changed every 48 hours with the constant presence of $TcdB_{1114-1835}$ and CHIR99021. Viability of cells was analyzed after six days.

Adenovirus Mediated KD.

All shRNAs were purchased from sigma TRC shRNA designed library. The knockdown efficiency was validated as described in FIG. 16, Panel B, C. ShRNA sequences showed the highest efficiency (shRNA #2 for FZD1 and shRNA #5 for FZD2) were used to generate adenoviruses. Briefly, adenoviruses expressing a control shRNA (CTGGAC-TTCCAGAAGAACA-3') (SEQ ID NO: 11), shRNAs against mouse FZD1 (TGGTGTGCAACGACAAGTTTG) (SEQ ID NO: 12), or FZD2 (CGCTTCTCAGAGGACGGT-TAT) (SEQ ID NO: 13) were constructed using the Block-it U6 adenoviral RNAi system (Life Technologies) followed by viral packaging and multiple rounds of amplification in 293A cells (Life Technologies) per manufacture's protocols.

Assessment of Viability of Colonic Organoids Using MTT Assay.

The viability of the organoids were assessed via the ability to reduce MTT as previously described (42). Briefly, MTT solution was added to the organoid culture to a final concentration of 500 µg/ml. After incubation at 37° C. for 2 hrs, the medium was discarded. For each well (20 µl of Matrigel, in 48-well plate), 60 µl of 2% SDS solution was added to solubilize the Matrigel (1 hour, 37° C.), followed by the addition of 300 µl of DMSO to solubilize reduced MTT (2 hours, 37° C.). The absorbance at 562 nm was measured on a microplate reader. Twenty µl of Matrigel without organoids were used as blank controls. Normal organoids without exposure to toxins were defined as 100% viable.

Immunohistochemistry (IHC) and Histology Analysis.

Colons from adult C57BL/6 mice (10-12 weeks old) were dissected out and subjected to cryosectioning with sections measuring 8-10 µm thickness. Colonic sections were fixed in cold acetone for 5 minutes and then washed three times with PBS. The colonic sections were then blocked with 5% goat serum in PBS for 30 minutes at room temperature, and incubated with primary antibodies (anti-TcdB: 1:600; anti-FZDs: 1:250; rabbit anti-NG2: 1:250) overnight, followed with biotinylated goat anti-chicken or rabbit IgG secondary antibodies (1:200, Vector Lab) for 1 hour at room temperature. They were then incubated with HRP-conjugated streptavidin (1:500, DAKO) for 30 minutes. Immuno-reactivity was visualized as a red color with 3-amino-9-thyl carbazole (DAKO). Cell nuclei were labeled as a blue color with Gill's Hematoxylin (1:3.5, Sigma). Frozen human colon tissue slides were purchased from BioChain Institute Inc., and subjected to IHC analysis. IHC analysis of Claudin3 was carried out using mouse colon tissues fixed in 10% formalin and embedded in paraffin following standard procedures (anti-Claudin3 antibody: 1:100) and detected with 3-Amino-9-Ethylcarbazole (AEC). Histology analysis was carried out with H&E staining of paraffin-embedded sections. Stained sections were coded and scored by blinded observers based on disruption of epithelium, inflammatory cell filtration, and edema, on a scale of 0 to 3 (mild to severe).

Competition Assays in Colon Tissues with Recombinant Proteins.

TcdB (40 nM) was pre-incubated with either human IgG1-Fc or FZD2-Fc (2.4 µM) for 30 minutes on ice. To generate the ex vivo colon segment, mice (C57BL/6, 6-8 weeks) were euthanized and the colon was exposed via laparotomy. A segment in the ascending colon (~2 cm long) was sealed by tying both ends with silk ligatures. The toxin samples (40 µl) were injected through a LV catheter into the sealed colon segment. The injection site was then sealed with a hemostat. The colon was covered with PBS-soaked gauze for 2 hours. The colon segment was then excised and its lumen was washed with PBS injected through a needle for three times, and then subjected to IHC analysis.

Colon Loop Ligation Assay.

All procedures were conducted in accordance with the guidelines of the Boston Children's Hospital IACUC. WT or FZD7$^{-/-}$ Mice (6-8 weeks) were anesthetized following overnight fasting. A midline laparotomy was performed to locate the ascending colon and seal a ~2 cm long loop with silk ligatures. Two µg of TcdB$_{1-1830}$ in 80 µl of normal saline or 80 µl of normal saline were injected through a LV catheter into the sealed colon segment, followed by closing the wounds with stitches. Mice were allowed to recover. After 8 hours, mice were euthanized and the ligated colon segments were excised out. The weight and length of ligated colon were measured and recorded. The colon segments were fixed and subjected to H&E staining and IHC.

Inhibition of Tumor Growth in Xenograft Models.

The effects of blocking Wnt signaling with TcdB$_{1114-1835}$ on tumor growth is assessed in vivo using a well-established mouse xenograft model. Liver cancer cell lines FOCUS and Huh7 cells are used. These cells lines express high levels of FZD2 and inhibiting Wnt signaling by FDZ antibodies can reduce growth of tumors formed by these cancer cells in mouse xenograft models (Gujral T S et al. *Cell*, 2014, 159:844-856). FOCUS or Huh7 cells (2×106 in suspension) are inoculated subcutaneously (s.c.) into athymic nude mice on day 0. Tumor growth is followed every 2 to 3 days. The size of tumor is measured using Vernier calipers. The tumor volumes are calculated using the formula: V=AB2/2 (A, axial diameter; B, rotational diameter). When tumors reach ~200 mm3, mice are divided into two groups (control and treatment). The treatment group are injected with TcdB$_{1114-1835}$ (20 mg/kg in saline) subcutaneously at the tumor site twice a week for up to three weeks. The control group are injected with saline. The tumor size are measured every 2-3 days. Tumor tissues are dissected out and subjected to immunohistochemical analysis to evaluate the markers for Wnt signaling and cellular proliferation and activity (e.g. β-catenin, Ki67).

Significantly reduced tumor sizes are observed in treated group than the control group, demonstrating that blocking Wnt signaling using TcdB$_{1114-1835}$ inhibited tumor growth in vivo.

TABLE 1

CSPG4/NG2

```
WT sequence:
TGAGGGTCCTGGCTTGAGGTCCGTCCTCCTTCTGCAGGGCTCCATGCTGGGGTGGCTCCAGCACCTGC
AGGCTGAGGCCCAGGAGAGTGGGGAAGTAG----------------GGCCCGGAGACACGGAGCA
GTGGAGGGGCCAGGGTGAGGCTGCCACCCTCAGGGACGCTGAAGTTTTGCGCCTCTAGTGGGAT
GGCAGCGGGCAGCACCTCCAGCTCCACAAGGAC  (SEQ ID NO: 30)
```

| Reads | Fraction | Fraction Cum_Sum | Seq | SEQ ID NO: |
|---|---|---|---|---|
| 231864 | 0.301963655 | 0.301963655 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGCCCGGAGACACGGAG----------------------- GGGCCAGGGTGAGGCTGCCACCCTCAGGGACGCTGAAGTT TTGCGCCTCTAGTGGGATGGCAGCGGGCAGCACCTCCAGC TCCACAAGGAC | 31 |
| 117150 | 0.152568066 | 0.454531721 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGCCCGGAGACACGGAGCA--------------- AGTGGAGGGGCCAGGGTGAGGCTGCCACCCTCAGGGACGC TGAAGTTTTGCGCCTCTAGTGGGATGGCAGCGGGCAGCAC CTCCAGCTCCACAAGGAC | 32 |
| 63230 | 0.082346384 | 0.536878104 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGCCCGGAGACACGGAGCA---------------- | 33 |

TABLE 1-continued

CSPG4/NG2

WT sequence:
TGAGGGTCCTGGCTTGAGGTCCGTCCTCCTTCTGCAGGGCTCCATGCTGGGGTGGCTCCAGCACCTGC
AGGCTGAGGCCCAGGAGAGTGGGGAAGTAG----------------GGCCCAGGAGACACGGAGCA
GTGGAGGGGCCAGGGTGAGGCTGCCACCCTCAGGGACGCTGAAGTTTTGCGCCTCTAGTGGGAT
GGCAGCGGGCAGCACCTCCAGCTCCACAAGGAC (SEQ ID NO: 30)

| Reads | Fraction | Fraction Cum_Sum | Seq | SEQ ID NO: |
|---|---|---|---|---|
| | | | GGAGGGGCCAGGGTGAGGCTGCCACCCTCAGGGACGCTGA AGTTTTGCGCCTCTAGTGGGATGGCAGCGGGCAGCACCTC CAGCTCCACAAGGAC | |
| 55508 | 0.072289784 | 0.609167889 | TGAGGGTCCTGGCTTGAGGTCCGTCCTCCTTCTGCAGGGCT CCATGCTGGGGTGGCTCCAGCACCTGCAGGCCGAGGCCCA GGAGAGTGGGGAAGTAGGGCCCGGAGACACGGAGGGCCG GCGATGCAGAGCA---------------- GTGGAGGGGCCAGGGTGAGGCTGCCACCCTCAGGGACGCT GAAGTTTTGCGCCTCTAGTGGGATGGCAGCGGGCAGCACC TCCAGCTCCACAAGGAC | 34 |
| 14095 | 0.018356354 | 0.627524243 | TGAGGGTCCTGGCTTGAGGTCCGTCCTCCTTCTGCAGGGCT CCATGCTGGGGTGGCTCCAGCACCTGCAGGCCGAGGCCCG GGAGAGTGGGGAAGTAG---------------- GGGCCGGCGATGCAGAGCA---------------- GTGGAGGGGCCAGGGTGAAGCTGCCACCCTCAGGGACACT GAAGTTTTGCACCTCCGGTGGGATGACAGTGGGCAGCACC TCCAGCTCCACAAGGAC | 35 |
| 10796 | 0.014059965 | 0.641584207 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGCCCGGAGACACGGAG---------------------- GGGCCAGGGTGAGGCTGCCACCCTCAGGGACGCTGAAGTT TTGCACCTCCGGTGGGATGACAGTGGGCAGCACCTCCAGC TCCACAAGGAC | 36 |
| 10407 (WT) | 0.655137565 | 0.013553358 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGGCCGGCGATGCAGAGCA---------------- GTGGAGGGGCCAGGGTGAAGCTGCCACCCTCAGGGACACT GAAGTTTTGCACCTCCGGTGGGATGACAGTGGGCAGCACC TCCAGCTCCACAAGGAC | 37 |
| 5631 | 0.007333425 | 0.662470991 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGCCCGGAGACACGGAGCA---------------- AGTGGAGGGGCCAGGGTGAGGCTGCCACCCTCAGGGACGC TGAAGTTTTGCACCTCCGGTGGGATGACAGTGGGCAGCAC CTCCAGCTCCACAAGGAC | 38 |
| 5043 | 0.006567655 | 0.669038645 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGCCCGGAGACACGGAG---------------------- GGGCCAGGGTGAGGCTGCCACCCTCAGGGACACTGAAGTT TTGCACCTCCGGTGGGATGACAGTGGGCAGCACCTCCAGC TCCACAAGGAC | 39 |
| 4255 | 0.005541418 | 0.674580063 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGCCCGGAGACACGGAGCA---------------- GTGGAGGGGCCAGGGTGAGGCTGCCACCCTCAGGGACGCT GAAGTTTTGCGCCTCTAGTGGGATGGCAGCGGGCAGCACC TCCAGCTCCACAAGGAC | 40 |
| 4059 | 0.005286161 | 0.679866225 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAGGGCCCGGAGACACGGAGGGCCG GCGATGCAGAGCA---------------- GTGGAGGGGCCAGGGTGAAGCTGCCACCCTCAGGGACACT GAAGTTTTGCACCTCCGGTGGGATGACAGTGGGCAGCACC TCCAGCTCCACAAGGAC | 41 |

TABLE 1-continued

CSPG4/NG2

WT sequence:
TGAGGGTCCTGGCTTGAGGTCCGTCCTCCTTCTGCAGGGCTCCATGCTGGGGTGGCTCCAGCACCTGC
AGGCTGAGGCCCAGGAGAGTGGGGAAGTAG----------------GGCCCGGAGACACGGAGCA
GTGGAGGGGCCAGGGTGAGGCTGCCACCCTCAGGGACGCTGAAGTTTTGCGCCTCTAGTGGGAT
GGCAGCGGGCAGCACCTCCAGCTCCACAAGGAC (SEQ ID NO: 30)

| Reads | Fraction | Fraction Cum_Sum | Seq | SEQ ID NO: |
|---|---|---|---|---|
| 3392 | 0.004417506 | 0.684283731 | TGAGGGTCCTGGCTTGAGGTCCGTCCTCCTTCTGCAGGGCT CCATGCTGGGGTGGCTCCAGCACCTGCAGGCCGAGGCCCG GGAGAGTGGGGAAGTAG---------------- GGGCCGGCGATGCAGAGCA---------------- GTGGAGGGGCCAGGGTGAGGCTGCCACCCTCAGGGACGCT GAAGTTTTGCGCCTCTAGTGGGATGGCAGCGGGCAGCACC TCCAGCTCCACAAGGAC | 42 |
| 3259 | 0.004244296 | 0.688528027 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGGCCGGCGATGCAGAGCA---------------- GTGGAGGGGCCAGGGTGAGGCTGCCACCCTCAGGGACGCT GAAGTTTTGCGCCTCTAGTGGGATGGCAGCGGGCAGCACC TCCAGCTCCACAAGGAC | 43 |
| 3258 | 0.004242994 | 0.692771022 | TGAGGGTCCTGGCTTGAGGTCCGTCCTCCTTCTGCAGGGCT CCATGCTGGGGTGGCTCCAGCACCTGCAGGCCGAGGCCCG GGAGAGTGGGGAAGTAG---------------- GGGCCGGCGATGCAGAGCA---------------- GTGGAGGGGCCAGGGTGAAGCTGCCACCCTCAGGGACACT GAAGTTTTGCGCCTCTAGTGGGATGGCAGCGGGCAGCACC TCCAGCTCCACAAGGAC | 44 |
| 2951 | 0.003843179 | 0.6966142 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGCCCGGAGACACGGAGCA---------------- GGAGGGGCCAGGGTGAGGCTGCCACCCTCAGGGACGCTGA AGTTTTGCACCTCCGGTGGGATGACAGTGGGCAGCACCTC CAGCTCCACAAGGAC | 45 |
| 2765 | 0.003600945 | 0.700215145 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAGGGCCCGGAGACACGGAGGGCCG GCGATGCAGAGCA---------------- GTGGAGGGGCCAGGGTGAGGCTGCCACCCTCAGGGACGCT GAAGTTTTGCACCTCCGGTGGGATGACAGTGGGCAGCACC TCCAGCTCCACAAGGAC | 46 |
| 2671 | 0.003478526 | 0.703693671 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGCCCGGAGACACGGAGCA---------------- AGTGGAGGGGCCAGGGTGAGGCTGCCACCCTCAGGGACAC TGAAGTTTTGCACCTCCGGTGGGATGACAGTGGGCAGCAC CTCCAGCTCCACAAGGAC | 47 |
| 2641 | 0.003439456 | 0.707133127 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGGCCGGCGATGCAGAGCA---------------- GTGGAGGGGCCAGGGTGAAGCTGCCACCCTCAGGGACACT GAAGTTTTGCGCCTCTAGTGGGATGGCAGCGGGCAGCACC TCCAGCTCCACAAGGAC | 48 |
| 2426 | 0.003159455 | 0.710292582 | TGAGGGTCCTGGCTTGAGGTCCGTCCTCCTTCTGCAGGGCT CCATGCTGGGGTGGCTCCAGCACCTGCAGGCCGAGGCCCG GGAGAGTGGGGAAGTAG---------------- GGCCCGGAGACACGGAG---------------------- GGGCCAGGGTGAGGCTGCCACCCTCAGGGACGCTGAAGTT TTGCGCCTCTAGTGGGATGGCAGCGGGCAGCACCTCCAGC TCCACAAGGAC | 49 |
| 2405 | 0.003132106 | 0.713424688 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGCCCGGAGACACGGAG---------------------- GGGCCAGGGTGAAGCTGCCACCCTCAGGGACACTGAAGTT | 50 |

TABLE 1-continued

CSPG4/NG2

WT sequence:
TGAGGGTCCTGGCTTGAGGTCCGTCCTCCTTCTGCAGGGCTCCATGCTGGGGTGGCTCCAGCACCTGC
AGGCTGAGGCCCAGGAGAGTGGGGAAGTAG---------------GGCCCGGAGACACGGGAGCA
GTGGAGGGGCCAGGGTGAGGCTGCCACCCTCAGGGACGCTGAAGTTTTGCGCCTCTAGTGGGAT
GGCAGCGGGCAGCACCTCCAGCTCCACAAGGAC (SEQ ID NO: 30)

| Reads | Fraction | Fraction Cum_Sum | Seq | SEQ ID NO: |
|---|---|---|---|---|
| | | | TTGCACCTCCGGTGGGATGACAGTGGGCAGCACCTCCAGC TCCACAAGGAC | |
| 2171 | 0.00282736 | 0.716252048 | TGAGGGTCCTGGCTTGAGGTCCGTCCTCCTTCTGCAGGGCT CCATGCTGGGGTGGCTCCAGCACCTGCAGGCCGAGGCCCG GGAGAGTGGGGAAGTAG---------------- GGGCCGGCGATGCAGAGCA---------------- GTGGAGGGGCCAGGGTGAAGCTGCCACCCTCAGGGACGCT GAAGTTTTGCGCCTCTAGTGGGATGGCAGCGGGCAGCACC TCCAGCTCCACAAGGAC | 51 |
| 2070 | 0.002695825 | 0.718947873 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGGCCGGCGATGCAGAGCA---------------- GTGGAGGGGCCAGGGTGAAGCTGCCACCCTCAGGGACGCT GAAGTTTTGCGCCTCTAGTGGGATGGCAGCGGGCAGCACC TCCAGCTCCACAAGGAC | 52 |
| 2006 | 0.002612476 | 0.721560349 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGCCCGGAGACACGGAGCA---------------- AGTGGAGGGGCCAGGGTGAAGCTGCCACCCTCAGGGACAC TGAAGTTTTGCACCTCCGGTGGGATGACAGTGGGCAGCAC CTCCAGCTCCACAAGGAC | 53 |
| 1958 | 0.002549964 | 0.724110313 | TGAGGGTCCTGGCTTGAGGTCCATCCTCCTTCTGCAGGGCT CCATGCTGGGGTGGCTCCAGCACCTGCAGGCCGAGGCCCG GGAGAGTGGGGAAGTAG---------------- GGGCCGGCGATGCAGAGCA---------------- GTGGAGGGGCCAGGGTGAAGCTGCCACCCTCAGGGACACT GAAGTTTTGCACCTCCGGTGGGATGACAGTGGGCAGCACC TCCAGCTCCACAAGGAC | 54 |
| 1874 | 0.002440568 | 0.726550881 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------GGCCCGGAGACAC---- -------------------- GGAGGGGCCAGGGTGAGGCTGCCACCCTCAGGGACACTGA AGTTTTGCGCCTCTAGTGGGATGGCAGCGGGCAGCACCTC CAGCTCCACAAGGAC | 55 |
| 1856 | 0.002417126 | 0.728968007 | TGAGGGTCCTGGCTTGAGGTCCGTCCTCCTTCTGCAGGGCT CCATGCTGGGGTGGCTCCAGCACCTGCAGGCTGAGGCCCG GGAGAGTGGGGAAGTAG---------------- GGGCCGGCGATGCAGAGCA---------------- GTGGAGGGGCCAGGGTGAAGCTGCCACCCTCAGGGACACT GAAGTTTTGCACCTCCGGTGGGATGACAGTGGGCAGCACC TCCAGCTCCACAAGGAC | 56 |
| 1529 | 0.001991264 | 0.730959271 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAGGGCCCGGAGACACGGAGGGCCG GCGATGCAGAGCA---------------- GTGGAGGGGCCAGGGTGAGGCTGCCACCCTCAGGGACACT GAAGTTTTGCACCTCCGGTGGGATGACAGTGGGCAGCACC TCCAGCTCCACAAGGAC | 57 |
| 1416 | 0.001844101 | 0.732803371 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGCCCGGAGACACGGAG---------------------- GGGCCAGGGTGAGGCTGCCACCCTCAGGGACGCTGAAGTT TTGCGCCTCTAGTGGGATGACAGTGGGCAGCACCTCCAGC TCCACAAGGAC | 58 |
| 1331 | 0.001733402 | 0.734536774 | TGAGGGTCCTGGCTTGAGGTCCGTCCTCCTTCTGCAGGGCT CCATGCTGGGGTGGCTCCAGCACCTGCAGGCTGAGGCCCA | 59 |

TABLE 1-continued

CSPG4/NG2

WT sequence:
TGAGGGTCCTGGCTTGAGGTCCGTCCTCCTTCTGCAGGGCTCCATGCTGGGGTGGCTCCAGCACCTGC
AGGCTGAGGCCCAGGAGAGTGGGGAAGTAG----------------GGCCCGGAGACACGGAGCA
GTGGAGGGGCCAGGGTGAGGCTGCCACCCTCAGGGACGCTGAAGTTTTGCGCCTCTAGTGGGAT
GGCAGCGGGCAGCACCTCCAGCTCCACAAGGAC (SEQ ID NO: 30)

| Reads | Fraction | Fraction Cum_Sum | Seq | SEQ ID NO: |
|---|---|---|---|---|
| | | | GGAGAGTGGGGAAGTAG----------------<br>GGCCCGGAGACACGGAGCA------------------<br>GGAGGGGCCAGGGTGAGGCTGCCACCCTCAGGGACACTGA<br>AGTTTTGCACCTCCGGTGGGATGACAGTGGGCAGCACCTC<br>CAGCTCCACAAGGAC | |
| 1254 | 0.001633123 | 0.736169897 | TGAGGGTCCTGGCTTGAGGTCCGTCCTCCTTCTGCAGGGCT<br>CCATGCTGGGGTGGCTCCAGCACCTGCAGGCCGAGGCCCG<br>GGAGAGTGGGGAAGTAG----------------<br>GGCCCGGAGACACGGAGCA--------------<br>AGTGGAGGGGCCAGGGTGAGGCTGCCACCCTCAGGGACGC<br>TGAAGTTTTGCGCCTCTAGTGGGATGGCAGCGGGCAGCAC<br>CTCCAGCTCCACAAGGAC | 60 |
| 1240 | 0.00161489 | 0.737784787 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAG----------------<br>GGCCCGGAGACACGGAGGGCCGGCGATGCAGAGCAGTGG<br>AGGGGCCAGGGTGAAGCTGCCACCCTCAGGGACACTGAAG<br>TTTTGCGCCTCTAGTGGGATGGCAGCGGGCAGCACCTCCA<br>GCTCCACAAGGAC | 61 |
| 1146 | 0.001492471 | 0.739277258 | TGAGGGTCCTGGCTTGAGGTCCGTCCTCCTTCTGCAGGGCT<br>CCATGCTGGGGTGGCTCCAGCACCTGCAGGCCGAGGCCCA<br>GGAGAGTGGGGAAGTAG----------------<br>GGCCCGGAGACACGGAG----------------------<br>GGGCCAGGGTGAGGCTGCCACCCTCAGGGACGCTGAAGTT<br>TTGCGCCTCTAGTGGGATGGCAGCGGGCAGCACCTCCAGC<br>TCCACAAGGAC | 62 |
| 1128 | 0.001469029 | 0.740746288 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAG----------------<br>GGCCCGGAGACACGGAG----------------------<br>GGGCCAGGGTGAGGCTGCCACCCTCAGGGACGCTGAAGTT<br>TTGCGCCTCTAGTGGGATGGCAGTGGGCAGCACCTCCAGC<br>TCCACAAGGAC | 63 |
| 1025 | 0.001334889 | 0.742081177 | TGAGGGTCCTGGCTTGAGGTCCATCCTCCTTCTGCAGGGCT<br>CCATGCTGGGGTGGCTCCAGCACCTGCAGGCTGAGGCCCA<br>GGAGAGTGGGGAAGTAG----------------<br>GGCCCGGAGACACGGAG----------------------<br>GGGCCAGGGTGAGGCTGCCACCCTCAGGGACGCTGAAGTT<br>TTGCGCCTCTAGTGGGATGGCAGCGGGCAGCACCTCCAGC<br>TCCACAAGGAC | 64 |
| 997 | 0.001298424 | 0.743379601 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAGGGCCCGGAGACACGGAGGGCCG<br>GCGATGCAGAGCA----------------<br>GTGGAGGGGCCAGGGTGAAGCTGCCACCCTCAGGGACGCT<br>GAAGTTTTGCGCCTCTAGTGGGATGGCAGCGGGCAGCACC<br>TCCAGCTCCACAAGGAC | 65 |
| 937 | 0.001220284 | 0.744599885 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAG----------------<br>GGCCCGGAGACACGGAGCA--------------<br>AGTGGAGGGGCCAGGGTGAGGCTGCCACCCTCAGGGACAC<br>TGAAGTTTTGCGCCTCTAGTGGGATGGCAGCGGGCAGCAC<br>CTCCAGCTCCACAAGGAC | 66 |
| 867 | 0.001129121 | 0.745729006 | TGAGGGTCCTGGCTTGAGGTCCGTCCTCCTTCTGCAGGGCT<br>CCATGCTGGGGTGGCTCCAGCACCTGCAGGCTGAGGCCCG<br>GGAGAGTGGGGAAGTAG----------------<br>GGCCCGGAGACACGGAG----------------------<br>GGGCCAGGGTGAGGCTGCCACCCTCAGGGACGCTGAAGTT<br>TTGCGCCTCTAGTGGGATGGCAGCGGGCAGCACCTCCAGC<br>TCCACAAGGAC | 67 |

TABLE 1-continued

CSPG4/NG2

WT sequence:
TGAGGGTCCTGGCTTGAGGTCCGTCCTCCTTCTGCAGGGCTCCATGCTGGGGTGGCTCCAGCACCTGC
AGGCTGAGGCCCAGGAGAGTGGGGAAGTAG---------------GGCCCAGGAGACACGGAGCA
GTGGAGGGGCCAGGGTGAGGCTGCCACCCTCAGGGACGCTGAAGTTTTGCGCCTCTAGTGGGAT
GGCAGCGGGCAGCACCTCCAGCTCCACAAGGAC (SEQ ID NO: 30)

| Reads | Fraction | Fraction Cum_Sum | Seq | SEQ ID NO: |
|-------|----------|------------------|-----|------------|
| 830 | 0.001080935 | 0.74680994 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAG---------------<br>GGCCCGGAGACACGGAGCA------------------<br>GGAGGGGCCAGGGTGAAGCTGCCACCCTCAGGGACACTGA<br>AGTTTTGCACCTCCGGTGGGATGACAGTGGGCAGCACCTC<br>CAGCTCCACAAGGAC | 68 |
| 781 | 0.00101712 | 0.747827061 | TGAGGGTCCTGGCTTGAGGTCCGTCCTCCTTCTGCAGGGCT<br>CCATGCTGGGGCGGCTCCAGCACCTGCAGGCTGAGGCCCA<br>GGAGAGTGGGGAAGTAG---------------GGCCCGGAGACAC----<br>--------------------<br>GGAGGGGCCAGGGTGAGGCTGCCACCCTCAGGGACGCTGA<br>AGTTTTGCGCCTCTAGTGGGATGGCAGCGGGCAGCACCTC<br>CAGCTCCACAAGGAC | 69 |
| 771 | 0.001004097 | 0.748831158 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAG---------------<br>GGCCCGGAGACACGGA-----------------------<br>GGGGCCAGGGTGAAGCTGCCACCCTCAGGGACGCTGAAGT<br>TTTGCGCCTCTAGTGGGATGGCAGCGGGCAGCACCTCCAG<br>CTCCACAAGGAC | 70 |
| 767 | 0.000998888 | 0.749830046 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAG---------------<br>GGCCCGGAGACACGGAG----------------------<br>GGGCCAGGGTGAGGCTGCCACCCTCAGGGACGCTGAAGTT<br>TTGCGCCTCTAGTGGGATGGCAGCGGGCAGCCCCTCCAGC<br>TCCACAAGGAC | 71 |
| 759 | 0.000988469 | 0.750818515 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAG---------------GGCCCGGAGACAC----<br>--------------------<br>GGAGGGGCCAGGGTGAGGCTGCCACCCTCAGGGACGCTGA<br>AGTTTTGCGCCTCTAGTGGGATGGCGGCGGGCAGCACCTC<br>CAGCTCCACAAGGAC | 72 |
| 752 | 0.000979353 | 0.751797868 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAG---------------<br>GGCCCGGAGACACGGAGCA---------------<br>AGTGGAGGGGCCAGGGTGAGGCTGCCACCCTCAGGGACGC<br>TGAAGTTTTGCGCCTCTAGTGGGATGACAGTGGGCAGCAC<br>CTCCAGCTCCACAAGGAC | 73 |
| 731 | 0.000952004 | 0.752749872 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAG---------------<br>GGCCCGGAGACACGGAG----------------------<br>GGGCCAGGGTGAGGCTGCCACCCTCAGGGACGCTGAAGTT<br>TTGCGCCTCTAGTGGGATGGCAGCGGGCAGCGCCTCCAGC<br>TCCACAAGGAC | 74 |
| 705 | 0.000918143 | 0.753668015 | TGAGGGTCCTGGCTTGAGGTCCGTCCTCCTTCTGCAGGGCT<br><br>CCATGCTGGGGTGGCCCCAGCACCTGCAGGCTGAGGCCCA<br>GGAGAGTGGGGAAGTAG---------------<br>GGCCCGGAGACACGGAG----------------------<br>GGGCCAGGGTGAGGCTGCCACCCTCAGGGACGCTGAAGTT<br>TTGCGCCTCTAGTGGGATGGCAGCGGGCAGCACCTCCAGC<br>TCCACAAGGAC | 75 |
| 687 | 0.000894701 | 0.754562716 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAG---------------GGCCCGGAGACAC---- | 76 |

TABLE 1-continued

CSPG4/NG2

WT sequence:
TGAGGGTCCTGGCTTGAGGTCCGTCCTCCTTCTGCAGGGCTCCATGCTGGGGTGGCTCCAGCACCTGC
AGGCTGAGGCCCAGGAGAGTGGGGAAGTAG---------------GGCCCGGAGACACGGAGCA
GTGGAGGGGCCAGGGTGAGGCTGCCACCCTCAGGGACGCTGAAGTTTTGCGCCTCTAGTGGGAT
GGCAGCGGGCAGCACCTCCAGCTCCACAAGGAC (SEQ ID NO: 30)

| Reads | Fraction | Fraction Cum_Sum | Seq | SEQ ID NO: |
|---|---|---|---|---|
| | | | -------------------<br>GGAGGGGCCAGGGTGAGGCTGCCACCCTCAGGGACGCTGA<br>AGTTTTGCGCCTCTAGTGGGGTGGCAGCGGGCAGCACCTC<br>CAGCTCCACAAGGAC | |
| 685 | 0.000892097 | 0.755454813 | TGAGGGTCCTGGCTTGAGGTCCGTCCTCCTTCTGCAGGGCT<br>CCATGCTGGGGTGGCTCCAGCACCTGCAGGCCGAGGCCCG<br>GGAGAGTGGGGAAGTAG----------------<br>GGCCCGGAGACACGGAGCA------------------<br>GGAGGGGCCAGGGTGAGGCTGCCACCCTCAGGGACGCTGA<br>AGTTTTGCGCCTCTAGTGGGATGGCAGCGGGCAGCACCTC<br>CAGCTCCACAAGGAC | 77 |
| 667 | 0.000868655 | 0.756323468 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAG----------------<br>GGCCCGGAGACACGGAGGG-----------------------<br>GCCAGGGTGAAGCTGCCACCCTCAGGGACACTGAAGTTTT<br>GCGCCTCTAGTGGGATGGCAGCGGGCAGCACCTCCAGCTC<br>CACAAGGAC | 78 |
| 620 | 0.000807445 | 0.757130913 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAG----------------<br>GGCCCGGAGGCACGGAG-----------------------<br>GGGCCAGGGTGAGGCTGCCACCCTCAGGGACGCTGAAGTT<br>TTGCGCCTCTAGTGGGATGGCAGCGGGCAGCACCTCCAGC<br>TCCACAAGGAC | 79 |
| 604 | 0.000786608 | 0.757917521 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGGGTGGGGAAGTAG----------------GGCCCGGAGACAC----<br>-------------------<br>GGAGGGGCCAGGGTGAGGCTGCCACCCTCAGGGACGCTGA<br>AGTTTTGCGCCTCTAGTGGGATGGCAGCGGGCAGCACCTC<br>CAGCTCCACAAGGAC | 80 |
| 604 | 0.000786608 | 0.758704129 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAG----------------GGCCCGGAGA-------<br>CA-----------------<br>CGGAGGGGCCAGGGTGAGGCTGCCACCCTCAGGGACGCTG<br>AAGTTTTGCGCCTCCGGTGGGATGACAGTGGGCAGCACCT<br>CCAGCTCCACAAGGAC | 81 |
| 600 | 0.000781399 | 0.759485527 | TGAGGGTCCTGGCTTGAGGTCCGTCCTCCTCTGCAGGGCT<br>CCATGCTGGGGTGGCTCCAGCACCTGCAGGCTGAGGCCCA<br>GGAGAGTGGGGAAGTAG----------------<br>GGCCCGGAGACACGGAG-----------------------<br>GGGCCAGGGTGAGGCTGCCACCCTCAGGGACGCTGAAGTT<br>TTGCGCCTCTAGTGGGATGGCAGCGGGCAGCACCTCCAGC<br>TCCACAAGGAC | 82 |
| 587 | 0.000764468 | 0.760249995 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAG----------------<br>GGCCCGGAGACACGGAG-----------------------<br>GGGCCAGGGTGGGCTGCCACCCTCAGGGACGCTGAAGTT<br>TTGCGCCTCTAGTGGGATGGCAGCGGGCAGCACCTCCAGC<br>TCCACAAGGAC | 83 |
| 586 | 0.000763166 | 0.761013161 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAG----------------GGCCCGGAGACAC----<br>-------------------<br>GGAGGGGCCAGGGTGAGGCTGCCGCCCTCAGGGACGCTGA<br>AGTTTTGCGCCTCTAGTGGGATGGCAGCGGGCAGCACCTC<br>CAGCTCCACAAGGAC | 84 |

TABLE 1-continued

CSPG4/NG2

WT sequence:
TGAGGGTCCTGGCTTGAGGTCCGTCCTCCTTCTGCAGGGCTCCATGCTGGGGTGGCTCCAGCACCTGC
AGGCTGAGGCCCAGGAGAGTGGGGAAGTAG----------------GGCCCGGAGACACGGAGCA
GTGGAGGGGCCAGGGTGAGGCTGCCACCCTCAGGGACGCTGAAGTTTTGCGCCTCTAGTGGGAT
GGCAGCGGGCAGCACCTCCAGCTCCACAAGGAC (SEQ ID NO: 30)

| Reads | Fraction | Fraction Cum_Sum | Seq | SEQ ID NO: |
|---|---|---|---|---|
| 582 | 0.000757957 | 0.761771118 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGCCCGGAGACACGGAG---------------------- GGGCCAGGGTGAGGCTGCCACCCTCAGGGACGCTGAGGTT TTGCGCCTCTAGTGGGATGGCAGCGGGCAGCACCTCCAGC TCCACAAGGAC | 85 |
| 577 | 0.000751445 | 0.762522563 | TGAGGGTCCTGGCTTGAGGTCCGTCCTCCTTCCGCAGGGCT CCATGCTGGGGTGGCTCCAGCACCTGCAGGCTGAGGCCCA GGAGAGTGGGGAAGTAG---------------- GGCCCGGAGACACGGAG---------------------- GGGCCAGGGTGAGGCTGCCACCCTCAGGGACGCTGAAGTT TTGCGCCTCTAGTGGGATGGCAGCGGGCAGCACCTCCAGC TCCACAAGGAC | 86 |
| 575 | 0.00074884 | 0.763271403 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAGGTAG---------------GGCCCGGAGACAC---- -------------------- GGAGGGGCCAGGGTGAGGCTGCCACCCTCAGGGACGCTGA AGTTTTGCGCCTCTAGTGGGATGGCAGCGGGCAGCACCTC CAGCTCCACAAGGAC | 87 |
| 572 | 0.000744933 | 0.764016336 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGCCCGGAGACACGGAGCA--------------- AGTGGAGGGGCCAGGGTGAAGCTGCCACCCTCAGGGACAC TGAAGTTTTGCGCCTCTAGTGGGATGGCAGCGGGCAGCAC CTCCAGCTCCACAAGGAC | 88 |
| 567 | 0.000738422 | 0.764754758 | TGAGGGTCCTGGCTTGAGGTCCGTCCTCCTTCTGCAGGGCT CCATGCTGGGGTGGCTCCAGCACCCGCAGGCTGAGGCCCA GGAGAGTGGGGAAGTAG---------------- GGCCCGGAGACACGGAG---------------------- GGGCCAGGGTGAGGCTGCCACCCTCAGGGACGCTGAAGTT TTGCGCCTCTAGTGGGATGGCAGCGGGCAGCACCTCCAGC TCCACAAGGAC | 89 |
| 564 | 0.000734515 | 0.765489273 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGCCCGGAGACACGGAG---------------------- GGGCCAGGGTGAGGCCGCCACCCTCAGGGACGCTGAAGTT TTGCGCCTCTAGTGGGATGGCAGCGGGCAGCACCTCCAGC TCCACAAGGAC | 90 |
| 563 | 0.000733212 | 0.766222485 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------GGCCCGGAGACGC---- -------------------- GGAGGGGCCAGGGTGAGGCTGCCACCCTCAGGGACGCTGA AGTTTTGCGCCTCTAGTGGGATGGCAGCGGGCAGCACCTC CAGCTCCACAAGGAC | 91 |
| 561 | 0.000730608 | 0.766953093 | TGAGGGTCCTGGCTTGAGGTCCGTCCTCCTTCTGCAGGGCT CCATGCTGGGGTGGCTCCAGCACCTGCAGGCTGAGGCCCA GGGGAGTGGGGAAGTAG---------------GGCCCGGAGACAC---- -------------------- GGAGGGGCCAGGGTGAGGCTGCCACCCTCAGGGACGCTGA AGTTTTGCGCCTCTAGTGGGATGGCAGCGGGCAGCACCTC CAGCTCCACAAGGAC | 92 |
| 561 | 0.000730608 | 0.7676837 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGCCCGGAGACACGGAG---------------------- GGGCCAGGGTGAGGCTGCCACCCTCAGGGGCGCTGAAGTT | 93 |

TABLE 1-continued

CSPG4/NG2

WT sequence:
TGAGGGTCCTGGCTTGAGGTCCGTCCTCCTTCTGCAGGGCTCCATGCTGGGGTGGCTCCAGCACCTGC
AGGCTGAGGCCCAGGAGAGTGGGGAAGTAG---------------GGCCCGGAGACACGGAGCA
GTGGAGGGGCCAGGGTGAGGCTGCCACCCTCAGGGACGCTGAAGTTTTGCGCCTCTAGTGGGAT
GGCAGCGGGCAGCACCTCCAGCTCCACAAGGAC (SEQ ID NO: 30)

| Reads | Fraction | Fraction Cum_Sum | Seq | SEQ ID NO: |
|---|---|---|---|---|
| | | | TTGCGCCTCTAGTGGGATGGCAGCGGGCAGCACCTCCAGC<br>TCCACAAGGAC | |
| 560 | 0.000729305 | 0.768413006 | TGAGGGTCCTGGCTTGAGGTCCGTCCCCCTTCTGCAGGGCT<br>CCATGCTGGGGTGGCTCCAGCACCTGCAGGCTGAGGCCCA<br>GGAGAGTGGGGAAGTAG---------------<br>GGCCCGGAGACACGGAG----------------------<br>GGGCCAGGGTGAGGCTGCCACCCTCAGGGACGCTGAAGTT<br>TTGCGCCTCTAGTGGGATGGCAGCGGGCAGCACCTCCAGC<br>TCCACAAGGAC | 94 |
| 549 | 0.00071498 | 0.769127985 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAG---------------GGCCCGGAGACAC----<br>--------------------<br>GGAGGGGCCAGGGTGAGGCTGCCACCCTCAGGGACGCTGA<br>AGTTTTGCGCCTCTAGTGGGATGGCAGCGGGCAGCACCTC<br>CAGCTCCACAAGGAC | 95 |
| 547 | 0.000712375 | 0.76984036 | TGAGGGTCCTGGCTTGAGGTCCGTCCTCCTTCTGCAGGGCT<br>CCATGCTGGGGTGGCTCCAGCACCTGCAGGCCGAGGCCCA<br>GGAGAGTGGGGAAGTAG---------------<br>GGCCCGGAGACACGGAGCA---------------<br>AGTGGAGGGGCCAGGGTGAGGCTGCCACCCTCAGGGACGC<br>TGAAGTTTTGCGCCTCTAGTGGGATGGCAGCGGGCAGCAC<br>CTCCAGCTCCACAAGGAC | 96 |
| 546 | 0.000711073 | 0.770551433 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAG---------------<br>GGCCCGGAGACACGGAG----------------------<br>GGGCCAGGGTGAGGCTGCCACCCTCAGGGACGCTGAAGTT<br>TTGCGCCCCTAGTGGGATGGCAGCGGGCAGCACCTCCAGC<br>TCCACAAGGAC | 97 |
| 540 | 0.000703259 | 0.771254692 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAG---------------<br>GGCCCGGAGACACGGAG----------------------<br>GGGCCAGGGTGAGGCTGCCACCCTCAGGGACGCTGAAGTT<br>TTGCGCCTCTAGTGGGATGGCAGCGGGCGGCACCTCCAGC<br>TCCACAAGGAC | 98 |
| 537 | 0.000699352 | 0.771954043 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAG---------------<br>GGCCCGGAGACACGGAGCA---------------<br>AGTGGAGGGGCCAGGGTGAAGCTGCCACCCTCAGGGACGC<br>TGAAGTTTTGCGCCTCTAGTGGGATGGCAGCGGGCAGCAC<br>CTCCAGCTCCACAAGGAC | 99 |
| 530 | 0.000690235 | 0.772644279 | TGAGGGTCCTGGCTTGAGGCCCGTCCTCCTTCTGCAGGGCT<br>CCATGCTGGGGTGGCTCCAGCACCTGCAGGCTGAGGCCCA<br>GGAGAGTGGGGAAGTAG---------------<br>GGCCCGGAGACACGGAG----------------------<br>GGGCCAGGGTGAGGCTGCCACCCTCAGGGACGCTGAAGTT<br>TTGCGCCTCTAGTGGGATGGCAGCGGGCAGCACCTCCAGC<br>TCCACAAGGAC | 100 |
| 524 | 0.000682421 | 0.7733267 | TGAGGGTCCTGGCTTGAGGTCCGTCCTCCTTCTGCAGGGCT<br>CCATGCTGGGGTGGCTCCAGCACCTGCAGGCTGAGGCCCG<br>GGAGAGTGGGGAAGTAG---------------<br>GGGCCGGCGATGCAGAGCA---------------<br>GTGGAGGGGCCAGGGTGAGGCTGCCACCCTCAGGGACGCT<br>GAAGTTTTGCGCCTCTAGTGGGATGGCAGCGGGCAGCACC<br>TCCAGCTCCACAAGGAC | 101 |
| 522 | 0.000679817 | 0.774006517 | TGAGGGTCCTGGCTTGAGGTCCATCCTCCTTCTGCAGGGCT<br>CCATGCTGGGGTGGCTCCAGCACCTGCAGGCTGAGGCCCA | 102 |

TABLE 1-continued

CSPG4/NG2

WT sequence:
TGAGGGTCCTGGCTTGAGGTCCGTCCTCCTTCTGCAGGGCTCCATGCTGGGGTGGCTCCAGCACCTGC
AGGCTGAGGCCCAGGAGAGTGGGGAAGTAG----------------GGCCCGGAGACACGGAGCA
GTGGAGGGGCCAGGGTGAGGCTGCCACCCTCAGGGACGCTGAAGTTTTGCGCCTCTAGTGGGAT
GGCAGCGGGCAGCACCTCCAGCTCCACAAGGAC (SEQ ID NO: 30)

| Reads | Fraction | Fraction Cum_Sum | Seq | SEQ ID NO: |
|---|---|---|---|---|
| | | | GGAGAGTGGGGAAGTAG----------------<br>GGCCCGGAGACACGGAGCA---------------<br>AGTGGAGGGGCCAGGGTGAGGCTGCCACCCTCAGGGACGC<br>TGAAGTTTTGCGCCTCTAGTGGGATGGCAGCGGGCAGCAC<br>CTCCAGCTCCACAAGGAC | |
| 502 | 0.00065377 | 0.774660287 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAG----------------<br>GGCCCGGAGACACGGAGCA-----------------<br>GGAGGGGCCAGGGTGAGGCTGCCACCCTCAGGGACACTGA<br>AGTTTTGCGCCTCTAGTGGGATGGCAGCGGGCAGCACCTC<br>CAGCTCCACAAGGAC | 103 |
| 501 | 0.000652468 | 0.775312755 | TGAGGGTCCTGGCTTGAGGTCCGTCCTCCTTCTGCAGGGCT<br>CCATGCTGGGGTGGCTCCAGCACCTGCAGGCTGGGGCCCA<br>GGAGAGTGGGGAAGTAG----------------GGCCCGGAGACAC----<br>--------------------<br>GGAGGGGCCAGGGTGAGGCTGCCACCCTCAGGGACGCTGA<br>AGTTTTGCGCCTCTAGTGGGATGGCAGCGGGCAGCACCTC<br>CAGCTCCACAAGGAC | 104 |
| 501 | 0.000652468 | 0.775965223 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAG----------------<br>GGCCCGGAGACACGGAG----------------------<br>GGGCCAGGGTGAGGCTGCCACCCTCAGGGACGCTGAAGTT<br>TTGCACCTCCGGTGGGATGGCAGCGGGCAGCACCTCCAGC<br>TCCACAAGGAC | 105 |
| 501 | 0.000652468 | 0.77661769 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAG----------------<br>GGCCCGGAGACACGGAG----------------------<br>GGGCCAGGGTGAGGCTGCCACCCTCAGGGACGCTGAAGTT<br>TTGCGCCTCTAGTGGGATGGCAGCGGGCAGCACCTCCAGC<br>TCCACAAGGAC | 106 |
| 501 | 0.000652468 | 0.777270158 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAG----------------<br>GGCCCGGAGACACGGAGCA---------------<br>AGTGGAGGGGCCAGGGTGAGGCTGCCACCCTCAGGGACGC<br>TGAAGTTTTGCGCCTCTAGTGGGATGGCAGTGGGCAGCAC<br>CTCCAGCTCCACAAGGAC | 107 |
| 497 | 0.000647258 | 0.777917417 | TGAGGGTCCTGGCTTGAGGGCCGTCCTCCTTCTGCAGGGCT<br>CCATGCTGGGGTGGCTCCAGCACCTGCAGGCTGAGGCCCA<br>GGAGAGTGGGGAAGTAG----------------<br>GGCCCGGAGACACGGAG----------------------<br>GGGCCAGGGTGAGGCTGCCACCCTCAGGGACGCTGAAGTT<br>TTGCGCCTCTAGTGGGATGGCAGCGGGCAGCACCTCCAGC<br>TCCACAAGGAC | 108 |
| 488 | 0.000635537 | 0.778552954 | TGAGGGTCCTGGCTTGAGGTCCGTCCTCCTTCTGCAGGGCT<br>CCATGCTGGGGTGGCTCCAGCACCTGCAGGCTGAGGCCCA<br>GGAGAGTGGGGAAGTAG----------------<br>GGCCCGGAGACACGGAGGGCCGGCGATGCAGAGCAGTGG<br>AGGGGCCAGGGTGAGGCTGCCACCCTCAGGGACACTGAAG<br>TTTTGCGCCTCTAGTGGGATGGCAGCGGGCAGCACCTCCA<br>GCTCCACAAGGAC | 109 |
| 488 | 0.000635537 | 0.779188492 | TGAGGGTCCTGGCTTGAGGTCCGTCCTCCTTCTGCAGGGCT<br>CCATGCTGGGGTGGCTCCAGCACCTGCAGGCCGAGGCCCG<br>GGAGAGTGGGGAAGTAGGGCCCGGAGACACGGAGGGCCG<br>GCGATGCAGAGCA---------------<br>GTGGAGGGGCCAGGGTGAGGCTGCCACCCTCAGGGACGCT<br>GAAGTTTTGCGCCTCTAGTGGGATGGCAGCGGGCAGCACC<br>TCCAGCTCCACAAGGAC | 110 |

TABLE 1-continued

CSPG4/NG2

WT sequence:
TGAGGGTCCTGGCTTGAGGTCCGTCCTCCTTCTGCAGGGCTCCATGCTGGGGTGGCTCCAGCACCTGC
AGGCTGAGGCCCAGGAGAGTGGGGAAGTAG----------------GGCCCGGAGACACGGGAGCA
GTGGAGGGGCCAGGGTGAGGCTGCCACCCTCAGGGACGCTGAAGTTTTGCGCCTCTAGTGGGAT
GGCAGCGGGCAGCACCTCCAGCTCCACAAGGAC (SEQ ID NO: 30)

| Reads | Fraction | Fraction Cum_Sum | Seq | SEQ ID NO: |
|---|---|---|---|---|
| 484 | 0.000630328 | 0.77981882 | TGAGGGTCCTGGCTTGAGGTCCGTCCTCCTTCTGCAGGGCC CCATGCTGGGGTGGCTCCAGCACCTGCAGGCTGAGGCCCA GGAGAGTGGGGAAGTAG---------------- GGCCCGGAGACACGGAG---------------------- GGGCCAGGGTGAGGCTGCCACCCTCAGGGACGCTGAAGTT TTGCGCCTCTAGTGGGATGGCAGCGGGCAGCACCTCCAGC TCCACAAGGAC | 111 |
| 466 | 0.000606886 | 0.780425706 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG----------------GGCCCGGAGACAC---- -------------------- GGAGGGGCCAGGGTGAGGCTGCCACCCCCAGGGACGCTG AAGTTTTGCGCCTCTAGTGGGATGGCAGCGGGCAGCACCT CCAGCTCCACAAGGAC | 112 |
| 461 | 0.000600375 | 0.78102608 | TGAGGGTCCTGGCTTGAGGTCCGTCCTCCTTCTGCAGGGCT CCATGCTGGGGTGGCTCCGGCACCTGCAGGCTGAGGCCCA GGAGAGTGGGGAAGTAG---------------- GGCCCGGAGACACGGAG---------------------- GGGCCAGGGTGAGGCTGCCACCCTCAGGGACGCTGAAGTT TTGCGCCTCTAGTGGGATGGCAGCGGGCAGCACCTCCAGC TCCACAAGGAC | 113 |
| 459 | 0.00059777 | 0.78162385 | TGAGGGTCCTGGCTTGAGGTCCGTCCTCCTTCTGCAGGGCT CCATGCTGGGGTGGCTCCAGCACCTGCAGGCTGAGGCCCG GGAGAGTGGGGAAGTAG---------------- GGGCCGGCGATGCAGAGCA--------------- GTGGAGGGGCCAGGGTGAAGCTGCCACCCTCAGGGACACT GAAGTTTTGCGCCTCTAGTGGGATGGCAGCGGGCAGCACC TCCAGCTCCACAAGGAC | 114 |
| 458 | 0.000596468 | 0.782220318 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGCCCGGAGACACGGGG---------------------- GGGCCAGGGTGAGGCTGCCACCCTCAGGGACGCTGAAGTT TTGCGCCTCTAGTGGGATGGCAGCGGGCAGCACCTCCAGC TCCACAAGGAC | 115 |
| 454 | 0.000591258 | 0.782811576 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG----------------GGCCCGGGGACAC---- -------------------- GGAGGGGCCAGGGTGAGGCTGCCACCCTCAGGGACGCTGA AGTTTTGCGCCTCTAGTGGGATGGCAGCGGGCAGCACCTC CAGCTCCACAAGGAC | 116 |
| 452 | 0.000588654 | 0.78340023 | TGAGGGTCCTGGCTTGAGGTCCGCCCTCCTTCTGCAGGGCT CCATGCTGGGGTGGCTCCAGCACCTGCAGGCTGAGGCCCA GGAGAGTGGGGAAGTAG----------------GGCCCGGAGACAC---- -------------------- GGAGGGGCCAGGGTGAGGCTGCCACCCTCAGGGACGCTGA AGTTTTGCGCCTCTAGTGGGATGGCAGCGGGCAGCACCTC CAGCTCCACAAGGAC | 117 |
| 451 | 0.000587351 | 0.783987581 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGCCCGGAGACACGGAG---------------------- GGGCCAGGGCGAGGCTGCCACCCTCAGGGACGCTGAAGTT TTGCGCCTCTAGTGGGATGGCAGCGGGCAGCACCTCCAGC TCCACAAGGAC | 118 |
| 449 | 0.000584747 | 0.784572328 | TGAGGGTCCTGGCTTGAGGTCCGTCCTCCTTCTGCAGGGCT CCATGCTGGGGTGGCTCCAGCACCTGCAGGCCGAGGCCCG GGAGAGTGGGGAAGTAG---------------- GGGCCGGCGATGCAGAGCA--------------- | 119 |

TABLE 1-continued

CSPG4/NG2

WT sequence:
TGAGGGTCCTGGCTTGAGGTCCGTCCTCCTTCTGCAGGGCTCCATGCTGGGGTGGCTCCAGCACCTGC
AGGCTGAGGCCCAGGAGAGTGGGGAAGTAG---------------GGCCCGGAGACACGGGAGCA
GTGGAGGGGCCAGGGTGAGGCTGCCACCCTCAGGGACGCTGAAGTTTTGCGCCTCTAGTGGGAT
GGCAGCGGGCAGCACCTCCAGCTCCACAAGGAC (SEQ ID NO: 30)

| Reads | Fraction | Fraction Cum_Sum | Seq | SEQ ID NO: |
|---|---|---|---|---|
| | | | GTGGAGGGGCCAGGGTGAAGCTGCCACCCTCAGGGACACT GAAGTTTTGCACCTCCGGTGGGATGGCAGCGGGCAGCACC TCCAGCTCCACAAGGAC | |
| 448 | 0.000583444 | 0.785155772 | TGAGGGTCCTGGCTTGAGGTCCGTCCTCCTTCTGCAGGGCT CCGTGCTGGGGTGGCTCCAGCACCTGCAGGCTGAGGCCCA GGAGAGTGGGGAAGTAG---------------- GGCCCGGAGACACGGAG---------------------- GGGCCAGGGTGAGGCTGCCACCCTCAGGGACGCTGAAGTT TTGCGCCTCTAGTGGGATGGCAGCGGGCAGCACCTCCAGC TCCACAAGGAC | 120 |
| 443 | 0.000576933 | 0.785732704 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG----------------GGCCCGGAGACAC---- -------------------- GGAGGGGCCGGGGTGAGGCTGCCACCCTCAGGGACGCTGA AGTTTTGCGCCTCTAGTGGGATGGCAGCGGGCAGCACCTC CAGCTCCACAAGGAC | 121 |
| 435 | 0.000566514 | 0.786299218 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGCCCGGAGACACGGAG---------------------- CCAGGGTGAGGCTGCCACCCTCAGGGACGCTGAAGTTTTG CGCCTCTAGTGGGATGGCAGCGGGCAGCACCTCCAGCTCC ACAAGGAC | 122 |
| 435 | 0.000566514 | 0.786865732 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGCCCGGAGACACGGAGCA--------------- AGTGGAGGGGCCAGGGTGAGGCTGCCACCCTCAGGGACGC TGAAGTTTTGCGCCTCTAGTGGGATGGCAGCGGGCAGCGC CTCCAGCTCCACAAGGAC | 123 |
| 431 | 0.000561305 | 0.787427037 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGCCCGGAGACACGGAG---------------------- GGGCCAGGGTGAGGCTGCCACCCTCGGGGACGCTGAAGTT TTGCGCCTCTAGTGGGATGGCAGCGGGCAGCACCTCCAGC TCCACAAGGAC | 124 |
| 431 | 0.000561305 | 0.787988342 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGCCCGGAGACACGGAG---------------------- GGGCCAGGGTGAGGCTGCCACCCTCAGGGACGCTGAAGCT TTGCGCCTCTAGTGGGATGGCAGCGGGCAGCACCTCCAGC TCCACAAGGAC | 125 |
| 426 | 0.000554793 | 0.788543135 | TGAGGGTCCTGGCTTGAGGTCCGTCCTCCTTCTGCAGGGCT CCATGCTGGGGTGGCTCCAGCGCCTGCAGGCTGAGGCCCA GGAGAGTGGGGAAGTAG---------------GGCCCGGAGACAC---- -------------------- GGAGGGGCCAGGGTGAGGCTGCCACCCTCAGGGACGCTGA AGTTTTGCGCCTCTAGTGGGATGGCAGCGGGCAGCACCTC CAGCTCCACAAGGAC | 126 |
| 421 | 0.000548281 | 0.789091416 | TGAGGGTCCTGGCTTGAGGTCCGTCCTCCTTCTGCAGGGCT CCATGCTGGGGTGGCTCCAGCACCTGCAGGCTGAGGCCCG GGAGAGTGGGGAAGTAG---------------- GGCCCGGAGACACGGAGCA--------------- AGTGGAGGGGCCAGGGTGAGGCTGCCACCCTCAGGGACGC TGAAGTTTTGCGCCTCTAGTGGGATGGCAGCGGGCAGCAC CTCCAGCTCCACAAGGAC | 127 |

TABLE 1-continued

CSPG4/NG2

WT sequence:
TGAGGGTCCTGGCTTGAGGTCCGTCCTCCTTCTGCAGGGCTCCATGCTGGGGTGGCTCCAGCACCTGC
AGGCTGAGGCCCAGGAGAGTGGGGAAGTAG---------------GGCCCGGAGACACGGAGCA
GTGGAGGGGCCAGGGTGAGGCTGCCACCCTCAGGGACGCTGAAGTTTTGCGCCTCTAGTGGGAT
GGCAGCGGGCAGCACCTCCAGCTCCACAAGGAC (SEQ ID NO: 30)

| Reads | Fraction | Fraction Cum_Sum | Seq | SEQ ID NO: |
|---|---|---|---|---|
| 410 | 0.000533956 | 0.789625371 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGCCCGGAGACACGGAGCA------------------ GGAGGGGCCAGGGTGAGGCTGCCACCCTCAGGGACGCTGA AGTTTTGCGCCTCTAGTGGGATGACAGTGGGCAGCACCTC CAGCTCCACAAGGAC | 128 |
| 408 | 0.000531351 | 0.790156723 | TGAGGGTCCTGGCTTGAGGTCCGTCCTCCTTCTGCAGGGCT CCATGCTGGGGTGGCTCCAGCACCTGCAGGCTGAGGCCCA GGAGAGTGGGGAAGTAG---------------- GGCCCGGAGACACGGAG---------------------- GGGCCAGGGTGAGGCTGCCACCCTCAGGGACGCTGAAGTT TTGCGCCTCTAGTGGGACGGCAGCGGGCAGCACCTCCAGC TCCACAAGGAC | 129 |
| 401 | 0.000522235 | 0.790678957 | TGAGGGTCCTGGCTTGAGGTCCGTCCTCCTTCTGCAGGGCT CCATGCCGGGGTGGCTCCAGCACCTGCAGGCTGAGGCCCA GGAGAGTGGGGAAGTAG---------------- GGCCCGGAGACACGGAG---------------------- GGGCCAGGGTGAGGCTGCCACCCTCAGGGACGCTGAAGTT TTGCGCCTCTAGTGGGATGGCAGCGGGCAGCACCTCCAGC TCCACAAGGAC | 130 |

TABLE 2

FZD2

WT sequence:
TTCCTGTGCTCCATGTACGCACCCGTGTGCACCGTGCTGGAACAGGCCATCCCGCCGTGCCGCTCTATC
TGTGAGCGCGCGCGCCAGGGCTGCGAAGCCCTCATGAACAAGTTCGGTTTTCAGTGGCCCGAGCGCCT
GCGCTGCGAGCACTTCCCGCGCCAC----------GGCGCCGAGCAGATCTGCGTCGGCCAGAACCACTCCGAGGACGGAGCT (SEQ ID NO: 131)

| Reads | Fraction | Fraction Cum_Sum | Seq | SEQ ID NO: |
|---|---|---|---|---|
| 106541 | 0.138930038 | 0.138930038 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGCGC------------------ CGAGCAGATCTGCGTCGGCCAGAACCACTCCGAG GA CGGAGCT | 132 |
| 66146 | 0.08625474 | 0.225184778 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGCGGC----------------- GCCGAGCAGATCTGCGTCGGCCAGAACCACTCCGA G GACGGAGCT | 133 |
| 42820 | 0.05583751 | 0.281022288 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACT----------T---- CCCACGCGCCGAGCAGATCTGCGTCGGCCAGAA CCACTCCGAGGACGGAGCT | 134 |
| 34007 | 0.044345311 | 0.325367599 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT | 135 |

TABLE 2-continued

FZD2

WT sequence:
TTCCTGTGCTCCATGTACGCACCCGTGTGCACCGTGCTGGAACAGGCCATCCCGCCGTGCCGCTCTATC
TGTGAGCGCGCGCGCCAGGGCTGCGAAGCCCTCATGAACAAGTTCGGTTTTTCAGTGGCCCGAGCGCCT
GCGCTGCGAGCACTTCCCGCGCCAC----------
GGCGCCGAGCAGATCTGCGTCGGCCAGAACCACTCCGAGGACGGAGCT (SEQ ID NO: 131)

| Reads | Fraction | Fraction Cum_Sum | Seq | SEQ ID NO: |
|---|---|---|---|---|
| | | | GAACAAGTTCGGTTTTCAGTGGCCCGAGCGCCTGC GCTGCGAGCAC-----------T---- TCCACGGCGCCGAGCAGATCTGCGTCGGCCAGAAC CACTCCGAGGACGGAGCT | |
| 28239 (WT) | 0.036823808 | 0.362191407 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGCGCCAC---------- GGCGCCGAGCAGATCTGCGTCGGCCAGAACCACTC CGAGGACGGAGCT | 136 |
| 13147 | 0.017143759 | 0.379335166 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGC-----------T---- CGAGCAGATCTGCGTCGGCCAGAACCACTCCGAG GACGGAGCT | 137 |
| 10667 | 0.013909825 | 0.393244991 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCG--------------------- AGCAGATCTGCGTCGGCCAGAACCACTCCGAGGA CGGAGCT | 138 |
| 10071 | 0.013132638 | 0.40637763 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGCGAG-------------------- CAGATCTGCGTCGGCCAGAACCACTCCGAGGACG GAGCT | 139 |
| 9638 | 0.012568004 | 0.418945633 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCG-------------------------------- AGCAGATCTGCGTCGGCCAGAACCACTCCGAGGA CGGAGCT | 140 |
| 6967 | 0.009085006 | 0.428030639 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGCG----------------- CCGAGCAGATCTGCGTCGGCCAGAACCACTCAGA GGACGGAGCT | 141 |
| 6806 | 0.008875061 | 0.4369057 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGCGCG---------------- CCGAGCAGATCTGCGTCGGCCAGAACCACTCCGAG GACGGAGCT | 142 |
| 6659 | 0.008683372 | 0.445589071 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTC------------------- GGCGCCGAGCAGATCTGCGTCGGCCAGAACCACTC CGAGGACGGAGCT | 143 |

TABLE 2-continued

FZD2

WT sequence:
TTCCTGTGCTCCATGTACGCACCCGTGTGCACCGTGCTGGAACAGGCCATCCCGCCGTGCCGCTCTATC
TGTGAGCGCGCGCGCCAGGGCTGCGAAGCCCTCATGAACAAGTTCGGTTTTCAGTGGCCCGAGCGCCT
GCGCTGCGAGCACTTCCCGCGCCAC----------
GGCGCCGAGCAGATCTGCGTCGGCCAGAACCACTCCGAGGACGGAGCT (SEQ ID NO: 131)

| Reads | Fraction | Fraction Cum_Sum | Seq | SEQ ID NO: |
|---|---|---|---|---|
| 6624 | 0.008637732 | 0.454226803 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGC-------------- TCGGCGCCGAGCAGATCTGCGTCGGCCAGAACCAC TCCGAGGACGGAGCT | 144 |
| 6445 | 0.008404315 | 0.462631118 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGCGCA---------- CGGCGCCGAGCAGATCTGCGTCGGCCAGAACCACT CCGAGGACGGAGCT | 145 |
| 6441 | 0.008399099 | 0.471030216 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGGCGC---------------- CGAGCAGATCTGCGTCGGCCAGAACCACTCCGAG GAC GGAGCT | 146 |
| 6377 | 0.008315642 | 0.479345859 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGCGC-------------- GGCGCCGAGCAGATCTGCGTCGGCCAGAACCACTC CGAGGACGGAGCT | 147 |
| 6151 | 0.008020937 | 0.487366796 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCG------------ CCACGGCGCCGAGCAGATCTGCGTCGGCCAGAAC CACTCCGAGGACGGAGCT | 148 |
| 5924 | 0.007724928 | 0.495091724 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGCGGC--------- CACGGCGCCGAGCAGATCTGCGTCGGCCAGAACC ACTCCGAGGACGGAGCT | 149 |
| 5376 | 0.007010333 | 0.502102057 | TTCCTGTGCTCCATGTACGCACCCGTGTGCACCGT GCTGGAACAGGCCATCCCGCCGTGCCGCTCT--------- --------------------------------------- ------------ GCACGGCGCCGAGCAGATCTGCGTCGGCCAGAAC CACTCCGAGGACGGAGCT | 150 |
| 4830 | 0.006298346 | 0.508400403 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTGCCCG-------------- CGGCGCCGAGCAGATCTGCGTCGGCCAGAACCACT CCGAGGACGGAGCT | 151 |
| 4704 | 0.006134041 | 0.514534444 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGCGGG-------------- | 152 |

TABLE 2-continued

FZD2

WT sequence:
TTCCTGTGCTCCATGTACGCACCCGTGTGCACCGTGCTGGAACAGGCCATCCCGCCGTGCCGCTCTATC
TGTGAGCGCGCGCGCCAGGGCTGCGAAGCCCTCATGAACAAGTTCGGTTTTCAGTGGCCCGAGCGCCT
GCGCTGCGAGCACTTCCCGCGCCAC----------
GGCGCCGAGCAGATCTGCGTCGGCCAGAACCACTCCGAGGACGGAGCT (SEQ ID NO: 131)

| Reads | Fraction | Fraction Cum_Sum | Seq | SEQ ID NO: |
|---|---|---|---|---|
| | | | CGCCGAGCAGATCTGCGTCGGCCAGAACCACTCCG<br>AG<br>GACGGAGCT | |
| 4248 | 0.005539415 | 0.520073859 | TTCCTGTGCTCCATGTACGCACCCGTGTGCACCGT<br>GCTGGAACAGGCCATCCCGCCGTGCCGCTCTATCT<br>GTGAGCGCGCGCGCCAGGGCTGCGAAGCCCTCAT<br>GAACAAGTTCGGTTTTCAGTGGCCCGAGCGCCTGC<br>GCTGCGAGCACTTCCCGCG---------------<br>GCGCCGAGCAGATCTGCGTCGGCCAGAACCACTCA<br>GAGGACGGAGCT | 153 |
| 3937 | 0.005133869 | 0.525207728 | TTCCTGTGCTCCATGTACGCACCCGTGTGCACCGT<br>GCTGGAACAGGCCATCCCGCCGTGCCGCTCTATCT<br>GTGAGCGCGCGCGCCAGGGCTGCGAAGCCCTCAT<br>GAACAAGTTCGGTTTTCAGTGGCCCGAGCGCCTGC<br>GCTGCGAGCACTTCCCGCG--------------------<br>GGCAGATCTGCGTCGGCCAGAACCACTCCGAGGA<br>CG<br>GAGCT | 154 |
| 3733 | 0.004867852 | 0.53007558 | TTCCTGTGCTCCATGTACGCACCCGTGTGCACCGT<br>GCTGGAACAGGCCATCCCGCCGTGCCGCTCTATCT<br>GTGAGCGCGCGCGCCAGGGCTGCGAAGCCCTCAT<br>GAACAAGTTCGGTTTTCAGTGGCCCGAGCGCCTGC<br>GCTGCGAGCAC----------------<br>TTCACGCGCCGAGCAGATCTGCGTCGGCCAGAAC<br>CACTCCGAGGACGGAGCT | 155 |
| 3662 | 0.004775268 | 0.534850848 | TTCCTGTGCTCCATGTACGCACCCGTGTGCACCGT<br>GCTGGAACAGGCCATCCCGCCGTGCCGCTCTATCT<br>GTGAGCGCGCGCGCCAGGGCTGCGAAGCCCTCAT<br>GAACAAGTTCGGTTTTCAGTGGCCCGAGCGCCTGC<br>GCTGCGAGCACTTCCCGC--------------------<br>GGGCCAGATCTGCGTCGGCCAGAACCACTCCGAG<br>GACGGAGCT | 156 |
| 3300 | 0.004303218 | 0.539154066 | TTCCTGTGCTCCATGTACGCACCCGTGTGCACCGT<br>GCTGGAACAGGCCATCCCGCCGTGCCGCTCTATCT<br>GTGAGCGCGCGCGCCAGGGCTGCGAAGCCCTCAT<br>GAACAAGTTCGGTTTTCAGTGGCCCGAGCGCCTGC<br>GCTGCGAGCACTTCCCGCG------------------------<br>GATCTGCGTCGGCCAGAACCACTCCGAGGACGGA<br>GCT | 157 |
| 3257 | 0.004247146 | 0.543401211 | TTCCTGTGCTCCATGTACGCACCCGTGTGCACCGT<br>GCTGGAACAGGCCATCCCGCCGTGCCGCTCTATCT<br>GTGAGCGCGCGCGCCAGGGCTGCGAAGCCCTCAT<br>GAACAAGTTCGGTTTTCAGTGGCCCGAGCGCCTGC<br>GCTGCGAGCACTTCCCGCG-----------<br>ACGGCGCCGAGCAGATCTGCGTCGGCCAGAACCA<br>CTCCGAGGACGGAGCT | 158 |
| 3149 | 0.004106313 | 0.547507524 | TTCCTGTGCTCCATGTACGCACCCGTGTGCACCGT<br>GCTGGAACAGGCCATCCCGCCGTGCCGCTCTATCT<br>GTGAGCGCGCGCGCCAGGGCTGCGAAGCCCTCAT<br>GAACAAGTTCGGTTTTCAGTGGCCCGAGCGCCTGC<br>GCTGCGAGCACT----------G----<br>CCCACGGCGCCGAGCAGATCTGCGTCGGCCAGAA<br>CCACTCCGAGGACGGAGCT | 159 |
| 2894 | 0.003773792 | 0.551281316 | TTCCTGTGCTCCATGTACGCACCCGTGTGCACCGT<br>GCTGGAACAGGCCATCCCGCCGTGCCGCTCTATCT<br>GTGAGCGCGCGCGCCAGGGCTGCGAAGCCCTCAT<br>GAACAAGTTCGGTTTTCAGTGGCCCGAGCGCC------<br>-----------------------------------GAGCAGAT<br>CTGCGTCGGCCAGAACCACTCCGAGGACGGAGCT | 160 |

TABLE 2-continued

FZD2

WT sequence:
TTCCTGTGCTCCATGTACGCACCCGTGTGCACCGTGCTGGAACAGGCCATCCCGCCGTGCCGCTCTATC
TGTGAGCGCGCGCGCCAGGGCTGCGAAGCCCTCATGAACAAGTTCGGTTTTCAGTGGCCCGAGCGCCT
GCGCTGCGAGCACTTCCCGCGCCAC----------
GGCGCCGAGCAGATCTGCGTCGGCCAGAACCACTCCGAGGACGGAGCT (SEQ ID NO: 131)

| Reads | Fraction | Fraction Cum_Sum | Seq | SEQ ID NO: |
|---|---|---|---|---|
| 2874 | 0.003747711 | 0.555029027 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGCG------------------ TCGGCCAGA--------------- ACCACTCCGAGGACGGAGCT | 161 |
| 2853 | 0.003720327 | 0.558749355 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCG------------------------------ -------------------------------- ATCTGCGTCGGCCAGAACCACTCCGAGGACGGAG CT | 162 |
| 2806 | 0.003659039 | 0.562408394 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGC------------- ------------------------------------ AGATCTGCGTCGGCCAGAACCACTCCGAGGACGG AGCT | 163 |
| 2696 | 0.003515599 | 0.565923992 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGA------------------------- GCGCCGAGCAGATCTGCGTCGGCCAGAACCACTCC GAGGACGGAGCT | 164 |
| 2657 | 0.003464742 | 0.569388734 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCACG--------------- GCGCCGAGCAGATCTGCGTCGGCCAGAACCACTCA GAGGACGGAGCT | 165 |
| 2600 | 0.003390414 | 0.572779148 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTT------------------------- CCCGCAGATCTGCGTCGGCCAGAACCACTCCGAGG ACGGAGCT | 166 |
| 2318 | 0.003022684 | 0.575801833 | TTCCTGTGCTCCATGTACGCACCCGTGTGCA---------- --------------------------------------------- -------------------------------------- CCGAGCAGATCTGCGTCGGCCAGAACCACTCCGAG GACGGAGCT | 167 |
| 2217 | 0.00289098 | 0.578692813 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTC----------------------------- GATCTGCGTCGGCCAGAACCACTCCGAGGACGGA GCT | 168 |
| 2135 | 0.002784051 | 0.581476864 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCC-ACG--------------- GCGCCGAGCAGATCTGCGTCGGCCAGAACCACTCA GAGGACGGAGCT | 169 |

TABLE 2-continued

FZD2

WT sequence:
TTCCTGTGCTCCATGTACGCACCCGTGTGCACCGTGCTGGAACAGGCCATCCCGCCGTGCCGCTCTATC
TGTGAGCGCGCGCGCCAGGGCTGCGAAGCCCTCATGAACAAGTTCGGTTTTCAGTGGCCCGAGCGCCT
GCGCTGCGAGCACTTCCCGCGCCAC----------
GGCGCCGAGCAGATCTGCGTCGGCCAGAACCACTCCGAGGACGGAGCT (SEQ ID NO: 131)

| Reads | Fraction | Fraction Cum_Sum | Seq | SEQ ID NO: |
|---|---|---|---|---|
| 2110 | 0.002751451 | 0.584228316 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCC--------------------- CGAGCAGATCTGCGTCGGCCAGAACCACTCCGAG GACGGAGCT | 170 |
| 2073 | 0.002703203 | 0.586931519 | TTCCTGTGCTCCATGTACGCACCCGTGTGCACCGT GCTGGAACAGGCCATCCCGCCGTGCCGCTCTATCT GTGAGCGTGCGCGCCAGGGCTGCGAAGCCCTCATG AACAAGTTCGGTTTTCAGTGGCCCGAGCGCCTGCG CTGCGAGCACTTC--------------------- CCGAGCAGATCTGCGTCGGCCAGAACCACTCCGAG GACGGAGCT | 171 |
| 2037 | 0.002656259 | 0.589587778 | TTCCTGTGCTCCATGTACGCACCCGTGTGCACCGT GCTGGAACAGGCCATCCCGCCGTGCCGCTCTATCT GTGA---------------------------------- ----------------------------------- GCCGAGCAGATCTGCGTCGGCCAGAACCACTCCGA GGACGGAGCT | 172 |
| 1985 | 0.002588451 | 0.592176229 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GC-------------------------- AGATCTGCGTCGGCCAGAACCACTCCGAGGACGG AGCT | 173 |
| 1966 | 0.002563675 | 0.594739903 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGA CGCAGATCTGCGTCGGCCAGAACCACTCCGAGGAC GGAGCT | 174 |
| 1922 | 0.002506298 | 0.597246201 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCT--------------------------------- CGAGCAGATCTGCGTCGGCCAGAACCACTCCGAG GACGGAGCT | 175 |
| 1876 | 0.002446314 | 0.599692516 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGCGCC--------- ACGGCGCCGAGCAGATCTGCGTCGGCCAGAACCA CTCAGAGGACGGAGCT | 176 |
| 1874 | 0.002443706 | 0.602136222 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTG--------------------- --------------------- GCACGGCGCCGAGCAGATCTGCGTCGGCCAGAAC CACTCCGAGGACGGAGCT | 177 |
| 1865 | 0.00243197 | 0.604568192 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGC----------------- | 178 |

TABLE 2-continued

FZD2

WT sequence:
TTCCTGTGCTCCATGTACGCACCCGTGTGCACCGTGCTGGAACAGGCCATCCCGCCGTGCCGCTCTATC
TGTGAGCGCGCGCGCCAGGGCTGCGAAGCCCTCATGAACAAGTTCGGTTTTCAGTGGCCCGAGCGCCT
GCGCTGCGAGCACTTCCCGCGCCAC----------
GGCGCCGAGCAGATCTGCGTCGGCCAGAACCACTCCGAGGACGGAGCT (SEQ ID NO: 131)

| Reads | Fraction | Fraction Cum_Sum | Seq | SEQ ID NO: |
|---|---|---|---|---|
| | | | GCCGTGCAGATCTGCGTCGGCCAGAACCACTCCGAGGACGGAGCT | |
| 1778 | 0.002318522 | 0.606886713 | TTCCTGTGCTCCATGTACGCACCCGTGTGCACCGTGCTGGAACAGGCCATCCCGCCGTGCCGCTCTATCTGTGAGCGCGCGCGCCAGGGCTGCGAAGCCCTCATGAACAAGTTCGGTTTTCAGTGGCCCGAGCGCCTGCGCTGCGAGCACTTC------------------TCGGCGCCGAGCAGATCTGCGTCGGCCAGAACCACTCCGAGGACGGAGCT | 179 |
| 1745 | 0.002275489 | 0.609162203 | TTCCTGTGCTCCATGTACGCACCCGTGTGCACCGTGCTGGAACAGGCCATCCCGCCGTGCCGCTCTATCTGTGAGCGCGCGCGCCAGGGCTGCGAAGCCCTCATGAACAC--------------------CGA-----------------------------GCAGATCTGCGTCGGCCAGAACCACTCCGAGGACGGAGCT | 180 |
| 1589 | 0.002072065 | 0.611234267 | TTCCTGTGCTCCATGTACGCACCCGTGTGCACCGTGCTGGAACAGGCCATCCCGCCGTGCCGCTCTATCTGTGAGCGCGCGCGCCAGGGCTGCGAAGCCCTCATGAACAAGTTCGGTTTTCAGTGGCCCGAGCGCCTGCGCTGCGAGCACTTCCCGCGGCGAGCAGATCTGCGTCGGCCAGAACCACTCCGAGGACGGAGCT | 181 |
| 1562 | 0.002036856 | 0.613271124 | TTCCTGTGCTCCATGTACGCACCCGTGTGCACCGTGCTGGAACAGGCCATCCCGCCGTGCCGCTCTATCTGTGAGCGCGCGCGCCAGGGCTGCGAAGCCCTCATGAACAAGTTCGGTTTTCAGTGGCCCGAGCGCCTGCGCTGCGAGCAC-----------------TCCACGGCGCCGAGCAGATCTGCGTCGGCCAGAACCACTCCGAGGACGGAGCT | 182 |
| 1541 | 0.002009472 | 0.615280596 | TTCCTGTGCTCCATGTACGCACCCGTGTGCACCGTGC----------------------------------------------------------------------------------AGATCTGCGTCGGCCAGAACCACTCCGAGGACGGAGCT | 183 |
| 1420 | 0.001851688 | 0.617132284 | TTCCTGTGCTCCATGTACGCACCCGTGTGCACCGTGCTGGAACAGGCCATCCCGCCGTGCCGCTCTATCTGTGAGCGCGCGCGCCAGGGCTGCGAAGCCCTCATGAACAAGTTCGGTTTTCAGTGGCCCGAGCGCCTGCGCTGCGAGC---------------------ACGGCGCCGAGCAGATCTGCGTCGGCCAGAACCACTCCGAGGACGGAGCT | 184 |
| 1318 | 0.001718679 | 0.618850963 | TTCCTGTGCTCCATGTACGCACCCGTGTGCACCGTGCTGGAACAGGCCATCCCGCCGTGCCGCTCTATCTGTGAGCGCGCGCGCCAGGGCTGCGAAGCCCTCATGAACAAGTTCGGTTTTCAGTGGCCCGAGCGCCTGCGCTGCGAGCACTTCCCGCGCG---------------------GATCTGCGTCGGCCAGAACCACTCCGAGGACGGAGCT | 185 |
| 1300 | 0.001695207 | 0.62054617 | TTCCTGTGCTCCATGTACGCACCCGTGTGCACCGTGCTGGAACAGGCCATCCCGCCGTGCCGCTCTATCTGTGAGCGCGCGCGCCAGGGCTGCGAAGCCCTCATGAACAAGTTCGGTTTTCAGTGGCCCGAGCGCCTGCGCTGCGAGCACTTCCCGAT------------------CGGCCAGA---------------ACCACTCCGAGGACGGAGCT | 186 |
| 1283 | 0.001673039 | 0.622219209 | TTCCTGTGCTCCATGTACGCACCCGTGTGCACCGTGCTGGAACAGGCCATCCCGCCGTGCCGCTCTATCTGTGAGCGCGCGCGCCAGGGCTGCGAAGCCCTCAT | 187 |

TABLE 2-continued

FZD2

WT sequence:
TTCCTGTGCTCCATGTACGCACCCGTGTGCACCGTGCTGGAACAGGCCATCCCGCCGTGCCGCTCTATC
TGTGAGCGCGCGCGCCAGGGCTGCGAAGCCCTCATGAACAAGTTCGGTTTTCAGTGGCCCGAGCGCCT
GCGCTGCGAGCACTTCCCGCGCCAC----------
GGCGCCGAGCAGATCTGCGTCGGCCAGAACCACTCCGAGGACGGAGCT (SEQ ID NO: 131)

| Reads | Fraction | Fraction Cum_Sum | Seq | SEQ ID NO: |
|---|---|---|---|---|
|  |  |  | GAACAAGTTCGGTTTTCAGTGGCCCGAGCGCCTGC<br>GCTGCGAGCACTTCCCGCCG---------<br>CCACGGCGCCGAGCAGATCTGCGTCGGCCAGAAC<br>CACTCCGAGGACGGAGCT |  |
| 1271 | 0.001657391 | 0.623876599 | TTCCTGTGCTCCATGTACGCACCCGTGTGCACCGT<br>GCTGGAACAGGCCATCCCGCCGTGCCGCTCTATCT<br>GTGAGCGCGCGCGCCAGGGCTGCGAAGCCCTCAT<br>GAACAAGTTCGGTTTTCAGTGGCCCGAGCGCCTGC<br>GCTGC------------------------<br>CACGGCGCCGAGCAGATCTGCGTCGGCCAGAACC<br>ACTCCGAGGACGGAGCT | 188 |
| 1248 | 0.001627399 | 0.625503998 | TTCCTGTGCTCCATGTACGCACCCGTGTGCACCGT<br>GCTGGAACAGGCCATCCCGCCGTGCCGCTCTATCT<br>GTGAGCGCGCGCGCCAGGGCTGCGAAGCCCTCAT<br>GAACAAGTTCGGTTTTCAGTGGCCCGAGCGCCTGC<br>GCTGCGAGCACTTCC--------------<br>CCACGGCGCCGAGCAGATCTGCGTCGGCCAGAAC<br>CACTCCGAGGACGGAGCT | 189 |
| 1215 | 0.001584367 | 0.627088365 | TTCCTGTGCTCCATGTACGCACCCGTGTGCACCGT<br>GCTGGAACAGGCCATCCCGCCGTGCCGCTCTATCT<br>GTGAGCGCGCGCGCCAGGGCTGCGAAGCCCTCAT<br>GAACAAGTTCGGTTTTCAGTGGCCCGAGCGCCTGC<br>GCTGCGAGCACT----------------<br>CCCACGGCGCCGAGCAGATCTGCGTCGGCCAGAA<br>CCACTCCGAGGACGGAGCT | 190 |
| 1190 | 0.001551766 | 0.628640131 | TTCCTGTGCTCCATGTACGCACCCGTGTGCACCGT<br>GCTGGAACAGGCCATCCCGCCGTGCCGCTCTATCT<br>GTGAGCGCGCGCGCCAGGGCTGCGAAGCCCTCAT<br>GAACAAGTTCGGTTTTCAGTGGCCCGAGCGCCTGC<br>GCTGCGAGCACTTCCCGC--------------------<br>GGGCCAGA---------------<br>ACCACTCCGAGGACGGAGCT | 191 |
| 1184 | 0.001543942 | 0.630184073 | TCCTGTGCTCCATGTACGCACCCGTGTGCACCGT<br>GCTGGAACAGGCCATCCCGCCGTGCCGCTCTATCT<br>GTGAGCGCGCGCGCCAGGGCTGCGAAGCCCTCAT<br>GAACAAGTTCGGTTTTCAGTGGCCCGAGCGCCTGC<br>GCTGCGAGCACTTCCC-------------<br>GCACGGCGCCGAGCAGATCTGCGTCGGCCAGAAC<br>CACTCCGAGGACGGAGCT | 192 |
| 1179 | 0.001537422 | 0.631721496 | TTCCTGTGCTCCATGTACGCACCCGTGTGCACCGT<br>GCTGGAACAGGCCATCCCGCCGTGCCGCTCTATCT<br>GTGAGCGCGCGCGCCAGGGCTGCGAAGCCCTCAT<br>GAACAAGTTCGGTTTTCAGTGGCCCGAGCGCCTGC<br>GCTGC-------------------------------------<br>GTCGGCCAGAACCACTCCGAGGACGGAGCT | 193 |
| 1155 | 0.001506126 | 0.633227622 | TTCCTGTGCTCCATGTACGCACCCGTGTGCACCGT<br>GCTGGAACAGGCCATCCCGCCGTGCCGCTCTATCT<br>GTGAGCGCGCGCGCCAGGGCTGCGAAGCCCTCAT<br>GAACAAGTTCGGTTTTCAGTGGCCCGAGCGCCTGC<br>GCTGCGAGCACT----------T----<br>TCCACGGCGCCGAGCAGATCTGCGTCGGCCAGAAC<br>CACTCCGAGGACGGAGCT | 194 |
| 1151 | 0.00150091 | 0.634728532 | TTCCTGTGCTCCATGTACGCACCCGTGTGCACCGT<br>GCTGGAACAGGCCATCCCGCCGTGCCGCTCTATCT<br>GTGAGCGCGCGCGCCAGGGCTGCGAAGCCCTCAT<br>GAACAAGTTCGGTTTTCAGTGGCCCGAGCGCCTGC<br>GCTGCGAGCACTTCCCG--------------------<br>CGGCCAGA---------------<br>ACCACTCCGAGGACGGAGCT | 195 |

TABLE 2-continued

FZD2

WT sequence:
TTCCTGTGCTCCATGTACGCACCCGTGTGCACCGTGCTGGAACAGGCCATCCCGCCGTGCCGCTCTATC
TGTGAGCGCGCGCGCCAGGGCTGCGAAGCCCTCATGAACAAGTTCGGTTTTCAGTGGCCCGAGCGCCT
GCGCTGCGAGCACTTCCCGCGCCAC----------
GGCGCCGAGCAGATCTGCGTCGGCCAGAACCACTCCGAGGACGGAGCT (SEQ ID NO: 131)

| Reads | Fraction | Fraction Cum_Sum | Seq | SEQ ID NO: |
|---|---|---|---|---|
| 1139 | 0.001485262 | 0.636213794 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCG------------------------------ ---------------------- AGCAGATCTGCGTCGGCCAGAACCACTCCGAGGA CGGAGCT | 196 |
| 1122 | 0.001463094 | 0.637676888 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGCG----------------- GGAAGCAGATCTGCGTCGGCCAGAACCACTCCGA GGACGGAGCT | 197 |
| 1110 | 0.001447446 | 0.639124334 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCTCAT--------------------- ------------GAACCACTCCGAGGACGGAGCT | 198 |
| 1060 | 0.001382246 | 0.64050658 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGC------------ CCACGGCGCCGAGCAGATCTGCGTCGGCCAGAAC CACTCCGAGGACGGAGCT | 199 |
| 1052 | 0.001371814 | 0.641878394 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGCGCCGG--A--------------- AGATCTGCGTCGGCCAGAACCACTCCGAGGACGG AGCT | 200 |
| 1035 | 0.001349646 | 0.643228039 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGCGCCGAGCACTTCCACGG CGCCGAGCAGATCTGCGTCGGCCAGAACCACTCCG AGGACGGAGCT | 201 |
| 1018 | 0.001327477 | 0.644555517 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGCGC-------------------- AGATCTGCGTCGGCCAGAACCACTCCGAGGACGG AGCT | 202 |
| 1003 | 0.001307917 | 0.645863434 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGCGCG--------------- TCCGAGCAGATCTGCGTCGGCCAGAACCACTCCGA GGACGGAGCT | 203 |
| 983 | 0.001281837 | 0.647145271 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGCGAG--------------- | 204 |

TABLE 2-continued

FZD2

WT sequence:
TTCCTGTGCTCCATGTACGCACCCGTGTGCACCGTGCTGGAACAGGCCATCCCGCCGTGCCGCTCTATC
TGTGAGCGCGCGCGCCAGGGCTGCGAAGCCCTCATGAACAAGTTCGGTTTTCAGTGGCCCGAGCGCCT
GCGCTGCGAGCACTTCCCGCGCCAC----------
GGCGCCGAGCAGATCTGCGTCGGCCAGAACCACTCCGAGGACGGAGCT (SEQ ID NO: 131)

| Reads | Fraction | Fraction Cum_Sum | Seq | SEQ ID NO: |
|---|---|---|---|---|
|  |  |  | CCGAGCAGATCTGCGTCGGCCAGAACCACTCCGAGGACGGAGCT |  |
| 925 | 0.001206205 | 0.648351476 | TTCCTGTGCTCCATGTACGCACCCGTGTGCACCGTGCTGGAACAGGCCATCCCGCCGTGCCGCTCTATCTGTGAGCGCGCGCGCCAGGGCTGCGAAGCCCTCATGAACAAGTTCGGTTTTCAGTGGCC---------------------------------------ACGGCGCCGAGCAGATCTGCGTCGGCCAGAACCACTCCGAGGACGGAGCT | 205 |
| 877 | 0.001143613 | 0.649495089 | TTCCTGTGCTCCATGTACGCACCCGTGTGCACCGTGCTGGAACAGGCCATCCCGCCGTGCCGCTCTATCTGTGAGCGCGCGCGCCAGGGCTGCGAAGCCCTCATGAACAAGTTCGGTTTTCAGTGGCCCGAGCGCCTGCGCTGCGAGCACTTCC----------------CGCCGAGCAGATCTGCGTCGGCCAGAACCACTCAGGACGGAGCT | 206 |
| 875 | 0.001141005 | 0.650636094 | TTCCTGTGCTCCATGTACGCACCCGTGTGCACCGTGCTGGAACAGGCCATCCCGCCGTGCCGCTCTATCTGTGAGCGCGCGCGCCAGGGCTGCGAAGCCCTCATGAACAAGTTCGGTTTTCAGTGGCCCGAGCGCCTGCGCTGCGAGCACTTC------------------GAGCAGATCTGCGTCGGCCAGAACCACTCCGAGGACGGAGCT | 207 |
| 875 | 0.001141005 | 0.651777099 | TTCCTGTGCTCCATGTACGCACCCGTGTGCACCGTGCTGGAACAGGCCATCCCGCCG--------------------------------------------------------------AGCAGATCTGCGTCGGCCAGAACCACTCCGAGGACGGAGCT | 208 |
| 863 | 0.001125357 | 0.652902455 | TTCCTGTGCTCCATGTACGCACCCGTGTGCACCGTGCTGGAACAGGCCATCCCGCCGTGCCGCTCTATCTGTGAGC--GCGCGCCAGGGCTGCGAAGCCCTCATGAACAAGTTCGGTTTTCAGTGGCCCGAGCGCCTGCGCTGCGAGCACTTCCCGCGCCGAGCAGATCTGCGTCGGCCAGAACCACTCCGAGGACGGAGCT | 209 |
| 852 | 0.001111013 | 0.654013468 | TTCCTGTGCTCCATGTACGCACCCGTGTGCACCGTGCTGGAACAGGCCATCCCGCCGTGCCGCTCTATCTGTGAGCGCGCGCGCCA-GGCTGCGAAGCCCTCATGAACAAGTTCGGTTTTCAGTGGCCCGAGCGCCTGCGCTGCGAGCACTTCCCGCGC-----------------CGAGCAGATCTGCGTCGGCCAGAACCACTCCGAGGACGGAGCT | 210 |
| 838 | 0.001092757 | 0.655106224 | TTCCTGTGCTCCATGTACGCACCCGTGTGCACCGTGCTGGAACAGGCCATCCCGCCGTGCCGCTCTATCTGTGAGCGCGCGCGCCAGGGCTGCGAAGCCCTCATGAACAAGTTCGGTTTTCAGTGGCCCGAGCGCCTGCGCTGCGAGCACTTCCCGCGCGCCA--------CGGCGCCGAGCAGATCTGCGTCGGCCAGAACCACTCCGAGGACGGAGCT | 211 |
| 836 | 0.001090149 | 0.656196373 | TTCCTGTGCTCCATGTACGCACCCGTGTGCACCGTGCTGGAACAGGCCATCCCGCCGTGCCGCTCTATCTGTGAGCGCGCGCGCCAGGGCTGCGAAGCCCTCATGAACAAGTTCGGTTTTCAGTGGCCCGAGCGCCTGCGCTGCGAGCACTTCCCGCTCG-------------GCGCCGTGCAGATCTGCGTCGGCCAGAACCACTCCGAGGACGGAGCT | 212 |

TABLE 2-continued

FZD2

WT sequence:
TTCCTGTGCTCCATGTACGCACCCGTGTGCACCGTGCTGGAACAGGCCATCCCGCCGTGCCGCTCTATC
TGTGAGCGCGCGCGCCAGGGCTGCGAAGCCCTCATGAACAAGTTCGGTTTTCAGTGGCCCGAGCGCCT
GCGCTGCGAGCACTTCCCGCGCCAC----------
GGCGCCGAGCAGATCTGCGTCGGCCAGAACCACTCCGAGGACGGAGCT (SEQ ID NO: 131)

| Reads | Fraction | Fraction Cum_Sum | Seq | SEQ ID NO: |
|---|---|---|---|---|
| 782 | 0.001019732 | 0.657216105 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGGGCA-GA---- TCCACGGCGCCGAGCAGATCTGCGTCGGCCAGAAC CACTCCGAGGACGGAGCT | 213 |
| 697 | 0.000908892 | 0.658124997 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCG--------------------------- CCGAGCAGATCTGCGTCGGCCAGAACCACTCCGAG GACGGAGCT | 214 |
| 697 | 0.000908892 | 0.659033888 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCC------------------- CGAGCAGATCTGCGTCGGCCAGAACCACTCAGAG GACGGAGCT | 215 |
| 690 | 0.000899764 | 0.659933652 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGCGC--------------- CGAGCAGATCTGCGTCGGCCGGAACCACTCC GAGGACGGAGCT | 216 |
| 686 | 0.000894548 | 0.6608282 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTC----------------------- TGCGTCGGCCAGAACCACTCCGAGGACGGAGCT | 217 |
| 680 | 0.000886724 | 0.661714924 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCAAGCACTTCCCGCGCCAG-- ATCTGCTCGGCGCCGTGGAGATCTGCGTCGGCCAG AACCACTCCGAGGACGGAGCT | 218 |
| 660 | 0.000860644 | 0.662575567 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACG--------------- TCCACGGCGCCGAGCAGATCTGCGTCGGCCAGAAC CACTCCGAGGACGGAGCT | 219 |
| 659 | 0.00085934 | 0.663434907 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGCG------------------ AGCAGATCTGCGTCGGCCAGAACCACTCAGAGGA CG GAGCT | 220 |
| 657 | 0.000856732 | 0.664291638 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGC-------------------------- | 221 |

TABLE 2-continued

FZD2

WT sequence:
TTCCTGTGCTCCATGTACGCACCCGTGTGCACCGTGCTGGAACAGGCCATCCCGCCGTGCCGCTCTATC
TGTGAGCGCGCGCGCCAGGGCTGCGAAGCCCTCATGAACAAGTTCGGTTTTCAGTGGCCCGAGCGCCT
GCGCTGCGAGCACTTCCCGCGCCAC----------
GGCGCCGAGCAGATCTGCGTCGGCCAGAACCACTCCGAGGACGGAGCT (SEQ ID NO: 131)

| Reads | Fraction | Fraction Cum_Sum | Seq | SEQ ID NO: |
|---|---|---|---|---|
| | | | AGATCTGCGTCGGCCAGAACCACTCAGAGGACGG AGCT | |
| 594 | 0.000774579 | 0.665066217 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGC--------------------- CACGGCGCCGAGCAGATCTGCGTCGGCCAGAACC ACTCCGAGGACGGAGCT | T. |
| 582 | 0.000758931 | 0.665825149 | TTCCTGTGCTCCATGTACGC----------------------- ------------------------------------------------- ------------------------------------------------- CGAGCAGATCTGCGTCGGCCAGAACCACTCCGAG GACGGAGCT | 223 |
| 580 | 0.000756323 | 0.666581472 | TTCCTGTGCTCCATGTACGCACCCGTGTGCACCGT GCTGGAACAGGCCATCCCGCCGTGCCGCTCTATCT GTGAGCGCGCGCGCCAGGGCTGCGGAGCCCTCAT GAACAAGTTCGGTTTTCAGTGGCCCGAGCGCCTGC GCTGCGAGCACTTC----------------------- CCGCGCCGAGCAGATCTGCGTCGGCCAGAACCACT CCGAGGACGGAGCT | 224 |
| 577 | 0.000752411 | 0.667333883 | TTCCTGTGCTCCATGTACGCACCCGTGTGCACCGT GCTGGAACAGGCCATCCCGCCGTGCCGCTCTATCT GTGAGAGCGCGCGCCAGGGCTGCGAAGCCCTCAT GAACAAGTTCGGTTTTCAGTGGCCCGAGCGCCTGC GCTGCGAGCAC-----------T---- TCCACGGCGCCGAGCAGATCTGCGTCGGCCAGAGC CACTCCGAGGACGGAGCT | 225 |
| 564 | 0.000735459 | 0.668069342 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCGCT------------T---- CCCACGGCGCCGAGCAGATCTGCGTCGGCCAGAA CCACTCCGAGGACGGAGCT | 226 |
| 564 | 0.000735459 | 0.668804801 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GC-------------------------- CGAGCAGATCTGCGTCGGCCAGAACCACTCCGAG GACGGAGCT | 227 |
| 562 | 0.000732851 | 0.669537652 | TTCCTGTGCTCCATGTACGCACCCGTGTGCACCGT GCTGGAACAGGCCATCCCGCCGTGCCGCTCTATCT GTGAGC---------------------------------- -------------------------------------------- AGATCTGCGTCGGCCAGAACCACTCCGAGGACGG AGCT | 228 |
| 552 | 0.000719811 | 0.670257463 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAA- CCCTCATGAACAAGTTCGGTTTTCAGTGGCCCGAG CGCCTGCGCTGCGAGCACTTC----------------------- ----------------------- TGCGTCGGCCAGAACCACTCCGAGGACGGAGCT | 229 |
| 551 | 0.000718507 | 0.67097597 | TTCCTGTGCTCCATGTACGCACCCGTGTGCACCGT GCTGGAACAGGCCATCCCGCCGTGCCGCTCTATCT GTGAGCGCGCGCGCCAGGGCTGCGAAGCCCTCAT GAACAAGTTCGGTTTTCAGTGGCCCGAGCGCCTGC GCTGCGAGCACTTCCCGCGGC---------------- | 230 |

TABLE 2-continued

FZD2

WT sequence:
TTCCTGTGCTCCATGTACGCACCCGTGTGCACCGTGCTGGAACAGGCCATCCCGCCGTGCCGCTCTATC
TGTGAGCGCGCGCGCCAGGGCTGCGAAGCCCTCATGAACAAGTTCGGTTTTCAGTGGCCCGAGCGCCT
GCGCTGCGAGCACTTCCCGCGCCAC----------
GGCGCCGAGCAGATCTGCGTCGGCCAGAACCACTCCGAGGACGGAGCT (SEQ ID NO: 131)

| Reads | Fraction | Fraction Cum_Sum | Seq | SEQ ID NO: |
|---|---|---|---|---|
| | | | GCCGAGCAGATCTGCGTCGGTCAGAACCACTCCGAGGACGGAGCT | |
| 546 | 0.000711987 | 0.671687957 | TTCCTGTGCTCCATGTACGCACCCGTGTGCACCGTGCTGGAACAGGCCATCCCGCCGTGCCGCTCTATCTGTGAGCGCGCGCGCCAGGGCTGCGAAGCCCTCATGAACAAGTTCGGTTTTCAGTGGCCCGAGCGCCTGCGCTGCGAGCAC---------------T----TCCACGGCGCCGAGCAGATCTGCGTCGGCCAGAGCCACTCCGAGGACGGAGCT | 231 |

TABLE 3

UGP2

WT Sequence:
AATTTTCATTGTAACAACATACCTTTAATGAAACATTTTTTTCCAAATGTCACATCTCCTGAAACTGTGA
GGTGATCCAATTCAAGCAT--------A-
TCTGGTATACTTTCAAATCTTCTTAGATAATCTTGAACCTTACAGAAA
AGGAGAAACATAAAAATTTGTCTCAAATGGGTTCAAAGAAAGACAGGAAAAATATTAACAAGAAAG
TTTAACTGAACTGTAGAAACCTTTTTTGGCAAAGCTCAGGTCCTCT (SEQ ID NO: 232)

| Reads | Fraction | Fraction Cum_Sum | Seq | SEQ ID NO: |
|---|---|---|---|---|
| 295658 | 0.302416711 | 0.302416711 | AATTTTCATTGTAACAACATACCTTTAATGAAACATTTTTTTCCAAATGTCACATCTCCTGAAACTGTGAGGTGATCCAATTCAAGCAT----------TCTGGTATACTTTCAAATCTTCTTAGATAATCTTGAACCTTACAGAAAAGGAGAAACATAAAAATTTGTCTCAAATGGGTTCAAAGAAAGACAGGAAAAATATTAACAAGAAAGTTTAACTGAACTGTAGAAACCTTTTTTGGCAAAGCTCAGGTCCTCT | 233 |
| 196681 | 0.201177107 | 0.503593818 | AATTTTCATTGTAACAACATACCTTTAATGAAACATTTTTTTCCAAATGTCACATCTCCTGAAACTGTGAGGTGATCCAATTCAAGCATATACTTGAATTCTGGTATACTTTCAAATCTTCTTAGATAATCTTGAACCTTACAGAAAAGGAGAAACATAAAAATTTGTCTCAAATGGGTTCAAAGAAAGACAGGAAAAATATTAACAAGAAAGTTTAACTGAACTGTAGAAACCTTTTTTGGCAAAGCTCAGGTCCTCT | 234 |
| 178981 (WT) | 0.183072487 | 0.686666305 | AATTTTCATTGTAACAACATACCTTTAATGAAACATTTTTTTCCAAATGTCACATCTCCTGAAACTGTGAGGTGATCCAATTCAAGCAT--------A-TCTGGTATACTTTCAAATCTTCTTAGATAATCTTGAACCTTACAGAAAAGGAGAAACATAAAAATTTGTCTCAAATGGGTTCAAAGAAAGACAGGAAAAATATTAACAAGAAAGTTTAACTGAACTGTAGAAACCTTTTTTGGCAAAGCTCAGGTCCTCT | 235 |
| 1354 | 0.001384952 | 0.688051258 | AATTTTCATTGTAACAACATACCTTTAATGAAACATTTTTTTCCAAATGTCACATCTCCTGAAACTGTGAGGTGATCCAATTCAAGCAT----------TCTGGTATACTTTCAAATCTTCTTAGATAATCTTGAACCTTACAGAAAAGGAGAAACATAAAAATTTGTCTCAAATGGGTTCAAAGAAAGACAGGAAAAATATTAACAAGAAAGTTTAACTGAACTGTAGAAACCTTTTTTGGCAAAGCTCAGGTCCTCT | 236 |
| 1142 | 0.001168106 | 0.689219364 | AATTTTCATTGTAACAACATACCTTTAATGAAACATTTTTTTCCAAATGTCACATCTCCTGAAACTGTGAGGTGATCCAATTCAAGCAT----------TCTGGTATACTTTCAAATCTTCTTAGATAATCTTGAACCTTACAGAAAAGGAGAAACATAAAAATTTGTCT | 237 |

TABLE 3-continued

UGP2

WT Sequence:
AATTTTCATTGTAACAACATACCTTTAATGAAACATTTTTTCCAAATGTCACATCTCCTGAAACTGTGA
GGTGATCCAATTCAAGCAT--------A-
TCTGGTATACTTTCAAATCTTCTTAGATAATCTTGAACCTTACAGAAA
AGGAGAAACATAAAAATTTGTCTCAAATGGGTTCAAAGAAAGACAGGAAAAATATTAACAAGAAAG
TTTAACTGAACTGTAGAAACCTTTTTGGCAAAGCTCAGGTCCTCT (SEQ ID NO: 232)

| Reads | Fraction | Fraction Cum_Sum | Seq | SEQ ID NO: |
|---|---|---|---|---|
| | | | CAAATGGGTTCAAAGAAGGACAGGAAAAATATTA<br>ACAAGAAAGTTTAACTGAACTGTAGAAACCTTTTT<br>TGGCAAAGCTCAGGTCCTCT | |
| 998 | 0.001020814 | 0.690240178 | AATTTTCATTGTAACAACATACCTTTAATGAAACA<br>TTTTTTCCAAATGTCACATCTCCTGAAACTGTGAGG<br>TGATCCAATTCAAGCAT----------<br>TCTGGTATACTTTCAAATCTTCTTAGATAATCTTGA<br>ACCTTACAGAAAAGGAGAAACATAAAAATTTGTCT<br>CAAATGGGTTCAAAGAAAGACAGGAAAAATATTA<br>ACAAGAAAGTTTAACTGAACTGTAGAAGCCTTTTT<br>TGGCAAAGCTCAGGTCCTCT | 238 |
| 992 | 0.001014677 | 0.691254855 | AATTTTCATTGTAACAACATACCTTTAATGAAACA<br>TTTTTTCCAAATGTCACATCTCCTGAAACTGTGAGG<br>TGATCCAATTCAAGCAT----------<br>TCTGGTATACTTTCAAATCTTCTTAGATAATCTTGA<br>ACCTTACAGAAAAGGAGAAACATAAAAATTTGTCT<br>CAAATGGGTTCAAGGAAAGACAGGAAAAATATTA<br>ACAAGAAAGTTTAACTGAACTGTAGAAACCTTTTT<br>TGGCAAAGCTCAGGTCCTCT | 239 |
| 990 | 0.001012631 | 0.692267486 | AATTTTCATTGTAACAACATACCTTTAATGAAACA<br>TTTTTTCCAAATGTCACATCTCCTGAAACTGTGAGG<br>TGATCCAATTCAAGCAT----------<br>TCTGGTATACTTTCAAATCTTCTTAGATAATCTTGA<br>ACCTTACAGAAAAGGAGAAACATAAAAATTTGTCT<br>CAAATGGGTTCAAAGAAAGACAGGAAAAATATTA<br>ACAAGAAAGTTTAACTGAGCTGTAGAAACCTTTTT<br>TGGCAAAGCTCAGGTCCTCT | 240 |
| 971 | 0.000993197 | 0.693260683 | AATTTTCATTGTAACAACATACCTTTAATGAAACA<br>TTTTTTCCAAATGTCACATCTCCTGAAACTGTGAGG<br>TGATCCAATTCAA--------------<br>TCTGGTATACTTTCAAATCTTCTTAGATAATCTTGA<br>ACCTTACAGAAAAGGAGAAACATAAAAATTTGTCT<br>CAAATGGGTTCAAAGAAAGACAGGAAAAATATTA<br>ACAAGAAAGTTTAACTGAACTGTAGAAACCTTTTT<br>TGGCAAAGCTCAGGTCCTCT | 241 |
| 971 | 0.000993197 | 0.69425388 | AATTTTCATTGTAACAACATACCTTTAATGAAACA<br>TTTTTTCCAAATGTCACATCTCCTGAAACTGTGAGG<br>TGATCCAATTCAAGCAT----------<br>TCTGGTATACTTTCAAATCTTCTTAGATAATCTTGA<br>GCCTTACAGAAAAGGAGAAACATAAAAATTTGTCT<br>CAAATGGGTTCAAAGAAAGACAGGAAAAATATTA<br>ACAAGAAAGTTTAACTGAACTGTAGAAACCTTTTT<br>TGGCAAAGCTCAGGTCCTCT | 242 |
| 950 | 0.000971717 | 0.695225597 | AATTTTCATTGTAACAACATACCTTTAATGAAACA<br>TTTTTTCCAAATGTCACATCTCCTGAAACTGTGAGG<br>TGATCCAATTCAAGC----------<br>ATTCTGGTATACTTTCAAATCTTCTTAGATAATCTT<br>GAACCTTACAGAAAAGGAGAAACATAAAAATTTG<br>TCTCAAATGGGTTCAAAGAAAGGCAGGAAAAATA<br>TTAACAAGAAAGTTTAACTGAACTGTAGAAACCTT<br>TTTGGCAAAGCTCAGGTCCTCT | 243 |
| 942 | 0.000963534 | 0.696189131 | AATTTTCATTGTAACAACATACCTTTAATGAAACA<br>TTTTTTCCAAATGCCACATCTCCTGAAACTGTGAG<br>GTGATCCAATTCAAGC----------<br>ATTCTGGTATACTTTCAAATCTTCTTAGATAATCTT<br>GAACCTTACAGAAAAGGAGAAACATAAAAATTTG<br>TCTCAAATGGGTTCAAAGAAAGACAGGAAAAATA<br>TTAACAAGAAAGTTTAACTGAACTGTAGAAACCTT<br>TTTGGCAAAGCTCAGGTCCTCT | 244 |

TABLE 3-continued

UGP2

WT Sequence:
AATTTTCATTGTAACAACATACCTTTAATGAAACATTTTTTCCAAATGTCACATCTCCTGAAACTGTGA
GGTGATCCAATTCAAGCAT--------A-
TCTGGTATACTTTCAAATCTTCTTAGATAATCTTGAACCTTACAGAAA
AGGAGAAACATAAAAATTTGTCTCAAATGGGTTCAAAGAAAGACAGGAAAAATATTAACAAGAAAG
TTTAACTGAACTGTAGAAACCTTTTTTGGCAAAGCTCAGGTCCTCT (SEQ ID NO: 232)

| Reads | Fraction | Fraction Cum_Sum | Seq | SEQ ID NO: |
|---|---|---|---|---|
| 939 | 0.000960465 | 0.697149596 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGATAATCTTGA ACCTTACAGAAAAGGAGAAACATAAAAATTTGTCT CAAATGGGTTCAAAGAAAGACGGGAAAAATATTA ACAAGAAAGTTTAACTGAACTGTAGAAACCTTTTT TGGCAAAGCTCAGGTCCTCT | 245 |
| 914 | 0.000934894 | 0.69808449 | AATTTTCATTGTAACAACATACCTTTAATGAAACA TTTTTTCCAAATGTCACATCTCCTGAAACTGTGAGG TGATCCAATTCAAGC---------- ATTCTGGTATACTTTCAAATCTTCTTAGATAATCTT GAACCTTACAGAAAAGGAGAAACATAAAAATTTG CCTCAAATGGGTTCAAAGAAAGACAGGAAAAATA TTAACAAGAAAGTTTAACTGAACTGTAGAAACCTT TTTTGGCAAAGCTCAGGTCCTCT | 246 |
| 898 | 0.000918528 | 0.699003018 | AATTTTCATTGTAACAACATACCTTTAATGAAACA TTTTTTCCAAATGTCACATCTCCTGAAACTGTGAGG TGATCCAATTCAAGC---------- ATTCTGGTATACTTTCAAATCTTCTTAGATAATCTT GAACCTTACAGAAAAGGAGAAGCATAAAAATTTG TCTCAAATGGGTTCAAAGAAAGACAGGAAAAATA TTAACAAGAAAGTTTAACTGAACTGTAGAAACCTT TTTTGGCAAAGCTCAGGTCCTCT | 247 |
| 886 | 0.000906254 | 0.699909272 | AATTTTCATTGTAACAACATACCTTTAATGAAACA TTTTTTCCAAATGTCACATCTCCTGAAACTGTGAGG TGATCCAATTCAAGC---------- ATTCTGGTATACTTTCAAATCTTCTTAGATAATCTT GAACCTTACAGAAAAGGAGAAACATAAAAATTTG TCTCAAATGGGTTCAAAGAAAGACAGGAAAAATA TTAACAAGAAGGTTTAACTGAACTGTAGAAACCTT TTTTGGCAAAGCTCAGGTCCTCT | 248 |
| 880 | 0.000900117 | 0.700809389 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGATAATCTTGA ACCTTACAGAAAAGGAGAAACATAAAAATTTGTCT CAAATGGGCTCAAAGAAAGACAGGAAAAATATTA ACAAGAAAGTTTAACTGAACTGTAGAAACCTTTTT TGGCAAAGCTCAGGTCCTCT | 249 |
| 875 | 0.000895002 | 0.701704391 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGATAATCTTGA ACCTTACAGAGAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 250 |
| 874 | 0.00089398 | 0.702598371 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGATAATCTTGA ACCTTACGGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 251 |
| 857 | 0.000876591 | 0.703474962 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGATAATCTTGA ACCTTACAGAAAAGGAGAAACATAAAAATTTGTCT | 252 |

TABLE 3-continued

UGP2

WT Sequence:
AATTTTCATTGTAACAACATACCTTTAATGAAACATTTTTTCCAAATGTCACATCTCCTGAAACTGTGA
GGTGATCCAATTCAAGCAT--------A-
TCTGGTATACTTTCAAATCTTCTTAGATAATCTTGAACCTTACAGAAA
AGGAGAAACATAAAAATTTGTCTCAAATGGGTTCAAAGAAAGACAGGAAAAATATTAACAAGAAAG
TTTAACTGAACTGTAGAAACCTTTTTGGCAAAGCTCAGGTCCTCT (SEQ ID NO: 232)

| Reads | Fraction | Fraction Cum_Sum | Seq | SEQ ID NO: |
|---|---|---|---|---|
| | | | CAAATGGGTTCAAAGAAAGACAGGAAAAATATTA ACAAGAAAGTTTAACTGAACTGTAGAGACCTTTTT TGGCAAAGCTCAGGTCCTCT | |
| 847 | 0.000866362 | 0.704341324 | AATTTTCATTGTAACAACATACCTTTAATGAAACA TTTTTTCCAAATGTCACATCTCCTGAAACTGTGAGG TGATCCAATTCAAGC---------- ATTCTGGTATACTTTCAAATCTTCTTAGATAATCTT GAACCTTACAGAAAGGAGGAACATAAAAATTTG TCTCAAATGGGTTCAAAGAAAGACAGGAAAAATA TTAACAAGAAAGTTTAACTGAACTGTAGAAACCTT TTTTGGCAAAGCTCAGGTCCTCT | 253 |
| 847 | 0.000866362 | 0.705207687 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGATAATCTTGA ACCTTACAGAAAAGGAGAAACATAAAAATTTGTCT CAAATGGGTCCAAAGAAAGACAGGAAAAATATTA ACAAGAAAGTTTAACTGAACTGTAGAAACCTTTTT TGGCAAAGCTCAGGTCCTCT | 254 |
| 846 | 0.000865339 | 0.706073026 | AATTTTCATTGTAACAACATACCTTTAATGAAACA TTTTTTCCAAATGTCACATCTCCTGAAACTGTGAGG TGATCCAATTCAAGC---------- ATTCTGGTATACTTTCAAATCTTCTTAGATAATCTT GAACCTTACAGAAAAGGAGAAACATAAAAATTTG TCTCAAATGGGTTCAAAGAGAGACAGGAAAAATA TTAACAAGAAAGTTTAACTGAACTGTAGAAACCTT TTTTGGCAAAGCTCAGGTCCTCT | 255 |
| 842 | 0.000861248 | 0.706934274 | AATTTTCATTGTAACAACATACCTTTAATGAAACA TTTTTTCCAAATGTCACATCTCCTGAAACTGTGAGG TGATCCAATTCAAGCATATACTTGAATTCTGGTAT ACTTTCAAATCTTCTTAGATAATCTTGAACCTTACA GAAAGGGAGAAACATAAAAATTTGTCTCAAATGG GTTCAAAGAAAGACAGGAAAAATATTAACAAGAA AGTTTAACTGAACTGTAGAAACCTTTTTGGCAAA GCTCAGGTCCTCT | 256 |
| 837 | 0.000856134 | 0.707790408 | AATTTTCATTGTAACAACATACCTTTAATGAAACA TTTTTTCCAAATGTCACATCTCCTGAAACTGTGAGG TGATCCAATTCAAGC---------- ATTCTGGTATACCTTCAAATCTTCTTAGATAATCTT GAACCTTACAGAAAAGGAGAAACATAAAAATTTG TCTCAAATGGGTTCAAAGAAAGACAGGAAAAATA TTAACAAGAAAGTTTAACTGAACTGTAGAAACCTT TTTTGGCAAAGCTCAGGTCCTCT | 257 |
| 834 | 0.000853065 | 0.708643473 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGATAATCTTGA ACCTTACAGAAAAGGAGAAACATAAAAATTTGTCT CAAATGGGTTCAAAGAAAGACAGGAAAAATATTA ACAAGAAAGTTTAACTGAACTGTAGAAACC- TTTTTGGCAAAGCTCAGGTCCTCT | 258 |
| 833 | 0.000852042 | 0.709495515 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGATAATCTTGA ACCTTACAGAAAAGGAGAAACATAAAAATTTGTCT CAAATGGGTTCAAAGAAAGACAGGAAAAATATTA ACAAGAAAGTTTAACTGAACTGTAGAAACCCTTTT TGGCAAAGCTCAGGTCCTCT | 259 |

TABLE 3-continued

UGP2

WT Sequence:
AATTTTCATTGTAACAACATACCTTTAATGAAACATTTTTTCCAAATGTCACATCTCCTGAAACTGTGA
GGTGATCCAATTCAAGCAT--------A-
TCTGGTATACTTTCAAATCTTCTTAGATAATCTTGAACCTTACAGAAA
AGGAGAAACATAAAAATTTGTCTCAAATGGGTTCAAAGAAAGACAGGAAAAATATTAACAAGAAAG
TTTAACTGAACTGTAGAAACCTTTTTTGGCAAAGCTCAGGTCCTCT (SEQ ID NO: 232)

| Reads | Fraction | Fraction Cum_Sum | Seq | SEQ ID NO: |
|---|---|---|---|---|
| 826 | 0.000844882 | 0.710340398 | AATTTTCATTGTAACAACATACCTTTAATGAAACATTTTTTCCAAATGTCGCATCTCCTGAAACTGTGAGGTGATCCAATTCAAGCAT----------TCTGGTATACTTTCAAATCTTCTTAGATAATCTTGAACCTTACAGAAAAGGAGAAACATAAAAATTTGTCTCAAATGGGTTCAAAGAAAGACAGGAAAAATATTAACAAGAAAGTTTAACTGAACTGTAGAAACCTTTTTTGGCAAAGCTCAGGTCCTCT | 260 |
| 820 | 0.000838745 | 0.711179143 | AATTTTCATTGTAACAACATACCTTTAATGAAACATTTTTTCCAAATGTCACATCTCCTGAAACTGTGAGGTGATCCAATTCAAGCAT----------TCTGGTATACTTTCAAATCTTCTTAGATAATCTTGAACCTTACAGAAAAGGAGAAACATAAAAATTTGTCTCAAATGGGTTCGAAGAAAGACAGGAAAAATATTAACAAGAAAGTTTAACTGAACTGTAGAAACCTTTTTTGGCAAAGCTCAGGTCCTCT | 261 |
| 813 | 0.000831585 | 0.712010728 | AATTTTCATTGTAACAACATACCTTTAATGAAACATTTTTTCCAAATGTCACATCTCCTGAAACTGTGAGGTGATCCAATTCAAGCAT----------TCTGGTATACTTTCAAATCTTCTTAGATAATCTTGAACCTTACAGAAAAGGAGAAACATAAAAATTTGTCTCAAATGGGTTCAAAGAAAGACAGGAAGAATATTAACAAGAAAGTTTAACTGAACTGTAGAAACCTTTTTTGGCAAAGCTCAGGTCCTCT | 262 |
| 804 | 0.000822379 | 0.712833107 | AATTTTCATTGTAACAACATACCTTTAATGAAACATTTTTTCCAAATGTCACATCTCCTGAAACTGTGAGGTGATCCAATTCAAGCAT----------TCTGGTATACTTTCAAATCTTCTTAGATAATCTTGAACCTTACAGAAAAGGAGAAACATAAAAATTTGTCTCAAATGGGTTCAAAGAAAGACAGGAAAAATATTAACAAGAAAGTTTAACTGAACTGTAGGAACCTTTTTTGGCAAAGCTCAGGTCCTCT | 263 |
| 794 | 0.000812151 | 0.713645258 | AATTTTCATTGTAACAACATACCTTTAATGAAACATTTTTTCCAAATGTCACATCTCCTGAAACTGTGAGGTGATCCAATTCAAGCATA---------TCTGGTATACTTTCAAATCTTCTTAGATAATCTTGAACCTTACAGAAAGGGAGAAACATAAAAATTTGTCTCAAATGGGTTCAAAGAAAGACAGGAAAAATATTAACAAGAAAGTTTAACTGAACTGTAGAAACCTTTTTTGGCAAAGCTCAGGTCCTCT | 264 |
| 792 | 0.000810105 | 0.714455363 | AATTTTCATTGTAACAACATACCTTTAATGAAACATTTTTTCCAAATGTCACATCTCCTGAAACTGTGAGGTGATCCAATTCAAGCAT----------TCTGGTATACTTTCAAATCTTCTTAGATAATCTTGAACCTTACAGAAAAGGAGAAACATAAAAATTTGTCTCAAATGGGTTCAAAGAAAGACAGGAAAAATATTAACAAGAAAGTTTAACTGGACTGTAGAAACCTTTTTTGGCAAAGCTCAGGTCCTCT | 265 |
| 786 | 0.000803968 | 0.715259331 | AATTTTCATTGTAACAACATACCTTTAATGAAACATTTTTTCCAAATGTCACATCCCCTGAAACTGTGAGGTGATCCAATTCAAGCAT----------TCTGGTATACTTTCAAATCTTCTTAGATAATCTTGAACCTTACAGAAAAGGAGAAACATAAAAATTTGTCTCAAATGGGTTCAAAGAAAGACAGGAAAAATATTAACAAGAAAGTTTAACTGAACTGTAGAAACCTTTTTTGGCAAAGCTCAGGTCCTCT | 266 |
| 750 | 0.000767145 | 0.716026476 | AATTTTCATTGTAACAACATACCTTTAATGAAACATTTTTTCCAAATGTCACATCTCCTGAAACTGTGAGGTGATCCAATTCAAGCAT----------TCTGGTATACTTTCAAATCTTCTTAGATAATCTTGAACCTTACAGAAAAGGAGAAACATAAAAATTTGTCT | 267 |

TABLE 3-continued

UGP2

WT Sequence:
AATTTTCATTGTAACAACATACCTTTAATGAAACATTTTTTCCAAATGTCACATCTCCTGAAACTGTGA
GGTGATCCAATTCAAGCAT--------A-
TCTGGTATACTTTCAAATCTTCTTAGATAATCTTGAACCTTACAGAAA
AGGAGAAACATAAAAATTTGTCTCAAATGGGTTCAAAGAAAGACAGGAAAAATATTAACAAGAAAG
TTTAACTGAACTGTAGAAACCTTTTTGGCAAAGCTCAGGTCCTCT (SEQ ID NO: 232)

| Reads | Fraction | Fraction Cum_Sum | Seq | SEQ ID NO: |
|---|---|---|---|---|
| | | | CAAATGGGTTCAAAGAAAGACAGGAAAAATATTA ACAAGGAAGTTTAACTGAACTGTAGAAACCTTTTT TGGCAAAGCTCAGGTCCTCT | |
| 746 | 0.000763053 | 0.716789529 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGATAATCTTGA ACCTTACAGAAAGGAGAAACATAAAAATTTGTCT CAAATGGGTTCAAAGGAAGACAGGAAAAATATTA ACAAGAAAGTTTAACTGAACTGTAGAAACCTTTTT TGGCAAAGCTCAGGTCCTCT | 268 |
| 745 | 0.000762031 | 0.71755156 | AATTTTCATTGTAACAACATACCTTTAATGAAACA TTTTTTCCAAATGTCACATCTCCTGAAACTGTGGGG TGATCCAATTCAAGCAT---------- TCTGGTATACTTTCAAATCTTCTTAGATAATCTTGA ACCTTACAGAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 269 |
| 733 | 0.000749756 | 0.718301316 | AATTTTCATTGTAACAACATACCTTTAATGAAACA TTTTTTCCAAATGTCACATCTCCTGAAACTGTGAGG TGATCCAATTCAAGCATATACTTGAATTCTGGTAT ACTTTCAAATCTTCTTAGATAATCTTGAACCTTACA GAAAAGGAGAAACATAAAAATTTGTCTCAAATGG GTTCAAAGAAGGACAGGAAAAATATTAACAAGAA AGTTTAACTGAACTGTAGAAACCTTTTTGGCAAA GCTCAGGTCCTCT | 270 |
| 730 | 0.000746688 | 0.719048004 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGATAATCTTGA ACCTTACAGAAGAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 271 |
| 718 | 0.000734413 | 0.719782417 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGATAATCTTGA ACCTTACAGAAAAGGAGAAACATAAAAATTTGTCT CAAATGGGTTCAAAGAAAGACAGGGAAAAATATTA ACAAGAAAGTTTAACTGAACTGTAGAAACCTTTTT TGGCAAAGCTCAGGTCCTCT | 272 |
| 707 | 0.000723162 | 0.720505579 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGATAATCTTGA ACCTTACAGAAAAGGAGAAACATAAAAATTCGTC TCAAATGGGTTCAAAGAAAGACAGGAAAAATATT AACAAGAAAGTTTAACTGAACTGTAGAAACCTTTT TTGGCAAAGCTCAGGTCCTCT | 273 |
| 707 | 0.000723162 | 0.721228741 | AATTTTCATTGTAACAACATACCTTTAATGAAACA TTTTTTCCAAATGTCACATCTCCTGAAACTGCGAG GTGATCCAATTCAAGCAT---------- TCTGGTATACTTTCAAATCTTCTTAGATAATCTTGA ACCTTACAGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 274 |

TABLE 3-continued

UGP2

WT Sequence:
AATTTTCATTGTAACAACATACCTTTAATGAAACATTTTTTCCAAATGTCACATCTCCTGAAACTGTGA
GGTGATCCAATTCAAGCAT--------A-
TCTGGTATACTTTCAAATCTTCTTAGATAATCTTGAACCTTACAGAAA
AGGAGAAACATAAAAATTTGTCTCAAATGGGTTCAAAGAAAGACAGGAAAAATATTAACAAGAAAG
TTTAACTGAACTGTAGAAACCTTTTTTGGCAAAGCTCAGGTCCTCT (SEQ ID NO: 232)

| Reads | Fraction | Fraction Cum_Sum | Seq | SEQ ID NO: |
|---|---|---|---|---|
| 704 | 0.000720093 | 0.721948835 | AATTTTCATTGTAACAAAATACCTTTAATGAAACA TTTTTTCCAAATGTCACATCTCCTGAAACTGTGAGG TGATCCAATTCAAGCAT---------- TCTGGTATACTTTCAAATCTTCTTAGATAATCTTGA ACCTTACAGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 275 |
| 701 | 0.000717025 | 0.722665859 | AATTTTCATTGTAACAACATACCTTTAATGAAACA TTTTTTCCAAATGTCACATCTCCTGAAACTGTGAGG CGATCCAATTCAAGCAT---------- TCTGGTATACTTTCAAATCTTCTTAGATAATCTTGA ACCTTACAGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 276 |
| 699 | 0.000714979 | 0.723380838 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGATAATCTTGA ACCTTACAGAAAAGGAGAAACGTAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 277 |
| 698 | 0.000713956 | 0.724094795 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGATAATCTTGA ACCTTACAGAAAAGGGGAAACATAAAAATTTGTCT CAAATGGGTCAAAGAAAGACAGGAAAAATATTA ACAAGAAAGTTTAACTGAACTGTAGAAACCTTTTT TGGCAAAGCTCAGGTCCTCT | 278 |
| 696 | 0.00071191 | 0.724806705 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGATAATCTTGA ACCTTACAGAAAAGGAGAAACATAAAAATTTGTC CCAAATGGGTTCAAAGAAAGACAGGAAAAATATT AACAAGAAAGTTTAACTGAACTGTAGAAACCTTTT TTGGCAAAGCTCAGGTCCTCT | 279 |
| 696 | 0.00071191 | 0.725518616 | AATTTTCATTGTAACAACATACCTTTAATGAAACA TTTTTTCCAAATGTCACACCTCCTGAAACTGTGAG GTGATCCAATTCAAGCAT---------- TCTGGTATACTTTCAAATCTTCTTAGATAATCTTGA ACCTTACAGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 280 |
| 689 | 0.00070475 | 0.726223366 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGATAATCTTGG ACCTTACAGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 281 |
| 681 | 0.000696568 | 0.726919934 | AATTTTCATTGTAACAACATACCTTTAATGAAACA TTTTTTCCAAATGTCACATCTCCTGAAACTGTGAGG TGATCCAATTCAAGCATA--------- TCTGGTATACTTTCAAATCTTCTTAGATAATCTTGA ACCTTACAGAAAAGGAGAAACATAAAAATTTGTCT | 282 |

TABLE 3-continued

UGP2

WT Sequence:
AATTTTCATTGTAACAACATACCTTTAATGAAACATTTTTTCCAAATGTCACATCTCCTGAAACTGTGA
GGTGATCCAATTCAAGCAT--------A-
TCTGGTATACTTTCAAATCTTCTTAGATAATCTTGAACCTTACAGAAA
AGGAGAAACATAAAAATTTGTCTCAAATGGGTTCAAAGAAAGACAGGAAAAATATTAACAAGAAAG
TTTAACTGAACTGTAGAAACCTTTTTTGGCAAAGCTCAGGTCCTCT (SEQ ID NO: 232)

| Reads | Fraction | Fraction Cum_Sum | Seq | SEQ ID NO: |
|---|---|---|---|---|
| | | | CAAATGGGTTCAAAGAAGGACAGGAAAAATATTA ACAAGAAAGTTTAACTGAACTGTAGAAACCTTTTT TGGCAAAGCTCAGGTCCTCT | |
| 670 | 0.000685316 | 0.72760525 | AATTTTCATTGTAACAACATACCTTTAATGAAACA TTTTTTCCAAATGTCACATCTCCTGAAACTGTGAGG TGATCCAATTCAAGCATATACTTGAATTCTGGTAT ACTTTCAAATCTTCTTAGATAATCTTGAACCTTACA GAAAAGGAGAAACATAAAAATTTGTCTCAAATGG GCTCAAAGAAAGACAGGAAAAATATTAACAAGAA AGTTTAACTGAACTGTAGAAACCTTTTTTGGCAAA GCTCAGGTCCTCT | 283 |
| 667 | 0.000682248 | 0.728287497 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGATAATCTTGA ACCTTACAGAAAAGGAGAAACATAAAAATTTGTCT CAAGTGGGTTCAAAGAAAGACAGGAAAAATATTA ACAAGAAAGTTTAACTGAACTGTAGAAACCTTTTT TGGCAAAGCTCAGGTCCTCT | 284 |
| 664 | 0.000679179 | 0.728966676 | AATTTTCATTGTAACAACATACCTTTAATGAAACA TTTTTTCCAAATGTCACATCTCCTGAAACCGTGAG GTGATCCAATTCAAGCAT---------- TCTGGTATACTTTCAAATCTTCTTAGATAATCTTGA ACCTTACAGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 285 |
| 663 | 0.000678156 | 0.729644832 | AATTTTCATTGTAACAACATACCTTTAATGAAACA TTTTTTCCAAATGTCACGTCTCCTGAAACTGTGAGG TGATCCAATTCAAGCAT---------- TCTGGTATACTTTCAAATCTTCTTAGATAATCTTGA ACCTTACAGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 286 |
| 661 | 0.00067611 | 0.730320943 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGATAATCTTGA ACCTTACAGAAAAGGAGAGACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 287 |
| 661 | 0.00067611 | 0.730997053 | AATTTTCATTGTAACAACATACCTTTAATGAAACA TTTTTTCCAAATGTAACATCTCCTGAAACTGTGAG GTGATCCAATTCAAGCAT---------- TCTGGTATACTTTCAAATCTTCTTAGATAATCTTGA ACCTTACAGAAAAGGAGAAACATAAAAATTTGTCT CAAATGGGTCAAAGAAAGACAGGAAAAATATTA ACAAGAAAGTTTAACTGAACTGTAGAAACCTTTTT TGGCAAAGCTCAGGTCCTCT | 288 |
| 660 | 0.000675088 | 0.731672141 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGATAATCTTGA ACCTTACAGAAAAGGAGAAACATAAAAATTTGTCT CAAATGGGTTCAAAGAAAGACAGGAAAAATATTA ACAAGAAAGTTTAACTGAACCGTAGAAACCTTTTT TGGCAAAGCTCAGGTCCTCT | 289 |

TABLE 3-continued

UGP2

WT Sequence:
AATTTTCATTGTAACAACATACCTTTAATGAAACATTTTTTCCAAATGTCACATCTCCTGAAACTGTGA
GGTGATCCAATTCAAGCAT--------A-
TCTGGTATACTTTCAAATCTTCTTAGATAATCTTGAACCTTACAGAAA
AGGAGAAACATAAAAATTTGTCTCAAATGGGTTCAAAGAAAGACAGGAAAAATATTAACAAGAAAG
TTTAACTGAACTGTAGAAACCTTTTTTGGCAAAGCTCAGGTCCTCT (SEQ ID NO: 232)

| Reads | Fraction | Fraction Cum_Sum | Seq | SEQ ID NO: |
|---|---|---|---|---|
| 658 | 0.000673042 | 0.732345182 | AATTTTCATTGTAACAACATACCTTTAATGAAGCA TTTTTTCCAAATGTCACATCTCCTGAAACTGTGAGG TGATCCAATTCAAGCAT---------- TCTGGTATACTTTCAAATCTTCTTAGATAATCTTGA ACCTTACAGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 290 |
| 651 | 0.000665882 | 0.733011064 | AATTTTCATTGTAACAACATACCTTTAATGAAACA TTTTTTCCAAATGTCACATCTCCTGAAACTGTGAGG TGATCCAATTCGAGCAT---------- TCTGGTATACTTTCAAATCTTCTTAGATAATCTTGA ACCTTACAGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 291 |
| 648 | 0.000662813 | 0.733673877 | AATTTTCATTGTAACAACATACCTTTAATGAAACA TTTTTTCCAAATGTCACATCTCCTGAAACTGTGAGG TGATCCAATTCAAGCATATACTTGAATTCTGGTAT ACTTTCAAATCTTCTTAGATAATCTTGAACCTTACA GAAAAGGAGAAACATAAAAATTTGTCTCAAATGG GTTCAAAGAAAGACAGGAAAAATATTAACAAGAA AGTTTAACTGAGCTGTAGAAACCTTTTTTGGCAAA GCTCAGGTCCTCT | 292 |
| 646 | 0.000660767 | 0.734334645 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGATAACCTTGA ACCTTACAGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 293 |
| 643 | 0.000657699 | 0.734992344 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGATAATCTTGA ACCCTACAGAAAAGGAGAAACATAAAAATTTGTC TCAAATGGGTTCAAAGAAAGACAGGAAAAATATT AACAAGAAAGTTTAACTGAACTGTAGAAACCTTTT TTGGCAAAGCTCAGGTCCTCT | 294 |
| 643 | 0.000657699 | 0.735650043 | AATTTTCATTGTAACAACATACCTTTAATGAAACA TTTTTTCCAAATGTCACATCTCCTGAAACTGTGAGG TGATCCAATTCAAGCATATACTTGAATTCTGGTAT ACTTTCAAATCTTCTTAGATAATCTTGAACCTTACA GAAAAGGAGAAACATAAAAATTTGTCTCAAATGG GTTCAAAGAAAGACAGGAAAAATATTAACAAGAA AGTTTAACTGAACTGTAGAAGCCTTTTTGGCAAA GCTCAGGTCCTCT | 295 |
| 642 | 0.000656676 | 0.736306719 | AATTTTCATTGTAACAACATACCTTTAATGAAACA TTTTTTCCAAATGTCACATCTCCCGAAACTGTGAG GTGATCCAATTCAAGCAT---------- TCTGGTATACTTTCAAATCTTCTTAGATAATCTTGA ACCTTACAGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 296 |
| 638 | 0.000652585 | 0.736959303 | AATTTTCATTGTAACAACATACCTTTAATGAAACA TTTTTTCCAAATGTCACATCTCCTGAGACTGTGAGG TGATCCAATTCAAGCAT---------- TCTGGTATACTTTCAAATCTTCTTAGATAATCTTGA ACCTTACAGAAAAGGAGAAACATAAAAATTTGTCT | 297 |

TABLE 3-continued

| | | UGP2 | | |
|---|---|---|---|---|

WT Sequence:
AATTTTCATTGTAACAACATACCTTTAATGAAACATTTTTTCCAAATGTCACATCTCCTGAAACTGTGA
GGTGATCCAATTCAAGCAT--------A-
TCTGGTATACTTTCAAATCTTCTTAGATAATCTTGAACCTTACAGAAA
AGGAGAAACATAAAAATTTGTCTCAAATGGGTTCAAAGAAAGACAGGAAAAATATTAACAAGAAAG
TTTAACTGAACTGTAGAAACCTTTTTGGCAAAGCTCAGGTCCTCT (SEQ ID NO: 232)

| Reads | Fraction | Fraction Cum_Sum | Seq | SEQ ID NO: |
|---|---|---|---|---|
| | | | CAAATGGGTTCAAAGAAAGACAGGAAAAATATTA ACAAGAAAGTTTAACTGAACTGTAGAAACCTTTTT TGGCAAAGCTCAGGTCCTCT | |
| 638 | 0.000652585 | 0.737611888 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGATAATCTTGA ACCTTACAGAAAAGGAGAAACATAAAAATTTGTCT CAAATGGGTTCAAAGAAAGACAGGAAAAATATTA ACAAGAAAGCTTAACTGAACTGTAGAAACCTTTTT TGGCAAAGCTCAGGTCCTCT | 298 |
| 635 | 0.000649516 | 0.738261404 | AATTTTCATTGTAACAACATACCTTTAATGAAACA TTTTTTCCAAATGTCACATCTCCTGAAACTGTGAGG TGATCCAATTCAAGCATATACTTGAATTCTGGTAT ACTTTCAAATCTTCTTAGATAATCTTGAACCTTACA GAAAAGGAGAAACATAAAAATTTGTCTCAAATGG GTTCAAGGAAAGACAGGAAAAATATTAACAAGAA AGTTTAACTGAACTGTAGAAACCTTTTTGGCAAA GCTCAGGTCCTCT | 299 |
| 633 | 0.00064747 | 0.738908874 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGATAATCTCGA ACCTTACAGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 300 |
| 632 | 0.000646447 | 0.739555322 | AATTTTCATTGTAACAACATACCTTTAATGAAACA TTTTTTCCAAATGTCACATCTCCTGAAACTGTGAGG TGATCCAATTCAAGCATATACTTGAATTCTGGTAT ACTTTCAAATCTTCTTAGATAATCTTGAACCTTACA GAAAAGGAGAAACATAAAAATTTGTCTCAAATGG GTTCAAAGAAAGACGGGAAAAATATTAACAAGAA AGTTTAACTGAACTGTAGAAACCTTTTTGGCAAA GCTCAGGTCCTCT | 301 |
| 631 | 0.000645425 | 0.740200746 | AATTTTCATTGTAACAACATACCTTTAATGAAACA TTTTTTCCAAATGTCACATCTCCTGAAGCTGTGAGG TGATCCAATTCAAGCAT---------- TCTGGTATACTTTCAAATCTTCTTAGATAATCTTGA ACCTTACAGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 302 |
| 629 | 0.000643379 | 0.740844125 | AATTTTCATTGTAACAACATACCTTTAATGAAACA TTTTTTCCAAATGTCACATCTCCTGAAACTGTGAGG TGATCCAATTCAAGCATA---------- TCTGGTATACTTTCAAATCTTCTTAGATAATCTTGA ACCTTACAGAAAAGGAGAAACATAAAAATTTGTCT CAAATGGGTTCAAAGAAAGACAGGAAAAATATTA ACAAGAAAGTTTAACTGAACTGTAGAAGCCTTTTT TGGCAAAGCTCAGGTCCTCT | 303 |
| 627 | 0.000641333 | 0.741485459 | AATTTTCATTGTAACAACATACCTTTAATGAAACA TTTTTTCCAAATGTCACATCTCCTGAAACTGTGAGG TGGTCCAATTCAAGCAT---------- TCTGGTATACTTTCAAATCTTCTTAGATAATCTTGA ACCTTACAGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 304 |

TABLE 3-continued

UGP2

WT Sequence:
AATTTTCATTGTAACAACATACCTTTAATGAAACATTTTTTCCAAATGTCACATCTCCTGAAACTGTGA
GGTGATCCAATTCAAGCAT--------A-
TCTGGTATACTTTCAAATCTTCTTAGATAATCTTGAACCTTACAGAAA
AGGAGAAACATAAAAATTTGTCTCAAATGGGTTCAAAGAAAGACAGGAAAAATATTAACAAGAAAG
TTTAACTGAACTGTAGAAACCTTTTTTGGCAAAGCTCAGGTCCTCT (SEQ ID NO: 232)

| Reads | Fraction | Fraction Cum_Sum | Seq | SEQ ID NO: |
|---|---|---|---|---|
| 624 | 0.000638265 | 0.742123723 | AATTTTCATTGTAACAACATACCTTTAATGAAACATTTTTTCCAAATGTCACATCTCCTGAAACTGTGAGGTGATCCAATTCAAGCATATACTTGAATTCTGGTATACTTTCAAATCTTCTTAGATAATCTTGAGCCTTACAGAAAGGAGAAACATAAAAATTTGTCTCAAATGGGTTCAAAGAAAGACAGGAAAAATATTAACAAGAAAGTTTAACTGAACTGTAGAAACCTTTTTTGGCAAAGCTCAGGTCCTCT | 305 |
| 620 | 0.000634173 | 0.742757896 | AATTTTCATTGTAACAACATACCTTTAATGAAACATTTTTTCCAAATGTCACATCTCCTGAAACTGTGAGGTGATCCAATTCAAGCATATACTTGAATTCTGGTATACTTTCAAATCTTCTTAGATAATCTTGAACCTTACAGAAAGGAGAAGCATAAAAATTTGTCTCAAATGGGTTCAAAGAAAGACAGGAAAAATATTAACAAGAAAGTTTAACTGAACTGTAGAAACCTTTTTTGGCAAAGCTCAGGTCCTCT | 306 |
| 607 | 0.000620876 | 0.743378772 | AATTTTCATTGTAACAACATACCTTTAATGAAACATTTTTTCCAAATGTCACATCTCCTGAAACTGTGAGGTGATCCAATTCAAGCATA----------TCTGGTATACTTTCAAATCTTCTTAGATAATCTTGAACCTTACAGAAAGGAGAAACATAAAAATTTGTCTCAAATGGGTTCAAGGAAAGACAGGAAAAATATTAACAAGAAAGTTTAACTGAACTGTAGAAACCTTTTTTGGCAAAGCTCAGGTCCTCT | 307 |
| 604 | 0.000617807 | 0.74399658 | AATTTTCATTGTAACAACATACCTTTAATGAAACATTTTTTCCAAATGCCACATCTCCTGAAACTGTGAGGTGATCCAATTCAAGCATATACTTGAATTCTGGTATACTTTCAAATCTTCTTAGATAATCTTGAACCTTACAGAAAAGGAGAAACATAAAAATTTGTCTCAAATGGGTTCAAAGAAAGACAGGAAAAATATTAACAAGAAGTTTAACTGAACTGTAGAAACCTTTTTTGGCAAAGCTCAGGTCCTCT | 308 |
| 599 | 0.000612693 | 0.744609273 | AATTTTCATTGTAACAACATACCTTTAATGAAACATTTTTTCCAAATGTCACATCTCCTGAAACTGTGAGGTGATCCAATTCAAGCAT----------TCTGGTATACTTTCAAATCTTCTTAGATAATCTTGAACCTTACAGAAAAGGAGAAACATAAAAATTTGTCTCAAATGGGTTCAAAGAAAGACAGGAAAAATATTAACAAGAAAGTTTAGCTGAACTGTAGAAACCTTTTTTGGCAAAGCTCAGGTCCTCT | 309 |
| 597 | 0.000610647 | 0.74521992 | AATTTTCATTGTAACAACATACCTTTAATGAAACATTTTTTCCAAATGTCACATCTCCTGAAACTGTGAGGTGATCCAATTCAAGCAT----------TCTGGTATACTCTCAAATCTTCTTAGATAATCTTGAACCTTACAGAAAAGGAGAAACATAAAAATTTGTCTCAAATGGGTTCAAAGAAAGACAGGAAAAATATTAACAAGAAAGTTTAACTGAACTGTAGAAACCTTTTTTGGCAAAGCTCAGGTCCTCT | 310 |
| 594 | 0.000607579 | 0.745827499 | AATTTTCATTGTAACAACATACCTTTAATGAAACATTTTTTCCAAATGTCACATCTCCTGAAACTGTGAGGTGATCCAATTCAAGCAT----------TCTGGTATACTTTCAAATCTTCTTAGATAATCTTGAACCTTACAGAAAAGGAGAAACATAAAAATTTGTCTCAAATGGGTTCAAAGAAAGACAGGAAAAATATTAACAAGAAAGTTTAACTGAACTGTGGAAACCTTTTTTGGCAAAGCTCAGGTCCTCT | 311 |
| 585 | 0.000598373 | 0.746425872 | AATTTTCATTGTAACAACATACCTTTAATGAAACATTTTTTCCAAATGTCACATCTCCTGAAACTGTGAGGTGATCCAATTCAAGCATATACTTGAATTCTGGTATACTTTCAAATCTTCTTAGATAATCTTGAACCTTACAGAAAGGAGAAACATAAAAATTTGTCTCAAATGG | 312 |

TABLE 3-continued

UGP2

WT Sequence:
AATTTTCATTGTAACAACATACCTTTAATGAAACATTTTTTCCAAATGTCACATCTCCTGAAACTGTGA
GGTGATCCAATTCAAGCAT--------A-
TCTGGTATACTTTCAAATCTTCTTAGATAATCTTGAACCTTACAGAAA
AGGAGAAACATAAAAATTTGTCTCAAATGGGTTCAAAGAAAGACAGGAAAAATATTAACAAGAAAG
TTTAACTGAACTGTAGAAACCTTTTTTGGCAAAGCTCAGGTCCTCT (SEQ ID NO: 232)

| Reads | Fraction | Fraction Cum_Sum | Seq | SEQ ID NO: |
|---|---|---|---|---|
| | | | GTTCAAAGAAAGACAGGAAAAATATTAACAAGAA AGTTTAACTGAACTGTAGAAACCTTTTTTGGCAAA GCTCAGGTCCTCT | |
| 584 | 0.00059735 | 0.747023222 | AATTTTCATTGTAACAACATACCTTTAATGAAACA TTTTTTCCAAATGTCACATCTCCTGAAACTGTGAGG TGATCCAATTCAAGCATA---------- TCTGGTATACTTTCAAATCTTCTTAGATAATCTTGA ACCTTACAGAAAAGGAGAAACATAAAAATTTGTCT CAAATGGGCTCAAAGAAAGACAGGAAAAATATTA ACAAGAAAGTTTAACTGAACTGTAGAAACCTTTTT TGGCAAAGCTCAGGTCCTCT | 313 |
| 584 | 0.00059735 | 0.747620572 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGATAATCTTGA ACCTTACAGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 314 |
| 582 | 0.000595304 | 0.748215877 | AATTTTCATTGTAACAACATACCTTTAATGAAACA TTTTTTCCAAATGTCACATCTCCTGAAACTGTGAGG TGATCCAATTCAAGCATA---------- TCTGGTATACTTTCAAATCTTCTTAGATAATCTTGA ACCTTACAGAAAAGGAGAAACATAAAAATTTGTCT CAAATGGGTTCAAAGAAAGACGGGAAAAATATTA ACAAGAAAGTTTAACTGAACTGTAGAAACCTTTTT TGGCAAAGCTCAGGTCCTCT | 315 |
| 581 | 0.000594282 | 0.748810158 | AATTTTCATTGTAACAACATACCTTTAATGAAACA TTTTTTCCAAATGTCACATCTCCTGAAACTGTGAGG TGATCCAATTCAAGCATATACTTGAATTCTGGTAT ACTTTCAAATCTTCTTAGATAATCTTGAACCTTACG GAAAAGGAGAAACATAAAAATTTGTCTCAAATGG GTTCAAAGAAAGACAGGAAAAATATTAACAAGAA AGTTTAACTGAACTGTAGAAACCTTTTTTGGCAAA GCTCAGGTCCTCT | 316 |
| 578 | 0.000591213 | 0.749401371 | AATTTTCATTGTAACAACATACCTTTAATGAAACA TTTTTTCCAAACGTCACATCTCCTGAAACTGTGAG GTGATCCAATTCAAGCAT---------- TCTGGTATACTTTCAAATCTTCTTAGATAATCTTGA ACCTTACAGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 317 |
| 577 | 0.00059019 | 0.749991561 | AATTTTCATTGTAACAACATACCTTTAATGAGACA TTTTTTCCAAATGTCACATCTCCTGAAACTGTGAGG TGATCCAATTCAAGCAT---------- TCTGGTATACTTTCAAATCTTCTTAGATAATCTTGA ACCTTACAGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 318 |
| 573 | 0.000586099 | 0.75057766 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCCTCTTAGATAATCTTGA ACCTTACAGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 319 |

TABLE 3-continued

UGP2

WT Sequence:
AATTTTCATTGTAACAACATACCTTTAATGAAACATTTTTTCCAAATGTCACATCTCCTGAAACTGTGA
GGTGATCCAATTCAAGCAT--------A-
TCTGGTATACTTTCAAATCTTCTTAGATAATCTTGAACCTTACAGAAA
AGGAGAAACATAAAAATTTGTCTCAAATGGGTTCAAAGAAAGACAGGAAAAATATTAACAAGAAAG
TTTAACTGAACTGTAGAAACCTTTTTTGGCAAAGCTCAGGTCCTCT (SEQ ID NO: 232)

| Reads | Fraction | Fraction Cum_Sum | Seq | SEQ ID NO: |
|---|---|---|---|---|
| 573 | 0.000586099 | 0.751163759 | AATTTTCATTGTAACAACATACCTTTAATGAAACA TTTTTTCCAAATGTCACATCTCCTGAAACTGTGAGG TGATCCAATTCAAGCATA---------- TCTGGTATACTTTCAAATCTTCTTAGATAATCTTGA ACCTTACAGAAAAGGAGAAACATAAAAATTTGTCT CAAATGGGTTCAAAGAAAGACAGGAAAAATATTA ACAAGAAAGTTTAACTGAGCTGTAGAAACCTTTTT TGGCAAAGCTCAGGTCCTCT | 320 |
| 573 | 0.000586099 | 0.751749858 | AATTTTCATTGTAACAACATACCTTTAATGAAACA TTTTTTCCAAATGTCACATCTCCTGAAACTGTGAGG TGATCCAATTCAAGCATATACTTGAATTCTGGTAT ACTTTCAAATCTTCTTAGATAATCTTGAACCTTACA GAAAAGGAGAAACATAAAAATTTGCCTCAAATGG GTTCAAAGAAAGACAGGAAAAATATTAACAAGAA AGTTTAACTGAACTGTAGAAACCTTTTTTGGCAAA GCTCAGGTCCTCT | 321 |
| 570 | 0.00058303 | 0.752332888 | AATTTTCATTGTAACAACATACCTTTAATGAAACA TTTTTTCCAAATGTCACATCTCCTGAAACTGTGAGG TGATCCAATTCAAGCATATACTTGAATTCTGGTAT ACTTTCAAATCTTCTTAGATAATCTTGAACCTTACA GAAAAGGAGAAACATAAAAATTTGTCTCAAATGG GTTCAAAGAAAGACAGGAAAAATATTAACAAGAA GGTTTAACTGAACTGTAGAAACCTTTTTTGGCAAA GCTCAGGTCCTCT | 322 |
| 568 | 0.000580984 | 0.752913872 | AATTTTCATTGTAACAACATACCTTTAATGAAACA TTTTCTCCAAATGTCACATCTCCTGAAACTGTGAG GTGATCCAATTCAAGCAT---------- TCTGGTATACTTTCAAATCTTCTTAGATAATCTTGA ACCTTACAGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 323 |
| 568 | 0.000580984 | 0.753494857 | AATTTTCATTGTAACAACATACCTTTAACGAAACA TTTTTTCCAAATGTCACATCTCCTGAAACTGTGAGG TGATCCAATTCAAGCAT---------- TCTGGTATACTTTCAAATCTTCTTAGATAATCTTGA ACCTTACAGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 324 |
| 567 | 0.000579962 | 0.754074818 | AATTTTCATTGTAACAACATACCTTTAATGAAACA TTTTTTCCAAATGTCACATCTCCTGAAACTGTGAGG TGATCCAATTCAAGCATATACTTGAATTCTGGTAT ACTTTCAAATCTTCTTAGATAATCTTGAACCTTACA GAAAAGGAGAAACATAAAAATTTGTCTCAAATGG GTTCAAAGAAAGGCAGGAAAAATATTAACAAGAA AGTTTAACTGAACTGTAGAAACCTTTTTTGGCAAA GCTCAGGTCCTCT | 325 |
| 566 | 0.000578939 | 0.754653757 | AATTTTCATTGTAACAACATACCTTTAATGAAACA TTTTTTCCAAATGTCACATCTCCTGAAACTGTGAGG TGATCCAATTCAAGCATATACTTGAATTCTGGTAT ACTTTCAAATCTTCTTAGATAATCTTGAACCTTACA GAAAAGGAGGAACATAAAAATTTGTCTCAAATGG GTTCAAAGAAAGACAGGAAAAATATTAACAAGAA AGTTTAACTGAACTGTAGAAACCTTTTTTGGCAAA GCTCAGGTCCTCT | 326 |
| 564 | 0.000576893 | 0.75523065 | AATTTTCATTGTAACAACATACCTTTAATGAAACA TTTTTTCCAAATGTCACATCTCCTGAAACTGTGAGG TGATCCAATTCAAGCAT---------- TCTGGCATACTTTCAAATCTTCTTAGATAATCTTGA ACCTTACAGAAAAGGAGAAACATAAAAATTTGTCT | 327 |

TABLE 3-continued

UGP2

WT Sequence:
AATTTTCATTGTAACAACATACCTTTAATGAAACATTTTTTCCAAATGTCACATCTCCTGAAACTGTGA
GGTGATCCAATTCAAGCAT--------A-
TCTGGTATACTTTCAAATCTTCTTAGATAATCTTGAACCTTACAGAAA
AGGAGAAACATAAAAATTTGTCTCAAATGGGTTCAAAGAAAGACAGGAAAAATATTAACAAGAAAG
TTTAACTGAACTGTAGAAACCTTTTTTGGCAAAGCTCAGGTCCTCT (SEQ ID NO: 232)

| Reads | Fraction | Fraction Cum_Sum | Seq | SEQ ID NO: |
|---|---|---|---|---|
|  |  |  | CAAATGGGTTCAAAGAAAGACAGGAAAAATATTA ACAAGAAAGTTTAACTGAACTGTAGAAACCTTTTT TGGCAAAGCTCAGGTCCTCT |  |
| 564 | 0.000576893 | 0.755807543 | AATTTTCATTGTAACAACATACCTTTAATGAAACA TTTTTTCCAAATGTCACATCTCCTGAAACTGTGAGG TGATCCAATTCAAGCATATACTTGAATTCTGGTAT ACTTTCAAATCTTCTTAGATAATCTTGAACCTTACA GAAAGGAGAAACATAAAAATTTGTCTCAAATGG GTTCAAAGAGAGACAGGAAAAATATTAACAAGAA AGTTTAACTGAACTGTAGAAACCTTTTTTGGCAAA GCTCAGGTCCTCT | 328 |
| 562 | 0.000574847 | 0.75638239 | AATTTTCATTGTAACAACATACCTTTAATGAAACA TTTTTTCCAAATGTCACATCTCCTGAAACTGTGAGG TGATCCAATTCAAGCAT---------- TCTGGTATACTTTCAAATCTTCTTAGGTAATCTTGA ACCTTACAGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 329 |
| 559 | 0.000571779 | 0.756954169 | AATTTTCATTGTAACAACATACCTTTAATGAAACA TTTTTTCCAAATGTCACATCTCCTGAAACTGTGAGG TGATCCAATTCAAGCAT---------- CCTGGTATACTTTCAAATCTTCTTAGATAATCTTGA ACCTTACAGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 330 |
| 559 | 0.000571779 | 0.757525947 | AATTTTCATTGTAACAACATACCTTTAATGAAACA TTTTTTCCAAATGTCACATCTCCTGAAACTGTGAGG TGATCCAATTCAAGCATA--------- TCTGGTATACTTTCAAATCTTCTTAGATAATCTTGA GCCTTACAGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 331 |
| 558 | 0.000570756 | 0.758096703 | AATTTTCATTGTAACAACATACCTTTAATGAAACA TTTTTTCCAAATGTCACATCTCCTGAAACTGTGAGG TGATCCAATTCAAGCATA--------- TCTGGTATACTTTCAAATCTTCTTAGATAATCTTGA ACCTTACGGAAAAGGAGAAACATAAAAATTTGTCT CAAATGGGTTCAAAGAAAGACAGGAAAAATATTA ACAAGAAAGTTTAACTGAACTGTAGAAACCTTTTT TGGCAAAGCTCAGGTCCTCT | 332 |

TABLE 4

EMC4

WT Sequence:
AGCTCAGTTAGAAGCAGGGAGTTGGGAATTCCGTTCATGTGATTTAGCATCAGTGATATGGCAAATGT
GGGACTAAGGGTAGTGATCAGAGGGTTAAAATTGTGTGTTTTGTTTTAGCGCTGCTGGGACATCG-CC--
TTGGGTCCCCTCAAACAGATTCCCATGAATCTCTTCATCATGTACATGGCAGGCAATACTATCTCCATC
TTCCCTACTATGATGGTGTGTATGATGGCCTGG (SEQ ID NO: 333)

| Reads | Fraction | Fraction Cum_Sum | Seq | SEQ ID NO: |
|---|---|---|---|---|
| 202135 (WT) | 0.185140407 | 0.185140407 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT | 334 |

TABLE 4-continued

EMC4

WT Sequence:
AGCTCAGTTAGAAGCAGGGAGTTGGGAATTCCGTTCATGTGATTTAGCATCAGTGATATGGCAAATGT
GGGACTAAGGGTAGTGATCAGAGGGTTAAAATTGTGTGTTTTGTTTTAGCGCTGCTGGGACATCG-CC--
TTGGGTCCCCTCAAACAGATTCCCATGAATCTCTTCATCATGTACATGGCAGGCAATACTATCTCCATC
TTCCCTACTATGATGGTGTGTATGATGGCCTGG (SEQ ID NO: 333)

| Reads | Fraction | Fraction Cum_Sum | Seq | SEQ ID NO: |
|---|---|---|---|---|
|  |  |  | GTTTTGTTTTAGCGCTGCTGGGACATCG-CC-- TTGGGTCCCCTCAAACAGATTCCCATGAATCTCTTC ATCATGTACATGGCAGGCAATACTATCTCCATCTT CCCTACTATGATGGTGTGTATGATGGCCTGG |  |
| 94677 | 0.086716988 | 0.271857394 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCG-TT---- GGGTCCCCTCAAACAGATTCCCATGAATCTCTTCA TCATGTACATGGCAGGCAATACTATCTCCATCTTC CCTACTATGATGGTGTGTATGATGGCCTGG | 335 |
| 35489 | 0.032505246 | 0.30436264 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTG-------------C-- TTGGGTCCCCTCAAACAGATTCCCATGAATCTCTTC ATCATGTACATGGCAGGCAATACTATCTCCATCTT CCCTACTATGATGGTGTGTATGATGGCCTGG | 336 |
| 31794 | 0.029120905 | 0.333483545 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGG--------------- TCCCCTCAAACAGATTCCCATGAATCTCTTCATCAT GTACATGGCAGGCAATACTATCTCCATCTTCCCTA CTATGATGGTGTGTATGATGGCCTGG | 337 |
| 21465 | 0.01966032 | 0.353143865 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCA----------- ------- AACAGATTCCCATGAATCTCTTCATCATGTACATG GCAGGCAATACTATCTCCATCTTCCCTACTATGAT GGTGTGTATGATGGCCTGG | 338 |
| 18219 | 0.016687229 | 0.369831094 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCC----- TTGGGTCCCCTCAAACAGATTCCCATGAATCTCTTC ATCATGTACATGGCAGGCAATACTATCTCCATCTT CCCTACTATGATGGTGTGTATGATGGCCTGG | 339 |
| 17040 | 0.015607354 | 0.385438448 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCG--C-- TTGGGTCCCCTCAAACAGATTCCCATGAATCTCTTC ATCATGTACATGGCAGGCAATACTATCTCCATCTT CCCTACTATGATGGTGTGTATGATGGCCTGG | 340 |
| 9631 | 0.008821269 | 0.394259718 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCG------ TGGGTCCCCTCAAACAGATTCCCATGAATCTCTTC ATCATGTACATGGCAGGCAATACTATCTCCATCTT CCCTACTATGATGGTGTGTATGATGGCCTGG | 341 |
| 8354 | 0.007651634 | 0.401911351 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACCTTG-------- GGTCCCCTCAAACAGATTCCCATGAATCTCTTCAT CATGTACATGGCAGGCAATACTATCTCCATCTTCC CTACTATGATGGTGTGTATGATGGCCTGG | 342 |

TABLE 4-continued

EMC4

WT Sequence:
AGCTCAGTTAGAAGCAGGGAGTTGGGAATTCCGTTCATGTGATTTAGCATCAGTGATATGGCAAATGT
GGGACTAAGGGTAGTGATCAGAGGGTTAAAATTGTGTGTTTTGTTTTAGCGCTGCTGGGACATCG-CC--
TTGGGTCCCCTCAAACAGATTCCCATGAATCTCTTCATCATGTACATGGCAGGCAATACTATCTCCATC
TTCCCTACTATGATGGTGTGTATGATGGCCTGG (SEQ ID NO: 333)

| Reads | Fraction | Fraction Cum_Sum | Seq | SEQ ID NO: |
|---|---|---|---|---|
| 8144 | 0.007459289 | 0.409370641 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCT--- GTTTGGGTCCCCTCAAACAGATTCCCATGAATCTC TTCATCATGTACATGGCAGGCAATACTATCTCCAT CTTCCCTACTATGATGGTGTGTATGATGGCCTGG | 343 |
| 6912 | 0.00633087 | 0.415701511 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCC------------ CCTCAAACAGATTCCCATGAATCTCTTCATCATGT ACATGGCAGGCAATACTATCTCCATCTTCCCTACT ATGATGGTGTGTATGATGGCCTGG | 344 |
| 6520 | 0.005971828 | 0.421673339 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGG---------------- TCCCCTCAAACAGATTCCCATGAATCTCTTCATCAT GTACATGGCAGGCAATACTATCTCCATCTTCCCTA CTATGATGGTGTGTATGATGGCCTGG | 345 |
| 5469 | 0.005009191 | 0.42668253 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACACCT------ TGGGTCCCCTCAAACAGATTCCCATGAATCTCTTC ATCATGTACATGGCAGGCAATACTATCTCCATCTT CCCTACTATGATGGTGTGTATGATGGCCTGG | 346 |
| 5428 | 0.004971638 | 0.431654169 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCG-------- GGTCCCCTCAAACAGATTCCCATGAATCTCTTCAT CATGTACATGGCAGGCAATACTATCTCCATCTTCC CTACTATGATGGTGTGTATGATGGCCTGG | 347 |
| 4620 | 0.004231571 | 0.43588574 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGAC---------------- CCCTCAAACAGATTCCCATGAATCTCTTCATCATGT ACATGGCAGGCAATACTATCTCCATCTTCCCTACT ATGATGGTGTGTATGATGGCCTGG | 348 |
| 4419 | 0.004047471 | 0.439933211 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGT--------------- TTGGGTCCCCTCAAACAGATTCCCATGAATCTCTTC ATCATGTACATGGCAGGCAATACTATCTCCATCTT CCCTACTATGATGGTGTGTATGATGGCCTGG | 349 |
| 4007 | 0.00367011 | 0.44360332 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTG-----------CC-- TTGGGTCCCCTCAAACAGATTCCCATGAATCTCTTC ATCATGTACATGGCAGGCAATACTATCTCCATCTT CCCTACTATGATGGTGTGTATGATGGCCTGG | 350 |
| 3721 | 0.003408155 | 0.447011476 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCT--------------- | 351 |

TABLE 4-continued

EMC4

WT Sequence:
AGCTCAGTTAGAAGCAGGGAGTTGGGAATTCCGTTCATGTGATTTAGCATCAGTGATATGGCAAATGT
GGGACTAAGGGTAGTGATCAGAGGGTTAAAATTGTGTGTTTTGTTTTAGCGCTGCTGGGACATCG-CC--
TTGGGTCCCCTCAAACAGATTCCCATGAATCTCTTCATCATGTACATGGCAGGCAATACTATCTCCATC
TTCCCTACTATGATGGTGTGTATGATGGCCTGG (SEQ ID NO: 333)

| Reads | Fraction | Fraction Cum_Sum | Seq | SEQ ID NO: |
|---|---|---|---|---|
| | | | CAAACAGATTCCCATGAATCTCTTCATCATGTACA TGGCAGGCAATACTATCTCCATCTTCCCTACTATG ATGGTGTGTATGATGGCCTGG | |
| 3663 | 0.003355032 | 0.450366507 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCG-------- GTCCCCTCAAACAGATTCCCATGAATCTCTTCATC ATGTACATGGCAGGCAATACTATCTCCATCTTCCC TACTATGATGGTGTGTATGATGGCCTGG | 352 |
| 3649 | 0.003342209 | 0.453708716 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATTG------- GGTCCCCTCAAACAGATTCCCATGAATCTCTTCAT CATGTACATGGCAGGCAATACTATCTCCATCTTCC CTACTATGATGGTGTGTATGATGGCCTGG | 353 |
| 3556 | 0.003257028 | 0.456965744 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACAGAT--------------- --------- TCCCATGAATCTCTTCATCATGTACATGGCAGGCA ATACTATCTCCATCTTCCCTACTATGATGGTGTGTA TGATGGCCTGG | 354 |
| 3549 | 0.003250616 | 0.46021636 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCGGCC-- TTGGGTCCCCTCAAACAGATTCCCATGAATCTCTTC ATCATGTACATGGCAGGCAATACTATCTCCATCTT CCCTACTATGATGGTGTGTATGATGGCCTGG | 355 |
| 3539 | 0.003241457 | 0.463457817 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCG--------------- -- AACAGATTCCCATGAATCTCTTCATCATGTACATG GCAGGCAATACTATCTCCATCTTCCCTACTATGAT GGTGTGTATGATGGCCTGG | 356 |
| 3379 | 0.003094909 | 0.466552726 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGAC-----CC-- TTGGGTCCCCTCAAACAGATTCCCATGAATCTCTTC ATCATGTACATGGCAGGCAATACTATCTCCATCTT CCCTACTATGATGGTGTGTATGATGGCCTGG | 357 |
| 3239 | 0.00296668 | 0.469519405 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATC------------------ ----------------------------------------- --------------- TTCCCTACTATGATGGTGTGTATGATGGCCTGG | 358 |
| 2964 | 0.0027148 | 0.472234206 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCT-GC-- TTGGGTCCCCTCAAACAGATTCCCATGAATCTCTTC ATCATGTACATGGCAGGCAATACTATCTCCATCTT CCCTACTA TGATGGTGTGTATGATGGCCTGG | 359 |

TABLE 4-continued

EMC4

WT Sequence:
AGCTCAGTTAGAAGCAGGGAGTTGGGAATTCCGTTCATGTGATTTAGCATCAGTGATATGGCAAATGT
GGGACTAAGGGTAGTGATCAGAGGGTTAAAATTGTGTGTTTTGTTTTAGCGCTGCTGGGACATCG-CC--
TTGGGTCCCCTCAAACAGATTCCCATGAATCTCTTCATCATGTACATGGCAGGCAATACTATCTCCATC
TTCCCTACTATGATGGTGTGTATGATGGCCTGG (SEQ ID NO: 333)

| Reads | Fraction | Fraction Cum_Sum | Seq | SEQ ID NO: |
|---|---|---|---|---|
| 2901 | 0.002657097 | 0.474891303 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGG--------------- GTCCCCTCAAACAGATTCCCATGAATCTCTTCATC ATGTACATGGCAGGCAATACTATCTCCATCTTCCC TACTATGATGGTGTGTATGATGGCCTGG | 360 |
| 2804 | 0.002568252 | 0.477459555 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCT---------GT-- TTGGGTCCCCTCAAACAGATTCCCATGAATCTCTTC ATCATGTACATGGCAGGCAATACTATCTCCATCTT CCCTACTATGATGGTGTGTATGATGGCCTGG | 361 |
| 2776 | 0.002542607 | 0.480002162 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCG-GG------ GTCCCCTCAAACAGATTCCCATGAATCTCTTCATC ATGTACATGGCAGGCAATACTATCTCCATCTTCCC TACTATGATGGTGTGTATGATGGCCTGG | 362 |
| 2690 | 0.002463837 | 0.482465999 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCG-CCC- TTGGGTCCCCTCAAACAGATTCCCATGAATCTCTTC ATCATGTACATGGCAGGCAATACTATCTCCATCTT CCCTACTATGATGGTGTGTATGATGGCCTGG | 363 |
| 2539 | 0.002325532 | 0.484791531 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCC--C-- TTGGGTCCCCTCAAACAGATTCCCATGAATCTCTTC ATCATGTACATGGCAGGCAATACTATCTCCATCTT CCCTACTATGATGGTGTGTATGATGGCCTGG | 364 |
| 2469 | 0.002261418 | 0.487052949 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACA-------------------- AACAGATTCCCATGAATCTCTTCATCATGTACATG GCAGGCAATACTATCTCCATCTTCCCTACTATGAT GGTGTGTATGATGGCCTGG | 365 |
| 2415 | 0.002211958 | 0.489264906 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGAC---------------- CCTCAAACAGATTCCCATGAATCTCTTCATCATGT ACATGGCAGGCAATACTATCTCCATCTTCCCTACT ATGATGGTGTGTATGATGGCCTGG | 366 |
| 2191 | 0.002006791 | 0.491271697 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCT----------------- GTCCCCTCAAACAGATTCCCATGAATCTCTTCATC ATGTACATGGCAGGCAATACTATCTCCATCTTCCC TACTATGATGGTGTGTATGATGGCCTGG | 367 |
| 2168 | 0.001985724 | 0.493257422 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCG--------------- | 368 |

TABLE 4-continued

EMC4

WT Sequence:
AGCTCAGTTAGAAGCAGGGAGTTGGGAATTCCGTTCATGTGATTTAGCATCAGTGATATGGCAAATGT
GGGACTAAGGGTAGTGATCAGAGGGTTAAAATTGTGTGTTTTGTTTTAGCGCTGCTGGGACATCG- CC--
TTGGGTCCCCTCAAACAGATTCCCATGAATCTCTTCATCATGTACATGGCAGGCAATACTATCTCCATC
TTCCCTACTATGATGGTGTGTATGATGGCCTGG (SEQ ID NO: 333)

| Reads | Fraction | Fraction Cum_Sum | Seq | SEQ ID NO: |
|---|---|---|---|---|
| | | | CAAACAGATTCCCATGAATCTCTTCATCATGTACA TGGCAGGCAATACTATCTCCATCTTCCCTACTATG ATGGTGTGTATGATGGCCTGG | |
| 2013 | 0.001843756 | 0.495101178 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTT------------------------ GGGTCCCCTCAAACAGATTCCCATGAATCTCTTCA TCATGTACATGGCAGGCAATACTATCTCCATCTTC CCTACTATGATGGTGTGTATGATGGCCTGG | 369 |
| 1979 | 0.001812615 | 0.496913792 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCG------------ CCTCAAACAGATTCCCATGAATCTCTTCATCATGT ACATGGCAGGCAATACTATCTCCATCTTCCCTACT ATGATGGTGTGTATGATGGCCTGG | 370 |
| 1944 | 0.001780557 | 0.49869435 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACAT-------------------------- CTCTTCATCATGTACATGGCAGGCAATACTATCTC CATCTTCCCTACTATGATGGTGTGTATGATGGCCTG G | 371 |
| 1901 | 0.001741173 | 0.500435522 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATGA---------------- ---------------- ATCTCTTCATCATGTACATGGCAGGCAATACTATC TCCATCTTCCCTACTATGATGGTGTGTATGATGGCC TGG | 372 |
| 1769 | 0.001620271 | 0.502055793 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCT ---TG--- GGTCCCCTCAAACAGATTCCCATGAATCTCTTCAT CATGTACATGGCAGGCAATACTATCTCCATCTTCC CTACTATGATGGTGTGTATGATGGCCTGG | 373 |
| 1760 | 0.001612027 | 0.50366782 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGC---------------C-- TTGGGTCCCCTCAAACAGATTCCCATGAATCTCTTC ATCATGTACATGGCAGGCAATACTATCTCCATCTT CCCTACTATGATGGTGTGTATGATGGCCTGG | 374 |
| 1737 | 0.001590961 | 0.505258781 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATC------------------ --------------------------- ATGTACATGGCAGGCAATACTATCTCCATCTTCCC TACTATGATGGTGTGTATGATGGCCTGG | 375 |
| 1714 | 0.001569895 | 0.506828675 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCG--------- TCCCCTCAAACAGATTCCCATGAATCTCTTCATCAT GTACATGGCAGGCAATACTATCTCCATCTTCCCTA CTATGATGGTGTGTATGATGGCCTGG | 376 |

TABLE 4-continued

EMC4

WT Sequence:
AGCTCAGTTAGAAGCAGGGAGTTGGGAATTCCGTTCATGTGATTTAGCATCAGTGATATGGCAAATGT
GGGACTAAGGGTAGTGATCAGAGGGTTAAAATTGTGTGTTTTGTTTTAGCGCTGCTGGGACATCG-CC--
TTGGGTCCCCTCAAACAGATTCCCATGAATCTCTTCATCATGTACATGGCAGGCAATACTATCTCCATC
TTCCCTACTATGATGGTGTGTATGATGGCCTGG (SEQ ID NO: 333)

| Reads | Fraction | Fraction Cum_Sum | Seq | SEQ ID NO: |
|---|---|---|---|---|
| 1706 | 0.001562567 | 0.508391243 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTG---------CC-- TTGGGTCCCCTCAAACAGATTCCCATGAATCTCTTC ATCATGTACATGGCAGGCAATACTATCTCCATCTT CCCTACTATGATGGTGTGTATGATGGCCTGG | 377 |
| 1652 | 0.001513107 | 0.50990435 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACAT----------------- ----------------------------------- GGCAGGCAATACTATCTCCATCTTCCCTACTATGA TGGTGTGTATGATGGCCTGG | 378 |
| 1582 | 0.001448993 | 0.511353343 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCT------------------------ CAAACAGATTCCCATGAATCTCTTCATCATGTACA TGGCAGGCAATACTATCTCCATCTTCCCTACTATG ATGGTGTGTATGATGGCCTGG | 379 |
| 1527 | 0.001398617 | 0.512751959 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATC------------------ ----------------------------------------- ------------ TCCATCTTCCCTACTATGATGGTGTGTATGATGGCC TGG | 380 |
| 1521 | 0.001393121 | 0.514145081 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCG----------- CCCTCAAACAGATTCCCATGAATCTCTTCATCATGT ACATGGCAGGCAATACTATCTCCATCTTCCCTACT ATGATGGTGTGTATGATGGCCTGG | 381 |
| 1489 | 0.001363812 | 0.515508892 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCG---------- CCCCTCAAACAGATTCCCATGAATCTCTTCATCAT GTACATGGCAGGCAATACTATCTCCATCTTCCCTA CTATGATGGTGTGTATGATGGCCTGG | 382 |
| 1430 | 0.001309772 | 0.516818664 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCG---------------- --- ACAGATTCCCATGAATCTCTTCATCATGTACATGG CAGGCAATACTATCTCCATCTTCCCTACTATGATG GTGTGTATGATGGCCTGG | 383 |
| 1409 | 0.001290538 | 0.518109202 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCC---------------- ------------ CATGAATCTCTTCATCATGTACATGGCAGGCAATA CTATCTCCATCTTCCCTACTATGATGGTGTGTATGA TGGCCTGG | 384 |

TABLE 4-continued

EMC4

WT Sequence:
AGCTCAGTTAGAAGCAGGGAGTTGGGAATTCCGTTCATGTGATTTAGCATCAGTGATATGGCAAATGT
GGGACTAAGGGTAGTGATCAGAGGGTTAAAATTGTGTGTTTTTGTTTTAGCGCTGCTGGGACATCG-CC--
TTGGGTCCCCTCAAACAGATTCCCATGAATCTCTTCATCATGTACATGGCAGGCAATACTATCTCCATC
TTCCCTACTATGATGGTGTGTATGATGGCCTGG (SEQ ID NO: 333)

| Reads | Fraction | Fraction Cum_Sum | Seq | SEQ ID NO: |
|---|---|---|---|---|
| 1371 | 0.001255733 | 0.519364935 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCG-------------- CTCAAACAGATTCCCATGAATCTCTTCATCATGTA CATGGCAGGCAATACTATCTCCATCTTCCCTACTAT GATGGTGTGTATGATGGCCTGG | 385 |
| 1265 | 0.001158645 | 0.520523579 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCG---TTT- GGGTCCCCTCAAACAGATTCCCATGAATCTCTTCA TCATGTACATGGCAGGCAATACTATCTCCATCTTC CCTACTATGATGGTGTGTATGATGGCCTGG | 386 |
| 1256 | 0.001150401 | 0.52167398 | AGCTCAGTTAGAAGCAGGGAGTTGGGAATTCCGTT CATGTGATTTAGCATCAGTGATATGGCAAATGTGG GACTAAGGGTAGTGATCAGA------------------------ ------------------------- GGGTCCCCTCAAACAGATTCCCATGAATCTCTTCA TCATGTACATGGCAGGCAATACTATCTCCATCTTC CCTACTATGATGGTGTGTATGATGGCCTGG | 387 |
| 1234 | 0.522804231 | 0.001130251 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTG---------------- TTGGGTCCCCTCAAACAGATTCCCATGAATCTCTTC ATCATGTACATGGCAGGCAATACTATCTCCATCTT CCCTACTATGATGGTGTGTATGATGGCCTGG | 388 |
| 1194 | 0.001093614 | 0.523897845 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGA---------------------- --- TTCCCATGAATCTCTTCATCATGTACATGGCAGGC AATACTATCTCCATCTTCCCTACTATGATGGTGTGT ATGATGGCCTGG | 389 |
| 1180 | 0.001080791 | 0.524978636 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACA-------------------- ------------------------------------------- ATACTATCTCCATCTTCCCTACTATGATGGTGTGTA TGATGGCCTGG | 390 |
| 1135 | 0.001039574 | 0.52601821 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCT------------CC-- TTGGGTCCCCTCAAACAGATTCCCATGAATCTCTTC ATCATGTACATGGCAGGCAATACTATCTCCATCTT CCCTACTATGATGGTGTGTATGATGGCCTGG | 391 |
| 1114 | 0.00102034 | 0.52703855 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGC------------------------ --- AGATTCCCATGAATCTCTTCATCATGTACATGGCA GGCAATACTATCTCCATCTTCCCTACTATGATGGT GTATGATGGCCTGG | 392 |
| 1095 | 0.001002937 | 0.528041488 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT | 393 |

TABLE 4-continued

EMC4

WT Sequence:
AGCTCAGTTAGAAGCAGGGAGTTGGGAATTCCGTTCATGTGATTTAGCATCAGTGATATGGCAAATGT
GGGACTAAGGGTAGTGATCAGAGGGTTAAAATTGTGTGTTTTGTTTTAGCGCTGCTGGGACATCG-CC--
TTGGGTCCCCTCAAACAGATTCCCATGAATCTCTTCATCATGTACATGGCAGGCAATACTATCTCCATC
TTCCCTACTATGATGGTGTGTATGATGGCCTGG (SEQ ID NO: 333)

| Reads | Fraction | Fraction Cum_Sum | Seq | SEQ ID NO: |
|---|---|---|---|---|
| | | | GTTTTGTTTTAGCGCTGCTGGGACATCG---AT GTCCCCTCAAACAGATTCCCATGAATCTCTTCATC ATGTACATGGCAGGCAATACTATCTCCATCTTCCC TACTATGATGGTGTGTATGATGGCCTGG | |
| 1086 | 0.000994694 | 0.529036182 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCG--- CTTTGGGTCCCCTCAAACAGATTCCCATGAATCTCT TCATCATGTACATGGCAGGCAATACTATCTCCATC TTCCCTACTATGATGGTGTGTATGATGGCCTGG | 394 |
| 1042 | 0.000954393 | 0.529990575 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCC--------------- TCAAACAGATTCCCATGAATCTCTTCATCATGTAC ATGGCAGGCAATACTATCTCCATCTTCCCTACTAT GATGGTGTGTATGATGGCCTGG | 395 |
| 1022 | 0.000936075 | 0.53092665 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCA--------------- ------ GATTCCCATGAATCTCTTCATCATGTACATGGCAG GCAATACTATCTCCATCTTCCCTACTATGATGGTGT GTATGATGGCCTGG | 396 |
| 999 | 0.000915009 | 0.531841659 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCT---------CC-- TTGGGTCCCCTCAAACAGATTCCCATGAATCTCTTC ATCATGTACATGGCAGGCAATACTATCTCCATCTT CCCTACTATGATGGTGTGTATGATGGCCTGG | 397 |
| 993 | 0.000909513 | 0.532751172 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCG--------------- ---- CAGATTCCCATGAATCTCTTCATCATGTACATGGC AGGCAATACTATCTCCATCTTCCCTACTATGATGGT GTGTATGATGGCCTGG | 398 |
| 982 | 0.000899438 | 0.53365061 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCG----------------C-- TTGGGTCCCCTCAAACAGATTCCCATGAATCTCTTC ATCATGTACATGGCAGGCAATACTATCTCCATCTT CCCTACTATGATGGTGTGTATGATGGCCTGG | 399 |
| 940 | 0.000860969 | 0.534511579 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCG--------------- - AAACAGATTCCCATGAATCTCTTCATCATGTACAT GGCAGGCAATACTATCTCCATCTTCCCTACTATGA TGGTGTGTATGATGGCCTGG | 400 |
| 909 | 0.000832575 | 0.535344154 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGAC--------------- CTCAAACAGATTCCCATGAATCTCTTCATCATGTA | 401 |

TABLE 4-continued

EMC4

WT Sequence:
AGCTCAGTTAGAAGCAGGGAGTTGGGAATTCCGTTCATGTGATTTAGCATCAGTGATATGGCAAATGT
GGGACTAAGGGTAGTGATCAGAGGGTTAAAATTGTGTGTTTTGTTTTAGCGCTGCTGGGACATCG-CC--
TTGGGTCCCCTCAAACAGATTCCCATGAATCTCTTCATCATGTACATGGCAGGCAATACTATCTCCATC
TTCCCTACTATGATGGTGTGTATGATGGCCTGG (SEQ ID NO: 333)

| Reads | Fraction | Fraction Cum_Sum | Seq | SEQ ID NO: |
|---|---|---|---|---|
| | | | CATGGCAGGCAATACTATCTCCATCTTCCCTACTAT GATGGTGTGTATGATGGCCTGG | |
| 908 | 0.000831659 | 0.536175814 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGC----------------C-- TTGGGTCCCCTCAAACAGATTCCCATGAATCTCTTC ATCATGTACATGGCAGGCAATACTATCTCCATCTT CCCTACTATGATGGTGTGTATGATGGCCTGG | 402 |
| 902 | 0.000826164 | 0.537001977 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTT------------------------- GGGTCCCCTCAAACAGATTCCCATGAATCTCTTCA TCATGTACATGGCAGGCAATACTATCTCCATCTTC CCTACTATGATGGTGTGTATGATGGCCTGG | 403 |
| 882 | 0.000807845 | 0.537809823 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTT------------------------- GTCCCCTCAAACAGATTCCCATGAATCTCTTCATC ATGTACATGGCAGGCAATACTATCTCCATCTTCCC TACTATGATGGTGTGTATGATGGCCTGG | 404 |
| 859 | 0.000786779 | 0.538596602 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGG------------------- ------------ TGTGTATGATGGCCTGG | 405 |
| 806 | 0.000738235 | 0.539334837 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACAT-------------- ------------------------ ACTATCTCCATCTTCCCTACTATGATGGTGTGTATG ATGGCCTGG | 406 |
| 799 | 0.000731824 | 0.540066661 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCG-CC-- TTGGGTCCCCTCAAACAGATTCCCATGAATCTCTTC ATCATGTACATGGCGGGCAATACTATCTCCATCTT CCCTACTATGATGGTGTGTATGATGGCCTGG | 407 |
| 792 | 0.000725412 | 0.540792073 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCG--------------- -------- ATTCCCATGAATCTCTTCATCATGTACATGGCAGG CAATACTATCTCCATCTTCCCTACTATGATGGTGTG TATGATGGCCTGG | 408 |
| 754 | 0.000690607 | 0.54148268 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGC------------------------ -------------------- CATGAATCTCTTCATCATGTACATGGCAGGCAATA CTATCTCCATCTTCCCTACTATGATGGTGTGTATGA TGGCCTGG | 409 |

TABLE 4-continued

EMC4

WT Sequence:
AGCTCAGTTAGAAGCAGGGAGTTGGGAATTCCGTTCATGTGATTTAGCATCAGTGATATGGCAAATGT
GGGACTAAGGGTAGTGATCAGAGGGTTAAAATTGTGTGTTTTGTTTTAGCGCTGCTGGGACATCG-CC--
TTGGGTCCCCTCAAACAGATTCCCATGAATCTCTTCATCATGTACATGGCAGGCAATACTATCTCCATC
TTCCCTACTATGATGGTGTGTATGATGGCCTGG (SEQ ID NO: 333)

| Reads | Fraction | Fraction Cum_Sum | Seq | SEQ ID NO: |
|---|---|---|---|---|
| 749 | 0.000686027 | 0.542168708 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGC------------------------- AAACAGATTCCCATGAATCTCTTCATCATGTACAT GGCAGGCAATACTATCTCCATCTTCCCTACTATGA TGGTGTGTATGATGGCCTGG | 410 |
| 721 | 0.000660382 | 0.542829089 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGGCATCG-CC TTGGGTCCCCTCAAACAGATTCCCATGAATCTCTTC ATCATGTACATGGCAGGCAATACTATCTCCATCTT CCCTACTATGATGGTGTGTATGATGGCCTGG | 411 |
| 715 | 0.000654886 | 0.543483975 | AGCTCAGTTAGAAGCAGGGAGTTGGGAATTCCGTT CACGTGATTTAGCATCAGTGATATGGCAAATGTGG GACTAAGGGTAGTGATCAGAGGGTTAAAATTGTGT GTTTTGTTTTAGCGCTGCTGGGACATCG-CC TTGGGTCCCCTCAAACAGATTCCCATGAATCTCTTC ATCATGTACATGGCAGGCAATACTATCTCCATCTT CCCTACTATGATGGTGTGTATGATGGCCTGG | 412 |
| 707 | 0.000647559 | 0.544131534 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCGTCC-- TTGGGTCCCCTCAAACAGATTCCCATGAATCTCTTC ATCATGTACATGGCAGGCAATACTATCTCCATCTT CCCTACTATGATGGTGTGTATGATGGCCTGG | 413 |
| 700 | 0.000641147 | 0.544772681 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCG-CC-- TTGGGTCCCCTCAAACAGATTCCCATGAATCTCCT CATCATGTACATGGCAGGCAATACTATCTCCATCT TCCCTACTATGATGGTGTGTATGATGGCCTGG | 414 |
| 694 | 0.000635652 | 0.545408333 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCT---GT------ CCCCTCAAACAGATTCCCATGAATCTCTTCATCAT GTACATGGCAGGCAATACTATCTCCATCTTCCCTA CTATGATGGTGTGTATGATGGCCTGG | 415 |
| 689 | 0.000631072 | 0.546039405 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTG------------------------- CCCCTCAAACAGATTCCCATGAATCTCTTCATCAT GTACATGGCAGGCAATACTATCTCCATCTTCCCTA CTATGATGGTGTGTATGATGGCCTGG | 416 |
| 687 | 0.00062924 | 0.546668645 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTT---------------------------------- ------------------------- GGTAGGCAATACTATCTCCATCTTCCCTACTATGAT GGTGTGTATGATGGCCTGG | 417 |
| 685 | 0.000627408 | 0.547296053 | AGCTCAGTTAGAAGCAGGGAGTTGGGAATTCCGCT CATGTGATTTAGCATCAGTGATATGGCAAATGTGG GACTAAGGGTAGTGATCAGAGGGTTAAAATTGTGT GTTTTGTTTTAGCGCTGCTGGGACATCG-CC-- TTGGGTCCCCTCAAACAGATTCCCATGAATCTCTTC | 418 |

TABLE 4-continued

EMC4

WT Sequence:
AGCTCAGTTAGAAGCAGGGAGTTGGGAATTCCGTTCATGTGATTTAGCATCAGTGATATGGCAAATGT
GGGACTAAGGGTAGTGATCAGAGGGTTAAAATTGTGTGTTTTGTTTTAGCGCTGCTGGGACATCG-CC--
TTGGGTCCCCTCAAACAGATTCCCATGAATCTCTTCATCATGTACATGGCAGGCAATACTATCTCCATC
TTCCCTACTATGATGGTGTGTATGATGGCCTGG (SEQ ID NO: 333)

| Reads | Fraction | Fraction Cum_Sum | Seq | SEQ ID NO: |
|---|---|---|---|---|
| | | | ATCATGTACATGGCAGGCAATACTATCTCCATCTT CCCTACTATGATGGTGTGTATGATGGCCTGG | |
| 675 | 0.000618249 | 0.547914302 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGG---------CC-- TTGGGTCCCCTCAAACAGATTCCCATGAATCTCTTC ATCATGTACATGGCAGGCAATACTATCTCCATCTT CCCTACTATGATGGTGTGTATGATGGCCTGG | 419 |
| 665 | 0.00060909 | 0.548523392 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGT---- ------------------------- GTGTCCCCTCAAACAGATTCCCATGAATCTCTTCAT CATGTACATGGCAGGCAATACTATCTCCATCTTCC CTACTATGATGGTGTGTATGATGGCCTGG | 420 |
| 661 | 0.000605426 | 0.549128818 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGC--------------------- TGGGTCCCCTCAAACAGATTCCCATGAATCTCTTC ATCATGTACATGGCAGGCAATACTATCTCCATCTT CCCTACTATGATGGTGTGTATGATGGCCTGG | 421 |
| 656 | 0.000600846 | 0.549729665 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCG-CC-- TTGGGTCCCCTCAAACAGATTCCCATGAATCTCTTC ATCATGTACGTGGCAGGCAATACTATCTCCATCTT CCCTACTATGATGGTGTGTATGATGGCCTGG | 422 |
| 651 | 0.000596267 | 0.550325932 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATGG--------- GTCCCCTCAAACAGATTCCCATGAATCTCTTCATC ATGTACATGGCAGGCAATACTATCTCCATCTTCCC TACTATGATGGTGTGTATGATGGCCTGG | 423 |
| 651 | 0.000596267 | 0.550922199 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACAT------------- ----------------CT-- TCATCATGTACATGGCAGGCAATACTATCTCCATC TTCCCTACTATGATGGTGTGTATGATGGCCTGG | 424 |
| 644 | 0.000589855 | 0.551512054 | AGCTCAGTTAGAAGCAGGGAGTTGGGAATTCCGTT CATGCGATTTAGCATCAGTGATATGGCAAATGTGG GACTAAGGGTAGTGATCAGAGGGTTAAAATTGTGT GTTTTGTTTTAGCGCTGCTGGGACATCG-CC-- TTGGGTCCCCTCAAACAGATTCCCATGAATCTCTTC ATCATGTACATGGCAGGCAATACTATCTCCATCTT CCCTACTATGATGGTGTGTATGATGGCCTGG | 425 |
| 641 | 0.000587108 | 0.552099162 | AGCTCAGTTAGAAGCAGGGAGTTGGGAATTCCGTC CATGTGATTTAGCATCAGTGATATGGCAAATGTGG GACTAAGGGTAGTGATCAGAGGGTTAAAATTGTGT GTTTTGTTTTAGCGCTGCTGGGACATCG-CC-- TTGGGTCCCCTCAAACAGATTCCCATGAATCTCTTC ATCATGTACATGGCAGGCAATACTATCTCCATCTT CCCTACTATGATGGTGTGTATGATGGCCTGG | 426 |
| 637 | 0.000583444 | 0.552682606 | AGCTCAGTTAGAAGCAGGGAGTTGGGAATTCCGTT CATGTGATTTAGCATCAGTGATATGGCAAATGTGG | 427 |

TABLE 4-continued

EMC4

WT Sequence:
AGCTCAGTTAGAAGCAGGGAGTTGGGAATTCCGTTCATGTGATTTAGCATCAGTGATATGGCAAATGT
GGGACTAAGGGTAGTGATCAGAGGGTTAAAATTGTGTGTTTTGTTTTAGCGCTGCTGGGACATCG-CC--
TTGGGTCCCCTCAAACAGATTCCCATGAATCTCTTCATCATGTACATGGCAGGCAATACTATCTCCATC
TTCCCTACTATGATGGTGTGTATGATGGCCTGG (SEQ ID NO: 333)

| Reads | Fraction | Fraction Cum_Sum | Seq | SEQ ID NO: |
|---|---|---|---|---|
| | | | GACTAAGGGTAGTGATCAGAGGGTTAAAATTGTGT GTTTTGTTTTAGCGCTGCTGGGACATCGACC-- TTGGGTCCCCTCAAACAGATTCCCATGAATCTCTTC ATCATGTACATGGCAGGCAATACTATCTCCATCTT CCCTACTATGATGGTGTGTATGATGGCCTGG | |
| 632 | 0.000578864 | 0.55326147 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCG-CC-- TTGGGTCCCCTCAAACAGATTCCCATGAATCTCTTC ATCATGTACATGGCAGGCAATACTATCTCCATCTT CCCTACTATGGTGGTGTGTATGATGGCCTGG | 428 |
| 631 | 0.000577948 | 0.553839418 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGCGT GTTTTGTTTTAGCGCTGCTGGGACATCG-CC-- TTGGGTCCCCTCAAACAGATTCCCATGAATCTCTTC ATCATGTACATGGCAGGCAATACTATCTCCATCTT CCCTACTATGATGGTGTGTATGATGGCCTGG | 429 |
| 628 | 0.000575201 | 0.554414619 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGGACATCC-------------- --- CTCAAACAGATTCCCATGAATCTCTTCATCATGTA CATGGCAGGCAATACTATCTCCATCTTCCCTACTAT GATGGTGTGTATGATGGCCTGG | 430 |
| 626 | 0.000573369 | 0.554987988 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GCTTTGTTTTAGCGCTGCTGGGACATCG -CC-- TTGGGTCCCCTCAAACAGATTCCCATGAATCTCTTC ATCATGTACATGGCAGGCAATACTATCTCCATCTT CCCTACTATGATGGTGTGTATGATGGCCTGG | 431 |
| 621 | 0.000568789 | 0.555556777 | AGCTCAGTTAGAAGCAGGGAGTTGGGAATTCCGTT CATGTGATTTAGCATCAGTGATATGGCAAATGTGG GACTAAGGGTAGTGATCAGAGGGTTAAAATTGTGT GTTTTGTTTTAGCGCTGCTGGG--------CC-- TTGGGTCCCCTCAAACAGATTCCCATGAATCTCTTC ATCATGTACATGGCAGGCAATACTATCTCCATCTT CCCTACTATGATGGTGTGTATGATGGCCTGG | 432 |
| 617 | 0.000565125 | 0.556121902 | AGCTCAGTTAGAAGCAGGGAGTT--------------------- ---------------------------------------- ----------------------------- GGGTCCCCTCAAACAGATTCCCATGAATCTCTTCA TCATGTACATGGCAGGCAATACTATCTCCATCTTC CCTACTATGATGGTGTGTATGATGGCCTGG | 433 |

TABLE 5

SGMS1

WT Sequence:
GACTATTGCAAATCTCTCCCCCTTTCAGATTCCCCTCGGCGACTCTGGTGGTATCACTGGATTTGCTGG
CTTCTCAGCGTAGTTGGAATCTTCTGTATTCTCTTAGCGCATGACCACTACA--C-
TGTGGACGTGGTGG
TGGCATATTACATCACCACGAGACTCTTCTGGTGGTATCACACTATGGCCAATCAGCAAGTGAGTTTC
CCCGCTTTTGATTTTAGCTTCTGTTGTTTCTGGCTT (SEQ ID NO: 434)

| Reads | Fraction | Fraction Cum_Sum | Seq | SEQ ID NO: |
|---|---|---|---|---|
| 226590 | 0.198527189 | 0.198527189 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACA--A- CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 435 |
| 101436 (WT) | 0.088873313 | 0.287400502 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACA--C-- TGTGGACGTGGTGGTGGCATATTACATCACCACGA GACTCTTCTGGTGGTATCACACTATGGCCAATCAG CAAGTGAGTTTCCCCGCTTTTGATTTTAGCTTCTGT TGTTTCTGGCTT | 436 |
| 67864 | 0.059459152 | 0.346859654 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCA--------- CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 437 |
| 56625 | 0.049612084 | 0.396471738 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTA------ CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 438 |
| 20086 | 0.017598381 | 0.414070118 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCAT------------------ GACGTGGTGGTGGCATATTACATCACCACGAGACT CTTCTGGTGGTATCACACTATGGCCAATCAGCAAG TGAGTTTCCCCGCTTTTGATTTTAGCTTCTGTTGTTT CTGGCTT | 439 |
| 15031 | 0.013169435 | 0.427239553 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACA----- TGTGGACGTGGTGGTGGCATATTACATCACCACGA GACTCTTCTGGTGGTATCACACTATGGCCAATCAG CAAGTGAGTTTCCCCGCTTTTGATTTTAGCTTCTGT TGTTTCTGGCTT | 440 |
| 13287 | 0.011641426 | 0.438880979 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATG----------------- GACGTGGTGGTGGCATATTACATCACCACGAGACT CTTCTGGTGGTATCACACTATGGCCAATCAGCAAG TGAGTTTCCCCGCTTTTGATTTTAGCTTCTGTTGTTT CTGGCTT | 441 |
| 10732 | 0.009402859 | 0.448283838 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATG----------------- TGGACGTGGTGGTGGCATATTACATCACCACGAGA | 442 |

TABLE 5-continued

SGMS1

WT Sequence:
GACTATTGCAAATCTCTCCCCCTTTCAGATTCCCCTCGGCGACTCTGGTGGTATCACTGGATTTGCTGG
CTTCTCAGCGTAGTTGGAATCTTCTGTATTCTCTTAGCGCATGACCACTACA--C-
TGTGGACGTGGTGG
TGGCATATTACATCACCACGAGACTCTTCTGGTGGTATCACACTATGGCCAATCAGCAAGTGAGTTTC
CCCGCTTTTGATTTTAGCTTCTGTTGTTTCTGGCTT (SEQ ID NO: 434)

| Reads | Fraction | Fraction Cum_Sum | Seq | SEQ ID NO: |
|---|---|---|---|---|
|  |  |  | CTCTTCTGGTGGTATCACACTATGGCCAATCAGCA AGTGAGTTTCCCCGCTTTTGATTTTAGCTTCTGTTG TTTCTGGCTT |  |
| 10690 | 0.009366061 | 0.457649899 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACAC-------GT---- GGTGGTGGCATATTACATCACCACGAGACTCTTCT GGTGGTATCACACTATGGCCAATCAGCAAGTGAGT TTCCCCGCTTTTGATTTTAGCTTCTGTTGTTTCTGGC TT | 443 |
| 10577 | 0.009267055 | 0.466916954 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACAG-------GA- CGTGGTGGTGGCATATTACATCACCACGAGACTCT TCTGGTGGTATCACACTATGGCCAATCAGCAAGTG AGTTTCCCCGCTTTTGATTTTAGCTTCTGTTGTTTCT GGCTT | 444 |
| 9132 | 0.008001016 | 0.47491797 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACAG-------AC-- GTGGTGGTGGCATATTACATCACCACGAGACTCTT CTGGTGGTATCACACTATGGCCAATCAGCAAGTGA GTTTCCCCGCTTTTGATTTTAGCTTCTGTTGTTTCTG GCTT | 445 |
| 7889 | 0.00691196 | 0.48182993 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATG----------A- CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 446 |
| 7547 | 0.006612316 | 0.488442246 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTA----------CG--- TGGTGGTGGCATATTACATCACCACGAGACTCTTC TGGTGGTATCACACTATGGCCAATCAGCAAGTGAG TTTCCCCGCTTTTGATTTTAGCTTC TGTTGTTTCTGGCTT | 447 |
| 6500 | 0.005694985 | 0.494137232 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC ----------------------------------- GCATATTACATCACCACGAGACTCTTCTGGTGGTA TCACACTATGGCCAATCAGCAAGTGAGTTTCCCCG CTTTTGATTTTAGCTTCTGTTGTTTCTGGCTT | 448 |
| 6114 | 0.005356791 | 0.499494022 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCAC---C--A- CTGTGGACGTGGTGGTGGCATATTACATCACCACG AGACTCTTCTGGTGGTATCACACTATGGCCAATCA GCAAGTGAGTTTCCCCGCTTTTGATTTAGCTTCTG TTGTTTCTGGCTT | 449 |
| 6031 | 0.00528407 | 0.504778093 | GACTATTGCAAATCTCTCCCCCTTTCAGATTCCCCT CGGCGACTCTGGTGGTATCACTGGATTTGCTGGCT | 450 |

TABLE 5-continued

SGMS1

WT Sequence:
GACTATTGCAAATCTCTCCCCCTTTCAGATTCCCCTCGGCGACTCTGGTGGTATCACTGGATTTGCTGG
CTTCTCAGCGTAGTTGGAATCTTCTGTATTCTCTTAGCGCATGACCACTACA--C-
TGTGGACGTGGTGG
TGGCATATTACATCACCACGAGACTCTTCTGGTGGTATCACACTATGGCCAATCAGCAAGTGAGTTTC
CCCGCTTTTGATTTTAGCTTCTGTTGTTTCTGGCTT (SEQ ID NO: 434)

| Reads | Fraction | Fraction Cum_Sum | Seq | SEQ ID NO: |
|---|---|---|---|---|
|  |  |  | TCTCAGCGTAGTTGGAATCTTCTGTATTCTCTTAGC GCATGACCACTACAT------- GGACGTGGTGGTGGCATATTACATCACCACGAGAC TCTTCTGGTGGTATCACACTATGGCCAATCAGCAA GTGAGTTTCCCCGCTTTTGATTTTAGCTTCTGTTGT TTCTGGCTT |  |
| 5783 | 0.005066785 | 0.509844877 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACA----------------------- TATTACATCACCACGAGACTCTTCTGGTGGTATCA CACTATGGCCAATCAGCAAGTGAGTTTCCCCGCTT TTGATTTTAGCTTCTGTTGTTTCTGGCTT | 451 |
| 5581 | 0.004889802 | 0.514734679 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACA------------------------------ TCACCACGAGACTCTTCTGGTGGTATCACACTATG GCCAATCAGCAAGTGAGTTTCCCCGCTTTTGATTTT AGCTTCTGTTGTTTCTGGCTT | 452 |
| 5246 | 0.004596291 | 0.519330971 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTAC---- CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 453 |
| 4878 | 0.004273867 | 0.523604838 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACA--A- CTGTGGACGTGGTGGTGGCATATTACATCACCACG AGACTCTTCTGGTGGTATCACACTATGGCCAATCA GCAAGTGAGTTTCCCCGATTTTGATTTTAGCTTCTG TTGTTTCTGGCTT | 454 |
| 4313 | 0.003778842 | 0.52738368 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACAA-------CG--- TGGTGGCATATTACATCACCACGAGACTCTTC TGGTGGTATCACACTATGGCCAATCAGCAAGTGAG TTTCCCCGCTTTTGATTTAGCTTCTGTTGTTTCTGG CTT | 455 |
| 4253 | 0.003726273 | 0.531109953 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTAC---A--- GTGGACGTGGTGGTGGCATATTACATCACCACGAG ACTCTTCTGGTGGTATCACACTATGGCCAATCAGC AAGTGAGTTTCCCCGCTTTTGATTTTAGCTTCTGTT GTTTCTGGCTT | 456 |
| 3729 | 0.003267169 | 0.534377122 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCAC--------------- GTGGTGGTGGCATATTACATCACCACGAGACTCTT CTGGTGGTATCACACTATGGCCAATCAGCAAGTGA GTTTCCCCGCTTTTGATTTTAGCTTCTGTTGTTTCTG GCTT | 457 |

TABLE 5-continued

SGMS1

WT Sequence:
GACTATTGCAAATCTCTCCCCCTTTCAGATTCCCCTCGGCGACTCTGGTGGTATCACTGGATTTGCTGG
CTTCTCAGCGTAGTTGGAATCTTCTGTATTCTCTTAGCGCATGACCACTACA--C-
TGTGGACGTGGTGG
TGGCATATTACATCACCACGAGACTCTTCTGGTGGTATCACACTATGGCCAATCAGCAAGTGAGTTTC
CCCGCTTTTGATTTTAGCTTCTGTTGTTTCTGGCTT (SEQ ID NO: 434)

| Reads | Fraction | Fraction Cum_Sum | Seq | SEQ ID NO: |
|---|---|---|---|---|
| 3658 | 0.003204963 | 0.537582084 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACA-- CACTGTGGACGTGGTGGTGGCATATTACATCACCA CGAGACTCTTCTGGTGGTATCACACTATGGCCAAT CAGCAAGTGAGTTTCCCCGCTTTTGATTTTAGCTTC TGTTGTTTCTGGCTT | 458 |
| 3401 | 0.002979792 | 0.540561876 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCAC--------------------------------- -------- GAGACTCTTCTGGTGGTATCACACTATGGCCAATC AGCAAGTGAGTTTCCCCGCTTTTGATTTTAGCTTCT GTTGTTTCTGGCTT | 459 |
| 3320 | 0.002908823 | 0.543470699 | GACTATTGCAAATCTCTCCCCCTTTCAGATTCCCCT CGGCGACTCTGGTGGTATCACTGGATTTGCTGGCT TCTCAGCGTAGTTGGAATCTT------------------------ --------- CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 460 |
| 2894 | 0.002535583 | 0.546006282 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGTCCACTA------ CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 461 |
| 2830 | 0.002479509 | 0.548485791 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACAG-------TG----G- TGGTGGCATATTACATCACCACGAGACTCTTCTGG TGGTATCACACTATGGCCAATCAGCAAGTGAGTTT CCCCGCTTTTGATTTTAGCTTCTGTTGTTTCTGGCTT | 462 |
| 2375 | 0.00208086 | 0.550566651 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACAG-------G------- TGGTGGCATATTACATCACCACGAGACTCTTCTGG TGGTATCACACTATGGCCAATCAGCAAGTGAGTTT CCCCGCTTTTGATTTTAGCTTCTGTTGTTTCTGGCTT | 463 |
| 2304 | 0.002018653 | 0.552585304 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACACCT--- GTGGACGTGGTGGTGGCATATTACATCACCACGAG ACTCTTCTGGTGGTATCACACTATGGCCAATCAGC AAGTGAGTTTCCCCGCTTTTGATTTTAGCTTCTGTT GTTTCTGGCTT | 464 |
| 2219 | 0.00194418 | 0.554529485 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACA---- | 465 |

TABLE 5-continued

SGMS1

WT Sequence:
GACTATTGCAAATCTCTCCCCCTTTCAGATTCCCCTCGGCGACTCTGGTGGTATCACTGGATTTGCTGG
CTTCTCAGCGTAGTTGGAATCTTCTGTATTCTCTTAGCGCATGACCACTACA--C-
TGTGGACGTGGTGG
TGGCATATTACATCACCACGAGACTCTTCTGGTGGTATCACACTATGGCCAATCAGCAAGTGAGTTTC
CCCGCTTTTGATTTTAGCTTCTGTTGTTTCTGGCTT (SEQ ID NO: 434)

| Reads | Fraction | Fraction Cum_Sum | Seq | SEQ ID NO: |
|---|---|---|---|---|
|  |  |  | CTGTGGACGTGGTGGTGGCATATTACATCACCACG AGACTCTTCTGGTGGTATCACACTATGGCCAATCA GCAAGTGAGTTTCCCCGATTTTGATTTTAGCTTCTG TTGTTTCTGGCTT |  |
| 2165 | 0.001896868 | 0.556426353 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAG-- ------------------------ CGTGGTGGTGGCATATTACATCACCACGAGACTCT TCTGGTGGTATCACACTATGGCCAATCAGCAAGTG AGTTTCCCCGCTTTTGATTTTAGCTTCTGTTGTTTCT GGCTT | 466 |
| 1999 | 0.001751427 | 0.55817778 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGAC----------- CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 467 |
| 1942 | 0.001701486 | 0.559879266 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATG---------------------- GTGGTGGCATATTACATCACCACGAGACTCTTCTG GTGGTATCACACTATGGCCAATCAGCAAGTGAGTT TCCCCGCTTTTGATTTAGCTTCTGTTGTTTCTGGCT T | 468 |
| 1918 | 0.001680459 | 0.561559725 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATG------------ CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 469 |
| 1780 | 0.00155955 | 0.563119275 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCA-------------------------- TATTACATCACCACGAGACTCTTCTGGTGGTATCA CACTATGGCCAATCAGCAAGTGAGTTTCCCCGCTT TTGATTTTAGCTTCTGTTGTTTCTGGCTT | 470 |
| 1714 | 0.001501724 | 0.564620999 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTAC------- GTGGACGTGGTGGTGGCATATTACATCACCACGAG ACTCTTCTGGTGGTATCACACTATGGCCAATCAGC AAGTGAGTTTCCCCGCTTTTGATTTTAGCTTCTGTT GTTTCTGGCTT | 471 |
| 1570 | 0.001375558 | 0.565996557 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACT--A- CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 472 |

TABLE 5-continued

SGMS1

WT Sequence:
GACTATTGCAAATCTCTCCCCCTTTCAGATTCCCCTCGGCGACTCTGGTGGTATCACTGGATTTGCTGG
CTTCTCAGCGTAGTTGGAATCTTCTGTATTCTCTTAGCGCATGACCACTACA--C-
TGTGGACGTGGTGG
TGGCATATTACATCACCACGAGACTCTTCTGGTGGTATCACACTATGGCCAATCAGCAAGTGAGTTTC
CCCGCTTTTGATTTTAGCTTCTGTTGTTTCTGGCTT (SEQ ID NO: 434)

| Reads | Fraction | Fraction Cum_Sum | Seq | SEQ ID NO: |
|---|---|---|---|---|
| 1534 | 0.001344017 | 0.567340573 | GACTATTGCAAATCTCTCCCCCTTTCAGATTCCCCT CGGCGACTCTGGTGGTATCAC------------------------ ----------------------------------------------- -------------------------------------------- -------- ACTATGGCCAATCAGCAAGTGAGTTTCCCCGCTTTT GATTTTAGCTTCTGTTGTTTCTGGCTT | 473 |
| 1529 | 0.001339636 | 0.568680209 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACT--------- GTGGACGTGGTGGTGGCATATTACATCACCACGAG ACTCTTCTGGTGGTATCACACTATGGCCAATCAGC AAGTGAGTTTCCCCGATTTTGATTTTAGCTTCTGTT GTTTCTGGCTT | 474 |
| 1493 | 0.001308094 | 0.569988303 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGAC---------A- CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 475 |
| 1481 | 0.001297581 | 0.571285884 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATG------------------------- GTGGCATATTACATCACCACGAGACTCTTCTGGTG GTATCACACTATGGCCAATCAGCAAGTGAGTTTCC CCGCTTTTGATTTTAGCTTCTGTTGTTTCTGGCTT | 476 |
| 1465 | 0.001283562 | 0.572569446 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACA-- AACTGTGGACGTGGTGGTGGCATATTACATCACCA CGAGACTCTTCTGGTGGTATCACACTATGGCCAAT CAGCAAGTGAGTTTCCCCGCTTTTGATTTTAGCTTC TGTTGTTTCTGGCTT | 477 |
| 1403 | 0.001229241 | 0.573798687 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCAT------------ GGACGTGGTGGTGGCATATTACATCACCACGAGAC TCTTCTGGTGGTATCACACTATGGCCAATCAGCAA GTGAGTTTCCCCGCTTTTGATTTAGCTTCTGTTGT TTCTGGCTT | 478 |
| 1381 | 0.001209965 | 0.575008652 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCT------------ ------------ CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 479 |
| 1358 | 0.001189814 | 0.576198466 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCA--------- TGTGGACGTGGTGGTGGCATATTACATCACCACGA GACTCTTCTGGTGGTATCACACTATGGCCAATCAG | 480 |

TABLE 5-continued

SGMS1

WT Sequence:
GACTATTGCAAATCTCTCCCCCTTTCAGATTCCCCTCGGCGACTCTGGTGGTATCACTGGATTTGCTGGCTTCTCAGCGTAGTTGGAATCTTCTGTATTCTCTTAGCGCATGACCACTACA--C-TGTGGACGTGGTGGTGGCATATTACATCACCACGAGACTCTTCTGGTGGTATCACACTATGGCCAATCAGCAAGTGAGTTTCCCCGCTTTTGATTTTAGCTTCTGTTGTTTCTGGCTT (SEQ ID NO: 434)

| Reads | Fraction | Fraction Cum_Sum | Seq | SEQ ID NO: |
|---|---|---|---|---|
|  |  |  | CAAGTGAGTTTCCCCGCTTTTGATTTTAGCTTCTGTTGTTTCTGGCTT |  |
| 1322 | 0.001158272 | 0.577356738 | GACTATTGCAAATCTCTCCCCCTTTCAGATTCCCCTCGGCGACTCTGGTGGTATCACTGGATTTGCTGGCTTCTCAGCGTAGTTGGAATCTTCTGTATTCTCTTAGCGCATCACC----------------------------------------ACGAGACTCTTCTGGTGGTATCACACTATGGCCAATCAGCAAGTGAGTTTCCCCGCTTTTGATTTAGCTTCTGTTGTTTCTGGCTT | 481 |
| 1191 | 0.001043497 | 0.578400235 | GACTATTGCAAATCTCTCCCCCTTTCAGATTCCCCTCGGCGACTCTGGTGGTATCACTGGATTTGCTGGCTTCTCAGCGTAGTTGGAATCTTCTGTATTCTCTTAGCGCATGACCACTAC------TGTGGACGTGGTGGTGGCATATTACATCACCACGAGACTCTTCTGGTGGTATCACACTATGGCCAATCAGCAAGTGAGTTTCCCCGATTTTGATTTTAGCTTCTGTTGTTTCTGGCTT | 482 |
| 1185 | 0.00103824 | 0.579438474 | GACTATTGCAAATCTCTCCCCCTTTCAGATTCCCCTCGGCGACTCTGGTGGTATCACTGGATTTGCTGGCTTCTCAGCGTAGTTGGAATCTTCTGTATT--------------------------CTGTGGACGTGGTGGTGGCATATTACATCACCACGAGACTCTTCTGGTGGTATCACACTATGGCCAATCAGCAAGTGAGTTTCCCCGCTTTTGATTTTAGCTTCTGTTGTTTCTGGCTT | 483 |
| 1160 | 0.001016336 | 0.58045481 | GACTATTGCAAATCTCTCCCCCTTTCAGATTCCCCTCGGCGACTCTGGTGGTATCACTGGATTTGCTGGCTTCTCAGCGTAGTTGGAATCTTCTGTATTCTCTTAGCGCATGACCACT-----A---GTGGACGTGGTGGTGGCATATTACATCACCACGAGACTCTTCTGGTGGTATCACACTATGGCCAATCAGCAAGTGAGTTTCCCCGCTTTTGATTTTAGCTTCTGTTGTTTCTGGCTT | 484 |
| 1105 | 0.000968148 | 0.581422958 | GACTATTGCAAATCTCTCCCCCTTTCAGATTCCCCTCGGCGACTCTGGTGGTATCACTGGATTTGCTGGCTTCTCAGCGTAGTTGGAATCTTCTGTATTCTCTTAGCGCATGACCACTAAGA-------CG---TGGTGGTGGCATATTACATCACCACGAGACTCTTCTGGTGGTATCACACTATGGCCAATCAGCAAGTGAGTTTCCCCGCTTTTGATTTAGCTTCTGTTGTTTCTGGCTT | 485 |
| 1086 | 0.000951501 | 0.582374458 | GACTATTGCAAATCTCTCCCCCTTTCAGATTCCCCTCGGCGACTCTGGTGGTATCACTGGATTTGCTGGCTTCTCAGCGTAGTTGGAATCTTCTGTATTCTCTTAGCGCATGACCACTACAT---CTGTGGACGTGGTGGTGGCATATTACATCACCACGAGACTCTTCTGGTGGTATCACACTATGGCCAATCAGCAAGTGAGTTTCCCCGCTTTTGATTTTAGCTTCTGTTGTTTCTGGCTT | 486 |
| 1084 | 0.000949748 | 0.583324207 | GACTATTGCAAATCTCTCCCCCTTTCAGATTCCCCTCGGCGACTCTGGTGGTATCACTGGATTTGCTGGCTTCTCAGCGTAGTTGGAATCTTCTGTATTCTCTTAGCGCATGACCACTACA---GCTGTGGACGTGGTGGTGGCATATTACATCACCACGAGACTCTTCTGGTGGTATCACACTATGGCCAATCAGCAAGTGAGTTTCCCCGCTTTTGATTTTAGCTTCTGTTGTTTCTGGCTT | 487 |
| 1072 | 0.000939235 | 0.584263441 | GACTATTGCAAATCTCTCCCCCTTTCAGATTCCCCTCGGCGACTCTGGTGGTATCACTGGATTTGCTGGCT | 488 |

TABLE 5-continued

SGMS1

WT Sequence:
GACTATTGCAAATCTCTCCCCCTTTCAGATTCCCCTCGGCGACTCTGGTGGTATCACTGGATTTGCTGG
CTTCTCAGCGTAGTTGGAATCTTCTGTATTCTCTTAGCGCATGACCACTACA--C-
TGTGGACGTGGTGG
TGGCATATTACATCACCACGAGACTCTTCTGGTGGTATCACACTATGGCCAATCAGCAAGTGAGTTTC
CCCGCTTTTGATTTTAGCTTCTGTTGTTTCTGGCTT (SEQ ID NO: 434)

| Reads | Fraction | Fraction Cum_Sum | Seq | SEQ ID NO: |
|---|---|---|---|---|
| | | | TCTCAGCGTAGTTGGAATCTTCTGTATTCTCTTAGC GCATGACCAC----------- TGGACGTGGTGGTGGCATATTACATCACCACGAGA CTCTTCTGGTGGTATCACACTATGGCCAATCAGCA AGTGAGTTTCCCCGCTTTTGATTTTAGCTTCTGTTG TTTCTGGCTT | |
| 1065 | 0.000933101 | 0.585196543 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC G---------------- CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 489 |
| 1058 | 0.000926968 | 0.586123511 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACT------- CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 490 |
| 1042 | 0.00091295 | 0.587036461 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCA--------------- CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 491 |
| 1036 | 0.000907693 | 0.587944154 | GACTATTGCAAATCTCTCCCCCTTTCAGATTCCCCT CGGCGACTCTGGTGGTATCACTGGATTTGCTGGCT TCTCAGCGTAGT-------------------------- ------------ TGGACGTGGTGGTGGCATATTACATCACCACGAGA CTCTTCTGGTGGTATCACACTATGGCCAATCAGCA AGTGAGTTTCCCCGCTTTTGATTTTAGCTTCTGTTG TTTCTGGCTT | 492 |
| 1036 | 0.000907693 | 0.588851847 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACAT-------GG------ TGGTGGCATATTACATCACCACGAGACTCTTCTGG TGGTATCACACTATGGCCAATCAGCAAGTGAGTTT CCCCGCTTTTGATTTTAGCTTCTGTTGTTTCTGGCTT | 493 |
| 1028 | 0.000900684 | 0.589752531 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACA--------------------- CATATTACATCACCACGAGACTCTTCTGGTGGTAT CACACTATGGCCAATCAGCAAGTGAGTTTCCCCGC TTTTGATTTTAGCTTCTGTTGTTTCTGGCTT | 494 |
| 1003 | 0.00087878 | 0.590631311 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACC---------------- GTGGTGGTGGCATATTACATCACCACGAGACTCTT CTGGTGGTATCACACTATGGCCAATCAGCAAGTGA GTTTCCCCGCTTTTGATTTTAGCTTCTGTTGTTTCTG GCTT | 495 |

TABLE 5-continued

SGMS1

WT Sequence:
GACTATTGCAAATCTCTCCCCCTTTCAGATTCCCCTCGGCGACTCTGGTGGTATCACTGGATTTGCTGG
CTTCTCAGCGTAGTTGGAATCTTCTGTATTCTCTTAGCGCATGACCACTACA--C-
TGTGGACGTGGTGG
TGGCATATTACATCACCACGAGACTCTTCTGGTGGTATCACACTATGGCCAATCAGCAAGTGAGTTTC
CCCGCTTTTGATTTTAGCTTCTGTTGTTTCTGGCTT (SEQ ID NO: 434)

| Reads | Fraction | Fraction Cum_Sum | Seq | SEQ ID NO: |
|---|---|---|---|---|
| 969 | 0.000848991 | 0.591480302 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGAC------------- GTGGACGTGGTGGTGGCATATTACATCACCACGAG ACTCTTCTGGTGGTATCACACTATGGCCAATCAGC AAGTGAGTTTCCCCGCTTTTGATTTTAGCTTCTGTT GTTTCTGGCTT | 496 |
| 945 | 0.000827963 | 0.592308265 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATG---ACTA------ CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 497 |
| 936 | 0.000820078 | 0.593128343 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTA--------------------------- TTACATCACCACGAGACTCTTCTGGTGGTATCACA CTATGGCCAATCAGCAAGTGAGTTTCCCCGCTTTT GATTTTAGCTTCTGTTGTTTCTGGCTT | 498 |
| 929 | 0.000813945 | 0.593942288 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATG-------------------- TGGTGGTGGCATATTACATCACCACGAGACTCTTC TGGTGGTATCACACTATGGCCAATCAGCAAGTGAG TTTCCCCGCTTTTGATTTTAGCTTCTGTTGTTTCTGG CTT | 499 |
| 927 | 0.000812193 | 0.59475448 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GC--------------------- ACGTGGTGGTGGCATATTACATCACCACGAGACTC TTCTGGTGGTATCACACTATGGCCAATCAGCAAGT GAGTTTCCCCGCTTTTGATTTTAGCTTCTGTTGTTT CTGGCTT | 500 |
| 896 | 0.000785032 | 0.595539512 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC G--------------------- CGTGGTGGTGGCATATTACATCACCACGAGACTCT TCTGGTGGTATCACACTATGGCCAATCAGCAAGTG AGTTTCCCCGCTTTTGATTTTAGCTTCTGTTGTTTCT GGCTT | 501 |
| 878 | 0.000769261 | 0.596308773 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTA----A- CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 502 |
| 856 | 0.000749986 | 0.597058759 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACAT-------G--------- GTGGCATATTACATCACCACGAGACTCTTCTGGTG | 503 |

TABLE 5-continued

SGMS1

WT Sequence:
GACTATTGCAAATCTCTCCCCCTTTCAGATTCCCCTCGGCGACTCTGGTGGTATCACTGGATTTGCTGG
CTTCTCAGCGTAGTTGGAATCTTCTGTATTCTCTTAGCGCATGACCACTACA--C-
TGTGGACGTGGTGG
TGGCATATTACATCACCACGAGACTCTTCTGGTGGTATCACACTATGGCCAATCAGCAAGTGAGTTTC
CCCGCTTTTGATTTTAGCTTCTGTTGTTTCTGGCTT (SEQ ID NO: 434)

| Reads | Fraction | Fraction Cum_Sum | Seq | SEQ ID NO: |
|---|---|---|---|---|
| | | | GTATCACACTATGGCCAATCAGCAAGTGAGTTTCC CCGCTTTTGATTTTAGCTTCTGTTGTTTCTGGCTT | |
| 837 | 0.000733339 | 0.597792098 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACAG--------------------CATATTACATCACCACGAGACTCTTCTGGTGGTAT CACACTATGGCCAATCAGCAAGTGAGTTTCCCCGC TTTTGATTTTAGCTTCTGTTGTTTCTGGCTT | 504 |
| 816 | 0.00071494 | 0.598507038 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACA--A-CTGTGGACGTGGTGGTGGCATATTACATCACCACG AGACTCTTCTGGTGGTATCACGCTATGGCCAATCA GCAAGTGAGTTTCCCCGCTTTTGATTTTAGCTTCTG TTGTTTCTGGCTT | 505 |
| 815 | 0.000714064 | 0.599221101 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACGT------CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 506 |
| 809 | 0.000708807 | 0.599929908 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCAC--------CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 507 |
| 808 | 0.00070793 | 0.600637838 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTGGTG-------GT----------GGCATATTACATCACCACGAGACTCTTCTGGTGGT ATCACACTATGGCCAATCAGCAAGTGAGTTTCCCC GCTTTTGATTTTAGCTTCTGTTGTTTCTGGCTT | 508 |
| 790 | 0.00069216 | 0.601329998 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACA--A-CTGTGGACGTGGTGGTGGCATATTACATCGCCACG AGACTCTTCTGGTGGTATCACACTATGGCCAATCA GCAAGTGAGTTTCCCCGCTTTTGATTTTAGCTTCTG TTGTTTCTGGCTT | 509 |
| 775 | 0.000679017 | 0.602009016 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCAT-----------A-CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 510 |
| 747 | 0.000654485 | 0.602663501 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCA-------------------------- | 511 |

TABLE 5-continued

SGMS1

WT Sequence:
GACTATTGCAAATCTCTCCCCCTTTCAGATTCCCCTCGGCGACTCTGGTGGTATCACTGGATTTGCTGG
CTTCTCAGCGTAGTTGGAATCTTCTGTATTCTCTTAGCGCATGACCACTACA--C-
TGTGGACGTGGTGG
TGGCATATTACATCACCACGAGACTCTTCTGGTGGTATCACACTATGGCCAATCAGCAAGTGAGTTTC
CCCGCTTTTGATTTTAGCTTCTGTTGTTTCTGGCTT (SEQ ID NO: 434)

| Reads | Fraction | Fraction Cum_Sum | Seq | SEQ ID NO: |
|---|---|---|---|---|
| | | | TCACCACGAGACTCTTCTGGTGGTATCACACTATG GCCAATCAGCAAGTGAGTTTCCCCGCTTTTGATTTT AGCTTCTGTTGTTTCTGGCTT | |
| 745 | 0.000652733 | 0.603316234 | GACTATTGCAAATCTCTCCCCCTTTCAGATTCCCCT CGGCGACTCTGGTGGTATCACTGGATTTGCTGGCT TCTCAGCGTAGTTGGAATCTTC------------------------ ----------- TGGACGTGGTGGTGGCATATTACATCACCACGAGA CTCTTCTGGTGGTATCACACTATGGCCAATCAGCA AGTGAGTTTCCCCGCTTTTGATTTTAGCTTCTGTTG TTTCTGGCTT | 512 |
| 739 | 0.000647476 | 0.60396371 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC G-------------------- TGGACGTGGTGGTGGCATATTACATCACCACGAGA CTCTTCTGGTGGTATCACACTATGGCCAATCAGCA AGTGAGTTTCCCCGCTTTTGATTTTAGCTTCTGTTG TTTCTG GCTT | 513 |
| 739 | 0.000647476 | 0.604611186 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTAT--------- GGACGTGGTGGTGGCATATTACATCACCACGAGAC TCTTCTGGTGGTATCACACTATGGCCAATCAGCAA GTGAGTTTCCCCGCTTTTGATTTAGCTTCTGTTGT TTCTGGCTT | 514 |
| 731 | 0.000640467 | 0.605251653 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATG--------A--A- CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 515 |
| 720 | 0.000630829 | 0.605882482 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCACGTCCA--------- CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 516 |
| 713 | 0.000624696 | 0.606507178 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCAT---------------------- GGCATATTACATCACCACGAGACTCTTCTGGTGGT ATCACACTATGGCCAATCAGCAAGTGAGTTTCCCC GCTTTTGATTTTAGCTTCTGTTGTTTCTGGCTT | 517 |
| 707 | 0.000619439 | 0.607126617 | GACTATTGCAAATCTCTCCCCCTTTCAGATTCCCCT CAAGTGAGTTTCCCCGCTTTTGATTTTAGCTTCTGT CGGCGACTCTGGTGGTATCACTGGATTTGCTGGCT TCTCAGCGTAGTTGGAATCTTCTGTATTCTCTTAGC GCATGACCACTA------- TGTGGACGTGGTGGTGGCATATTACATCACCACGA GACTCTTCTGGTGGTATCACACTATGGCCAATCAG TGTTTCTGGCTT | 518 |
| 707 | 0.000619439 | 0.607746056 | GACTATTGCAAATCTCTCCCCCTTTCAGATTCCCCT CGGCGACTCTGGTGGTATCACTGGATTTGCTGGCT | 519 |

TABLE 5-continued

SGMS1

WT Sequence:
GACTATTGCAAATCTCTCCCCCTTTCAGATTCCCCTCGGCGACTCTGGTGGTATCACTGGATTTGCTGG
CTTCTCAGCGTAGTTGGAATCTTCTGTATTCTCTTAGCGCATGACCACTACA--C-
TGTGGACGTGGTGG
TGGCATATTACATCACCACGAGACTCTTCTGGTGGTATCACACTATGGCCAATCAGCAAGTGAGTTTC
CCCGCTTTTGATTTTAGCTTCTGTTGTTTCTGGCTT (SEQ ID NO: 434)

| Reads | Fraction | Fraction Cum_Sum | Seq | SEQ ID NO: |
|---|---|---|---|---|
| | | | TCTCAGCGTAGTTGGAATCTTCTGTATTCTCTTAGC GCATGACCAC------A- CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | |
| 701 | 0.000614182 | 0.608360238 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACC---------- CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 520 |
| 687 | 0.000601916 | 0.608962155 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCAC--------- GTGGACGTGGTGGTGGCATATTACATCACCACGAG ACTCTTCTGGTGGTATCACACTATGGCCAATCAGC AAGTGAGTTTCCCCGCTTTTGATTTTAGCTTCTGTT GTTTCTGGCTT | 521 |
| 683 | 0.000598412 | 0.609560566 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACGA-------CG--- TGGTGGTGGCATATTACATCACCACGAGACTCTTC TGGTGGTATCACACTATGGCCAATCAGCAAGTGAG TTTCCCCGCTTTTGATTTTAGCTTCTGTTGTTTCTGG CTT | 522 |
| 676 | 0.000592278 | 0.610152845 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACAG-------G---------- TGGCATATTACATCACCACGAGACTCTTCTGGTGG TATCACACTATGGCCAATCAGCAAGTGAGTTTCCC CGCTTTTGATTTTAGCTTCTGTTGTTTCTGGCTT | 523 |
| 663 | 0.000580889 | 0.610733733 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACA--A- CTGTGGACGTGGTGGTGGCATATTACATCACCACG AGACTCTTCTGGTGGTATCACACTATGGCCAATCA GCAAGTGGGTTTCCCCGCTTTTGATTTTAGCTTCTG TTGTTTCTGGCTT | 524 |
| 652 | 0.000571251 | 0.611304984 | GACTATTGCAAATCTCTCCCCCTTTCAGATTCCCCT CGGCGACTCTGGTGGTATCACTGGATTTGCTGGCT TCTCAGCGTAGTTGGAATCTTCCGTATTCTCTTAGC GCATGACCACTACA--A- CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 525 |
| 645 | 0.000565118 | 0.611870102 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGGCCACTACA--A- CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 526 |

TABLE 5-continued

SGMS1

WT Sequence:
GACTATTGCAAATCTCTCCCCCTTTCAGATTCCCCTCGGCGACTCTGGTGGTATCACTGGATTTGCTGG
CTTCTCAGCGTAGTTGGAATCTTCTGTATTCTCTTAGCGCATGACCACTACA--C-
TGTGGACGTGGTGG
TGGCATATTACATCACCACGAGACTCTTCTGGTGGTATCACACTATGGCCAATCAGCAAGTGAGTTTC
CCCGCTTTTGATTTTAGCTTCTGTTGTTTCTGGCTT (SEQ ID NO: 434)

| Reads | Fraction | Fraction Cum_Sum | Seq | SEQ ID NO: |
|---|---|---|---|---|
| 641 | 0.000561613 | 0.612431715 | GACTATTGCAAATCTCTCCCCCTTTCAGATTCCCCT CGGCGACTCTGGTGGTATCACTGGATTTGCTGGCC TCTCAGCGTAGTTGGAATCTTCTGTATTCTCTTAGC GCATGACCACTACA--A- CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 527 |
| 637 | 0.000558109 | 0.612989823 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCAC------A--- GTGGACGTGGTGGTGGCATATTACATCACCACGAG ACTCTTCTGGTGGTATCACACTATGGCCAATCAGC AAGTGAGTTTCCCCGCTTTTGATTTTAGCTTCTGTT GTTTCTGG CTT | 528 |
| 634 | 0.00055548 | 0.613545304 | GACTATTGCAAATCTCTCCCCCTTTCAGATTCCCCT CGGCGACTCTGGTGGTATCACTGGATTTGCTGGCT CCTCAGCGTAGTTGGAATCTTCTGTATTCTCTTAGC GCATGACCACTACA--A- CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 529 |
| 628 | 0.000550223 | 0.614095527 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCAT-------------- CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 530 |
| 626 | 0.000548471 | 0.614643998 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACG--------- GACGTGGTGGTGGCATATTACATCACCACGAGACT CTTCTGGTGGTATCACACTATGGCCAATCAGCAAG TGAGTTTCCCCGCTTTTGATTTTAGCTTCTGTTGTTT CTGGCTT | 531 |
| 616 | 0.000539709 | 0.615183707 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACC--A- CTGTGGACGTGGTGGTGGCATATTACATCACCACG AGACTCTTCTGGTGGTATCACACTATGGCCAATCA GCAAGTGAGTTTCCCCGCTTTTGATTTTAGCTTCTG TTGTTTCTGGCTT | 532 |
| 616 | 0.000539709 | 0.615723416 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTACA--A- CTGTGGACGTGGTGGTGGCATATTACATCACCACG AGACTCTTCTGGTGGTATCACACTATGGCCAATCG GCAAGTGAGTTTCCCCGCTTTTGATTTTAGCTTCTG TTGTTTCTGGCTT | 533 |
| 615 | 0.000538833 | 0.61626225 | GACTATTGCAAATCTCTCCCCCTTTCAGATTCCCCT CGGCGACTCTGGTGGTATCACTGGATTTGCTGGCT TCTCAGCGTAGTTGGAATCTTCTGTATTCTCTTAGC GCATGACCACTAC---- | 534 |

TABLE 5-continued

SGMS1

WT Sequence:
GACTATTGCAAATCTCTCCCCCTTTCAGATTCCCCTCGGCGACTCTGGTGGTATCACTGGATTTGCTGG
CTTCTCAGCGTAGTTGGAATCTTCTGTATTCTCTTAGCGCATGACCACTACA--C-
TGTGGACGTGGTGG
TGGCATATTACATCACCACGAGACTCTTCTGGTGGTATCACACTATGGCCAATCAGCAAGTGAGTTTC
CCCGCTTTTGATTTTAGCTTCTGTTGTTTCTGGCTT (SEQ ID NO: 434)

| Reads | Fraction | Fraction Cum_Sum | Seq | SEQ ID NO: |
|---|---|---|---|---|
| | | | GCTGTGGACGTGGTGGTGGCATATTACATCACCAC GAGACTCTTCTGGTGGTATCACACTATGGCCAATC AGCAAGTGAGTTTCCCCGCTTTTGATTTTAGCTTCT GTTGTTTCTGGCTT | |

TABLE 6

IL1RAPL2

WT sequence:
TCCTCATCCCCAAGACTGCTATTGACTGAGGTAAAATATGAATTTGACACCATGCTGAGTTACCTTATA
CCACACAA---------CATCAGGCTCCTGATCGGACTTTTTAAAGTCATCCATGTCTGGACAGGAGATCTCC
TTTCTTTTAGTGACTTCAGATTT--------------TTCTAAATAGC-GGATCCTGCTGTTGTAGCACAGG
CCTGATTCATT----------------------------------------------CTCTGCAACAGTCAAGGACA (SEQ ID NO: 535)

| Reads | Fraction | Fraction Cum_Sum | Seq | SEQ ID NO: |
|---|---|---|---|---|
| 233692 (WT) | 0.275762621 | 0.275762621 | TCCTCATCCCCAAGACTGCTATTGACTGAGGTAAA ATATGAATTTGACACCATGCTGAGTTACCTTATAC CACACAA-------- CATCAGGCTCCTGATCGGACTTTTTAAAGTCATCC ATGTCTGGACAGGAGATCTCCTTTCTTTTAGTGACT TCAGATTT--------------TTCTAAATAGC- GGATCCTGCTGTTGTAGCACAGG------- CCTGATTCATT------------------------------------- --------- CTCTGCAACAGTCAAGGACA | 536 |
| 32827 | 0.038736711 | 0.314499333 | TCCTCATCCCCAAGACTGCTATTGACTGAGGTAAA ATATGAATTTGACACCATGCTGAGTTACCTTATAC CACACAA------- CCATCAGGCTCCTGATCGGACTTTTTAAAGTCATC CATGTCTGGACAGGAGATCTCCTTTCTTTTAGTGAC TTCAGATTT--------------TTCTAAATAGC- GGATCCTGCTGTTGTAGCACAGG------- CCTGATTCATT------------------------------------- --------- CTCTGCAACAGTCAAGGACA | 537 |
| 26161 | 0.030870659 | 0.345369991 | TCCTCATCCCCAAGACTGCTATTGACTGAGGTAAA ATATGAATTTGACACCATGCTGAGTTACCTTATAC CACA-------------- CAGGCTCCTGATCGGACTTTTTAAAGTCATCCATG TCTGGACAGGAGATCTCCTTTCTTTTAGTGACTTCA GATTT-------------TTCTAAATAGC- GGATCCTGCTGTTGTAGCACAGG------- CCTGATTCATT------------------------------------- --------- CTCTGCAACAGTCAAGGACA | 538 |
| 18043 | 0.021291208 | 0.366661199 | TCCTCATCCCCAAGACTGCTATTGACTGAGGTAAA ATATGAATTTGACACCATGCTGAGTTACCTTATAC CACACAA------- CTATCAGGCTCCTGATCGGACTTTTTAAAGTCATCC ATGTCTGGACAGGAGATCTCCTTTCTTTTAGTGACT TCAGATTT--------------TTCTAAATAGC- GGATCCTGCTGTTGTAGCACAGG------- CCTGATTCATT------------------------------------- --------- CTCTGCAACAGTCAAGGACA | 539 |
| 15983 | 0.018860355 | 0.385521554 | TCCTCATCCCCAAGACTGCTATTGACTGAGGTAAA ATATGAATTTGACACCATGCTGAGTTACCTTATAC CACACAA------ | 540 |

TABLE 6-continued

IL1RAPL2

WT sequence:
TCCTCATCCCCAAGACTGCTATTGACTGAGGTAAAATATGAATTTGACACCATGCTGAGTTACCTTATA
CCACACAA---------CATCAGGCTCCTGATCGGACTTTTTAAAGTCATCCATGTCTGGACAGGAGATCTCC
TTTCTTTTAGTGACTTCAGATTT--------------TTCTAAATAGC-GGATCCTGCTGTTGTAGCACAGG
CCTGATTCATT-----------------------------------------CTCTGCAACAGTCAAGGACA (SEQ ID NO: 535)

| Reads | Fraction | Fraction Cum_Sum | Seq | SEQ ID NO: |
|---|---|---|---|---|
| | | | CAATCAGGCTCCTGATCGGACTTTTTAAAGTCATC CATGTCTGGACAGGAGATCTCCTTTCTTTTAGTGAC TTCAGATTT--------------TTCTAAATAGC- GGATCCTGCTGTTGTAGCACAGG------- CCTGATTCATT------------------------------------ CTCTGCAACAGTCAAGGACA | |
| 11590 | 0.013676501 | 0.399198054 | TCCTCATCCCCAAGACTGCTATTGACTGAGGTAAA ATATGAATTTGACACCATGCTGAGTTACCTTATAC CACAC----------- ATCAGGCTCCTGATCGGACTTTTTAAAGTCATCCA TGTCTGGACAGGAGATCTCCTTTCTTTTAGTGACTT CAGATTT--------------TTCTAAATAGC- GGATCCTGCTGTTGTAGCACAGG------- CCTGATTCATT------------------------------------ -------- CTCTGCAACAGTCAAGGACA | 541 |
| 10519 | 0.012412693 | 0.411610747 | TCCTCATCCCCAAGACTGCTATTGACTGAGGTAAA ATATGAATTTGACACCATGCTGAGTTACCTTATAC CACACAA---------- TCAGGCTCCTGATCGGACTTTTTAAAGTCATCCAT GTCTGGACAGGAGATCTCCTTTCTTTTAGTGACTTC AGATTT--------------TTCTAAATAGC- GGATCCTGCTGTTGTAGCACAGG------- CCTGATTCATT------------------------------------ -------- CTCTGCAACAGTCAAGGACA | 542 |
| 9660 | 0.011399051 | 0.423009798 | TCCTCATCCCCAAGACTGCTATTGACTGAGGTAAA ATATGAATTTGACACCATGCTGAGTTACCTTATAC CACACAA------- CGATCAGGCTCCTGATCGGACTTTTTAAAGTCATC CATGTCTGGACAGGAGATCTCCTTTCTTTTAGTGAC TTCAGATTT--------------TTCTAAATAGC- GGATCCTGCTGTTGTAGCACAGG------- CCTGATTCATT------------------------------------ -------- CTCTGCAACAGTCAAGGACA | 543 |
| 8642 | 0.010197784 | 0.433207582 | TCCTCATCCCCAAGACTGCTATTGACTGAGGTAAA ATATGAATTTGACACCATGCTGAGTTACCTTATAC CA---------------- CAGGCTCCTGATCGGACTTTTTAAAGTCATCCATG TCTGGACAGGAGATCTCCTTTCTTTTAGTGACTTCA GATTT--------------TTCTAAATAGC- GGATCCTGCTGTTGTAGCACAGG------- CCTGATTCATT------------------------------------ -------- CTCTGCAACAGTCAAGGACA | 544 |
| 8162 | 0.009631372 | 0.442838954 | TCCTCATCCCCAAGACTGCTATTGACTGAGGTAAA ATATGAATTTGACACCATGCTGAGTTACCTTATAC CACACAA---------- CCAGGCTCCTGATCGGACTTTTTAAAGTCATCCAT GTCTGGACAGGAGATCTCCTTTCTTTTAGTGACTTC AGATTT--------------TTCTAAATAGC- GGATCCTGCTGTTGTAGCACAGG------- CCTGATTCATT------------------------------------ -------- CTCTGCAACAGTCAAGGACA | 545 |
| 8041 | 0.009488589 | 0.452327542 | TCCTCATCCCCAAGACTGCTATTGACTGAGGTAAA ATATGAATTTGACACCATGCTGAGTTACCTTATAC CACACAA-------C- ATCAGGCTCCTGATCGGACTTTTTAAAGTCATCCA TGTCTGGACAGGAGATCTCCTTTCTTTTAGTGACTT CAGATTT--------------TTCTAAATAGC- GGATCCTGCTGTTGTAGCACAGG------- | 546 |

TABLE 6-continued

IL1RAPL2

WT sequence:
TCCTCATCCCCAAGACTGCTATTGACTGAGGTAAAATATGAATTTGACACCATGCTGAGTTACCTTATA
CCACACAA---------CATCAGGCTCCTGATCGGACTTTTTAAAGTCATCCATGTCTGGACAGGAGATCTCC
TTTCTTTTAGTGACTTCAGATTT--------------TTCTAAATAGC-GGATCCTGCTGTTGTAGCACAGG
CCTGATTCATT---------------------------------------------CTCTGCAACAGTCAAGGACA (SEQ ID NO: 535)

| Reads | Fraction | Fraction Cum_Sum | Seq | SEQ ID NO: |
|---|---|---|---|---|
|  |  |  | CCTGATTCATT---------------------------------------<br>--------<br>ATCTGCAACAGTCAAGGACA |  |
| 8011 | 0.009453188 | 0.46178073 | TCCTCATCCCCAAGACTGCTATTGACTGAGGTAAA<br>ATATGAATTTGACACCATGCTGAGTTACCTTATAC<br>CACA-------------<br>TCAGGCTCCTGATCGGACTTTTTAAAGTCATCCAT<br>GTCTGGACAGGAGATCTCCTTTCTTTTAGTGACTTC<br>AGATTT--------------TTCTAAATAGC-<br>GGATCCTGCTGTTGTAGCACAGG-------<br>CCTGATTCATT---------------------------------------<br>--------<br>CTCTGCAACAGTCAAGGACA | 547 |
| 8002 | 0.009442568 | 0.471223297 | TCCTCATCCCCAAGACTGCTATTGACTGAGGTAAA<br>ATATGAATTTGACACCATGCTGAGTTACCTTATAC<br>CACA-------------<br>ATCAGGCTCCTGATCGGACTTTTTAAAGTCATCCA<br>TGTCTGGACAGGAGATCTCCTTTCTTTTAGTGACTT<br>CAGATTT--------------TTCTAAATAGC-<br>GGATCCTGCTGTTGTAGCACAGG-------<br>CCTGATTCATT---------------------------------------<br>--------<br>CTCTGCAACAGTCAAGGACA | 548 |
| 7538 | 0.008895036 | 0.480118333 | TCCTCATCCCCAAGACTGCTATTGACTGAGGTAAA<br>ATATGAATTTGACACCATGCTGAGTTACCTTATAC<br>CACACAA-----------<br>CAGGCTCCTGATCGGACTTTTTAAAGTCATCCATG<br>TCTGGACAGGAGATCTCCTTTCTTTTAGTGACTTCA<br>GATTT--------------TTCTAAATAGC-<br>GGATCCTGCTGTTGTAGCACAGG-------<br>CCTGATTCATT---------------------------------------<br>CTCTGCAACAGTCAAGGACA | 549 |
| 5582 | 0.006586905 | 0.486705238 | TCCTCATCCCCAAGACTGCTATTGACTGAGGTAAA<br>ATATGAATTTGACACCATGCTGAGTTACCTTATAC-<br>-----------------<br>CAGGCTCCTGATCGGACTTTTTAAAGTCATCCATG<br>TCTGGACAGGAGATCTCCTTTCTTTTAGTGACTTCA<br>GATTT--------------TTCTAAATAGC-<br>GGATCCTGCTGTTGTAGCACAGG-------<br>CCTGATTCATT---------------------------------------<br>--------<br>CTCTGCAACAGTCAAGGACA | 550 |
| 5070 | 0.005982732 | 0.492687969 | TCCTCATCCCCAAGACTGCTATTGACTGAGGTAAA<br>ATATGAATTTGACACCATGCTGAGTTACCTTATAC<br>CACACAA---------------<br>CTCCTGATCGGACTTTTTAAAGTCATCCATGTCTGG<br>ACAGGAGATCTCCTTTCTTTTAGTGACTTCAGATTT<br>--------------TTCTAAATAGC-<br>GGATCCTGCTGTTGTAGCACAGG-------<br>CCTGATTCATT---------------------------------------<br>--------<br>CTCTGCAACAGTCAAGGACA | 551 |
| 4681 | 0.005523701 | 0.498211671 | TCCTCATCCCCAAGACTGCTATTGACTGAGGTAAA<br>ATATGAATTTGACACCATGCTGAGTTACCTTATAC-<br>-----------------<br>CTGATCGGACTTTTTAAAGTCATCCATGTCTGGAC<br>AGGAGATCTCCTTTCTTTTAGTGACTTCAGATTT----<br>-----------TTCTAAATAGC-<br>GGATCCTGCTGTTGTAGCACAGG-------<br>CCTGATTCATT---------------------------------------<br>CTCTGCAACAGTCAAGGACA | 552 |

TABLE 6-continued

IL1RAPL2

WT sequence:
TCCTCATCCCCAAGACTGCTATTGACTGAGGTAAAATATGAATTTGACACCATGCTGAGTTACCTTATA
CCACACAA---------CATCAGGCTCCTGATCGGACTTTTTAAAGTCATCCATGTCTGGACAGGAGATCTCC
TTTCTTTTAGTGACTTCAGATTT--------------TTCTAAATAGC-GGATCCTGCTGTTGTAGCACAGG
CCTGATTCATT----------------------------------------CTCTGCAACAGTCAAGGACA (SEQ ID NO: 535)

| Reads | Fraction | Fraction Cum_Sum | Seq | SEQ ID NO: |
|---|---|---|---|---|
| 4127 | 0.004869967 | 0.503081638 | TCCTCATCCCCAAGACTGCTATTGACTGAGGTAAA ATATGAATTTGACACCATGCTGAGTTACCTTAT----- -------------- ATCAGGCTCCTGATCGGACTTTTTAAAGTCATCCA TGTCTGGACAGGAGATCTCCTTTCTTTTAGTGACTT CAGATTT--------------TTCTAAATAGC- GGATCCTGCTGTTGTAGCACAGG------- CCTGATTCATT------------------------------------ -------- CTCTGCAACAGTCAAGGACA | 553 |
| 4064 | 0.004795625 | 0.507877263 | TCCTCATCCCCAAGACTGCTATTGACTGAGGTAAA ATATGAATTTGACACCATGCTGAGTTAC--------------- ----------------- CTGATCGGACTTTTTAAAGTCATCCATGTCTGGAC AGGAGATCTCCTTTCTTTTAGTGACTTCAGATTT---- -----------TTCTAAATAGC- GGATCCTGCTGTTGTAGCACAGG------- CCTGATTCATT------------------------------------ -------- CTCTGCAACAGTCAAGGACA | 554 |
| 2841 | 0.003352454 | 0.511229717 | TCCTCATCCCCAAGACTGCTATTGACTGAGGTAAA ATATGAATTTGACACCATGCTGAGTTACCTT--------- ---------------------- ATCGGACTTTTTAAAGTCATCCATGTCTGGACAGG AGATCTCCTTTCTTTTAGTGACTTCAGATTT----------- ---TTCTAAATAGC- GGATCCTGCTGTTGTAGCACAGG------- CCTGATTCATT------------------------------------ CTCTGCAACAGTCAAGGACA | 555 |
| 2809 | 0.003314693 | 0.51454441 | TCCTCATCCCCAAGACTGCTATTGACTGAGGTAAA ATATGAATTTGACACCATGCTGAGTTACCTTATAC CACA------------------ CTCCTGATCGGACTTTTTAAAGTCATCCATGTCTGG ACAGGAGATCTCCTTTCTTTTAGTGACTTCAGATTT ---------------TTCTAAATAGC- GGATCCTGCTGTTGTAGCACAGG------- CCTGATTCATT------------------------------------ -------- CTCTGCAACAGTCAAGGACA | 556 |
| 2573 | 0.003036207 | 0.517580616 | TCCTCATCCCCAAGACTGCTATTGACTGAGGTAAA ATATGAATTTGACACCATGCTGAGTTACCTTATAC CACACAA------------- GGCTCCTGATCGGACTTTTTAAAGTCATCCATGTCT GGACAGGAGATCTCCTTTCTTTTAGTGACTTCAGA TTT--------------TTCTAAATAGC- GGATCCTGCTGTTGTAGCACAGG------- CCTGATTCATT------------------------------------ -------- CTCTGCAACAGTCAAGGACA | 557 |
| 2513 | 0.002965405 | 0.520546022 | TCCTCATCCCCAAGACTGCTATTGACTGAGGTAAA ATATGAATTTGACACCATGCTGAGTTACCTTATAC- --------------------- TCCTGATCGGACTTTTTAAAGTCATCCATGTCTGGA CAGGAGATCTCCTTTCTTTTAGTGACTTCAGATTT-- -------------TTCTAAATAGC- GGATCCTGCTGTTGTAGCACAGG------- CCTGATTCATT------------------------------------ CTCTGCAACAGTCAAGGACA | 558 |
| 2419 | 0.002854483 | 0.523400504 | TCCTCATCCCCAAGACTGCTATTGACTGAGGTAAA ATATGAATTTGACACCATGCTGAGTTACCTTATAC C--------------- ATCAGGCTCCTGATCGGACTTTTTAAAGTCATCCA TGTCTGGACAGGAGATCTCCTTTCTTTTAGTGACTT | 559 |

TABLE 6-continued

IL1RAPL2

WT sequence:
TCCTCATCCCCAAGACTGCTATTGACTGAGGTAAAATATGAATTTGACACCATGCTGAGTTACCTTATA
CCACACAA---------CATCAGGCTCCTGATCGGACTTTTTAAAGTCATCCATGTCTGGACAGGAGATCTCC
TTTCTTTTAGTGACTTCAGATTT--------------TTCTAAATAGC-GGATCCTGCTGTTGTAGCACAGG
CCTGATTCATT---------------------------------------CTCTGCAACAGTCAAGGACA (SEQ ID NO: 535)

| Reads | Fraction | Fraction Cum_Sum | Seq | SEQ ID NO: |
|---|---|---|---|---|
| | | | CAGATTT--------------TTCTAAATAGC-GGATCCTGCTGTTGTAGCACAGG-------CCTGATTCATT---------------------------------------CTCTGCAACAGTCAAGGACA | |
| 2369 | 0.002795481 | 0.526195986 | TCCTCATCCCCAAGACTGCTATTGACTGAGGTAAAATATGAATTTGACACCATGCTGAGTTACCTT--------------------ATCAGGCTCCTGATCGGACTTTTTAAAGTCATCCATGTCTGGACAGGAGATCTCCTTTCTTTTAGTGACTTCAGATTT--------------TTCTAAATAGC-GGATCCTGCTGTTGTAGCACAGG-------CCTGATTCATT---------------------------------------CTCTGCAACAGTCAAGGACA | 560 |
| 2241 | 0.002644438 | 0.528840424 | TCCTCATCCCCAAGACTGCTATTGACTGAGGTAAAATATGAATTTGACACCATGCTGAGTTACCTTATACCACACAA---------ATCAGGCTCCTGATCGGACTTTTTAAAGTCATCCATGTCTGGACAGGAGATCTCCTTTCTTTTAGTGACTTCAGATTT--------------TTCTAAATAGC-GGATCCTGCTGTTGTAGCACAGG-------CCTGATTCATT---------------------------------------CTCTGCAACAGTCAAGGACA | 561 |
| 2224 | 0.002624378 | 0.531464802 | TCCTCATCCCCAAGACTGCTATTGACTGAGGTAAAATATGAATTTGACACCATGCTGAGTTACCTTATACCACACAA-----------------CTGATCGGACTTTTTAAAGTCATCCATGTCTGGACAGGAGATCTCCTTTCTTTTAGTGACTTCAGATTT--------------TTCTAAATAGC-GGATCCTGCTGTTGTAGCACAGG-------CCTGATTCATT---------------------------------------CTCTGCAACAGTCAAGGACA | 562 |
| 2223 | 0.002623198 | 0.534087999 | TCCTCATCCCCAAGACTGCTATTGACTGAGGTAAAATATGAATTTGACACCATGCTGAGTTACCTTATACCACA----------CCATCAGGCTCCTGATCGGACTTTTTAAAGTCATCCATGTCTGGACAGGAGATCTCCTTTCTTTTAGTGACTTCAGATTT--------------TTCTAAATAGC-GGATCCTGCTGTTGTAGCACAGG-------CCTGATTCATT---------------------------------------CTCTGCAACAGTCAAGGACA | 563 |
| 2018 | 0.002381292 | 0.536469292 | TCCTCATCCCCAAGACTGCTATTGACTGAGGTAAAATATGAATTTGACACCATGCTG-------------------------AGGCTCCTGATCGGACTTTTTAAAGTCATCCATGTCTGGACAGGAGATCTCCTTTCTTTTAGTGACTTCAGATTT--------------TTCTAAATAGC-GGATCCTGCTGTTGTAGCACAGG-------CCTGATTCATT---------------------------------------CTCTGCAACAGTCAAGGACA | 564 |
| 1964 | 0.002317571 | 0.538786863 | TCCTCATCCCCAAGACTGCTATTGACTGAGGTAAAATATGAATTTGACACCATGCTGAGTTACCTTATAC---------------CGATCAGGCTCCTGATCGGACTTTTTAAAGTCATCCATGTCTGGACAGGAGATCTCCTTTCTTTTAGTGACTTCAGATTT--------------TTCTAAATAGC-GGATCCTGCTGTTGTAGCACAGG-------CCTGATTCATT | 565 |

TABLE 6-continued

IL1RAPL2

WT sequence:
TCCTCATCCCCAAGACTGCTATTGACTGAGGTAAAATATGAATTTGACACCATGCTGAGTTACCTTATA
CCACACAA---------CATCAGGCTCCTGATCGGACTTTTTAAAGTCATCCATGTCTGGACAGGAGATCTCC
TTTCTTTTAGTGACTTCAGATTT--------------TTCTAAATAGC-GGATCCTGCTGTTGTAGCACAGG
CCTGATTCATT----------------------------------------CTCTGCAACAGTCAAGGACA (SEQ ID NO: 535)

| Reads | Fraction | Fraction Cum_Sum | Seq | SEQ ID NO: |
|---|---|---|---|---|
| | | | --------<br>CTCTGCAACAGTCAAGGACA | |
| 1908 | 0.002251489 | 0.541038352 | TCCTCATCCCCAAGACTGCTATTGACTGAGGTAAA<br>ATATGAATTTGACACCATGCTGAGTTACCTTATAC-<br>----------------<br>ATCAGGCTCCTGATCGGACTTTTTAAAGTCATCCA<br>TGTCTGGACAGGAGATCTCCTTTCTTTTAGTGACTT<br>CAGATTT--------------TTCTAAATAGC-<br>GGATCCTGCTGTTGTAGCACAGG-------<br>CCTGATTCATT---------------------------------<br>--------<br>CTCTGCAACAGTCAAGGACA | 566 |
| 1860 | 0.002194848 | 0.5432332 | TCCTCATCCCCAAGACTGCTATTGACTGAGGTAAA<br>ATATGAATTTGACACCATGCTGAGTTACCTTATAC<br>CA-------------------<br>CTCCTGATCGGACTTTTTAAAGTCATCCATGTCTGG<br>ACAGGAGATCTCCTTTCTTTTAGTGACTTCAGATTT<br>---------------TTCTAAATAGC-<br>GGATCCTGCTGTTGTAGCACAGG-------<br>CCTGATTCATT---------------------------------<br>--------<br>CTCTGCAACAGTCAAGGACA | 567 |
| 1699 | 0.002004864 | 0.545238064 | TCCTCATCCCCAAGACTGCTATTGACTGAGGTAAA<br>ATATGAATTTGACACCATGCTGAG----------------------<br>----------------<br>ATCGGACTTTTTAAAGTCATCCATGTCTGGACAGG<br>AGATCTCCTTTCTTTTAGTGACTTCAGATTT-----------<br>---TTCTAAATAGC-<br>GGATCCTGCTGTTGTAGCACAGG-------<br>CCTGATTCATT---------------------------------<br>--------<br>CTCTGCAACAGTCAAGGACA | 568 |
| 1610 | 0.001899842 | 0.547137906 | TCCTCATCCCCAAGACTG-------<br>CTGACCAAAGCCTATATTTTGGGACGTGGATGA-<br>TGAGAGTAAACTACACCTTCTGCCCATTTTAGCTTC<br>CTGCTCTCACCTCCAACA------------<br>AGAATAAGAGATGTGCCAACTTTCTCTGGGTGCAT<br>ACTTGCTGCCATGCACTGTTCTGGGTACCAGGATA<br>GAGCATTAAAAGGGCAGATGCAGTCCCTGCTTCCA<br>TGAAGGGTCATAAATTCCTTCCTGGGCCTTATAGT<br>TAGCCTTCATCACTCTGCAACAGTCAAGGACA | 569 |
| 1536 | 0.00181252 | 0.548950426 | TCCTCATCCCCAAGACTGCTATTGACTGAGGTAAA<br>ATATGAATTTGACACCATGCTGAGTTACCTTATAC<br>CACACAA-------------------------<br>CTTTTTAAAGTCATCCATGTCTGGACAGGAGATCT<br>CCTTTCTTTTAGTGACTTCAGATTT--------------<br>TTCTAAATAGC-GGATCCTGCTGTTGTAGCACAGG--<br>-----CCTGATTCATT-----------------------------<br>---------------<br>-CTCTGCAACAGTCAAGGACA | 570 |
| 1413 | 0.001667377 | 0.550617803 | TCCTCATCCCCAAGACTGCTATTGACTGAGGTAAA<br>ATATGAATTTGACACCATGCTGA------------------------<br>--------<br>GCTCCTGATCGGACTTTTTAAAGTCATCCATGTCTG<br>GACAGGAGATCTCCTTTCTTTTAGTGACTTCAGATT<br>T--------------TTCTAAATAGC-<br>GGATCCTGCTGTTGTAGCACAGG-------<br>CCTGATTCATT---------------------------------<br>--------<br>CTCTGCAACAGTCAAGGACA | 571 |
| 1402 | 0.001654396 | 0.552272199 | TCCTCATCCCCAAGACTGCTATTGACTGAGGTAAA<br>ATATGAATTTGACACCATGCTGAGTTACCTTA------- | 572 |

TABLE 6-continued

IL1RAPL2

WT sequence:
TCCTCATCCCCAAGACTGCTATTGACTGAGGTAAAATATGAATTTGACACCATGCTGAGTTACCTTATA
CCACACAA---------CATCAGGCTCCTGATCGGACTTTTTAAAGTCATCCATGTCTGGACAGGAGATCTCC
TTTCTTTTAGTGACTTCAGATTT--------------TTCTAAATAGC-GGATCCTGCTGTTGTAGCACAGG
CCTGATTCATT---------------------------------------------CTCTGCAACAGTCAAGGACA (SEQ ID NO: 535)

| Reads | Fraction | Fraction Cum_Sum | Seq | SEQ ID NO: |
|---|---|---|---|---|
| | | | ---------------------TGATCGGACTTTTTAAAGTCATCCATGTCTGGACA--------------GGAGATCTCCTTTCTTTTAGTGACTTCAGATTTTTCTAAATAGC-GGATCCTGCTGTTGTAGCACAGG-------CCTGATTCATT-----------------------------------CTCTGCAACAGTCAAGGACA | |
| 1338 | 0.001578875 | 0.553851074 | TCCTCATCCCCAAGACTGCTATTGACTGAGGTAAAATATGAATTTGACACCATGCTGAGTTACCTTATACCACAC---------------------ATCGGACTTTTTAAAGTCATCCATGTCTGGACAGGAGATCTCCTTTCTTTTAGTGACTTCAGATTT--------------TTCTAAATAGC-GGATCCTGCTGTTGTAGCACAGG-------CCTGATTCATT-----------------------------------CTCTGCAACAGTCAAGGACA | 573 |
| 1302 | 0.001536394 | 0.555387467 | TCCTCATCCCCAAGACTGCTATTGACTGAGGTAAAATATGAATTTGACACCATGCTGAGTTACCTTATACCACA---------------------------CTTTTTAAAGTCATCCATGTCTGGACAGGAGATCTCCTTTCTTTTAGTGACTTCAGATTT--------------TTCTAAATAGC-GGATCCTGCTGTTGTAGCACAGG--------CCTGATTCATT-------------------------------CTCTGCAACAGTCAAGGACA | 574 |
| 1255 | 0.001480933 | 0.5568684 | TCCTCATCCCCAAGACTGCTATTGACTGAGGTAAAATATGAATTTGACACCATGCTGA-----------------------------------------TCGGACTTTTTAAAGTCATCCATGTCTGGACAGGAGATCTCCTTTCTTTTAGTGACTTCAGATTT-------------TTCTAAATAGC-GGATCCTGCTGTTGTAGCACAGG-------CCTGATTCATT-----------------------------------CTCTGCAACAGTCAAGGACA | 575 |
| 1243 | 0.001466772 | 0.558335172 | TCCTCATCCCCAAGACTGCTATTGACTGAGGTAAAATATGAATTTGACACCATGCTGAGTTAC-----------------------------CTCCTGATCGGACTTTTTAAAGTCATCCATGTCTGGACAGGAGATCTCCTTTCTTTTAGTGACTTCAGATTT--------------TTCTAAATAGC-GGATCCTGCTGTTGTAGCACAGG-------CCTGATTCATT-----------------------------------CTCTGCAACAGTCAAGGACA | 576 |
| 1200 | 0.001416031 | 0.559751203 | TCCTCATCCCCAAGACTGCTATTGACTGAGGTAAAATATGAATTTGACACCATGCTGAG---------------------------------TGATCGGACTTTTTAAAGTCATCCATGTCTGGACAGGGAGATCTCCTTTCTTTTAGTGACTTCAGATTT--------------TTCTAAATAGC-GGATCCTGCTGTTGTAGCACAGG-------CCTGATTCATT-----------------------------------CTCTGCAACAGTCAAGGACA | 577 |
| 1197 | 0.001412491 | 0.561163694 | TCCTCATCCCCAAGACTGCTATTGACTGAGGTAAAATATGAATTTGACACCATGCTGAGTTACCTTA-------------------------TCCTGATCGGACTTTTTAAAGTCATCCATGTCTGGACAGGAGATCTCCTTTCTTTTAGTGACTTCAGATTT------------TTCTAAATAGC-GGATCCTGCTGTTGTAGCACAGG-------CCTGATTCATT------------------------------ | 578 |

TABLE 6-continued

IL1RAPL2

WT sequence:
TCCTCATCCCCAAGACTGCTATTGACTGAGGTAAAATATGAATTTGACACCATGCTGAGTTACCTTATA
CCACACAA---------CATCAGGCTCCTGATCGGACTTTTTAAAGTCATCCATGTCTGGACAGGAGATCTCC
TTTCTTTTAGTGACTTCAGATTT--------------TTCTAAATAGC-GGATCCTGCTGTTGTAGCACAGG
CCTGATTCATT-------------------------------------CTCTGCAACAGTCAAGGACA (SEQ ID NO: 535)

| Reads | Fraction | Fraction Cum_Sum | Seq | SEQ ID NO: |
|---|---|---|---|---|
| | | | ------------<br>CTCTGCAACAGTCAAGGACA | |
| 1177 | 0.001388891 | 0.562552585 | TCCTCATCCCCAAGACTGCTATTGACTGAGGTAAA<br>ATATGAATTTGACACCATGCTGAGTTACCTTATAC<br>CACACAA---------<br>CTCAGGCTCCTGATCGGACTTTTTAAAGTCATCCAT<br>GTCTGGACAGGAGATCTCCTTTCTTTTAGTGACTTC<br>AGATTT--------------TTCTAAATAGC-<br>GGATCCTGCTGTTGTAGCACAGG-------<br>CCTGATTCATT-------------------------------<br>------------<br>CTCTGCAACAGTCAAGGACA | 579 |
| 1172 | 0.00138299 | 0.563935575 | TCCTCATCCCCAAGACTGCTATTGACTGAGGTAAA<br>ATATGAATTTGACACCATGCTGAGTTACCTTATAC<br>CACA----------<br>CGATCAGGCTCCTGATCGGACTTTTTAAAGTCATC<br>CATGTCTGGACAGGAGATCTCCTTTCTTTTAGTGAC<br>TTCAGATTT--------------TTCTAAATAGC-<br>GGATCCTGCTGTTGTAGCACAGG-------<br>CCTGATTCATT-------------------------------<br>------------<br>CTCTGCAACAGTCAAGGACA | 580 |
| 1138 | 0.00134287 | 0.565278445 | TCCTCATCCCCAAGACTGCTATTGACTGAGGTAAA<br>ATATGAATTTGACACCATGCTGAGTTACCTTATAC<br>CA----------------------<br>CTGATCGGACTTTTTAAAGTCATCCATGTCTGGAC<br>AGGAGATCTCCTTTCTTTTAGTGACTTCAGATTT----<br>-----------TTCTAAATAGC-<br>GGATCCTGCTGTTGTAGCACAGG-------<br>CCTGATTCATT-------------------------------<br>CTCTGCAACAGTCAAGGACA | 581 |
| 1130 | 0.001333429 | 0.566611874 | TCCTCATCCCCAAGACTGCTATTGACTGAGGTAAA<br>ATATGAATTTGACACCATGCTGAGTTACCTTATAC<br>CACACAA-------<br>CCATCAGGCTCCTGATCGGACTTTTTAAAGTCATC<br>CATGTCTGGACAGGAGATCTCCTTTCTTTTAGTGAC<br>TTCAGATTT--------------TTCTAAATAGC-<br>GGATCCTGCTGTTGTAGCACAGG-------<br>CCTGATTCATT-------------------------------<br>------------<br>ATCTGCAACAGTCAAGGACA | 582 |
| 1125 | 0.001327529 | 0.567939403 | TCCTCATCCCCAAGACTGCTATTGACTGAGGTAAA<br>ATATGAATTTGACACCATGCTGAGTTACCTTATAC-<br>-------------<br>CAATCAGGCTCCTGATCGGACTTTTTAAAGTCATC<br>CATGTCTGGACAGGAGATCTCCTTTCTTTTAGTGAC<br>TTCAGATTT--------------TTCTAAATAGC-<br>GGATCCTGCTGTTGTAGCACAGG-------<br>CCTGATTCATT-------------------------------<br>------------<br>CTCTGCAACAGTCAAGGACA | 583 |
| 1075 | 0.001268528 | 0.569207931 | TCCTCATCCCCAAGACTGCTATTGACTGAGGTAAA<br>ATATGAATTTGACACCATGCTGAGTTACCTTATAC<br>CACACA------------<br>CAGGCTCCTGATCGGACTTTTTAAAGTCATCCATG<br>TCTGGACAGGAGATCTCCTTTCTTTTAGTGACTTCA<br>GATTT--------------TTCTAAATAGC-<br>GGATCCTGCTGTTGTAGCACAGG-------<br>CCTGATTCATT-------------------------------<br>------------<br>CTCTGCAACAGTCAAGGACA | 584 |

TABLE 6-continued

IL1RAPL2

WT sequence:
TCCTCATCCCCAAGACTGCTATTGACTGAGGTAAAATATGAATTTGACACCATGCTGAGTTACCTTATA
CCACACAA---------CATCAGGCTCCTGATCGGACTTTTTAAAGTCATCCATGTCTGGACAGGAGATCTCC
TTTCTTTTAGTGACTTCAGATTT--------------TTCTAAATAGC-GGATCCTGCTGTTGTAGCACAGG
CCTGATTCATT---------------------------------------------CTCTGCAACAGTCAAGGACA (SEQ ID NO: 535)

| Reads | Fraction | Fraction Cum_Sum | Seq | SEQ ID NO: |
|---|---|---|---|---|
| 1074 | 0.001267348 | 0.570475279 | TCCTCATCCCCAAGACTGCTATTGACTGAGGTAAA<br>ATATGAATTTGACACCATGCTGAGTTACCTTATAC<br>CACACAA--------------<br>CCTCCTGATCGGACTTTTTAAAGTCATCCATGTCTG<br>GACAGGAGATCTCCTTTCTTTTAGTGACTTCAGATT<br>T--------------TTCTAAATAGC-<br>GGATCCTGCTGTTGTAGCACAGG-------<br>CCTGATTCATT-------------------------------<br>------------<br>CTCTGCAACAGTCAAGGACA | 585 |
| 1040 | 0.001227227 | 0.571702506 | TCCTCATCCCCAAGACTGCTATTGACTGAGGTAAA<br>ATATGAATTTGACACCATGCTGAGTTACCTTATAC-<br>------------------------<br>TGATCGGACTTTTTAAAGTCATCCATGTCTGGACA<br>GGAGATCTCCTTTCTTTTAGTGACTTCAGATTT------<br>----------TTCTAAATAGC-<br>GGATCCTGCTGTTGTAGCACAGG-------<br>CCTGATTCATT-------------------------------<br>------------<br>CTCTGCAACAGTCAAGGACA | 586 |
| 1023 | 0.001207167 | 0.572909673 | TCCTCATCCCCAAGACTGCTATTGACTGAGGTAAA<br>ATATGAATTTGACACCATGCTGAGTT-------------------<br>------<br>ATCAGGCTCCTGATCGGACTTTTTAAAGTCATCCA<br>TGTCTGGACAGGAGATCTCCTTTCTTTTAGTGACTT<br>CAGATTT--------------TTCTAAATAGC-<br>GGATCCTGCTGTTGTAGCACAGG-------<br>CCTGATTCATT-------------------------------<br>------------<br>CTCTGCAACAGTCAAGGACA | 587 |
| 1005 | 0.001185926 | 0.574095599 | TCCTCATCCCCAAGACTGCTATTGACTGAGGTAAA<br>ATATGAATTTGACACCATGCTGAG----------------------<br>-----------<br>TCCTGATCGGACTTTTTAAAGTCATCCATGTCTGGA<br>CAGGAGATCTCCTTTCTTTTAGTGACTTCAGATTT<br>-------------TTCTAAATAGC-<br>GGATCCTGCTGTTGTAGCACAGG-------<br>CCTGATTCATT-------------------------------<br>------------<br>CTCTGCAACAGTCAAGGACA | 588 |
| 1003 | 0.001183566 | 0.575279165 | TCCTCATCCCCAAGACTGCTATTGACTGAGGTAAA<br>ATATGAATTTGACACCATGCTGAGTTACCTTATAC<br>CACACAA----------------<br>CCTGATCGGACTTTTTAAAGTCATCCATGTCTGGA<br>CAGGAGATCTCCTTTCTTTTAGTGACTTCAGATTT--<br>--------------TTCTAAATAGC-<br>GGATCCTGCTGTTGTAGCACAGG-------<br>CCTGATTCATT-------------------------------<br>------------<br>CTCTGCAACAGTCAAGGACA | 589 |
| 972 | 0.001146985 | 0.57642615 | TCCTCATCCCCAAGACTGCTATTGACTGAGGTAAA<br>ATATGAATTTGACACCATGCTGAGT--------------------<br>---------------<br>TGATCGGACTTTTTAAAGTCATCCATGTCTGGACA<br>GGGAGATCTCCTTTCTTTTAGTGACTTCAGATTT------<br>----------TTCTAAATAGC-<br>GGATCCTGCTGTTGTAGCACAGG-------<br>CCTGATTCATT-------------------------------<br>------------<br>CTCTGCAACAGTCAAGGACA | 590 |
| 969 | 0.001143445 | 0.577569595 | TCCTCATCCCCAAGACTGCTATTGACTGAGGTAAA<br>ATATGAATTTGACACCATGCTGAGTTACCTTATAC-<br>------------------ | 591 |

TABLE 6-continued

IL1RAPL2

WT sequence:
TCCTCATCCCCAAGACTGCTATTGACTGAGGTAAAATATGAATTTGACACCATGCTGAGTTACCTTATA
CCACACAA---------CATCAGGCTCCTGATCGGACTTTTTAAAGTCATCCATGTCTGGACAGGAGATCTCC
TTTCTTTTAGTGACTTCAGATTT--------------TTCTAAATAGC-GGATCCTGCTGTTGTAGCACAGG
CCTGATTCATT---------------------------------------CTCTGCAACAGTCAAGGACA (SEQ ID NO: 535)

| Reads | Fraction | Fraction Cum_Sum | Seq | SEQ ID NO: |
|---|---|---|---|---|
| | | | AGGCTCCTGATCGGACTTTTTAAAGTCATCCATGT<br>CTGGACAGGAGATCTCCTTTCTTTTAGTGACTTCAG<br>ATTT--------------TTCTAAATAGC-<br>GGATCCTGCTGTTGTAGCACAGG-------<br>CCTGATTCATT-------------------------------<br>------------<br>CTCTGCAACAGTCAAGGACA | |
| 937 | 0.001105684 | 0.578675279 | TCCTCATCCCCAAGACTGCTATTGACTGAGGTAAA<br>ATATGAATTTGACACCATGCTGAGTTACCT-----------<br>-------------------<br>TGATCGGACTTTTTAAAGTCATCCATGTCTGGACA<br>GGAGATCTCCTTTCTTTTAGTGACTTCAGATTT------<br>----------TTCTAAATAGC-<br>GGATCCTGCTGTTGTAGCACAGG-------<br>CCTGATTCATT-------------------------------<br>------------<br>CTCTGCAACAGTCAAGGACA | 592 |
| 909 | 0.001072644 | 0.579747923 | TCCTCATCCCCAAGACTGCTATTGACTGAGGTAAA<br>ATATGAATTTGACACCATGCTGAGTTACCTTATAC-<br>---------------------<br>CTCCTGATCGGACTTTTTAAAGTCATCCATGTCTGG<br>ACAGGAGATCTCCTTTCTTTTAGTGACTTCAGATTT<br>---------------TTCTAAATAGC-<br>GGATCCTGCTGTTGTAGCACAGG-------<br>CCTGATTCATT-------------------------------<br>------------<br>CTCTGCAACAGTCAAGGACA | 593 |
| 884 | 0.001043143 | 0.580791066 | TCCTCATCCCCAAGACTGCTATTGACTGAGGTAAA<br>ATATGAATTTGACACCATGCTGAG----------------------<br>--------------------------<br>TTAAAGTCATCCATGTCTGGACAGGAGATCTCCTT<br>TCTTTTAGTGACTTCAGATTT--------------<br>TTCTAAATAGC-GGATCCTGCTGTTGTAGCACAGG--<br>------CCTGATTCATT-------------------------------<br>------------<br>-CTCTGCAACAGTCAAGGACA | 594 |
| 883 | 0.001041963 | 0.581833029 | TCCTCATCCCCAAGACTGCTATTGACTGAGGTAAA<br>ATATGAATTTGACACCATGCTGAGTT------------------<br>--------------------------<br>ACTTTTTAAAGTCATCCATGTCTGGACAGGAGATC<br>TCCTTTCTTTTAGTGACTTCAGATTT--------------<br>TTCTAAATAGC-GGATCCTGCTGTTGTAGCACAGG--<br>------CCTGATTCATT-------------------------------<br>------------<br>-CTCTGCAACAGTCAAGGACA | 595 |
| 878 | 0.001036063 | 0.582869091 | TCCTCATCCCCAAGACTGCTATTGACTGAGGTAAA<br>ATATGAATTTGACACCATGCTGAGTTACCTTATAC<br>CACACAA-------------------<br>CATCGGACTTTTTAAAGTCATCCATGTCTGGACAG<br>GAGATCTCCTTTCTTTTAGTGACTTCAGATTT---------<br>-----TTCTAAATAGC-<br>GGATCCTGCTGTTGTAGCACAGG-------<br>CCTGATTCATT-------------------------------<br>------------<br>CTCTGCAACAGTCAAGGACA | 596 |
| 857 | 0.001011282 | 0.583880374 | TCCTCATCCCCAAGACTGCTATTGACTGAGGTAAA<br>ATATGAATTTGACACCATGCTGAGTTACCTTATAC<br>CACA---------------------<br>CTGATCGGACTTTTTAAAGTCATCCATGTCTGGAC<br>AGGAGATCTCCTTTCTTTTAGTGACTTCAGATTT----<br>------------TTCTAAATAGC-<br>GGATCCTGCTGTTGTAGCACAGG-------<br>CCTGATTCATT------------------------------- | 597 |

TABLE 6-continued

IL1RAPL2

WT sequence:
TCCTCATCCCCAAGACTGCTATTGACTGAGGTAAAATATGAATTTGACACCATGCTGAGTTACCTTATA
CCACACAA---------CATCAGGCTCCTGATCGGACTTTTTAAAGTCATCCATGTCTGGACAGGAGATCTCC
TTTCTTTTAGTGACTTCAGATTT--------------TTCTAAATAGC-GGATCCTGCTGTTGTAGCACAGG
CCTGATTCATT---------------------------------------CTCTGCAACAGTCAAGGACA (SEQ ID NO: 535)

| Reads | Fraction | Fraction Cum_Sum | Seq | SEQ ID NO: |
|---|---|---|---|---|
| | | | ------------<br>CTCTGCAACAGTCAAGGACA | |
| 851 | 0.001004202 | 0.584884576 | TCCTCATCCCCAAGACTGCTATTGACTGAGGTAAA<br>ATATGAATTTGACACCATGCTGAGTTACCTTATAC<br>CACACAA-------------<br>CGCTCCTGATCGGACTTTTTAAAGTCATCCATGTCT<br>GGACAGGAGATCTCCTTTCTTTTAGTGACTTCAGA<br>TTT--------------TTCTAAATAGC-<br>GGATCCTGCTGTTGTAGCACAGG-------<br>CCTGATTCATT-------------------------------<br>------------<br>CTCTGCAACAGTCAAGGACA | 598 |
| 846 | 0.000998302 | 0.585882878 | TCCTCATCCCCAAGACTGCTATTGACTGAGGTAAA<br>ATATGAATTTGACACCATGCTGAGTTACCTTATAC<br>CACACAA------<br>CAAATCAGGCTCCTGATCGGACTTTTTAAAGTCAT<br>CCATGTCTGGACAGGAGATCTCCTTTCTTTTAGTGA<br>CTTCAGATTT--------------TTCTAAATAGC-<br>GGATCCTGCTGTTGTAGCACAGG-------<br>CCTGATTCATT-------------------------------<br>------------<br>CTCTGCAACAGTCAAGGACA | 599 |
| 840 | 0.000991222 | 0.586874099 | TCCTCATCCCCAAGACTGCTATTGACTGAGGTAAA<br>ATATGAATTTGACACCATGCTGAGTT-------------------<br>--------------------<br>CGGACTTTTTAAAGTCATCCATGTCTGGACAGGAG<br>ATCTCCTTTCTTTTAGTGACTTCAGATTT--------------<br>TTCTAAATAGC-GGATCCTGCTGTTGTAGCACAGG--<br>-----CCTGATTCATT-------------------------------<br>-CTCTGCAACAGTCAAGGACA | 600 |
| 834 | 0.000984142 | 0.587858241 | TCCTCATCCCCAAGACTGCTATTGACTGAGGGAAA<br>ATATGAATTTGACACCATGCTGAGTTACCTTATAC<br>CACACAA--------<br>CATCAGGCTCCTGATCGGACTTTTTAAAGTCATCC<br>ATGTCTGGACAGGAGATCTCCTTTCTTTTAGTGACT<br>TCAGATTT--------------TTCTAAATAGC-<br>GGATCCTGCTGTTGTAGCACAGG-------<br>CCTGATTCATT-------------------------------<br>CTCTGCAACAGTCAAGGACA | 601 |
| 833 | 0.000982962 | 0.588841203 | TCCTCATCCCCAAGACTGCTATTGACTGAGGTAAA<br>ATATGAATTTGACACCATGCTGAGTTACC-------------<br>-------------------------------<br>TTAAAGTCATCCATGTCTGGACAGGAGATCTCCTT<br>TCTTTTAGTGACTTCAGATTT--------------<br>TTCTAAATAGC-GGATCCTGCTGTTGTAGCACAGG--<br>-----CCTGATTCATT-------------------------------<br>------------<br>-CTCTGCAACAGTCAAGGACA | 602 |
| 830 | 0.000979422 | 0.589820624 | TCCTCATCCCCAAGACTGCTATTGACTGAGGTAAA<br>ATATGAATTTGACACCATGCTGAGTTACCTTATAC<br>CACA-------------<br>CAGGCTCCTGATCGGACTTTTTAAAGTCATCCATG<br>TCTGGACAGGAGATCTCCTTTCTTTTAGTGACTTCA<br>GATTT--------------TTCTAAATAGC-<br>GGATCCTGCTGTTGTAGCACAGG-------<br>CCTGATTCATT-------------------------------<br>------------<br>ATCTGCAACAGTCAAGGACA | 603 |
| 816 | 0.000962901 | 0.590783525 | TCCTCATCCCCAAGACTGCTATTGACTGAGGTAAA<br>ATATGAATTTGACACCATGCTGAGTTACCTTATAC<br>CACA----------------------------------------<br>------------------------------------------ | 604 |

TABLE 6-continued

IL1RAPL2

WT sequence:
TCCTCATCCCCAAGACTGCTATTGACTGAGGTAAAATATGAATTTGACACCATGCTGAGTTACCTTATA
CCACACAA---------CATCAGGCTCCTGATCGGACTTTTTAAAGTCATCCATGTCTGGACAGGAGATCTCC
TTTCTTTTAGTGACTTCAGATTT--------------TTCTAAATAGC-GGATCCTGCTGTTGTAGCACAGG
CCTGATTCATT---------------------------------------------CTCTGCAACAGTCAAGGACA (SEQ ID NO: 535)

| Reads | Fraction | Fraction Cum_Sum | Seq | SEQ ID NO: |
|---|---|---|---|---|
| | | | CAGG-------CCTGATTCATT-------------------------<br>------------------<br>CTCTGCAACAGTCAAGGACA | |
| 793 | 0.000935761 | 0.591719286 | TCCTCATCCCCAAGACTGCTATTGACTGAGGTAAA<br>ATATGAATTTGACACCATGCTGAGTTA----------------<br>-------------<br>CTCCTGATCGGACTTTTTAAAGTCATCCATGTCTGG<br>ACAGGAGATCTCCTTTCTTTTAGTGACTTCAGATTT<br>--------------TTCTAAATAGC-<br>GGATCCTGCTGTTGTAGCACAGG-------<br>CCTGATTCATT-------------------------<br>------------<br>CTCTGCAACAGTCAAGGACA | 605 |
| 786 | 0.0009275 | 0.592646786 | TCCTCATCCCCAAGACTGCTATTGACTGAGGTAAA<br>ATATGAATTTGACACCATGCTGAGTTACCTTATAC<br>CACA----------------------<br>TCGGACTTTTTAAAGTCATCCATGTCTGGACAGGA<br>GATCTCCTTTCTTTTAGTGACTTCAGATTT-------------<br>-TTCTAAATAGC-GGATCCTGCTGTTGTAGCACAGG-<br>------CCTGATTCATT-------------------------<br>------------<br>--CTCTGCAACAGTCAAGGACA | 606 |
| 783 | 0.00092396 | 0.593570747 | TCCTCATCCCCAAGACTGCTATTGACTGAGGTAAA<br>ATATGAATTTGACACCATGCTGAGTTACCTTATAC<br>CACAC---------<br>ACATCAGGCTCCTGATCGGACTTTTTAAAGTCATC<br>CATGTCTGGACAGGAGATCTCCTTTCTTTTAGTGAC<br>TTCAGATTT--------------TTCTAAATAGC-<br>GGATCCTGCTGTTGTAGCACAGG-------<br>CCTGATTCATT-------------------------<br>------------<br>CTCTGCAACAGTCAAGGACA | 607 |
| 768 | 0.00090626 | 0.594477007 | TCCTCATCCCCAAGACTGCTATTGACTGAGGTAAA<br>ATATGAATTTGACACCATGCTGAGTTACCTTATAC<br>CACACAA------------------<br>CGATCGGACTTTTTAAAGTCATCCATGTCTGGACA<br>GGAGATCTCCTTTCTTTTAGTGACTTCAGATTT------<br>---------TTCTAAATAGC-<br>GGATCCTGCTGTTGTAGCACAGG-------<br>CCTGATTCATT-------------------------<br>------------<br>CTCTGCAACAGTCAAGGACA | 608 |
| 758 | 0.00089446 | 0.595371466 | TCCTCATCCCCAAGACTGCTATTGACTGAGGTAAA<br>ATATGAATTTGACACCATGCTGAGTTACCTTAT-----<br>------------------------<br>ATCGGACTTTTTAAAGTCATCCATGTCTGGACAGG<br>AGATCTCCTTTCTTTTAGTGACTTCAGATTT-----------<br>---TTCTAAATAGC-<br>GGATCCTGCTGTTGTAGCACAGG-------<br>CCTGATTCATT-------------------------<br>------------<br>CTCTGCAACAGTCAAGGACA | 609 |
| 751 | 0.000886199 | 0.596257666 | TCCTCATCCCCAAGACTGCTATTGACTGAGGCAAA<br>ATATGAATTTGACACCATGCTGAGTTACCTTATAC<br>CACACAA--------<br>CATCAGGCTCCTGATCGGACTTTTTAAAGTCATCC<br>ATGTCTGGACAGGAGATCTCCTTTCTTTTAGTGACT<br>TCAGATTT--------------TTCTAAATAGC-<br>GGATCCTGCTGTTGTAGCACAGG-------<br>CCTGATTCATT-------------------------<br>------------<br>CTCTGCAACAGTCAAGGACA | 610 |

TABLE 6-continued

IL1RAPL2

WT sequence:
TCCTCATCCCCAAGACTGCTATTGACTGAGGTAAAATATGAATTTGACACCATGCTGAGTTACCTTATA
CCACACAA---------CATCAGGCTCCTGATCGGACTTTTTAAAGTCATCCATGTCTGGACAGGAGATCTCC
TTTCTTTTAGTGACTTCAGATTT--------------TTCTAAATAGC-GGATCCTGCTGTTGTAGCACAGG
CCTGATTCATT---------------------------------------------CTCTGCAACAGTCAAGGACA (SEQ ID NO: 535)

| Reads | Fraction | Fraction Cum_Sum | Seq | SEQ ID NO: |
|---|---|---|---|---|
| 749 | 0.000883839 | 0.597141505 | TCCTCATCCCCAAGACTGCTATTGACTGAGGTAAA ATATGAATTTGACACCATGCTGAG--------------------- --------------------- GACTTTTTAAAGTCATCCATGTCTGGACAGGAGAT CTCCTTTCTTTTAGTGACTTCAGATTT-------------- TTCTAAATAGC-GGATCCTGCTGTTGTAGCACAGG-- -----CCTGATTCATT------------------------------- ------------ -CTCTGCAACAGTCAAGGACA | 611 |
| 743 | 0.000876759 | 0.598018264 | TCCTCATCCCCAAGACTGCTATTGACTGAGGTAAA ATATGAATTTGACACCATGCTGAGTTACCTTATAC C------------------------------- ACTTTTTAAAGTCATCCATGTCTGGACAGGAGATC TCCTTTCTTTTAGTGACTTCAGATTT-------------- TTCTAAATAGC-GGATCCTGCTGTTGTAGCACAGG-- -----CCTGATTCATT------------------------------- -CTCTGCAACAGTCAAGGACA | 612 |
| 713 | 0.000841358 | 0.598859623 | TCCTCATCCCCAAGACTGCTATTGACTGAGGTAAA ATATGAATTTGACACCAT----------------------------- ------- GCTCCTGATCGGACTTTTTAAAGTCATCCATGTCTG GACAGGAGATCTCCTTTCTTTTAGTGACTTCAGATT T--------------TTCTAAATAGC- GGATCCTGCTGTTGTAGCACAGG------- CCTGATTCATT------------------------------- ------------ CTCTGCAACAGTCAAGGACA | 613 |
| 711 | 0.000838998 | 0.599698621 | TCCTCATCCCCAAGACTGCTATTGACTGAGGTAAA ATATGAATTTGACACCATGCTGAGTTACCTTATAC- -CA---------- CCATCAGGCTCCTGATCGGACTTTTTAAAGTCATC CATGTCTGGACAGGAGATCTCCTTTCTTTTAGTGAC TTCAGATTT--------------TTCTAAATAGC- GGATCCTGCTGTTGTAGCACAGG------- CCTGATTCATT------------------------------- ------------ CTCTGCAACAGTCAAGGACA | 614 |
| 700 | 0.000826018 | 0.60052464 | TCCTCATCCCCAAGACTGCTATTGACTGAGGTAAA ATATGAATTTGACACCATGCTGAGTTACCTTATAC CACA-------------------- CCTGATCGGACTTTTTAAAGTCATCCATGTCTGGA CAGGAGATCTCCTTTCTTTTAGTGACTTCAGATTT-- --------------TTCTAAATAGC- GGATCCTGCTGTTGTAGCACAGG------- CCTGATTCATT------------------------------- ------------ CTCTGCAACAGTCAAGGACA | 615 |
| 688 | 0.000811858 | 0.601336497 | TCCTCATCCCCAAGACTGCTATTGACTGAGGTAAA ATATGAATTTGACACCATGCTGAGTTACCTTA------- ------------- ATCAGGCTCCTGATCGGACTTTTTAAAGTCATCCA TGTCTGGACAGGAGATCTCCTTTCTTTTAGTGACTT CAGATTT--------------TTCTAAATAGC- GGATCCTGCTGTTGTAGCACAGG------- CCTGATTCATT------------------------------- CTCTGCAACAGTCAAGGACA | 616 |
| 686 | 0.000809498 | 0.602145995 | TCCTCATCCCCAAGACTGCTATTGACTGAGGTAAA ATATGAATTTGACACCATGCTGAG--------------------- --------------------- ACTTTTTAAAGTCATCCATGTCTGGACAGGAGATC TCCTTTCTTTTAGTGACTTCAGATTT-------------- TTCTAAATAGC-GGATCCTGCTGTTGTAGCACAGG-- -----CCTGATTCATT------------------------------- | 617 |

TABLE 6-continued

IL1RAPL2

WT sequence:
TCCTCATCCCCAAGACTGCTATTGACTGAGGTAAAATATGAATTTGACACCATGCTGAGTTACCTTATA
CCACACAA---------CATCAGGCTCCTGATCGGACTTTTTAAAGTCATCCATGTCTGGACAGGAGATCTCC
TTTCTTTTAGTGACTTCAGATTT--------------TTCTAAATAGC-GGATCCTGCTGTTGTAGCACAGG
CCTGATTCATT---------------------------------------CTCTGCAACAGTCAAGGACA (SEQ ID NO: 535)

| Reads | Fraction | Fraction Cum_Sum | Seq | SEQ ID NO: |
|---|---|---|---|---|
|  |  |  | ------------<br>-CTCTGCAACAGTCAAGGACA |  |
| 682 | 0.000804778 | 0.602950773 | TCCTCATCCCCAAGACTGCTATTGACTGAGGTAAA<br>ATATGAATTTGACACCATGCTGAGTTACCTTATAC<br>CACACA----------------<br>CTCCTGATCGGACTTTTTAAAGTCATCCATGTCTGG<br>ACAGGAGATCTCCTTTCTTTTAGTGACTTCAGATTT<br>---------------TTCTAAATAGC-<br>GGATCCTGCTGTTGTAGCACAGG-------<br>CCTGATTCATT-------------------------------<br>------------<br>CTCTGCAACAGTCAAGGACA | 618 |
| 670 | 0.000790617 | 0.60374139 | TCCTCATCCCCAAGACTGCTATTGACTGAGGTAAA<br>ATATGAATTTGACACCATGCTGAGTTAC---------------<br>---------<br>ATCAGGCTCCTGATCGGACTTTTTAAAGTCATCCA<br>TGTCTGGACAGGAGATCTCCTTTCTTTTAGTGACTT<br>CAGATTT--------------TTCTAAATAGC-<br>GGATCCTGCTGTTGTAGCACAGG-------<br>CCTGATTCATT-------------------------------<br>------------<br>CTCTGCAACAGTCAAGGACA | 619 |
| 663 | 0.000782357 | 0.604523747 | TCCTCATCCCCAAGACTGCTATTGACTGAGGTAAA<br>ATATGAATTTGACACCATGCTGAGTTACCTTATAC-<br>-----------------------------<br>CGGACTTTTTAAAGTCATCCATGTCTGGACAGGAG<br>ATCTCCTTTCTTTTAGTGACTTCAGATTT--------------<br>TTCTAAATAGC-GGATCCTGCTGTTGTAGCACAGG--<br>------CCTGATTCATT-------------------------------<br>------------<br>-CTCTGCAACAGTCAAGGACA | 620 |
| 655 | 0.000772917 | 0.605296664 | TCCTCATCCCCAAGACTGCTATTGACTGAGGTAAA<br>ATATGAATTTGACACCATGCTGAGTTACCTTATAC<br>CACACA--------<br>ACATCAGGCTCCTGATCGGACCTTTTTAAAGTCATC<br>CATGTCTGGACAGGAGATCTCCTTTCTTTTAGTGAC<br>TTCAGATTT--------------TTCTAAATAGC-<br>GGATCCTGCTGTTGTAGCACAGG-------<br>CCTGATTCATT-------------------------------<br>------------<br>CTCTGCAACAGTCAAGGACA | 621 |
| 650 | 0.000767017 | 0.606063681 | TCCTCATCCCCAAGACTGCTATTGACTGAGGTAAA<br>ATATGAATTTGACGCCATGCTGAGTTACCTTATAC<br>CACACAA--------<br>CATCAGGCTCCTGATCGGACTTTTTAAAGTCATCC<br>ATGTCTGGACAGGAGATCTCCTTTCTTTTAGTGACT<br>TCAGATTT--------------TTCTAAATAGC-<br>GGATCCTGCTGTTGTAGCACAGG-------<br>CCTGATTCATT-------------------------------<br>------------<br>CTCTGCAACAGTCAAGGACA | 622 |
| 647 | 0.000763477 | 0.606827158 | TCCTCATCCCCAAGACTGCTATTGACTGAGGTAAA<br>ATATGAATTTGACACCATGCTGAGTTACCTTATAC<br>CACACAA--------<br>CATCAGGCTCCTGATCGGACTTTTTAAAGTCATCC<br>ATGTCTGGACAGGAGATCTCCTTTCTTTTAGTGACT<br>TCAGATTT--------------TTCTAAATAGC-<br>GGATCCTGCTGTTGTAGCGCAGG-------<br>CCTGATTCATT-------------------------------<br>------------<br>CTCTGCAACAGTCAAGGACA | 623 |

TABLE 6-continued

IL1RAPL2

WT sequence:
TCCTCATCCCCAAGACTGCTATTGACTGAGGTAAAATATGAATTTGACACCATGCTGAGTTACCTTATA
CCACACAA---------CATCAGGCTCCTGATCGGACTTTTTAAAGTCATCCATGTCTGGACAGGAGATCTCC
TTTCTTTTAGTGACTTCAGATTT--------------TTCTAAATAGC-GGATCCTGCTGTTGTAGCACAGG
CCTGATTCATT---------------------------------------CTCTGCAACAGTCAAGGACA (SEQ ID NO: 535)

| Reads | Fraction | Fraction Cum_Sum | Seq | SEQ ID NO: |
|---|---|---|---|---|
| 641 | 0.000756397 | 0.607583555 | TCCTCATCCCCAAGACTGCTATTGACTGAGGTAAA ATATGAATTTGACACCATGCTGAGTTACCTTATAC CACACAA-------- CATCAGGCTCCTGATCGGACTTTTTAAAGTCATCC ATGTCTGGACAGGAGATCTCCTTTCCTTTAGTGACT TCAGATTT--------------TTCTAAATAGC- GGATCCTGCTGTTGTAGCACAGG------- CCTGATTCATT------------------------------ CTCTGCAACAGTCAAGGACA | 624 |
| 633 | 0.000746956 | 0.608330511 | TCCTCATCCCCAAGACTGCTATTGACTGAGGTAAA ATATGAATTTGACACCATGCTGAGTTACCTTATAC CACACAA------- CATCAGGCTCCTGATCGGACTTTTTAAAGTCATCC ATGTCTGGACAGGAGATCTCCTTTCTTTTAGTGACT TCAGATTT--------------TTCTAAATAGC- GGATCCTGCTGTCGTAGCACAGG------- CCTGATTCATT------------------------------ ------------ CTCTGCAACAGTCAAGGACA | 625 |
| 631 | 0.000744596 | 0.609075107 | TCCTCATCCCCAAGACTGCTATTGACTGAGGTAAA ATATGAATTTGACACCATGCTGAGTTACCTTATAC CACACAA--------------- GCTCCTGATCGGACTTTTTAAAGTCATCCATGTCTG GACAGGAGATCTCCTTTCTTTTAGTGACTTCAGATT T--------------TTCTAAATAGC- GGATCCTGCTGTTGTAGCACAGG------- CCTGATTCATT------------------------------ CTCTGCAACAGTCAAGGACA | 626 |
| 628 | 0.000741056 | 0.609816164 | TCCTCATCCCCAAGACTGCTATTGACTGAGGTAAA ATATGAATTTGACACCATGCTGAGTTACCTTATAC CACACAA------ CTTATCAGGCTCCTGATCGGACTTTTTAAAGTCATC CATGTCTGGACAGGAGATCTCCTTTCTTTTAGTGAC TTCAGATTT--------------TTCTAAATAGC- GGATCCTGCTGTTGTAGCACAGG------- CCTGATTCATT------------------------------ ------------ CTCTGCAACAGTCAAGGACA | 627 |
| 611 | 0.000720996 | 0.61053716 | TCCTCATCCCCAAGACTGCTATTGACTGAGGTAAA ATATGAATTTGACACCATGCTGAGTTACCTTATAC CACA------------------------ CGGACTTTTTAAAGTCATCCATGTCTGGACAGGAG ATCTCCTTTCTTTTAGTGACTTCAGATTT-------------- TTCTAAATAGC-GGATCCTGCTGTTGTAGCACAGG-- -----CCTGATTCATT------------------------------ ------------ -CTCTGCAACAGTCAAGGACA | 628 |
| 610 | 0.000719816 | 0.611256975 | TCCTCATCCCCAAGACTGCTATTGACTGAGGTAAA ATATGAATTTGACACCATGCTGAGTT------------------ ------------------ ATCGGACTTTTTAAAGTCATCCATGTCTGGACAGG AGATCTCCTTTCTTTTAGTGACTTCAGATTT---------- ---TTCTAAATAGC- GGATCCTGCTGTTGTAGCACAGG------- CCTGATTCATT------------------------------ ------------ CTCTGCAACAGTCAAGGACA | 629 |
| 610 | 0.000719816 | 0.611976791 | TCCTCATCCCCAAGACTGCTATTGACTGAGGTAAA ATATGAATTTGACACCATGCTGAGTTACCTTATAC CACACAA------- CTATCAGGCTCCTGATCGGACTTTTTAAAGTCATCC ATGTCTGGACAGGAGATCTCCTTTCTTTTAGTGACT TCAGATTT--------------TTCTAAATAGC- | 630 |

TABLE 6-continued

IL1RAPL2

WT sequence:
TCCTCATCCCCAAGACTGCTATTGACTGAGGTAAAATATGAATTTGACACCATGCTGAGTTACCTTATA
CCACACAA---------CATCAGGCTCCTGATCGGACTTTTTAAAGTCATCCATGTCTGGACAGGAGATCTCC
TTTCTTTTAGTGACTTCAGATTT--------------TTCTAAATAGC-GGATCCTGCTGTTGTAGCACAGG
CCTGATTCATT---------------------------------------------CTCTGCAACAGTCAAGGACA (SEQ ID NO: 535)

| Reads | Fraction | Fraction Cum_Sum | Seq | SEQ ID NO: |
|---|---|---|---|---|
| | | | GGATCCTGCTGTTGTAGCACAGG-------<br>CCTGATTCATT--------------------------------<br>------------<br>ATCTGCAACAGTCAAGGACA | |
| 610 | 0.000719816 | 0.612696607 | TCCTCATCCCCAAGACTGCTATTGACTGAGGTAAA<br>ATATGAATTTGACACCATGCTGAGTTACCTTATAC<br>CACACAA--------<br>CATCAGGCTCCTGATCGGACTTTTTAAAGTCATCC<br>ATGTCTGGACAGGAGATCTCCCTTCTTTTAGTGACT<br>TCAGATTT--------------TTCTAAATAGC-<br>GGATCCTGCTGTTGTAGCACAGG-------<br>CCTGATTCATT--------------------------------<br>CTCTGCAACAGTCAAGGACA | 631 |
| 601 | 0.000709196 | 0.613405803 | TCCTCATCCCCAAGACTGCTATTGACTGAGGTAAA<br>ATATGAATTTGACACCATGCTGAGTTACCTTATAC<br>CACAC------------------------------------<br>AAGTCATCCATGTCTGGACAGGAGATCTCCTTTCT<br>TTTAGTGACTTCAGATTT--------------<br>TTCTAAATAGC-GGATCCTGCTGTTGTAGCACAGG--<br>------CCTGATTCATT--------------------------------<br>------------<br>-CTCTGCAACAGTCAAGGACA | 632 |
| 597 | 0.000704475 | 0.614110278 | TCCTCATCCCCAAGACTGCTATTGACTGAGGTAAA<br>ATATGAATTTGACACCATGCTG-------------------------<br>--<br>ATCAGGCTCCTGATCGGACTTTTTAAAGTCATCCA<br>TGTCTGGACAGGAGATCTCCTTTCTTTTAGTGACTT<br>CAGATTT--------------TTCTAAATAGC-<br>GGATCCTGCTGTTGTAGCACAGG-------<br>CCTGATTCATT--------------------------------<br>------------<br>CTCTGCAACAGTCAAGGACA | 633 |
| 596 | 0.000703295 | 0.614813574 | TCCTCATCCCCAAGACTGCTATTGACTGAGGTAAA<br>ATATGAATTTGACACCATGCTGAGTTACCTTATAC<br>CACACAA-------<br>CAATCAGGCTCCTGATCGGACTTTTTAAAGTCATC<br>CATGTCTGGACAGGAGATCTCCTTTCTTTTAGTGAC<br>TTCAGATTT--------------TTCTAAATAGC-<br>GGATCCTGCTGTTGTAGCACAGG-------<br>CCTGATTCATT--------------------------------<br>------------<br>ATCTGCAACAGTCAAGGACA | 634 |
| 595 | 0.000702115 | 0.615515689 | TCCTCATCCCCAAGACTGCTATTGACTGAGGTAAA<br>ATATGAATTTGACACCATGCTGAGTTACCTTATAC<br>CACAC----------------------------------------<br>--------------<br>AGGAGATCTCCTTTCTTTTAGTGACTTCAGATTT----<br>----------TTCTAAATAGC-<br>GGATCCTGCTGTTGTAGCACAGG-------<br>CCTGATTCATT--------------------------------<br>------------<br>CTCTGCAACAGTCAAGGACA | 635 |

REFERENCES

1. D. M. Lyerly, H. C. Krivan, T. D. Wilkins, *Clinical Microbiology Reviews* 1, 1 (January, 1988).
2. M. Rupnik, M. H. Wilcox, D. N. Gerding, *Nat Rev Microbiol* 7, 526 (July, 2009).
3. F. C. Lessa et al., *The New England Journal of Medicine* 372, 825 (Feb. 26, 2015).
4. T. Jank, K. Aktories, *Trends Microbiol* 16, 222 (May, 2008).
5. D. E. Voth, J. D. Ballard, *Clinical Microbiology Reviews* 18, 247 (April, 2005).
6. X. Sun, T. Savidge, H. Feng, *Toxins (Basel)* 2, 1848 (July, 2010).
7. I. Just et al., *Nature* 375, 500 (Jun. 8, 1995).

8. D. Drudy, S. Fanning, L. Kyne, *Int J Infect Dis* 11, 5 (January, 2007).
9. D. Lyras et al., *Nature* 458, 1176 (Apr. 30, 2009).
10. S. A. Kuehne et al., *Nature* 467, 711 (Oct. 7, 2010).
11. G. P. Carter et al., *MBio* 6, e00551 (2015).
12. P. Yuan et al., *Cell Res* 25, 157 (February, 2015).
13. N. Terada et al., *Histochem Cell Biol* 126, 483 (October, 2006).
14. M. E. LaFrance et al., *Proceedings of the National Academy of Sciences of the United States of America* 112, 7073 (Jun. 2, 2015).
15. O. Shalem et al., *Science* 343, 84 (Jan. 3, 2014).
16. J. A. Doudna, E. Charpentier, *Science* 346, 1258096 (Nov. 28, 2014).
17. A. Greco et al., *Nature Structural & Molecular Biology* 13, 460 (May, 2006).
18. L. A. Barroso, J. S. Moncrief, D. M. Lyerly, T. D. Wilkins, *Microbial Pathogenesis* 16, 297 (April, 1994).
19. S. Genisyuerek et al., *Molecular Microbiology* 79, 1643 (March, 2011).
20. A. Olling et al., *PLoS ONE* 6, e17623 (2011).
21. B. Schorch et al., *Proceedings of the National Academy of Sciences of the United States of America* 111, 6431 (Apr. 29, 2014).
22. A. B. Ryder et al., *Journal of Clinical Microbiology* 48, 4129 (November, 2010).
23. M. Flores-Diaz et al., *The Journal of Biological Chemistry* 272, 23784 (Sep. 19, 1997).
24. B. T. MacDonald, X. He, *Cold Spring Harb Perspect Biol* 4, (December, 2012).
25. A. Gregorieff, H. Clevers, *Genes Dev* 19, 877 (Apr. 15, 2005).
26. W. B. Stallcup, F. J. Huang, *Cell Adh Migr* 2, 192 (July-September, 2008).
27. P. Orth et al., *The Journal of Biological Chemistry* 289, 18008 (Jun. 27, 2014).
28. N. Sagara, G. Toda, M. Hirai, M. Terada, M. Katoh, *Biochemical and Biophysical Research Communications* 252, 117 (Nov. 9, 1998).
29. K. Ueno et al., *Neoplasia* 10, 697 (July, 2008).
30. T. Sato et al., *Nature* 459, 262 (May 14, 2009).
31. D. J. Flanagan et al., *Stem Cell Reports* 4, 759 (May 12, 2015).
32. H. Yu, X. Ye, N. Guo, J. Nathans, *Development* 139, 4383 (Dec. 1, 2012).
33. M. Richard, T. Boulin, V. J. Robert, J. E. Richmond, J. L. Bessereau, *Proceedings of the National Academy of Sciences of the United States of America* 110, E1055 (Mar. 12, 2013).
34. T. Satoh, A. Ohba, Z. Liu, T. Inagaki, A. K. Satoh, *Elife* 4, (2015).
35. J. C. Hsieh, A. Rattner, P. M. Smallwood, J. Nathans, *Proceedings of the National Academy of Sciences of the United States of America* 96, 3546 (Mar. 30, 1999).
36. M. Dong et al., *The Journal of Cell Biology* 162, 1293 (Sep. 29, 2003).
37. G. Yang et al., *BMC Microbiol* 8, 192 (2008).
38. E. Tillet, F. Ruggiero, A. Nishiyama, W. B. Stallcup, *The Journal of Biological Chemistry* 272, 10769 (Apr. 18, 1997).
39. B. T. MacDonald, C. Yokota, K. Tamai, X. Zeng, X. He, *The Journal of Biological Chemistry* 283, 16115 (Jun. 6, 2008).
40. H. Miyoshi, T. S. Stappenbeck, *Nature Protocols* 8, 2471 (December, 2013).
41. N. Wang et al., *PLoS ONE* 9, e93608 (2014).
42. T. Grabinger et al., *Cell Death Dis* 5, e1228 (2014)

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method of treating cancer, the method comprising administering to a subject in need thereof, a therapeutically effective amount of an isolated polypeptide comprising the amino acid sequence of any one of SEQ ID NOs: 18-20, wherein the isolated polypeptide does not comprise the amino acid sequence of SEQ ID NO: 27.

2. The method of claim 1, wherein the method further comprises administering to the subject an agent that blocks Wnt signaling.

3. The method of claim 2, wherein the agent is a Frizzled antibody.

4. The method of claim 1, wherein the polypeptide is cyclized.

5. The method of claim 1, wherein the polypeptide further comprises a fusion domain.

6. The method of claim 5, wherein the fusion domain comprises an immunoglobulin heavy chain constant region (Fc).

7. The method of claim 6, wherein the fusion domain is an Fc portion of human IgG1.

8. The method of claim 7, wherein the polypeptide comprises the amino acid sequence of SEQ ID NO:21, SEQ ID NO: 22, or SEQ ID NO: 23.

9. The method of claim 1, wherein the cancer is selected from a group consisting of colon cancer, lung cancer, liver cancer, and breast cancer.

10. The method of claim 1, wherein the cancer is metastatic cancer.

11. The method of claim 2, wherein the agent is a Dkk family protein.

12. The method of claim 2, wherein the agent is a Secreted Frizzled Related Protein (sFRP).

13. The method of claim 2, wherein the agent is Draxin.

14. The method of claim 2, wherein the agent is IGFBP-4.

15. The method of claim 2, wherein the agent is a SOST/Sclerostin.

16. The method of claim 2, wherein the agent is USAG1.

17. The method of claim 2, wherein the agent is WIF-1.

18. The method of claim 1, wherein the polypeptide is PEGylated.

* * * * *

UNITED STATES PATENT AND TRADEMARK OFFICE
CERTIFICATE OF CORRECTION

PATENT NO. : 10,913,786 B2
APPLICATION NO. : 16/086159
DATED : February 9, 2021
INVENTOR(S) : Min Dong et al.

It is certified that error appears in the above-identified patent and that said Letters Patent is hereby corrected as shown below:

In the Specification

At Column 1, Line 19, please replace the paragraph titled "GOVERNMENT SUPPORT" with the following paragraph:

FEDERALLY SPONSORED RESEARCH
This invention was made with government support under Grant Nos. NS080833, AI132387, DK034854, and HD018655, awarded by the National Institutes of Health. The Government has certain rights in the invention.

Signed and Sealed this
Fifteenth Day of August, 2023

Katherine Kelly Vidal
*Director of the United States Patent and Trademark Office*